US012723283B2

(12) United States Patent
Feng et al.

(10) Patent No.: US 12,723,283 B2
(45) Date of Patent: Sep. 1, 2026

(54) COMBINATION OF SOYBEAN WHOLE GENOME SNP LOCI, GENE CHIP AND APPLICATION THEREOF

(71) Applicant: Northeast Institute of Geography and Agroecology, Chinese Academy of Sciences, Changchun city (CN)

(72) Inventors: Xianzhong Feng, Changchun city (CN); Hui Yu, Changchun city (CN); Jiantian Leng, Changchun city (CN); Huangkai Zhou, Changchun city (CN); Guang Li, Changchun city (CN); Kuanqiang Tang, Changchun city (CN); Beifang Zhao, Changchun city (CN)

(73) Assignee: NORTHEAST INSTITUTE OF GEOGRAPHY AND AGROECOLOGY, CHINESE ACADEMY OF SCIENCES, Changchun City (CN)

( * ) Notice: Subject to any disclaimer, the term of this patent is extended or adjusted under 35 U.S.C. 154(b) by 1435 days.

(21) Appl. No.: 17/386,594

(22) Filed: Jul. 28, 2021

(65) Prior Publication Data

US 2022/0205053 A1 Jun. 30, 2022

(30) Foreign Application Priority Data

Dec. 31, 2020 (CN) ......................... 202011633836.7

(51) Int. Cl.

| | |
|---|---|
| ***C12Q 1/6895*** | (2018.01) |
| ***C12Q 1/6837*** | (2018.01) |
| ***C40B 40/06*** | (2006.01) |
| ***G16B 20/20*** | (2019.01) |

(52) U.S. Cl.

CPC ......... *C12Q 1/6895* (2013.01); *C12Q 1/6837* (2013.01); *G16B 20/20* (2019.02); *C12Q 2600/156* (2013.01); *C40B 40/06* (2013.01)

(58) Field of Classification Search

None

See application file for complete search history.

(56) References Cited

U.S. PATENT DOCUMENTS

2014/0007304 A1 1/2014 Wang et al.

FOREIGN PATENT DOCUMENTS

| | | |
|---|---|---|
| CN | 105567857 A | 5/2016 |
| CN | 110698551 A | 1/2020 |
| CN | 111676308 A | 9/2020 |

OTHER PUBLICATIONS

Elshire et al., "A Robust, Simple Genotyping-by-Sequencing (GBS) Approach for High Diversity Species," PLoS ONE 2011, 6(5): e19379. (Year: 2011).*

Song, Q., et al., "Development and Evaluation of SoySNP50K, a High-Density Genotyping Array for Soybean." PLos One, Jan. 2013, 8(1): e54985, pp. 1-12.

Wang, J., et al., "Development and application of a novel genome-wide SNP array reveals domestication history in soybean." Scientific Reports, 2016, 6(1): 20728, pp. 1-10.

Wang, Y., et al., "Genotyping of Soybean Cultivars with Medium-Density Array Reveals the Population Structure and QTNs Underlying Maturity and Seed Traits." Frontiers in Plant Science, May 2018, 9(610): pp. 1-16.

* cited by examiner

*Primary Examiner* — Kaijiang Zhang

(74) *Attorney, Agent, or Firm* — SALIWANCHIK, LLOYD & EISENSCHENK

(57) ABSTRACT

The present invention relates to a combination of soybean whole genome SNP loci, a gene chip and an application thereof. The combination of soybean whole genome SNP loci includes 20,648 SNP loci, which are shown as S00001-20648. The gene chip provided by the present invention has extremely high coverage on functional genes, the SNP marker loci cover 17,096 functional genes of soybean, accounting for about 31% of the total number of soybean genes, and the SNP marker loci are located in gene coding regions. Among the 20,648 SNP marker loci, 17,588 SNP marker loci are located on genes, accounting for 85% of the total number of the SNP marker loci. Therefore, when those SNP marker loci are applied in molecular assisted breeding or whole genome selective breeding, they can accelerate the breeding process.

2 Claims, 1 Drawing Sheet

COMBINATION OF SOYBEAN WHOLE GENOME SNP LOCI, GENE CHIP AND APPLICATION THEREOF

CROSS-REFERENCE TO A RELATED APPLICATION

This application claims priority to Chinese Application No. 202011633836.7 filed Dec. 31, 2020, which is incorporated herein.

TECHNICAL FIELD

The present invention belongs to the field of molecular plant breeding, and particularly relates to a combination of soybean whole genome single nucleotide polymorphism (SNP) loci, a gene chip and an application thereof.

BACKGROUND ART

The development of SNP markers is based on DNA sequencing. In over 10 years since the advent of the ROCH-454 sequencer in 2005, the next-generation sequencing technology has been continuously improved, the genomic sequencing efficiency has been greatly improved, the sequencing cost has been greatly reduced, and the whole genome sequences of a lot of species has been completed, thus the progress of functional genome research has been greatly promoted.

Soybean is the most important cash crop as well as the most important food crop in the world. It is the top-priority subject for the researchers in molecular biology to carry out resequencing on different varieties of soybean, utilize the SNP markers discovered in the resequencing to carry out association analysis on important agronomic traits through genome-wide association study (GWAS), ascertain candidate gene loci related to important agronomic traits, and establish a set of efficient, rapid, matured and stable, low-cost and high-throughput genotyping methods.

Presently, SNP gene chips have been developed in many crop species to provide important super-high density molecular markers for use in application scenarios such as marker-assisted major gene selection, backcross breeding and its background selection, polygene pyramiding breeding, seed purity detection, transgenic component identification, genome-wide association study, QTL analysis, species evolution analysis, and germplasm resource identification, etc. However, the SNP gene chips mainly have the following shortcomings:

1) At present, large-scale genotyping mostly employs solid-state chips or simplified genomic sequencing based on next-generation sequencing, wherein solid-state chips are difficult to manufacture and involve high costs, special testing instruments have to be used, and specific analysis software has to be used to analyze the genotyping results, therefore the gene chips are subject to many restrictive conditions and inconvenient to use; however, the simplified genomic sequencing involves high costs, results in serious loss of loci and high sequencing data volume, and has high requirements for software and hardware for data storage, analysis and computation.
2) At present, the chips do not have uniform coverage on the chromosomes, and the markers are mostly distributed in non-gene coding regions where more variation information exists, such as chromosome duplication regions, but fewer markers are distributed in autosome regions where more soybean genes are distributed at shorter intervals, e.g., on the two sides of chromosomes.
3) Most of the chips available at present do not have high coverage on functional genes, but usually cover non-coding regions of the genes.

SUMMARY

In order to overcome the drawbacks in the prior art, the present invention provides a combination of soybean whole genome SNP loci, a gene chip and an application thereof.

In order to attain the object described above, the present invention employs the following technical solution:

A combination of soybean whole genome SNP loci, includes 20,648 SNP loci, and each of SNP loci includes two different nucleotide variation positions for detecting allelic changes of the locus, wherein the physical positions of the 20,648 SNP loci are determined on the basis of the whole genome sequence alignment of soybean variety Williams82, the version number of the whole genome sequence of the soybean variety Williams82 is *Glycine max* Wm82.a2.v1, the whole genome sequence of the soybean variety Williams82 can be obtained from the website phytozome.jgi-.doc.gov; the variation information of the SNP loci is represented in the form of chromosome number_physical position reference genotype/allelotype, and the 20,648 SNP loci are shown as S00001-20648:

S00001: Chr01_00027982 T/A; S00002: Chr01_00090638 C/T; S00003: Chr01_00100506 A/C; S00004: Chr01_00206445 T/A; S00005: Chr01_00225250 C/A; S00006: Chr01_00250005 A/T; S00007: Chr01_00281981 G/C; S00008: Chr01_00318908 A/C; S00009: Chr01_00333333 G/A; S00010: Chr01_00369910 C/A; S00011: Chr01_00376944 C/T; S00012: Chr01_00411506 G/A; S00013: Chr01_00425943 A/G; S00014: Chr01_00450291 C/A; S00015: Chr01_00506115 T/A; S00016: Chr01_00526691 G/T; S00017: Chr01_00560840 T/C; S00018: Chr01_00577219 G/T; S00019: Chr01_00604949 T/G; S00020: Chr01_00636059 C/T; S00021: Chr01_00650169 T/A; S00022: Chr01_00682203 T/C; S00023: Chr01_00708215 A/G; S00024: Chr01_00766278 T/C; S00025: Chr01_00775950 G/A; S00026: Chr01_00804370 G/A; S00027: Chr01_00827803 T/C; S00028: Chr01_00853962 A/T; S00029: Chr01_00882953 T/C; S00030: Chr01_00901990 C/T; S00031: Chr01_00925792 T/C; S00032: Chr01_00955453 T/C; S00033: Chr01_00975163 C/T; S00034: Chr01_01001775 A/G; S00035: Chr01_01031087 T/A; S00036: Chr01_01051083 A/C; S00037: Chr01_01085131 T/G; S00038: Chr01_01122432 T/C; S00039: Chr01_01125953 G/A; S00040: Chr01_01157437 G/T; S00041: Chr01_01182456 C/T; S00042: Chr01_01204481 C/A; S00043: Chr01_01232243 C/T; S00044: Chr01_01268322 T/C; S00045: Chr01_01278719 T/G; S00046: Chr01_01302531 C/A; S00047: Chr01_01328355 G/T; S00048: Chr01_01374300 G/A; S00049: Chr01_01389286 A/G; S00050: Chr01_01405027 A/G; S00051: Chr01_01430369 T/C; S00052: Chr01_01460795 C/A; S00053: Chr01_01481215 A/G; S00054: Chr01_01501284 G/A; S00055: Chr01_01533882 A/G; S00056: Chr01_01550268 C/T; S00057: Chr01_01575046 A/T; S00058: Chr01_01600023 T/G; S00059:

Chr01_01636901 T/C; S00060: Chr01_01656913 T/A; S00061: Chr01_01722575 C/T; S00062: Chr01_01734976 A/T; S00063: Chr01_01750365 T/A; S00064: Chr01_01783216 T/C; S00065: Chr01_01804602 T/G; S00066: Chr01_01835364 T/C; S00067: Chr01_01866165 G/A; S00068: Chr01_01906477 T/C; S00069: Chr01_01930184 C/T; S00070: Chr01_01976387 C/T; S00071: Chr01_02006014 C/T; S00072: Chr01_02067319 C/T; S00073: Chr01_02096999 A/G; S00074: Chr01_02105415 T/C; S00075: Chr01_02125068 T/A; S00076: Chr01_02151194 C/G; S00077: Chr01_02197864 A/G; S00078: Chr01_02240242 A/G; S00079: Chr01_02285551 T/C; S00080: Chr01_02300212 T/C; S00081: Chr01_02329051 A/G; S00082: Chr01_02350193 G/A; S00083: Chr01_02484626 T/G; S00084: Chr01_02531497 C/A; S00085: Chr01_02601764 A/C; S00086: Chr01_02699954 G/C; S00087: Chr01_02701606 T/G; S00088: Chr01_02731154 A/C; S00089: Chr01_02753365 C/A; S00090: Chr01_02782130 G/A; S00091: Chr01_02801633 G/C; S00092: Chr01_02836721 T/C; S00093: Chr01_02852655 A/T; S00094: Chr01_02877051 T/C; S00095: Chr01_02931250 A/T; S00096: Chr01_03038334 G/A; S00097: Chr01_03051719 T/C; S00098: Chr01_03134270 T/A; S00099: Chr01_03150979 C/T; S00100: Chr01_03178485 G/A; S00101: Chr01_03205217 T/C; S00102: Chr01_03243133 T/C; S00103: Chr01_03269913 C/T; S00104: Chr01_03282656 G/A; S00105: Chr01_03333666 T/G; S00106: Chr01_03375794 G/A; S00107: Chr01_03405220 T/A; S00108: Chr01_03425236 A/G; S00109: Chr01_03457861 C/G; S00110: Chr01_03487438 C/G; S00111: Chr01_03503569 C/T; S00112: Chr01_03525014 C/T; S00113: Chr01_03554669 G/T; S00114: Chr01_03577700 C/T; S00115: Chr01_03601592 G/T; S00116: Chr01_03627505 A/C; S00117: Chr01_03678971 A/G; S00118: Chr01_03719793 G/T; S00119: Chr01_03738252 C/A; S00120: Chr01_03756528 T/C; S00121: Chr01_03789943 T/C; S00122: Chr01_03811218 G/T; S00123: Chr01_03825426 T/C; S00124: Chr01_03860954 G/A; S00125: Chr01_03919954 T/A; S00126: Chr01_03925056 A/G; S00127: Chr01_03958157 T/C; S00128: Chr01_03989108 A/T; S00129: Chr01_04002673 A/G; S00130: Chr01_04026903 G/A; S00131: Chr01_04050717 A/T; S00132: Chr01_04092615 G/A; S00133: Chr01_04116778 T/C; S00134: Chr01_04125368 C/T; S00135: Chr01_04216824 C/G; S00136: Chr01_04235320 T/C; S00137: Chr01_04292947 C/T; S00138: Chr01_04301032 T/C; S00139: Chr01_04336522 G/A; S00140: Chr01_04360128 T/A; S00141: Chr01_04389727 T/C; S00142: Chr01_04412167 C/A; S00143: Chr01_04458779 C/T; S00144: Chr01_04485510 A/T; S00145: Chr01_04501467 T/C; S00146: Chr01_04608177 A/G; S00147: Chr01_04649541 A/C; S00148: Chr01_04665547 G/A; S00149: Chr01_04680711 G/A; S00150: Chr01_04708131 T/C; S00151: Chr01_04729599 C/T; S00152: Chr01_04773298 T/C; S00153: Chr01_04789690 G/A; S00154: Chr01_04845249 G/A; S00155: Chr01_04878492 G/A; S00156: Chr01_04922689 C/T; S00157: Chr01_04972988 C/T; S00158: Chr01_05031302 T/C; S00159: Chr01_05061368 G/C; S00160: Chr01_05132918 G/A; S00161: Chr01_05150023 C/A; S00162: Chr01_05227745 G/T; S00163: Chr01_05277986 T/C; S00164: Chr01_05300175 T/A; S00165: Chr01_05337442 G/C; S00166: Chr01_05354735 G/T; S00167: Chr01_05380884 T/C; S00168: Chr01_05450109 T/A; S00169: Chr01_05485137 T/C; S00170: Chr01_05503873 C/T; S00171: Chr01_05552328 A/G; S00172: Chr01_05585344 G/C; S00173: Chr01_05600608 G/T; S00174: Chr01_05630889 T/C; S00175: Chr01_05662837 G/A; S00176: Chr01_05681039 A/C; S00177: Chr01_05711023 A/C; S00178: Chr01_05736760 G/A; S00179: Chr01_05763995 G/T; S00180: Chr01_05814531 A/T; S00181: Chr01_05871704 C/A; S00182: Chr01_05875750 A/G; S00183: Chr01_05937344 G/A; S00184: Chr01_05994862 T/C; S00185: Chr01_06015676 T/C; S00186: Chr01_06029873 G/A; S00187: Chr01_06092615 A/G; S00188: Chr01_06200362 G/A; S00189: Chr01_06318897 G/T; S00190: Chr01_06328630 G/A; S00191: Chr01_06375907 A/T; S00192: Chr01_06429741 G/C; S00193: Chr01_06450531 G/A; S00194: Chr01_06569806 G/A; S00195: Chr01_06622467 G/A; S00196: Chr01_06626877 T/A; S00197: Chr01_06755296 C/A; S00198: Chr01_06788246 G/A; S00199: Chr01_06803234 A/T; S00200: Chr01_06825019 A/G; S00201: Chr01_06966548 T/A; S00202: Chr01_06997343 C/T; S00203: Chr01_07002322 C/T; S00204: Chr01_07072636 A/G; S00205: Chr01_07093982 A/C; S00206: Chr01_07108044 T/G; S00207: Chr01_07178778 G/A; S00208: Chr01_07221676 C/T; S00209: Chr01_07267380 A/G; S00210: Chr01_07308162 A/C; S00211: Chr01_07338918 A/G; S00212: Chr01_07374336 A/T; S00213: Chr01_07375671 G/A; S00214: Chr01_07509056 T/C; S00215: Chr01_07525790 A/G; S00216: Chr01_07574464 C/T; S00217: Chr01_07578412 A/G; S00218: Chr01_07602390 T/C; S00219: Chr01_07636779 C/G; S00220: Chr01_07650352 T/G; S00221: Chr01_07677753 C/G; S00222: Chr01_07770949 C/T; S00223: Chr01_07925219 A/T; S00224: Chr01_08004113 A/C; S00225: Chr01_08059308 A/G; S00226: Chr01_08138663 C/T; S00227: Chr01_08293319 G/A; S00228: Chr01_08350508 C/T; S00229: Chr01_08445735 C/G; S00230: Chr01_08533425 T/C; S00231: Chr01_08571833 G/A; S00232: Chr01_08656269 T/C; S00233: Chr01_08775411 T/G; S00234: Chr01_08888035 A/G; S00235: Chr01_08919940 G/C; S00236: Chr01_08982023 G/A; S00237: Chr01_09053888 C/T; S00238: Chr01_09140033 C/G; S00239: Chr01_09297338 G/A; S00240: Chr01_09354935 T/C; S00241: Chr01_09427666 G/A; S00242: Chr01_09509480 C/T; S00243: Chr01_09580260 A/G; S00244: Chr01_09741202 G/A; S00245: Chr01_09893535 C/G; S00246: Chr01_09959126 T/A; S00247: Chr01_10049737 T/A; S00248: Chr01_10075501 G/T; S00249: Chr01_10105865 C/T; S00250: Chr01_10182057 G/A; S00251: Chr01_10403696 G/A; S00252: Chr01_10564361 A/G; S00253: Chr01_10638496 A/C; S00254: Chr01_10708262 G/A; S00255: Chr01_10779637 G/A; S00256: Chr01_10851811 A/G; S00257: Chr01_10925619 C/T; S00258: Chr01_11087672 T/C; S00259: Chr01_11225614 C/T; S00260:

Chr01_11302156 T/C; S00261: Chr01_11453541 C/T; S00262: Chr01_11526154 G/A; S00263: Chr01_11645398 T/A; S00264: Chr01_11712374 T/C; S00265: Chr01_11725054 C/T; S00266: Chr01_11775104 A/T; S00267: Chr01_11919826 T/C; S00268: Chr01_11958171 G/A; S00269: Chr01_12015243 A/G; S00270: Chr01_12047539 A/G; S00271: Chr01_12055194 A/G; S00272: Chr01_12156444 A/C; S00273: Chr01_12227734 A/C; S00274: Chr01_12382884 G/C; S00275: Chr01_12450018 T/C; S00276: Chr01_12565594 A/G; S00277: Chr01_12624608 C/T; S00278: Chr01_12625848 T/G; S00279: Chr01_12650051 A/G; S00280: Chr01_12780255 A/G; S00281: Chr01_12801349 T/G; S00282: Chr01_12905537 A/G; S00283: Chr01_12925087 C/T; S00284: Chr01_13044304 A/G; S00285: Chr01_13104339 A/T; S00286: Chr01_13130620 C/T; S00287: Chr01_13296442 A/T; S00288: Chr01_13344930 T/C; S00289: Chr01_13350634 G/A; S00290: Chr01_13392050 C/T; S00291: Chr01_13455948 T/C; S00292: Chr01_13550069 T/C; S00293: Chr01_13625149 A/G; S00294: Chr01_13775215 C/T; S00295: Chr01_13871850 A/C; S00296: Chr01_13894047 A/G; S00297: Chr01_13900070 A/G; S00298: Chr01_13975046 C/A; S00299: Chr01_14074688 C/G; S00300: Chr01_14077385 T/G; S00301: Chr01_14194993 T/G; S00302: Chr01_14200515 G/A; S00303: Chr01_14275486 C/A; S00304: Chr01_14447110 T/A; S00305: Chr01_14450721 G/A; S00306: Chr01_14475167 T/C; S00307: Chr01_14565224 C/T; S00308: Chr01_14660961 T/C; S00309: Chr01_14675639 A/G; S00310: Chr01_14759984 T/A; S00311: Chr01_14775185 G/A; S00312: Chr01_14850661 C/T; S00313: Chr01_15373312 G/T; S00314: Chr01_15587629 C/T; S00315: Chr01_15675345 G/C; S00316: Chr01_15998034 A/C; S00317: Chr01_16555547 T/C; S00318: Chr01_16596049 C/T; S00319: Chr01_16600310 A/C; S00320: Chr01_16825742 G/T; S00321: Chr01_16900145 T/C; S00322: Chr01_16975377 G/A; S00323: Chr01_17050437 A/G; S00324: Chr01_17154560 C/G; S00325: Chr01_17413412 G/A; S00326: Chr01_17475011 G/T; S00327: Chr01_17700086 C/T; S00328: Chr01_17775284 T/A; S00329: Chr01_17925161 T/C; S00330: Chr01_18070034 C/T; S00331: Chr01_18076267 T/C; S00332: Chr01_18234896 T/C; S00333: Chr01_18400215 C/T; S00334: Chr01_18475024 A/T; S00335: Chr01_18550025 A/G; S00336: Chr01_18632361 T/C; S00337: Chr01_18746682 C/T; S00338: Chr01_18750871 G/T; S00339: Chr01_18775339 T/C; S00340: Chr01_18850423 T/A; S00341: Chr01_18984839 G/A; S00342: Chr01_19000227 T/A; S00343: Chr01_19075469 T/A; S00344: Chr01_19150185 T/G; S00345: Chr01_19225435 C/T; S00346: Chr01_19662445 A/T; S00347: Chr01_19675019 A/T; S00348: Chr01_19804342 A/C; S00349: Chr01_19950120 G/T; S00350: Chr01_19977723 G/A; S00351: Chr01_20058324 T/C; S00352: Chr01_20180391 C/T; S00353: Chr01_20275618 C/T; S00354: Chr01_20438714 C/T; S00355: Chr01_20637005 A/T; S00356: Chr01_20707509 T/C; S00357: Chr01_20800062 G/C; S00358: Chr01_21025045 C/G; S00359: Chr01_21213341 C/A; S00360: Chr01_21340508 C/G; S00361: Chr01_21440454 C/A; S00362: Chr01_21783619 T/A; S00363: Chr01_21815499 T/C; S00364: Chr01_21825013 A/G; S00365: Chr01_21975362 T/G; S00366: Chr01_22123660 C/A; S00367: Chr01_22126372 G/A; S00368: Chr01_22275005 G/A; S00369: Chr01_22426002 C/G; S00370: Chr01_22725021 T/A; S00371: Chr01_22868767 A/G; S00372: Chr01_22875205 G/C; S00373: Chr01_23010006 T/C; S00374: Chr01_23043888 T/A; S00375: Chr01_23126719 G/A; S00376: Chr01_23324663 G/A; S00377: Chr01_23398551 G/A; S00378: Chr01_23400665 T/C; S00379: Chr01_23476004 T/C; S00380: Chr01_23550069 A/G; S00381: Chr01_23676697 A/G; S00382: Chr01_23700455 C/T; S00383: Chr01_23813016 C/T; S00384: Chr01_23842194 C/T; S00385: Chr01_23900885 T/C; S00386: Chr01_24054517 G/A; S00387: Chr01_24239348 C/G; S00388: Chr01_24259671 C/A; S00389: Chr01_24334947 T/C; S00390: Chr01_24492586 G/A; S00391: Chr01_24552637 A/T; S00392: Chr01_24630509 G/A; S00393: Chr01_24702021 C/G; S00394: Chr01_24789361 G/A; S00395: Chr01_24853279 A/T; S00396: Chr01_25009879 C/T; S00397: Chr01_25085584 G/A; S00398: Chr01_25190805 C/G; S00399: Chr01_25211998 T/G; S00400: Chr01_25278472 T/A; S00401: Chr01_25370996 C/T; S00402: Chr01_25529267 C/T; S00403: Chr01_25601427 G/A; S00404: Chr01_25626349 T/G; S00405: Chr01_25851808 G/C; S00406: Chr01_25927052 T/C; S00407: Chr01_26015020 A/C; S00408: Chr01_26081859 C/T; S00409: Chr01_26150113 G/A; S00410: Chr01_26244279 G/A; S00411: Chr01_26325631 C/T; S00412: Chr01_26466551 C/T; S00413: Chr01_26530221 G/A; S00414: Chr01_26649112 G/A; S00415: Chr01_26657083 C/A; S00416: Chr01_26733462 C/T; S00417: Chr01_26877565 G/A; S00418: Chr01_26971380 A/G; S00419: Chr01_27108303 T/A; S00420: Chr01_27129040 A/C; S00421: Chr01_27200081 C/G; S00422: Chr01_27277066 T/C; S00423: Chr01_27318772 C/A; S00424: Chr01_27325394 C/T; S00425: Chr01_27418687 T/C; S00426: Chr01_27549087 G/A; S00427: Chr01_27551480 T/C; S00428: Chr01_27575051 G/C; S00429: Chr01_27742262 A/G; S00430: Chr01_27750349 A/G; S00431: Chr01_27871375 G/A; S00432: Chr01_27893663 A/G; S00433: Chr01_27900429 G/C; S00434: Chr01_27925687 G/A; S00435: Chr01_28005385 G/C; S00436: Chr01_28025252 C/T; S00437: Chr01_28177477 T/A; S00438: Chr01_28200328 A/G; S00439: Chr01_28331066 G/T; S00440: Chr01_28350273 T/A; S00441: Chr01_28500432 T/C; S00442: Chr01_28623574 C/T; S00443: Chr01_28632132 T/C; S00444: Chr01_28761661 G/A; S00445: Chr01_28817299 G/A; S00446: Chr01_28827376 C/T; S00447: Chr01_29050487 G/A; S00448: Chr01_29125424 A/G; S00449: Chr01_29201595 C/T; S00450: Chr01_29289571 C/T; S00451: Chr01_29300754 G/A; S00452: Chr01_29550337 T/C; S00453: Chr01_29578764 C/T; S00454: Chr01_29725756 A/G; S00455: Chr01_29875182 C/A; S00456: Chr01_29956518 T/G; S00457: Chr01_30250377 A/T; S00458: Chr01_30400067 T/A; S00459: Chr01_30475257 A/G; S00460: Chr01_30929130 G/A; S00461:

Chr01_31299431 C/A; S00462: Chr01_31300268 G/A; S00463: Chr01_31375567 A/T; S00464: Chr01_31567118 T/A; S00465: Chr01_31725522 C/T; S00466: Chr01_32008744 T/A; S00467: Chr01_32025799 T/C; S00468: Chr01_32131508 G/A; S00469: Chr01_32302282 C/T; S00470: Chr01_32375089 A/T; S00471: Chr01_32452952 G/A; S00472: Chr01_32525465 G/A; S00473: Chr01_32600233 C/T; S00474: Chr01_32701560 T/C; S00475: Chr01_32726446 A/G; S00476: Chr01_32802260 T/G; S00477: Chr01_32932972 C/T; S00478: Chr01_32998938 T/C; S00479: Chr01_33020908 C/T; S00480: Chr01_33025485 T/A; S00481: Chr01_33116273 T/C; S00482: Chr01_33125813 G/A; S00483: Chr01_33200588 G/A; S00484: Chr01_33275331 C/T; S00485: Chr01_33363893 T/C; S00486: Chr01_33443107 G/A; S00487: Chr01_33509352 T/A; S00488: Chr01_33599975 C/T; S00489: Chr01_33700648 G/A; S00490: Chr01_33789166 A/G; S00491: Chr01_33858398 G/C; S00492: Chr01_33904198 C/T; S00493: Chr01_33985509 T/C; S00494: Chr01_34000012 C/T; S00495: Chr01_34082645 A/C; S00496: Chr01_34132635 G/C; S00497: Chr01_34350946 A/G; S00498: Chr01_34426159 G/A; S00499: Chr01_34460214 G/A; S00500: Chr01_34477111 T/G; S00501: Chr01_34502425 T/C; S00502: Chr01_34575621 C/G; S00503: Chr01_34678156 C/T; S00504: Chr01_34756773 T/C; S00505: Chr01_34925134 G/T; S00506: Chr01_35002114 G/A; S00507: Chr01_35078391 C/A; S00508: Chr01_35150398 G/T; S00509: Chr01_35250030 C/T; S00510: Chr01_35325215 A/C; S00511: Chr01_35425560 G/A; S00512: Chr01_35501230 T/A; S00513: Chr01_35575846 G/A; S00514: Chr01_35714964 T/C; S00515: Chr01_35729457 T/C; S00516: Chr01_35856822 C/G; S00517: Chr01_35958283 C/T; S00518: Chr01_36051595 C/G; S00519: Chr01_36076816 T/C; S00520: Chr01_36151508 T/A; S00521: Chr01_36300263 T/A; S00522: Chr01_36420185 A/G; S00523: Chr01_36500647 G/A; S00524: Chr01_36579875 C/T; S00525: Chr01_36786717 G/A; S00526: Chr01_36970319 T/G; S00527: Chr01_36982210 A/G; S00528: Chr01_37000896 T/C; S00529: Chr01_37086325 A/G; S00530: Chr01_37100272 C/T; S00531: Chr01_37193882 A/G; S00532: Chr01_37201792 T/G; S00533: Chr01_37230438 A/G; S00534: Chr01_37319224 G/T; S00535: Chr01_37329604 T/C; S00536: Chr01_37357060 C/A; S00537: Chr01_37389379 C/T; S00538: Chr01_37429842 C/T; S00539: Chr01_37495974 C/T; S00540: Chr01_37500076 C/T; S00541: Chr01_37577846 A/G; S00542: Chr01_37610313 A/G; S00543: Chr01_37692594 T/C; S00544: Chr01_37716604 C/T; S00545: Chr01_37738386 C/T; S00546: Chr01_37755091 C/T; S00547: Chr01_37818478 G/A; S00548: Chr01_37826117 G/A; S00549: Chr01_37902998 T/C; S00550: Chr01_38052757 A/G; S00551: Chr01_38076553 T/A; S00552: Chr01_38102076 T/G; S00553: Chr01_38162112 C/A; S00554: Chr01_38250800 T/A; S00555: Chr01_38353737 A/T; S00556: Chr01_38403745 T/C; S00557: Chr01_38425002 A/G; S00558: Chr01_38588043 A/G; S00559: Chr01_38607302 T/C; S00560: Chr01_38675062 T/A; S00561: Chr01_38755673 A/G; S00562: Chr01_38782697 G/T; S00563: Chr01_38850874 T/C; S00564: Chr01_38934425 G/T; S00565: Chr01_38952241 T/C; S00566: Chr01_39100017 A/G; S00567: Chr01_39286434 G/A; S00568: Chr01_39306935 T/A; S00569: Chr01_39440429 A/T; S00570: Chr01_39450786 A/G; S00571: Chr01_39573984 C/T; S00572: Chr01_39586209 A/G; S00573: Chr01_39600198 G/A; S00574: Chr01_39628619 G/C; S00575: Chr01_39688109 C/T; S00576: Chr01_39766170 A/G; S00577: Chr01_39802257 A/G; S00578: Chr01_39860894 C/T; S00579: Chr01_39914433 C/T; S00580: Chr01_39969229 G/C; S00581: Chr01_39989946 C/T; S00582: Chr01_40040195 C/T; S00583: Chr01_40069526 T/G; S00584: Chr01_40130345 T/C; S00585: Chr01_40192106 G/C; S00586: Chr01_40207276 A/G; S00587: Chr01_40319041 C/T; S00588: Chr01_40367011 G/A; S00589: Chr01_40375157 A/C; S00590: Chr01_40498454 T/C; S00591: Chr01_40513982 A/C; S00592: Chr01_40581958 T/C; S00593: Chr01_40630406 T/A; S00594: Chr01_40699972 G/T; S00595: Chr01_40700227 T/A; S00596: Chr01_40763919 C/G; S00597: Chr01_40778034 T/G; S00598: Chr01_40807385 C/G; S00599: Chr01_40826487 A/G; S00600: Chr01_40862452 T/C; S00601: Chr01_40882839 C/A; S00602: Chr01_40904985 C/A; S00603: Chr01_40927642 C/T; S00604: Chr01_40966577 C/A; S00605: Chr01_40976248 A/G; S00606: Chr01_41075167 T/C; S00607: Chr01_41160332 G/C; S00608: Chr01_41197558 C/T; S00609: Chr01_41240276 C/T; S00610: Chr01_41271382 C/G; S00611: Chr01_41291184 C/A; S00612: Chr01_41328136 C/T; S00613: Chr01_41351074 A/G; S00614: Chr01_41380949 T/C; S00615: Chr01_41470321 T/A; S00616: Chr01_41475011 T/A; S00617: Chr01_41550746 T/C; S00618: Chr01_41625723 G/T; S00619: Chr01_41650148 T/C; S00620: Chr01_41809598 T/C; S00621: Chr01_41828455 T/C; S00622: Chr01_41857458 A/G; S00623: Chr01_41912398 C/T; S00624: Chr01_41926831 A/C; S00625: Chr01_42007719 A/G; S00626: Chr01_42067123 G/C; S00627: Chr01_42284533 T/A; S00628: Chr01_42337744 T/C; S00629: Chr01_42446780 A/T; S00630: Chr01_42450382 G/A; S00631: Chr01_42529392 A/G; S00632: Chr01_42557864 C/A; S00633: Chr01_42575031 A/G; S00634: Chr01_42655454 G/A; S00635: Chr01_42734677 A/C; S00636: Chr01_42763750 C/G; S00637: Chr01_42787480 C/T; S00638: Chr01_42832197 A/G; S00639: Chr01_42886515 A/T; S00640: Chr01_42908212 C/A; S00641: Chr01_42973007 C/T; S00642: Chr01_42993934 G/T; S00643: Chr01_43009054 T/G; S00644: Chr01_43073364 A/C; S00645: Chr01_43076094 G/A; S00646: Chr01_43107952 C/T; S00647: Chr01_43125116 A/T; S00648: Chr01_43219027 G/A; S00649: Chr01_43225309 T/C; S00650: Chr01_43316094 C/T; S00651: Chr01_43394731 T/G; S00652: Chr01_43400634 C/T; S00653: Chr01_43435398 G/A; S00654: Chr01_43455210 T/G; S00655: Chr01_43475059 C/G; S00656: Chr01_43513716 T/G; S00657: Chr01_43526938 T/G; S00658: Chr01_43570871 A/T; S00659: Chr01_43598512 T/G; S00660: Chr01_43603147 C/T; S00661: Chr01_43632115 A/G; S00662:

Chr01_43689182 T/A; S00663: Chr01_43713568 A/T; S00664: Chr01_43873912 G/T; S00665: Chr01_43935166 C/T; S00666: Chr01_43955296 T/C; S00667: Chr01_44006033 C/T; S00668: Chr01_44083864 T/G; S00669: Chr01_44106093 G/A; S00670: Chr01_44129261 C/T; S00671: Chr01_44205650 C/A; S00672: Chr01_44261394 T/C; S00673: Chr01_44287852 T/C; S00674: Chr01_44313026 T/G; S00675: Chr01_44327313 G/A; S00676: Chr01_44350139 G/A; S00677: Chr01_44472270 T/C; S00678: Chr01_44503626 G/A; S00679: Chr01_44553308 G/A; S00680: Chr01_44586060 A/C; S00681: Chr01_44639670 G/T; S00682: Chr01_44666969 C/A; S00683: Chr01_44685993 A/C; S00684: Chr01_44701457 A/C; S00685: Chr01_44736785 G/T; S00686: Chr01_44779235 C/A; S00687: Chr01_44820113 C/T; S00688: Chr01_44841385 T/A; S00689: Chr01_44856299 T/C; S00690: Chr01_44902075 C/T; S00691: Chr01_44957117 C/T; S00692: Chr01_44988039 G/A; S00693: Chr01_45000008 G/A; S00694: Chr01_45077780 T/C; S00695: Chr01_45100800 T/C; S00696: Chr01_45185076 A/G; S00697: Chr01_45222105 G/A; S00698: Chr01_45231907 G/T; S00699: Chr01_45250841 C/A; S00700: Chr01_45292957 T/G; S00701: Chr01_45356184 G/A; S00702: Chr01_45425695 C/T; S00703: Chr01_45501408 A/G; S00704: Chr01_45583404 T/C; S00705: Chr01_45625481 T/G; S00706: Chr01_45661863 G/A; S00707: Chr01_45677056 A/T; S00708: Chr01_45702927 G/A; S00709: Chr01_45779620 T/A; S00710: Chr01_45802234 C/T; S00711: Chr01_45876744 T/C; S00712: Chr01_45950215 A/T; S00713: Chr01_46036919 A/C; S00714: Chr01_46055846 G/A; S00715: Chr01_46159351 A/G; S00716: Chr01_46195305 C/T; S00717: Chr01_46332194 C/T; S00718: Chr01_46400594 C/T; S00719: Chr01_46475550 T/A; S00720: Chr01_46551084 C/G; S00721: Chr01_46626420 C/T; S00722: Chr01_46700299 A/G; S00723: Chr01_46780090 C/G; S00724: Chr01_46850782 T/A; S00725: Chr01_46933166 C/T; S00726: Chr01_47000199 G/A; S00727: Chr01_47076357 G/C; S00728: Chr01_47154232 G/A; S00729: Chr01_47312518 A/G; S00730: Chr01_47417257 C/A; S00731: Chr01_47460755 A/G; S00732: Chr01_47475300 C/T; S00733: Chr01_47550534 G/A; S00734: Chr01_47641338 A/G; S00735: Chr01_47702611 C/T; S00736: Chr01_47726965 C/G; S00737: Chr01_47803490 A/G; S00738: Chr01_47863542 A/G; S00739: Chr01_47882760 A/T; S00740: Chr01_47921219 A/G; S00741: Chr01_47957886 T/G; S00742: Chr01_47987679 G/C; S00743: Chr01_48006283 A/T; S00744: Chr01_48069631 T/C; S00745: Chr01_48096144 T/C; S00746: Chr01_48127166 T/C; S00747: Chr01_48153557 G/C; S00748: Chr01_48175228 A/T; S00749: Chr01_48254397 T/C; S00750: Chr01_48359406 A/G; S00751: Chr01_48383407 A/T; S00752: Chr01_48400021 A/T; S00753: Chr01_48510140 C/T; S00754: Chr01_48550251 G/A; S00755: Chr01_48613811 C/T; S00756: Chr01_48625074 G/A; S00757: Chr01_48709312 T/G; S00758: Chr01_48809126 G/A; S00759: Chr01_48826125 C/G; S00760: Chr01_48859582 G/A; S00761: Chr01_48877702 C/T; S00762: Chr01_48920296 G/A; S00763: Chr01_48955198 T/G; S00764: Chr01_48981188 A/T; S00765: Chr01_49008235 C/T; S00766: Chr01_49039826 A/T; S00767: Chr01_49051009 G/A; S00768: Chr01_49095991 T/A; S00769: Chr01_49120937 C/T; S00770: Chr01_49139189 T/A; S00771: Chr01_49155060 A/G; S00772: Chr01_49196559 A/G; S00773: Chr01_49200548 A/T; S00774: Chr01_49242529 T/C; S00775: Chr01_49254257 T/C; S00776: Chr01_49300479 C/T; S00777: Chr01_49350084 T/G; S00778: Chr01_49376415 A/G; S00779: Chr01_49404575 A/C; S00780: Chr01_49441366 A/G; S00781: Chr01_49480081 T/C; S00782: Chr01_49503164 A/C; S00783: Chr01_49558080 A/G; S00784: Chr01_49576766 T/A; S00785: Chr01_49625003 A/G; S00786: Chr01_49650075 T/A; S00787: Chr01_49678451 C/T; S00788: Chr01_49822870 G/T; S00789: Chr01_49869514 T/A; S00790: Chr01_49891865 A/G; S00791: Chr01_49903973 A/G; S00792: Chr01_49933665 A/C; S00793: Chr01_49951429 G/A; S00794: Chr01_49997432 T/G; S00795: Chr01_50001182 G/A; S00796: Chr01_50030807 G/A; S00797: Chr01_50067658 A/G; S00798: Chr01_50079414 T/C; S00799: Chr01_50103534 T/C; S00800: Chr01_50157010 G/A; S00801: Chr01_50189557 G/A; S00802: Chr01_50206929 C/T; S00803: Chr01_50225146 G/C; S00804: Chr01_50251932 G/C; S00805: Chr01_50275183 G/A; S00806: Chr01_50306503 T/C; S00807: Chr01_50340661 G/A; S00808: Chr01_50367387 C/T; S00809: Chr01_50400004 G/C; S00810: Chr01_50431852 C/T; S00811: Chr01_50469539 A/C; S00812: Chr01_50498657 T/A; S00813: Chr01_50502058 A/G; S00814: Chr01_50525268 G/C; S00815: Chr01_50572793 T/C; S00816: Chr01_50583756 T/C; S00817: Chr01_50602779 A/C; S00818: Chr01_50625356 C/A; S00819: Chr01_50653236 T/G; S00820: Chr01_50689878 A/G; S00821: Chr01_50702185 T/C; S00822: Chr01_50726398 G/C; S00823: Chr01_50767372 G/A; S00824: Chr01_50776387 G/A; S00825: Chr01_50834469 G/A; S00826: Chr01_50851685 C/T; S00827: Chr01_50876771 T/A; S00828: Chr01_50912999 T/C; S00829: Chr01_50926203 T/C; S00830: Chr01_50951257 G/A; S00831: Chr01_51007163 A/G; S00832: Chr01_51025509 T/A; S00833: Chr01_51052418 C/T; S00834: Chr01_51098557 T/C; S00835: Chr01_51100171 G/A; S00836: Chr01_51134158 C/T; S00837: Chr01_51165863 A/G; S00838: Chr01_51175986 T/C; S00839: Chr01_51234168 A/G; S00840: Chr01_51258108 A/G; S00841: Chr01_51315364 A/G; S00842: Chr01_51325418 A/C; S00843: Chr01_51408405 A/G; S00844: Chr01_51488831 C/A; S00845: Chr01_51507836 T/G; S00846: Chr01_51528414 T/C; S00847: Chr01_51553036 G/A; S00848: Chr01_51600690 G/C; S00849: Chr01_51634033 A/G; S00850: Chr01_51670162 G/C; S00851: Chr01_51685788 A/G; S00852: Chr01_51704662 T/C; S00853: Chr01_51728584 T/A; S00854: Chr01_51750816 G/C; S00855: Chr01_51775991 C/T; S00856: Chr01_51801724 A/T; S00857: Chr01_51838674 A/G; S00858: Chr01_51854907 A/G; S00859: Chr01_51880489 T/C; S00860: Chr01_51903437 A/G; S00861: Chr01_52011140 G/A; S00862: Chr01_52078418 C/T; S00863:

Chr01_52176571 C/G; S00864: Chr01_52202383 A/G; S00865: Chr01_52238119 G/A; S00866: Chr01_52250882 G/A; S00867: Chr01_52275421 G/A; S00868: Chr01_52306999 G/A; S00869: Chr01_52335650 T/G; S00870: Chr01_52378237 C/T; S00871: Chr01_52404094 T/A; S00872: Chr01_52425459 A/T; S00873: Chr01_52501265 T/C; S00874: Chr01_52533804 T/C; S00875: Chr01_52551294 C/G; S00876: Chr01_52575882 G/A; S00877: Chr01_52602686 C/G; S00878: Chr01_52631317 G/A; S00879: Chr01_52660145 C/T; S00880: Chr01_52702147 G/A; S00881: Chr01_52749540 T/C; S00882: Chr01_52750188 C/A; S00883: Chr01_52777403 A/G; S00884: Chr01_52806626 C/T; S00885: Chr01_52834522 C/T; S00886: Chr01_52854004 G/T; S00887: Chr01_52879428 G/A; S00888: Chr01_52914925 T/A; S00889: Chr01_52942422 C/G; S00890: Chr01_52952348 C/T; S00891: Chr01_52980806 T/A; S00892: Chr01_53054125 G/A; S00893: Chr01_53076252 G/A; S00894: Chr01_53127107 T/C; S00895: Chr01_53150925 C/T; S00896: Chr01_53196369 C/T; S00897: Chr01_53271286 G/C; S00898: Chr01_53339091 G/A; S00899: Chr01_53423278 T/G; S00900: Chr01_53429911 G/A; S00901: Chr01_53481392 T/A; S00902: Chr01_53509482 G/A; S00903: Chr01_53535466 G/T; S00904: Chr01_53556013 T/A; S00905: Chr01_53580094 C/T; S00906: Chr01_53602160 G/C; S00907: Chr01_53631984 A/C; S00908: Chr01_53662828 C/G; S00909: Chr01_53686448 A/G; S00910: Chr01_53712558 G/A; S00911: Chr01_53726089 C/T; S00912: Chr01_53753509 A/T; S00913: Chr01_53787487 G/C; S00914: Chr01_53808282 C/A; S00915: Chr01_53884130 C/A; S00916: Chr01_53979152 C/T; S00917: Chr01_54065323 C/T; S00918: Chr01_54109018 G/A; S00919: Chr01_54126679 T/C; S00920: Chr01_54150350 G/A; S00921: Chr01_54183817 G/A; S00922: Chr01_54252843 C/T; S00923: Chr01_54335459 C/T; S00924: Chr01_54377691 T/A; S00925: Chr01_54456679 C/T; S00926: Chr01_54477239 C/T; S00927: Chr01_54501366 T/C; S00928: Chr01_54530855 C/G; S00929: Chr01_54558891 G/A; S00930: Chr01_54576534 G/A; S00931: Chr01_54602258 C/G; S00932: Chr01_54627771 T/A; S00933: Chr01_54654504 C/T; S00934: Chr01_54681333 G/T; S00935: Chr01_54703190 A/G; S00936: Chr01_54741695 C/T; S00937: Chr01_54752138 G/A; S00938: Chr01_54776105 A/G; S00939: Chr01_54820966 T/A; S00940: Chr01_54829269 G/C; S00941: Chr01_54850038 A/G; S00942: Chr01_54880501 G/C; S00943: Chr01_54903440 C/T; S00944: Chr01_54926017 T/A; S00945: Chr01_54951239 C/T; S00946: Chr01_54975247 C/G; S00947: Chr01_55002164 A/G; S00948: Chr01_55042294 C/T; S00949: Chr01_55072851 G/C; S00950: Chr01_55108277 A/G; S00951: Chr01_55125854 C/T; S00952: Chr01_55163470 G/A; S00953: Chr01_55177993 G/A; S00954: Chr01_55204845 C/T; S00955: Chr01_55226199 C/A; S00956: Chr01_55269597 G/C; S00957: Chr01_55286149 T/G; S00958: Chr01_55315611 A/G; S00959: Chr01_55325371 A/G; S00960: Chr01_55350876 A/G; S00961: Chr01_55385766 C/T; S00962: Chr01_55410265 A/G; S00963: Chr01_55427568 T/A; S00964: Chr01_55452801 G/A; S00965: Chr01_55477941 C/T; S00966: Chr01_55505809 G/A; S00967: Chr01_55547694 T/A; S00968: Chr01_55550640 T/A; S00969: Chr01_55580915 C/T; S00970: Chr01_55600308 T/C; S00971: Chr01_55632327 G/A; S00972: Chr01_55650253 C/T; S00973: Chr01_55675627 T/G; S00974: Chr01_55715065 C/T; S00975: Chr01_55725167 T/C; S00976: Chr01_55751731 G/C; S00977: Chr01_55776049 C/A; S00978: Chr01_55802420 A/G; S00979: Chr01_55834302 A/C; S00980: Chr01_55850309 G/A; S00981: Chr01_55875716 C/G; S00982: Chr01_55900359 G/A; S00983: Chr01_55929275 A/G; S00984: Chr01_55961196 G/C; S00985: Chr01_55975922 G/C; S00986: Chr01_56011818 T/C; S00987: Chr01_56025005 T/A; S00988: Chr01_56086832 C/A; S00989: Chr01_56109410 T/G; S00990: Chr01_56168061 G/A; S00991: Chr01_56188382 C/G; S00992: Chr01_56205269 G/T; S00993: Chr01_56234675 T/C; S00994: Chr01_56261162 C/A; S00995: Chr01_56277865 C/A; S00996: Chr01_56304223 A/T; S00997: Chr01_56325416 G/A; S00998: Chr01_56351328 T/C; S00999: Chr01_56392557 G/A; S01000: Chr01_56407141 C/T; S01001: Chr01_56444479 A/T; S01002: Chr01_56450246 T/C; S01003: Chr01_56489882 C/T; S01004: Chr01_56508892 G/A; S01005: Chr01_56540433 A/G; S01006: Chr01_56554790 C/T; S01007: Chr01_56577627 C/A; S01008: Chr01_56601944 G/A; S01009: Chr01_56634790 G/A; S01010: Chr01_56651009 C/T; S01011: Chr01_56676508 T/G; S01012: Chr01_56720355 C/T; S01013: Chr01_56728888 A/C; S01014: Chr01_56754757 A/C; S01015: Chr01_56777671 T/C; S01016: Chr01_56816004 G/C; S01017: Chr01_56825127 A/T; S01018: Chr02_00009978 C/T; S01019: Chr02_00041144 G/A; S01020: Chr02_00076929 C/A; S01021: Chr02_00109513 C/A; S01022: Chr02_00129266 C/T; S01023: Chr02_00157840 A/G; S01024: Chr02_00175683 C/T; S01025: Chr02_00204208 G/T; S01026: Chr02_00230791 G/C; S01027: Chr02_00263409 G/A; S01028: Chr02_00277173 A/C; S01029: Chr02_00330064 A/G; S01030: Chr02_00351278 C/T; S01031: Chr02_00381160 T/C; S01032: Chr02_00400760 T/G; S01033: Chr02_00434019 A/G; S01034: Chr02_00474929 T/G; S01035: Chr02_00475192 T/C; S01036: Chr02_00503569 T/A; S01037: Chr02_00531882 T/A; S01038: Chr02_00564318 C/T; S01039: Chr02_00587323 A/C; S01040: Chr02_00605426 C/A; S01041: Chr02_00626869 A/T; S01042: Chr02_00662230 G/A; S01043: Chr02_00688019 A/G; S01044: Chr02_00702221 C/T; S01045: Chr02_00740912 A/G; S01046: Chr02_00751390 G/T; S01047: Chr02_00777458 G/A; S01048: Chr02_00800750 G/T; S01049: Chr02_00826621 A/G; S01050: Chr02_00853589 C/T; S01051: Chr02_00876997 A/G; S01052: Chr02_00914056 C/A; S01053: Chr02_00941235 C/A; S01054: Chr02_00950577 C/A; S01055: Chr02_00980499 T/C; S01056: Chr02_01000468 G/A; S01057: Chr02_01026085 T/A; S01058: Chr02_01058364 G/A; S01059: Chr02_01078593 C/T; S01060: Chr02_01101578 G/A; S01061: Chr02_01170166 C/T; S01062: Chr02_01198816 C/G; S01063: Chr02_01243854 A/C; S01064:

Chr02_01250261 C/T; S01065: Chr02_01275126 G/T; S01066: Chr02_01310323 C/G; S01067: Chr02_01333828 A/G; S01068: Chr02_01410853 C/G; S01069: Chr02_01427644 T/G; S01070: Chr02_01450107 T/G; S01071: Chr02_01482658 T/G; S01072: Chr02_01511454 A/G; S01073: Chr02_01540964 C/T; S01074: Chr02_01552812 C/T; S01075: Chr02_01578371 T/C; S01076: Chr02_01605253 T/A; S01077: Chr02_01627916 G/A; S01078: Chr02_01702651 T/G; S01079: Chr02_01806075 G/A; S01080: Chr02_01831450 T/C; S01081: Chr02_01855048 C/T; S01082: Chr02_01889836 T/C; S01083: Chr02_01901619 A/G; S01084: Chr02_01930865 A/G; S01085: Chr02_01956250 C/G; S01086: Chr02_01983899 A/G; S01087: Chr02_02063251 A/C; S01088: Chr02_02134018 A/G; S01089: Chr02_02153770 T/A; S01090: Chr02_02177579 C/T; S01091: Chr02_02205451 C/T; S01092: Chr02_02231449 A/C; S01093: Chr02_02250172 T/A; S01094: Chr02_02332331 T/A; S01095: Chr02_02351482 T/C; S01096: Chr02_02381927 G/A; S01097: Chr02_02401426 C/T; S01098: Chr02_02442452 T/C; S01099: Chr02_02473519 T/G; S01100: Chr02_02475854 C/T; S01101: Chr02_02504452 A/C; S01102: Chr02_02576855 A/G; S01103: Chr02_02605405 T/A; S01104: Chr02_02625631 T/C; S01105: Chr02_02661597 G/T; S01106: Chr02_02713442 T/C; S01107: Chr02_02729755 G/C; S01108: Chr02_02758471 C/G; S01109: Chr02_02775112 A/T; S01110: Chr02_02814480 C/T; S01111: Chr02_02851902 A/G; S01112: Chr02_02896075 A/T; S01113: Chr02_02908715 C/T; S01114: Chr02_02926640 A/T; S01115: Chr02_02950682 T/C; S01116: Chr02_02986388 A/T; S01117: Chr02_03024338 T/A; S01118: Chr02_03025808 A/G; S01119: Chr02_03054072 T/C; S01120: Chr02_03086465 T/A; S01121: Chr02_03100017 G/A; S01122: Chr02_03134153 C/A; S01123: Chr02_03158953 T/A; S01124: Chr02_03175139 T/G; S01125: Chr02_03200625 A/G; S01126: Chr02_03231033 G/A; S01127: Chr02_03256602 G/C; S01128: Chr02_03275900 G/A; S01129: Chr02_03300719 C/T; S01130: Chr02_03328577 A/G; S01131: Chr02_03363813 T/A; S01132: Chr02_03388507 T/A; S01133: Chr02_03402910 A/T; S01134: Chr02_03432500 T/C; S01135: Chr02_03457111 G/A; S01136: Chr02_03484428 G/T; S01137: Chr02_03511948 A/G; S01138: Chr02_03576931 T/C; S01139: Chr02_03613242 G/T; S01140: Chr02_03625047 C/T; S01141: Chr02_03650992 G/A; S01142: Chr02_03684957 A/G; S01143: Chr02_03708186 G/T; S01144: Chr02_03736684 T/C; S01145: Chr02_03753269 G/C; S01146: Chr02_03776967 T/C; S01147: Chr02_03821348 C/T; S01148: Chr02_03831168 T/C; S01149: Chr02_03851809 T/G; S01150: Chr02_03875740 C/T; S01151: Chr02_03912545 G/A; S01152: Chr02_03943603 G/T; S01153: Chr02_03952555 C/A; S01154: Chr02_03975424 C/A; S01155: Chr02_04001584 T/A; S01156: Chr02_04029254 A/C; S01157: Chr02_04050670 A/G; S01158: Chr02_04076567 C/T; S01159: Chr02_04100565 G/T; S01160: Chr02_04126743 C/T; S01161: Chr02_04150842 G/T; S01162: Chr02_04175010 A/T; S01163: Chr02_04214239 A/C; S01164: Chr02_04234113 A/G; S01165: Chr02_04250062 A/G; S01166: Chr02_04277591 A/G; S01167: Chr02_04300890 T/C; S01168: Chr02_04329490 G/A; S01169: Chr02_04357786 A/G; S01170: Chr02_04379130 C/A; S01171: Chr02_04402607 A/G; S01172: Chr02_04425394 G/C; S01173: Chr02_04450412 T/A; S01174: Chr02_04490403 A/G; S01175: Chr02_04502006 A/G; S01176: Chr02_04526649 A/T; S01177: Chr02_04565865 T/A; S01178: Chr02_04577590 A/G; S01179: Chr02_04601159 C/T; S01180: Chr02_04650971 G/A; S01181: Chr02_04681104 G/A; S01182: Chr02_04702366 C/T; S01183: Chr02_04726332 T/C; S01184: Chr02_04788707 C/A; S01185: Chr02_04800624 A/G; S01186: Chr02_04843348 G/T; S01187: Chr02_04860108 A/G; S01188: Chr02_04880939 A/G; S01189: Chr02_04935232 T/C; S01190: Chr02_04951067 C/G; S01191: Chr02_04975293 A/C; S01192: Chr02_05005980 G/A; S01193: Chr02_05065480 C/T; S01194: Chr02_05085075 C/T; S01195: Chr02_05107435 C/T; S01196: Chr02_05126448 A/G; S01197: Chr02_05184206 T/C; S01198: Chr02_05200074 C/T; S01199: Chr02_05225452 C/T; S01200: Chr02_05250738 G/C; S01201: Chr02_05284208 A/G; S01202: Chr02_05302707 C/T; S01203: Chr02_05351331 T/C; S01204: Chr02_05378324 C/G; S01205: Chr02_05434082 C/A; S01206: Chr02_05458522 A/C; S01207: Chr02_05475390 A/T; S01208: Chr02_05508750 A/G; S01209: Chr02_05531209 G/A; S01210: Chr02_05551479 G/A; S01211: Chr02_05591646 G/A; S01212: Chr02_05605910 T/G; S01213: Chr02_05647968 T/C; S01214: Chr02_05654145 G/A; S01215: Chr02_05675722 C/T; S01216: Chr02_05701942 G/A; S01217: Chr02_05728076 G/A; S01218: Chr02_05759207 G/C; S01219: Chr02_05803390 A/T; S01220: Chr02_05827023 A/C; S01221: Chr02_05852326 G/A; S01222: Chr02_05880019 C/A; S01223: Chr02_05900136 G/A; S01224: Chr02_05926544 G/A; S01225: Chr02_05951992 G/A; S01226: Chr02_05975820 A/C; S01227: Chr02_06015651 T/C; S01228: Chr02_06026591 A/G; S01229: Chr02_06088462 T/C; S01230: Chr02_06144520 T/C; S01231: Chr02_06159370 T/A; S01232: Chr02_06219243 C/T; S01233: Chr02_06245979 C/T; S01234: Chr02_06250011 A/T; S01235: Chr02_06277824 A/C; S01236: Chr02_06300927 C/T; S01237: Chr02_06326769 T/A; S01238: Chr02_06353562 G/T; S01239: Chr02_06387459 T/G; S01240: Chr02_06400615 C/T; S01241: Chr02_06436618 A/T; S01242: Chr02_06454031 T/C; S01243: Chr02_06481533 A/T; S01244: Chr02_06503409 G/A; S01245: Chr02_06528102 G/C; S01246: Chr02_06551737 G/A; S01247: Chr02_06581305 G/T; S01248: Chr02_06617656 T/C; S01249: Chr02_06633114 T/C; S01250: Chr02_06658886 G/A; S01251: Chr02_06675538 A/T; S01252: Chr02_06706782 C/G; S01253: Chr02_06726921 G/T; S01254: Chr02_06753706 A/T; S01255: Chr02_06777662 T/C; S01256: Chr02_06803214 T/A; S01257: Chr02_06827865 T/C; S01258: Chr02_06852415 T/C; S01259: Chr02_06878062 A/G; S01260: Chr02_06910331 C/T; S01261: Chr02_06934962 A/T; S01262: Chr02_06964302 A/G; S01263: Chr02_07009229 A/C; S01264: Chr02_07025058 C/G; S01265:

Chr02_07054447 G/T; S01266: Chr02_07080073 A/G; S01267: Chr02_07118150 G/T; S01268: Chr02_07145800 G/C; S01269: Chr02_07160589 A/G; S01270: Chr02_07181578 T/C; S01271: Chr02_07207615 T/G; S01272: Chr02_07241169 C/T; S01273: Chr02_07263449 C/T; S01274: Chr02_07302171 T/C; S01275: Chr02_07327931 C/T; S01276: Chr02_07354922 T/C; S01277: Chr02_07378707 G/A; S01278: Chr02_07406183 G/A; S01279: Chr02_07427003 T/C; S01280: Chr02_07458860 C/T; S01281: Chr02_07527226 G/A; S01282: Chr02_97557303 G/A; S01283: Chr02_07577546 A/G; S01284: Chr02_07615529 G/T; S01285: Chr02_07637412 G/A; S01286: Chr02_07690977 A/G: S01287: Chr02_07722999 C/T; S01288: Chr02_07725023 T/C; S01289: Chr02_07784330 T/C; S01290: Chr02_07802661 G/T; S01291: Chr02_07836496 A/T; S01292: Chr02_07852038 A/G; S01293: Chr02_07921597 C/T; S01294: Chr02_07928221 T/C; S01295: Chr02_07957612 G/T; S01296: Chr02_07976541 G/A; S01297: Chr02_08000367 C/T; S01298: Chr02_08025046 T/A; S01299: Chr02_08058961 C/T; S01300: Chr02_08124168 G/A; S01301: Chr02_08130023 T/A; S01302: Chr02_08156995 T/C; S01303: Chr02_08175874 T/C; S01304: Chr02_08213905 G/A; S01305: Chr02_08244754 G/A; S01306: Chr02_08275939 T/C; S01307: Chr02_08312806 A/T; S01308: Chr02_08334746 T/A; S01309: Chr02_08370417 C/T; S01310: Chr02_08390343 T/C; S01311: Chr02_08410168 C/T; S01312: Chr02_08440899 T/G; S01313: Chr02_08452292 T/C; S01314: Chr02_08483458 G/T; S01315: Chr02_08505964 T/C; S01316: Chr02_08528271 G/A; S01317: Chr02_08593791 T/C; S01318: Chr02_08600130 T/C; S01319: Chr02_08625020 A/G; S01320: Chr02_08722138 G/A; S01321: Chr02_08744076 T/C; S01322: Chr02_08758401 G/A; S01323: Chr02_08791211 C/T; S01324: Chr02_08840665 C/A; S01325: Chr02_08923676 C/A; S01326: Chr02_08961396 C/T; S01327: Chr02_08975125 C/T; S01328: Chr02_09036084 T/A; S01329: Chr02_09103804 T/A; S01330: Chr02_09169402 G/C; S01331: Chr02_09176744 A/T; S01332: Chr02_09220693 C/A; S01333: Chr02_09258611 A/G; S01334: Chr02_09275110 G/A; S01335: Chr02_09369049 G/C; S01336: Chr02_09377706 C/G; S01337: Chr02_09402204 G/C; S01338: Chr02_09445716 C/T; S01339: Chr02_09453561 T/A; S01340: Chr02_09475097 A/T; S01341: Chr02_09528594 C/G; S01342: Chr02_09600618 C/G; S01343: Chr02_09635853 G/A; S01344: Chr02_09659990 T/C; S01345: Chr02_09675960 C/T; S01346: Chr02_09708873 A/T; S01347: Chr02_09729311 C/T; S01348. Chr02_09763022 G/A; S01349: Chr02_09786636 G/C; S01350: Chr02_09807517 G/T; S01351: Chr02_09836732 A/G; S01352: Chr02_09858422 G/A; S01353: Chr02_09879479 C/T; S01354: Chr02_09904314 A/G; S01355: Chr02_09940459 C/A; S01356: Chr02_09954226 A/C; S01357: Chr02_09983124 G/A; S01358: Chr02_10000263 T/C; S01359: Chr02_10025323 T/C; S01360: Chr02_10075061 G/T; S01361: Chr02_10113138 T/C; S01362: Chr02_10141061 T/A; S01363: Chr02_10151059 G/A; S01364: Chr02_10177077 A/G; S01365: Chr02_10216169 T/C;

S01366: Chr02_10253514 T/C; S01367: Chr02_10279884 C/T; S01368: Chr02_10304650 T/A; S01369: Chr02_10328728 T/C; S01370: Chr02_10350783 A/G; S01371: Chr02_10384204 A/C; S01372: Chr02_10404552 T/G; S01373: Chr02_10435506 C/T; S01374: Chr02_10484147 T/C; S01375: Chr02_10510106 G/A; S01376: Chr02_10550119 G/A; S01377: Chr02_10605923 C/G; S01378: Chr02_10630134 A/G; S01379: Chr02_10655342 T/C; S01380: Chr02_10677776 A/T; S01381: Chr02_10701918 T/A; S01382: Chr02_10728282 A/G; S01383: Chr02_10753044 G/A; S01384: Chr02_10783970 C/T; S01385: Chr02_10808885 G/T; S01386: Chr02_10846777 C/T; S01387: Chr02_10855760 G/A; S01388: Chr02_10895236 C/T; S01389: Chr02_10900886 T/G; S01390: Chr02_10925940 A/G; S01391: Chr02_10950871 G/A; S01392: Chr02_11020666 T/G; S01393: Chr02_11034945 G/A; S01394: Chr02_11050044 G/A; S01395: Chr02_11075770 A/G; S01396: Chr02_11107518 A/G; S01397: Chr02_11159988 G/T; S01398: Chr02_11191938 C/T; S01399: Chr02_11228119 A/T; S01400: Chr02_11251542 T/C; S01401: Chr02_11276103 A/G; S01402: Chr02_11311215 C/T; S01403: Chr02_11329341 T/C; S01404: Chr02_11352590 G/A; S01405: Chr02_11377219 C/T; S01406: Chr02_11402509 C/T; S01407: Chr02_11493953 C/T; S01408: Chr02_11523541 G/A; S01409: Chr02_11551590 A/T; S01410: Chr02_11611855 A/G; S01411: Chr02_11677676 A/G; S01412: Chr02_11709751 G/A; S01413: Chr02_11727612 C/G; S01414: Chr02_11751540 A/G; S01415: Chr02_11775217 G/A; S01416: Chr02_11800948 G/A; S01417: Chr02_11825881 C/G; S01418: Chr02_11862643 G/A; S01419: Chr02_11894492 G/T; S01420: Chr02_11907659 C/T; S01421: Chr02_11927284 C/T; S01422: Chr02_11954368 T/A; S01423: Chr02_12029221 T/A; S01424: Chr02_12087053 T/A; S01425: Chr02_12107308 G/A; S01426: Chr02_12134439 T/C; S01427: Chr02_12162493 A/G; S01428: Chr02_12195965 C/G; S01429: Chr02_12229404 T/A; S01430: Chr02_12280886 A/G; S01431: Chr02_12300521 C/T; S01432: Chr02_12354352 T/A; S01433: Chr02_12384785 C/T; S01434: Chr02_12407462 G/A; S01435: Chr02_12442328 T/C; S01436: Chr02_12450652 G/T; S01437: Chr02_12502697 T/A; S01438: Chr02_12531538 C/T; S01439: Chr02_12586568 C/T; S01440: Chr02_12604560 T/C; S01441: Chr02_12678747 C/T; S01442: Chr02_12749216 C/A; S01443: Chr02_12798614 C/T; S01444: Chr02_12800348 C/T; S01445: Chr02_12982535 T/G; S01446: Chr02_13012397 G/C; S01447: Chr02_13082300 G/A; S01448: Chr02_13151764 G/A; S01449: Chr02_13294039 C/T; S01450: Chr02_13325357 C/T; S01451: Chr02_13357583 G/C; S01452: Chr02_13425523 C/T; S01453: Chr02_13501133 T/C; S01454: Chr02_13604595 T/C; S01455: Chr02_13658313 A/C; S01456: Chr02_13731660 G/T; S01457: Chr02_13752589 T/C; S01458: Chr02_13775908 C/T; S01459: Chr02_13865859 C/T; S01460: Chr02_13886746 T/C; S01461: Chr02_13922538 T/G; S01462: Chr02_13961541 C/T; S01463: Chr02_13979499 T/C; S01464: Chr02_14025228 A/G; S01465: Chr02_14111951 C/T; S01466:

Chr02_14132624 A/G; S01467: Chr02_14185805 A/C; S01468: Chr02_14262611 G/A; S01469: Chr02_14283834 G/A; S01470: Chr02_14304514 T/C; S01471: Chr02_14349056 C/A; S01472: Chr02_14365591 G/T; S01473: Chr02_14382881 C/T; S01474: Chr02_14414245 A/G; S01475: Chr02_14477995 A/C; S01476: Chr02_14501714 G/T; S01477: Chr02_14531600 C/T; S01478: Chr02_14552511 C/A; S01479: Chr02_14611514 T/C; S01480: Chr02_14625332 T/A; S01481: Chr02_14655711 G/A; S01482: Chr02_14678818 T/C; S01483: Chr02_14717871 A/G; S01484: Chr02_14731071 C/A; S01485: Chr02_14758307 G/C; S01486: Chr02_14781935 T/C; S01487: Chr02_14822012 G/C; S01488: Chr02_14827663 C/T; S01489: Chr02_14859510 T/A; S01490: Chr02_14884030 C/T; S01491: Chr02_14908964 T/G; S01492: Chr02_14936155 A/C; S01493: Chr02_14977622 C/G; S01494: Chr02_15009796 A/T; S01495: Chr02_15034734 A/G; S01496: Chr02_15054185 C/G; S01497: Chr02_15075831 A/T; S01498: Chr02_15169938 C/T; S01499: Chr02_15179119 G/A; S01500: Chr02_15207649 T/C; S01501: Chr02_15259884 G/T; S01502: Chr02_15286780 A/G; S01503: Chr02_15310684 A/C; S01504: Chr02_15368870 A/G; S01505: Chr02_15417200 T/G; S01506: Chr02_15425037 T/G; S01507: Chr02_15462179 T/A; S01508: Chr02_15482341 T/A; S01509: Chr02_15527683 C/T; S01510: Chr02_15552879 A/G; S01511: Chr02_15581360 C/G; S01512: Chr02_15603859 T/C; S01513: Chr02_15630855 C/T; S01514: Chr02_15652036 A/G; S01515: Chr02_15693475 C/T; S01516: Chr02_15702444 C/T; S01517: Chr02_15762383 G/A; S01518: Chr02_15802678 A/G; S01519: Chr02_15918292 C/G; S01520: Chr02_15932969 T/G; S01521: Chr02_16001938 T/C; S01522: Chr02_16227226 T/C; S01523: Chr02_16312448 G/C; S01524: Chr02_16345029 T/C; S01525: Chr02_16494317 A/C; S01526: Chr02_16503809 T/C; S01527: Chr02_16579534 T/G; S01528: Chr02_16702618 T/G; S01529: Chr02_16788636 C/G; S01530: Chr02_16806704 G/A; S01531: Chr02_16876242 G/T; S01532: Chr02_16953156 A/G; S01533: Chr02_17027333 T/C; S01534: Chr02_17064844 T/C; S01535: Chr02_17152957 A/G; S01536: Chr02_17228881 C/T; S01537: Chr02_17311644 A/C; S01538: Chr02_17450072 A/T; S01539: Chr02_17525329 T/C; S01540: Chr02_17757492 A/T; S01541: Chr02_17827009 G/A; S01542: Chr02_18067387 A/G; S01543: Chr02_18125569 C/A; S01544: Chr02_18275085 A/G; S01545: Chr02_18504972 A/G; S01546: Chr02_18726082 T/C; S01547: Chr02_18750960 A/G; S01548: Chr02_18901881 G/A; S01549: Chr02_19051066 G/A; S01550: Chr02_19206723 A/G; S01551: Chr02_19281007 T/C; S01552: Chr02_19500259 G/A; S01553: Chr02_19584237 C/T; S01554: Chr02_19708461 A/G; S01555: Chr02_19725913 T/C; S01556: Chr02_20025629 T/C; S01557: Chr02_20177645 G/A; S01558: Chr02_20259848 G/A; S01559: Chr02_20331212 T/C; S01560: Chr02_20475853 A/G; S01561: Chr02_20631191 A/C; S01562: Chr02_20700008 T/G; S01563: Chr02_20918336 T/C; S01564: Chr02_21079736 A/G; S01565: Chr02_21225849 G/A; S01566: Chr02_21301061 T/C; S01567: Chr02_21458305 G/A; S01568: Chr02_21511369 G/A; S01569: Chr02_21525224 T/A; S01570: Chr02_21600253 A/G; S01571: Chr02_21677719 T/C; S01572: Chr02_21907559 C/A; S01573: Chr02_22057884 C/A; S01574: Chr02_22303747 T/C; S01575: Chr02_22775332 T/A; S01576: Chr02_23146905 A/G; S01577: Chr02_23225173 C/T; S01578: Chr02_23530213 T/C; S01579: Chr02_23750757 A/C; S01580: Chr02_23827055 A/T; S01581: Chr02_23904920 A/G; S01582: Chr02_23927244 G/C; 501583: Chr02_24095663 C/T; S01584: Chr02_24226747 T/C; S01585: Chr02_24452565 C/T; S01586: Chr02_24527529 A/G; S01587: Chr02_24602804 A/G; S01588: Chr02_24750527 G/A; S01589: Chr02_24825216 T/C; S01590: Chr02_24979564 G/T; S01591: Chr02_25064037 C/T; S01592: Chr02_25147150 T/C; S01593: Chr02_25150251 A/G; S01594: Chr02_25302799 C/T; S01595: Chr02_25499659 T/G; S01596: Chr02_25503405 G/A; S01597: Chr02_25538266 T/C; S01598: Chr02_25608385 G/C; S01599: Chr02_25625668 C/T; S01600: Chr02_25701461 A/G; S01601: Chr02_25775658 G/A; S01602: Chr02_25902092 A/G; S01603: Chr02_25926694 A/G; S01604: Chr02_26004533 A/G; S01605: Chr02_26055194 C/G; S01606: Chr02_26113946 C/T; S01607: Chr02_26130926 T/C; S01608: Chr02_26188273 C/T; S01609: Chr02_26246727 A/G; S01610: Chr02_26251322 A/G; S01611: Chr02_26331830 T/C; S01612: Chr02_26355873 C/T; S01613: Chr02_26375043 C/G; S01614: Chr02_26450017 A/G; S01615: Chr02_26593086 A/C; S01616: Chr02_26655947 T/A; S01617: Chr02_26732063 T/G; S01618: Chr02_26750369 T/C; S01619: Chr02_26875655 G/T; S01620: Chr02_26917590 C/T; S01621: Chr02_26942716 A/G; S01622: Chr02_26982799 G/T; S01623: Chr02_27041225 A/C; S01624: Chr02_27105618 G/A; S01625: Chr02_27194938 G/A; S01626: Chr02_27229775 G/T; S01627: Chr02_27327628 G/T; S01628: Chr02_27353200 G/A; S01629: Chr02_27425273 T/A; S01630: Chr02_27552134 G/A; 501631: Chr02_27661167 C/T; S01632: Chr02_27825152 T/C; S01633: Chr02_27959497 A/G; S01634: Chr02_27975213 G/A; S01635: Chr02_28086119 T/C; S01636: Chr02_28125203 G/A; S01637: Chr02_28204202 A/G; S01638: Chr02_28292252 T/C; S01639: Chr02_28351068 C/A; S01640: Chr02_28426331 T/A; S01641: Chr02_28508509 G/T; S01642: Chr02_28629666 G/A; S01643: Chr02_28652004 C/A; S01644: Chr02_28726135 C/A; S01645: Chr02_28814460 G/A; S01646: Chr02_28903890 G/A; S01647: Chr02_29025631 T/G; S01648: Chr02_29125339 T/C; S01649: Chr02_29237305 T/C; S01650: Chr02_29250059 C/T; S01651: Chr02_29326021 A/G; S01652: Chr02_29445747 G/T; S01653: Chr02_29450123 G/A; S01654: Chr02_29535994 T/A; S01655: Chr02_29598955 C/T; S01656: Chr02_29600053 A/T; S01657: Chr02_29698667 A/G; S01658: Chr02_29700046 A/G; S01659: Chr02_29775087 A/G; S01660: Chr02_29850533 G/A; S01661: Chr02_30019557 A/G; S01662: Chr02_30025246 G/A; S01663: Chr02_30216072 G/A; S01664: Chr02_30334071 G/A; S01665: Chr02_30471217 G/A; S01666: Chr02_30478808 T/C; S01667:

Chr02_30551690 G/T; S01668: Chr02_30626690 T/G; S01669: Chr02_30708916 G/A; S01670: Chr02_30792672 C/G; S01671: Chr02_30802133 C/A; S01672: Chr02_30932636 G/A; S01673: Chr02_30951255 T/C; S01674: Chr02_31061572 T/G; S01675: Chr02_31115094 C/T; S01676: Chr02_31139937 C/T; S01677: Chr02_31150024 G/T; S01678: Chr02_31199600 G/A; S01679: Chr02_31200169 A/G; S01680: Chr02_31236629 A/G; S01681: Chr02_31251713 G/A; S01682: Chr02_31366319 G/T; S01683: Chr02_31376020 T/G; S01684: Chr02_31509124 T/C; S01685: Chr02_31595574 A/C; S01686: Chr02_31600052 G/C; S01687: Chr02_31723543 C/G; S01688: Chr02_31745245 C/T; S01689: Chr02_31799868 G/A; S01690: Chr02_31800084 T/A; S01691: Chr02_31825334 C/A; S01692: Chr02_31999799 C/T; S01693: Chr02_32000004 C/T; S01694: Chr02_32040548 G/A; S01695: Chr02_32054261 A/G; S01696: Chr02_32139213 C/T; S01697: Chr02_32160719 G/A; S01698: Chr02_32186856 T/C; S01699: Chr02_32244736 T/G; S01700: Chr02_32250507 A/G; S01701: Chr02_32275445 A/G; S01702: Chr02_32350138 T/C; S01703: Chr02_32425063 A/G; S01704: Chr02_32552305 T/C; S01705: Chr02_32579142 A/T; S01706: Chr02_32607816 A/G; S01707: Chr02_32749175 A/G; S01708: Chr02_32750507 G/C; S01709: Chr02_32827019 G/A; S01710: Chr02_32932059 T/G; S01711: Chr02_33105476 A/T; S01712: Chr02_33200011 G/A; S01713: Chr02_33350036 T/C; S01714: Chr02_33427439 C/T; S01715: Chr02_33478904 G/T; S01716: Chr02_33500058 C/T; S01717: Chr02_33575990 G/T; S01718: Chr02_33726794 C/T; S01719: Chr02_33827735 T/C; S01720: Chr02_33850090 C/T; S01721: Chr02_33933718 T/A; S01722: Chr02_34053527 T/A; S01723: Chr02_34075754 T/A; S01724: Chr02_34273149 G/C; S01725: Chr02_34275789 A/G; S01726: Chr02_34352721 C/A; S01727: Chr02_34375140 C/A; S01728: Chr02_34506902 G/A; S01729: Chr02_34525103 C/T; S01730: Chr02_34600312 T/A; S01731: Chr02_34721731 C/A; S01732: Chr02_34766981 A/G; S01733: Chr02_34775430 T/C; S01734: Chr02_34925142 G/A; S01735: Chr02_35003205 C/T; S01736: Chr02_35065511 C/T; S01737: Chr02_35187151 G/T; S01738: Chr02_35267196 A/T; S01739: Chr02_35299621 A/G; S01740: Chr02_35311209 T/C; S01741: Chr02_35325900 A/G; S01742: Chr02_35351343 T/A; S01743: Chr02_35500730 A/G; S01744: Chr02_35583866 G/A; S01745: Chr02_35659700 C/T; S01746: Chr02_35678966 C/T; S01747: Chr02_35700392 G/A; S01748: Chr02_35783525 A/G; S01749: Chr02_35802216 T/C; S01750: Chr02_35825000 A/G; S01751: Chr02_35930610 C/A; S01752: Chr02_35950084 A/T; S01753: Chr02_36025167 A/T; S01754: Chr02_36125727 C/T; S01755: Chr02_36150780 A/G; S01756: Chr02_36183513 G/T; S01757: Chr02_36201368 T/G; S01758: Chr02_36288185 A/T; S01759: Chr02_36300067 G/A; S01760: Chr02_36411657 T/C; S01761: Chr02_36474306 A/G; S01762: Chr02_36475062 G/A; S01763: Chr02_36517635 G/T; S01764: Chr02_36567330 T/C; S01765: Chr02_36577954 A/G; S01766: Chr02_36639436 G/A; S01767: Chr02_36665533 T/C; S01768: Chr02_36738436 A/C; S01769: Chr02_36756088 A/G; S01770: Chr02_36793036 A/C; S01771: Chr02_36801797 G/C; S01772: Chr02_36836301 G/T; S01773: Chr02_36856775 A/G; S01774: Chr02_36887104 T/G; S01775: Chr02_36900250 C/T; S01776: Chr02_37009046 C/T; S01777: Chr02_37064827 T/C; S01778: Chr02_37122980 G/A; S01779: Chr02_37133659 C/T; S01780: Chr02_37235724 C/T; S01781: Chr02_37251234 A/T; S01782: Chr02_37275061 A/G; S01783: Chr02_37353395 T/A; S01784: Chr02_37425200 G/A; S01785: Chr02_37521892 C/T; S01786: Chr02_37525789 A/T; S01787: Chr02_37650261 T/G; S01788: Chr02_37725313 T/G; S01789: Chr02_37873784 A/G; S01790: Chr02_37875545 G/A; S01791: Chr02_37950321 C/T; S01792: Chr02_38089530 C/T; S01793: Chr02_38100814 T/A; S01794: Chr02_38255920 A/T; S01795: Chr02_38326821 C/T; S01796: Chr02_38446388 G/C; S01797: Chr02_38456423 A/G; S01798: Chr02_38539450 A/G; S01799: Chr02_38550468 G/T; S01800: Chr02_38613149 A/C; S01801: Chr02_38654561 A/G; S01802: Chr02_38708487 A/G; S01803: Chr02_38739602 A/G; S01804: Chr02_38754838 A/T; S01805: Chr02_38778781 G/C; S01806: Chr02_38801289 A/C; S01807: Chr02_38827243 A/G; S01808: Chr02_38856739 C/A; S01809: Chr02_38904196 G/A; S01810: Chr02_38935935 A/G; S01811: Chr02_38957458 T/C; S01812: Chr02_38982515 G/A; S01813: Chr02_39004142 A/C; S01814: Chr02_39040332 C/T; S01815: Chr02_39065375 C/T; S01816: Chr02_39079008 G/A; S01817: Chr02_39130231 A/G; S01818: Chr02_39166507 C/T; S01819: Chr02_39242633 G/A; S01820: Chr02_39262305 T/C; S01821: Chr02_39293435 G/A; S01822: Chr02_39317703 A/G; S01823: Chr02_39326434 A/G; S01824: Chr02_39351374 A/G; S01825: Chr02_39420347 A/G; S01826: Chr02_39450322 C/T; S01827: Chr02_39492055 T/C; S01828: Chr02_39534972 G/A; S01829: Chr02_39560572 T/A; S01830: Chr02_39584924 C/G; S01831: Chr02_39600089 G/C; S01832: Chr02_39627302 A/G; S01833: Chr02_39661019 C/T; S01834: Chr02_39675930 A/G; S01835: Chr02_39711360 C/G; S01836: Chr02_39736473 T/C; S01837: Chr02_39752443 C/T; S01838: Chr02_39778310 G/A; S01839: Chr02_39800129 A/G; S01840: Chr02_39876854 C/T; S01841: Chr02_39911236 C/T; S01842: Chr02_39946882 T/C; S01843: Chr02_39950530 A/C; S01844: Chr02_39979964 T/A; S01845: Chr02_40017547 T/A; S01846: Chr02_40029226 T/C; S01847: Chr02_40058782 A/G; S01848: Chr02_40080611 C/T; S01849: Chr02_40114918 C/T; S01850: Chr02_40132801 C/T; S01851: Chr02_40150270 C/T; S01852: Chr02_40181565 A/G; S01853: Chr02_40232088 T/G; S01854: Chr02_40276722 T/C; S01855: Chr02_40306189 G/C; S01856: Chr02_40329606 T/C; S01857: Chr02_40370217 G/A; S01858: Chr02_40383752 C/T; S01859: Chr02_40403311 T/C; S01860: Chr02_40488413 C/A; S01861: Chr02_40532534 A/C; S01862: Chr02_40564346 G/A; S01863: Chr02_40589440 C/T; S01864: Chr02_40604577 A/T; S01865: Chr02_40658010 A/G; S01866: Chr02_40683769 C/T; S01867: Chr02_40701107 C/A; S01868:

Chr02_40726991 A/G; S01869: Chr02_40757373 A/T; S01870: Chr02_40784801 T/C; S01871: Chr02_40800066 G/C; S01872: Chr02_40831974 C/A; S01873: Chr02_40859063 T/C; S01874: Chr02_40881964 T/C; S01875: Chr02_40902499 C/T; S01876: Chr02_40933954 A/G; S01877: Chr02_40955346 G/T; S01878: Chr02_40977632 T/G; S01879: Chr02_41000605 G/A; S01880: Chr02_41032570 C/A; S01881: Chr02_41066386 A/G; S01882: Chr02_41077148 A/G; S01883: Chr02_41104941 T/A; S01884: Chr02_41157668 G/A; S01885: Chr02_41176241 G/A; S01886: Chr02_41200248 C/T; S01887: Chr02_41225633 G/A; S01888: Chr02_41251656 C/T; S01889: Chr02_41277787 T/C; S01890: Chr02_41300703 T/C; S01891: Chr02_41334871 G/C; S01892: Chr02_41350974 T/C; S01893: Chr02_41388471 C/G; S01894: Chr02_41403721 G/A; S01895: Chr02_41432839 T/C; S01896: Chr02_41450686 A/T; S01897: Chr02_41481363 G/A; S01898: Chr02_41553711 C/T; S01899: Chr02_41627797 C/T; S01900: Chr02_41689128 G/A; S01901: Chr02_41726764 C/T; S01902: Chr02_41788292 C/T; S01903: Chr02_41829756 A/C; S01904: Chr02_41850275 G/A; S01905: Chr02_41903360 G/A; S01906: Chr02_41931882 G/A; S01907: Chr02_41950542 T/G; S01908: Chr02_42088883 A/C; S01909: Chr02_42111201 T/A; S01910: Chr02_42129852 G/C; S01911: Chr02_42167404 G/A; S01912: Chr02_42184891 G/C; S01913: Chr02_42230180 A/G: S01914: Chr02_42257077 G/A; S01915: Chr02_42284967 C/T; S01916: Chr02_42301205 G/A; S01917: Chr02_42328787 C/G; S01918: Chr02_42354167 T/C; S01919: Chr02_42377138 G/A; S01920: Chr02_42438225 C/T; S01921: Chr02_42456049 G/A; S01922: Chr02_42482035 G/T; S01923: Chr02_42523277 C/T; S01924: Chr02_42536360 A/G; S01925: Chr02_42566645 C/G; S01926: Chr02_42581000 T/A; S01927: Chr02_42610766 G/A; S01928: Chr02_42627794 T/A; S01929: Chr02_42688615 C/T; S01930: Chr02_42702674 T/C; S01931: Chr02_42725006 A/G; S01932: Chr02_42800843 C/T; S01933: Chr02_212863495 T/C; S01934: Chr02_42894473 T/C; S01935: Chr02_42900979 C/T; S01936: Chr02_42925266 T/G; S01937: Chr02_42953049 C/T; S01938: Chr02_42977015 T/G; S01939: Chr02_43011936 C/A; S01940: Chr02_43025467 A/T; S01941: Chr02_43073363 T/C; S01942: Chr02_213083523 G/T; S01943: Chr02_43103807 G/A; S01944: Chr02_43128153 C/T; S01945: Chr02_43160129 T/C; S01946: Chr02_43185933 A/G; S01947: Chr02_43201186 A/G; S01948: Chr02_43230817 G/T; S01949: Chr02_43259724 A/C; S01950: Chr02_43323401 T/C; S01951: Chr02_43334252 C/T; S01952: Chr02_43367206 A/G; S01953: Chr02_43376970 T/C; S01954: Chr02_43405956 T/A; S01955: Chr02_43425791 C/T; S01956: Chr02_43481138 C/T; S01957: Chr02_43506583 A/G; S01958: Chr02_43559616 G/A; S01959: Chr02_43594093 C/T; S01960: Chr02_43663544 G/A; S01961: Chr02_43779773 A/G; S01962: Chr02_43803934 T/G; S01963: Chr02_43825349 A/G; S01964: Chr02_43850610 A/G; S01965: Chr02_43890012 G/A; S01966: Chr02_43901102 T/C; S01967: Chr02_43927200 G/A; S01968: Chr02_43997544 G/T; S01969: Chr02_44009320 A/T; S01970: Chr02_44041696 T/C; S01971: Chr02_44058992 C/G; S01972: Chr02_44075057 A/C; S01973: Chr02_44113985 G/A; S01974: Chr02_44131383 A/C; S01975: Chr02_44178519 C/T; S01976: Chr02_44201142 T/G; S01977: Chr02_44226209 A/G; S01978: Chr02_44267515 A/G; S01979: Chr02_44278342 C/T; S01980: Chr02_44300161 C/T; S01981: Chr02_44339616 T/G; S01982: Chr02_44355651 G/C; S01983: Chr02_44376849 A/C; S01984: Chr02_44405175 C/A; S01985: Chr02_44426269 G/A; S01986: Chr02_44450267 G/A; S01987: Chr02_44490248 A/G; S01988: Chr02_44517329 T/A; S01989: Chr02_44525186 G/A; S01990: Chr02_44623749 A/C; S01991: Chr02_44633434 T/C; S01992: Chr02_44651523 T/G; S01993: Chr02_44695753 C/G; S01994: Chr02_44702951 C/T; S01995: Chr02_44726820 T/C; S01996: Chr02_44753024 C/G; S01997: Chr02_44777006 C/T; S01998: Chr02_44812660 C/T; S01999: Chr02_44827147 A/G; S02000: Chr02_44850928 C/G; S02001: Chr02_44889728 C/T; S02002: Chr02_44902984 T/C; S02003: Chr02_44927745 G/A; S02004: Chr02_44953925 G/C; S02005: Chr02_44980787 C/T; S02006: Chr02_215012265 C/T; S02007: Chr02_45035957 T/C; S02008: Chr02_215065088 G/C; S02009: Chr02_45083910 G/C; S02010: Chr02_45106877 G/A; S02011: Chr02_215133116 G/C; S02012: Chr02_45151358 C/T; S02013: Chr02_45184130 A/G; S02014: Chr02_45202529 G/A; S02015: Chr02_45225277 A/T; S02016: Chr02_45263062 A/G; S02017: Chr02_45276438 T/A: S02018: Chr02_45300532 A/T; S02019: Chr02_45331693 T/C; S02020: Chr02_45420952 G/A; S02021: Chr02_45437663 T/C; S02022: Chr02_45460408 A/G; S02023: Chr02_45476100 A/G; S02024: Chr02_45500945 C/T; S02025: Chr02_45541258 T/C; S02026: Chr02_45563808 A/T; S02027: Chr02_45576128 T/A; S02028: Chr02_45606962 A/G; S02029: Chr02_45625797 T/C; S02030: Chr02_45673121 C/T; S02031: Chr02_45675678 C/T; S02032: Chr02_45701878 T/C; S02033: Chr02_45743013 T/C; S02034: Chr02_45752056 G/A; S02035: Chr02_45786998 T/G; S02036: Chr02_45800675 T/A; S02037: Chr02_45828485 T/C; S02038: Chr02_45855719 C/T; S02039: Chr02_45878211 T/G; S02040: Chr02_45973293 A/T; S02041: Chr02_45981336 G/A; S02042: Chr02_46000020 C/A; S02043: Chr02_46043264 T/C; S02044: Chr02_46050021 C/T; S02045: Chr02_46197659 A/C; S02046: Chr02_46268763 G/C; S02047: Chr02_46283047 C/A; S02048: Chr02_46314964 A/T; S02049: Chr02_46327188 T/A; S02050: Chr02_46352910 G/A; S02051: Chr02_46378297 G/A; S02052: Chr02_46404567 A/C; S02053: Chr02_46427657 A/T; S02054: Chr02_46451976 C/T; S02055: Chr02_46476012 T/C; S02056: Chr02_46513566 A/T; S02057: Chr02_46529972 C/T; S02058: Chr02_46557062 T/A; S02059: Chr02_46575417 G/A; S02060: Chr02_46601831 A/T; S02061: Chr02_46647075 T/C; S02062: Chr02_46651539 C/G; S02063: Chr02_46675597 G/A; S02064: Chr02_46700813 T/G; S02065: Chr02_46728440 A/G; S02066: Chr02_46776729 C/T; S02067: Chr02_46864092 G/A; S02068: Chr02_46888215 G/A; S02069:

Chr02_46906445 C/T; S02070: Chr02_46947115 G/A; S02071: Chr02_46966884 T/G; S02072: Chr02_46980186 T/C; S02073: Chr02_47007874 C/T; S02074: Chr02_47056849 G/A; S02075: Chr02_47075851 T/G; S02076: Chr02_47112718 G/A; S02077: Chr02_47127707 T/C; S02078: Chr02_47158778 C/T; S02079: Chr02_47177511 A/G; S02080: Chr02_47200274 G/A; S02081: Chr02_47227119 A/G; S02082: Chr02_47256997 C/T; S02083: Chr02_47283243 T/C; S02084: Chr02_47300435 T/A; S02085: Chr02_47327219 T/G; S02086: Chr02_47356394 T/A; S02087: Chr02_217376166 A/T; S02088: Chr02_47404217 G/A; S02089: Chr02_47431520 G/A; S02090: Chr02_47453543 T/C; S02091: Chr02_47479060 C/T; S02092: Chr02_217501756 C/T; S02093: Chr02_47525859 A/C; S02094: Chr02_47555159 A/C; S02095: Chr02_47592455 T/C; S02096: Chr02_47626392 C/T; S02097: Chr02_47682431 G/A; S02098: Chr02_47704887 T/A; S02099: Chr02_47734043 C/T; S02100: Chr02_47751944 T/C; S02101: Chr02_47779385 G/A; S02102: Chr02_47807886 G/A; S02103: Chr02_47825751 G/A; S02104: Chr02_47854571 C/G; S02105: Chr02_47881101 A/G; S02106: Chr02_47904254 C/A; S02107: Chr02_47926539 T/C; S02108: Chr02_47951719 T/C; S02109: Chr02_48012289 A/G; S02110: Chr02_48043523 G/A; S02111: Chr02_48056517 C/G; S02112: Chr02_48094100 C/T; S02113: Chr02_48100079 A/G; S02114: Chr02_48125864 T/C; S02115: Chr02_48156171 C/T; S02116: Chr02_48175896 C/T; S02117: Chr02_48201784 T/G; S02118: Chr02_48226815 G/A; S02119: Chr02_48268910 C/T; S02120: Chr02_48284401 T/G; S02121: Chr02_48304951 G/T; S02122: Chr02_48327552 A/G; S02123: Chr02_48352600 T/A; S02124: Chr02_48376363 T/A; S02125: Chr02_48411988 T/C; S02126: Chr02_48435041 G/A; S02127: Chr02_48457817 A/G; S02128: Chr02_48491652 G/A; S02129: Chr02_48505982 C/A; S02130: Chr02_48539098 T/C; S02131: Chr02_48551358 C/T; S02132: Chr03_00043232 C/T; S02133: Chr03_00053784 G/T; S02134: Chr03_00076396 G/A; S02135: Chr03_00114996 C/T; S02136: Chr03_00129878 T/A; S02137: Chr03_00155260 C/T; S02138: Chr03_00177571 T/A; S02139: Chr03_00204258 A/G; S02140: Chr03_00225286 G/C; S02141: Chr03_00253508 T/C; S02142: Chr03_00281750 A/C; S02143: Chr03_00301066 A/C; S02144: Chr03_00333082 G/C; S02145: Chr03_00350024 C/A; S02146: Chr03_00376613 T/A; S02147: Chr03_00401093 G/C; S02148: Chr03_00430947 C/T; S02149: Chr03_00450091 C/T; S02150: Chr03_00484619 C/G; S02151: Chr03_00507039 T/C; S02152: Chr03_00525137 T/C; S02153: Chr03_00558044 C/G; S02154: Chr03_00580641 T/A; S02155: Chr03_00601714 A/T; S02156: Chr03_00630212 T/G; S02157: Chr03_00650331 A/T; S02158: Chr03_00698819 G/T; S02159: Chr03_00722933 A/G; S02160: Chr03_00750370 C/T; S02161: Chr03_00779021 C/T; S02162: Chr03_00803054 G/C; S02163: Chr03_00825755 G/A; S02164: Chr03_00850491 A/C; S02165: Chr03_00888998 T/C; S02166: Chr03_00909851 T/C; S02167: Chr03_00925941 A/G; S02168: Chr03_00951467 T/C; S02169: Chr03_00979152 G/A; S02170: Chr03_01004948 A/C; S02171: Chr03_01039288 C/T; S02172: Chr03_01072541 A/G; S02173: Chr03_01076445 A/G; S02174: Chr03_01100384 T/C; S02175: Chr03_01140747 A/G; S02176: Chr03_01160306 A/G; S02177: Chr03_01197358 T/C; S02178: Chr03_01216786 T/C; S02179: Chr03_01226256 T/C; S02180: Chr03_01280334 A/C; S02181: Chr03_01324758 T/C; S02182: Chr03_01371986 C/A; S02183: Chr03_01381218 C/T; S02184: Chr03_01404553 G/A; S02185: Chr03_01432952 T/A; S02186: Chr03_01452056 C/T; S02187: Chr03_01485365 A/G; S02188: Chr03_01509091 C/A; S02189: Chr03_01536380 C/T; S02190: Chr03_01555305 T/G; S02191: Chr03_01579835 C/A; S02192: Chr03_01606252 G/A; S02193: Chr03_01633588 C/A; S02194: Chr03_01688207 A/C; S02195: Chr03_01717039 C/T; S02196: Chr03_01730161 A/G; S02197: Chr03_01757249 G/A; S02198: Chr03_01781289 C/T; S02199: Chr03_01842018 C/G; S02200: Chr03_01851626 T/G; S02201: Chr03_01875617 G/A; S02202: Chr03_01917125 G/T; S02203: Chr03_01968306 G/A; S02204: Chr03_02000327 C/T; S02205: Chr03_02043169 C/T; S02206: Chr03_02068518 C/G; S02207: Chr03_02087097 C/T; S02208: Chr03_02100913 T/C; S02209: Chr03_02125496 T/G; S02210: Chr03_02150599 A/G; S02211: Chr03_02187767 G/A; S02212: Chr03_02202492 C/T; S02213: Chr03_02237422 T/C; S02214: Chr03_02250983 C/T; S02215: Chr03_02287828 T/C; S02216: Chr03_02302545 A/C; S02217: Chr03_02331398 G/A; S02218: Chr03_02357646 C/A; S02219: Chr03_02408121 C/A; S02220: Chr03_02429062 C/T; S02221: Chr03_02450947 A/G; S02222: Chr03_02488291 C/G; S02223: Chr03_02505045 G/A; S02224: Chr03_02531823 T/C; S02225: Chr03_02550027 G/A; S02226: Chr03_02608120 G/A; S02227: Chr03_02626350 C/A; S02228: Chr03_02769677 C/G; S02229: Chr03_02787417 T/C; S02230: Chr03_02801265 T/A; S02231: Chr03_02834232 T/C; S02232: Chr03_02886359 T/C; S02233: Chr03_02908572 A/G; S02234: Chr03_02930446 T/A; S02235: Chr03_02953887 C/T; S02236: Chr03_02985484 C/T; S02237: Chr03_03005377 C/T; S02238: Chr03_03029797 A/G; S02239: Chr03_03057146 C/T; S02240: Chr03_03092420 C/T; S02241: Chr03_03100461 A/G; S02242: Chr03_03128831 G/C; S02243: Chr03_03178665 G/C; S02244: Chr03_03238219 T/C; S02245: Chr03_03253919 G/T; S02246: Chr03_03327118 G/A; S02247: Chr03_93355927 A/T; S02248: Chr03_03403141 A/G; S02249: Chr03_03427144 A/G; S02250: Chr03_03458537 T/C; S02251: Chr03_03483680 G/T; S02252: Chr03_03516313 G/A; S02253: Chr03_03540421 C/T; S02254: Chr03_03554295 G/T; S02255: Chr03_03603515 G/A; S02256: Chr03_03633977 T/C; S02257: Chr03_03651035 C/T; S02258: Chr03_03691818 C/T; S02259: Chr03_03740804 G/A; S02260: Chr03_03786906 C/T; S02261: Chr03_03811959 G/C; S02262: Chr03_03826007 A/G; S02263: Chr03_03850117 G/A; S02264: Chr03_03886674 C/T; S02265: Chr03_03902061 C/T; S02266: Chr03_03927694 C/T; S02267: Chr03_03953113 G/C; S02268: Chr03_93975034 A/G; S02269: Chr03_04026229 C/A; S02270:

Chr03_04055040 A/C; S02271: Chr03_04123272 T/C; S02272: Chr03_04126504 T/C; S02273: Chr03_04201067 A/C; S02274: Chr03_04266483 C/G; S02275: Chr03_04275186 A/T; S02276: Chr03_04309319 C/T; S02277: Chr03_04325664 A/G; S02278: Chr03_04361323 G/T; S02279: Chr03_04375541 G/C; S02280: Chr03_04402344 T/C; S02281: Chr03_04434164 G/C; S02282: Chr03_04474012 T/A; S02283: Chr03_04475947 C/G; S02284: Chr03_04517165 T/C; S02285: Chr03_04542039 C/G; S02286: Chr03_04566926 C/A; S02287: Chr03_04594019 G/C; S02288: Chr03_04607877 G/A; S02289: Chr03_04638998 T/C; S02290: Chr03_04656720 T/C; S02291: Chr03_04686084 C/A; S02292: Chr03_04704648 G/A; S02293: Chr03_04726872 C/A; S02294: Chr03_04752667 C/G; S02295: Chr03_04780729 G/T; S02296: Chr03_04807631 C/T; S02297: Chr03_04828604 C/A; S02298: Chr03_04852343 A/C; S02299: Chr03_04891117 A/C; S02300: Chr03_04914238 T/A; S02301: Chr03_04958329 C/T; S02302: Chr03_04978476 T/C; S02303: Chr03_05009142 A/G; S02304: Chr03_05032943 C/T; S02305: Chr03_05050657 A/G; S02306: Chr03_05115378 C/T; S02307: Chr03_05125410 C/T; S02308: Chr03_05151333 T/G; S02309: Chr03_05176521 G/C; S02310: Chr03_05210627 C/T; S02311: Chr03_05230334 C/T; S02312: Chr03_05250137 A/G; S02313: Chr03_05284320 C/T; S02314: Chr03_05309175 T/A; S02315: Chr03_05350954 T/C; S02316: Chr03_05393497 T/G; S02317: Chr03_05407462 T/C; S02318: Chr03_05442430 C/T; S02319: Chr03_05450012 G/C; S02320: Chr03_05475540 A/T; S02321: Chr03_05504471 T/C; S02322: Chr03_05525457 G/C; S02323: Chr03_05570073 C/T; S02324: Chr03_05575826 C/T; S02325: Chr03_05621695 C/T; S02326: Chr03_05652547 G/A; S02327: Chr03_05683834 T/C; S02328: Chr03_05702004 G/T; S02329: Chr03_05744104 T/C; S02330: Chr03_05761252 T/C; S02331: Chr03_05782106 A/G; S02332: Chr03_05818267 T/C; S02333: Chr03_05840443 G/A; S02334: Chr03_05898879 G/A; S02335: Chr03_05910027 A/C; S02336: Chr03_05927371 T/C; S02337: Chr03_05977223 G/A; S02338: Chr03_06004158 G/A; S02339: Chr03_06039516 A/T; S02340: Chr03_06117091 C/T; S02341: Chr03_06127579 C/T; S02342: Chr03_06152595 T/A; S02343: Chr03_06185023 T/A; S02344: Chr03_06235821 G/A; S02345: Chr03_06266824 G/A; S02346: Chr03_06313681 T/A; S02347: Chr03_06331184 T/C; S02348: Chr03_06373474 C/T; S02349: Chr03_06378166 C/T; S02350: Chr03_06400516 T/C; S02351: Chr03_06475291 G/A; S02352: Chr03_06526065 G/A; S02353: Chr03_06554906 C/T; S02354: Chr03_06593304 A/G; S02355: Chr03_06603605 G/T; S02356: Chr03_06631908 C/A; S02357: Chr03_06684584 T/C; S02358: Chr03_06700029 C/G; S02359: Chr03_06742866 A/C; S02360: Chr03_06813576 G/A; S02361: Chr03_06854504 T/C; S02362: Chr03_06904143 G/A; S02363: Chr03_06925266 A/G; S02364: Chr03_06952111 C/T; S02365: Chr03_06995484 C/T; S02366: Chr03_07000179 T/C; S02367: Chr03_07048480 C/T; S02368: Chr03_07071278 T/C; S02369: Chr03_07087660 C/T; S02370: Chr03_07337136 G/T; S02371: Chr03_07454850 T/G; S02372: Chr03_07500926 A/G; S02373: Chr03_07562600 T/G; S02374: Chr03_07580819 C/T; S02375: Chr03_07602284 C/T; S02376: Chr03_07646473 G/A; S02377: Chr03_07659302 T/G; S02378: Chr03_07678715 G/A; S02379: Chr03_07700978 G/A; S02380: Chr03_07739139 A/G; S02381: Chr03_07750182 T/G; S02382: Chr03_07780849 C/T; S02383: Chr03_07838302 C/T; S02384: Chr03_07857134 C/T; S02385: Chr03_07933011 A/G; S02386: Chr03_08004233 A/G; S02387: Chr03_08043417 C/T; S02388: Chr03_08073776 A/G; S02389: Chr03_08117624 A/T; S02390: Chr03_08169726 T/C; S02391: Chr03_08179072 G/A; S02392: Chr03_08206014 A/T; S02393: Chr03_08236660 C/G; S02394: Chr03_08252251 G/A; S02395: Chr03_08283603 T/G; S02396: Chr03_08314042 G/A; S02397: Chr03_08329958 C/T; S02398: Chr03_08350052 C/T; S02399: Chr03_08468970 G/A; S02400: Chr03_08490197 A/G; S02401: Chr03_08500028 T/C; S02402: Chr03_08525055 A/G; S02403: Chr03_08600715 T/C; S02404: Chr03_08645993 C/T; S02405: Chr03_08686487 C/T; S02406: Chr03_08707991 T/C; S02407: Chr03_08754621 G/A; S02408: Chr03_08808524 C/T; S02409: Chr03_08826859 C/T; S02410: Chr03_08925950 C/T; S02411: Chr03_09020263 C/T; S02412: Chr03_09030089 T/C; S02413: Chr03_09050574 A/G; S02414: Chr03_09084306 G/A; S02415: Chr03_09204998 T/A; S02416: Chr03_09286947 A/G; S02417: Chr03_09300102 G/A; S02418: Chr03_09378733 G/T; S02419: Chr03_09401627 A/T; S02420: Chr03_09478846 A/G; S02421: Chr03_09547633 G/A; S02422: Chr03_09609105 C/T; S02423: Chr03_09655278 A/T; S02424: Chr03_09707952 G/A; S02425: Chr03_09753678 A/G; S02426: Chr03_09785755 C/A; S02427: Chr03_09897295 C/T; S02428: Chr03_09984410 G/A; S02429: Chr03_10011363 C/A; S02430: Chr03_10026181 A/T; S02431: Chr03_10163547 G/A; S02432: Chr03_10175181 C/T; S02433: Chr03_10250747 T/G; S02434: Chr03_10344117 T/A; S02435: Chr03_10350224 G/A; S02436: Chr03_10427488 G/A; S02437: Chr03_10450026 G/T; S02438: Chr03_10525236 G/A; S02439: Chr03_10603728 A/T; S02440: Chr03_10644274 A/T; S02441: Chr03_10674120 G/A; S02442: Chr03_10675224 C/G; S02443: Chr03_10816468 A/G; S02444: Chr03_10825483 A/G; S02445: Chr03_11275044 G/T; S02446: Chr03_11410770 T/A; S02447: Chr03_11432494 G/A; S02448: Chr03_11451665 G/C; S02449: Chr03_11475021 G/A; S02450: Chr03_11684810 G/A; S02451: Chr03_11700209 A/T; S02452: Chr03_11850248 T/C; S02453: Chr03_11925083 T/G; S02454: Chr03_12065254 G/A; S02455: Chr03_12300123 A/G; S02456: Chr03_12375163 G/T; S02457: Chr03_12722440 G/A; S02458: Chr03_12725438 T/A; S02459: Chr03_12874828 A/G; S02460: Chr03_12875935 C/T; S02461: Chr03_13131030 A/G; S02462: Chr03_13168933 C/A; S02463: Chr03_13225866 G/A; S02464: Chr03_13350524 G/A; S02465: Chr03_13375163 C/G; S02466: Chr03_13439433 A/G; S02467: Chr03_13450354 T/G; S02468: Chr03_13548354 G/T; S02469: Chr03_13567056 G/A; S02470: Chr03_13666918 T/C; S02471:

Chr03_13675036 G/T; S02472: Chr03_13811209 G/A; S02473: Chr03_13894481 C/T; S02474: Chr03_13900025 G/A; S02475: Chr03_14005056 A/T; S02476: Chr03_14073403 A/G; S02477: Chr03_14075000 T/C; S02478: Chr03_14163126 A/G; S02479: Chr03_14467894 A/G; S02480: Chr03_14478745 G/C; S02481: Chr03_14503582 G/A; S02482: Chr03_14580237 C/T; S02483: Chr03_14601109 T/A; S02484: Chr03_14700103 C/T; S02485: Chr03_14777212 C/A; S02486: Chr03_15092586 C/T; S02487: Chr03_15225080 G/A; S02488: Chr03_15525017 A/G; S02489: Chr03_15707317 G/T; S02490: Chr03_15737998 A/G; S02491: Chr03_15755050 C/A; S02492: Chr03_15850169 A/G; S02493: Chr03_16207103 C/T; S02494: Chr03_16225425 G/T; S02495: Chr03_16326622 T/A; S02496: Chr03_16489463 G/T; S02497: Chr03_16513739 G/A; S02498: Chr03_16650034 G/A; S02499: Chr03_16766701 A/G; S02500: Chr03_16844893 T/C; S02501: Chr03_16851619 A/C; S02502: Chr03_16886235 A/G; S02503: Chr03_16941708 C/T; S02504: Chr03_16964685 T/C; S02505: Chr03_17022980 T/C; S02506: Chr03_17027193 C/G; S02507: Chr03_17052961 T/C; S02508: Chr03_17107500 T/A; S02509: Chr03_17129847 G/C; S02510: Chr03_17204522 G/T; S02511: Chr03_17310283 T/G; S02512: Chr03_17400498 G/C; S02513: Chr03_17492608 G/A; S02514: Chr03_17501591 G/A; S02515: Chr03_17634773 G/A; S02516: Chr03_17650348 G/C; S02517: Chr03_17784858 T/G; S02518: Chr03_17846721 T/C; S02519: Chr03_17852180 G/T; S02520: Chr03_18030983 G/A; S02521: Chr03_18107159 G/A; S02522: Chr03_18264422 G/A; S02523: Chr03_18332942 G/T; S02524: Chr03_18402549 A/G; S02525: Chr03_18515528 A/G; S02526: Chr03_18551501 C/T; S02527: Chr03_18597824 C/T; S02528: Chr03_18608511 C/T; S02529: Chr03_18686370 A/G; S02530: Chr03_18700439 C/T; S02531: Chr03_18726118 T/C; S02532: Chr03_18815271 T/A; S02533: Chr03_18839544 G/A; S02534: Chr03_18902361 G/A; S02535: Chr03_18925276 T/C; S02536: Chr03_19014898 A/G; S02537: Chr03_19025927 C/G; S02538: Chr03_19167082 T/C; S02539: Chr03_19180823 A/T; S02540: Chr03_19248979 G/A; S02541: Chr03_19250042 T/C; S02542: Chr03_19365011 A/C; S02543: Chr03_19375066 T/C; S02544: Chr03_19450140 C/G; S02545: Chr03_19613129 C/A; S02546: Chr03_19634138 A/G; S02547: Chr03_19664478 G/A; S02548: Chr03_19692559 G/C; S02549: Chr03_19700107 A/G; S02550: Chr03_19877176 G/C; S02551: Chr03_19982691 A/T; S02552: Chr03_20035077 C/T; S02553: Chr03_20052999 T/C; S02554: Chr03_20118790 T/A; S02555: Chr03_20190001 T/C; S02556: Chr03_20202019 A/G; S02557: Chr03_20236623 T/C; S02558: Chr03_20391401 G/A; S02559: Chr03_20418529 A/T; S02560: Chr03_20425227 T/A; S02561: Chr03_20521062 C/T; S02562: Chr03_20525364 G/A; S02563: Chr03_20675019 A/C; S02564: Chr03_20761879 G/A; S02565: Chr03_20900316 A/G; S02566: Chr03_21086603 C/T; S02567: Chr03_21102664 T/C; S02568: Chr03_21271763 A/T; S02569: Chr03_21275077 A/T; S02570: Chr03_21425443 C/T; S02571: Chr03_21510706 T/C; S02572: Chr03_21525016 A/G; S02573: Chr03_21679961 C/T; S02574: Chr03_21759235 A/G; S02575: Chr03_21811597 G/T; S02576: Chr03_21825465 C/A; S02577: Chr03_21875131 T/A; S02578: Chr03_21945332 G/A; S02579: Chr03_21956330 C/T; S02580: Chr03_21978307 C/T; S02581: Chr03_22005191 C/T; S02582: Chr03_22025079 T/C; S02583: Chr03_22258867 T/C; S02584: Chr03_22348254 C/T; S02585: Chr03_22434548 A/G; S02586: Chr03_22676211 C/T; S02587: Chr03_22828389 T/G; S02588: Chr03_22883387 T/C; S02589: Chr03_22900148 G/A; S02590: Chr03_22976030 A/G; S02591: Chr03_23025614 A/G; S02592: Chr03_23050653 C/T; S02593: Chr03_23142376 C/T; S02594: Chr03_23215081 C/T; S02595: Chr03_23225075 T/G; S02596: Chr03_23291468 G/T; S02597: Chr03_23308572 T/C; S02598: Chr03_23353530 A/G; S02599: Chr03_23376572 A/G; S02600: Chr03_23400189 A/G; S02601: Chr03_23475566 G/A; S02602: Chr03_23694878 A/T; S02603: Chr03_23700777 C/G; S02604: Chr03_23775048 C/T; S02605: Chr03_23850058 G/C; S02606: Chr03_23957356 G/A; S02607: Chr03_23975433 T/A; S02608: Chr03_24143218 A/G; S02609: Chr03_24183100 G/A; S02610: Chr03_24200399 G/A; S02611: Chr03_24275027 A/G; S02612: Chr03_24417772 T/G; S02613: Chr03_24466946 C/G; S02614: Chr03_24499646 T/C; S02615: Chr03_24501907 A/C; S02616: Chr03_24588768 T/A; S02617: Chr03_24600014 C/T; S02618: Chr03_24700003 T/C; S02619: Chr03_24785105 C/T; S02620: Chr03_24800356 A/C; S02621: Chr03_24875012 G/A; S02622: Chr03_25087434 C/A; S02623: Chr03_25137329 T/C; S02624: Chr03_25150645 C/T; S02625: Chr03_25262968 T/A; S02626: Chr03_25275220 C/T; S02627: Chr03_25357483 T/A; S02628: Chr03_25375252 G/A; S02629: Chr03_25485377 C/T; S02630: Chr03_25507584 T/G; S02631: Chr03_25549148 C/T; S02632: Chr03_25552344 G/A; S02633: Chr03_25575268 G/A; S02634: Chr03_25660505 G/C; S02635: Chr03_25675261 A/G; S02636: Chr03_25891807 T/G; S02637: Chr03_25921286 T/C; S02638: Chr03_25949489 G/A; S02639: Chr03_25959844 T/C; S02640: Chr03_25979474 A/C; S02641: Chr03_26013031 G/C; S02642: Chr03_26056996 A/G; S02643: Chr03_26085842 A/G; S02644: Chr03_26189898 G/A; S02645: Chr03_26213930 C/G; S02646: Chr03_26225056 G/A; S02647: Chr03_26331678 A/G; S02648: Chr03_26474231 C/T; S02649: Chr03_26534058 T/C; S02650: Chr03_26554495 A/G; S02651: Chr03_26582330 A/G; S02652: Chr03_26673314 G/A; S02653: Chr03_26675597 C/T; S02654: Chr03_26722389 T/C; S02655: Chr03_26725241 C/T; S02656: Chr03_26750948 T/C; S02657: Chr03_26775057 G/A; S02658: Chr03_26850749 T/A; S02659: Chr03_26895226 G/A; S02660: Chr03_26900029 C/A; S02661: Chr03_26974151 G/A; S02662: Chr03_26982673 A/C; S02663: Chr03_27013368 C/T; S02664: Chr03_27026241 T/C; S02665: Chr03_27060204 T/C; S02666: Chr03_27082205 T/C; S02667: Chr03_27134087 C/T; S02668: Chr03_27150031 C/G; S02669: Chr03_27181444 G/A; S02670: Chr03_27200151 A/T; S02671: Chr03_27227587 C/T; S02672:

Chr03_27276804 T/C; S02673: Chr03_27300018 T/C; S02674: Chr03_27375070 A/C; S02675: Chr03_27513076 A/G; S02676: Chr03_27568206 T/C; S02677: Chr03_27610249 A/G; S02678: Chr03_27639080 A/T; S02679: Chr03_27663908 C/A; S02680: Chr03_27675007 A/G; S02681: Chr03_27840829 C/G; S02682: Chr03_27923496 T/C; S02683: Chr03_27953393 C/T; S02684: Chr03_28013333 G/A; S02685: Chr03_28025071 T/C; S02686: Chr03_28125344 C/T; S02687: Chr03_28185318 C/T; S02688: Chr03_28265800 A/G; S02689: Chr03_28318224 A/G; S02690: Chr03_28345239 G/C; S02691: Chr03_28383770 C/G; S02692: Chr03_28403844 A/G; S02693: Chr03_28449805 G/A; S02694: Chr03_28467077 C/A; S02695: Chr03_28479403 A/G; S02696: Chr03_28509421 G/A; S02697: Chr03_28531592 T/C; S02698: Chr03_28552237 A/G; S02699: Chr03_28575287 C/A; S02700: Chr03_28605992 T/A; S02701: Chr03_28656001 T/C; S02702: Chr03_28700956 A/G; S02703: Chr03_28725047 T/C; S02704: Chr03_28760048 A/C; S02705: Chr03_28841895 T/G; S02706: Chr03_28851441 A/T; S02707: Chr03_28878230 A/G; S02708: Chr03_28932716 C/G; S02709: Chr03_28952175 T/C; S02710: Chr03_28980446 T/C; S02711: Chr03_29000132 A/C; S02712: Chr03_29055432 T/A; S02713: Chr03_29090404 T/C; S02714: Chr03_29180493 G/T; S02715: Chr03_29225126 T/G; S02716: Chr03_29253094 A/G; S02717: Chr03_29328790 A/T; S02718: Chr03_29375199 G/A; S02719: Chr03_29420855 G/A; S02720: Chr03_29450392 A/C; S02721: Chr03_29532753 T/A; S02722: Chr03_29564070 T/A; S02723: Chr03_29578891 G/A; S02724: Chr03_29645112 T/C; S02725: Chr03_29676525 T/G; S02726: Chr03_29711970 G/A; S02727: Chr03_29748914 C/A; S02728: Chr03_29757107 A/G; S02729: Chr03_29786220 G/T; S02730: Chr03_29819202 G/C; S02731: Chr03_29833250 G/A; S02732: Chr03_29976919 A/T; S02733: Chr03_30065075 T/G; S02734: Chr03_30128104 T/C; S02735: Chr03_30201013 G/A; S02736: Chr03_30311351 G/A; S02737: Chr03_30377562 G/A; S02738: Chr03_30455017 G/T; S02739: Chr03_30532752 C/G; S02740: Chr03_30610340 T/C; S02741: Chr03_30693895 T/C; S02742: Chr03_30820359 C/T; S02743: Chr03_30837594 A/G; S02744: Chr03_30897927 C/T; S02745: Chr03_30927448 G/A; S02746: Chr03_30953864 A/G; S02747: Chr03_31002306 A/G; S02748: Chr03_31071719 A/C; S02749: Chr03_31115254 T/A; S02750: Chr03_31164461 T/G; S02751: Chr03_31175433 G/A; S02752: Chr03_31360305 A/G; S02753: Chr03_31379557 A/G; S02754: Chr03_31452820 T/A; S02755: Chr03_31529370 T/C; S02756: Chr03_31683825 C/T; S02757: Chr03_31761678 G/A; S02758: Chr03_31853050 G/A; S02759: Chr03_31930740 G/C; S02760: Chr03_31966204 G/T; S02761: Chr03_32001316 A/C; S02762: Chr03_32049025 G/A; S02763: Chr03_32051441 C/A; S02764: Chr03_32076067 G/T; S02765: Chr03_32102060 C/T; S02766: Chr03_32127776 C/T; S02767: Chr03_32154761 A/G; S02768: Chr03_32229034 T/C; S02769: Chr03_32387164 C/G; S02770: Chr03_32408556 A/G; S02771: Chr03_32562777 C/T; S02772: Chr03_32676245 T/C; S02773: Chr03_32737429 A/G; S02774: Chr03_32752459 A/G; S02775: Chr03_32809310 A/G; S02776: Chr03_32859102 A/G; S02777: Chr03_32895847 G/T; S02778: Chr03_32902523 C/T; S02779: Chr03_32937595 A/G; S02780: Chr03_32971133 G/A; S02781: Chr03_32977907 T/A; S02782: Chr03_33037342 T/C; S02783: Chr03_33056162 G/A; S02784: Chr03_33103625 T/G; S02785: Chr03_33136358 C/T; S02786: Chr03_33177061 A/G; S02787: Chr03_33270553 C/T; S02788: Chr03_33280183 G/A; S02789: Chr03_33300817 T/A; S02790: Chr03_33337475 T/C; S02791: Chr03_33383860 G/A; S02792: Chr03_33418640 A/G; S02793: Chr03_33428956 C/G; S02794: Chr03_33466999 A/T; S02795: Chr03_33478683 G/A; S02796: Chr03_33525823 T/A; S02797: Chr03_33561143 A/G; S02798: Chr03_33604283 T/C; S02799: Chr03_33641088 G/A; S02800: Chr03_33651460 T/C; S02801: Chr03_33744602 G/C; S02802: Chr03_33763642 C/T; S02803: Chr03_33840122 A/G; S02804: Chr03_33878307 G/A; S02805: Chr03_33909938 G/A; S02806: Chr03_33930711 C/T; S02807: Chr03_33982680 T/C; S02808: Chr03_34025261 T/C; S02809: Chr03_34059598 T/C; S02810: Chr03_34077256 C/A; S02811: Chr03_34108558 G/C; S02812: Chr03_34127589 T/C; S02813: Chr03_34150044 C/T; S02814: Chr03_34203827 T/A; S02815: Chr03_34231801 G/A; 502816: Chr03_34250276 T/C; S02817: Chr03_34278750 T/G; S02818: Chr03_34300104 G/T; S02819: Chr03_34353123 G/T; S02820: Chr03_34377175 A/G; S02821: Chr03_34442572 C/T; S02822: Chr03_34450388 G/A; S02823: Chr03_34491935 A/G; S02824: Chr03_34532040 G/A; S02825: Chr03_34590720 G/A; S02826: Chr03_34612476 G/A; S02827: Chr03_34635500 A/T; S02828: Chr03_34664203 C/A; S02829: Chr03_34691323 T/C; S02830: Chr03_34713653 T/A; S02831: Chr03_34736991 G/A; S02832: Chr03_34750595 C/T; S02833: Chr03_34784744 G/T; S02834: Chr03_34801273 G/A; S02835: Chr03_34851073 A/C; S02836: Chr03_34886505 A/G; S02837: Chr03_34910684 C/T; S02838: Chr03_34928316 C/A; S02839: Chr03_34958033 C/A; S02840: Chr03_34993772 C/T; S02841: Chr03_35003120 C/T; S02842: Chr03_35025938 C/G; S02843: Chr03_35065466 G/A; S02844: Chr03_35075678 C/T; S02845: Chr03_35104287 A/C; S02846: Chr03_35143998 T/G; S02847: Chr03_35161975 A/T; S02848: Chr03_35187943 T/C; S02849: Chr03_35200081 T/A; S02850: Chr03_35229509 G/A; S02851: Chr03_35252476 A/G; S02852: Chr03_35281607 C/T; S02853: Chr03_35309254 G/A; S02854: Chr03_35337240 T/A; S02855: Chr03_35351071 T/C; S02856: Chr03_35377125 A/G; S02857: Chr03_35410412 C/A; S02858: Chr03_35458306 C/G; S02859: Chr03_35481036 C/T; S02860: Chr03_35510105 C/T; S02861: Chr03_35526378 C/G; S02862: Chr03_35550015 G/A; S02863: Chr03_35635849 A/G; S02864: Chr03_35671327 A/T; S02865: Chr03_35697656 T/A; S02866: Chr03_35704426 A/G; S02867: Chr03_35729726 G/C; S02868: Chr03_35758171 T/C; S02869: Chr03_35795083 G/A; S02870: Chr03_35801057 A/C; S02871: Chr03_35836637 G/A; S02872: Chr03_35854897 A/G; S02873:

Chr03_35877582 A/G; S02874: Chr03_35909535 C/T; S02875: Chr03_35928452 G/A; S02876: Chr03_35980956 T/C; S02877: Chr03_36001942 T/C; S02878: Chr03_36025667 G/A; S02879: Chr03_36050264 C/T; S02880: Chr03_36075687 G/C; S02881: Chr03_36105105 C/T; S02882: Chr03_36130023 G/T; S02883: Chr03_36157751 T/C; S02884: Chr03_36183523 A/C; S02885: Chr03_36202956 C/T; S02886: Chr03_36242540 A/G; S02887: Chr03_36250365 C/T; S02888: Chr03_36287324 C/T; S02889: Chr03_36339214 C/T; S02890: Chr03_36373619 A/G; 502891: Chr03_36397972 C/T; S02892: Chr03_36421392 A/G; S02893: Chr03_36426626 T/C; S02894: Chr03_36451021 G/A; S02895: Chr03_36475034 T/A; S02896: Chr03_36504983 C/A; S02897: Chr03_36548103 A/G; S02898: Chr03_36611113 C/A; S02899: Chr03_36676760 C/T; S02900: Chr03_36700811 C/A; S02901: Chr03_36727120 A/G; S02902: Chr03_36761629 C/G; S02903: Chr03_36789422 G/C; S02904: Chr03_36860656 C/T; S02905: Chr03_36903387 C/A; S02906: Chr03_36925522 T/A; S02907: Chr03_36953906 A/G; S02908: Chr03_37015622 C/A; S02909: Chr03_37027494 C/A; S02910: Chr03_37112674 A/G; S02911: Chr03_37191690 T/C; S02912: Chr03_37223992 G/A; S02913: Chr03_37229914 T/C; S02914: Chr03_37328249 G/A; S02915: Chr03_37359614 T/G; S02916: Chr03_37411093 C/T; S02917: Chr03_37425219 T/G; S02918: Chr03_37451797 G/C; S02919: Chr03_37484920 G/A; S02920: Chr03_37520039 T/C; S02921: Chr03_37527828 C/T; S02922: Chr03_37561486 A/C; S02923: Chr03_37585621 T/A; S02924: Chr03_37606306 C/T; S02925: Chr03_37628040 A/G; S02926: Chr03_37665819 T/A; S02927: Chr03_37675014 T/C; S02928: Chr03_37706557 T/A; S02929: Chr03_37754024 T/C; S02930: Chr03_37778193 A/G; S02931: Chr03_37801799 C/G; S02932: Chr03_37825537 G/A; S02933: Chr03_37851384 T/C; S02934: Chr03_37892774 T/C; S02935: Chr03_37902609 T/C; S02936: Chr03_37938275 A/G; S02937: Chr03_37957535 G/A; S02938: Chr03_37981188 A/C; S02939: Chr03_38005003 G/A; S02940: Chr03_38028840 G/T; S02941: Chr03_38050001 G/T; S02942: Chr03_38082875 T/A; S02943: Chr03_38101474 T/C; S02944: Chr03_38125759 T/C; S02945: Chr03_38157657 C/T; S02946: Chr03_38180937 T/A; S02947: Chr03_38201477 C/T; S02948: Chr03_38225932 T/C; S02949: Chr03_38254870 T/C; S02950: Chr03_38299775 G/T; S02951: Chr03_38305381 G/A; S02952: Chr03_38325682 G/A; S02953: Chr03_38355833 C/T; S02954: Chr03_38386368 T/C; S02955: Chr03_38419731 G/C; S02956: Chr03_38445075 C/T; S02957: Chr03_38455758 T/C; S02958: Chr03_38476968 G/A; S02959: Chr03_38506584 G/T; S02960: Chr03_38526989 G/A; S02961: Chr03_38551569 A/G; S02962: Chr03_38579634 G/A; S02963: Chr03_38601323 T/C; S02964: Chr03_38644367 A/G; S02965: Chr03_38654695 A/T; S02966: Chr03_38675853 G/A; S02967: Chr03_38703846 C/A; S02968: Chr03_38741334 G/A; S02969: Chr03_38750327 G/A; S02970: Chr03_38782632 G/A; S02971: Chr03_38811359 G/C; S02972: Chr03_38831804 A/T; S02973: Chr03_38853807 C/T; S02974: Chr03_38876199 T/A; S02975: Chr03_38904011 A/T; S02976: Chr03_38925672 G/A; S02977: Chr03_38952250 A/T; S02978: Chr03_38991943 C/T; S02979: Chr03_39016240 G/A; S02980: Chr03_39039639 T/C; S02981: Chr03_39050775 A/G; S02982: Chr03_39081328 G/A; S02983: Chr03_39102792 T/G; S02984: Chr03_39127235 G/T; S02985: Chr03_39157969 G/A; S02986: Chr03_39180498 G/C; S02987: Chr03_39204585 A/G; S02988: Chr03_39226969 T/C; S02989: Chr03_39250645 T/C; S02990: Chr03_39286435 A/T; S02991: Chr03_39301022 C/A; S02992: Chr03_39335220 A/G; S02993: Chr03_39352385 A/G; S02994: Chr03_39376532 G/A; S02995: Chr03_39407484 A/G; S02996: Chr03_39426838 T/G; S02997: Chr03_39473503 G/T; S02998: Chr03_39479334 T/A; S02999: Chr03_39504468 T/A; S03000: Chr03_39554527 G/C; S03001: Chr03_39579634 T/G; S03002: Chr03_39600787 C/T; S03003: Chr03_39630784 T/C; S03004: Chr03_39687289 T/C; S03005: Chr03_39704728 T/C; S03006: Chr03_39727905 T/G; S03007: Chr03_39758872 T/C; S03008: Chr03_39787241 A/G; S03009: Chr03_39806763 T/C; S03010: Chr03_39827617 T/C; S03011: Chr03_39882991 C/T; S03012: Chr03_39957969 T/C; S03013: Chr03_39976930 T/A; S03014: Chr03_210000917 A/T; S03015: Chr03_40028464 A/G; S03016: Chr03_40051318 T/A; S03017: Chr03_210120540 T/C; S03018: Chr03_40127610 G/A; S03019: Chr03_40152251 A/T; S03020: Chr03_40182579 A/G; S03021: Chr03_40201341 G/A; S03022: Chr03_40225852 G/A; S03023: Chr03_40250096 T/C; S03024: Chr03_40326562 A/C; S03025: Chr03_40389920 G/T; S03026: Chr03_40401264 T/C; S03027: Chr03_40475505 A/G; S03028: Chr03_40558941 T/G; S03029: Chr03_40583244 G/C; S03030: Chr03_40672151 A/G; S03031: Chr03_40682204 A/C; S03032: Chr03_40765554 A/C; S03033: Chr03_40888354 T/C; S03034: Chr03_40913421 T/C; S03035: Chr03_40932092 G/A; S03036: Chr03_210955744 C/T; S03037: Chr03_40981424 C/G; S03038: Chr03_41139176 T/A; S03039: Chr03_41220278 C/T; S03040: Chr03_41228895 G/T; S03041: Chr03_41251378 C/T; S03042: Chr03_41324086 T/C; S03043: Chr03_41331499 C/T; S03044: Chr03_41387227 G/A; S03045: Chr03_41400680 T/C; S03046: Chr03_41437738 G/A; S03047: Chr03_41450833 C/T; S03048: Chr03_41475662 C/A; S03049: Chr03_41508785 A/G; S03050: Chr03_41548247 A/G; S03051: Chr03_41551652 G/A; S03052: Chr03_41602591 T/A; S03053: Chr03_41625069 A/G; S03054: Chr03_41699009 G/A; S03055: Chr03_41700467 T/A; S03056: Chr03_41726717 T/C; S03057: Chr03_41771283 A/G; S03058: Chr03_41795286 T/G; S03059: Chr03_41803925 C/T; S03060: Chr03_41865300 G/C; S03061: Chr03_41889902 C/G; S03062: Chr03_41961254 C/T; S03063: Chr03_41975193 A/G; S03064: Chr03_42001647 G/A; S03065: Chr03_42025006 G/T; S03066: Chr03_42083901 G/T; S03067: Chr03_42127054 A/C; S03068: Chr03_42152917 A/C; S03069: Chr03_42179233 A/T; S03070: Chr03_42235000 A/G; S03071: Chr03_42260470 T/G; S03072: Chr03_42275385 A/T; S03073: Chr03_42326268 T/A; S03074:

Chr03_42365077 T/C; S03075: Chr03_42378516 G/A; S03076: Chr03_42406569 A/G; S03077: Chr03_42430222 T/C; S03078: Chr03_42456210 A/G; S03079: Chr03_42476022 G/A; S03080: Chr03_42505702 C/A; S03081: Chr03_42530214 C/G; S03082: Chr03_42551193 G/A; S03083: Chr03_42575014 A/C; S03084: Chr03_42610487 C/T; S03085: Chr03_42634344 G/C; S03086: Chr03_42654295 C/T; S03087: Chr03_42692363 C/T; S03088: Chr03_42700765 G/C; S03089: Chr03_42726960 C/G; S03090: Chr03_42754587 T/C; S03091: Chr03_42776266 A/G; S03092: Chr03_42802419 A/G; S03093: Chr03_42828606 T/G; S03094: Chr03_42850931 G/A; S03095: Chr03_42889191 C/T; S03096: Chr03_42902162 C/A; S03097: Chr03_42938364 A/T; S03098: Chr03_42963333 A/G; S03099: Chr03_42980712 G/A; S03100: Chr03_43040119 C/G; S03101: Chr03_43061605 C/G; S03102: Chr03_43086875 T/A; S03103: Chr03_43104855 T/C; S03104: Chr03_43127220 T/C; S03105: Chr03_43150360 A/G; S03106: Chr03_43196378 A/T; S03107: Chr03_43201351 A/G; S03108: Chr03_43232301 A/C; S03109: Chr03_43250942 T/C; S03110: Chr03_43288252 T/A; S03111: Chr03_43324840 G/T; S03112: Chr03_43331880 A/T; S03113: Chr03_43352021 T/C; S03114: Chr03_43375857 A/T; S03115: Chr03_43400925 C/G; S03116: Chr03_43447330 G/A; S03117: Chr03_43456702 G/A; S03118: Chr03_43479607 A/G; S03119: Chr03_43508720 T/A; S03120: Chr03_43545764 T/C; S03121: Chr03_43553389 C/T; S03122: Chr03_43580780 T/C; S03123: Chr03_213610628 C/T; S03124: Chr03_43630368 G/T; S03125: Chr03_43670969 A/G; S03126: Chr03_43695078 G/A; S03127: Chr03_43703324 A/C; S03128: Chr03_43726576 T/C; S03129: Chr03_43750939 A/T; S03130: Chr03_43775000 C/T; S03131: Chr03_43801402 A/T; S03132: Chr03_43828061 G/A; S03133: Chr03_43852958 T/C; S03134: Chr03_43875561 T/C; S03135: Chr03_43901278 G/A; S03136: Chr03_43934883 C/G; S03137: Chr03_43953323 A/G; S03138: Chr03_43984693 A/C; S03139: Chr03_44007560 C/T; S03140: Chr03_44032388 A/G; S03141: Chr03_44064771 C/T; S03142: Chr03_44089904 G/A; S03143: Chr03_44114451 G/A; S03144: Chr03_44125039 T/G; S03145: Chr03_44155645 G/A; S03146: Chr03_44176052 C/A; S03147: Chr03_44202514 C/G; S03148: Chr03_44226218 C/T; S03149: Chr03_44251291 G/A; S03150: Chr03_44281955 T/G; S03151: Chr03_44300948 C/T; S03152: Chr03_44328629 G/A; S03153: Chr03_44350014 A/G; S03154: Chr03_44381349 G/C; S03155: Chr03_44400465 G/A; S03156: Chr03_44431530 T/C; S03157: Chr03_44450282 C/T; S03158: Chr03_44475689 T/C; S03159: Chr03_44500041 G/C; S03160: Chr03_214529531 A/T; S03161: Chr03_44550993 C/G; S03162: Chr03_44581620 A/G; S03163: Chr03_44602100 T/A; S03164: Chr03_44627607 T/A; S03165: Chr03_44668318 T/C; S03166: Chr03_44689057 T/G; S03167: Chr03_44704477 T/C; S03168: Chr03_44725448 T/G; S03169: Chr03_44750514 T/C; S03170: Chr03_44777470 G/T; S03171: Chr03_44800197 C/T; S03172: Chr03_44833104 A/G; S03173: Chr03_44850673 C/G; S03174: Chr03_44881299 G/A; S03175: Chr03_44904696 C/T; S03176: Chr03_44931010 G/A; S03177: Chr03_44950456 C/T; S03178: Chr03_44975858 T/C; S03179: Chr03_45003578 G/T; S03180: Chr03_45053687 G/A; S03181: Chr03_45081603 C/T; S03182: Chr03_45104017 C/A; S03183: Chr03_45125385 G/A; S03184: Chr03_45151144 A/G; S03185: Chr03_45176175 C/T; S03186: Chr03_45200054 A/C; S03187: Chr03_45233937 T/C; S03188: Chr03_45252972 T/C; S03189: Chr03_45280678 A/T; S03190: Chr03_45301350 C/T; S03191: Chr03_45330859 G/A; S03192: Chr03_45354036 T/C; S03193: Chr03_45381133 G/A; S03194: Chr03_45403769 A/C; S03195: Chr03_45425998 G/T; S03196: Chr03_45462673 C/G; S03197: Chr03_45477579 C/T; S03198: Chr03_45508694 G/A; S03199: Chr03_45525754 A/G; S03200: Chr03_45557433 A/C; S03201: Chr03_45575031 G/A; S03202: Chr03_45601584 A/C; S03203: Chr03_45644558 T/C; S03204: Chr03_45659041 C/G; S03205: Chr03_45721970 A/G; S03206: Chr03_45730193 G/A; S03207: Chr03_45763210 A/G; S03208: Chr03_45778731 A/G; S03209: Chr04_00003024 A/G; S03210: Chr04_00035743 C/G; S03211: Chr04_00054135 T/C; S03212: Chr04_00075018 G/A; S03213: Chr04_00102947 C/A; S03214: Chr04_00134959 A/G; S03215: Chr04_00150103 A/G; S03216: Chr04_00187935 T/G; S03217: Chr04_00206997 G/A; S03218: Chr04_00235504 T/A; S03219: Chr04_00321728 A/G; S03220: Chr04_00334792 A/T; S03221: Chr04_00362208 A/G; S03222: Chr04_00386084 T/C; S03223: Chr04_00425074 C/T; S03224: Chr04_00463274 T/A; S03225: Chr04_00475155 G/A; S03226: Chr04_00506089 T/A; S03227: Chr04_00525028 T/A; S03228: Chr04_00555955 C/G; S03229: Chr04_00575851 T/G; S03230: Chr04_00661515 A/G; S03231: Chr04_00726838 C/T; S03232: Chr04_00753010 G/A; S03233: Chr04_00853348 T/G; S03234: Chr04_00914276 A/T; S03235: Chr04_00988853 T/C; S03236: Chr04_01005018 C/T; S03237: Chr04_01033248 G/A; S03238: Chr04_01051432 A/G; S03239: Chr04_01077434 C/G; S03240: Chr04_01120155 C/T; S03241: Chr04_01128091 G/A; S03242: Chr04_01153469 T/C; S03243: Chr04_01175093 G/T; S03244: Chr04_01272492 T/C; S03245: Chr04_01288048 C/T; S03246: Chr04_01375204 C/A; S03247: Chr04_01404047 C/T; S03248: Chr04_01458547 C/A; S03249: Chr04_01566547 G/T; S03250: Chr04_01597557 G/T; S03251: Chr04_01601042 T/A; S03252: Chr04_01630689 G/A; S03253: Chr04_01650965 G/C; S03254: Chr04_01744771 C/A; S03255: Chr04_01769084 T/G; S03256: Chr04_01775055 G/T; S03257: Chr04_01834955 T/G; S03258: Chr04_01867698 C/T; S03259: Chr04_01886636 G/A; S03260: Chr04_01906362 A/C; S03261: Chr04_01929171 G/A; S03262: Chr04_01954234 T/G; S03263: Chr04_01975063 C/T; S03264: Chr04_02046116 C/T; S03265: Chr04_02062813 T/C; S03266: Chr04_02075540 C/T; 503267: Chr04_02102753 T/C; S03268: Chr04_02140716 C/T; S03269: Chr04_02155529 G/A; S03270: Chr04_02175371 T/C; S03271: Chr04_02204158 T/A; S03272: Chr04_02236262 C/T; S03273: Chr04_02250264 A/T; S03274: Chr04_02286172 C/A; S03275:

Chr04_02309526 T/C; S03276: Chr04_02353160 A/C; S03277: Chr04_02384219 T/G; S03278: Chr04_02406107 G/T; S03279: Chr04_02425281 A/G; S03280: Chr04_02464452 A/G; S03281: Chr04_02483791 C/T; S03282: Chr04_02500653 C/A; S03283: Chr04_02552472 A/T; S03284: Chr04_02575064 C/A; S03285: Chr04_02616241 G/A; S03286: Chr04_02627371 A/G; S03287: Chr04_02650360 C/A; S03288: Chr04_02675545 A/G; S03289: Chr04_02705166 T/C; S03290: Chr04_02736409 A/C; S03291: Chr04_02751613 T/C; S03292: Chr04_02777705 T/C; S03293: Chr04_02804237 C/G; S03294: Chr04_02825113 A/T; S03295: Chr04_02854924 C/T; S03296: Chr04_02877836 T/A; S03297: Chr04_02900161 T/C; S03298: Chr04_02925585 A/G; S03299: Chr04_02970295 G/A; S03300: Chr04_02978040 T/A; S03301: Chr04_03002668 G/A; S03302: Chr04_03025152 C/T; S03303: Chr04_03070244 G/A; S03304: Chr04_03076875 T/C; S03305: Chr04_03100270 G/T; S03306: Chr04_03125194 C/G; S03307: Chr04_03152780 G/T; S03308: Chr04_03175161 T/C; S03309: Chr04_03206910 T/C; S03310: Chr04_03258515 G/A; S03311: Chr04_03308493 G/A; S03312: Chr04_03326762 A/C; S03313: Chr04_03350250 C/A; S03314: Chr04_03405224 A/T; S03315: Chr04_03425900 T/C; S03316: Chr04_03453431 G/A; S03317: Chr04_03475123 G/C; S03318: Chr04_03500545 T/C; S03319: Chr04_03536354 A/C; S03320: Chr04_03573816 A/T; S03321: Chr04_03588697 C/A; S03322: Chr04_03608128 A/T; S03323: Chr04_03660929 C/A; S03324: Chr04_03680128 C/T; S03325: Chr04_03705291 C/T; S03326: Chr04_03725767 T/C; S03327: Chr04_03759591 G/T; S03328: Chr04_03776475 A/T; S03329: Chr04_03810429 C/A; S03330: Chr04_03841306 G/A; S03331: Chr04_03858914 C/T; S03332: Chr04_03875045 T/G; S03333: Chr04_03901073 A/C; S03334: Chr04_03951578 A/T; S03335: Chr04_03977462 G/C; S03336: Chr04_04000319 C/T; S03337: Chr04_04030575 T/C; S03338: Chr04_04054808 T/G; S03339: Chr04_04076681 G/A; S03340: Chr04_04102302 G/C; S03341: Chr04_04131272 A/T; S03342: Chr04_04156104 C/A; S03343: Chr04_04180463 A/G; S03344: Chr04_04205108 G/T; S03345: Chr04_04230043 C/G; S03346: Chr04_04272399 T/A; S03347: Chr04_04285505 T/A; S03348: Chr04_04313026 A/G; S03349: Chr04_04329418 A/G; S03350: Chr04_04351303 A/G; S03351: Chr04_04383427 T/G; S03352: Chr04_04410103 A/G; S03353: Chr04_04427382 C/T; S03354: Chr04_04458704 G/A; S03355: Chr04_04521490 A/T; S03356: Chr04_04532237 T/C; S03357: Chr04_04557116 G/T; S03358: Chr04_04578082 G/A; S03359: Chr04_04608241 A/G; S03360: Chr04_04626486 C/G; S03361: Chr04_04662641 T/C; S03362: Chr04_04683479 C/T; S03363: Chr04_04706140 C/A; S03364: Chr04_04733713 C/A; S03365: Chr04_04750267 A/G; S03366: Chr04_04778350 C/T; S03367: Chr04_04871066 G/T; S03368: Chr04_04887975 T/C; S03369: Chr04_04901121 G/A; S03370: Chr04_04967977 A/G; S03371: Chr04_04976236 A/G; S03372: Chr04_05017067 A/T; S03373: Chr04_05069331 T/G; S03374: Chr04_05080864 C/T; S03375: Chr04_05106548 T/C; S03376: Chr04_05138579 A/T; S03377: Chr04_05155506 T/C; S03378: Chr04_05175354 G/A; S03379: Chr04_05244213 G/C; S03380: Chr04_05257081 G/A; S03381: Chr04_05276150 T/C; S03382: Chr04_05321180 T/G; S03383: Chr04_05340675 A/G; S03384: Chr04_05359808 G/T; S03385: Chr04_05432335 C/G; S03386: Chr04_05460424 A/T; S03387: Chr04_05527316 A/T; S03388: Chr04_05570126 A/G; S03389: Chr04_05607322 G/A; S03390: Chr04_05629959 T/G; S03391: Chr04_05650162 A/G; S03392: Chr04_05735837 A/T; S03393: Chr04_05762278 C/T; S03394: Chr04_05784670 G/C; S03395: Chr04_05816885 G/A; S03396: Chr04_05839404 A/T; S03397: Chr04_05878849 C/T; S03398: Chr04_05900416 C/T; S03399: Chr04_05925621 G/A; S03400: Chr04_05956250 A/G; S03401: Chr04_06068510 T/C; S03402: Chr04_06076228 G/A; S03403: Chr04_06144091 T/C; S03404: Chr04_06151552 G/A; S03405: Chr04_06182948 G/C; S03406: Chr04_06202903 A/T; S03407: Chr04_06261418 A/G; S03408: Chr04_06298617 A/G; S03409: Chr04_06315806 C/A; S03410: Chr04_06326706 G/A; S03411: Chr04_06353684 C/A; S03412: Chr04_06380579 C/G; S03413: Chr04_06412165 C/T; S03414: Chr04_06435379 G/A; S03415: Chr04_06452778 A/G; S03416: Chr04_06479934 T/C; S03417: Chr04_06513553 T/C; S03418: Chr04_06545493 A/T; S03419: Chr04_06559520 T/C; S03420: Chr04_06629918 A/T; S03421: Chr04_06654495 C/T; S03422: Chr04_06709507 T/C; S03423: Chr04_06732902 A/G; S03424: Chr04_06777106 A/T; S03425: Chr04_06806702 A/G; S03426: Chr04_06893781 C/G; S03427: Chr04_06943829 G/T; S03428: Chr04_06950318 A/G; S03429: Chr04_06995484 A/T; S03430: Chr04_07002708 A/G; S03431: Chr04_07030432 C/T; S03432: Chr04_07050805 G/C; S03433: Chr04_07075297 A/T; S03434: Chr04_07132701 C/T; S03435: Chr04_07153221 G/T; S03436: Chr04_07185743 T/C; S03437: Chr04_07201061 G/A; S03438: Chr04_07230081 T/C; S03439: Chr04_07250319 C/T; S03440: Chr04_07292591 A/C; S03441: Chr04_07304895 T/G; S03442: Chr04_07326831 T/C; S03443: Chr04_07350278 T/C; S03444: Chr04_07377900 T/C; S03445: Chr04_07433248 C/A; S03446: Chr04_07467876 C/T; 503447: Chr04_07536574 T/C; S03448: Chr04_07608019 G/T; S03449: Chr04_07744741 A/G; S03450: Chr04_07753853 A/T; S03451: Chr04_07827745 T/G; S03452: Chr04_07947209 G/C; S03453: Chr04_07952258 G/T; S03454: Chr04_07990022 A/T; S03455: Chr04_08020382 T/C; S03456: Chr04_08029471 G/T; S03457: Chr04_08053340 C/A; S03458: Chr04_08089953 T/C; 503459: Chr04_08104094 G/C; S03460: Chr04_08133705 C/A; 503461: Chr04_08150071 T/C; 503462: Chr04_08188825 C/A; S03463: Chr04_08222889 G/A; S03464: Chr04_08233645 A/G; S03465: Chr04_08259632 C/T; S03466: Chr04_08291114 T/A; S03467: Chr04_08315400 T/C; S03468: Chr04_08328248 G/T; S03469: Chr04_08354618 G/T; S03470: Chr04_08375562 C/T; S03471: Chr04_08406527 G/T; S03472: Chr04_08439237 T/G; S03473: Chr04_08460910 G/C; S03474: Chr04_08477484 C/T; S03475: Chr04_08520847 G/A; S03476:

Chr04_08531136 A/T; S03477: Chr04_08569889 T/A; S03478: Chr04_08577960 A/G; S03479: Chr04_08600187 T/C; S03480: Chr04_08627986 T/C; S03481: Chr04_08667076 A/C; S03482: Chr04_08706066 G/A; S03483: Chr04_08744131 C/T; S03484: Chr04_08777894 A/G; S03485: Chr04_08802375 G/A; S03486: Chr04_08834618 G/T; S03487: Chr04_08858816 C/T; S03488: Chr04_08887618 A/C; S03489: Chr04_08902700 C/T; S03490: Chr04_08935672 A/G; S03491: Chr04_08979191 T/C; S03492: Chr04_09031250 T/C; S03493: Chr04_09061992 G/A; S03494: Chr04_09106520 T/C; S03495: Chr04_09127590 C/T; S03496: Chr04_09150218 T/C; S03497: Chr04_09178742 G/A; S03498: Chr04_09221110 G/A; S03499: Chr04_09231883 T/C; S03500: Chr04_09267903 G/A; S03501: Chr04_09277319 T/G; S03502: Chr04_09308835 T/C; S03503: Chr04_09326798 T/C; S03504: Chr04_09354807 C/T; S03505: Chr04_09378161 A/G; S03506: Chr04_09412752 G/T; S03507: Chr04_09444040 C/T; S03508: Chr04_09450136 C/T; S03509: Chr04_09479291 C/T; S03510: Chr04_09501636 G/A; S03511: Chr04_09534814 C/G; S03512: Chr04_09555350 G/T; S03513: Chr04_09611974 A/T; S03514: Chr04_09625416 A/G; S03515: Chr04_09701999 C/G; S03516: Chr04_09726940 G/A; S03517: Chr04_09754156 C/T; S03518: Chr04_09800635 A/T; S03519: Chr04_09877995 G/A; S03520: Chr04_09914276 T/A; S03521: Chr04_09925311 G/A; S03522: Chr04_10057616 G/T; S03523: Chr04_10075089 A/G; S03524: Chr04_10102893 A/G; S03525: Chr04_10126905 G/A; S03526: Chr04_10444529 G/A; S03527: Chr04_10450193 A/G; S03528: Chr04_10600256 G/T; S03529: Chr04_10789432 T/A; S03530: Chr04_10800410 G/A; S03531: Chr04_10907421 T/C; S03532: Chr04_10952963 G/C; S03533: Chr04_10983124 T/A; S03534: Chr04_11000130 T/C; S03535: Chr04_11161188 G/T; S03536: Chr04_11186208 G/A; S03537: Chr04_11225993 C/T; S03538: Chr04_11252437 C/T; S03539: Chr04_11277367 G/A; S03540: Chr04_11300064 C/T; S03541: Chr04_11416598 C/A; S03542: Chr04_11425102 A/C; S03543: Chr04_11500214 T/A; S03544: Chr04_11595080 A/G; S03545: Chr04_11656669 C/G; S03546: Chr04_11950233 C/A; S03547: Chr04_12039123 A/T; S03548: Chr04_12143138 T/C; S03549: Chr04_12159916 G/C; S03550: Chr04_12194763 A/G; S03551: Chr04_12200022 A/T; S03552: Chr04_12225297 G/A; S03553: Chr04_12251193 C/T; S03554: Chr04_12285946 A/G; S03555: Chr04_12306575 C/T; S03556: Chr04_12325007 T/A; S03557: Chr04_12438204 A/T; S03558: Chr04_12495433 C/T; S03559: Chr04_12504367 T/C; S03560: Chr04_12562978 A/G; S03561: Chr04_12581872 C/A; S03562: Chr04_12609618 G/T; S03563: Chr04_12643390 A/G; S03564: Chr04_12650459 C/G; S03565: Chr04_12698867 C/T; S03566: Chr04_12758806 A/T; S03567: Chr04_12832786 G/C; S03568: Chr04_12897766 T/C; S03569: Chr04_12901974 T/C; S03570: Chr04_12932416 G/A; S03571: Chr04_12954966 G/A; S03572: Chr04_12991694 A/G; S03573: Chr04_13145679 A/G; S03574: Chr04_13219455 A/G; S03575: Chr04_13270716 T/C; S03576: Chr04_13277548 T/G; S03577: Chr04_13311659 C/T; S03578: Chr04_13330319 T/G; S03579: Chr04_13428566 C/T; S03580: Chr04_13488853 A/G; S03581: Chr04_13565652 G/A; S03582: Chr04_13575150 T/C; S03583: Chr04_13700145 C/G; S03584: Chr04_13725652 C/T; S03585: Chr04_13755707 G/A; S03586: Chr04_13777214 C/T; S03587: Chr04_13818399 C/T; S03588: Chr04_13825405 C/A; S03589: Chr04_13913892 T/G; S03590: Chr04_14028764 C/T; S03591: Chr04_14197035 A/T; S03592: Chr04_14201286 C/T; S03593: Chr04_14347352 C/A; S03594: Chr04_14401242 T/C; S03595: Chr04_14443525 A/C; S03596: Chr04_14450114 T/A; S03597: Chr04_14622323 A/T; S03598: Chr04_14625180 T/G; S03599: Chr04_14712065 A/G; S03600: Chr04_14738912 G/C; S03601: Chr04_14750215 A/G; S03602: Chr04_14801035 T/A; S03603: Chr04_14881149 A/G; S03604: Chr04_14900010 A/T; S03605: Chr04_15116450 T/A; S03606: Chr04_15154456 A/T; S03607: Chr04_15177972 C/T; S03608: Chr04_15251492 T/C; S03609: Chr04_15326576 G/T; S03610: Chr04_15351140 G/C; S03611: Chr04_15375115 C/G; S03612: Chr04_15474141 A/C; S03613: Chr04_15529677 T/A; S03614: Chr04_15582665 A/G; S03615: Chr04_15620165 G/A; S03616: Chr04_15666766 T/A; S03617: Chr04_15675153 C/A; S03618: Chr04_15770776 C/T; S03619: Chr04_15798157 T/C; S03620: Chr04_15808206 T/G; S03621: Chr04_15847864 T/A; S03622: Chr04_15852291 T/C; S03623: Chr04_15932980 T/C; S03624: Chr04_15953123 G/A; S03625: Chr04_15991442 G/C; S03626: Chr04_16018596 G/C; S03627: Chr04_16025559 G/T; S03628: Chr04_16077156 A/C; S03629: Chr04_16123347 C/T; S03630: Chr04_16125890 C/T; S03631: Chr04_16200137 A/G; S03632: Chr04_16285170 G/A; S03633: Chr04_16329993 T/A; S03634: Chr04_16369381 T/C; S03635: Chr04_16387326 A/G; S03636: Chr04_16400513 G/C; S03637: Chr04_16473219 A/G; S03638: Chr04_16501251 G/A; S03639: Chr04_16529340 T/A; S03640: Chr04_16625245 A/G; S03641: Chr04_16713671 C/T; S03642: Chr04_16730936 T/C; S03643: Chr04_16809386 C/T; S03644: Chr04_16825355 T/G; S03645: Chr04_17003221 T/C; S03646: Chr04_17030559 T/C; S03647: Chr04_17058634 C/T; S03648: Chr04_17100075 G/A; S03649: Chr04_17127789 C/A; S03650: Chr04_17182592 T/G; S03651: Chr04_17255383 T/C; S03652: Chr04_17275484 C/T; S03653: Chr04_17387363 C/A; S03654: Chr04_17504709 G/A; S03655: Chr04_17525251 G/A; S03656: Chr04_17600294 T/G; S03657: Chr04_17688864 A/G; S03658: Chr04_17760225 T/C; S03659: Chr04_17777645 A/G; S03660: Chr04_17866441 C/T; S03661: Chr04_17903805 G/A; S03662: Chr04_17928514 T/C; S03663: Chr04_17968046 T/C; S03664: Chr04_17975375 A/C; S03665: Chr04_18029103 G/A; S03666: Chr04_18077075 A/G; S03667: Chr04_18108878 G/A; S03668: Chr04_18133889 T/C; S03669: Chr04_18194185 T/A; S03670: Chr04_18283509 A/C; S03671: Chr04_18313616 C/T; S03672: Chr04_18356975 T/C; S03673: Chr04_18375447 A/G; S03674: Chr04_18425256 G/T; S03675: Chr04_18451720 A/C; S03676: Chr04_18476324 C/G; S03677:

Chr04_18565313 C/T; S03678: Chr04_18602390 G/A; S03679: Chr04_18633070 G/A; S03680: Chr04_18657339 T/C; S03681: Chr04_18690694 T/C; S03682: Chr04_18755115 A/T; S03683: Chr04_18775184 G/A; S03684: Chr04_18884905 C/T; S03685: Chr04_18902909 T/G; S03686: Chr04_18925003 C/T; S03687: Chr04_19018722 A/T; S03688: Chr04_19026960 C/T; S03689: Chr04_19194236 T/A; S03690: Chr04_19203437 G/A; S03691: Chr04_19320784 C/T; S03692: Chr04_19325025 A/G; S03693: Chr04_19428889 G/A; S03694: Chr04_19450083 C/T; S03695: Chr04_19556728 A/G; S03696: Chr04_19578640 C/T; S03697: Chr04_19600055 A/G; S03698: Chr04_19687111 A/G; S03699: Chr04_19775251 A/C; S03700: Chr04_19850051 A/G; S03701: Chr04_19964773 A/T; S03702: Chr04_20050029 C/T; S03703: Chr04_20171360 T/G; S03704: Chr04_20177900 C/T; S03705: Chr04_20222568 A/T; S03706: Chr04_20225060 G/A; S03707: Chr04_20345232 C/T; S03708: Chr04_20352273 C/T; S03709: Chr04_20444791 A/T; S03710: Chr04_20450521 C/G; S03711: Chr04_20554507 T/C; S03712: Chr04_20612558 T/G; S03713: Chr04_20850837 G/A; S03714: Chr04_20928342 G/A; S03715: Chr04_21002013 T/C; S03716: Chr04_21075400 T/C; S03717: Chr04_21150720 T/G; S03718: Chr04_21230407 G/A; S03719: Chr04_21413638 A/G; S03720: Chr04_21437632 C/T; S03721: Chr04_21450019 T/C; S03722: Chr04_21525031 T/G; S03723: Chr04_21676235 G/A; S03724: Chr04_21700295 T/C; S03725: Chr04_21775355 G/T; S03726: Chr04_21800068 C/G; S03727: Chr04_22051521 C/T; S03728: Chr04_22082438 A/G; S03729: Chr04_22315424 A/G; S03730: Chr04_22407827 C/T; S03731: Chr04_22477042 T/C; S03732: Chr04_22550147 G/A; S03733: Chr04_22604138 T/G; S03734: Chr04_22718133 C/T; S03735: Chr04_22725062 T/A; S03736: Chr04_22819950 T/A; S03737: Chr04_22898405 G/A; S03738: Chr04_22900381 C/T; S03739: Chr04_22967133 T/G; S03740: Chr04_23029978 C/T; S03741: Chr04_23055569 C/T; S03742: Chr04_23150000 G/T; S03743: Chr04_23246125 A/G; S03744: Chr04_23277331 T/G; S03745: Chr04_23300140 G/A; S03746: Chr04_23450129 G/A; S03747: Chr04_23525187 A/G; S03748: Chr04_23666863 G/A; S03749: Chr04_23679566 G/T; S03750: Chr04_23725376 C/T; S03751: Chr04_23761020 C/T; S03752: Chr04_23790879 C/T; S03753: Chr04_23838529 A/C; S03754: Chr04_23910068 T/C; S03755: Chr04_23931556 A/G; S03756: Chr04_24036032 G/A; S03757: Chr04_24050251 G/A; S03758: Chr04_24128871 C/T; S03759: Chr04_24361650 A/G; S03760: Chr04_24438365 A/G; S03761: Chr04_24700032 A/C; S03762: Chr04_24854164 T/G; S03763: Chr04_24975146 A/G; S03764: Chr04_25125143 A/G; S03765: Chr04_25200286 T/C; S03766: Chr04_25295954 C/A; S03767: Chr04_25358809 A/T; S03768: Chr04_25375022 T/A; S03769: Chr04_25525001 A/C; S03770: Chr04_25600048 C/T; S03771: Chr04_25681258 C/T; S03772: Chr04_25775457 C/A; S03773: Chr04_25856224 T/C; S03774: Chr04_26075075 T/C; S03775: Chr04_26215519 A/G; S03776: Chr04_26231551 A/G; S03777: Chr04_26324467 G/A; S03778: Chr04_26325522 A/G; S03779: Chr04_26350993 T/C; S03780: Chr04_26377271 A/G; S03781: Chr04_26450392 G/T; S03782: Chr04_26616238 A/G; S03783: Chr04_26679403 C/T; S03784: Chr04_26747531 T/C; S03785: Chr04_26750077 C/T; S03786: Chr04_26825261 C/T; S03787: Chr04_26902560 C/T; S03788: Chr04_27126858 T/C; S03789: Chr04_27358459 C/G; S03790: Chr04_27375514 A/G; S03791: Chr04_27451075 G/A; S03792: Chr04_27600424 T/C; S03793: Chr04_27908507 G/T; S03794: Chr04_27975152 G/C; S03795: Chr04_28127358 A/T; S03796: Chr04_28200067 A/G; S03797: Chr04_28428426 A/C; S03798: Chr04_28689477 C/G; S03799: Chr04_28700807 A/G; S03800: Chr04_28851145 T/C; S03801: Chr04_29000116 A/T; S03802: Chr04_29150196 A/C; S03803: Chr04_29377597 T/G; S03804: Chr04_29506733 T/C; S03805: Chr04_29676665 A/G; S03806: Chr04_29977221 T/C; S03807: Chr04_30261987 G/A; S03808: Chr04_30303179 G/C; S03809: Chr04_30325157 T/A; S03810: Chr04_30475085 C/T; S03811: Chr04_30625256 T/C; S03812: Chr04_30850999 T/C; S03813: Chr04_30925553 T/C; S03814: Chr04_31021978 A/G; S03815: Chr04_31176441 T/C; S03816: Chr04_31351418 G/A; S03817: Chr04_31425443 T/C; S03818: Chr04_31508906 A/C; S03819: Chr04_31725746 A/G; S03820: Chr04_31876292 T/C; S03821: Chr04_31950441 C/G; S03822: Chr04_32025113 T/C; S03823: Chr04_32100034 A/G; S03824: Chr04_32250246 C/T; S03825: Chr04_32325672 T/C; S03826: Chr04_32403697 C/T; S03827: Chr04_32475071 C/T; S03828: Chr04_32625324 T/C; S03829: Chr04_32801457 A/G; S03830: Chr04_32894839 T/C; S03831: Chr04_32902913 T/C; S03832: Chr04_33006957 A/G; S03833: Chr04_33150055 A/G; S03834: Chr04_33250099 T/C; S03835: Chr04_33375233 C/A; S03836: Chr04_33442291 G/A; S03837: Chr04_33450548 C/G; S03838: Chr04_33526058 A/G; S03839: Chr04_33672827 A/G; S03840: Chr04_33697462 T/G; S03841: Chr04_33700033 A/G; S03842: Chr04_33775693 T/C; S03843: Chr04_33851930 G/A; S03844: Chr04_33925730 A/G; S03845: Chr04_34000271 T/C; S03846: Chr04_34025260 A/G; S03847: Chr04_34221542 C/T; S03848: Chr04_34228463 T/C; S03849: Chr04_34305572 T/A; S03850: Chr04_34327535 A/G; S03851: Chr04_34400576 G/A; S03852: Chr04_34613160 G/A; S03853: Chr04_34831476 A/G; S03854: Chr04_34850213 T/G; S03855: Chr04_34925835 A/C; S03856: Chr04_35087024 G/A; S03857: Chr04_35103194 A/T; S03858: Chr04_35239285 T/C; S03859: Chr04_35253697 G/T; S03860: Chr04_35401248 G/A; S03861: Chr04_35850791 G/T; S03862: Chr04_35932639 A/G; S03863: Chr04_35952202 T/G; S03864: Chr04_36025347 C/T; S03865: Chr04_36100735 A/G; S03866: Chr04_36313277 G/A; S03867: Chr04_36326033 G/A; S03868: Chr04_36417169 A/T; S03869: Chr04_36426215 T/C; S03870: Chr04_36520262 C/T; S03871: Chr04_36554187 A/G; S03872: Chr04_36575041 A/T; S03873: Chr04_36725079 T/C; S03874: Chr04_36822354 A/G; S03875: Chr04_36826649 T/C; S03876: Chr04_36980675 G/A; S03877: Chr04_37040449 A/T; S03878:

Chr04_37068001 T/G; S03879: Chr04_37120651 G/T; S03880: Chr04_37125052 A/G; S03881: Chr04_37200214 C/A; S03882: Chr04_37275109 A/C; S03883: Chr04_37500017 A/G; S03884: Chr04_37675138 T/A; S03885: Chr04_37750173 A/G; S03886: Chr04_37976395 A/T; S03887: Chr04_38050069 C/T; S03888: Chr04_38125703 T/C; S03889: Chr04_38269932 T/C; S03890: Chr04_38277052 T/A; S03891: Chr04_38350126 T/C; S03892: Chr04_38555548 A/G; S03893: Chr04_38725402 C/A; S03894: Chr04_38875563 A/G; S03895: Chr04_38971578 T/C; S03896: Chr04_38984499 T/G; S03897: Chr04_39000492 T/C; S03898: Chr04_39104802 G/T; S03899: Chr04_39125034 T/C; S03900: Chr04_39210780 T/C; S03901: Chr04_39289776 UT: S03902: Chr04_39300310 G/A; S03903: Chr04_39375739 T/G; S03904: Chr04_39452804 A/G; S03905: Chr04_39477562 C/A; S03906: Chr04_39603189 C/G; S03907: Chr04_39633453 T/C; S03908: Chr04_39655962 A/G; S03909: Chr04_39744152 C/A; S03910: Chr04_39752034 T/A; S03911: Chr04_39809470 T/C; S03912: Chr04_39842686 C/T; S03913: Chr04_39851695 A/G; S03914: Chr04_39924884 G/A; S03915: Chr04_39946088 A/C; S03916: Chr04_39979540 C/T; S03917: Chr04_40001925 G/A; S03918: Chr04_40052227 G/T; S03919: Chr04_40104847 C/T; S03920: Chr04_40147912 C/T; S03921: Chr04_40213259 A/G; S03922: Chr04_40237128 A/C; S03923: Chr04_40279991 A/G; S03924: Chr04_40327952 A/G; S03925: Chr04_40391367 C/A; S03926: Chr04_40466217 T/A; S03927: Chr04_40484516 T/C; S03928: Chr04_40501510 C/T; S03929: Chr04_40580513 A/T; S03930: Chr04_40600047 A/T; S03931: Chr04_40706268 C/T; S03932: Chr04_40730838 G/A; S03933: Chr04_40803705 C/A; S03934: Chr04_40847261 T/A; S03935: Chr04_40914112 C/A; S03936: Chr04_40973838 A/G; S03937: Chr04_41028535 G/A; S03938: Chr04_41086234 T/C; S03939: Chr04_41150080 A/C; S03940: Chr04_41264511 G/A; S03941: Chr04_41290074 A/G; S03942: Chr04_41351782 A/G; S03943: Chr04_41375751 T/A; S03944: Chr04_41400002 C/T; S03945: Chr04_41484075 A/T; S03946: Chr04_41523408 G/A; S03947: Chr04_41536915 A/G; S03948: Chr04_41560797 T/A; S03949: Chr04_41629407 C/T; S03950: Chr04_41685095 C/A; S03951: Chr04_41734586 T/A; S03952: Chr04_211757081 T/A; S03953: Chr04_41808537 T/C; S03954: Chr04_41837660 G/A; S03955: Chr04_41882682 C/T; S03956: Chr04_41900015 T/C; S03957: Chr04_41995829 G/A; S03958: Chr04_42009788 G/T; S03959: Chr04_42056183 C/T; S03960: Chr04_42119993 C/A; S03961: Chr04_42134349 T/C; S03962: Chr04_42179376 T/C; S03963: Chr04_42225530 C/G; S03964: Chr04_42279202 G/A; S03965: Chr04_42330667 A/G; S03966: Chr04_42356343 G/C; S03967: Chr04_42381069 A/T; S03968: Chr04_42416681 C/T; S03969: Chr04_42465390 T/C; S03970: Chr04_42617143 A/C; S03971: Chr04_42638214 T/C; S03972: Chr04_42657545 A/G; S03973: Chr04_42715602 A/G; S03974: Chr04_42784990 G/A; S03975: Chr04_42815840 G/C; S03976: Chr04_42848787 T/G; S03977: Chr04_42859299 C/T; S03978: Chr04_42901457 G/A; S03979: Chr04_43002386 G/A; S03980: Chr04_43125219 G/C; S03981: Chr04_43150051 G/A; S03982: Chr04_43257083 C/G; S03983: Chr04_43279404 C/A; S03984: Chr04_43300012 C/G; S03985: Chr04_43375234 G/A; S03986: Chr04_43480478 C/T; S03987: Chr04_43547218 A/G; S03988: Chr04_43554888 C/T; S03989: Chr04_43611185 A/G; S03990: Chr04_43632103 C/G; S03991: Chr04_43656037 A/G; S03992: Chr04_213699129 C/T; S03993: Chr04_43700987 G/A; S03994: Chr04_43755007 T/A; S03995: Chr04_43775000 C/A; S03996: Chr04_43857056 C/T; S03997: Chr04_43905757 G/A; S03998: Chr04_213928645 T/A; S03999: Chr04_43954546 G/A; S04000: Chr04_44000761 C/T; S04001: Chr04_44032620 C/T; S04002: Chr04_44077654 T/C; S04003: Chr04_44117962 A/G; S04004: Chr04_44127785 G/A; S04005: Chr04_44159087 A/G; S04006: Chr04_44191827 C/T; S04007: Chr04_44202428 C/G; S04008: Chr04_44285724 T/G; S04009: Chr04_214313136 A/C; S04010: Chr04_44325216 G/A; S04011: Chr04_44358686 C/T; S04012: Chr04_44392150 C/T; S04013: Chr04_44400037 G/C; S04014: Chr04_44426179 C/A; S04015: Chr04_44458679 G/C; S04016: Chr04_44476706 A/T; S04017: Chr04_44514431 T/A; S04018: Chr04_44592458 A/G; S04019: Chr04_44612012 T/C; S04020: Chr04_44625161 A/T; S04021: Chr04_44651892 C/G; S04022: Chr04_44693997 T/C; S04023: Chr04_44700506 A/G; S04024: Chr04_44740558 G/T; S04025: Chr04_44753356 C/G; S04026: Chr04_44801618 T/C; S04027: Chr04_44857508 C/T; S04028: Chr04_44931055 A/G; S04029: Chr04_44986524 G/A; S04030: Chr04_45000521 G/T; S04031: Chr04_45044704 T/C; S04032: Chr04_45062368 C/T; S04033: Chr04_45076011 T/C; S04034: Chr04_45150594 A/G; S04035: Chr04_45176896 A/T; S04036: Chr04_45211877 C/T; S04037: Chr04_45234196 A/G; S04038: Chr04_45291815 C/T; S04039: Chr04_45300157 A/T; S04040: Chr04_45335177 T/C; S04041: Chr04_45354975 G/A; S04042: Chr04_45384175 A/T; S04043: Chr04_45408520 C/T; S04044: Chr04_45429209 C/T; S04045: Chr04_45498316 G/A; S04046: Chr04_45546221 A/G; S04047: Chr04_45569116 G/A; S04048: Chr04_45575047 T/C; S04049: Chr04_45658472 T/G; S04050: Chr04_45777978 T/C; S04051: Chr04_45803001 G/A; S04052: Chr04_45836181 A/T; S04053: Chr04_45855170 A/G; S04054: Chr04_45877175 C/A; S04055: Chr04_45919097 C/A; S04056: Chr04_45927321 G/A; S04057: Chr04_45965159 G/T; S04058: Chr04_45983488 C/G; S04059: Chr04_46003119 T/C; S04060: Chr04_46027902 T/C; S04061: Chr04_46050879 A/T; S04062: Chr04_46077634 G/A; S04063: Chr04_46102658 G/T; S04064: Chr04_46132170 G/T; S04065: Chr04_46152626 C/T; S04066: Chr04_46177201 A/G; S04067: Chr04_46213322 G/A; S04068: Chr04_46238255 T/A; S04069: Chr04_46254878 T/G; S04070: Chr04_46279312 G/A; S04071: Chr04_46307814 A/G; S04072: Chr04_46326314 A/G; S04073: Chr04_46357424 G/A; S04074: Chr04_46377067 C/T; S04075: Chr04_46400670 C/T; S04076: Chr04_46434792 C/T; S04077: Chr04_46451480 G/A; S04078: Chr04_46484456 A/T; S04079:

Chr04_46506299 T/C; S04080: Chr04_46525679 G/T; S04081: Chr04_46559968 G/C; S04082: Chr04_46582419 C/T; S04083: Chr04_46609130 T/C; S04084: Chr04_46654744 T/C; S04085: Chr04_46682467 T/C; S04086: Chr04_46705184 T/C; S04087: Chr04_46726078 A/T; S04088: Chr04_46750345 G/A; S04089: Chr04_46788348 C/T; S04090: Chr04_46807960 C/T; S04091: Chr04_46832902 C/T; S04092: Chr04_46850873 G/A; S04093: Chr04_46878018 G/A; S04094: Chr04_46955233 C/T; S04095: Chr04_46997620 A/G; S04096: Chr04_47001664 T/C; S04097: Chr04_47041279 C/T; S04098: Chr04_47113140 T/C; S04099: Chr04_47157109 C/A; S04100: Chr04_47179171 A/C; S04101: Chr04_47247075 C/T; S04102: Chr04_217254706 T/C; S04103: Chr04_47281231 G/C; S04104: Chr04_47311823 C/G; S04105: Chr04_47350308 G/A; S04106: Chr04_47376541 G/A; S04107: Chr04_217405915 T/A; S04108: Chr04_47426257 C/T; S04109: Chr04_47454952 G/A; S04110: Chr04_47483393 T/C; S04111: Chr04_47506354 A/G; S04112: Chr04_47537209 C/G; S04113: Chr04_47555835 G/C; S04114: Chr04_47587959 G/A; S04115: Chr04_47602898 T/C; S04116: Chr04_47627449 T/G; S04117: Chr04_47652057 T/C; S04118: Chr04_47678145 C/T; S04119: Chr04_47718677 A/G; S04120: Chr04_47733011 C/T; S04121: Chr04_47754234 G/A; S04122: Chr04_47775179 C/A; S04123: Chr04_47811052 C/T; S04124: Chr04_47831991 A/T; S04125: Chr04_47856446 G/C; S04126: Chr04_47875842 T/A; S04127: Chr04_47900156 A/T; S04128: Chr04_47925101 G/A; S04129: Chr04_47950851 T/C; S04130: Chr04_48001707 A/G; S04131: Chr04_48029104 G/T; S04132: Chr04_48061350 T/C; S04133: Chr04_48080149 A/T; S04134: Chr04_48109645 C/T; S04135: Chr04_48133794 A/G; S04136: Chr04_48158453 C/T; S04137: Chr04_48190085 T/G; S04138: Chr04_48218119 T/C; S04139: Chr04_48232808 G/T; S04140: Chr04_48263847 A/G; S04141: Chr04_48279338 T/C; S04142: Chr04_48314013 T/G; S04143: Chr04_48340200 C/A; S04144: Chr04_48365430 C/G; S04145: Chr04_48382310 G/A; S04146: Chr04_48401759 A/T; S04147: Chr04_48428892 G/A; S04148: Chr04_48451513 A/G; S04149: Chr04_48485665 A/C; S04150: Chr04_48503520 A/C; S04151: Chr04_48525231 T/C; S04152: Chr04_48550747 A/T; S04153: Chr04_48590176 T/C; S04154: Chr04_48603821 C/T; S04155: Chr04_48633564 G/A; S04156: Chr04_48673776 G/A; S04157: Chr04_48675097 C/A; S04158: Chr04_48707587 T/C; S04159: Chr04_48726633 T/A; S04160: Chr04_48759118 T/A; S04161: Chr04_48857980 G/C; S04162: Chr04_48887076 A/C; S04163: Chr04_48990921 A/G; S04164: Chr04_49015711 C/T; S04165: Chr04_49026072 A/G; S04166: Chr04_49054117 C/T; S04167: Chr04_49086282 A/T; S04168: Chr04_49133954 C/G; S04169: Chr04_49161893 C/T; S04170: Chr04_49182724 A/G; S04171: Chr04_49204713 T/C; S04172: Chr04_49239890 A/C; S04173: Chr04_49255924 A/G; S04174: Chr04_49298913 A/G; S04175: Chr04_49304403 C/T; S04176: Chr04_49351611 C/T; S04177: Chr04_49412311 C/A; S04178: Chr04_49431330 G/A; S04179: Chr04_49451089

G/C; S04180: Chr04_49482174 T/C; S04181: Chr04_49501143 A/G; S04182: Chr04_49528291 C/T; S04183: Chr04_49550167 G/A; S04184: Chr04_49575208 G/A; S04185: Chr04_49601333 C/T; S04186: Chr04_49625290 C/T; S04187: Chr04_49655228 T/C; S04188: Chr04_49680910 C/T; S04189: Chr04_49706352 T/C; S04190: Chr04_49754179 A/G; S04191: Chr04_49779017 T/C; S04192: Chr04_49803507 A/G; S04193: Chr04_49828162 A/G; S04194: Chr04_49852574 C/A; S04195: Chr04_49883170 C/G; S04196: Chr04_49900038 A/T; S04197: Chr04_49941402 G/A; S04198: Chr04_49952672 C/G; S04199: Chr04_50019800 G/C; S04200: Chr04_50038531 T/C; S04201: Chr04_50053684 G/A; S04202: Chr04_50089211 T/C; S04203: Chr04_50101328 T/C; S04204: Chr04_50131254 T/A; S04205: Chr04_50213997 T/C; S04206: Chr04_50227631 A/G; S04207: Chr04_50258974 A/T; S04208: Chr04_50280579 C/A; S04209: Chr04_50308155 C/T; S04210: Chr04_50333842 T/C; S04211: Chr04_50350312 C/T; S04212: Chr04_50402455 T/G; S04213: Chr04_50425328 C/T; S04214: Chr04_50452014 G/T; S04215: Chr04_50479009 G/T; S04216: Chr04_50500064 T/C; S04217: Chr04_50618497 C/T; S04218: Chr04_50679514 G/C; S04219: Chr04_50757517 G/A; S04220: Chr04_50780516 C/T; S04221: Chr04_50809572 T/C; S04222: Chr04_50826899 C/T; S04223: Chr04_50850178 G/A; S04224: Chr04_50878264 G/A; S04225: Chr04_50902845 T/G; S04226: Chr04_50925825 A/G; S04227: Chr04_50994851 A/T; S04228: Chr04_51001982 A/G; S04229: Chr04_51027741 T/C; S04230: Chr04_51054060 A/G; S04231: Chr04_51082928 T/C; S04232: Chr04_51103827 T/C; S04233: Chr04_51134738 C/G; S04234: Chr04_51158072 A/C; S04235: Chr04_51176069 C/G; S04236: Chr04_51201999 T/A; S04237: Chr04_51226385 C/T; S04238: Chr04_51252852 C/G; S04239: Chr04_51292305 T/A; S04240: Chr04_51305043 A/T; S04241: Chr04_51335430 G/A; S04242: Chr04_51351370 C/A; S04243: Chr04_51375575 G/A; S04244: Chr04_51466056 A/G; S04245: Chr04_51504477 C/T; S04246: Chr04_51526078 C/T; S04247: Chr04_51554352 C/A; S04248: Chr04_51579450 G/A; S04249: Chr04_51612008 C/T; S04250: Chr04_51659941 G/C; S04251: Chr04_51687662 T/C; S04252: Chr04_51711380 C/G; S04253: Chr04_51725549 G/A; S04254: Chr04_51762243 A/G; S04255: Chr04_51790499 G/A; S04256: Chr04_51809325 A/G; S04257: Chr04_51825483 C/T; S04258: Chr04_51850144 T/G; S04259: Chr04_51886730 G/A; S04260: Chr04_51904549 C/A; S04261: Chr04_51926547 C/T; S04262: Chr04_51965401 G/A; S04263: Chr04_51989018 T/A; S04264: Chr04_52005841 A/G; S04265: Chr04_52093150 C/T; S04266: Chr04_52100424 A/T; S04267: Chr04_52188714 C/T; S04268: Chr04_52200804 C/T; S04269: Chr04_52225506 A/C; S04270: Chr04_52316114 G/T; S04271: Chr04_52388024 G/A; S04272: Chr05_00012184 G/A; S04273: Chr05_00062130 C/A; S04274: Chr05_00084921 C/T; S04275: Chr05_00107911 G/A; S04276: Chr05_00132830 A/G; S04277: Chr05_00151961 T/C; S04278: Chr05_00179266 A/G; S04279: Chr05_00200110 C/T; S04280:

Chr05_00227559 C/A; S04281: Chr05_00254210 T/A; S04282: Chr05_00285830 A/G; S04283: Chr05_00300276 C/T; S04284: Chr05_00328234 G/A; S04285: Chr05_00399491 T/C; S04286: Chr05_00402447 T/C; S04287: Chr05_00430730 T/G; S04288: Chr05_00451090 T/C; S04289: Chr05_00476344 T/A; S04290: Chr05_00500497 T/C; S04291: Chr05_00552066 C/T; S04292: Chr05_00615750 A/G; S04293: Chr05_00645804 T/A; S04294: Chr05_00651653 T/A; S04295: Chr05_00683189 C/T; S04296: Chr05_00710098 T/C; S04297: Chr05_00728199 A/T; S04298: Chr05_00750395 C/T; S04299: Chr05_00790268 T/C; S04300: Chr05_00819507 C/T; S04301: Chr05_00829318 C/T; S04302: Chr05_00850447 G/A; S04303: Chr05_00880642 C/A; S04304: Chr05_00900284 A/G; S04305: Chr05_00933168 T/C; S04306: Chr05_00962409 G/T; S04307: Chr05_00992883 A/T; S04308: Chr05_01013568 C/T; S04309: Chr05_01025323 G/C; S04310: Chr05_01129082 G/A; S04311: Chr05_01176194 G/A; S04312: Chr05_01205640 G/C; S04313: Chr05_01264187 A/C; S04314: Chr05_01280292 T/A; S04315: Chr05_01313878 G/A; S04316: Chr05_01340399 G/A; S04317: Chr05_01358556 C/T; S04318: Chr05_01449857 C/T; S04319: Chr05_01457241 G/A; S04320: Chr05_01475484 C/G; S04321: Chr05_01502343 G/A; S04322: Chr05_01545337 G/C; S04323: Chr05_01562735 C/T; S04324: Chr05_01576964 T/A; S04325: Chr05_01606995 A/C; S04326: Chr05_01626178 C/T; S04327: Chr05_01661385 C/T; S04328: Chr05_01692088 A/C; S04329: Chr05_01700777 C/T; S04330: Chr05_01725871 T/C; S04331: Chr05_01753704 C/A; S04332: Chr05_01781250 A/T; S04333: Chr05_01801496 T/A; S04334: Chr05_01826579 C/T; S04335: Chr05_01929421 C/T; S04336: Chr05_01952577 C/T; S04337: Chr05_02013895 A/G; S04338: Chr05_02086063 C/G; S04339: Chr05_02105142 A/C; S04340: Chr05_02141202 A/T; S04341: Chr05_02167334 C/T; S04342: Chr05_02178871 A/G; S04343: Chr05_02200890 A/T; S04344: Chr05_02241453 A/T; S04345: Chr05_02281930 T/A; S04346: Chr05_92301238 A/G; S04347: Chr05_02338209 G/C; S04348: Chr05_02354272 C/T; S04349: Chr05_02406095 T/C; S04350: Chr05_02428992 A/C; S04351: Chr05_02451005 C/T; S04352: Chr05_02477128 A/G; S04353: Chr05_02505712 C/A; S04354: Chr05_02525824 G/C; S04355: Chr05_02582742 G/A; S04356: Chr05_02612793 A/G; S04357: Chr05_02626909 T/C; S04358: Chr05_02667653 G/A; S04359: Chr05_02680630 T/C; S04360: Chr05_02708914 G/T; S04361: Chr05_02729896 A/T; S04362: Chr05_02753677 C/A; S04363: Chr05_02786703 T/C; S04364: Chr05_02803320 G/A; S04365: Chr05_02826141 A/T; S04366: Chr05_02851236 G/A; S04367: Chr05_02883123 G/A; S04368: Chr05_02906386 C/G; S04369: Chr05_02928145 G/A; S04370: Chr05_02963065 C/T; S04371: Chr05_02989398 A/C; S04372: Chr05_03037780 G/T; S04373: Chr05_03053748 T/A; S04374: Chr05_03075773 G/A; S04375: Chr05_03100788 C/T; S04376: Chr05_03128952 G/A; S04377: Chr05_03152430 A/G; S04378: Chr05_03177702 T/C; S04379: Chr05_03200799 G/A; S04380: Chr05_03242150 T/G; S04381: Chr05_03261123 C/T; S04382: Chr05_03280123 G/T; S04383: Chr05_03307133 G/T; S04384: Chr05_03335419 C/A; S04385: Chr05_03355678 A/C; S04386: Chr05_03377432 C/T; S04387: Chr05_03410868 G/A; S04388: Chr05_03431358 A/G; S04389: Chr05_03458186 C/T; S04390: Chr05_03483076 A/T; S04391: Chr05_03505974 C/T; S04392: Chr05_03531115 T/G; S04393: Chr05_03561223 A/T; S04394: Chr05_03614833 G/A; S04395: Chr05_03644217 G/T; S04396: Chr05_03670860 G/A; S04397: Chr05_03680548 G/A; S04398: Chr05_03701358 C/A; S04399: Chr05_03725956 C/A; S04400: Chr05_03753535 G/C; S04401: Chr05_03776582 T/C; S04402: Chr05_03814056 A/C; S04403: Chr05_03848321 G/A; S04404: Chr05_03902580 G/T; S04405: Chr05_03925871 C/T; S04406: Chr05_04015253 G/A; S04407: Chr05_04078364 A/C; S04408: Chr05_04105092 T/C; S04409: Chr05_04138708 C/A; S04410: Chr05_04150568 C/T; S04411: Chr05_04176187 A/C; S04412: Chr05_04254989 G/A; S04413: Chr05_04276732 T/C; S04414: Chr05_04303558 T/A; S04415: Chr05_04352303 C/A; S04416: Chr05_04379100 G/A; S04417: Chr05_04400059 C/A; S04418: Chr05_04449221 T/A; S04419: Chr05_04462985 T/A; S04420: Chr05_04497032 A/G; S04421: Chr05_04501169 G/T; S04422: Chr05_04537868 A/T; S04423: Chr05_04553295 G/A; S04424: Chr05_04576304 A/G; S04425: Chr05_04600518 G/A; S04426: Chr05_04634347 T/C; S04427: Chr05_04652161 G/T; S04428: Chr05_04678859 A/T; S04429: Chr05_04716071 A/C; S04430: Chr05_04725073 T/A; S04431: Chr05_04794781 G/A; S04432: Chr05_04813177 A/C; S04433: Chr05_04840924 G/A; S04434: Chr05_04851610 C/T; S04435: Chr05_04892911 G/C; S04436: Chr05_05000732 G/T; S04437: Chr05_05035397 A/G; S04438: Chr05_05050818 C/A; S04439: Chr05_05146158 A/G; S04440: Chr05_05150312 A/T; S04441: Chr05_05194243 G/C; S04442: Chr05_05215429 C/A; S04443: Chr05_05237210 C/T; S04444: Chr05_05262227 A/G; S04445: Chr05_05276418 T/C; S04446: Chr05_05305851 T/A; S04447: Chr05_05325721 T/G; S04448: Chr05_05350571 T/G; S04449: Chr05_05379985 A/G; S04450: Chr05_05412174 G/A; S04451: Chr05_05473437 C/T; S04452: Chr05_05481028 T/C; S04453: Chr05_05558466 C/T; S04454: Chr05_05575650 A/G; S04455: Chr05_05613716 T/C; S04456: Chr05_05626085 A/G; S04457: Chr05_05655191 A/G; S04458: Chr05_05676224 A/G; S04459: Chr05_05709990 C/G; S04460: Chr05_05758957 A/G; S04461: Chr05_05797843 A/G; S04462: Chr05_05802102 G/A; S04463: Chr05_05843476 A/T; S04464: Chr05_05857973 T/C; S04465: Chr05_05953531 A/C; S04466: Chr05_06010911 A/G; S04467: Chr05_06051401 G/A; S04468: Chr05_06126077 A/G; S04469: Chr05_06206488 T/C; S04470: Chr05_06275238 A/C; S04471: Chr05_06352583 T/C; S04472: Chr05_06432723 T/C; S04473: Chr05_06658730 T/G; S04474: Chr05_06730320 T/C; S04475: Chr05_06823448 A/G; S04476: Chr05_06833337 C/T; S04477: Chr05_06850859 T/A; S04478: Chr05_07038187 A/G; S04479: Chr05_07118032 A/G; S04480: Chr05_07198178 G/A; S04481:

Chr05_07237768 A/G; S04482: Chr05_07327393 C/T; S04483: Chr05_07403498 G/A; S04484: Chr05_07478549 C/T; S04485: Chr05_07639901 G/A; S04486: Chr05_07663474 G/C; S04487: Chr05_07677592 A/T; S04488: Chr05_07784857 C/T; S04489: Chr05_07810558 G/A; S04490: Chr05_07856405 C/T; S04491: Chr05_07879449 A/G; S04492: Chr05_08046486 T/G; S04493: Chr05_08215946 C/T; S04494: Chr05_08227583 T/A; S04495: Chr05_08320646 A/C; S04496: Chr05_08380180 A/G; S04497: Chr05_08413351 G/A; S04498: Chr05_08552858 C/A; S04499: Chr05_08703290 C/A; S04500: Chr05_08784416 C/T; S04501: Chr05_08850538 G/A; S04502: Chr05_08937657 T/C; S04503: Chr05_09075194 G/A; S04504: Chr05_09230748 C/T; S04505: Chr05_09306011 C/T; S04506: Chr05_09375832 G/A; S04507: Chr05_09454156 G/T; S04508: Chr05_09677994 G/A; S04509: Chr05_09750287 C/A; S04510: Chr05_09828221 C/T; S04511: Chr05_09950950 C/T; S04512: Chr05_09981599 A/T; S04513: Chr05_10053123 T/C; S04514: Chr05_10161902 A/G; S04515: Chr05_10226327 C/T; S04516: Chr05_10309039 A/G; S04517: Chr05_10381441 A/G; S04518: Chr05_10467846 T/C; S04519: Chr05_10543713 G/A; S04520: Chr05_10550647 G/A; S04521: Chr05_10626520 T/C; S04522: Chr05_10775619 C/T; S04523: Chr05_10850514 T/C; S04524: Chr05_10927067 T/C; S04525: Chr05_11006049 G/A; S04526: Chr05_11082581 A/G; S04527: Chr05_11151477 A/G; S04528: Chr05_11232982 G/T; S04529: Chr05_11320014 G/A; S04530: Chr05_11406908 C/T; S04531: Chr05_11679420 A/G; S04532: Chr05_11910963 G/A; S04533: Chr05_12070393 C/A; S04534: Chr05_12078377 T/C; S04535: Chr05_12652407 G/A; S04536: Chr05_12750070 G/T; S04537: Chr05_12849181 G/A; S04538: Chr05_12850545 G/A; S04539: Chr05_13088208 T/C; S04540: Chr05_13150021 T/C; S04541: Chr05_13315571 G/A; S04542: Chr05_13603345 A/C; S04543: Chr05_13685639 T/A; S04544: Chr05_13906822 C/G; S04545: Chr05_14050149 G/A; S04546: Chr05_14125350 G/A; S04547: Chr05_14429875 C/T; S04548: Chr05_14592668 T/C; S04549: Chr05_14875185 G/C; S04550: Chr05_15332888 T/G; S04551: Chr05_15404352 T/C; S04552: Chr05_15480600 A/G; S04553: Chr05_15642477 A/G; S04554: Chr05_15724051 C/T; S04555: Chr05_16077781 A/G; S04556: Chr05_16451874 T/A; S04557: Chr05_16529267 T/C; S04558: Chr05_17058970 C/T; S04559: Chr05_17208467 T/G; S04560: Chr05_17288898 G/A; S04561: Chr05_17429290 A/G; S04562: Chr05_17506173 C/T; S04563: Chr05_17735436 C/T; S04564: Chr05_17953870 G/A; S04565: Chr05_18110536 G/A; S04566: Chr05_18181942 C/T; S04567: Chr05_18702101 T/C; S04568: Chr05_18929941 T/C; S04569: Chr05_19248633 A/G; S04570: Chr05_19302857 G/A; S04571: Chr05_19386464 G/C; S04572: Chr05_19452429 C/T; S04573: Chr05_19686086 C/A; S04574: Chr05_19758558 C/T; S04575: Chr05_19827470 G/A; S04576: Chr05_19912621 C/T; S04577: Chr05_19978330 C/T; S04578: Chr05_20137134 A/G; S04579: Chr05_20273594 C/G; S04580: Chr05_20293404 C/T; S04581: Chr05_20301713 C/T;

S04582: Chr05_20621542 G/T; S04583: Chr05_20631179 G/A; S04584: Chr05_20703641 A/G; S04585: Chr05_20925786 A/G; S04586: Chr05_21234864 C/T; S04587: Chr05_21610100 A/G; S04588: Chr05_21751510 A/T; S04589: Chr05_21879882 T/C; S04590: Chr05_21901444 A/G; S04591: Chr05_22058564 A/G; S04592: Chr05_22132472 A/C; S04593: Chr05_22256126 C/T; S04594: Chr05_22500310 G/A; S04595: Chr05_22588713 A/G; S04596: Chr05_22705815 G/A; S04597: Chr05_22734785 G/A; S04598: Chr05_22958793 T/C; S04599: Chr05_23033304 C/A; S04600: Chr05_23176248 A/G; S04601: Chr05_23403704 T/C; S04602: Chr05_23529971 G/A; S04603: Chr05_23554153 A/G; S04604: Chr05_23630966 C/T; S04605: Chr05_23712499 A/G; S04606: Chr05_23779082 C/T; S04607: Chr05_23852322 C/T; S04608: Chr05_23925440 C/T; S04609: Chr05_24006769 T/A; S04610: Chr05_24232186 A/G; S04611: Chr05_24310746 A/G; S04612: Chr05_24544617 C/T; S04613: Chr05_24675661 A/T; S04614: Chr05_24751380 A/C; S04615: Chr05_24905880 A/G; S04616: Chr05_24990004 C/A; S04617: Chr05_25069027 T/C; S04618: Chr05_25351885 A/T; S04619: Chr05_25558259 A/G; S04620: Chr05_25583053 C/T; S04621: Chr05_25677478 T/C; S04622: Chr05_25750555 A/C; S04623: Chr05_25827606 A/T; S04624: Chr05_25975217 C/T; S04625: Chr05_26054778 T/A; S04626: Chr05_26153481 G/A; S04627: Chr05_26254893 A/G; S04628: Chr05_26354581 C/T; S04629: Chr05_26428725 T/C; S04630: Chr05_26577341 T/C; S04631: Chr05_26659689 G/A; S04632: Chr05_26741322 C/T; S04633: Chr05_26871834 A/C; S04634: Chr05_26897202 A/G; S04635: Chr05_26900195 G/C; S04636: Chr05_26992744 C/T; S04637: Chr05_27055313 A/T; S04638: Chr05_27082454 A/T; S04639: Chr05_27107327 G/A; S04640: Chr05_27128179 T/C; S04641: Chr05_27167484 C/T; S04642: Chr05_27184841 C/A; S04643: Chr05_27200056 A/G; S04644: Chr05_27290052 A/G; S04645: Chr05_27352879 G/A; S04646: Chr05_27611411 T/G; S04647: Chr05_27637698 T/A; S04648: Chr05_27658903 A/G; S04649: Chr05_27694369 A/T; S04650: Chr05_27708277 C/T; S04651: Chr05_27728032 T/A; S04652: Chr05_27752781 T/A; S04653: Chr05_27802865 G/A; S04654: Chr05_27877681 A/C; S04655: Chr05_27903879 C/T; S04656: Chr05_27927585 G/A; S04657: Chr05_28002461 A/G; S04658: Chr05_28025455 T/C; S04659: Chr05_28050943 G/T; S04660: Chr05_28138248 C/T; S04661: Chr05_28150604 C/G; S04662: Chr05_28300238 T/C; S04663: Chr05_28356380 T/C; S04664: Chr05_28385952 T/C; S04665: Chr05_28424704 T/G; S04666: Chr05_28425055 G/A; S04667: Chr05_28450023 T/A; S04668: Chr05_28535594 T/A; S04669: Chr05_28570815 A/G; S04670: Chr05_28577714 G/T; S04671: Chr05_28607782 G/A; S04672: Chr05_28625208 C/T; S04673: Chr05_28765460 A/G; S04674: Chr05_28776800 C/A; S04675: Chr05_28805428 G/C; S04676: Chr05_28829948 T/G; S04677: Chr05_28860381 T/C; S04678: Chr05_28875019 A/G; S04679: Chr05_28964066 A/G; S04680: Chr05_28985901 G/A; S04681: Chr05_29030745 A/T; S04682:

Chr05_29155250 T/G; S04683: Chr05_29182647 A/G; S04684: Chr05_29213311 G/A; S04685: Chr05_29265465 G/T; S04686: Chr05_29278149 G/T; S04687: Chr05_29402087 A/C; S04688: Chr05_29425896 C/T; S04689: Chr05_29513582 G/T; S04690: Chr05_29567385 A/T; S04691: Chr05_29611278 A/G; S04692: Chr05_29625287 T/G; S04693: Chr05_29729933 C/T; S04694: Chr05_29750275 A/G; S04695: Chr05_29775190 G/A; S04696: Chr05_29852709 G/A; S04697: Chr05_29889474 A/T; S04698: Chr05_29900000 G/A; S04699: Chr05_29980003 G/A; S04700: Chr05_30050530 G/C; S04701: Chr05_30186388 C/G; S04702: Chr05_30201810 A/C; S04703: Chr05_30305206 G/A; S04704: Chr05_30449912 C/T; S04705: Chr05_30509152 G/A; S04706: Chr05_30584144 C/T; S04707: Chr05_30655034 G/A; S04708: Chr05_30727861 G/A; S04709: Chr05_30812796 C/G; S04710: Chr05_30934033 A/T; S04711: Chr05_30962476 G/A; S04712: Chr05_30989882 C/A; S04713: Chr05_31108177 A/G; S04714: Chr05_31126124 C/A; S04715: Chr05_31164234 G/A; S04716: Chr05_31203470 G/A; S04717: Chr05_31235182 C/T; S04718: Chr05_31256689 A/T; S04719: Chr05_31278594 G/T; S04720: Chr05_31321892 C/T; S04721: Chr05_31325272 C/G; S04722: Chr05_31365575 T/C; S04723: Chr05_31384199 G/A; S04724: Chr05_31402552 G/C; S04725: Chr05_31429682 A/G; S04726: Chr05_31453659 A/T; S04727: Chr05_31475312 C/A; S04728: Chr05_31548041 A/T; S04729: Chr05_31563741 A/G; S04730: Chr05_31580487 A/G; S04731: Chr05_31601400 C/T; S04732: Chr05_31628393 A/T; S04733: Chr05_31658505 T/C; S04734: Chr05_31678681 A/G; S04735: Chr05_31712778 A/G; S04736: Chr05_31741630 T/G; S04737: Chr05_31756235 A/G; S04738: Chr05_31775728 A/G; S04739: Chr05_31800564 T/A; S04740: Chr05_31842390 A/C; S04741: Chr05_31850128 A/T; S04742: Chr05_31875974 C/T; S04743: Chr05_31927085 A/T; S04744: Chr05_31950317 G/C; S04745: Chr05_31986274 C/T; S04746: Chr05_32003690 T/G; S04747: Chr05_32025567 C/G; S04748: Chr05_32075424 C/T; S04749: Chr05_32106084 T/C; S04750: Chr05_32127005 C/T; S04751: Chr05_32150188 A/G; S04752: Chr05_32176403 T/A; S04753: Chr05_32291512 C/T; S04754: Chr05_32313730 A/T; S04755: Chr05_32328898 G/A; S04756: Chr05_32382011 G/T; S04757: Chr05_32401803 A/G; S04758: Chr05_32463831 G/A; S04759: Chr05_32500439 T/C; S04760: Chr05_32593081 C/G; S04761: Chr05_32611932 C/T; S04762: Chr05_32625538 T/C; S04763: Chr05_32660260 C/G; S04764: Chr05_32708943 T/C; S04765: Chr05_32729251 C/T; S04766: Chr05_32813954 C/T; S04767: Chr05_32825822 C/T; S04768: Chr05_32857267 T/A; S04769: Chr05_32876712 T/A; S04770: Chr05_32927498 A/C; S04771: Chr05_32950458 T/C; S04772: Chr05_32989487 T/C; S04773: Chr05_33002251 G/A; S04774: Chr05_33027200 T/A; S04775: Chr05_33054818 T/A; S04776: Chr05_33075008 T/C; S04777: Chr05_33135555 C/T; S04778: Chr05_33173656 T/C; S04779: Chr05_33186319 A/G; S04780: Chr05_33216054 C/T; S04781: Chr05_33229042 G/T; S04782: Chr05_33257198 G/A; S04783: Chr05_33285068 T/C; S04784: Chr05_33323893 T/C; S04785: Chr05_33325105 C/T; S04786: Chr05_33359743 G/A; S04787: Chr05_33376715 C/T; S04788: Chr05_33422406 G/T; S04789: Chr05_33438894 G/T; S04790: Chr05_33468570 A/T; S04791: Chr05_33479307 T/A; S04792: Chr05_33512311 G/T; S04793: Chr05_33525340 G/T; S04794: Chr05_33561622 G/T; S04795: Chr05_33577553 G/A; S04796: Chr05_33630915 A/G; S04797: Chr05_33662474 G/A; S04798: Chr05_33727311 A/C; S04799: Chr05_33844667 A/G; S04800: Chr05_33852440 T/C; S04801: Chr05_33893210 C/A; S04802: Chr05_33920665 A/C; S04803: Chr05_33926353 T/C; S04804: Chr05_33953345 C/T; S04805: Chr05_33978681 T/A; S04806: Chr05_34000026 G/A; S04807: Chr05_34025706 G/A; S04808: Chr05_34063554 C/T; S04809: Chr05_34110946 A/G; S04810: Chr05_34141257 G/A; S04811: Chr05_34187667 T/C; S04812: Chr05_34202168 A/C; S04813: Chr05_34231673 C/T; S04814: Chr05_34291992 C/T; S04815: Chr05_34329856 T/A; S04816: Chr05_34351206 C/G; S04817: Chr05_34377218 G/A; S04818: Chr05_34408599 T/C; S04819: Chr05_34436459 C/T; S04820: Chr05_34458367 C/G; S04821: Chr05_34477111 G/A; S04822: Chr05_34519869 G/A; S04823: Chr05_34539965 C/T; S04824: Chr05_34563715 G/C; S04825: Chr05_34589911 T/C; S04826: Chr05_34618963 T/C; S04827: Chr05_34635952 G/A; S04828: Chr05_34655847 T/A; S04829: Chr05_34683729 C/T; S04830: Chr05_34700023 A/T; S04831: Chr05_34728441 C/G; S04832: Chr05_34765686 C/T; S04833: Chr05_34785485 A/C; S04834: Chr05_34809039 G/A; S04835: Chr05_34828078 G/T; S04836: Chr05_34851012 G/T; S04837: Chr05_34875607 T/A; S04838: Chr05_34904125 C/T; S04839: Chr05_34929210 T/C; S04840: Chr05_34955082 G/C; S04841: Chr05_34977447 C/T; S04842: Chr05_35002639 T/C; S04843: Chr05_35032946 C/G; S04844: Chr05_35063128 G/C; S04845: Chr05_35086101 C/T; S04846: Chr05_35110713 A/T; S04847: Chr05_35128563 A/T; S04848: Chr05_35154022 T/C; S04849: Chr05_35176081 A/G; S04850: Chr05_35250550 A/C; S04851: Chr05_35283498 T/G; S04852: Chr05_35303156 C/T; S04853: Chr05_35325544 T/A; S04854: Chr05_35350881 T/C; S04855: Chr05_35375296 T/G; S04856: Chr05_35406649 G/A; S04857: Chr05_35458763 A/C; S04858: Chr05_35478909 A/T; S04859: Chr05_35500987 C/T; S04860: Chr05_35526062 A/T; S04861: Chr05_35551637 T/A; S04862: Chr05_35580527 T/C; S04863: Chr05_35612803 G/A; S04864: Chr05_35626345 G/A; S04865: Chr05_35653092 T/C; S04866: Chr05_35675029 C/A; S04867: Chr05_35714405 A/G; S04868: Chr05_35737861 C/A; S04869: Chr05_35767006 A/T; S04870: Chr05_35778664 A/T; S04871: Chr05_35800521 T/G; S04872: Chr05_35832768 T/G; S04873: Chr05_35863818 C/G; S04874: Chr05_35881224 A/G; S04875: Chr05_35904850 C/T; S04876: Chr05_35925254 C/T; S04877: Chr05_35960704 A/T; S04878: Chr05_35996170 T/G; S04879: Chr05_36006824 G/A; S04880: Chr05_36043172 G/T; S04881: Chr05_36062464 G/A; S04882: Chr05_36108741 T/C; S04883:

Chr05_36130315 A/T; S04884: Chr05_36150115 C/T; S04885: Chr05_36188922 G/C; S04886: Chr05_36200612 C/A; S04887: Chr05_36258726 G/C; S04888: Chr05_36275125 G/T; S04889: Chr05_36301282 T/C; S04890: Chr05_36327288 A/G; S04891: Chr05_36371924 C/T; S04892: Chr05_36379413 G/C; S04893: Chr05_36413081 A/G; S04894: Chr05_36425647 T/G; S04895: Chr05_36503023 C/T; S04896: Chr05_36525124 C/T; S04897: Chr05_36585315 C/T; S04898: Chr05_36618895 T/C; S04899: Chr05_36626182 T/C; S04900: Chr05_36652668 C/T; S04901: Chr05_36675113 C/T; S04902: Chr05_36703586 A/C; S04903: Chr05_36725068 G/C; S04904: Chr05_36768890 C/T; S04905: Chr05_36808143 A/G; S04906: Chr05_36826270 C/G; S04907: Chr05_36852724 T/C; S04908: Chr05_36885618 G/C; S04909: Chr05_36902012 A/G; S04910: Chr05_36938897 C/T; S04911: Chr05_36951563 T/C; S04912: Chr05_36978072 C/T; S04913: Chr05_37004641 A/C; S04914: Chr05_37032954 G/C; S04915: Chr05_37050946 A/C; S04916: Chr05_37075852 T/C; S04917: Chr05_37100163 A/T; S04918: Chr05_37133483 A/C; S04919: Chr05_37156964 C/T; S04920: Chr05_37177049 A/G; S04921: Chr05_37204086 T/C; S04922: Chr05_37233051 T/C; S04923: Chr05_37251796 C/T; S04924: Chr05_37275359 C/T; S04925: Chr05_37308482 G/A; S04926: Chr05_37325007 A/G; S04927: Chr05_37351265 G/A; S04928: Chr05_37375076 G/T; S04929: Chr05_37414974 C/A; S04930: Chr05_37437023 C/T; S04931: Chr05_37486454 A/G; S04932: Chr05_37500397 C/A; S04933: Chr05_37527633 T/C; S04934: Chr05_37557447 C/G; S04935: Chr05_37580263 T/G; S04936: Chr05_37602253 G/A; S04937: Chr05_37653121 C/T; S04938: Chr05_37677335 C/T; S04939: Chr05_37700114 G/T; S04940: Chr05_37737672 C/G; S04941: Chr05_37752676 C/G; S04942: Chr05_37794902 T/C; S04943: Chr05_37807589 C/T; S04944: Chr05_37827649 C/G; S04945: Chr05_37873188 T/C; S04946: Chr05_37879985 T/G; S04947: Chr05_37900941 C/T; S04948: Chr05_37928222 T/G; S04949: Chr05_37952922 C/T; S04950: Chr05_37983944 C/G; S04951: Chr05_38002803 C/G; S04952: Chr05_38027056 A/T; S04953: Chr05_38063211 C/T; S04954: Chr05_38076147 A/G; S04955: Chr05_38103476 C/T; S04956: Chr05_38131027 G/T; S04957: Chr05_38159403 G/C; S04958: Chr05_38176866 C/G; S04959: Chr05_38211371 C/T; S04960: Chr05_38240988 G/C; S04961: Chr05_38253929 A/G; S04962: Chr05_38276191 G/A; S04963: Chr05_38303728 A/G; S04964: Chr05_38325944 G/C; S04965: Chr05_38371806 G/A; S04966: Chr05_38376405 C/A; S04967: Chr05_38413745 T/C; S04968: Chr05_38425854 G/A; S04969: Chr05_38463608 G/C; S04970: Chr05_38503919 T/C; S04971: Chr05_38531878 G/C; S04972: Chr05_38573344 A/G; S04973: Chr05_38576297 C/T; S04974: Chr05_38613119 A/G; S04975: Chr05_38647010 C/A; S04976: Chr05_38682782 T/C; S04977: Chr05_38716654 C/T; S04978: Chr05_38738345 A/G; S04979: Chr05_38753737 T/G; S04980: Chr05_38776491 G/C; S04981: Chr05_38801909 C/G; S04982: Chr05_38851166 T/A; S04983: Chr05_38876287 C/T; S04984: Chr05_38918842 G/A; S04985: Chr05_38925468 A/G; S04986: Chr05_38950282 C/G; S04987: Chr05_38978246 G/A; S04988: Chr05_39002106 G/C; S04989: Chr05_39025546 A/T; S04990: Chr05_39050149 T/C; S04991: Chr05_39082477 A/C; S04992: Chr05_39103534 C/G; S04993: Chr05_39132561 A/G; S04994: Chr05_39151100 C/A; S04995: Chr05_39177730 A/T; S04996: Chr05_39207458 A/C; S04997: Chr05_39236266 T/C; S04998: Chr05_39259175 G/T; S04999: Chr05_39283464 G/C; S05000: Chr05_39300926 A/G; S05001: Chr05_39328136 C/G; S05002: Chr05_39351508 C/G; S05003: Chr05_39379438 A/T; S05004: Chr05_39400826 A/T; S05005: Chr05_39431910 A/G; S05006: Chr05_39459721 T/C; S05007: Chr05_39479733 G/A; S05008: Chr05_39512317 C/T; S05009: Chr05_39525975 C/A; S05010: Chr05_39554094 A/C; S05011: Chr05_39577818 C/A; S05012: Chr05_39604331 C/T; S05013: Chr05_39631574 A/T; S05014: Chr05_39677974 T/C; S05015: Chr05_39705287 C/A; S05016: Chr05_39735401 T/C; S05017: Chr05_39754206 C/T; S05018: Chr05_39788521 C/T; S05019: Chr05_39802393 G/T; S05020: Chr05_39825204 A/C; S05021: Chr05_39853057 G/T; S05022: Chr05_39878522 G/A; S05023: Chr05_39900025 C/T; S05024: Chr05_39931972 C/T; S05025: Chr05_39952692 T/A; S05026: Chr05_39981196 C/T; S05027: Chr05_40019733 C/G; S05028: Chr05_40035311 A/T; S05029: Chr05_40051231 C/T; S05030: Chr05_40075652 T/C; S05031: Chr05_40103927 G/A; S05032: Chr05_40147705 G/C; S05033: Chr05_40153989 G/T; S05034: Chr05_40175831 C/T; S05035: Chr05_40209793 A/G; S05036: Chr05_40232854 T/A; S05037: Chr05_40259517 G/C; S05038: Chr05_40279242 G/C; S05039: Chr05_40301194 G/A; S05040: Chr05_40326384 T/C; S05041: Chr05_40352046 C/A; S05042: Chr05_40377846 A/T; S05043: Chr05_40400283 A/T; S05044: Chr05_40433784 A/G; S05045: Chr05_40458413 G/A; S05046: Chr05_40476259 G/A; S05047: Chr05_40502528 G/C; S05048: Chr05_40542212 G/A: S05049: Chr05_40555155 G/C; S05050: Chr05_40575091 A/T; S05051: Chr05_40632858 G/A; S05052: Chr05_40663600 A/G; S05053: Chr05_40678064 G/A; S05054: Chr05_40712109 G/T; S05055: Chr05_40735855 A/G; S05056: Chr05_40750218 T/C; S05057: Chr05_40775318 C/T; S05058: Chr05_40800762 C/G; S05059: Chr05_40825147 G/A; S05060: Chr05_40852815 G/A; S05061: Chr05_40887544 A/T; S05062: Chr05_40900878 C/G; S05063: Chr05_40925229 T/C; S05064: Chr05_40960402 C/T; S05065: Chr05_40999995 A/T; S05066: Chr05_41002052 C/T; S05067: Chr05_41025065 A/G; S05068: Chr05_41056100 A/G; S05069: Chr05_41088440 G/T; S05070: Chr05_41100620 G/A; S05071: Chr05_41126529 G/C; S05072: Chr05_41165218 A/G; S05073: Chr05_41175611 C/T; S05074: Chr05_41213590 A/G; S05075: Chr05_41231598 C/T; S05076: Chr05_41254151 G/A; S05077: Chr05_41278787 T/G; S05078: Chr05_41301894 G/C; S05079: Chr05_41330573 A/G; S05080: Chr05_41360321 T/C; S05081: Chr05_41384000 T/C; S05082: Chr05_41402038 G/A; S05083: Chr05_41436677 T/G; S05084:

Chr05_41452307 G/A; S05085: Chr05_41484954 A/G; S05086: Chr05_41500302 A/G; S05087: Chr05_41535966 T/C; S05088: Chr05_41550014 G/A; S05089: Chr05_41586392 A/G; S05090: Chr05_41612855 T/A; S05091: Chr05_41626230 C/T; S05092: Chr05_41702646 G/A; S05093: Chr05_41738018 T/C; S05094: Chr05_41750076 T/A; S05095: Chr05_41777763 A/C; S05096: Chr05_41807289 A/C; S05097: Chr05_41827957 T/C; S05098: Chr05_41853265 G/A; S05099: Chr05_41876563 C/T; S05100: Chr05_41912828 T/C; S05101: Chr05_41926765 A/G; S05102: Chr05_41984546 A/G; S05103: Chr05_42019019 G/T; S05104: Chr05_42058688 C/A; S05105: Chr05_42090637 C/G; S05106: Chr05_42116847 G/A; S05107: Chr05_42186608 T/C; S05108: Chr05_42233705 A/G; S05109: Chr06_00019074 G/T; S05110: Chr06_00048114 T/A; S05111: Chr06_00074139 A/G; S05112: Chr06_00093660 C/T; S05113: Chr06_00109808 A/G; S05114: Chr06_00138106 C/G; S05115: Chr06_00150690 A/G; S05116: Chr06_00191524 C/T; S05117: Chr06_00203440 G/T; S05118: Chr06_00225240 T/A; S05119: Chr06_00257626 C/G; S05120: Chr06_00279422 T/G; S05121: Chr06_00318048 T/G; S05122: Chr06_00330666 C/T; S05123: Chr06_00381641 T/C; S05124: Chr06_00404788 C/T; S05125: Chr06_00432211 G/A; S05126: Chr06_00452705 A/G; S05127: Chr06_00476575 G/A; S05128: Chr06_00500052 C/A; S05129: Chr06_00526813 T/C; S05130: Chr06_00562136 T/C; S05131: Chr06_00593504 C/T; S05132: Chr06_00603885 C/G; S05133: Chr06_00634977 G/T; S05134: Chr06_00650709 T/C; S05135: Chr06_00675014 C/T; S05136: Chr06_00709362 C/T; S05137: Chr06_00731361 T/A; S05138: Chr06_00751998 C/T; S05139: Chr06_00801327 A/T; S05140: Chr06_00828502 A/G; S05141: Chr06_00850694 C/T; S05142: Chr06_00875297 C/T; S05143: Chr06_00902346 C/A; S05144: Chr06_00928245 G/A; S05145: Chr06_00970242 T/C; S05146: Chr06_00976127 A/G; S05147: Chr06_01009336 T/C; S05148: Chr06_01025155 T/C; S05149: Chr06_01052684 A/G; S05150: Chr06_01078386 C/T; S05151: Chr06_01103138 G/A; S05152: Chr06_01129202 C/A; S05153: Chr06_01150126 A/T; S05154: Chr06_01193990 G/T; S05155: Chr06_01203733 A/G; S05156: Chr06_01230529 C/T; S05157: Chr06_01260234 T/C; S05158: Chr06_01280468 C/T; S05159: Chr06_01303128 A/C; S05160: Chr06_01330490 G/T; S05161: Chr06_01353416 G/A; S05162: Chr06_01385091 C/T; S05163: Chr06_01404953 C/T; S05164: Chr06_01443698 G/C; S05165: Chr06_01451868 C/T; S05166: Chr06_01475861 G/A; S05167: Chr06_01500182 C/T; S05168: Chr06_01532614 C/T; S05169: Chr06_01554080 C/G; S05170: Chr06_01578794 G/C; S05171: Chr06_01617930 T/G; S05172: Chr06_01627366 C/T; S05173: Chr06_01673727 T/G; S05174: Chr06_01678912 T/A; S05175: Chr06_01756279 A/C; S05176: Chr06_01780193 A/C; S05177: Chr06_01809855 C/A; S05178: Chr06_01828468 G/A; S05179: Chr06_01850177 G/A; S05180: Chr06_01948936 C/A; S05181: Chr06_01959954 G/A; S05182: Chr06_91977842 A/T; S05183: Chr06_02080379 T/G; S05184: Chr06_02100577 T/C;

S05185: Chr06_02158432 G/C; S05186: Chr06_02175064 A/T; S05187: Chr06_02262891 T/C; S05188: Chr06_02333551 C/T; S05189: Chr06_02358960 A/T; S05190: Chr06_02481568 C/A; S05191: Chr06_02503419 T/C; S05192: Chr06_02526376 T/A; S05193: Chr06_02551517 T/G; S05194: Chr06_02577457 C/T; S05195: Chr06_02604226 G/C; S05196: Chr06_02636926 T/C; S05197: Chr06_02650044 C/T; S05198: Chr06_02678061 C/T; S05199: Chr06_02714420 G/A; S05200: Chr06_02725187 G/C; S05201: Chr06_02772954 G/A; S05202: Chr06_02778790 C/T; S05203: Chr06_02851250 A/G; S05204: Chr06_02903709 C/T; S05205: Chr06_02925179 T/A; S05206: Chr06_02952199 C/A; S05207: Chr06_02986499 C/A; S05208: Chr06_03001711 C/T; S05209: Chr06_03025776 C/T; S05210: Chr06_03055022 A/G; S05211: Chr06_03085367 T/C; S05212: Chr06_03109449 A/G; S05213: Chr06_03132988 T/A; S05214: Chr06_03150859 T/C; S05215: Chr06_03179722 T/G; S05216: Chr06_03214790 G/A; S05217: Chr06_03226536 A/C; S05218: Chr06_03264626 T/G; S05219: Chr06_03286909 C/T; S05220: Chr06_03315550 A/G; S05221: Chr06_03325111 T/A; S05222: Chr06_03353659 G/A; S05223: Chr06_03375231 T/G; S05224: Chr06_03403481 C/T; S05225: Chr06_03430462 T/A; S05226: Chr06_03453914 C/T; S05227: Chr06_03475035 A/G; S05228: Chr06_03510973 C/T; S05229: Chr06_03525384 T/G; S05230: Chr06_03565789 A/G; S05231: Chr06_03588330 T/C; S05232: Chr06_03603322 C/T; S05233: Chr06_03629797 G/A; S05234: Chr06_03664310 C/T; S05235: Chr06_03679994 C/T; S05236: Chr06_03709181 A/T; S05237: Chr06_03735481 T/C; S05238: Chr06_03772035 G/T; S05239: Chr06_03786244 G/C; S05240: Chr06_03805578 G/A; S05241: Chr06_03833610 A/T; S05242: Chr06_03865212 G/A; S05243: Chr06_03894475 G/C; S05244: Chr06_03989711 T/A; S05245: Chr06_04000044 C/T; S05246: Chr06_04134589 A/T; S05247: Chr06_04157597 G/A; S05248: Chr06_04187283 A/C; S05249: Chr06_04241219 G/A; S05250: Chr06_04298131 C/T; S05251: Chr06_04319355 C/T; S05252: Chr06_34334059 T/C; S05253: Chr06_04351486 G/A; S05254: Chr06_04377598 T/C; S05255: Chr06_04400562 G/C; S05256: Chr06_04425096 A/G; S05257: Chr06_04450232 T/C; S05258: Chr06_04544520 C/T; S05259: Chr06_04554132 C/T; S05260: Chr06_04580363 C/G; S05261: Chr06_04600186 G/A; S05262: Chr06_04649188 T/C; S05263: Chr06_04651121 G/A; S05264: Chr06_04677628 G/A; S05265: Chr06_04701496 T/A; S05266: Chr06_04777730 G/A; S05267: Chr06_04801511 T/C; S05268: Chr06_04826081 A/G; S05269: Chr06_04856687 A/C; S05270: Chr06_04889959 C/G; S05271: Chr06_04900070 G/A; S05272: Chr06_05040311 T/G; S05273: Chr06_05061040 C/T; S05274: Chr06_05084047 G/A; S05275: Chr06_05117063 A/G; S05276: Chr06_05125205 T/G; S05277: Chr06_05158703 G/A; S05278: Chr06_05177471 T/G; S05279: Chr06_05214248 T/C; S05280: Chr06_05229748 G/A; S05281: Chr06_05259344 A/G; S05282: Chr06_05283310 T/G; S05283: Chr06_05333040 A/G; S05284: Chr06_05362707 G/A; S05285:

Chr06_05381785 A/C; S05286: Chr06_05400582 T/C; S05287: Chr06_05425436 A/G; S05288: Chr06_05453753 T/C; S05289: Chr06_05549522 G/A; S05290: Chr06_05598412 T/C; S05291: Chr06_05606322 A/G; S05292: Chr06_05631221 A/G; S05293: Chr06_05680299 C/T; S05294: Chr06_05702098 G/A; S05295: Chr06_05766823 T/C; S05296: Chr06_05795046 G/A; S05297: Chr06_05800163 A/G; S05298: Chr06_05825918 T/G; S05299: Chr06_05853240 C/T; S05300: Chr06_05879284 G/T; S05301: Chr06_05902370 A/G; S05302: Chr06_05940354 G/C; S05303: Chr06_05951713 C/T; S05304: Chr06_05975521 A/C; S05305: Chr06_06036370 T/A; S05306: Chr06_06069381 G/A; S05307: Chr06_06078531 A/G; S05308: Chr06_06100733 A/C; S05309: Chr06_06134887 C/A; S05310: Chr06_06180013 A/G; S05311: Chr06_06202607 A/T; S05312: Chr06_06276968 G/A; S05313: Chr06_06321130 T/G; S05314: Chr06_06375053 T/C; S05315: Chr06_06400599 A/G; S05316: Chr06_06437316 T/C; S05317: Chr06_06466256 C/T; S05318: Chr06_06479162 A/T; S05319: Chr06_06500187 C/T; S05320: Chr06_06525169 G/A; S05321: Chr06_06555441 G/T; S05322: Chr06_06614307 C/T; S05323: Chr06_06632769 C/T; S05324: Chr06_06671220 T/C; S05325: Chr06_06688993 A/G; S05326: Chr06_06712017 G/C; S05327: Chr06_06734240 A/G; S05328: Chr06_06751407 C/T; S05329: Chr06_06790395 G/T; S05330: Chr06_06801037 C/T; S05331: Chr06_06825965 A/C; S05332: Chr06_06851835 T/A; S05333: Chr06_06875329 G/A; S05334: Chr06_06903296 C/T; S05335: Chr06_06958945 C/T; S05336: Chr06_06989576 A/G; S05337: Chr06_07006724 G/A; S05338: Chr06_07025567 T/C; S05339: Chr06_07051004 G/T; S05340: Chr06_07078527 A/G; S05341: Chr06_07103068 G/C; S05342: Chr06_07176781 A/G; S05343: Chr06_07200617 A/T; S05344: Chr06_07294477 T/C; S05345: Chr06_07305514 T/C; S05346: Chr06_07329187 T/G; S05347: Chr06_07354533 A/T; S05348: Chr06_07420490 A/C; S05349: Chr06_07469403 G/A; S05350: Chr06_07529058 G/A; S05351: Chr06_07550049 T/C; S05352: Chr06_07596671 A/C; S05353: Chr06_07686038 G/A; S05354: Chr06_07703276 A/G; S05355: Chr06_07738183 T/C; S05356: Chr06_07765820 G/A; S05357: Chr06_07783479 A/G; S05358: Chr06_07802387 T/A; S05359: Chr06_07825328 C/T; S05360: Chr06_07851267 C/T; S05361: Chr06_07877820 G/T; S05362: Chr06_07900374 G/A; S05363: Chr06_07951010 A/C; S05364: Chr06_07979076 T/G; S05365: Chr06_08010095 T/C; S05366: Chr06_08030288 G/A; S05367: Chr06_08053711 T/G; S05368: Chr06_08075462 G/T; S05369: Chr06_08100716 T/C; S05370: Chr06_08169261 A/G; S05371: Chr06_08176617 C/G; S05372: Chr06_08221934 C/T; S05373: Chr06_08237000 A/G; S05374: Chr06_08254974 G/C; S05375: Chr06_08310531 T/C; S05376: Chr06_08325839 A/T; S05377: Chr06_08409921 T/A; S05378: Chr06_08428438 C/T; S05379: Chr06_08454617 G/A; S05380: Chr06_08476105 G/A; S05381: Chr06_08500734 G/A; S05382: Chr06_08541078 T/C; S05383: Chr06_08595570 G/T; S05384: Chr06_08643225 T/A; S05385: Chr06_08687928 G/A; S05386: Chr06_08787044 C/A; S05387: Chr06_08809788 T/C; S05388: Chr06_08827357 G/A; S05389: Chr06_08871757 G/C; S05390: Chr06_08881834 A/G; S05391: Chr06_08901225 A/T; S05392: Chr06_08945772 A/T; S05393: Chr06_08956544 G/A; S05394: Chr06_08975824 T/A; S05395: Chr06_09000876 A/C; S05396: Chr06_09032958 G/A; S05397: Chr06_09052641 A/G; S05398: Chr06_09079105 C/T; S05399: Chr06_09104609 T/G; S05400: Chr06_09125060 A/G; S05401: Chr06_09157263 T/C; S05402: Chr06_09176350 C/T; S05403: Chr06_09201049 C/T; S05404: Chr06_09225812 A/G; S05405: Chr06_09251099 A/G; S05406: Chr06_09282894 G/A; S05407: Chr06_09300796 G/T; S05408: Chr06_09326825 C/T; S05409: Chr06_09350977 T/C; S05410: Chr06_09456904 G/T; S05411: Chr06_09562630 T/C; S05412: Chr06_09576998 T/C; S05413: Chr06_09616717 G/C; S05414: Chr06_09632469 T/C; S05415: Chr06_09712989 G/C; S05416: Chr06_09789267 G/C; S05417: Chr06_09886433 A/G; S05418: Chr06_09938533 C/T; S05419: Chr06_09960045 C/T; S05420: Chr06_10031982 C/A; S05421: Chr06_10050946 C/T; S05422: Chr06_10139236 T/C; S05423: Chr06_10211244 C/T; S05424: Chr06_10225001 T/A; S05425: Chr06_10303886 C/T; S05426: Chr06_10383778 G/A; S05427: Chr06_10409402 A/G; S05428: Chr06_10505562 T/A; S05429: Chr06_10565163 C/G; S05430: Chr06_10602080 C/G; S05431: Chr06_10632813 A/T; S05432: Chr06_10655999 G/C; S05433: Chr06_10685431 A/C; S05434: Chr06_10734711 C/T; S05435: Chr06_10751412 T/A; S05436: Chr06_10852720 A/G; S05437: Chr06_10877517 C/T; S05438: Chr06_10901582 G/A; S05439: Chr06_10935342 T/C; S05440: Chr06_10957150 T/A; S05441: Chr06_10988551 C/T; S05442: Chr06_11002280 G/A; S05443: Chr06_11029572 C/G; S05444: Chr06_11075142 T/C; S05445: Chr06_11126366 G/C; S05446: Chr06_11153460 G/C; S05447: Chr06_11175922 T/C; S05448: Chr06_11216844 A/G; S05449: Chr06_11240356 C/T; S05450: Chr06_11250802 T/C; S05451: Chr06_11275320 G/A; S05452: Chr06_11302872 G/T; S05453: Chr06_11328531 T/C; S05454: Chr06_11364909 T/C; S05455: Chr06_11375459 T/A; S05456: Chr06_11402477 C/T; S05457: Chr06_11439628 T/A; S05458: Chr06_11470469 G/A; S05459: Chr06_11503396 C/A; S05460: Chr06_11525246 C/A; S05461: Chr06_11652544 G/A; S05462: Chr06_11679077 T/A; S05463: Chr06_11702062 A/T; S05464: Chr06_11726799 G/T; S05465: Chr06_11812926 G/T; S05466: Chr06_11851152 A/C; S05467: Chr06_11878270 G/C; S05468: Chr06_11932555 G/A; S05469: Chr06_11951443 G/T; S05470: Chr06_11976726 T/C; S05471: Chr06_12053115 C/T; S05472: Chr06_12146173 G/A; S05473: Chr06_12157998 C/T; S05474: Chr06_12185351 G/C; S05475: Chr06_12205988 T/C; S05476: Chr06_12232760 G/A; S05477: Chr06_12283364 C/T; S05478: Chr06_12304360 T/G; S05479: Chr06_12360846 A/G; S05480: Chr06_12381008 A/T; S05481: Chr06_12410678 T/C; S05482: Chr06_12425353 C/T; S05483: Chr06_12450074 C/G; S05484: Chr06_12480464 T/C; S05485: Chr06_12519669 C/T; S05486:

Chr06_12525745 A/G; S05487: Chr06_12555111 T/C; S05488: Chr06_12575606 G/A; S05489: Chr06_12600363 A/C; S05490: Chr06_12635456 G/A; S05491: Chr06_12765451 A/G; S05492: Chr06_12784181 G/A; S05493: Chr06_12923084 A/T; S05494: Chr06_12937960 A/C; S05495: Chr06_12977788 T/C; S05496: Chr06_13003203 C/T; S05497: Chr06_13029242 G/T; S05498: Chr06_13093038 G/T; S05499: Chr06_13105258 A/T; S05500: Chr06_13127505 A/G; S05501: Chr06_13151489 G/A; S05502: Chr06_13175906 A/G; S05503: Chr06_13202926 A/G; S05504: Chr06_13231992 C/G; S05505: Chr06_13267654 A/G; S05506: Chr06_13280278 T/C; S05507: Chr06_13308460 A/T; S05508: Chr06_13329119 C/T; S05509: Chr06_13356169 A/T; S05510: Chr06_13378329 C/T; S05511: Chr06_13412419 A/T; S05512: Chr06_13432800 C/A; S05513: Chr06_13455439 A/C; S05514: Chr06_13481784 T/G; S05515: Chr06_13535265 C/G; S05516: Chr06_13558126 T/C; S05517: Chr06_13578554 C/A; S05518: Chr06_13606920 G/C; S05519: Chr06_13625975 T/C; S05520: Chr06_13672550 G/T; S05521: Chr06_13677844 T/C; S05522: Chr06_13700633 T/C; S05523: Chr06_13731044 T/C; S05524: Chr06_13751087 C/G; S05525: Chr06_13780690 T/A; S05526: Chr06_13803027 C/T; S05527: Chr06_13825006 A/G; S05528: Chr06_13850643 C/T; S05529: Chr06_13888424 A/C; S05530: Chr06_13906051 A/G; S05531: Chr06_13925452 T/C; S05532: Chr06_13958683 G/A; S05533: Chr06_14016121 C/A; S05534: Chr06_14033230 G/A; S05535: Chr06_14058279 G/T; S05536: Chr06_14101847 C/G; S05537: Chr06_14125130 G/A; S05538: Chr06_14155432 A/G; S05539: Chr06_14184751 C/T; S05540: Chr06_14243357 A/C; S05541: Chr06_14269400 G/T; S05542: Chr06_14276793 C/A; S05543: Chr06_14302825 C/A; S05544: Chr06_14325920 G/T; S05545: Chr06_14353258 G/A; S05546: Chr06_14402075 G/A; S05547: Chr06_14430560 A/G; S05548: Chr06_14468235 G/T; S05549: Chr06_14510740 C/T; S05550: Chr06_14526570 C/A; S05551: Chr06_14555400 C/T; S05552: Chr06_14584400 G/C; S05553: Chr06_14643520 G/A; S05554: Chr06_14657221 C/G; S05555: Chr06_14691651 G/A; S05556: Chr06_14712033 A/G; S05557: Chr06_14730541 T/C; S05558: Chr06_14771625 T/C; S05559: Chr06_14787304 T/A; S05560: Chr06_14818780 C/T; S05561: Chr06_14828870 T/G; S05562: Chr06_14871168 G/C; S05563: Chr06_14886441 T/C; S05564: Chr06_14901754 T/A; S05565: Chr06_14925159 C/G; S05566: Chr06_14961997 T/C; S05567: Chr06_14996182 T/A; S05568: Chr06_15015786 C/T; S05569: Chr06_15034972 G/A; S05570: Chr06_15050703 T/C; S05571: Chr06_15085147 T/A; S05572: Chr06_15109352 C/T; S05573: Chr06_15132070 C/G; S05574: Chr06_15164880 A/T; S05575: Chr06_15202835 G/A; S05576: Chr06_15231313 G/T; S05577: Chr06_15251974 A/C; S05578: Chr06_15275129 C/T; S05579: Chr06_15310130 C/A; S05580: Chr06_15326660 G/A; S05581: Chr06_15403340 C/T; S05582: Chr06_15492183 G/A; S05583: Chr06_15507866 A/G; S05584: Chr06_15525810 G/C; S05585: Chr06_15551665 C/T; S05586: Chr06_15581879 G/A; S05587: Chr06_15600922 G/A; S05588: Chr06_15643320 G/T; S05589: Chr06_15655528 G/A; S05590: Chr06_15681367 T/G; S05591: Chr06_15706603 T/C; S05592: Chr06_15756234 G/A; S05593: Chr06_15781134 C/T; S05594: Chr06_15829345 C/T; S05595: Chr06_15855130 G/A; S05596: Chr06_15904741 A/G; S05597: Chr06_15940062 T/C; S05598: Chr06_15968336 A/C; S05599: Chr06_15984245 G/A; S05600: Chr06_16011956 G/A; S05601: Chr06_16053105 G/C; S05602: Chr06_16081041 G/T; S05603: Chr06_16109700 C/A; S05604: Chr06_16128371 C/T; S05605: Chr06_16179965 A/C; S05606: Chr06_16202936 G/A; S05607: Chr06_16229672 C/G; S05608: Chr06_16257099 T/C; S05609: Chr06_16280647 T/C; S05610: Chr06_16310170 A/C; S05611: Chr06_16336380 G/A; S05612: Chr06_16357533 C/T; S05613: Chr06_16392200 G/A; S05614: Chr06_16400275 C/G; S05615: Chr06_16428664 T/C; S05616: Chr06_16450977 C/T; S05617: Chr06_16497995 C/T; S05618: Chr06_16506243 A/G; S05619: Chr06_16576391 G/C; S05620: Chr06_16635273 A/C; S05621: Chr06_16675861 A/T; S05622: Chr06_16704557 G/A; S05623: Chr06_16732606 A/G; S05624: Chr06_16770536 A/T; S05625: Chr06_16775800 C/A; S05626: Chr06_16812084 T/C; S05627: Chr06_16825044 G/A; S05628: Chr06_16853246 C/T; S05629: Chr06_16875657 T/C; S05630: Chr06_16956874 A/G; S05631: Chr06_16981860 C/G; S05632: Chr06_17060857 T/C; S05633: Chr06_17124812 A/G; S05634: Chr06_17125245 C/T; S05635: Chr06_17154269 G/A; S05636: Chr06_17175049 T/C; S05637: Chr06_17279302 G/A; S05638: Chr06_17313267 G/T; S05639: Chr06_17382650 T/C; S05640: Chr06_17425051 C/T; S05641: Chr06_17482009 A/G; S05642: Chr06_17500025 C/T; S05643: Chr06_17582094 G/A; S05644: Chr06_17602402 T/C; S05645: Chr06_17626369 T/A; S05646: Chr06_17690558 A/T; S05647: Chr06_17728900 A/G; S05648: Chr06_17771245 C/T; S05649: Chr06_17812012 G/T; S05650: Chr06_17825257 C/T; S05651: Chr06_17905233 A/G; S05652: Chr06_17937700 A/G; S05653: Chr06_17958233 C/G; S05654: Chr06_17991369 A/G; S05655: Chr06_18000674 C/G; S05656: Chr06_18025091 A/G; S05657: Chr06_18056527 A/G; S05658: Chr06_18266160 A/C; S05659: Chr06_18284677 G/A; S05660: Chr06_18318164 T/C; S05661: Chr06_18328218 C/A; S05662: Chr06_18352906 G/C; S05663: Chr06_18398199 G/C; S05664: Chr06_18404414 G/A; S05665: Chr06_18468005 C/T; S05666: Chr06_18521393 T/C; S05667: Chr06_18538343 T/C; S05668: Chr06_18559695 C/T; S05669: Chr06_18579426 G/T; S05670: Chr06_18607338 G/T; S05671: Chr06_18656351 C/A; S05672: Chr06_18694817 G/A; S05673: Chr06_18713502 C/T; S05674: Chr06_18731550 C/T; S05675: Chr06_18785434 C/T; S05676: Chr06_18819533 T/G; S05677: Chr06_18836142 C/A; S05678: Chr06_18882265 C/T; S05679: Chr06_18963439 G/A; S05680: Chr06_18999090 C/A; S05681: Chr06_19026173 T/C; S05682: Chr06_19081766 A/G; S05683: Chr06_19117684 A/C; S05684: Chr06_19151635 A/T; S05685: Chr06_19212609 C/G; S05686: Chr06_19249081 T/G; S05687:

Chr06_19251651 T/G; S05688: Chr06_19275883 T/C; S05689: Chr06_19310425 T/C; S05690: Chr06_19330891 C/T; S05691: Chr06_19353880 A/G; S05692: Chr06_19392205 G/T; S05693: Chr06_19445340 A/G; S05694: Chr06_19461588 T/C; S05695: Chr06_19587807 A/G; S05696: Chr06_19600014 T/C; S05697: Chr06_19676661 T/C; S05698: Chr06_19710411 A/G; S05699: Chr06_19759390 G/T; S05700: Chr06_19781007 C/T; S05701: Chr06_19823381 A/T; S05702: Chr06_19825754 T/G; S05703: Chr06_19913355 A/C; S05704: Chr06_19938863 T/C; S05705: Chr06_20012169 G/A; S05706: Chr06_20025137 A/G; S05707: Chr06_20052082 A/T; S05708: Chr06_20086903 A/G; S05709: Chr06_20207322 C/G; S05710: Chr06_20281872 G/A; S05711: Chr06_20308852 C/T; 505712: Chr06_20342987 G/T; S05713: Chr06_20350012 T/C; S05714: Chr06_20426277 C/T; S05715: Chr06_20500310 T/C; S05716: Chr06_20575483 A/G; S05717: Chr06_20627600 G/T; S05718: Chr06_20686541 T/A; S05719: Chr06_20706667 T/G; S05720: Chr06_20725485 C/T; S05721: Chr06_20760293 A/G; S05722: Chr06_20803414 C/T; S05723: Chr06_20868970 C/T; S05724: Chr06_20943000 C/T; S05725: Chr06_20963053 G/A; S05726: Chr06_20982760 C/G; S05727: Chr06_21000043 G/A; S05728: Chr06_21094533 G/A; S05729: Chr06_21100487 C/T; S05730: Chr06_21143967 T/C; S05731: Chr06_21162624 C/T; S05732: Chr06_21226068 C/A; S05733: Chr06_21251562 G/A; S05734: Chr06_21275222 A/G; S05735: Chr06_21371440 C/T; S05736: Chr06_21376481 T/C; S05737: Chr06_21421216 C/T; S05738: Chr06_21477394 G/A; S05739: Chr06_21523749 C/T; S05740: Chr06_21548965 A/G; S05741: Chr06_21553515 G/A; S05742: Chr06_21683017 G/T; S05743: Chr06_21714564 A/G; S05744: Chr06_21730721 A/G; S05745: Chr06_21816843 T/G; S05746: Chr06_21877970 T/C; S05747: Chr06_21901107 A/T; S05748: Chr06_21986774 A/G; S05749: Chr06_22013029 A/G; S05750: Chr06_22033385 T/G; S05751: Chr06_22066673 G/C; S05752: Chr06_22083396 A/G; S05753: Chr06_22137151 C/T; S05754: Chr06_22190356 C/T; S05755: Chr06_22200014 G/A; S05756: Chr06_22275061 A/T; S05757: Chr06_22374932 G/A; S05758: Chr06_22375184 G/A; S05759: Chr06_22445619 G/A; S05760: Chr06_22455712 A/G; S05761: Chr06_22475835 C/A; S05762: Chr06_22515711 G/A; S05763: Chr06_22650085 A/G; S05764: Chr06_22727044 T/C; S05765: Chr06_22802501 A/G; S05766: Chr06_22887996 T/C; S05767: Chr06_22939589 G/A; S05768: Chr06_23175315 C/T; S05769: Chr06_23318825 A/G; S05770: Chr06_23384252 A/G; S05771: Chr06_23410068 C/A; S05772: Chr06_23425567 T/C; S05773: Chr06_23650530 G/A; S05774: Chr06_23825052 G/T; S05775: Chr06_23902026 T/A; S05776: Chr06_23977725 A/G; S05777: Chr06_24104128 T/A; S05778: Chr06_24459622 A/G; S05779: Chr06_24475141 A/T; S05780: Chr06_24625346 A/G; S05781: Chr06_24925793 C/T; S05782: Chr06_25150268 A/G; S05783: Chr06_25284517 C/A; S05784: Chr06_25365872 G/T; S05785: Chr06_25383818 T/C; S05786: Chr06_25623277 C/T; S05787: Chr06_25625614 A/G;

S05788: Chr06_25657237 A/T; S05789: Chr06_25877614 C/G; S05790: Chr06_26100059 G/A; S05791: Chr06_26185803 A/T; S05792: Chr06_26237443 A/T; S05793: Chr06_26250415 T/A; S05794: Chr06_26328392 G/A; S05795: Chr06_26630579 T/C; S05796: Chr06_26741334 C/T; S05797: Chr06_26950335 T/C; S05798: Chr06_27101834 T/G; S05799: Chr06_27184190 T/C; S05800: Chr06_27250335 C/T; S05801: Chr06_27471473 C/T; S05802: Chr06_27475405 A/G; S05803: Chr06_27625128 A/G; S05804: Chr06_27775135 G/A; S05805: Chr06_27850284 T/A; S05806: Chr06_27943569 T/A; S05807: Chr06_27950335 C/T; S05808: Chr06_28025056 T/C; S05809: Chr06_28175922 T/C; S05810: Chr06_28259270 T/C; S05811: Chr06_28325023 A/G; S05812: Chr06_28625180 C/G; S05813: Chr06_28700152 A/T; S05814: Chr06_28775417 T/A; S05815: Chr06_28876383 G/C; S05816: Chr06_28900093 T/A; S05817: Chr06_28928355 G/T; S05818: Chr06_29025918 A/G; S05819: Chr06_29118322 T/C; S05820: Chr06_29126001 T/A; S05821: Chr06_29273871 G/A; S05822: Chr06_29303915 A/G; S05823: Chr06_29325698 T/C; S05824: Chr06_29419856 T/C; S05825: Chr06_29425173 T/C; S05826: Chr06_29500479 A/C; S05827: Chr06_29581847 A/G; S05828: Chi-06_29604201 G/A; S05829: Chr06_29678001 A/T; S05830: Chr06_29750516 T/C; S05831: Chr06_29999326 T/C; S05832: Chr06_30001186 G/C; S05833: Chr06_30025083 T/C; S05834: Chr06_30175020 A/C; S05835: Chr06_30301396 T/C; S05836: Chr06_30327133 T/C; S05837: Chr06_30400698 T/C; S05838: Chr06_30511066 A/G; S05839: Chr06_30599244 C/T; S05840: Chr06_30675585 G/A; S05841: Chr06_30791137 T/C; S05842: Chr06_30800206 G/C; S05843: Chr06_31082378 A/G; S05844: Chr06_31117491 T/A; S05845: Chr06_31131420 T/A; S05846: Chr06_31211714 C/T; S05847: Chr06_31300746 T/C; S05848: Chr06_31527450 T/C; S05849: Chr06_31692038 A/G; S05850: Chr06_32053121 A/G; S05851: Chr06_32147772 C/T; S05852: Chr06_32277895 T/G; S05853: Chr06_32507635 A/G; S05854: Chr06_32798694 A/T; S05855: Chr06_32864678 C/G; S05856: Chr06_32899600 T/A; S05857: Chr06_32972037 T/A; S05858: Chr06_33350249 A/G; S05859: Chr06_33725138 T/C; S05860: Chr06_33800346 G/A; S05861: Chr06_33879878 C/T; S05862: Chr06_34143896 A/T; S05863: Chr06_34280753 T/C; S05864: Chr06_34425599 T/C; S05865: Chr06_34507532 G/T; S05866: Chr06_34550464 G/C; S05867: Chr06_34598898 T/C; S05868: Chr06_34670480 T/C; S05869: Chr06_34727503 T/C; S05870: Chr06_34752628 T/G; S05871: Chr06_34873123 G/A; S05872: Chr06_34875665 G/C; S05873: Chr06_34920781 G/T; S05874: Chr06_34965593 T/C; S05875: Chr06_35015569 C/A; S05876: Chr06_35205457 T/C; S05877: Chr06_35226466 A/G; S05878: Chr06_35317466 G/A; S05879: Chr06_35346607 A/G; S05880: Chr06_35351147 T/C; S05881: Chr06_35536286 A/G; S05882: Chr06_35550072 T/G; S05883: Chr06_35718955 G/T; S05884: Chr06_35725504 A/C; S05885: Chr06_35857503 C/T; S05886: Chr06_35876823 A/C; S05887: Chr06_35983651 A/T; S05888:

Chr06_36049216 A/G; S05889: Chr06_36052389 G/A; S05890: Chr06_36126353 T/C; S05891: Chr06_36262458 G/A; S05892: Chr06_36314019 C/A; S05893: Chr06_36326722 A/T; S05894: Chr06_36400449 G/A; S05895: Chr06_36552194 G/A; S05896: Chr06_36695539 C/T; S05897: Chr06_36767467 A/G; S05898: Chr06_36827523 G/A; S05899: Chr06_36872226 T/C; S05900: Chr06_36960472 T/A; S05901: Chr06_36991039 G/T; S05902: Chr06_37000790 T/C; S05903: Chr06_37147745 C/T; S05904: Chr06_37150282 T/G; S05905: Chr06_37355113 T/C; S05906: Chr06_37523936 A/T; S05907: Chr06_37543838 G/A; S05908: Chr06_37624463 A/T; S05909: Chr06_37674927 C/T; S05910: Chr06_37699056 G/T; S05911: Chr06_37701202 T/C; S05912: Chr06_37822708 G/A; S05913: Chr06_37843637 G/T; S05914: Chr06_37851923 G/A; S05915: Chr06_37877807 T/C; S05916: Chr06_38094025 G/A; S05917: Chr06_38113568 T/C; S05918: Chr06_38243910 T/G; S05919: Chr06_38250210 G/A; S05920: Chr06_38325048 C/A; S05921: Chr06_38423630 G/T; S05922: Chr06_38472597 C/T; S05923: Chr06_38498189 G/T; S05924: Chr06_38506618 T/G; S05925: Chr06_38638331 G/A; S05926: Chr06_38653753 G/A; S05927: Chr06_38683568 C/T; S05928: Chr06_38732450 G/A; S05929: Chr06_38751189 T/A; S05930: Chr06_38800705 T/C; S05931: Chr06_38826635 T/A; S05932: Chr06_38900112 C/A; S05933: Chr06_38999689 A/T; S05934: Chr06_39001229 A/T; S05935: Chr06_39025143 A/G; S05936: Chr06_39110079 C/T; S05937: Chr06_39169441 C/A; S05938: Chr06_39233930 A/G; S05939: Chr06_39258771 T/A; S05940: Chr06_39282164 G/A; S05941: Chr06_39300255 G/A; S05942: Chr06_39427322 C/T; S05943: Chr06_39531582 A/C; S05944: Chr06_39583427 G/A; S05945: Chr06_39600813 A/G; S05946: Chr06_39690419 A/G; S05947: Chr06_39700140 C/T; S05948: Chr06_39809020 C/A; S05949: Chr06_39826905 A/G; S05950: Chr06_39916700 T/C; S05951: Chr06_39935150 C/T; S05952: Chr06_39950618 T/C; S05953: Chr06_39978228 A/T; S05954: Chr06_40078895 A/G; S05955: Chr06_40161331 G/C; S05956: Chr06_40186328 C/A; S05957: Chr06_40200058 A/T; S05958: Chr06_40285139 T/A; S05959: Chr06_40300404 G/A; S05960: Chr06_40325010 T/A; S05961: Chr06_40413347 T/C; S05962: Chr06_40430425 A/G; S05963: Chr06_40490983 C/T; S05964: Chr06_40505516 C/T; S05965: Chr06_40539746 A/C; S05966: Chr06_40552401 A/T; S05967: Chr06_40575154 C/G; S05968: Chr06_40757753 A/G; S05969: Chr06_40786438 A/T; S05970: Chr06_40800610 A/C; S05971: Chr06_40905871 A/G; S05972: Chr06_40943881 T/C; S05973: Chr06_40950020 C/T; S05974: Chr06_41100086 A/T; S05975: Chr06_41175045 A/G; S05976: Chr06_41369904 G/C; S05977: Chr06_41394446 A/T; S05978: Chr06_41408535 C/T; S05979: Chr06_41435815 A/T; S05980: Chr06_41485505 C/A; S05981: Chr06_41506872 C/T; S05982: Chr06_41535985 A/T; S05983: Chr06_41560898 C/T; S05984: Chr06_41612936 T/C; S05985: Chr06_41636834 G/T; S05986: Chr06_41655258 T/C; S05987: Chr06_41686491 G/A; S05988: Chr06_41706518 A/G; S05989: Chr06_41739381 A/T; S05990: Chr06_41768161 T/C; S05991: Chr06_41790617 G/A; S05992: Chr06_41822965 T/C; S05993: Chr06_41867315 T/C; S05994: Chr06_41883929 G/A; S05995: Chr06_41969840 T/G; S05996: Chr06_41999497 G/T; S05997: Chr06_42000621 C/T; S05998: Chr06_42027322 G/A; S05999: Chr06_42092757 A/G; S06000: Chr06_42121544 C/T; S06001: Chr06_42126616 T/C; S06002: Chr06_42157271 G/A; S06003: Chr06_42175204 G/T; S06004: Chr06_42252843 C/T; S06005: Chr06_42406773 G/A; S06006: Chr06_42487881 A/G; S06007: Chr06_42620001 T/C; S06008: Chr06_212668299 G/A; S06009: Chr06_42711036 T/C; S06010: Chr06_212897736 G/A; S06011: Chr06_213029922 C/T; S06012: Chr06_43075404 G/A; S06013: Chr06_43151183 C/T; S06014: Chr06_43227308 T/C; S06015: Chr06_43308122 A/T; S06016: Chr06_43433729 G/A; S06017: Chr06_43500761 T/C; S06018: Chr06_43541876 G/A; S06019: Chr06_43550043 G/A; S06020: Chr06_43638991 C/T; S06021: Chr06_43660283 A/G; S06022: Chr06_43737099 C/A; S06023: Chr06_43769047 G/T; S06024: Chr06_43776983 C/T; S06025: Chr06_43801510 T/A; S06026: Chr06_43864028 A/G; S06027: Chr06_43891732 A/T; S06028: Chr06_43943750 C/A; S06029: Chr06_43996760 C/T; S06030: Chr06_44000042 G/A; S06031: Chr06_44030750 C/T; S06032: Chr06_44052899 C/T; S06033: Chr06_44079315 A/G; S06034: Chr06_44160545 T/C; S06035: Chr06_44201706 C/T; S06036: Chr06_44352118 C/T; S06037: Chr06_44376931 A/G; S06038: Chr06_44410661 T/A; S06039: Chr06_44427481 G/C; S06040: Chr06_44468234 T/C; S06041: Chr06_44521053 T/A; S06042: Chr06_44551315 G/C; S06043: Chr06_44639758 C/T; S06044: Chr06_44663405 C/T; S06045: Chr06_44680491 G/T; S06046: Chr06_44721997 C/G; S06047: Chr06_44785999 C/G; S06048: Chr06_44830620 C/A; S06049: Chr06_44861066 C/T; S06050: Chr06_44936824 C/T; S06051: Chr06_45025317 T/C; S06052: Chr06_45088675 C/G; S06053: Chr06_45101959 C/G; S06054: Chr06_45141044 C/G; S06055: Chr06_45152566 T/C; S06056: Chr06_45233608 G/A; S06057: Chr06_45278177 C/T; S06058: Chr06_45344497 A/T; S06059: Chr06_45379105 T/A; S06060: Chr06_45403673 A/C; S06061: Chr06_45436808 T/G; S06062: Chr06_45464095 C/T; S06063: Chr06_45489483 A/T; S06064: Chr06_45500186 C/T; S06065: Chr06_45555148 G/A; S06066: Chr06_45578922 G/A; S06067: Chr06_45697193 T/G; S06068: Chr06_45721923 A/C; S06069: Chr06_45726691 G/C; S06070: Chr06_45756814 A/G; S06071: Chr06_45813342 G/A; S06072: Chr06_45848547 C/T; S06073: Chr06_45863095 T/C; S06074: Chr06_45888057 A/G; S06075: Chr06_45924762 T/C; S06076: Chr06_45925073 T/A; S06077: Chr06_45963486 G/A; S06078: Chr06_45983183 C/T; S06079: Chr06_46003609 C/T; S06080: Chr06_46084402 G/A; S06081: Chr06_46100745 G/A; S06082: Chr06_46135463 C/T; S06083: Chr06_46153054 A/T; S06084: Chr06_46179544 C/A; S06085: Chr06_46203833 C/T; S06086: Chr06_46282557 A/C; S06087: Chr06_46300207 G/T; S06088: Chr06_46328232 C/T; S06089:

Chr06_46355898 G/C; S06090: Chr06_46430692 T/A; S06091: Chr06_46464314 G/A; S06092: Chr06_46477684 G/C; S06093: Chr06_46517059 T/C; S06094: Chr06_46525752 A/G; S06095: Chr06_46573761 C/A; S06096: Chr06_46575887 T/G; S06097: Chr06_46608857 T/G; S06098: Chr06_46631868 G/A; S06099: Chr06_46654220 G/A; S06100: Chr06_46678957 G/T; S06101: Chr06_46703667 A/G; S06102: Chr06_46741895 T/C; S06103: Chr06_46772465 G/A; S06104: Chr06_46778730 G/T; S06105: Chr06_46800208 G/A; S06106: Chr06_46832993 T/C; S06107: Chr06_46856883 T/G; S06108: Chr06_46936677 T/C; S06109: Chr06_46951115 C/T; S06110: Chr06_46996145 C/T; S06111: Chr06_47001807 G/T; S06112: Chr06_47032480 C/T; S06113: Chr06_47060118 T/C; S06114: Chr06_47075364 C/G; S06115: Chr06_47102490 G/A; S06116: Chr06_47129262 G/A; S06117: Chr06_47195365 C/A; S06118: Chr06_47202165 G/A; S06119: Chr06_47256504 C/T; S06120: Chr06_47276721 G/A; S06121: Chr06_47302423 T/C; S06122: Chr06_47325249 C/T; S06123: Chr06_47361258 G/A; S06124: Chr06_47380588 T/G; S06125: Chr06_47404530 T/C; S06126: Chr06_47428824 G/A; S06127: Chr06_47459621 C/G; S06128: Chr06_47485220 A/G; S06129: Chr06_47527814 C/A; S06130: Chr06_47560414 G/T; S06131: Chr06_47585053 T/G; S06132: Chr06_47610343 T/A; S06133: Chr06_47628233 G/T; S06134: Chr06_47709944 T/G; S06135: Chr06_47737892 C/A; S06136: Chr06_47751729 G/A; S06137: Chr06_47775000 C/T; S06138: Chr06_47814558 T/C; S06139: Chr06_47832335 A/C; S06140: Chr06_47864934 C/A; S06141: Chr06_47878677 C/T; S06142: Chr06_47919971 C/G; S06143: Chr06_47929724 T/C; S06144: Chr06_47952252 C/T; S06145: Chr06_47975172 T/G; S06146: Chr06_48019540 G/T; S06147: Chr06_48026477 C/T; S06148: Chr06_48053039 C/T; S06149: Chr06_48081141 A/G; S06150: Chr06_48101685 G/A; S06151: Chr06_48130858 G/A; S06152: Chr06_48152602 T/C; S06153: Chr06_48178688 A/T; S06154: Chr06_48201170 T/C; S06155: Chr06_48242356 A/C; S06156: Chr06_48251790 C/T; S06157: Chr06_48301424 C/A; S06158: Chr06_48327039 G/C; S06159: Chr06_48357119 A/T; S06160: Chr06_48378512 G/A; S06161: Chr06_48411349 A/T; S06162: Chr06_48428377 C/T; S06163: Chr06_48460307 C/A; S06164: Chr06_48476672 G/A; S06165: Chr06_48523596 C/G; S06166: Chr06_48526587 A/G; S06167: Chr06_48556601 G/A; S06168: Chr06_48576624 A/G; S06169: Chr06_48606392 C/T; S06170: Chr06_48625035 A/T; S06171: Chr06_48657852 A/C; S06172: Chr06_48676425 A/G; S06173: Chr06_48702305 C/T; S06174: Chr06_48726044 C/T; S06175: Chr06_48750703 T/C; S06176: Chr06_48775006 T/C; S06177: Chr06_48800181 C/A; S06178: Chr06_48826451 A/T; S06179: Chr06_48860668 T/A; S06180: Chr06_48880873 G/A; S06181: Chr06_48910052 A/T; S06182: Chr06_48956197 T/A; S06183: Chr06_48976326 C/G; S06184: Chr06_49001498 G/C; S06185: Chr06_49049037 G/A; S06186: Chr06_49050190 G/A; S06187: Chr06_49075014 G/T; S06188: Chr06_49112020 A/T; S06189: Chr06_49159947 A/T; S06190: Chr06_49180762 C/T; S06191: Chr06_49266406 A/C; S06192: Chr06_49276640 T/C; S06193: Chr06_49317807 C/T; S06194: Chr06_49330470 G/A; S06195: Chr06_49350015 G/A; S06196: Chr06_49387163 T/A; S06197: Chr06_49404536 C/T; S06198: Chr06_49425648 G/A; S06199: Chr06_49450356 G/A; S06200: Chr06_49476030 C/T; S06201: Chr06_49530212 C/T; S06202: Chr06_49552884 C/T; S06203: Chr06_49584763 A/T; S06204: Chr06_49613395 T/A; S06205: Chr06_49631686 C/T; S06206: Chr06_49665071 C/A; S06207: Chr06_49694549 G/A; S06208: Chr06_49707587 G/C; S06209: Chr06_49727946 T/C; S06210: Chr06_49767935 A/T; S06211: Chr06_49783272 A/G; S06212: Chr06_49802475 C/G; S06213: Chr06_49834366 C/A; S06214: Chr06_49868372 T/G; S06215: Chr06_49877389 A/G; S06216: Chr06_49908711 A/T; S06217: Chr06_49925613 T/C; S06218: Chr06_49953938 A/G; S06219: Chr06_49982968 A/C; S06220: Chr06_50029281 A/G; S06221: Chr06_50051628 C/T; S06222: Chr06_50076398 A/G; S06223: Chr06_50119980 A/C; S06224: Chr06_50145253 C/T; S06225: Chr06_50163774 G/A; S06226: Chr06_50179369 A/G; S06227: Chr06_50219563 G/T; S06228: Chr06_50225458 A/C; S06229: Chr06_50253767 T/C; S06230: Chr06_50290434 C/A; S06231: Chr06_50305416 A/G; S06232: Chr06_50325512 G/A; S06233: Chr06_50363058 G/A; S06234: Chr06_50402260 A/G; S06235: Chr06_50452000 G/A; S06236: Chr06_50475185 A/T; S06237: Chr06_50502011 T/C; S06238: Chr06_50525361 A/T; S06239: Chr06_50555675 T/G; S06240: Chr06_50579276 G/A; S06241: Chr06_50604195 T/A; S06242: Chr06_50628255 G/T; S06243: Chr06_50661513 T/A; S06244: Chr06_50676044 T/A; S06245: Chr06_50704811 T/A; S06246: Chr06_50735240 C/T; S06247: Chr06_50771043 C/T; S06248: Chr06_50793984 C/T; S06249: Chr06_50826149 A/G; S06250: Chr06_50850872 G/T; S06251: Chr06_50881307 G/A; S06252: Chr06_50900908 C/A; S06253: Chr06_50925012 T/A; S06254: Chr06_50951817 A/G; S06255: Chr06_50975144 T/G; S06256: Chr06_51002402 G/T; S06257: Chr06_51025330 T/G; S06258: Chr06_51051522 T/A; S06259: Chr06_51076174 T/C; S06260: Chr06_51100303 C/A; S06261: Chr06_51130515 C/A; S06262: Chr06_51150774 A/G; S06263: Chr06_51175605 T/A; S06264: Chr06_51211110 A/G; S06265: Chr06_51232153 C/T; S06266: Chr06_51252360 G/A; S06267: Chr06_51282910 T/G; S06268: Chr06_51304115 C/T; S06269: Chr06_51326016 A/C; S06270: Chr06_51405245 C/T; S06271: Chr07_00003753 C/T; S06272: Chr07_00031692 A/G; S06273: Chr07_00054138 G/A; S06274: Chr07_00089336 T/G; S06275: Chr07_00100169 T/C; S06276: Chr07_00140995 G/A; S06277: Chr07_00158404 A/T; S06278: Chr07_00176543 C/A; S06279: Chr07_00200274 T/C; S06280: Chr07_00229726 C/A; S06281: Chr07_00250043 A/G; S06282: Chr07_00275422 T/C; S06283: Chr07_00304340 T/G; S06284: Chr07_00328463 G/A; S06285: Chr07_00355715 T/C; S06286: Chr07_00377557 G/C; S06287: Chr07_00400909 G/T; S06288: Chr07_00439330 T/C; S06289: Chr07_00451458 C/A; S06290:

Chr07_00475713 A/T; S06291: Chr07_00503796 G/C; S06292: Chr07_00529405 G/T; S06293: Chr07_00551899 G/T; S06294: Chr07_00575263 T/A; S06295: Chr07_00607996 T/A; S06296: Chr07_00628703 G/T; S06297: Chr07_00650604 T/C; S06298: Chr07_00695029 T/C; S06299: Chr07_00709198 A/G; S06300: Chr07_00729453 T/C; S06301: Chr07_00752325 G/A; S06302: Chr07_00776247 T/C; S06303: Chr07_00811226 G/A; S06304: Chr07_00827594 T/A; S06305: Chr07_00850794 G/T; S06306: Chr07_00875040 C/T; S06307: Chr07_00900238 T/G; S06308: Chr07_00927243 A/T; S06309: Chr07_00951082 T/C; S06310: Chr07_00978182 A/G; S06311: Chr07_01003896 C/A; S06312: Chr07_01029490 A/G; S06313: Chr07_01055607 C/T; S06314: Chr07_01075893 C/T; S06315: Chr07_01107510 C/T; S06316: Chr07_01125150 T/C; S06317: Chr07_01152708 T/C; S06318: Chr07_01179019 C/T; S06319: Chr07_01210984 A/C; S06320: Chr07_01245892 T/C; S06321: Chr07_01260234 G/A; S06322: Chr07_01279847 A/G; S06323: Chr07_01306761 G/T; S06324: Chr07_01326460 T/C; S06325: Chr07_01357653 C/A; S06326: Chr07_01385267 G/A; S06327: Chr07_01435920 C/A; S06328: Chr07_01456122 C/G; S06329: Chr07_01493545 A/T; S06330: Chr07_01502417 C/A; S06331: Chr07_01526641 A/T; S06332: Chr07_01550880 C/T; S06333: Chr07_01575519 A/G; S06334: Chr07_01600217 G/A; S06335: Chr07_01630223 C/T; S06336: Chr07_01652158 T/C; S06337: Chr07_01677620 C/T; S06338: Chr07_01702402 T/C; S06339: Chr07_01726263 G/C; S06340: Chr07_01760006 C/G; S06341: Chr07_01791905 G/A; S06342: Chr07_01822745 C/T; S06343: Chr07_01827515 C/T; S06344: Chr07_01883918 A/G; S06345: Chr07_01905332 G/A; S06346: Chr07_01930445 C/T; S06347: Chr07_01952143 T/C; S06348: Chr07_01984938 G/A; S06349: Chr07_02007479 G/A; S06350: Chr07_02039762 T/C; S06351: Chr07_02052531 G/A; S06352: Chr07_02081663 A/G; S06353: Chr07_02100621 A/G; S06354: Chr07_02132339 G/A; S06355: Chr07_02175577 C/A; S06356: Chr07_02201482 C/T; S06357: Chr07_02258005 C/T; S06358: Chr07_02275798 T/C; S06359: Chr07_02308193 C/T; S06360: Chr07_02325417 T/C; S06361: Chr07_02354939 C/T; S06362: Chr07_02389514 C/T; S06363: Chr07_02411239 G/A; S06364: Chr07_02426231 A/T; S06365: Chr07_02457171 C/G; S06366: Chr07_02490851 C/T; S06367: Chr07_02522577 T/C; S06368: Chr07_02527345 C/A; S06369: Chr07_02551063 T/A; S06370: Chr07_02576558 A/C; S06371: Chr07_02600071 C/T; S06372: Chr07_02625120 G/A; S06373: Chr07_02656273 G/C; S06374: Chr07_02680645 T/G; S06375: Chr07_02702181 A/G; S06376: Chr07_02730149 C/G; S06377: Chr07_02750261 C/T; S06378: Chr07_02785573 C/T; S06379: Chr07_02817583 A/C; S06380: Chr07_02827311 A/G; S06381: Chr07_02851637 G/A; S06382: Chr07_02876608 T/C; S06383: Chr07_02903675 T/G; S06384: Chr07_02929341 T/C; S06385: Chr07_02950988 G/A; S06386: Chr07_02975819 A/T; S06387: Chr07_03003929 C/T; S06388: Chr07_03034806 A/G; S06389: Chr07_03057990 T/C; S06390: Chr07_03075531 C/T; S06391: Chr07_03107267 A/C; S06392: Chr07_03131148 G/A; S06393: Chr07_03160465 T/G; S06394: Chr07_03183645 A/C; S06395: Chr07_03204295 T/A; S06396: Chr07_03225068 T/A; S06397: Chr07_03278774 T/C; S06398: Chr07_03321186 C/T; S06399: Chr07_03326190 T/C; S06400: Chr07_03353625 A/G; S06401: Chr07_03395041 C/T; S06402: Chr07_03409307 G/A; S06403: Chr07_03474321 G/T; S06404: Chr07_03475424 C/T; S06405: Chr07_03500276 A/C; S06406: Chr07_03532597 T/G; S06407: Chr07_03551774 C/T; S06408: Chr07_03588243 A/T; S06409: Chr07_03612884 G/A; S06410: Chr07_03659527 C/G; S06411: Chr07_03711860 G/A; S06412: Chr07_03729155 T/G; S06413: Chr07_03767329 C/T; S06414: Chr07_03775378 A/T; S06415: Chr07_03800581 C/T; S06416: Chr07_03827939 G/T; S06417: Chr07_03863487 C/A; S06418: Chr07_03895518 C/T; S06419: Chr07_03902012 C/A; S06420: Chr07_03931360 G/T; S06421: Chr07_03957067 G/A; S06422: Chr07_03978150 A/T; S06423: Chr07_04005739 A/C; S06424: Chr07_04034586 T/A; S06425: Chr07_04099081 C/T; S06426: Chr07_04118381 T/A; S06427: Chr07_04139269 C/A; S06428: Chr07_04156317 A/C; S06429: Chr07_04188806 T/C; S06430: Chr07_04209856 T/C; S06431: Chr07_04226739 A/G; S06432: Chr07_04348601 G/C; S06433: Chr07_04385032 A/T; S06434: Chr07_04429330 C/T; S06435: Chr07_04450352 G/A; S06436: Chr07_04485511 C/A; S06437: Chr07_04502257 A/G; S06438: Chr07_04559152 T/C; S06439: Chr07_04578793 G/C; S06440: Chr07_04600619 G/T; S06441: Chr07_04636847 A/T; S06442: Chr07_04655437 A/G; S06443: Chr07_04745292 A/G; S06444: Chr07_04829631 A/C; S06445: Chr07_04870641 G/C; S06446: Chr07_04882996 G/A; S06447: Chr07_04902859 A/G; S06448: Chr07_04932267 T/C; S06449: Chr07_04955456 A/G; S06450: Chr07_04975739 G/A; S06451: Chr07_05017935 A/G; S06452: Chr07_05028260 A/G; S06453: Chr07_05063622 A/G; S06454: Chr07_05082788 T/C; S06455: Chr07_05101000 T/C; S06456: Chr07_05130765 T/C; S06457: Chr07_05187540 T/C; S06458: Chr07_05200496 T/G; S06459: Chr07_05249521 C/T; S06460: Chr07_05257022 A/G; S06461: Chr07_05276183 G/T; S06462: Chr07_05313302 T/G; S06463: Chr07_05332213 C/A; S06464: Chr07_05350074 T/C; S06465: Chr07_05380836 T/G; S06466: Chr07_05403591 C/T; S06467: Chr07_05432458 A/G; S06468: Chr07_05456321 C/G; S06469: Chr07_05477043 T/C; S06470: Chr07_05500763 G/C; S06471: Chr07_05528985 G/A; S06472: Chr07_05554657 T/C; S06473: Chr07_05575080 C/T; S06474: Chr07_05601319 A/C; S06475: Chr07_05641035 C/G; S06476: Chr07_05650442 A/C; S06477: Chr07_05696261 G/A; S06478: Chr07_05707757 C/T; S06479: Chr07_05725201 C/A; S06480: Chr07_05755117 A/G; S06481: Chr07_05788641 G/C; S06482: Chr07_05801938 G/C; S06483: Chr07_05825087 T/C; S06484: Chr07_05858750 A/T; S06485: Chr07_05885302 G/T; S06486: Chr07_05926053 C/T; S06487: Chr07_05954603 C/T; S06488: Chr07_05985913 C/T; S06489: Chr07_06000775 C/T; S06490: Chr07_06026285 G/C; S06491:

Chr07_06050545 G/A; S06492: Chr07_06075189 G/T; S06493: Chr07_06100909 C/A; S06494: Chr07_06129107 C/T; S06495: Chr07_06171429 A/G; S06496: Chr07_06176812 A/G; S06497: Chr07_06200435 A/G; S06498: Chr07_06225994 A/G; S06499: Chr07_06270980 C/T; S06500: Chr07_06275036 A/G; S06501: Chr07_06305208 G/C; S06502: Chr07_06348871 G/A; S06503: Chr07_06356163 C/T; S06504: Chr07_06381487 C/A; S06505: Chr07_06403275 C/T; S06506: Chr07_06429846 T/C; S06507: Chr07_06464916 A/T; S06508: Chr07_06475305 T/A; S06509: Chr07_06500796 G/C; S06510: Chr07_06525158 T/G; S06511: Chr07_06562483 A/G; S06512: Chr07_06575085 C/T; S06513: Chr07_06611806 C/G; S06514: Chr07_06641052 C/T; S06515: Chr07_06652459 A/T; S06516: Chr07_06676064 A/C; S06517: Chr07_06702898 T/C; S06518: Chr07_06726255 T/A; S06519: Chr07_06751675 A/T; S06520: Chr07_06775444 C/G; S06521: Chr07_06808192 T/A; S06522: Chr07_06825519 G/A; S06523: Chr07_06864441 T/C; S06524: Chr07_06875262 A/G; S06525: Chr07_06915501 G/T; S06526: Chr07_06931152 G/A; S06527: Chr07_06953583 G/A; S06528: Chr07_06981065 T/G; S06529: Chr07_07020942 G/A; S06530: Chr07_07025001 C/G; S06531: Chr07_07051921 G/A; S06532: Chr07_07086216 T/A; S06533: Chr07_07100004 G/T; S06534: Chr07_07125621 C/T; S06535: Chr07_07157440 G/A; S06536: Chr07_07175712 C/A; S06537: Chr07_07200900 A/G; S06538: Chr07_07238076 T/A; S06539: Chr07_07259943 G/T; S06540: Chr07_07281298 C/A; S06541: Chr07_07312553 C/T; S06542: Chr07_07336882 T/C; S06543: Chr07_07399663 C/T; S06544: Chr07_07423434 G/T; S06545: Chr07_07427962 G/A; S06546: Chr07_07469512 C/T; S06547: Chr07_07480182 C/A; S06548: Chr07_07522318 A/G; S06549: Chr07_07527765 T/C; S06550: Chr07_07553302 T/C; S06551: Chr07_07592304 A/T; S06552: Chr07_07611312 A/G; S06553: Chr07_07649500 T/C; S06554: Chr07_07659934 G/C; S06555: Chr07_07687523 G/C; S06556: Chr07_07717440 C/G; S06557: Chr07_07725790 C/T; S06558: Chr07_07753209 G/A; S06559: Chr07_07776980 A/G; S06560: Chr07_07804500 A/G; S06561: Chr07_07833239 T/A; S06562: Chr07_07850652 A/T; S06563: Chr07_07875054 A/C; S06564: Chr07_07911943 G/A; S06565: Chr07_07927375 A/G; S06566: Chr07_07965706 T/C; S06567: Chr07_08001374 C/T; S06568: Chr07_08026862 C/T; S06569: Chr07_08053922 A/G; S06570: Chr07_08082527 T/A; S06571: Chr07_08100005 C/T; S06572: Chr07_08129222 G/A; S06573: Chr07_08157112 G/T; S06574: Chr07_08184140 C/T; S06575: Chr07_08226456 G/C; S06576: Chr07_08251737 G/C; S06577: Chr07_08285590 C/G; S06578: Chr07_08302081 C/T; S06579: Chr07_08340342 C/G; S06580: Chr07_08351838 T/C; S06581: Chr07_08378739 A/G; S06582: Chr07_08420276 G/A; S06583: Chr07_08425687 T/C; S06584: Chr07_08451394 G/A; S06585: Chr07_08509917 C/T; S06586: Chr07_08527056 A/C; S06587: Chr07_08550911 T/C; S06588: Chr07_08589457 T/C; S06589: Chr07_08607183 C/G; S06590: Chr07_08632682 T/C; S06591: Chr07_08673517 T/A; S06592: Chr07_08678220 A/G; S06593: Chr07_08712450 C/T; S06594: Chr07_08726757 A/G; S06595: Chr07_08756022 A/G; S06596: Chr07_08782556 T/C; S06597: Chr07_08812051 C/T; S06598: Chr07_08844318 T/A; S06599: Chr07_08865392 T/C; S06600: Chr07_08889495 A/G; S06601: Chr07_08910037 T/C; S06602: Chr07_08937993 T/G; S06603: Chr07_08969595 G/T; S06604: Chr07_08975048 A/T; S06605: Chr07_09007029 T/G; S06606: Chr07_09026088 A/G; S06607: Chr07_09052198 G/A; S06608: Chr07_09081389 G/A; S06609: Chr07_09118550 C/T; S06610: Chr07_09125085 A/C; S06611: Chr07_09158284 G/A; S06612: Chr07_09185311 C/T; S06613: Chr07_09201345 A/G; S06614: Chr07_09231108 C/A; S06615: Chr07_09250685 G/A; S06616: Chr07_09326561 C/T; S06617: Chr07_09361618 T/G; S06618: Chr07_09399124 T/C; S06619: Chr07_09400201 T/C; S06620: Chr07_09444350 A/G; S06621: Chr07_09461523 A/G; S06622: Chr07_09483132 A/G; S06623: Chr07_09502688 C/A; S06624: Chr07_09525422 T/C; S06625: Chr07_09550118 T/C; S06626: Chr07_09579665 C/T; S06627: Chr07_09600965 T/C; S06628: Chr07_09665704 A/T; S06629: Chr07_09697569 A/G; S06630: Chr07_09700726 C/T; S06631: Chr07_09726521 T/G; S06632: Chr07_09751203 A/G; S06633: Chr07_09786699 G/A; S06634: Chr07_09810029 C/T; S06635: Chr07_09839875 T/A; S06636: Chr07_09853338 A/C; S06637: Chr07_09904049 A/T; S06638: Chr07_09930931 C/T; S06639: Chr07_09950191 T/C; S06640: Chr07_10075295 A/C; S06641: Chr07_10103866 C/T; S06642: Chr07_10160518 A/T; S06643: Chr07_10176276 T/C; S06644: Chr07_10214061 T/C; S06645: Chr07_10235420 T/A; S06646: Chr07_10281273 C/T; S06647: Chr07_10319564 G/T; S06648: Chr07_10332576 C/G; S06649: Chr07_10360859 C/T; S06650: Chr07_10424569 G/C; S06651: Chr07_10425016 C/T; S06652: Chr07_10450495 T/A; S06653: Chr07_10484000 A/T; S06654: Chr07_10500693 A/T; S06655: Chr07_10575269 T/G; S06656: Chr07_10602781 C/G; S06657: Chr07_10680967 A/G; S06658: Chr07_10728905 T/C; S06659: Chr07_10815953 A/G; S06660: Chr07_10870816 G/A; S06661: Chr07_10918261 A/C; S06662: Chr07_10925209 T/G; S06663: Chr07_11049244 T/C; S06664: Chr07_11050820 T/C; S06665: Chr07_11082237 A/G; S06666: Chr07_11182276 A/G; S06667: Chr07_11240910 C/G; S06668: Chr07_11281216 G/T; S06669: Chr07_11305725 T/C; S06670: Chr07_11351905 A/T; S06671: Chr07_11398937 A/G; S06672: Chr07_11403202 C/T; S06673: Chr07_11425301 T/C; S06674: Chr07_11500274 T/C; S06675: Chr07_11532482 C/T; S06676: Chr07_11555317 A/T; S06677: Chr07_11589875 A/C; S06678: Chr07_11618150 C/G; S06679: Chr07_11639968 C/T; S06680: Chr07_11664469 G/T; S06681: Chr07_11681897 A/G; S06682: Chr07_11703620 A/G; S06683: Chr07_11728142 G/A; S06684: Chr07_11783523 G/T; S06685: Chr07_11805085 C/T; S06686: Chr07_11830200 T/C; S06687: Chr07_11864490 C/T; S06688: Chr07_11932808 T/C; S06689: Chr07_11952346 A/G; S06690: Chr07_11975134 A/C; S06691: Chr07_12107480 C/T; S06692:

Chr07_12175108 T/A; S06693: Chr07_12214754 G/A; S06694: Chr07_12225181 G/T; S06695: Chr07_12300163 A/G; S06696: Chr07_12375241 A/G; S06697: Chr07_12467934 G/T; S06698: Chr07_12503588 G/A; S06699: Chr07_12526360 G/T; S06700: Chr07_12648922 C/T; S06701: Chr07_12650392 A/G; S06702: Chr07_12791812 A/C; S06703: Chr07_12832382 T/C; S06704: Chr07_13149332 G/C; S06705: Chr07_13150753 T/C; S06706: Chr07_13280058 G/A; S06707: Chr07_13352948 C/G; S06708: Chr07_13376654 T/A; S06709: Chr07_13413417 G/A; S06710: Chr07_13431779 T/A; S06711: Chr07_13502229 C/T; S06712: Chr07_13582379 A/C; S06713: Chr07_13600044 A/C; S06714: Chr07_13680710 A/G; S06715: Chr07_13762356 C/T; S06716: Chr07_13780560 C/T; S06717: Chr07_13851636 A/G; S06718: Chr07_13931117 G/A; S06719: Chr07_14004505 T/A; S06720: Chr07_14091972 C/G; S06721: Chr07_14110244 C/T; S06722: Chr07_14139498 C/G; S06723: Chr07_14156833 C/T; S06724: Chr07_14214046 A/G; S06725: Chr07_14262092 C/A; S06726: Chr07_14277104 C/T; S06727: Chr07_14305658 G/A; S06728: Chr07_14346374 T/C; S06729: Chr07_14351835 C/T; S06730: Chr07_14450279 A/G; S06731: Chr07_14523803 C/G; S06732: Chr07_14539505 A/G; S06733: Chr07_14614036 A/G; S06734: Chr07_14627258 G/T; S06735: Chr07_14705148 A/G; S06736: Chr07_14784346 A/G; S06737: Chr07_14888709 T/C; S06738: Chr07_14900699 C/T; S06739: Chr07_14943741 G/A; S06740: Chr07_14964006 G/A; S06741: Chr07_14990477 G/A; S06742: Chr07_15003142 T/C; S06743: Chr07_15031910 G/T; S06744: Chr07_15059227 A/C; S06745: Chr07_15078889 C/T; S06746: Chr07_15103581 G/A; S06747: Chr07_15190688 T/C; S06748: Chr07_15215367 C/T; S06749: Chr07_15225989 G/C; S06750: Chr07_15256045 T/A; S06751: Chr07_15283776 A/G; S06752: Chr07_15330277 C/T; S06753: Chr07_15350925 C/A; S06754: Chr07_15375316 A/C; S06755: Chr07_15402604 A/C; S06756: Chr07_15425056 T/C; S06757: Chr07_15467589 G/A; S06758: Chr07_15480093 T/C; S06759: Chr07_15500002 G/C; S06760: Chr07_15531750 T/C; S06761: Chr07_15553544 G/C; S06762: Chr07_15585048 A/G; S06763: Chr07_15608892 C/A; S06764: Chr07_15625840 T/C; S06765: Chr07_15674420 C/T; S06766: Chr07_15676282 G/A; S06767: Chr07_15718239 T/A; S06768: Chr07_15737200 T/A; S06769: Chr07_15770517 T/G; S06770: Chr07_15781705 A/G; S06771: Chr07_15801743 G/A; S06772: Chr07_15837174 T/A; S06773: Chr07_15863483 A/G; S06774: Chr07_15881825 A/C; S06775: Chr07_15922193 A/C; S06776: Chr07_15954986 G/A; S06777: Chr07_15986465 A/G; S06778: Chr07_16000393 C/T; S06779: Chr07_16032805 T/C; S06780: Chr07_16051598 G/A; S06781: Chr07_16077299 T/A; S06782: Chr07_16101942 A/C; S06783: Chr07_16130074 T/A; S06784: Chr07_16151007 G/A; S06785: Chr07_16180441 T/C; S06786: Chr07_16235287 C/A; S06787: Chr07_16257847 C/A; S06788: Chr07_16277399 G/C; S06789: Chr07_16373781 A/T; S06790: Chr07_16433144 C/T; S06791: Chr07_16507336 C/A; S06792: Chr07_16556477 A/T;

S06793: Chr07_16587815 A/T; S06794: Chr07_16604145 C/T; S06795: Chr07_16641749 G/C; S06796: Chr07_16651784 A/G; S06797: Chr07_16706167 T/C; S06798: Chr07_16800958 T/C; S06799: Chr07_16889053 A/T; S06800: Chr07_16923896 G/C; S06801: Chr07_16925918 A/C; S06802: Chr07_16978432 A/G; S06803: Chr07_17041292 G/A; S06804: Chr07_17060565 C/A; S06805: Chr07_17086618 C/T; S06806: Chr07_17112080 A/G; S06807: Chr07_17127199 A/G; S06808: Chr07_17167187 T/C; S06809: Chr07_17194140 G/A; S06810: Chr07_17202681 C/T; S06811: Chr07_17232236 A/T; S06812: Chr07_17259103 T/A; S06813: Chr07_17286914 T/C; S06814: Chr07_17332447 G/C; S06815: Chr07_17410962 C/A; S06816: Chr07_17490121 A/G; S06817: Chr07_17511124 G/C; S06818: Chr07_17527205 A/G; S06819: Chr07_17611814 C/T; S06820: Chr07_17625159 A/G; S06821: Chr07_17712114 C/A; S06822: Chr07_17737744 T/A; S06823: Chr07_17750116 G/T; S06824: Chr07_17784446 G/A; S06825: Chr07_17803696 A/G; S06826: Chr07_17882368 T/C; S06827: Chr07_17929278 T/C; S06828: Chr07_17950592 G/A; S06829: Chr07_17997359 G/A; S06830: Chr07_18011715 A/T; S06831: Chr07_18029377 T/C; S06832: Chr07_18051213 T/C; S06833: Chr07_18181793 G/C; S06834: Chr07_18272329 A/G; S06835: Chr07_18333925 T/C; S06836: Chr07_18352757 A/T; S06837: Chr07_18409146 A/T; S06838: Chr07_18454071 T/A; S06839: Chr07_18508664 G/C; S06840: Chr07_18525025 G/A; S06841: Chr07_18624669 G/A; S06842: Chr07_18633380 C/A; S06843: Chr07_18684233 C/T; S06844: Chr07_18724868 A/T; S06845: Chr07_18725089 T/A; S06846: Chr07_18770143 C/G; S06847: Chr07_18775842 C/T; S06848: Chr07_18937607 A/G; S06849: Chr07_18973094 G/A; S06850: Chr07_18984380 T/C; S06851: Chr07_19024233 C/A; S06852: Chr07_19025998 C/T; S06853: Chr07_19051769 A/G; S06854: Chr07_19075269 A/G; S06855: Chr07_19114746 C/G; S06856: Chr07_19164455 C/T; S06857: Chr07_19196212 A/G; S06858: Chr07_19218914 T/C; S06859: Chr07_19252040 G/A; S06860: Chr07_19340054 T/G; S06861: Chr07_19364460 C/T; S06862: Chr07_19435779 G/C; S06863: Chr07_19462449 G/T; S06864: Chr07_19475119 G/A; S06865: Chr07_19517440 C/A; S06866: Chr07_19554664 C/T; S06867: Chr07_19640899 C/G; S06868: Chr07_19650904 A/G; S06869: Chr07_19766129 G/C; S06870: Chr07_19817324 C/T; S06871: Chr07_19846202 C/T; S06872: Chr07_19882218 C/T; S06873: Chr07_19929766 C/T; S06874: Chr07_20011334 T/C; S06875: Chr07_20124708 G/A; S06876: Chr07_20149074 G/A; S06877: Chr07_20151291 T/G; S06878: Chr07_20181436 C/T; S06879: Chr07_20266548 T/G; S06880: Chr07_20280812 C/T; S06881: Chr07_20300284 T/A; S06882: Chr07_20425660 C/A; S06883: Chr07_20452156 G/A; S06884: Chr07_20659385 G/A; S06885: Chr07_20676579 T/A; S06886: Chr07_20700171 G/T; S06887: Chr07_20725032 C/T; S06888: Chr07_20800108 A/G; S06889: Chr07_20887936 G/A; S06890: Chr07_21030079 C/T; S06891: Chr07_21125087 T/C; S06892: Chr07_21200054 G/T; S06893:

Chr07_21335081 T/C; S06894: Chr07_21354607 T/C; S06895: Chr07_21428163 T/C; S06896: Chr07_21525563 C/A; S06897: Chr07_21655889 T/C; S06898: Chr07_21707572 G/T; S06899: Chr07_21785072 T/C; S06900: Chr07_21830869 G/T; S06901: Chr07_21850704 G/A; S06902: Chr07_22004033 A/G; S06903: Chr07_22075068 C/T; S06904: Chr07_22153459 G/T; S06905: Chr07_22301993 G/A; S06906: Chr07_22450332 A/G; S06907: Chr07_22525262 A/C; S06908: Chr07_22985153 C/G; S06909: Chr07_23453570 C/A; S06910: Chr07_23676106 C/T; S06911: Chr07_23825282 C/T; S06912: Chr07_23975062 G/A; S06913: Chr07_24050419 T/G; S06914: Chr07_24367242 T/C; S06915: Chr07_24450226 T/G; S06916: Chr07_24565204 C/T; S06917: Chr07_24789623 A/G; S06918: Chr07_24839873 G/A; S06919: Chr07_24850835 C/A; S06920: Chr07_25001407 G/A; S06921: Chr07_25025050 C/T; S06922: Chr07_25161343 A/C; S06923: Chr07_25325200 C/T; S06924: Chr07_25663764 C/T; S06925: Chr07_25681379 G/A; S06926: Chr07_25705095 G/A; S06927: Chr07_25800983 C/A; S06928: Chr07_25877378 G/A; S06929: Chr07_25958072 C/A; S06930: Chr07_26125231 T/G; S06931: Chr07_26275196 C/T; S06932: Chr07_26500773 T/C; S06933: Chr07_27014180 C/T; S06934: Chr07_27028461 C/T; S06935: Chr07_27051393 G/A; S06936: Chr07_27128169 C/T; S06937: Chr07_27150256 T/C; S06938: Chr07_27233175 C/T; S06939: Chr07_27250197 C/T; S06940: Chr07_27325378 A/G; S06941: Chr07_27447535 G/T; S06942: Chr07_27510947 T/C; S06943: Chr07_27525570 A/C; S06944: Chr07_27600303 G/C; S06945: Chr07_27746356 C/T; S06946: Chr07_27750520 T/C; S06947: Chr07_28011986 T/C; S06948: Chr07_28061766 A/G; S06949: Chr07_28075443 C/T; S06950: Chr07_28235346 G/C; S06951: Chr07_28393706 G/C; S06952: Chr07_28401355 A/G; S06953: Chr07_28475153 C/T; S06954: Chr07_28601000 G/A; S06955: Chr07_28625253 A/T; S06956: Chr07_28746097 A/C; S06957: Chr07_28750038 T/C; S06958: Chr07_29125586 G/C; S06959: Chr07_29349998 G/A; S06960: Chr07_29395701 C/T; S06961: Chr07_29403066 C/G; S06962: Chr07_29475322 A/G; S06963: Chr07_29616190 G/A; S06964: Chr07_29667335 G/T; S06965: Chr07_29725064 T/A; S06966: Chr07_29800251 C/T; S06967: Chr07_29876789 T/A; S06968: Chr07_29950961 C/A; S06969: Chr07_30027740 G/A; S06970: Chr07_30100016 A/T; S06971: Chr07_30278408 A/G; S06972: Chr07_30303370 G/A; S06973: Chr07_30424289 T/G; S06974: Chr07_30473399 A/G; S06975: Chr07_30477609 T/C; S06976: Chr07_30500412 G/A; S06977: Chr07_30726328 T/C; S06978: Chr07_30800375 C/G; S06979: Chr07_30880062 T/A; S06980: Chr07_31025120 G/A; S06981: Chr07_31273255 A/G; S06982: Chr07_31345631 A/G; S06983: Chr07_31356882 G/A; S06984: Chr07_31510343 G/A; S06985: Chr07_31619531 C/T; S06986: Chr07_31626777 G/C; S06987: Chr07_31702331 A/G; S06988: Chr07_31775253 C/T; S06989: Chr07_31851739 C/T; S06990: Chr07_31931814 A/C; S06991: Chr07_31950630 C/T; S06992: Chr07_32093256 G/A; S06993: Chr07_32476267 C/T; S06994: Chr07_32660548 G/A; S06995: Chr07_32675395 C/G; S06996: Chr07_32825163 T/A; S06997: Chr07_33008794 A/G; S06998: Chr07_33025203 T/C; S06999: Chr07_33308902 G/T; S07000: Chr07_33354419 A/G; S07001: Chr07_33408036 C/T; S07002: Chr07_33600060 A/G; S07003: Chr07_33727995 T/C; S07004: Chr07_33752477 C/A; S07005: Chr07_33825005 A/C; S07006: Chr07_33917785 G/C; S07007: Chr07_33926218 C/T; S07008: Chr07_34000412 T/G; S07009: Chr07_34084167 C/T; S07010: Chr07_34174926 C/T; S07011: Chr07_34204608 C/T; S07012: Chr07_34245133 A/G; S07013: Chr07_34250901 C/T; S07014: Chr07_34400927 T/A; S07015: Chr07_34444184 A/G; S07016: Chr07_34465885 C/G; S07017: Chr07_34492616 C/G; S07018: Chr07_34500177 C/A; S07019: Chr07_34526011 T/C; S07020: Chr07_34563433 C/T; S07021: Chr07_34648446 T/C; S07022: Chr07_34672248 C/A; S07023: Chr07_34708329 G/A; S07024: Chr07_34909883 C/T; S07025: Chr07_34930254 C/T; S07026: Chr07_35024223 G/C; S07027: Chr07_35036639 A/G; S07028: Chr07_35054584 C/T; S07029: Chr07_35115251 A/G; S07030: Chr07_35126702 G/A; S07031: Chr07_35201283 A/C; S07032: Chr07_35235952 G/A; S07033: Chr07_35298158 C/T; S07034: Chr07_35319941 A/C; S07035: Chr07_35354090 A/G; S07036: Chr07_35379563 T/A; S07037: Chr07_35425792 C/A; S07038: Chr07_35454406 T/C; S07039: Chr07_35533096 A/C; S07040: Chr07_35600813 A/G; S07041: Chr07_35625161 T/A; S07042: Chr07_35712247 C/T; S07043: Chr07_35734570 T/C; S07044: Chr07_35775381 G/A; S07045: Chr07_35811082 T/C; S07046: Chr07_35828543 G/A; S07047: Chr07_35856794 C/G; S07048: Chr07_35875783 T/A; S07049: Chr07_35977735 C/T; S07050: Chr07_36077613 G/C; S07051: Chr07_36110741 C/T; S07052: Chr07_36150398 A/C; S07053: Chr07_36194792 T/C; S07054: Chr07_36233399 T/C; S07055: Chr07_36278153 G/A; S07056: Chr07_36301325 C/T; S07057: Chr07_36329958 C/A; S07058: Chr07_36370213 G/T; S07059: Chr07_36385660 C/T; S07060: Chr07_36415244 G/A; S07061: Chr07_36429122 A/G; S07062: Chr07_36452777 G/A; S07063; Chr07_36481334 G/T; S07064: Chr07_36500282 G/C; S07065: Chr07_36528508 G/T; S07066: Chr07_36566471 T/C; S07067: Chr07_36593681 C/T; S07068: Chr07_36603312 C/T; S07069: Chr07_36648345 A/G; S07070: Chr07_36685237 A/T; S07071: Chr07_36705900 T/C; S07072: Chr07_36727557 C/G; S07073: Chr07_36760079 C/A; S07074: Chr07_36798631 T/C; S07075: Chr07_36835906 G/A; S07076: Chr07_36855472 G/T; S07077: Chr07_36889194 C/T; S07078: Chr07_36906380 C/T; S07079: Chr07_36934673 G/A; S07080: Chr07_36951473 T/C; S07081: Chr07_36979248 A/T; S07082: Chr07_37001237 G/C; S07083: Chr07_37047088 T/C; S07084: Chr07_37057389 T/C; S07085: Chr07_37077520 A/G; S07086: Chr07_37103918 G/A; S07087: Chr07_37126356 C/T; S07088: Chr07_37167628 A/G; S07089: Chr07_37177579 G/A; S07090: Chr07_37201660 A/G; S07091: Chr07_37252006 G/C; S07092: Chr07_37277056 T/C; S07093: Chr07_37320730 C/A; S07094:

Chr07_37325621 C/T; S07095: Chr07_37373812 T/G; S07096: Chr07_37376238 A/G; S07097: Chr07_37442276 T/G; S07098: Chr07_37451907 G/A; S07099; Chr07_37480945 G/A; S07100: Chr07_37504064 G/A; S07101: Chr07_37554164 C/T; S07102: Chr07_37579340 T/C; S07103: Chr07_37619334 C/T; S07104: Chr07_37626391 T/C; S07105: Chr07_37659410 T/C; S07106: Chr07_37678723 A/G; S07107: Chr07_37707182 C/T; S07108: Chr07_37730242 T/G; S07109: Chr07_37804073 T/C; S07110: Chr07_37827586 T/C; S07111: Chr07_37859003 T/C; S07112: Chr07_37875090 A/T; S07113: Chr07_37920578 C/G; S07114: Chr07_37926079 C/T; S07115: Chr07_38017255 A/G; S07116: Chr07_38039033 C/T; S07117: Chr07_38050549 A/T; S07118: Chr07_38087724 G/A; S07119: Chr07_38126914 G/A; S07120: Chr07_38179883 C/T; S07121: Chr07_38220586 A/G; S07122: Chr07_38232324 T/C; S07123: Chr07_38281113 A/G; S07124: Chr07_38313749 G/A; S07125: Chr07_38333638 T/G; S07126: Chr07_38390498 G/A; S07127: Chr07_38419431 A/G; S07128: Chr07_38491179 T/A; S07129: Chr07_38508688 A/T; S07130: Chr07_38592263 T/C; S07131: Chr07_38609181 C/A; S07132: Chr07_38647894 A/T; S07133: Chr07_38653177 T/C; S07134: Chr07_38724256 T/C; S07135: Chr07_38732597 C/G; S07136: Chr07_38806266 A/G; S07137: Chr07_38876850 A/G; S07138: Chr07_38903583 G/T; S07139: Chr07_38940229 G/T; S07140: Chr07_38985885 T/G; S07141: Chr07_39013676 C/T; S07142: Chr07_39031535 T/A; S07143: Chr07_39055019 C/G; S07144: Chr07_39089424 C/A; S07145: Chr07_39104700 G/T; S07146: Chr07_39135932 C/T; S07147: Chr07_39158581 C/A; S07148: Chr07_39175875 G/T; S07149: Chr07_39200003 A/G; S07150: Chr07_39289842 A/C; S07151: Chr07_39355101 A/T; S07152: Chr07_39460629 G/T; S07153: Chr07_39518504 T/C; S07154: Chr07_39679761 G/T; S07155: Chr07_39702229 G/A; S07156: Chr07_39765725 A/G; S07157: Chr07_39779807 T/C; S07158: Chr07_39867495 G/A; S07159: Chr07_39904516 C/T; S07160: Chr07_39952599 G/A; S07161: Chr07_40026319 C/G; S07162: Chr07_40100252 C/T; S07163: Chr07_40241181 A/G; S07164: Chr07_40268331 G/C; S07165: Chr07_40276058 C/T; S07166: Chr07_40323523 A/T; S07167: Chr07_40326412 C/A; S07168: Chr07_40390918 T/C; S07169: Chr07_40405156 C/T; S07170: Chr07_40455816 A/T; S07171: Chr07_40531449 C/T; S07172: Chr07_40550010 T/C; S07173: Chr07_40588419 C/T; S07174: Chr07_40654148 A/T; S07175: Chr07_40806467 C/G; S07176: Chr07_40885491 A/G; S07177: Chr07_40951249 C/T; S07178: Chr07_41078590 G/A; S07179: Chr07_41110215 G/T; S07180: Chr07_41184660 C/A; S07181: Chr07_41263843 G/A; S07182: Chr07_211371120 A/T; S07183: Chr07_41411439 G/A; S07184: Chr07_41492536 A/G; S07185: Chr07_41639094 G/A; S07186: Chr07_41715596 G/A; S07187: Chr07_41784061 T/C; S07188: Chr07_41809658 C/G; S07189: Chr07_41841823 G/A; S07190: Chr07_41858206 C/T; S07191: Chr07_41876743 C/T; S07192: Chr07_41911735 G/A; S07193: Chr07_42047915 A/G; S07194: Chr07_42060327 C/A; S07195: Chr07_42119515 T/G; S07196: Chr07_42143068 A/T; S07197: Chr07_42158530 G/A; S07198: Chr07_42178536 T/C; S07199: Chr07_42202999 C/T; S07200: Chr07_42225842 T/A; S07201: Chr07_42256379 T/A; S07202: Chr07_42294378 T/C; S07203: Chr07_42300022 A/G; S07204: Chr07_42332258 T/C; S07205: Chr07_42355840 A/G; S07206: Chr07_42376996 A/G; S07207: Chr07_212406426 C/A; S07208: Chr07_42432262 C/G; S07209: Chr07_42450640 G/A; S07210: Chr07_42477510 C/T; S07211: Chr07_42500713 A/G; S07212: Chr07_42525008 G/A; S07213: Chr07_42559646 C/T; S07214: Chr07_42584817 C/G; S07215: Chr07_42602750 A/G; S07216: Chr07_42630478 T/C; S07217: Chr07_42658523 A/G; S07218: Chr07_42689775 C/T; S07219: Chr07_42700692 G/T; S07220: Chr07_42732051 A/G; S07221: Chr07_42756900 A/G; S07222: Chr07_42782332 A/T; S07223: Chr07_42806260 T/C; S07224: Chr07_42836543 T/A; S07225: Chr07_42870671 G/A; S07226: Chr07_42875137 A/G; S07227: Chr07_42913186 A/G; S07228: Chr07_42925545 G/T; S07229: Chr07_42959812 A/G; S07230: Chr07_42975287 C/T; S07231: Chr07_43012916 A/G; S07232: Chr07_43029097 C/T; S07233: Chr07_43100729 G/A; S07234: Chr07_43127874 T/C; S07235: Chr07_43157898 A/C; S07236: Chr07_43196784 C/T; S07237: Chr07_43200777 C/A; S07238: Chr07_43276630 T/C; S07239: Chr07_213354699 C/T; S07240: Chr07_43478278 G/A; S07241: Chr07_43553458 T/C; S07242: Chr07_43576575 A/G; S07243: Chr07_43630320 A/G; S07244: Chr07_43671688 G/A; S07245: Chr07_213675593 T/C; S07246: Chr07_43708062 C/T; S07247: Chr07_43729887 T/C; S07248: Chr07_43750432 T/C; S07249: Chr07_43825613 C/T; S07250: Chr07_43894908 C/T; S07251: Chr07_43907976 G/T; S07252: Chr07_44052110 A/T; S07253: Chr07_44153004 A/C; S07254: Chr07_44212022 C/T; S07255: Chr07_44278969 T/C; S07256: Chr07_44302019 T/C; S07257: Chr07_44387267 G/A; S07258: Chr07_44404139 T/C; S07259: Chr07_44443942 T/A; S07260: Chr07_44471830 C/T; S07261: Chr07_44489360 G/A; S07262: Chr07_44501932 A/G; S07263: Chr07_44525779 A/G; S07264: Chr07_44583901 G/A; S07265: Chr07_44601082 G/A; S07266: Chr08_00015068 A/C; S07267: Chr08_00120227 G/C; S07268: Chr08_00132840 C/T; S07269: Chr08_00204169 A/G; S07270: Chr08_00276183 G/A; S07271: Chr08_00362713 A/G; S07272: Chr08_00398178 A/G; S07273: Chr08_00450593 C/T; S07274: Chr08_00480877 A/T; S07275: Chr08_00503004 C/T; S07276: Chr08_00541490 C/A; S07277: Chr08_00550416 A/T; S07278: Chr08_00643713 A/G; S07279: Chr08_00650002 G/A; S07280: Chr08_00676539 C/A; S07281: Chr08_00734307 A/T; S07282: Chr08_00762012 G/A; S07283: Chr08_00776002 C/T; S07284: Chr08_00806504 A/G; S07285: Chr08_00840319 A/G; S07286: Chr08_00888019 T/G; S07287: Chr08_00920550 G/C; S07288: Chr08_00928095 T/A; S07289: Chr08_01007813 G/A; S07290: Chr08_01028572 C/A; S07291: Chr08_01118989 T/G; S07292: Chr08_01130502 T/C; S07293: Chr08_01172508 A/G; S07294: Chr08_01186543 A/T; S07295:

Chr08_01244842 G/T; S07296: Chr08_01267184 G/A; S07297: Chr08_01284270 A/C; S07298: Chr08_01302384 C/T; S07299: Chr08_01362401 A/G; S07300: Chr08_01434637 C/T; S07301: Chr08_01451606 T/A; S07302: Chr08_01475369 C/A; S07303: Chr08_01510558 C/G; S07304: Chr08_01538510 C/T; S07305: Chr08_01562857 T/C; S07306: Chr08_01594729 A/G; S07307: Chr08_01609537 A/G; S07308: Chr08_01640079 C/T; S07309: Chr08_01665885 T/A; S07310: Chr08_01676920 C/T; S07311: Chr08_01716531 C/T; S07312: Chr08_01725102 C/G; S07313: Chr08_01752252 C/T; S07314: Chr08_01798324 C/T; S07315: Chr08_01801713 A/G; S07316: Chr08_01836310 T/A; S07317: Chr08_01859200 T/A; S07318: Chr08_01879216 C/G; S07319: Chr08_01900130 C/T; S07320: Chr08_01925854 A/C; S07321: Chr08_01963431 A/T; S07322: Chr08_01975564 C/T; S07323: Chr08_02004451 C/T; S07324: Chr08_02035798 A/T; S07325: Chr08_02050475 A/G; S07326: Chr08_02089797 T/C; S07327: Chr08_02104023 C/A; S07328: Chr08_02137749 G/A; S07329: Chr08_02178416 T/C; S07330: Chr08_02221627 G/T; S07331: Chr08_02226176 A/G; S07332: Chr08_02252281 A/G; S07333: Chr08_02283973 C/T; S07334: Chr08_02305002 G/T; S07335: Chr08_02330234 A/G; S07336: Chr08_02379267 A/C; S07337: Chr08_02456645 T/G; S07338: Chr08_02481972 T/C; S07339: Chr08_02506913 T/C; S07340: Chr08_02533754 T/G; S07341: Chr08_02550484 T/G; S07342: Chr08_02576632 G/A; S07343: Chr08_02621158 G/T; S07344: Chr08_02631092 T/C; S07345: Chr08_02650305 G/T; S07346: Chr08_02675488 A/G; S07347: Chr08_02701355 T/C; S07348: Chr08_02725636 A/T; S07349: Chr08_02755936 T/A; S07350: Chr08_02781099 A/C; S07351: Chr08_02801048 A/C; S07352: Chr08_02835430 T/C; S07353: Chr08_02867604 C/T; S07354: Chr08_02900041 G/A; S07355: Chr08_02930272 C/A; S07356: Chr08_02955658 C/T; S07357: Chr08_02975349 C/T; S07358: Chr08_03019130 C/A; S07359: Chr08_03031450 T/C; S07360: Chr08_03053356 T/G; S07361: Chr08_03075828 T/G; S07362: Chr08_03105253 A/T; S07363: Chr08_03148078 T/C; S07364: Chr08_03157761 A/G; S07365: Chr08_03180940 T/C; S07366: Chr08_03215670 G/C; S07367: Chr08_03251866 T/G; S07368: Chr08_03291093 G/A; S07369: Chr08_03305079 C/T; S07370: Chr08_03337868 C/T; S07371: Chr08_03350204 C/A; S07372: Chr08_03379901 C/A; S07373: Chr08_03440456 T/C; S07374: Chr08_03450747 C/G; S07375: Chr08_03476171 A/G; S07376: Chr08_03500989 A/C; S07377: Chr08_03526782 G/T; S07378: Chr08_03554666 C/T; S07379: Chr08_03583409 C/T; S07380: Chr08_03600196 T/A; S07381: Chr08_03625219 G/A; S07382: Chr08_03653388 C/T; S07383: Chr08_03684743 T/A; S07384: Chr08_03709318 A/C; S07385: Chr08_03725849 C/T; S07386: Chr08_03758873 G/A; S07387: Chr08_03777218 G/C; S07388: Chr08_03801869 T/G; S07389: Chr08_03836330 C/T; S07390: Chr08_03855501 A/T; S07391: Chr08_03875809 A/T; S07392: Chr08_03995984 C/A; S07393: Chr08_04031795 T/A; S07394: Chr08_04095981 A/G; S07395: Chr08_04114180 A/T; S07396: Chr08_04201119 G/A; S07397: Chr08_04305030 G/A; S07398: Chr08_04328340 C/A; S07399: Chr08_04375599 C/G; S07400: Chr08_04406262 A/G; S07401: Chr08_04492878 A/G; S07402: Chr08_04608510 C/G; S07403: Chr08_04652027 C/T; S07404: Chr08_04675338 T/A; S07405: Chr08_04708971 T/A; S07406: Chr08_04734232 T/C; S07407: Chr08_04753552 G/A; S07408: Chr08_04806560 G/C; S07409: Chr08_04830404 G/A; S07410: Chr08_04850421 G/A; S07411: Chr08_04884688 A/C; S07412: Chr08_04906185 C/G; S07413: Chr08_04952152 T/A; S07414: Chr08_04978614 G/A; S07415: Chr08_05001757 C/T; S07416: Chr08_05051964 A/G; S07417: Chr08_05075393 C/T; S07418: Chr08_05101732 A/G; S07419: Chr08_05132603 C/T; S07420: Chr08_05155810 A/G; S07421: Chr08_05175355 C/G; S07422: Chr08_05207194 A/G; S07423: Chr08_05241957 G/A; S07424: Chr08_05269266 T/C; S07425: Chr08_05277717 G/C; S07426: Chr08_05304449 C/T; S07427: Chr08_05325591 G/A; S07428: Chr08_05352401 C/T; S07429: Chr08_05377822 C/A; S07430: Chr08_05400773 A/T; S07431: Chr08_05477306 G/A; S07432: Chr08_05500592 G/A; S07433: Chr08_05595345 C/T; S07434: Chr08_05655781 C/A; S07435: Chr08_05691020 T/G; S07436: Chr08_05709264 A/G; S07437: Chr08_05734351 T/C; S07438: Chr08_05751160 G/A; S07439: Chr08_05827905 C/T; S07440: Chr08_05872790 G/A; S07441: Chr08_05926643 A/T; S07442: Chr08_06042191 A/T; S07443: Chr08_06141255 G/A; S07444: Chr08_06196373 G/T; S07445: Chr08_06230982 C/A; S07446: Chr08_06255768 G/A; S07447: Chr08_06375933 G/A; S07448: Chr08_06405767 C/G; S07449: Chr08_06488691 A/G; S07450: Chr08_06583080 C/T; S07451: Chr08_06633155 A/G; S07452: Chr08_06659330 A/G; S07453: Chr08_06730924 T/C; S07454: Chr08_06808988 C/T; S07455: Chr08_06865060 G/A; S07456: Chr08_06880158 G/A; S07457: Chr08_06904097 T/C; S07458: Chr08_06980073 T/C; S07459: Chr08_07058661 G/C; S07460: Chr08_07088574 G/C; S07461: Chr08_07101251 A/G; S07462: Chr08_07147630 A/G; S07463: Chr08_07160831 A/T; S07464: Chr08_07175086 C/A; S07465: Chr08_07238107 A/G; S07466: Chr08_07255548 T/A; S07467: Chr08_07389352 C/T; S07468: Chr08_07409094 C/G; S07469: Chr08_07425128 C/T; S07470: Chr08_07457393 C/A; S07471: Chr08_07478674 A/G; S07472: Chr08_07512438 A/C; S07473: Chr08_07525546 T/G; S07474: Chr08_07574487 C/G; S07475: Chr08_07636850 C/T; S07476: Chr08_07675196 A/G; S07477: Chr08_07719126 G/A; S07478: Chr08_07725294 T/C: 507479: Chr08_07750646 G/A; S07480: Chr08_07780496 T/C; S07481: Chr08_07805605 A/C; S07482: Chr08_07829061 G/C; S07483: Chr08_07852526 A/G; S07484: Chr08_07876236 T/C; S07485: Chr08_07903178 A/G; S07486: Chr08_07930183 A/G; S07487: Chr08_07980043 T/G; S07488: Chr08_08017355 T/C; S07489: Chr08_08065674 T/C; S07490: Chr08_08075299 C/T; S07491: Chr08_08157061 G/A; S07492: Chr08_08177398 C/T; S07493: Chr08_08285093 T/G; S07494: Chr08_08300308 T/C; S07495: Chr08_08325103 T/C; S07496:

Chr08_08353076 A/G; S07497: Chr08_08389585 G/A; S07498: Chr08_08435735 G/A; S07499: Chr08_08508773 C/T; S07500: Chr08_08529096 T/C; S07501: Chr08_08557979 C/T; S07502: Chr08_08577146 G/A; S07503: Chr08_08600306 A/G; S07504: Chr08_08635628 A/G; S07505: Chr08_08661143 A/G; S07506: Chr08_08710726 T/C; S07507: Chr08_08725772 A/C; S07508: Chr08_08753670 T/G; S07509: Chr08_08796231 T/C; S07510: Chr08_08803061 A/G; S07511: Chr08_08850154 A/G; S07512: Chr08_08894420 T/C; S07513: Chr08_08901194 C/T; S07514: Chr08_08980199 C/G; S07515: Chr08_09083041 T/C; S07516: Chr08_09127538 G/A; S07517: Chr08_09170262 A/G; S07518: Chr08_09185800 C/G; S07519: Chr08_09220290 G/A; S07520: Chr08_09229556 A/G; S07521: Chr08_09255753 G/A; S07522: Chr08_09290677 C/A; S07523: Chr08_09307384 C/G; S07524: Chr08_09332121 A/C; S07525: Chr08_09350254 G/A; S07526: Chr08_09377927 A/G; S07527: Chr08_09400097 T/C; S07528: Chr08_09429179 T/C; S07529: Chr08_09453145 C/T; S07530: Chr08_09481603 A/G; S07531: Chr08_09500023 C/A; S07532: Chr08_09526669 T/G; S07533: Chr08_09557139 G/A; S07534: Chr08_09587438 A/T; S07535: Chr08_09600023 T/C; S07536: Chr08_09634387 C/T; S07537: Chr08_09652503 G/A; S07538: Chr08_09688271 G/A; S07539: Chr08_09701254 A/C; S07540: Chr08_09742193 G/A; S07541: Chr08_09760834 C/G; S07542: Chr08_09776456 G/A; S07543: Chr08_09803231 G/A; S07544: Chr08_09831710 G/A; S07545: Chr08_09857468 G/T; S07546: Chr08_09877278 T/A; S07547: Chr08_09905369 T/C; S07548: Chr08_09929008 G/A; S07549: Chr08_09958064 G/A; S07550: Chr08_09986616 G/A; S07551: Chr08_10023493 G/A; S07552: Chr08_10029124 C/T; S07553: Chr08_10073881 T/C; S07554: Chr08_10078342 C/T; S07555: Chr08_10122655 G/A; S07556: Chr08_10138441 G/T; S07557: Chr08_10160041 T/G; S07558: Chr08_10181475 T/A; S07559: Chr08_10215938 C/T; S07560: Chr08_10239467 C/T; S07561: Chr08_10255462 A/G; S07562: Chr08_10282878 G/A; S07563: Chr08_10322783 C/A; S07564: Chr08_10326219 C/T; S07565: Chr08_10359085 C/T; S07566: Chr08_10380268 A/C; S07567: Chr08_10400375 A/G; S07568: Chr08_10427844 T/C; S07569: Chr08_10454108 G/A; S07570: Chr08_10476027 C/A; S07571: Chr08_10512155 A/T; S07572: Chr08_10567287 C/T; S07573: Chr08_10575914 G/A; S07574: Chr08_10605162 T/G; S07575: Chr08_10626087 A/T; S07576: Chr08_10661714 A/G; S07577: Chr08_10675535 C/T; S07578: Chr08_10706589 G/A; S07579: Chr08_10726725 G/A; S07580: Chr08_10750116 G/A; S07581: Chr08_10776647 G/A; S07582: Chr08_10800432 A/G; S07583: Chr08_10825001 A/G; S07584: Chr08_10854902 G/C; S07585: Chr08_10884305 T/C; S07586: Chr08_10921305 A/G; S07587: Chr08_10934355 T/C; S07588: Chr08_10950188 A/G; S07589: Chr08_10983386 G/A; S07590: Chr08_11000151 G/A; S07591: Chr08_11025700 G/C; S07592: Chr08_11051138 A/G; S07593: Chr08_11085357 T/C; S07594: Chr08_11120268 A/T; S07595: Chr08_11126340 A/G; S07596: Chr08_11157979 C/T; S07597: Chr08_11184227 A/G; S07598: Chr08_11200186 C/T; S07599: Chr08_11226159 T/C; S07600: Chr08_11251742 A/G; S07601: Chr08_11281022 G/C; S07602: Chr08_11313529 T/A; S07603: Chr08_11326261 A/G; S07604: Chr08_11361006 A/G; S07605: Chr08_11393239 T/G; S07606: Chr08_11411364 C/A; S07607: Chr08_11429653 T/A; S07608: Chr08_11458029 A/T; S07609: Chr08_11477277 T/C; S07610: Chr08_11503327 T/G; S07611: Chr08_11552159 C/T; S07612: Chr08_11578398 C/A; S07613: Chr08_11602284 C/T; S07614: Chr08_11633675 A/C; S07615: Chr08_11650132 T/G; S07616: Chr08_11684131 A/C; 507617: Chr08_11703834 A/T; S07618: Chr08_11726523 A/G; S07619: Chr08_11750314 C/T; S07620: Chr08_11794218 G/T; S07621: Chr08_11816042 A/T; S07622: Chr08_11828249 C/T; S07623: Chr08_11862279 G/A; S07624: Chr08_11878380 A/T; S07625: Chr08_11935782 G/C; S07626: Chr08_11956327 C/A; S07627: Chr08_12005130 G/A; S07628: Chr08_12029609 A/G; S07629: Chr08_12059378 G/C; S07630: Chr08_12078358 A/C; S07631: Chr08_12103141 A/T; S07632: Chr08_12126511 C/T; S07633: Chr08_12156768 G/A; S07634: Chr08_12179167 A/G; S07635: Chr08_12201023 C/T; S07636: Chr08_12229072 A/G; S07637: Chr08_12254745 T/A; S07638: Chr08_12280758 T/A; S07639: Chr08_12301275 T/A; S07640: Chr08_12350897 A/G; S07641: Chr08_12376039 A/G; S07642: Chr08_12406508 G/A; S07643: Chr08_12425932 T/A; S07644: Chr08_12451808 A/T; S07645: Chr08_12485777 A/T; S07646: Chr08_12525524 T/C; S07647: Chr08_12565242 C/T; S07648: Chr08_12577581 C/A; S07649: Chr08_12616101 C/T; S07650: Chr08_12639886 G/A; S07651: Chr08_12651519 C/T; S07652: Chr08_12693862 A/C; S07653: Chr08_12733917 T/A; S07654: Chr08_12765989 A/G; S07655: Chr08_12800542 C/T; S07656: Chr08_12827223 C/G; S07657: Chr08_12911328 T/C; S07658: Chr08_12972483 T/C; S07659: Chr08_13003989 G/C; S07660: Chr08_13060632 T/C; S07661: Chr08_13118740 C/A; S07662: Chr08_13135528 G/C; S07663: Chr08_13154465 T/A; S07664: Chr08_13202236 G/C; S07665: Chr08_13238634 A/C; S07666: Chr08_13250791 T/G; S07667: Chr08_13381998 C/T; S07668: Chr08_13400302 G/A; S07669: Chr08_13494276 A/G; S07670: Chr08_13514715 T/G; S07671: Chr08_13534982 T/C; S07672: Chr08_13575825 G/A; S07673: Chr08_13657413 C/T; S07674: Chr08_13690394 C/T; S07675: Chr08_13724657 G/A; S07676: Chr08_13726085 G/T; S07677: Chr08_13768959 C/G; S07678: Chr08_13806811 A/T; S07679: Chr08_13831480 C/T; S07680: Chr08_13852506 G/T; S07681: Chr08_13881296 T/C; S07682: Chr08_13901312 G/C; S07683: Chr08_13933262 G/T; S07684: Chr08_13964839 G/A; S07685: Chr08_13976232 G/A; S07686: Chr08_14061866 C/T; S07687: Chr08_14107787 C/T; S07688: Chr08_14160423 C/T; S07689: Chr08_14182484 C/A; S07690: Chr08_14205433 T/G; S07691: Chr08_14225008 A/G; S07692: Chr08_14251580 C/T; S07693: Chr08_14278513 A/C; S07694: Chr08_14301079 C/A; S07695: Chr08_14386629 C/T; S07696: Chr08_14464772 G/C; S07697:

Chr08_14483246 C/T; S07698: Chr08_14519320 C/T; S07699: Chr08_14567220 T/C; S07700: Chr08_14576068 A/G; S07701: Chr08_14602272 A/C; S07702: Chr08_14641559 G/A; S07703: Chr08_14657945 A/C; S07704: Chr08_14695348 A/G; S07705: Chr08_14714220 A/G; S07706: Chr08_14739967 C/T; S07707: Chr08_14752236 G/A; S07708: Chr08_14779196 T/C; S07709: Chr08_14805800 C/T; S07710: Chr08_14835484 T/C; S07711: Chr08_14853304 C/T; S07712: Chr08_14880462 T/A; S07713: Chr08_14902316 C/T; S07714: Chr08_14932204 G/A; S07715: Chr08_14958933 C/G; S07716: Chr08_14978261 C/T; S07717: Chr08_15012126 G/A; S07718: Chr08_15026461 G/A; S07719: Chr08_15053008 C/T; S07720: Chr08_15087356 T/C; S07721: Chr08_15101689 T/C; S07722: Chr08_15125250 T/C; S07723: Chr08_15156410 G/A; S07724: Chr08_15176404 A/C; S07725: Chr08_15210216 C/T; S07726: Chr08_15235416 C/A; S07727: Chr08_15252037 T/G; S07728: Chr08_15299083 G/A; S07729: Chr08_15352045 A/G; S07730: Chr08_15435229 A/C; S07731: Chr08_15470712 C/A; S07732: Chr08_15483748 G/T; S07733: Chr08_15502148 C/A; S07734: Chr08_15532658 C/G; S07735: Chr08_15563425 G/T; S07736: Chr08_15592774 G/A; S07737: Chr08_15605556 C/T; S07738: Chr08_15628819 G/A; S07739: Chr08_15671774 T/A; S07740: Chr08_15684208 T/C; S07741: Chr08_15700634 C/T; S07742: Chr08_15735293 C/G; S07743: Chr08_15753860 G/A; S07744: Chr08_15778462 C/G; S07745: Chr08_15809698 A/C; S07746: Chr08_15841775 A/G; S07747: Chr08_15859680 T/C; S07748: Chr08_15908699 C/T; S07749: Chr08_15926122 C/T; S07750: Chr08_15951560 C/T; S07751: Chr08_15975384 G/A; S07752: Chr08_16000060 A/G; S07753: Chr08_16026351 T/C; S07754: Chr08_16067973 T/A; S07755: Chr08_16078686 C/T; S07756: Chr08_16100386 C/T; S07757: Chr08_16130987 A/G; S07758: Chr08_16160119 A/G; S07759: Chr08_16189625 G/C; S07760: Chr08_16220068 T/C; S07761: Chr08_16225667 T/G; S07762: Chr08_16252187 T/C; S07763: Chr08_16297454 T/A; S07764: Chr08_16301107 T/C; S07765: Chr08_16332877 A/T; S07766: Chr08_16354631 A/C; S07767: Chr08_16376183 A/G; S07768: Chr08_16436211 G/A; S07769: Chr08_16450755 G/A; S07770: Chr08_16486359 C/T; S07771: Chr08_16537550 A/C; S07772: Chr08_16574354 C/G; S07773: Chr08_16575359 C/A; S07774: Chr08_16603309 A/G; S07775: Chr08_16630538 A/G; S07776: Chr08_16664356 A/G; S07777: Chr08_16683573 T/A; S07778: Chr08_16702150 G/A; S07779: Chr08_16748376 A/C; S07780: Chr08_16752387 A/G; S07781: Chr08_16795090 T/C; S07782: Chr08_16814361 A/G; S07783: Chr08_16871030 T/C; S07784: Chr08_16881624 A/G; S07785: Chr08_16903727 G/C; S07786: Chr08_16927960 A/G; S07787: Chr08_16950810 T/C; S07788: Chr08_16975905 A/G; S07789: Chr08_17001799 A/G; S07790: Chr08_17061314 A/G; S07791: Chr08_17104829 T/C; S07792: Chr08_17137743 G/T; S07793: Chr08_17156020 A/G; S07794: Chr08_17179595 G/A; S07795: Chr08_17203421 T/G; S07796: Chr08_17225326 G/C; S07797: Chr08_17250097 A/G; S07798: Chr08_17275894 G/A; S07799: Chr08_17318021 T/C; S07800: Chr08_17327163 G/A; S07801: Chr08_17367013 T/C; S07802: Chr08_17399876 A/T; S07803: Chr08_17400161 G/A; S07804: Chr08_17426206 G/C; S07805: Chr08_17451897 G/A; S07806: Chr08_17477170 G/C; S07807: Chr08_17514307 C/T; S07808: Chr08_17527164 C/A; S07809: Chr08_17551742 C/G; S07810: Chr08_17596139 G/C; S07811: Chr08_17615051 C/G; S07812: Chr08_17630180 A/G; S07813: Chr08_17659479 T/C; S07814: Chr08_17676116 C/G; S07815: Chr08_17705911 A/G; S07816: Chr08_17728101 A/G; S07817: Chr08_17770219 A/G; S07818: Chr08_17795098 C/A; S07819: Chr08_17844333 T/A; S07820: Chr08_17851770 T/C; S07821: Chr08_17876431 T/A; S07822: Chr08_17908686 G/C; S07823: Chr08_17942655 T/A; S07824: Chr08_17962700 A/G; S07825: Chr08_17981980 G/A; S07826: Chr08_18003446 T/A; S07827: Chr08_18047365 T/C; S07828: Chr08_18057969 T/C; S07829: Chr08_18075674 T/G; S07830: Chr08_18103327 C/A; S07831: Chr08_18127627 A/C; S07832: Chr08_18153985 G/C; S07833: Chr08_18184285 T/G; S07834: Chr08_18205066 G/A; S07835: Chr08_18225379 C/T; S07836: Chr08_18251153 A/G; S07837: Chr08_18275878 T/C; S07838: Chr08_18303703 A/G; S07839: Chr08_18333397 G/A; S07840: Chr08_18366408 C/G; S07841: Chr08_18384492 C/T; S07842: Chr08_18403174 A/G; S07843: Chr08_18471719 C/T; S07844: Chr08_18496532 T/A; S07845: Chr08_18511689 G/A; S07846: Chr08_18525024 C/T; S07847: Chr08_18552646 A/G; S07848: Chr08_18598586 C/T; S07849: Chr08_18602537 C/T; S07850: Chr08_18660733 G/A; S07851: Chr08_18686117 T/C; S07852: Chr08_18703168 A/G; S07853: Chr08_18728894 T/C; S07854: Chr08_18753100 G/A; S07855: Chr08_18775553 T/C; S07856: Chr08_18804305 A/G; S07857: Chr08_18839017 C/G; S07858: Chr08_18879647 C/T; S07859: Chr08_18917185 C/T; S07860: Chr08_18928021 C/T; S07861: Chr08_18963546 C/T; S07862: Chr08_18983386 C/T; S07863: Chr08_19000538 C/T; S07864: Chr08_19038118 T/C; S07865: Chr08_19056879 C/G; S07866: Chr08_19084194 C/A; S07867: Chr08_19141689 A/G; S07868: Chr08_19152704 A/T; S07869: Chr08_19222326 A/G; S07870: Chr08_19262396 G/T; S07871: Chr08_19302162 T/C; S07872: Chr08_19353170 G/A; S07873: Chr08_19375087 C/T; S07874: Chr08_19455698 G/A; S07875: Chr08_19492544 C/T; S07876: Chr08_19515266 G/T; S07877: Chr08_19536081 A/G; S07878: Chr08_19609533 G/C; S07879: Chr08_19699457 A/G; S07880: Chr08_19700059 G/A; S07881: Chr08_19746885 C/T; S07882: Chr08_19777852 G/A; S07883: Chr08_19853041 G/A; S07884: Chr08_19949817 C/T; S07885: Chr08_19958302 C/T; S07886: Chr08_19981721 T/C; S07887: Chr08_20009876 T/C; S07888: Chr08_20048607 G/A; S07889: Chr08_20051354 T/C; S07890: Chr08_20081602 G/A; S07891: Chr08_20140371 T/A; S07892: Chr08_20157209 G/C; S07893: Chr08_20272858 T/C; S07894: Chr08_20296336 A/G; S07895: Chr08_20301811 A/C; S07896: Chr08_20430185 C/G; S07897: Chr08_20451392 G/A; S07898:

Chr08_20502206 G/A; S07899: Chr08_20588642 C/T; S07900: Chr08_20603559 C/T; S07901: Chr08_20698278 C/T; S07902: Chr08_20804984 C/T; S07903: Chr08_20835594 C/A; S07904: Chr08_20920236 T/C; S07905: Chr08_20981270 A/G; S07906: Chr08_21045453 C/T; S07907: Chr08_21050565 G/A; S07908: Chr08_21149631 T/G; S07909: Chr08_21153685 A/G; S07910: Chr08_21180366 G/C; S07911: Chr08_21223078 G/A; S07912: Chr08_21229346 G/T; S07913: Chr08_21261261 A/G; S07914: Chr08_21277003 T/C; S07915: Chr08_21306156 T/A; S07916: Chr08_21373852 A/G; S07917: Chr08_21394781 T/C; S07918: Chr08_21403523 C/T; S07919: Chr08_21432061 G/T; S07920: Chr08_21506648 T/C; S07921: Chr08_21554329 G/A; S07922: Chr08_21639447 C/G; S07923: Chr08_21651195 A/T; S07924: Chr08_21749534 A/G; S07925: Chr08_21750423 G/A; S07926: Chr08_21802940 A/G; S07927: Chr08_21841129 T/C; S07928: Chr08_21851535 C/A; S07929: Chr08_21894218 G/T; S07930: Chr08_21904648 T/A; S07931: Chr08_21933521 T/A; S07932: Chr08_21989032 A/G; S07933: Chr08_22000009 G/A; S07934: Chr08_22078860 G/A; S07935: Chr08_22166780 G/C; S07936: Chr08_22224600 C/T; S07937: Chr08_22343819 G/A; S07938: Chr08_22350068 A/G; S07939: Chr08_22426734 C/T; S07940: Chr08_22504437 A/G; S07941: Chr08_22526698 T/C; S07942: Chr08_22559926 G/A; S07943: Chr08_22584814 G/T; S07944: Chr08_22602882 A/T; S07945: Chr08_22750629 A/G; S07946: Chr08_22826666 A/G; S07947: Chr08_22924099 T/C; S07948: Chr08_22925150 C/G; S07949: Chr08_23046391 G/C; S07950: Chr08_23061573 A/G; S07951: Chr08_23076812 A/C; S07952: Chr08_23120626 C/G; S07953: Chr08_23134722 C/G; S07954: Chr08_23153550 G/T; S07955: Chr08_23178219 C/T; S07956: Chr08_23269753 T/C; S07957: Chr08_23275118 C/T; S07958: Chr08_23341913 G/C; S07959: Chr08_23362799 G/A; S07960: Chr08_23379978 G/C; S07961: Chr08_23405741 A/T; S07962: Chr08_23430276 T/A; S07963: Chr08_23451517 A/G; S07964: Chr08_23519296 C/T; S07965: Chr08_23555292 C/T; S07966: Chr08_23575056 C/A; S07967: Chr08_23876955 A/G; S07968: Chr08_23950218 C/T; S07969: Chr08_24204980 A/G; S07970: Chr08_24229843 C/G; S07971: Chr08_24775525 A/G; S07972: Chr08_25038577 G/A; S07973: Chr08_25081612 G/C; S07974: Chr08_25170926 A/G; S07975: Chr08_25409352 C/T; S07976: Chr08_25551543 C/T; S07977: Chr08_25635569 T/A; S07978: Chr08_25701144 C/T; S07979: Chr08_26076794 G/T; S07980: Chr08_26185274 T/G; S07981: Chr08_26350020 C/T; S07982: Chr08_26425019 T/G; S07983: Chr08_26725470 G/T; S07984: Chr08_26750363 G/A; S07985: Chr08_26825195 C/T; S07986: Chr08_27050629 G/A; S07987: Chr08_27181848 C/A; S07988: Chr08_27350027 C/T; S07989: Chr08_27434638 C/T; S07990: Chr08_27783176 C/T; S07991: Chr08_27801464 C/T; S07992: Chr08_28288411 A/C; S07993: Chr08_28332744 T/C; S07994: Chr08_28536038 C/T; S07995: Chr08_28680432 G/A; S07996: Chr08_28758147 A/C; S07997: Chr08_28920201 A/G; S07998: Chr08_28932227 G/A; S07999: Chr08_28950074 G/C; S08000: Chr08_29034881 A/T; S08001: Chr08_29123842 A/G; S08002: Chr08_29176404 T/A; S08003: Chr08_29259194 T/A; S08004: Chr08_29476619 A/C; S08005: Chr08_29706132 T/C; S08006: Chr08_29850344 T/C; S08007: Chr08_29940925 A/G; S08008: Chr08_30025276 C/T; S08009: Chr08_30769487 G/T; S08010: Chr08_31000795 T/C; S08011: Chr08_31114820 T/G; S08012: Chr08_31125785 T/A; S08013: Chr08_31200539 A/G; S08014: Chr08_31276278 T/C; S08015: Chr08_31500356 A/C; S08016: Chr08_31575106 A/C; S08017: Chr08_31725194 T/C; S08018: Chr08_31863730 A/G; S08019: Chr08_31877344 A/G; S08020: Chr08_32098872 A/C; S08021: Chr08_32102415 T/C; S08022: Chr08_32176940 G/C; S08023: Chr08_32325082 C/A; S08024: Chr08_32447544 C/A; S08025: Chr08_32450303 G/T; S08026: Chr08_32676955 A/C; S08027: Chr08_32754148 A/G; S08028: Chr08_33043458 C/T; S08029: Chr08_33300231 C/T; S08030: Chr08_33401254 A/G; S08031: Chr08_33475078 T/C; S08032: Chr08_33550179 T/G; S08033: Chr08_33625289 T/A; S08034: Chr08_33992671 G/C; S08035: Chr08_34002052 C/T; S08036: Chr08_34120361 A/G; S08037: Chr08_34205130 C/T; S08038: Chr08_34275039 A/C; S08039: Chr08_34413628 G/A; S08040: Chr08_34497416 G/A; S08041: Chr08_34548384 T/C; S08042: Chr08_34575212 A/C; S08043: Chr08_34663883 G/A; S08044: Chr08_34699467 A/G; S08045: Chr08_34704474 T/C; S08046: Chr08_34726645 G/T; S08047: Chr08_34863980 C/T; S08048: Chr08_34900022 C/T; S08049: Chr08_34976194 C/A; S08050: Chr08_35000079 C/T; S08051: Chr08_35082500 A/T; S08052: Chr08_35110954 G/A; S08053: Chr08_35125270 T/A; S08054: Chr08_35211452 G/A; S08055: Chr08_35225469 T/A; S08056: Chr08_35334114 C/T; S08057: Chr08_35350018 G/A; S08058: Chr08_35434030 G/T; S08059: Chr08_35457406 A/G; S08060: Chr08_35499076 C/T; S08061: Chr08_35504849 G/A; S08062: Chr08_35561386 G/A; S08063: Chr08_35597336 G/A; S08064: Chr08_35628494 T/A; S08065: Chr08_35666718 G/A; S08066: Chr08_35676865 A/G; S08067: Chr08_35728358 C/T; S08068: Chr08_35776075 G/A; S08069: Chr08_35807624 T/G; S08070: Chr08_35829137 C/T; S08071: Chr08_35942457 T/C; S08072: Chr08_35969825 G/A; S08073: Chr08_36027105 G/A; S08074: Chr08_36195207 C/T; S08075: Chr08_36201209 C/A; S08076: Chr08_36279499 A/G; S08077: Chr08_36402237 G/A; S08078: Chr08_36429248 T/C; S08079: Chr08_36450032 C/A; S08080: Chr08_36551098 A/C; S08081: Chr08_36606061 C/T; S08082: Chr08_36661612 C/A; S08083: Chr08_36701529 G/A; S08084: Chr08_36775922 G/A; S08085: Chr08_36837508 C/T; S08086: Chr08_36850041 A/G; S08087: Chr08_36946411 A/C; S08088: Chr08_36962396 T/C; S08089: Chr08_37015012 G/T; S08090: Chr08_37025145 C/T; S08091: Chr08_37161210 T/C; S08092: Chr08_37376799 T/C; S08093: Chr08_37480557 A/T; S08094: Chr08_37500386 A/G; S08095: Chr08_37645259 G/C; S08096: Chr08_37683665 T/C; S08097: Chr08_37721781 T/C; S08098: Chr08_37746119 C/T; S08099:

Chr08_37750114 G/A; S08100: Chr08_37825383 T/A; S08101: Chr08_37904321 C/T; S08102: Chr08_37944593 G/A; S08103: Chr08_37950928 T/C; S08104: Chr08_38025004 C/T; S08105: Chr08_38101241 A/G; S08106: Chr08_38190719 A/G; S08107: Chr08_38229046 G/A; S08108: Chr08_38252773 A/G; S08109: Chr08_38325098 G/A; S08110: Chr08_38533579 G/A; S08111: Chr08_38550010 T/G; S08112: Chr08_38632911 T/A; S08113: Chr08_38715092 G/A; S08114: Chr08_38726509 C/G; S08115: Chr08_38828744 A/T; S08116: Chr08_38850879 T/A; S08117: Chr08_38926845 A/G; S08118: Chr08_39014451 C/A; S08119: Chr08_39163167 G/A; S08120: Chr08_39253444 C/T; S08121: Chr08_39323782 G/T; S08122: Chr08_39375977 T/A; S08123: Chr08_39452474 A/G; S08124: Chr08_39530153 C/T; S08125: Chr08_39610774 A/T; S08126: Chr08_39734796 A/G; S08127: Chr08_39778468 C/T; S08128: Chr08_39854066 A/G; S08129: Chr08_39900115 C/G; S08130: Chr08_40147400 T/A; S08131: Chr08_40269617 G/A; S08132: Chr08_40295072 A/G; S08133: Chr08_210302834 C/G; S08134: Chr08_40326592 G/C; S08135: Chr08_40354842 T/C; S08136: Chr08_40380256 T/A; S08137: Chr08_40423602 G/A; S08138: Chr08_40425685 C/T; S08139: Chr08_40470024 G/A; S08140: Chr08_40479894 A/G; S08141: Chr08_40526844 A/G; S08142: Chr08_40559466 G/A; S08143: Chr08_40575361 C/T; S08144: Chr08_40619910 A/G; S08145: Chr08_40684524 T/C; S08146: Chr08_40709663 A/G; S08147: Chr08_40732759 A/G; S08148: Chr08_40768008 C/T; S08149: Chr08_40796330 A/G; S08150: Chr08_40820397 A/C; S08151: Chr08_210841028 C/A; S08152: Chr08_40859845 T/G; S08153: Chr08_40875740 G/A; S08154: Chr08_40900743 C/T; S08155: Chr08_40943244 G/A; S08156: Chr08_40955313 T/C; S08157: Chr08_40983073 A/G; S08158: Chr08_41009813 C/G; S08159: Chr08_41036962 G/A; S08160: Chr08_41051079 T/C; S08161: Chr08_41079912 T/G; S08162: Chr08_41101336 G/A; S08163: Chr08_41192419 C/A; S08164: Chr08_41217767 C/G; S08165: Chr08_41258641 A/G; S08166: Chr08_41328845 A/C; S08167: Chr08_41363986 A/T; S08168: Chr08_41379672 C/T; S08169: Chr08_41401587 T/C; S08170: Chr08_41470627 T/C; S08171: Chr08_41479744 G/T; S08172: Chr08_41527173 A/G; S08173: Chr08_41570358 A/G; S08174: Chr08_41584919 G/A; S08175: Chr08_41600040 T/C; S08176: Chr08_211628110 A/G; S08177: Chr08_41767566 T/C; S08178: Chr08_41776708 G/A; S08179: Chr08_41807920 T/C; S08180: Chr08_41828898 C/T; S08181: Chr08_41866305 A/G; S08182: Chr08_41881061 T/C; S08183: Chr08_41900333 C/T; S08184: Chr08_41932498 T/C; S08185: Chr08_41965395 C/T; S08186: Chr08_41975184 A/G; S08187: Chr08_42029722 G/A; S08188: Chr08_42050572 C/T; S08189: Chr08_42078128 A/G; S08190: Chr08_42100034 C/T; S08191: Chr08_42125243 C/T; S08192: Chr08_42150086 C/A; S08193: Chr08_42220266 C/A; S08194: Chr08_42226089 A/T; S08195: Chr08_42266836 T/C; S08196: Chr08_42281579 A/T; S08197: Chr08_42323787 A/T; S08198: Chr08_42328967 G/T; S08199: Chr08_42350867 G/C; S08200: Chr08_42375016 G/T; S08201: Chr08_42408949 G/C; S08202: Chr08_42439047 A/G; S08203: Chr08_42469377 C/A; S08204: Chr08_42477134 T/C; S08205: Chr08_42529305 A/G; S08206: Chr08_42551495 A/C; S08207: Chr08_42586733 A/T; S08208: Chr08_42604839 A/G; S08209: Chr08_42644442 G/A; S08210: Chr08_42651773 G/A; S08211: Chr08_42680181 T/C; S08212: Chr08_42707972 T/C; S08213: Chr08_42727110 T/A; S08214: Chr08_42760680 T/C; S08215: Chr08_42779868 A/G; S08216: Chr08_42800842 C/T; S08217: Chr08_42835527 T/C; S08218: Chr08_42877469 A/T; S08219: Chr08_42904239 A/C; S08220: Chr08_42954805 C/T; S08221: Chr08_42977728 A/G; S08222: Chr08_43004601 C/T; S08223: Chr08_43031011 A/G; S08224: Chr08_43084528 A/G; S08225: Chr08_43135899 T/C; S08226: Chr08_43188511 G/A; S08227: Chr08_43206064 T/C; S08228: Chr08_213225141 G/A; S08229: Chr08_43262854 C/A; S08230: Chr08_43283434 T/C; S08231: Chr08_43300853 G/A; S08232: Chr08_43328129 A/G; S08233: Chr08_43361138 C/T; S08234: Chr08_43375195 T/G; S08235: Chr08_43407690 C/T; S08236: Chr08_43428478 T/C; S08237: Chr08_43453091 A/C; S08238: Chr08_43486465 C/T; S08239: Chr08_43509128 C/G; S08240: Chr08_43531348 C/T; S08241: Chr08_43555140 C/G; S08242: Chr08_43595438 G/A; S08243: Chr08_43600988 G/C; S08244: Chr08_43641093 G/A; S08245: Chr08_43650315 G/A; S08246: Chr08_43676380 A/T; S08247: Chr08_43700218 G/T; S08248: Chr08_43727122 A/G; S08249: Chr08_43750106 C/G; S08250: Chr08_43776832 C/A; S08251: Chr08_43808487 A/G; S08252: Chr08_43827238 G/A; S08253: Chr08_43850225 T/G; S08254: Chr08_43890131 G/A; S08255: Chr08_43900314 C/T; S08256: Chr08_43928516 G/T; S08257: Chr08_43984848 G/A; S08258: Chr08_214013959 A/C; S08259: Chr08_44032688 A/G; S08260: Chr08_44055501 G/A; S08261: Chr08_44084665 G/A; S08262: Chr08_44105812 T/A; S08263: Chr08_44126018 A/T; S08264: Chr08_44151440 G/T; S08265: Chr08_44186180 A/G; S08266: Chr08_44202939 A/G; S08267: Chr08_44250197 A/G; S08268: Chr08_44277657 G/A; S08269: Chr08_44305946 A/C; S08270: Chr08_44334755 A/G; S08271: Chr08_44350593 G/T; S08272: Chr08_44379816 G/C; S08273: Chr08_44403398 G/A; S08274: Chr08_44428411 A/G; S08275: Chr08_44516729 A/G; S08276: Chr08_44579046 A/T; S08277: Chr08_44611328 C/T; S08278: Chr08_44625940 T/C; S08279: Chr08_44673111 T/C; S08280: Chr08_44683661 G/A; S08281: Chr08_44706029 G/A; S08282: Chr08_214725861 C/T; S08283: Chr08_214754026 T/C; S08284: Chr08_44795785 G/A; S08285: Chr08_44802718 G/A; S08286: Chr08_44825547 T/C; S08287: Chr08_44857533 T/A; S08288: Chr08_44894555 T/C; S08289: Chr08_44908360 T/C; S08290: Chr08_44950147 T/A; S08291: Chr08_44983836 C/T; S08292: Chr08_45024521 G/C; S08293: Chr08_45025999 G/A; S08294: Chr08_45066445 A/G; S08295: Chr08_45075520 A/G; S08296: Chr08_45115984 T/A; S08297: Chr08_45131702 T/C; S08298: Chr08_45153171 C/T; S08299: Chr08_45184902 A/C; S08300:

Chr08_45200923 T/C; S08301: Chr08_45225436 C/T; S08302: Chr08_45298536 G/A; S08303: Chr08_45303701 C/A; S08304: Chr08_45339882 G/A; S08305: Chr08_45351242 T/C; S08306: Chr08_45376514 A/T; S08307: Chr08_45406448 C/T; S08308: Chr08_45427974 A/G; S08309: Chr08_45459064 G/T; S08310: Chr08_45490743 A/G; S08311: Chr08_45506182 T/C; S08312: Chr08_45528017 C/T; S08313: Chr08_45554101 T/C; S08314: Chr08_45575256 C/G; S08315: Chr08_45608194 A/C; S08316: Chr08_45628684 C/T; S08317: Chr08_45655349 G/A; S08318: Chr08_215683625 C/T; S08319: Chr08_45706910 C/T; S08320: Chr08_215813778 T/C; S08321: Chr08_45825770 T/A: 508322: Chr08_45913059 C/T; S08323: Chr08_45939398 G/A; S08324: Chr08_45958922 T/C; S08325: Chr08_46019539 G/A; S08326: Chr08_46056956 C/T; S08327: Chr08_46093989 G/C; S08328: Chr08_46102321 C/G; S08329: Chr08_46131824 C/T; S08330: Chr08_46150354 G/A; S08331: Chr08_46177116 C/A; S08332: Chr08_46207309 C/T; S08333: Chr08_46239110 G/A; S08334: Chr08_46278339 T/G; S08335: Chr08_46311293 A/G; S08336: Chr08_46326275 G/A; S08337: Chr08_46384244 T/G; S08338: Chr08_46400699 A/G; S08339: Chr08_46442484 T/C; S08340: Chr08_46454799 C/A; S08341: Chr08_46475714 G/T; S08342: Chr08_46502079 T/C; S08343: Chr08_46526970 A/T; S08344: Chr08_46550034 G/A; S08345: Chr08_46575050 A/T; S08346: Chr08_46603980 T/G; S08347: Chr08_46645467 A/G; S08348: Chr08_46658298 G/A; S08349: Chr08_46677591 A/G; S08350: Chr08_46703614 C/T; S08351: Chr08_46733062 G/T; S08352: Chr08_46753099 G/A; S08353: Chr08_46779549 T/C; S08354: Chr08_46816645 A/G; S08355: Chr08_46830264 G/C; S08356: Chr08_46863453 T/C; S08357: Chr08_46885184 G/A; S08358: Chr08_46900170 A/G; S08359: Chr08_46926890 C/G; S08360: Chr08_46957929 G/A; S08361: Chr08_46983774 T/A; S08362: Chr08_47002324 T/C; S08363: Chr08_47038818 C/T; S08364: Chr08_47061716 G/A; S08365: Chr08_47075030 C/T; S08366: Chr08_47100233 T/G; S08367: Chr08_47125227 C/T; S08368: Chr08_47153079 G/A; S08369: Chr08_47252094 C/T; S08370: Chr08_47284810 T/A; S08371: Chr08_47303020 A/G; S08372: Chr08_47332464 T/C; S08373: Chr08_47351566 C/T; S08374: Chr08_47407551 T/A; S08375: Chr08_47482551 T/G; S08376: Chr08_47512843 T/C; S08377: Chr08_47525277 T/A; S08378: Chr08_47550043 G/A; S08379: Chr08_47581457 C/T; S08380: Chr08_47621530 G/C; S08381: Chr08_47629848 G/C; S08382: Chr08_47650838 A/C; S08383: Chr08_47676602 G/A; S08384: Chr08_47707980 G/A; S08385: Chr08_47725261 A/G; S08386: Chr08_47755831 C/A; S08387: Chr08_47785545 T/C; S08388: Chr08_47806226 T/A; S08389: Chr09_00002953 G/A; S08390: Chr09_00028995 A/G; S08391: Chr09_00060198 T/C; S08392: Chr09_00076686 G/T; S08393: Chr09_00114974 A/C; S08394: Chr09_00195679 A/G; S08395: Chr09_00204723 T/C; S08396: Chr09_00288188 T/G; S08397: Chr09_00303511 C/G; S08398: Chr09_00325462 T/C; S08399: Chr09_00351277 G/C; S08400: Chr09_00378194 T/C;

S08401: Chr09_00403765 A/G; S08402: Chr09_00425069 G/A; S08403: Chr09_00458254 G/A; S08404: Chr09_00475009 G/A; S08405: Chr09_00500375 T/C; S08406: Chr09_00605773 T/C; S08407: Chr09_00627340 G/A; S08408: Chr09_00673239 G/A; S08409: Chr09_00675567 T/C; S08410: Chr09_00701222 G/C; S08411: Chr09_00734255 G/C; S08412: Chr09_00755326 G/A; S08413: Chr09_00782720 C/T; S08414: Chr09_00814007 T/C; S08415: Chr09_00835854 A/G; S08416: Chr09_00855241 T/A; S08417: Chr09_00876204 C/T; S08418: Chr09_00900042 A/T; S08419: Chr09_00925073 A/G; S08420: Chr09_00963684 G/A; S08421: Chr09_00975750 T/G; S08422: Chr09_01000051 T/C; S08423: Chr09_01026139 T/G; S08424: Chr09_01059283 G/A; S08425: Chr09_01102394 G/A; S08426: Chr09_01128170 C/T; S08427: Chr09_01152852 G/A; S08428: Chr09_01177323 G/A; S08429: Chr09_01204269 G/C; S08430: Chr09_01226192 A/G; S08431: Chr09_01251387 C/A; S08432: Chr09_01285174 C/G; S08433: Chr09_01304517 C/T; S08434: Chr09_01333114 G/T; S08435: Chr09_01396095 T/A; S08436: Chr09_01407771 T/C; S08437: Chr09_01431363 C/A; S08438: Chr09_01454953 A/G; S08439: Chr09_01480524 C/A; S08440: Chr09_01505756 G/C; S08441: Chr09_01528156 C/T; S08442: Chr09_01563510 G/C; S08443: Chr09_01578644 A/T; S08444: Chr09_01605548 C/T; S08445: Chr09_01630447 A/G; S08446: Chr09_01669891 A/G; S08447: Chr09_01676836 A/G; S08448: Chr09_01701943 T/A; S08449: Chr09_01731637 A/G; S08450: Chr09_01765287 A/C; S08451: Chr09_01777808 C/T; S08452: Chr09_01805211 A/G; S08453: Chr09_01826736 T/A; S08454: Chr09_01850879 T/C; S08455: Chr09_01880128 C/T; S08456: Chr09_01904702 G/A; S08457: Chr09_01950433 T/C; S08458: Chr09_02040426 C/A; S08459: Chr09_02075141 T/C; S08460: Chr09_02128381 G/A; S08461: Chr09_02155480 T/G; S08462: Chr09_02205078 T/C; S08463: Chr09_02226891 T/C; S08464: Chr09_02259045 A/G; S08465: Chr09_02288589 A/T; S08466: Chr09_02314878 T/G; S08467: Chr09_02332180 T/C; S08468: Chr09_02353616 T/A; S08469: Chr09_02406505 A/G; S08470: Chr09_02427715 G/A; S08471: Chr09_02516585 C/T; S08472: Chr09_02595423 G/A; S08473: Chr09_02610975 A/T; S08474: Chr09_02633976 A/T; S08475: Chr09_02675056 C/G; S08476: Chr09_02727793 A/G; S08477: Chr09_02756510 G/A; S08478: Chr09_02808435 C/G; S08479: Chr09_02835154 G/A; S08480: Chr09_02850421 C/T; 508481: Chr09_02878505 T/A; S08482: Chr09_02909053 A/G; S08483: Chr09_02928072 G/C; S08484: Chr09_02955383 C/T; S08485: Chr09_02986075 G/T; S08486: Chr09_03002034 G/A; S08487: Chr09_03145061 G/A; S08488: Chr09_03165826 A/G; S08489: Chr09_03217132 C/T; S08490: Chr09_03240453 A/G; S08491: Chr09_03251850 G/C; S08492: Chr09_03299167 A/G; S08493: Chr09_03305142 A/T; S08494: Chr09_03331704 T/C; S08495: Chr09_03354335 T/A; S08496: Chr09_03386210 A/G; S08497: Chr09_03403228 A/G; S08498: Chr09_03430900 G/A; S08499: Chr09_03456760 C/A; S08500: Chr09_03489006 A/G; S08501:

Chr09_03513916 G/A; S08502: Chr09_03579757 G/T; S08503: Chr09_03600378 G/A; S08504: Chr09_03625700 A/T; S08505: Chr09_03653595 G/A; S08506: Chr09_03698892 G/A; S08507: Chr09_03712567 G/A; S08508: Chr09_03729069 A/G; S08509: Chr09_03760572 T/C; S08510: Chr09_03785101 T/C; S08511: Chr09_03807228 T/C; S08512: Chr09_03840393 C/T; S08513: Chr09_03857924 C/T; S08514: Chr09_03889585 C/T; S08515: Chr09_03919138 G/A; S08516: Chr09_03930166 A/G; S08517: Chr09_03969344 A/G; S08518: Chr09_03976496 C/G; S08519: Chr09_04002199 T/A; S08520: Chr09_04075203 C/T; S08521: Chr09_04115542 C/A; S08522: Chr09_04151407 G/A; S08523: Chr09_04175068 G/A; S08524: Chr09_04201884 C/T; S08525: Chr09_04225663 G/A; S08526: Chr09_04265011 C/T; S08527: Chr09_04283906 A/C; S08528: Chr09_04301068 G/A; S08529: Chr09_04350271 C/T; S08530: Chr09_04383521 G/A; S08531: Chr09_04402120 T/C; S08532: Chr09_04447957 A/C; S08533: Chr09_04453300 C/G; S08534: Chr09_04482552 C/T; S08535: Chr09_04521054 T/A; S08536: Chr09_04557811 T/C; S08537: Chr09_04605238 C/T; S08538: Chr09_04625525 C/A; S08539: Chr09_04670190 G/A; S08540: Chr09_04689963 A/G; S08541: Chr09_04703638 A/G; S08542: Chr09_04737930 T/A; S08543: Chr09_04751458 G/C; S08544: Chr09_04781188 C/T; S08545: Chr09_04800261 C/T; S08546: Chr09_04860719 T/A; S08547: Chr09_04876617 T/G; S08548: Chr09_04931029 A/G; S08549: Chr09_04951282 A/G; S08550: Chr09_04998391 C/A; S08551: Chr09_05001601 A/T; S08552: Chr09_05032468 T/A; S08553: Chr09_05060043 T/C; S08554: Chr09_05083337 T/C; S08555: Chr09_05108019 A/G; S08556: Chr09_05131709 A/G; S08557: Chr09_05156275 A/G; S08558: Chr09_05186309 C/A; S08559: Chr09_05231664 G/A; S08560: Chr09_05251894 C/T; S08561: Chr09_05276892 T/C; S08562: Chr09_05367109 C/T; S08563: Chr09_05376819 G/A; S08564: Chr09_05418798 C/T; S08565: Chr09_05438479 T/G; S08566: Chr09_05474238 G/A; S08567: Chr09_05476989 T/A; S08568: Chr09_05500100 G/A; S08569: Chr09_05541629 A/G; S08570: Chr09_05553987 G/T; S08571: Chr09_05610817 G/A; S08572: Chr09_05652058 G/A; S08573: Chr09_05675060 G/C; S08574: Chr09_05709255 C/T; S08575: Chr09_05743646 T/A; S08576: Chr09_05775055 G/A; S08577: Chr09_05819671 G/A; S08578: Chr09_05841996 T/G; S08579: Chr09_05865206 G/C; S08580: Chr09_05895108 C/A; S08581: Chr09_05905708 C/T; S08582: Chr09_05926313 G/A; S08583: Chr09_05958312 C/T; S08584: Chr09_05975897 A/T; S08585: Chr09_06005546 C/T; S08586: Chr09_06025300 C/T; S08587: Chr09_06052910 T/G; S08588: Chr09_06075029 C/T; S08589: Chr09_06102563 G/C; S08590: Chr09_06126743 T/C; S08591: Chr09_06183293 A/C; S08592: Chr09_06212224 G/T; S08593: Chr09_06236415 C/T; S08594: Chr09_06263006 G/A; S08595: Chr09_06283810 T/C; S08596: Chr09_06305537 G/A; S08597: Chr09_06327113 G/A; S08598: Chr09_06360332 A/T; S08599: Chr09_06393612 G/T; S08600: Chr09_06411185 C/T; S08601: Chr09_06433420 A/T; S08602: Chr09_06469861 G/T; S08603: Chr09_06477186 T/A; S08604: Chr09_06511413 A/G; S08605: Chr09_06532643 A/G; S08606: Chr09_06551732 T/G; S08607: Chr09_06595419 A/T; S08608: Chr09_06624454 G/T; S08609: Chr09_06625017 C/T; S08610: Chr09_06653411 T/A; S08611: Chr09_06732432 A/G; S08612: Chr09_06800411 T/G; S08613: Chr09_06846610 A/T; S08614: Chr09_06880782 A/C; S08615: Chr09_06922223 G/A; S08616: Chr09_06955877 T/A; S08617: Chr09_06981135 T/C; S08618: Chr09_07027598 A/C; S08619: Chr09_07055829 T/C; S08620: Chr09_07149422 C/G; S08621: Chr09_07150100 G/A; S08622: Chr09_07179294 C/T; S08623: Chr09_07212490 G/T; S08624: Chr09_07230897 A/G; S08625: Chr09_07261543 G/A; S08626: Chr09_07290095 G/A; S08627: Chr09_07303360 C/T; S08628: Chr09_07368086 C/A; S08629: Chr09_07392217 G/T; S08630: Chr09_07418909 C/T; S08631: Chr09_07436051 A/C; S08632: Chr09_07480285 G/A; S08633: Chr09_07538099 C/T; S08634: Chr09_07550454 C/T; S08635: Chr09_07651136 G/A; S08636: Chr09_07708157 T/C; S08637: Chr09_07732560 G/T; S08638: Chr09_07756991 C/T; S08639: Chr09_07812135 A/G; S08640: Chr09_07864341 T/A; S08641: Chr09_07897366 A/G; S08642: Chr09_07901463 A/C; S08643: Chr09_07925617 A/G; S08644: Chr09_07979431 G/A; S08645: Chr09_08022739 C/A; S08646: Chr09_08027957 A/G; S08647: Chr09_08100548 G/C; S08648: Chr09_08139223 A/G; S08649: Chr09_08194478 C/T; S08650: Chr09_08200435 T/C; S08651: Chr09_08236384 A/T; S08652: Chr09_08255633 G/A; S08653: Chr09_08287154 C/A; S08654: Chr09_08305328 T/C; S08655: Chr09_08327492 C/T; S08656: Chr09_08352457 A/C; S08657: Chr09_08379373 G/T; S08658: Chr09_08437525 G/A; S08659: Chr09_08526491 T/C; S08660: Chr09_08609356 T/C; S08661: Chr09_08769879 A/C; S08662: Chr09_08805228 T/C; S08663: Chr09_08857388 A/G; S08664: Chr09_08893611 C/T; S08665: Chr09_08956891 A/T; S08666: Chr09_08975427 C/A; S08667: Chr09_09104545 C/G; S08668: Chr09_09126136 T/C; S08669: Chr09_09161720 G/A; S08670: Chr09_09175018 G/T; S08671: Chr09_09258161 A/G; S08672: Chr09_09295603 G/A; S08673: Chr09_09306827 T/A; S08674: Chr09_09364264 C/T; S08675: Chr09_09375672 G/A; S08676: Chr09_09502098 G/A; S08677: Chr09_09566382 A/T; S08678: Chr09_09591393 C/T; S08679: Chr09_09642026 T/C; S08680: Chr09_09655089 T/C; S08681: Chr09_09715264 C/A; S08682: Chr09_09725406 G/T; S08683: Chr09_09781869 G/A; S08684: Chr09_09800016 C/T; S08685: Chr09_09898879 A/G; S08686: Chr09_09961089 A/C; S08687: Chr09_09980046 C/A; S08688: Chr09_10000788 C/T; S08689: Chr09_10050327 C/T; S08690: Chr09_10080898 A/G; S08691: Chr09_10137293 T/C; S08692: Chr09_10150916 C/T; S08693: Chr09_10190098 A/G; S08694: Chr09_10217494 A/G; S08695: Chr09_10229342 C/T; S08696: Chr09_10263572 T/A; S08697: Chr09_10281975 A/G; S08698: Chr09_10375728 T/C; S08699: Chr09_10419114 G/T; S08700: Chr09_10467369 G/A; S08701: Chr09_10521904 T/G; S08702:

Chr09_10564903 C/T; S08703: Chr09_10603858 C/T; S08704: Chr09_10631703 T/A; S08705: Chr09_10662285 A/G; S08706: Chr09_10740415 C/T; S08707: Chr09_10778575 T/C; S08708: Chr09_10809892 G/A; S08709: Chr09_10888936 G/A; S08710: Chr09_10975021 G/A; S08711: Chr09_11144688 A/T; S08712: Chr09_11225420 A/T; S08713: Chr09_11302298 T/C; S08714: Chr09_11421875 G/A; S08715: Chr09_11469684 A/C; S08716: Chr09_11475563 T/G; S08717: Chr09_11503666 C/T; S08718: Chr09_11540528 C/T; S08719: Chr09_11605979 T/G; S08720: Chr09_11646865 G/A; S08721: Chr09_11650384 G/T; S08722: Chr09_11697763 C/T; S08723: Chr09_11704980 A/T; S08724: Chr09_11741334 T/A; S08725: Chr09_11758053 C/T; S08726: Chr09_11815695 T/A; S08727: Chr09_11866805 G/A; S08728: Chr09_11902503 A/G; S08729: Chr09_11936627 A/C; S08730: Chr09_12024490 C/A; S08731: Chr09_12025024 A/G; S08732: Chr09_12101122 A/G; S08733: Chr09_12182064 C/T; S08734: Chr09_12266641 A/C; S08735: Chr09_12289145 T/C; S08736: Chr09_12309248 T/C; S08737: Chr09_12353183 G/A; S08738: Chr09_12375038 A/G; S08739: Chr09_12468140 C/T; S08740: Chr09_12507989 T/G; S08741: Chr09_12536556 T/C; S08742: Chr09_12563549 G/A; S08743: Chr09_12575650 G/A; S08744: Chr09_12674356 G/A; S08745: Chr09_12701432 A/G; S08746: Chr09_12778379 C/T; S08747: Chr09_12821635 A/C; S08748: Chr09_12846899 G/A; S08749: Chr09_12857708 A/G; S08750: Chr09_12877886 G/A; S08751: Chr09_12938709 T/C; S08752: Chr09_12983801 G/C; S08753: Chr09_13011025 C/T; S08754: Chr09_13025221 G/T; S08755: Chr09_13144324 C/T; S08756: Chr09_13198938 G/C; S08757: Chr09_13231467 C/T; S08758: Chr09_13255530 G/A; S08759: Chr09_13492467 C/T; S08760: Chr09_13500009 A/T; S08761: Chr09_13727063 A/G; S08762: Chr09_13956286 C/T; S08763: Chr09_14100363 T/G; S08764: Chr09_14234460 A/G; S08765: Chr09_14250043 T/A; S08766: Chr09_14430335 T/C; S08767: Chr09_14529570 C/G; S08768: Chr09_14653650 G/A; S08769: Chr09_14675287 G/A; S08770: Chr09_14750503 A/T; S08771: Chr09_14876147 T/C; S08772: Chr09_15043355 C/T; S08773: Chr09_15050520 T/G; S08774: Chr09_15160511 C/G; S08775: Chr09_15189980 C/T; S08776: Chr09_15237106 C/T; S08777: Chr09_15538877 G/A; S08778: Chr09_15550104 A/T; S08779: Chr09_15654295 G/A; S08780: Chr09_15779438 A/G; S08781: Chr09_16202024 G/A; S08782: Chr09_16335588 T/C; S08783: Chr09_16425026 A/C; S08784: Chr09_16565312 C/T; S08785: Chr09_16650074 C/T; S08786: Chr09_16800362 G/A; S08787: Chr09_16877684 G/A; S08788: Chr09_17025140 G/A; S08789: Chr09_17306938 C/T; S08790: Chr09_17372519 G/A; S08791: Chr09_17494470 G/A; S08792: Chr09_17502647 A/G; S08793: Chr09_17833975 G/A; S08794: Chr09_17850673 G/A; S08795: Chr09_17994408 C/A; S08796: Chr09_18037242 A/C; S08797: Chr09_18100497 G/T; S08798: Chr09_18134122 C/T; S08799: Chr09_18157380 G/A; S08800: Chr09_18195249 A/G; S08801: Chr09_18309178 G/A; S08802: Chr09_18423361 T/C; S08803: Chr09_18469182 T/C; S08804: Chr09_18475615 A/G; S08805: Chr09_18563869 T/C; S08806: Chr09_18575783 A/T; S08807: Chr09_18683937 A/G; S08808: Chr09_18700441 A/G; S08809: Chr09_18803365 A/G; S08810: Chr09_18849901 T/C; S08811: Chr09_18851570 T/A; S08812: Chr09_18988655 A/G; S08813: Chr09_19046619 A/G; S08814: Chr09_19069769 G/C; S08815: Chr09_19075143 A/G; S08816: Chr09_19190155 T/G; S08817: Chr09_19200626 T/C; S08818: Chr09_19324331 T/C; S08819: Chr09_19329466 G/T; S08820: Chr09_19359190 A/G; S08821: Chr09_19422282 A/G; S08822: Chr09_19429348 G/A; S08823: Chr09_19499106 C/T; S08824: Chr09_19516522 T/C; S08825: Chr09_19536878 T/C; S08826: Chr09_19550162 C/T; S08827: Chr09_19579888 T/C; S08828: Chr09_19600666 A/T; S08829: Chr09_19725118 A/T; S08830: Chr09_19892455 G/A; S08831: Chr09_19968640 T/A; S08832: Chr09_19985890 T/C; S08833: Chr09_20062139 G/A; S08834: Chr09_20076149 A/G; S08835: Chr09_20134733 G/A; S08836: Chr09_20150362 G/A; S08837: Chr09_20294245 T/C; S08838: Chr09_20314513 G/C; S08839: Chr09_20337958 T/C; S08840: Chr09_20490764 G/C; S08841: Chr09_20502995 G/C; S08842: Chr09_20553798 T/G; S08843: Chr09_20575403 G/A; S08844: Chr09_20650082 C/A; S08845: Chr09_20725078 T/C; S08846: Chr09_20801032 C/T; S08847: Chr09_20875238 G/T; S08848: Chr09_21008507 A/G; S08849: Chr09_21082499 C/T; S08850: Chr09_21134729 A/G; S08851: Chr09_21189360 T/A; S08852: Chr09_21233375 A/G; S08853: Chr09_21297629 C/A; S08854: Chr09_21357060 G/A; S08855: Chr09_21401605 G/T; S08856: Chr09_21460686 T/C; S08857: Chr09_21481094 C/T; S08858: Chr09_21534262 A/G; S08859: Chr09_21593368 C/A; S08860: Chr09_21600107 C/G; S08861: Chr09_21698937 A/T; S08862: Chr09_21700433 C/G; S08863: Chr09_21725001 A/G; S08864: Chr09_21803103 G/A; S08865: Chr09_21825736 C/T; S08866: Chr09_21896149 G/A; S08867: Chr09_21938508 G/T; S08868: Chr09_21999566 A/G; S08869: Chr09_22042853 A/G; S08870: Chr09_22065348 T/C; S08871: Chr09_22089253 T/C; S08872: Chr09_22100490 C/T; S08873: Chr09_22175163 C/T; S08874: Chr09_22247359 G/C; S08875: Chr09_22254145 T/C; S08876: Chr09_22295624 C/T; S08877: Chr09_22300357 G/A; S08878: Chr09_22339556 T/C; S08879: Chr09_22377153 C/T; S08880: Chr09_22429587 G/T; S08881: Chr09_22525012 T/A; S08882: Chr09_22675546 C/A; S08883: Chr09_23022370 G/C; S08884: Chr09_23063825 T/C; S08885: Chr09_23075655 A/C; S08886: Chr09_23232030 A/G; S08887: Chr09_23342858 C/G; S08888: Chr09_23396205 G/A; S08889: Chr09_23422299 C/G; S08890: Chr09_23426346 C/T; S08891: Chr09_23450817 C/T; S08892: Chr09_23600625 A/T; S08893: Chr09_23675003 T/A; S08894: Chr09_23750354 T/C; S08895: Chr09_24125314 T/C; S08896: Chr09_24281553 G/A; S08897: Chr09_24640845 A/G; S08898: Chr09_24651345 C/T; S08899: Chr09_24713594 T/C; S08900: Chr09_24728923 C/T; S08901: Chr09_24750035 A/C; S08902: Chr09_24831904 A/G; S08903:

Chr09_24851891 T/C; S08904: Chr09_24947698 T/C; S08905: Chr09_24950505 T/C; S08906: Chr09_25014351 T/C; S08907: Chr09_25026076 A/G; S08908: Chr09_25101064 G/A; S08909: Chr09_25147048 G/A; S08910: Chr09_25150009 G/A; S08911: Chr09_25186767 A/G; S08912: Chr09_25200104 A/C; S08913: Chr09_25611447 C/T; S08914: Chr09_25853581 G/A; S08915: Chr09_26550635 C/T; S08916: Chr09_26651638 C/T; S08917: Chr09_26675167 G/A; S08918: Chr09_26825212 G/A; S08919: Chr09_26913186 C/T; S08920: Chr09_26925112 C/A; S08921: Chr09_27000979 T/G; S08922: Chr09_27256342 T/G; S08923: Chr09_27378919 G/A; S08924: Chr09_27402599 G/A; S08925: Chr09_27564171 A/G; S08926: Chr09_27591444 G/A; S08927: Chr09_27600138 C/T; S08928: Chr09_27696251 A/C; S08929: Chr09_27700585 T/C; S08930: Chr09_27725186 C/T; S08931: Chr09_27950327 C/T; S08932: Chr09_28025440 C/T; S08933: Chr09_28100046 T/C; S08934: Chr09_28296550 T/C; S08935: Chr09_28305625 G/A; S08936: Chr09_28371392 C/T; S08937: Chr09_28383557 G/A; S08938: Chr09_28411009 A/G; S08939: Chr09_28426149 T/C; S08940: Chr09_28503049 C/A; S08941: Chr09_28562618 T/C; S08942: Chr09_28583021 A/C; S08943: Chr09_28629244 G/C; S08944: Chr09_28660303 T/C; S08945: Chr09_28675015 C/A; S08946: Chr09_28767908 G/A; S08947: Chr09_28779077 C/T; S08948: Chr09_28800053 C/A; S08949: Chr09_28947214 T/A; S08950: Chr09_28953316 T/C; S08951: Chr09_29036312 T/C: S08952: Chr09_29064774 A/G; S08953: Chr09_29075837 T/A; S08954: Chr09_29155475 G/C; S08955: Chr09_29213150 G/A; S08956: Chr09_29278049 G/A; S08957: Chr09_29311469 A/G; S08958: Chr09_29337237 A/G; S08959: Chr09_29423474 C/T; S08960: Chr09_29425032 T/C; S08961: Chr09_29482911 G/A; S08962: Chr09_29608720 G/A; S08963: Chr09_29635620 A/C; S08964: Chr09_29824840 G/A; S08965: Chr09_29825526 G/A; S08966: Chr09_29907751 C/T; S08967: Chr09_29934738 C/T; S08968: Chr09_29997689 T/G; S08969: Chr09_30004589 A/T; S08970: Chr09_30052725 T/C; S08971: Chr09_30131314 G/T; S08972: Chr09_30151286 C/T; S08973: Chr09_30304438 A/C; S08974: Chr09_30325024 A/G; S08975: Chr09_30400109 T/G; S08976: Chr09_30625016 A/T; S08977: Chr09_30700208 A/G; S08978: Chr09_30853078 T/C; S08979: Chr09_30875007 A/G; S08980: Chr09_30950064 C/A; S08981: Chr09_31028451 G/T; S08982: Chr09_31085917 T/A; S08983: Chr09_31149543 G/T; S08984: Chr09_31171649 A/G; S08985: Chr09_31176267 T/G; S08986: Chr09_31200812 T/C; S08987: Chr09_31347137 G/A; S08988: Chr09_31404390 G/C; S08989: Chr09_31425148 T/C; S08990: Chr09_31720828 C/T; S08991: Chr09_31726953 C/G; S08992: Chr09_31827689 A/C; S08993: Chr09_31966227 A/G; S08994: Chr09_32033996 T/C; S08995: Chr09_32050754 G/C; S08996: Chr09_32169664 G/T; S08997: Chr09_32339931 G/A; S08998: Chr09_32365975 C/T; S08999: Chr09_32390523 T/A; S09000: Chr09_32401612 C/A; S09001: Chr09_32426760 G/A; S09002: Chr09_32468593 C/T; S09003: Chr09_32506948 G/T; S09004: Chr09_32529380 A/G; S09005: Chr09_32558110 A/G; S09006: Chr09_32593082 C/T; S09007: Chr09_32600318 A/T; S09008: Chr09_32639665 C/T; S09009: Chr09_32685328 T/C; S09010: Chr09_32747409 G/T; S09011: Chr09_32751399 G/A; S09012: Chr09_32775411 A/G; S09013: Chr09_32815949 T/C; S09014: Chr09_32900057 A/G; S09015: Chr09_33031675 C/T; S09016: Chr09_33064429 T/G; S09017: Chr09_33166539 C/T; S09018: Chr09_33269200 A/T; S09019: Chr09_33276768 C/T; S09020: Chr09_33352518 G/T; S09021: Chr09_33430138 A/G; S09022: Chr09_33502306 T/C; S09023: Chr09_33531083 G/A; S09024: Chr09_33561287 T/A; S09025: Chr09_33608343 G/A; S09026: Chr09_33629886 T/A; S09027: Chr09_33655484 C/T; S09028: Chr09_33718965 C/A; S09029: Chr09_33754256 A/C; S09030: Chr09_33837108 G/T; S09031: Chr09_33850023 A/T; S09032: Chr09_33886989 C/T; S09033: Chr09_33944821 T/C; S09034: Chr09_33970453 C/T; S09035: Chr09_33975460 G/A; S09036: Chr09_34040278 A/G; S09037: Chr09_34096160 G/A; S09038: Chr09_34132842 G/A; S09039: Chr09_34150595 G/T; S09040: Chr09_34253498 T/C; S09041: Chr09_34373966 T/C; S09042: Chr09_34377550 T/A; S09043: Chr09_34480943 C/G; S09044: Chr09_34552898 C/T; S09045: Chr09_34697128 G/T; S09046: Chr09_34771675 T/A; S09047: Chr09_34775188 A/T; S09048: Chr09_34856467 A/G; S09049: Chr09_34966945 C/G; S09050: Chr09_34981876 G/C; S09051: Chr09_35060295 G/A; S09052: Chr09_35126852 C/A; S09053: Chr09_35222332 C/T; S09054: Chr09_35354970 T/C; S09055: Chr09_35479215 C/T; S09056: Chr09_35501507 A/T; S09057: Chr09_35582172 C/T; S09058: Chr09_35674085 C/A; S09059: Chr09_35795261 T/G; S09060: Chr09_35830423 C/T; S09061: Chr09_35879535 G/A; S09062: Chr09_35900128 C/T; S09063: Chr09_35982073 T/C; S09064: Chr09_36009294 A/T; S09065: Chr09_36025772 G/A; S09066: Chr09_36057297 A/G; S09067: Chr09_36118746 T/C; S09068: Chr09_36203486 C/T; S09069: Chr09_36283225 C/T; S09070: Chr09_36309330 T/C; S09071: Chr09_36375263 C/T; S09072: Chr09_36476727 C/A; S09073: Chr09_36570837 A/G; S09074: Chr09_36575653 A/G; S09075: Chr09_36650146 A/G; S09076: Chr09_36750321 T/A; S09077: Chr09_36783286 C/T; S09078: Chr09_36800017 T/A; S09079: Chr09_36848827 A/G; S09080: Chr09_36886634 C/G; S09081: Chr09_36917470 G/T; S09082: Chr09_36928428 C/A; S09083: Chr09_36963321 G/C; S09084: Chr09_36995084 T/C; S09085: Chr09_37072226 T/C; S09086: Chr09_37080049 A/C; S09087: Chr09_37121298 T/A; S09088: Chr09_37140717 G/A; S09089: Chr09_37154864 G/A; S09090: Chr09_37220002 T/C; S09091: Chr09_37240271 G/A; S09092: Chr09_37286702 G/A; S09093: Chr09_37339792 G/A; S09094: Chr09_37368943 G/A; S09095: Chr09_37448542 G/A; S09096: Chr09_37450448 A/G; S09097: Chr09_37478262 C/T; S09098: Chr09_37502205 G/A; S09099: Chr09_37528718 C/A; S09100: Chr09_37567588 A/G; S09101: Chr09_37576078 A/T; S09102: Chr09_37605891 A/G; S09103: Chr09_37636447 A/C; S09104:

Chr09_37651938 G/T; S09105: Chr09_37711730 G/C; S09106: Chr09_37727135 G/A; S09107: Chr09_37756366 T/A; S09108: Chr09_37810921 T/A; S09109: Chr09_37834579 G/C; S09110: Chr09_37850874 C/T; S09111: Chr09_37877689 C/T; S09112: Chr09_37906096 G/T; S09113: Chr09_37928292 A/G; S09114: Chr09_37958299 A/G; S09115: Chr09_37989391 T/C; S09116: Chr09_38000599 C/T; S09117: Chr09_38034135 C/A; S09118: Chr09_38092957 T/C; S09119: Chr09_38104919 T/C; S09120: Chr09_38139511 T/C; S09121: Chr09_38162129 G/T; S09122: Chr09_38178519 C/G; S09123: Chr09_38249392 A/G; S09124: Chr09_38260592 A/G; S09125: Chr09_38285919 T/C; S09126: Chr09_38324331 T/C; S09127: Chr09_38345993 G/A; S09128: Chr09_38355169 A/C; S09129: Chr09_38376818 A/G; S09130: Chr09_38400114 T/C; S09131: Chr09_38430124 T/C; S09132: Chr09_38450086 C/A; S09133: Chr09_38476031 A/G; S09134: Chr09_38500459 C/T; S09135: Chr09_38542872 G/A; S09136: Chr09_38553476 G/T; 509137: Chr09_38588298 C/T; S09138: Chr09_38600017 C/T; S09139: Chr09_38625476 T/C; S09140: Chr09_38661600 A/T; S09141: Chr09_38693144 T/C; S09142: Chr09_38704736 C/A; S09143: Chr09_38751029 A/C; S09144: Chr09_38776058 C/T; S09145: Chr09_38803895 G/A; S09146: Chr09_38843968 T/A; S09147: Chr09_38859403 T/C; S09148: Chr09_38875376 C/T; S09149: Chr09_38902705 G/T; S09150: Chr09_38931781 A/G; S09151: Chr09_38958460 T/A; S09152: Chr09_38995828 G/A; S09153: Chr09_39035084 T/G; S09154: Chr09_39050813 C/A; S09155: Chr09_39077439 T/G; S09156: Chr09_39106030 T/G; S09157: Chr09_39137413 T/C; S09158: Chr09_39176369 T/C; S09159: Chr09_39200075 C/T; S09160: Chr09_39236551 G/A; S09161: Chr09_39287052 G/A; S09162: Chr09_39300088 G/A; S09163: Chr09_39343182 A/T; S09164: Chr09_39350396 T/C; S09165: Chr09_39375108 A/T; S09166: Chr09_39411135 T/G; S09167: Chr09_39426468 C/T; S09168: Chr09_39454893 A/G; S09169: Chr09_39506624 A/G; S09170: Chr09_39526243 T/G; S09171: Chr09_39554106 A/C; S09172: Chr09_39593645 T/C; S09173: Chr09_39608782 T/C; S09174: Chr09_39630721 C/T; S09175: Chr09_39653180 T/A; S09176: Chr09_39685266 A/G; S09177: Chr09_39708237 T/G; S09178: Chr09_39730897 T/C; S09179: Chr09_39758598 G/C; S09180: Chr09_39814026 G/A; S09181: Chr09_39834202 A/T; S09182: Chr09_39856135 A/G; S09183: Chr09_39887650 G/A; S09184: Chr09_39911526 C/G; S09185: Chr09_39929820 T/G; S09186: Chr09_39950531 A/G; S09187: Chr09_39978172 C/T; S09188: Chr09_40040735 A/G; S09189: Chr09_40052962 A/T; S09190: Chr09_40078265 T/A; S09191: Chr09_40110685 A/C; S09192: Chr09_40131093 G/T; S09193: Chr09_40151203 C/T; S09194: Chr09_40202004 A/T; S09195: Chr09_40237927 A/C; S09196: Chr09_40259931 T/A; S09197: Chr09_40280508 C/T; S09198: Chr09_40307142 A/G; S09199: Chr09_40330303 C/T; S09200: Chr09_40354801 C/T; S09201: Chr09_40375594 T/A; S09202: Chr09_40402692 A/C; S09203: Chr09_40442407 C/T; S09204: Chr09_40496435 A/G; S09205: Chr09_40521623 C/T; S09206: Chr09_40529107 C/T; S09207: Chr09_40617431 A/G; S09208: Chr09_40641857 A/T; S09209: Chr09_40691073 G/A; S09210: Chr09_40729013 C/T; S09211: Chr09_40750164 G/A; S09212: Chr09_40780865 T/C; S09213: Chr09_40804978 A/C; S09214: Chr09_40828976 G/C; S09215: Chr09_40860730 A/T; S09216: Chr09_40877516 G/C; S09217: Chr09_40901351 A/G; S09218: Chr09_40927352 C/T; S09219: Chr09_40958348 G/A; S09220: Chr09_40987277 T/C; S09221: Chr09_41022674 G/C; S09222: Chr09_41058607 C/T; S09223: Chr09_41076114 T/C; S09224: Chr09_41100368 C/A; S09225: Chr09_41138380 T/C; S09226: Chr09_41156689 T/A; S09227: Chr09_41175510 C/T; S09228: Chr09_41207254 T/C; S09229: Chr09_41240494 T/C; S09230: Chr09_41252734 G/A; S09231: Chr09_41275255 A/C; S09232: Chr09_41311400 C/A; S09233: Chr09_41340304 C/A; S09234: Chr09_41362084 A/T; S09235: Chr09_41379252 C/G; S09236: Chr09_41408433 T/C; S09237: Chr09_41455306 G/T; S09238: Chr09_41483379 A/G; S09239: Chr09_41512465 A/G; S09240: Chr09_41558984 G/A; S09241: Chr09_41576646 C/T; S09242: Chr09_41601643 G/T; S09243: Chr09_41625776 T/C; S09244: Chr09_41655117 C/T; S09245: Chr09_41676859 G/A; S09246: Chr09_41714149 T/C; S09247: Chr09_41736236 T/A; S09248: Chr09_41765659 T/C; S09249: Chr09_41777476 C/G; S09250: Chr09_41801924 G/C; S09251: Chr09_41890348 G/A; S09252: Chr09_41909827 G/A; S09253: Chr09_41943355 A/C; S09254: Chr09_41951129 A/G; S09255: Chr09_41975603 C/T; S09256: Chr09_42019575 G/A; S09257: Chr09_42026148 T/C; S09258: Chr09_42065704 A/G; S09259: Chr09_42076921 A/T; S09260: Chr09_42101163 A/G; S09261: Chr09_42125133 C/T; S09262: Chr09_42163428 G/C; S09263: Chr09_42181140 T/C; S09264: Chr09_42208510 A/T; S09265: Chr09_42225677 C/T; S09266: Chr09_42254662 T/C; S09267: Chr09_42275783 T/G; S09268: Chr09_42306347 G/C; S09269: Chr09_42356522 T/C; S09270: Chr09_42388395 A/C; S09271: Chr09_42400809 C/G; S09272: Chr09_42428481 C/T; S09273: Chr09_42451094 T/C; S09274: Chr09_42483007 T/G; S09275: Chr09_42501758 A/T; S09276: Chr09_42531569 A/G; S09277: Chr09_42586008 C/T; S09278: Chr09_42601477 C/A; S09279: Chr09_42625539 C/G; S09280: Chr09_42684069 A/C; S09281: Chr09_42700212 T/C; S09282: Chr09_42822295 G/T; S09283: Chr09_42884416 A/G; S09284: Chr09_42911741 T/G; S09285: Chr09_42936473 C/A; S09286: Chr09_42958916 G/A; S09287: Chr09_42978224 A/G; S09288: Chr09_43003730 T/C; S09289: Chr09_43036466 T/A; S09290: Chr09_43068878 T/C; S09291: Chr09_43079098 G/A; S09292: Chr09_43109498 A/T; S09293: Chr09_43171460 T/A; S09294: Chr09_43197206 C/T; S09295: Chr09_43202321 C/G; S09296: Chr09_43238096 A/C; S09297: Chr09_43254205 T/A; S09298: Chr09_43280223 A/T; S09299: Chr09_43312651 G/C; S09300: Chr09_43332242 T/C; S09301: Chr09_43356211 A/G; S09302: Chr09_43377796 T/C; S09303: Chr09_43411318 T/C; S09304: Chr09_43426615 T/C; S09305:

Chr09_43451029 A/T; S09306: Chr09_43476639 A/C; S09307: Chr09_43500250 C/T; S09308: Chr09_43535674 A/G; S09309: Chr09_43566747 T/A; S09310: Chr09_43575272 A/G; S09311: Chr09_43607313 G/A; S09312: Chr09_43625432 G/A; S09313: Chr09_43667129 C/T; S09314: Chr09_43684550 C/T; S09315: Chr09_43710531 G/A; S09316: Chr09_43729076 G/C; S09317: Chr09_43751430 A/T; S09318: Chr09_43775281 A/G; S09319: Chr09_43805003 G/T; S09320: Chr09_43825040 T/C; S09321: Chr09_43881483 G/C; S09322: Chr09_43906224 G/A; S09323: Chr09_43927286 T/A; S09324: Chr09_43950106 G/C; S09325: Chr09_43975062 T/A; S09326: Chr09_44001312 G/T; S09327: Chr09_44032744 C/T; S09328: Chr09_44053258 C/T; S09329: Chr09_44083939 T/C; S09330: Chr09_44123069 G/A; S09331: Chr09_44126777 G/A; S09332: Chr09_44153558 A/T; S09333: Chr09_44197329 C/G; S09334: Chr09_44201081 A/T; S09335: Chr09_44235949 T/C; S09336: Chr09_44252217 A/C; S09337: Chr09_44275367 G/A; S09338: Chr09_44322265 A/G; S09339: Chr09_44343635 C/T; S09340: Chr09_44359178 A/G; S09341: Chr09_44379328 A/G; S09342: Chr09_44863602 C/T; S09343: Chr09_214875331 T/C; S09344: Chr09_44900977 A/T; S09345: Chr09_44932188 A/G; S09346: Chr09_44953870 T/C; S09347: Chr09_44979888 C/T; S09348: Chr09_45007126 T/C; S09349: Chr09_45029019 C/T; S09350: Chr09_45063397 A/G; S09351: Chr09_45078319 C/G; S09352: Chr09_45107106 T/A; S09353: Chr09_45151699 T/A; S09354: Chr09_45178630 A/T; S09355: Chr09_45200360 G/A; S09356: Chr09_45232196 C/T; S09357: Chr09_45251551 T/A; S09358: Chr09_45275016 A/G; S09359: Chr09_45303326 G/T; S09360: Chr09_45327471 T/A; S09361: Chr09_45353617 G/A; S09362: Chr09_45378105 A/G; S09363: Chr09_45402140 T/G; S09364: Chr09_45425654 C/T; S09365: Chr09_45454849 C/A; S09366: Chr09_45475965 G/T; S09367: Chr09_45511560 G/A; S09368: Chr09_45525885 T/G; S09369: Chr09_45557174 A/G; S09370: Chr09_45581015 T/C; S09371: Chr09_45603386 G/T; S09372: Chr09_45628603 G/C; S09373: Chr09_45651299 A/G; S09374: Chr09_45676405 G/A; S09375: Chr09_45711122 T/G; S09376: Chr09_45728133 T/C; S09377: Chr09_45758856 G/C; S09378: Chr09_45781605 A/G; S09379: Chr09_45805533 T/G; S09380: Chr09_45833385 A/G; S09381: Chr09_45852678 C/T; S09382: Chr09_45885307 A/G; S09383: Chr09_45911888 C/T; S09384: Chr09_45930488 C/A; S09385: Chr09_45950233 T/G; S09386: Chr09_45975341 C/A; S09387: Chr09_46033797 G/T; S09388: Chr09_46099292 G/A; S09389: Chr09_46101422 A/C; S09390: Chr09_46183240 A/G; S09391: Chr09_46200899 C/A; S09392: Chr09_46229783 A/T; S09393: Chr09_46256221 T/C; S09394: Chr09_46276810 T/C; S09395: Chr09_46308505 G/A; S09396: Chr09_216327123 C/G; S09397: Chr09_46359395 A/G; S09398: Chr09_46379193 G/T; S09399: Chr09_46404352 C/G; S09400: Chr09_46431739 A/G; S09401: Chr09_46456356 T/G; S09402: Chr09_46478149 T/A; S09403: Chr09_46500751 A/G; S09404: Chr09_46544673 G/T; S09405: Chr09_46571264 A/C; S09406: Chr09_46589096 T/C; S09407: Chr09_46612186 G/C; S09408: Chr09_46625050 G/C; S09409: Chr09_46651352 G/A; S09410: Chr09_46684650 G/A; S09411: Chr09_46701581 T/C; S09412: Chr09_46725523 A/G; S09413: Chr09_46779824 C/G; S09414: Chr09_46802196 C/T; S09415: Chr09_46836433 A/G; S09416: Chr09_46851653 C/T; S09417: Chr09_46880576 T/G; S09418: Chr09_46900248 G/T; S09419: Chr09_46925401 T/G; S09420: Chr09_46965184 T/C; S09421: Chr09_46975246 A/G; S09422: Chr09_47003233 G/A; S09423: Chr09_47027982 A/G; S09424: Chr09_47058829 G/A; S09425: Chr09_47084097 T/C; S09426: Chr09_47101756 T/A; S09427: Chr09_47125390 A/T; S09428: Chr09_47156687 G/C; S09429: Chr09_47205981 C/T; S09430: Chr09_47240709 C/T; S09431: Chr09_47260219 A/C; S09432: Chr09_47276868 T/A; S09433: Chr09_47305353 C/T; S09434: Chr09_47334297 C/G; S09435: Chr09_47356242 A/T; S09436: Chr09_47381976 G/T; S09437: Chr09_47403473 C/T; S09438: Chr09_47445366 C/A; S09439: Chr09_47470970 C/A; S09440: Chr09_47476675 C/T; S09441: Chr09_47511149 T/C; S09442: Chr09_47527188 C/T; S09443: Chr09_217552020 C/G; S09444: Chr09_47575242 A/C; S09445: Chr09_47637297 C/T; S09446: Chr09_47658718 G/A; S09447: Chr09_47677967 G/A; S09448: Chr09_47702857 C/T; S09449: Chr09_47769078 C/T; S09450: Chr09_47793938 C/A; S09451: Chr09_47809273 C/T; S09452: Chr09_47834194 C/A; S09453: Chr09_47851096 G/T; S09454: Chr09_47887800 G/T; S09455: Chr09_47901013 C/T; S09456: Chr09_47925035 C/T; S09457: Chr09_47956413 A/G; S09458: Chr09_47977625 A/G; S09459: Chr09_48003816 T/G; S09460: Chr09_48025997 G/C; S09461: Chr09_48050776 A/G; S09462: Chr09_48092122 T/C; S09463: Chr09_48136269 C/T; S09464: Chr09_218163375 C/T; S09465: Chr09_48182699 G/A; S09466: Chr09_48200709 C/G; S09467: Chr09_48232863 G/A; S09468: Chr09_218251278 A/G; S09469: Chr09_48275347 A/T; S09470: Chr09_48313044 C/T; S09471: Chr09_48331479 G/C; S09472: Chr09_48352477 T/A; S09473: Chr09_48400007 G/A; S09474: Chr09_48434986 G/A; S09475: Chr09_48452084 T/A; S09476: Chr09_48480888 C/T; S09477: Chr09_48501664 T/C; S09478: Chr09_48528301 C/T; S09479: Chr09_48555625 T/C; S09480: Chr09_48583702 G/A; S09481: Chr09_48601330 C/T; S09482: Chr09_48626905 G/A; S09483: Chr09_48651907 A/G; S09484: Chr09_48679493 C/G; S09485: Chr09_48700323 G/A; S09486: Chr09_48727778 A/G; S09487: Chr09_48750063 C/T; S09488: Chr09_48775089 G/A; S09489: Chr09_48808081 A/C; S09490: Chr09_48844803 T/G; S09491: Chr09_48858116 T/C; S09492: Chr09_48876954 C/A; S09493: Chr09_48900188 C/T; S09494: Chr09_48925693 G/A; S09495: Chr09_48956993 G/A; S09496: Chr09_48977064 T/C; S09497: Chr09_49008838 C/A; S09498: Chr09_49052440 C/T; S09499: Chr09_49079942 T/G; S09500: Chr09_49114986 T/C; S09501: Chr09_49129665 A/T; S09502: Chr09_49162387 C/T; S09503: Chr09_49185455 A/G; S09504: Chr09_49206671 C/T; S09505: Chr09_49239490 C/T; S09506:

Chr09_49259384 A/G; S09507: Chr09_49278015 A/G; S09508: Chr09_49368888 A/T; S09509: Chr09_49375133 A/C; S09510: Chr09_49401161 A/G; S09511: Chr09_49432371 A/G; S09512: Chr09_49470356 T/A; S09513: Chr09_49475350 C/T; S09514: Chr09_49510534 C/G; S09515: Chr09_49544802 A/C; S09516: Chr09_49551816 G/A; S09517: Chr09_49580325 T/C; S09518: Chr09_49625678 C/T; S09519: Chr09_49660346 G/A; S09520: Chr09_49677336 G/T; S09521: Chr09_49708629 C/T; S09522: Chr09_49739393 A/G; S09523: Chr09_49758394 A/C; S09524: Chr09_49776992 G/A; S09525: Chr09_49808140 C/T; S09526: Chr09_49826056 C/T; S09527: Chr09_49864734 T/C; S09528: Chr09_49877487 G/A; S09529: Chr09_49901270 C/A; S09530: Chr09_49938447 G/C; S09531: Chr09_49994639 G/A; S09532: Chr09_50005547 G/A; S09533: Chr09_50027806 C/A; S09534: Chr09_50071699 G/A; S09535: Chr09_50085403 A/C; S09536: Chr09_50100692 T/A; S09537: Chr09_50125918 A/G; S09538: Chr09_50152298 A/T; S09539: Chr09_50188321 G/C; S09540: Chr10_00064869 G/A; S09541: Chr10_00131916 G/T; S09542: Chr10_00166537 A/G; S09543: Chr10_00199728 A/C; S09544: Chr10_00206189 C/T; S09545: Chr10_00245813 G/A; S09546: Chr10_00253244 A/G; S09547: Chr10_00286340 A/T; S09548: Chr10_00302850 A/G; S09549: Chr10_00331641 T/G; S09550: Chr10_00382390 T/C; S09551: Chr10_00410962 C/T; S09552: Chr10_00452951 C/T; S09553: Chr10_00501441 T/A; S09554: Chr10_00528032 G/A; S09555: Chr10_00589610 A/G; S09556: Chr10_00628767 A/G; S09557: Chr10_00663290 G/A; S09558: Chr10_00687854 T/G; S09559: Chr10_00737459 T/C; S09560: Chr10_00756664 C/T; S09561: Chr10_00789952 C/T; S09562: Chr10_00813882 C/T; S09563: Chr10_00863114 G/A; S09564: Chr10_00875596 G/A; S09565: Chr10_00902557 A/C; S09566: Chr10_00937326 G/A; S09567: Chr10_00976582 G/A; S09568: Chr10_01023556 C/A; S09569: Chr10_01027266 A/T; S09570: Chr10_01052592 A/G; S09571: Chr10_01083387 A/G; S09572: Chr10_01103213 T/C; S09573: Chr10_01125561 C/T; S09574: Chr10_01160187 C/T; S09575: Chr10_01176625 C/T; S09576: Chr10_01205750 C/G; S09577: Chr10_01258620 T/G; S09578: Chr10_01279062 G/A; S09579: Chr10_01307271 A/T; S09580: Chr10_01380442 T/C; S09581: Chr10_01459922 T/G; S09582: Chr10_01476384 T/C; S09583: Chr10_01507123 G/A; S09584: Chr10_01539137 G/C; S09585: Chr10_01550490 A/T; S09586: Chr10_01576816 G/T; S09587: Chr10_01622570 A/G; S09588: Chr10_01627898 C/A; S09589: Chr10_01662322 C/T; S09590: Chr10_01677025 A/G; S09591: Chr10_01707438 T/A; S09592: Chr10_01782661 G/C; S09593: Chr10_01818552 C/T; S09594: Chr10_01898584 C/G; S09595: Chr10_01903082 C/T; S09596: Chr10_01925335 A/G; S09597: Chr10_02004351 G/T; S09598: Chr10_02046258 A/G; S09599: Chr10_02058441 C/A; S09600: Chr10_02081993 C/T; S09601: Chr10_02129959 C/T; S09602: Chr10_02158340 T/C; S09603: Chr10_02176662 A/G; S09604: Chr10_02207059 C/T; S09605: Chr10_02226383 G/T; S09606: Chr10_02263081 C/T; S09607: Chr10_02281196 C/G; S09608: Chr10_02305332 G/A; S09609: Chr10_02326206 G/A; S09610: Chr10_02356846 A/T; S09611: Chr10_02375462 A/T; S09612: Chr10_02415527 C/A; S09613: Chr10_02431236 T/G; S09614: Chr10_02452668 A/T; S09615: Chr10_02489268 A/G; S09616: Chr10_02508817 G/A; S09617: Chr10_02525602 A/T; S09618: Chr10_02560868 G/A; S09619: Chr10_02591501 C/G; S09620: Chr10_02601476 T/A; S09621: Chr10_02626212 C/T; S09622: Chr10_02658545 A/G; S09623: Chr10_02706850 C/T; S09624: Chr10_02746072 T/G; S09625: Chr10_02750802 G/C; S09626: Chr10_02785162 G/A; S09627: Chr10_02809008 C/T; S09628: Chr10_02825776 T/C; S09629: Chr10_02870996 G/T; S09630: Chr10_02887410 A/T; S09631: Chr10_02901283 G/A; S09632: Chr10_02927284 T/A; S09633: Chr10_02988733 C/T; S09634: Chr10_03000207 G/A; S09635: Chr10_03032473 A/G; S09636: Chr10_03054709 A/G; S09637: Chr10_03083923 C/T; S09638: Chr10_03100684 G/A; S09639: Chr10_03125352 C/T; S09640: Chr10_03160142 G/C; S09641: Chr10_03210302 T/A; S09642: Chr10_03233657 T/C; S09643: Chr10_03256697 G/A; S09644: Chr10_03275422 T/C; S09645: Chr10_03303531 A/T; S09646: Chr10_03373357 C/T; S09647: Chr10_03381435 C/A; S09648: Chr10_03401521 T/C; S09649: Chr10_03429437 A/G; S09650: Chr10_03485289 T/C; S09651: Chr10_03500524 T/C; S09652: Chr10_03533037 C/T; S09653: Chr10_03557649 C/T; S09654: Chr10_03585931 T/A; S09655: Chr10_03600044 A/C; S09656: Chr10_03659889 C/G; S09657: Chr10_03687061 C/T; S09658: Chr10_03737967 T/C; S09659: Chr10_03755179 T/A; S09660: Chr10_03775180 C/A; S09661: Chr10_03809934 G/T; S09662: Chr10_03839587 A/G; S09663: Chr10_03853991 G/A; S09664: Chr10_03886434 G/A; S09665: Chr10_03904914 C/T; S09666: Chr10_03925349 C/T; S09667: Chr10_03950599 C/T; S09668: Chr10_03975901 A/T; S09669: Chr10_04003143 C/A; S09670: Chr10_04034865 A/T; S09671: Chr10_04050226 T/C; S09672: Chr10_04082641 A/T; S09673: Chr10_04109599 T/A; S09674: Chr10_04136828 C/A; S09675: Chr10_04156071 G/A; S09676: Chr10_04192117 A/C; S09677: Chr10_04201836 T/C; S09678: Chr10_04232312 A/T; S09679: Chr10_04256389 A/C; S09680: Chr10_04289419 A/G; S09681: Chr10_04304163 T/C; S09682: Chr10_04326635 T/C; S09683: Chr10_04376815 A/G; S09684: Chr10_04408823 C/T; S09685: Chr10_04426372 T/C; S09686: Chr10_04451517 A/C; S09687: Chr10_04486837 C/T; S09688: Chr10_04507985 C/A; S09689: Chr10_04528519 C/T; S09690: Chr10_04572747 C/T; S09691: Chr10_04575105 T/A; S09692: Chr10_04603708 A/G; S09693: Chr10_04625079 G/T; S09694: Chr10_04651103 C/G; S09695: Chr10_04731868 G/A; S09696: Chr10_04757977 A/G; S09697: Chr10_04789218 T/C; S09698: Chr10_04822348 C/G; S09699: Chr10_04841256 T/C; S09700: Chr10_04859188 A/T; S09701: Chr10_04876965 T/C; S09702: Chr10_04913352 G/A; S09703: Chr10_04927914 T/C; S09704: Chr10_04951035 C/T; S09705: Chr10_05007846 C/T; S09706: Chr10_05044844 A/G; S09707:

Chr10_05081367 &A; S09708: Chr10_05110455 T/G; S09709: Chr10_05140105 T/A; S09710: Chr10_05188945 T/G; S09711: Chr10_05203880 C/T; S09712: Chr10_05230218 G/A; S09713: Chr10_05260439 T/C; S09714: Chr10_05301426 A/T; S09715: Chr10_05329637 T/C; S09716: Chr10_05401966 A/G; S09717: Chr10_05426021 C/T; S09718: Chr10_05452787 C/T; S09719: Chr10_05484725 T/C; S09720: Chr10_05500462 T/C; S09721: Chr10_05561093 G/A; S09722: Chr10_05578693 A/G; S09723: Chr10_05627322 A/G; S09724: Chr10_05650957 T/C; S09725: Chr10_05752794 G/A; S09726: Chr10_05778169 A/G; S09727: Chr10_05870074 G/A; S09728: Chr10_05889177 C/T; S09729: Chr10_05908937 G/A; S09730: Chr10_05933423 G/T; S09731: Chr10_05963906 C/T; S09732: Chr10_06035554 T/C; S09733: Chr10_06179036 A/T; S09734: Chr10_06220146 C/T; S09735: Chr10_06226289 C/T; S09736: Chr10_06273532 A/T; S09737: Chr10_06276446 A/C; S09738: Chr10_06388276 C/T; S09739: Chr10_06402093 G/C; S09740: Chr10_06461723 G/C; S09741: Chr10_06537611 T/G; S09742: Chr10_06572774 G/C; S09743: Chr10_06588731 A/T; S09744: Chr10_06613923 G/C; S09745: Chr10_06649407 G/A; S09746: Chr10_06652651 C/T; S09747: Chr10_06697968 T/C; S09748: Chr10_06700374 T/C; S09749: Chr10_06728326 T/G; S09750: Chr10_06758839 T/C; S09751: Chr10_06777816 C/T; S09752: Chr10_06802519 A/T; S09753: Chr10_06837189 G/T; S09754: Chr10_06874720 T/A; S09755: Chr10_06891998 G/T; S09756: Chr10_06906543 T/G; S09757: Chr10_06932246 C/T; S09758: Chr10_07094110 C/T; S09759: Chr10_07111255 A/G; S09760: Chr10_07133472 G/T; S09761: Chr10_07150630 G/A; S09762: Chr10_07249979 T/G; S09763: Chr10_07254828 C/T; S09764: Chr10_07287437 A/G; S09765: Chr10_07301453 C/T; S09766: Chr10_07371770 A/C; S09767: Chr10_07401170 T/C; S09768: Chr10_07469178 G/A; S09769: Chr10_07479743 G/A; S09770: Chr10_07556039 T/C; S09771: Chr10_07678738 A/G; S09772: Chr10_07732215 A/C; S09773: Chr10_07768688 C/G; S09774: Chr10_07809194 C/A; S09775: Chr10_07840956 C/T; S09776: Chr10_07856251 T/A; S09777: Chr10_07876704 G/A; S09778: Chr10_07973707 G/A; S09779: Chr10_07975341 G/A; S09780: Chr10_08126940 T/C; S09781: Chr10_08253161 A/G; S09782: Chr10_08393631 A/T; S09783: Chr10_08400465 G/A; S09784: Chr10_08569472 T/C; S09785: Chr10_08575125 A/G; S09786: Chr10_08650572 G/A; S09787: Chr10_08747537 C/T; S09788: Chr10_08751358 G/T; S09789: Chr10_08866485 G/T; S09790: Chr10_08883787 C/G; S09791: Chr10_08904703 C/T; S09792: Chr10_08949081 A/G; S09793: Chr10_08960702 G/A; S09794: Chr10_08975130 A/G; S09795: Chr10_09056493 T/C; S09796: Chr10_09086505 T/A; S09797: Chr10_09145728 T/A; S09798: Chr10_09183665 A/G; S09799: Chr10_09218769 T/C; S09800: Chr10_09295958 C/T; S09801: Chr10_09351453 C/T; S09802: Chr10_09375092 T/G; S09803: Chr10_09454676 G/A; S09804: Chr10_09489155 C/T; S09805: Chr10_09501723 C/T; S09806: Chr10_09531778 C/T; S09807: Chr10_09552671 A/G; S09808: Chr10_09577332 C/T; S09809: Chr10_09600772 C/A; S09810: Chr10_09625617 G/T; S09811: Chr10_09707338 A/G; S09812: Chr10_09754856 A/G; S09813: Chr10_09793137 C/T; S09814: Chr10_09800068 C/T; S09815: Chr10_09891678 G/T; S09816: Chr10_09926977 C/A; S09817: Chr10_09956246 A/C; S09818: Chr10_10015707 A/G; S09819: Chr10_10031640 T/G; S09820: Chr10_10070324 G/C; S09821: Chr10_10127022 A/G; S09822: Chr10_10157336 C/G; S09823: Chr10_10256862 C/T; S09824: Chr10_10275333 A/T; S09825: Chr10_10385214 T/G; S09826: Chr10_10403525 A/G; S09827: Chr10_10446833 T/G; S09828: Chr10_10464522 G/A; S09829: Chr10_10479614 C/G; S09830: Chr10_10550520 C/T; S09831: Chr10_10607910 T/C; S09832: Chr10_10663261 T/G; S09833: Chr10_10700159 A/G; S09834: Chr10_10775290 T/C; S09835: Chr10_10868232 T/C; S09836: Chr10_10901189 T/C; S09837: Chr10_10947585 C/G; S09838: Chr10_11016593 C/T; S09839: Chr10_11085359 C/T; S09840: Chr10_11137806 T/C; S09841: Chr10_11168902 C/T; S09842: Chr10_11179221 C/T; S09843: Chr10_11221554 A/G; S09844: Chr10_11253037 T/A; S09845: Chr10_11275008 T/C; S09846: Chr10_11355748 G/A; S09847: Chr10_11439743 T/C; S09848: Chr10_11454714 T/C; S09849: Chr10_11626550 G/A; S09850: Chr10_11736395 A/G; S09851: Chr10_11761431 C/T; S09852: Chr10_11777200 C/G; S09853: Chr10_11820600 G/C; S09854: Chr10_11856991 G/A; S09855: Chr10_11878628 A/G; S09856: Chr10_11933171 A/C; S09857: Chr10_11961784 C/T; S09858: Chr10_11982977 A/G; S09859: Chr10_12050036 T/A; S09860: Chr10_12090698 G/A; S09861: Chr10_12100130 C/T; S09862: Chr10_12234164 A/G; S09863: Chr10_12266415 T/C; S09864: Chr10_12287805 A/C; S09865: Chr10_12300363 T/G; S09866: Chr10_12381326 A/C; S09867: Chr10_12424159 C/T; S09868: Chr10_12425641 A/C; S09869: Chr10_12471965 A/G; S09870: Chr10_12539016 C/T; S09871: Chr10_12622454 C/T; S09872: Chr10_12626734 A/G; S09873: Chr10_12686891 C/T; S09874: Chr10_12740249 C/T; S09875: Chr10_12750012 G/C; S09876: Chr10_12834195 T/C; S09877: Chr10_12869555 A/T; S09878: Chr10_12876000 C/T; S09879: Chr10_12928422 G/A; S09880: Chr10_12985764 T/A; S09881: Chr10_13000075 G/C; S09882: Chr10_13087478 C/T; S09883: Chr10_13142756 G/A; S09884: Chr10_13153732 T/C; S09885: Chr10_13225071 C/T; S09886: Chr10_13315297 A/G; S09887: Chr10_13353442 A/G; S09888: Chr10_13409537 T/C; S09889: Chr10_13430170 A/G; S09890: Chr10_13461080 G/A; S09891: Chr10_13509241 C/T; S09892: Chr10_13529378 T/G; S09893: Chr10_13553542 G/A; S09894: Chr10_13577780 T/C; S09895: Chr10_13600037 C/A; S09896: Chr10_13725368 C/T; S09897: Chr10_13841752 A/T; S09898: Chr10_13855624 G/A; S09899: Chr10_13876671 C/T; S09900: Chr10_13909152 G/A; S09901: Chr10_13925450 C/G; S09902: Chr10_14048086 G/T; S09903: Chr10_14076253 A/C; S09904: Chr10_14347042 A/G; S09905: Chr10_14350189 C/T; S09906: Chr10_14430405 C/T; S09907: Chr10_14516297 G/T; S09908:

Chr10_14760426 C/A; S09909: Chr10_14801490 G/T; S09910: Chr10_14875077 T/A; S09911: Chr10_14950064 G/C; S09912: Chr10_15102610 T/C; S09913: Chr10_15176464 C/T; S09914: Chr10_15475064 T/G; S09915: Chr10_15550212 T/C; S09916: Chr10_15925104 C/T; S09917: Chr10_16000097 C/T; S09918: Chr10_16089579 T/C; S09919: Chr10_16184887 C/T; S09920: Chr10_16200353 T/C; S09921: Chr10_16476716 T/A; S09922: Chr10_16512062 C/T; S09923: Chr10_16541295 G/A; S09924: Chr10_16605212 C/A; S09925: Chr10_16637226 C/T; S09926: Chr10_16681452 G/A; S09927: Chr10_16903565 G/T; S09928: Chr10_16950885 G/T; S09929: Chr10_16985773 G/T; S09930: Chr10_17075464 G/A; S09931: Chr10_17440536 C/T; S09932: Chr10_17458182 T/G; S09933: Chr10_17720303 A/G; S09934: Chr10_17725049 C/T; S09935: Chr10_17800042 G/A; S09936: Chr10_17888761 C/T; S09937: Chr10_17975137 T/G; S09938: Chr10_18078705 A/G; S09939: Chr10_18100547 T/C; S09940: Chr10_18176862 C/T; S09941: Chr10_18258995 C/A; S09942: Chr10_18334213 C/T; S09943: Chr10_18407364 T/C; S09944: Chr10_18501504 A/G; S09945: Chr10_18575802 G/A; S09946: Chr10_18651832 G/C; S09947: Chr10_18726860 C/T; S09948: Chr10_18839541 T/A; S09949: Chr10_18851363 A/T; S09950: Chr10_19000071 C/T; S09951: Chr10_19303180 C/T; S09952: Chr10_19375484 T/C; S09953: Chr10_19452215 A/G; S09954: Chr10_19525481 A/G; S09955: Chr10_19655756 C/T; S09956: Chr10_19677126 A/G; S09957: Chr10_19750240 G/A; S09958: Chr10_19900876 C/A; S09959: Chr10_20013842 G/A; S09960: Chr10_20238866 T/G; S09961: Chr10_20250968 T/C; S09962: Chr10_20551205 C/T; S09963: Chr10_20625053 C/T; S09964: Chr10_20775177 G/A; S09965: Chr10_21075009 C/T; S09966: Chr10_21160039 C/T; S09967: Chr10_21251020 G/A; S09968: Chr10_21325177 A/T; S09969: Chr10_21401108 C/T; S09970: Chr10_21482957 C/G; S09971: Chr10_21584402 G/A; S09972: Chr10_21757831 A/G; S09973: Chr10_21778430 T/C; S09974: Chr10_21867895 A/G; S09975: Chr10_22025515 G/A; S09976: Chr10_22554183 G/A; S09977: Chr10_22646224 A/G; S09978: Chr10_22707643 T/A; S09979: Chr10_22725529 A/T; S09980: Chr10_22800283 G/A; S09981: Chr10_22875563 A/G; S09982: Chr10_22967091 G/A; S09983: Chr10_23048073 G/A; S09984: Chr10_23097787 A/G; S09985: Chr10_23101593 C/A; S09986: Chr10_23175117 C/T; S09987: Chr10_23200003 A/C; S09988: Chr10_23337610 G/A; S09989: Chr10_23350095 C/A; S09990: Chr10_23428749 T/A; S09991: Chr10_23451971 G/A; S09992: Chr10_23610963 C/G; S09993: Chr10_23703043 G/A; S09994: Chr10_23916602 A/G; S09995: Chr10_23946187 C/T; S09996: Chr10_23961429 C/T; S09997: Chr10_24002695 T/G; S09998: Chr10_24026394 A/G; S09999: Chr10_24143408 T/C; S10000: Chr10_24151634 G/A; S10001: Chr10_24215804 C/T; S10002: Chr10_24239878 C/G; S10003: Chr10_24366080 A/G; S10004: Chr10_24391157 A/G; S10005: Chr10_24425628 A/G; S10006: Chr10_24461581 T/C; S10007: Chr10_24512941 C/A; S10008: Chr10_24600771 A/C; S10009: Chr10_24632092 T/G; S10010: Chr10_24650090 T/C; S10011: Chr10_24675367 T/A; S10012: Chr10_24750325 C/T; S10013: Chr10_24890117 C/A; S10014: Chr10_24900272 T/C; S10015: Chr10_24976161 C/A; S10016: Chr10_25056327 G/A; S10017: Chr10_25075034 A/T; S10018: Chr10_25197296 G/A; S10019: Chr10_25247054 C/T; S10020: Chr10_25250111 G/T; S10021: Chr10_25326995 A/T; S10022: Chr10_25359417 G/A; S10023: Chr10_25390674 T/A; S10024: Chr10_25429299 C/T; S10025: Chr10_25484894 T/C; S10026: Chr10_25501285 C/T; S10027: Chr10_25604453 T/C; S10028: Chr10_25626012 T/C; S10029: Chr10_25656154 G/C; S10030: Chr10_25710067 G/A; S10031: Chr10_25729051 T/A; S10032: Chr10_25754740 T/G; S10033: Chr10_25940434 A/T; S10034: Chr10_25960133 G/A; S10035: Chr10_26031665 C/T; S10036: Chr10_26050579 T/A; S10037: Chr10_26131654 C/A; S10038: Chr10_26184232 A/G; S10039: Chr10_26256624 A/G; S10040: Chr10_26425162 T/C; S10041: Chr10_26580883 A/G; S10042: Chr10_26600027 A/T; S10043: Chr10_26822657 G/A; S10044: Chr10_26825199 A/G; S10045: Chr10_26906809 A/G; S10046: Chr10_27193064 C/T; S10047: Chr10_27205290 C/A; S10048: Chr10_27225108 G/C; S10049: Chr10_27320829 T/A; S10050: Chr10_27371513 C/T; S10051: Chr10_27375101 T/C; S10052: Chr10_27471081 G/A; S10053: Chr10_27491364 C/T; S10054: Chr10_27518449 T/C; S10055: Chr10_27525154 C/T; S10056: Chr10_27715661 T/C; S10057: Chr10_27875025 A/G; S10058: Chr10_28056934 A/C; S10059: Chr10_28075031 C/T; S10060: Chr10_28150033 C/T; S10061: Chr10_28411408 A/G; S10062: Chr10_28484142 C/A; S10063: Chr10_28500025 T/C; S10064: Chr10_28619170 G/A; S10065: Chr10_28700943 C/T; S10066: Chr10_28728080 G/A; S10067: Chr10_28804777 G/A; S10068: Chr10_28898900 A/C; S10069: Chr10_28900908 T/G; S10070: Chr10_28925213 G/T; S10071: Chr10_29000494 T/C; S10072: Chr10_29075307 G/A; S10073: Chr10_29154904 G/T; S10074: Chr10_29280189 A/T; S10075: Chr10_29356797 A/G; S10076: Chr10_29388751 T/C; S10077: Chr10_29452328 A/T; S10078: Chr10_29479789 T/G; S10079: Chr10_29501754 A/T; S10080: Chr10_29532885 A/G; S10081: Chr10_29611934 G/T; S10082: Chr10_29640097 T/C; S10083: Chr10_29655355 G/A; S10084: Chr10_29675108 T/C; S10085: Chr10_29750211 G/A; S10086: Chr10_29837760 G/A; S10087: Chr10_29924128 G/T; S10088: Chr10_29951938 G/A; S10089: Chr10_30041206 G/A; S10090: Chr10_30103879 G/A; S10091: Chr10_30150996 C/T; S10092: Chr10_30175004 C/A; S10093: Chr10_30310423 G/C; S10094: Chr10_30334362 T/C; S10095: Chr10_30351362 A/G; S10096: Chr10_30383368 A/G; S10097: Chr10_30420235 A/C; S10098: Chr10_30454441 C/T; S10099: Chr10_30488493 C/T; S10100: Chr10_30523754 A/C; S10101: Chr10_30590003 A/G; S10102: Chr10_30662264 C/T; S10103: Chr10_30683547 C/T; S10104: Chr10_30707546 C/T; S10105: Chr10_30737649 A/G; S10106: Chr10_30759389 A/G; S10107: Chr10_30775139 T/C; S10108: Chr10_30877573 A/C; S10109:

Chr10_30924427 T/C; S10110: Chr10_30925614 G/A; S10111: Chr10_30988498 C/A; S10112: Chr10_31033919 A/T; S10113: Chr10_31052131 G/C; S10114: Chr10_31130906 A/G; S10115: Chr10_31236364 G/A; S10116: Chr10_31285896 C/G; S10117: Chr10_31344467 G/A; S10118: Chr10_31397508 T/C; S10119: Chr10_31425863 G/A; S10120: Chr10_31450043 C/G; S10121: Chr10_31525724 A/G; S10122: Chr10_31601369 G/C; S10123: Chr10_31675712 T/A; S10124: Chr10_31778948 T/C; S10125: Chr10_31817673 T/G; S10126: Chr10_31900041 T/C; S10127: Chr10_31976313 T/G; S10128: Chr10_32050545 A/G; S10129: Chr10_32143878 C/A; S10130: Chr10_32150193 T/G; S10131: Chr10_32227506 A/G; S10132: Chr10_32325859 C/T; S10133: Chr10_32350054 T/C; S10134: Chr10_32378019 T/A; S10135: Chr10_32479407 G/A; S10136: Chr10_32500087 T/G; S10137: Chr10_32585199 A/G; S10138: Chr10_32619117 T/C; S10139: Chr10_32669481 C/T; S10140: Chr10_32732809 C/A; S10141: Chr10_32750237 A/G; S10142: Chr10_32849902 A/T; S10143: Chr10_32921896 A/G; S10144: Chr10_32925180 G/A; S10145: Chr10_33085467 T/A; S10146: Chr10_33171264 C/G; S10147: Chr10_33175036 A/T; S10148: Chr10_33271086 T/A; S10149: Chr10_33275027 C/T; S10150: Chr10_33350079 C/T; S10151: Chr10_33449992 G/C; S10152: Chr10_33451135 G/T; S10153: Chr10_33475116 T/C; S10154: Chr10_33571953 A/G; S10155: Chr10_33633244 T/C; S10156: Chr10_33676230 A/G; S10157: Chr10_33700033 C/T; S10158: Chr10_33822159 A/G; S10159: Chr10_33829157 T/C; S10160: Chr10_33875429 G/A; S10161: Chr10_33975048 C/T; S10162: Chr10_34053368 T/C; S10163: Chr10_34094035 G/A; S10164: Chr10_34134413 T/A; S10165: Chr10_34152577 T/C; S10166: Chr10_34187987 T/C; S10167: Chr10_34259670 T/G; S10168: Chr10_34279046 G/A; S10169: Chr10_34434459 G/A; S10170: Chr10_34452495 T/C; S10171: Chr10_34527570 C/T; S10172: Chr10_34662678 G/T; S10173: Chr10_34675807 T/C; S10174: Chr10_34772371 A/C; S10175: Chr10_34775229 T/C; S10176: Chr10_34801370 A/T; S10177: Chr10_34825703 A/T; S10178: Chr10_34902872 C/A; S10179: Chr10_34991826 G/A; S10180: Chr10_35005082 T/G; S10181: Chr10_35028000 G/A; S10182: Chr10_35050781 C/T; S10183: Chr10_35127391 C/T; S10184: Chr10_35311577 T/C; S10185: Chr10_35334683 A/G; S10186: Chr10_35406142 G/C; S10187: Chr10_35425085 T/C; S10188: Chr10_35498911 C/T; S10189: Chr10_35535245 T/C; S10190: Chr10_35607889 T/C; S10191: Chr10_35669007 A/C; S10192: Chr10_35707835 C/T; S10193: Chr10_35770990 T/A; S10194: Chr10_35775207 C/T; S10195: Chr10_35850097 A/T; S10196: Chr10_35937831 A/G; S10197: Chr10_35998864 C/A; S10198: Chr10_36006766 C/T; S10199: Chr10_36025870 T/C; S10200: Chr10_36100582 G/A; S10201: Chr10_36255351 C/T; S10202: Chr10_36383595 A/C; S10203: Chr10_36475758 G/T; S10204: Chr10_36611969 T/C; S10205: Chr10_36720287 G/A; S10206: Chr10_36753790 A/G; S10207: Chr10_36778917 A/G; S10208: Chr10_36871464 A/G; S10209: Chr10_36877037 C/A; S10210: Chr10_36988741 A/G; S10211: Chr10_37091779 T/A; S10212: Chr10_37123783 G/T; S10213: Chr10_37143518 A/C; S10214: Chr10_37156755 A/T; S10215: Chr10_37177777 G/T; S10216: Chr10_37209642 G/C; S10217: Chr10_37235656 A/T; S10218: Chr10_37251364 C/A; S10219: Chr10_37290759 A/C; S10220: Chr10_37308624 A/G; S10221: Chr10_37325098 C/A; S10222: Chr10_37409877 A/G; S10223: Chr10_37500527 T/C; S10224: Chr10_37529225 C/T; S10225: Chr10_37623872 C/A; S10226: Chr10_37687246 G/A; S10227: Chr10_37754457 C/T; S10228: Chr10_37909468 A/T; S10229: Chr10_37995518 C/T; S10230: Chr10_38006503 A/G; S10231: Chr10_38077214 C/T; S10232: Chr10_38110297 T/C; S10233: Chr10_38135451 G/A; S10234: Chr10_38151029 T/A; S10235: Chr10_38182465 T/G; S10236: Chr10_38258505 C/G; S10237: Chr10_38292846 G/A; S10238: Chr10_38304953 T/G; S10239: Chr10_38328997 A/C; S10240: Chr10_38353592 T/C; S10241: Chr10_38377953 T/C; S10242: Chr10_38428843 A/G; S10243: Chr10_38471034 C/T; S10244: Chr10_38497661 A/G; S10245: Chr10_38561888 A/G; S10246: Chr10_38581395 A/G; S10247: Chr10_38601800 G/T; S10248: Chr10_38625128 A/G; S10249: Chr10_38651877 A/C; S10250: Chr10_38690236 A/G; S10251: Chr10_38700028 C/T; S10252: Chr10_38726672 A/T; S10253: Chr10_38757759 A/C; S10254: Chr10_38779021 A/T; S10255: Chr10_38864965 T/C; S10256: Chr10_38875293 C/G; S10257: Chr10_38902148 T/A; S10258: Chr10_38930229 G/A; S10259: Chr10_38952119 T/A; S10260: Chr10_39004024 A/T; S10261: Chr10_39025321 C/A; S10262: Chr10_39050391 G/C; S10263: Chr10_39112437 C/G; S10264: Chr10_39127726 C/T; S10265: Chr10_39153821 A/G; S10266: Chr10_39180542 C/T; S10267: Chr10_39200791 G/T; S10268: Chr10_39234048 T/C; S10269: Chr10_39251844 C/T; S10270: Chr10_39283634 T/C; S10271: Chr10_39300485 T/C; S10272: Chr10_39342020 A/T; S10273: Chr10_39350339 C/G; S10274: Chr10_39376902 C/T; S10275: Chr10_39402868 C/A; S10276: Chr10_39435023 A/G; S10277: Chr10_39485647 A/G; S10278: Chr10_39515259 C/T; S10279: Chr10_39538165 A/G; S10280: Chr10_39563111 T/C; S10281: Chr10_39581493 A/G; S10282: Chr10_39612920 G/C; S10283: Chr10_39627917 T/C; S10284: Chr10_39661494 C/T; S10285: Chr10_39675524 A/G; S10286: Chr10_39701112 C/A; S10287: Chr10_39746955 C/T; S10288: Chr10_39760882 T/A; S10289: Chr10_39830221 T/A; S10290: Chr10_39922426 C/T; S10291: Chr10_39927065 C/T; S10292: Chr10_39950285 A/T; S10293: Chr10_39986013 G/A; S10294: Chr10_40065790 T/C; S10295: Chr10_40128440 T/G; S10296: Chr10_40162329 A/T; S10297: Chr10_40186799 A/G; S10298: Chr10_40200023 G/A; S10299: Chr10_40225940 C/G; S10300: Chr10_40251290 G/T; S10301: Chr10_40276736 A/T; S10302: Chr10_40305728 G/C; S10303: Chr10_40328958 T/A; S10304: Chr10_40378675 T/C; S10305: Chr10_40403191 A/T; S10306: Chr10_40494875 G/A; S10307: Chr10_40505338 C/T; S10308: Chr10_40529196 T/A; S10309: Chr10_40555489 A/G; S10310:

Chr10_40581832 A/C; S10311: Chr10_40614858 C/A; S10312: Chr10_40628708 T/G; S10313: Chr10_40658871 A/G; S10314: Chr10_40700205 T/A; S10315: Chr10_40728594 C/G; S10316: Chr10_40751806 G/A; S10317: Chr10_40785928 A/G; S10318: Chr10_40804543 G/A; S10319: Chr10_40831716 T/A; S10320: Chr10_40852908 A/T; S10321: Chr10_40960388 A/C; S10322: Chr10_41028424 A/C; S10323: Chr10_41111336 C/T; S10324: Chr10_41137318 C/T; S10325: Chr10_41159679 A/G; S10326: Chr10_41186751 A/G; S10327: Chr10_41203308 A/T; S10328: Chr10_41235171 G/C; S10329: Chr10_41255642 T/C; S10330: Chr10_41289883 G/C; S10331: Chr10_41300038 T/A; S10332: Chr10_41371901 T/G; S10333: Chr10_41415143 T/A; S10334: Chr10_41442466 T/A; S10335: Chr10_41454822 A/G; S10336: Chr10_41489848 T/C; S10337: Chr10_41510808 G/C; S10338: Chr10_41545902 C/T; S10339: Chr10_41562169 C/T; S10340: Chr10_41583463 T/C; S10341: Chr10_41602441 G/A; S10342: Chr10_41625310 C/T; S10343: Chr10_41650204 T/A; S10344: Chr10_41758182 T/C; S10345: Chr10_41775237 G/A; S10346: Chr10_41816459 T/G; S10347: Chr10_41846566 T/C; S10348: Chr10_41860177 A/G; S10349: Chr10_41886631 A/G; S10350: Chr10_41947086 C/T; S10351: Chr10_42009160 T/C; S10352: Chr10_42036007 C/G; S10353: Chr10_42077455 T/C; S10354: Chr10_42100204 G/A; S10355: Chr10_42144203 C/G; S10356: Chr10_42157572 C/A; S10357: Chr10_42182903 C/T; S10358: Chr10_42200041 A/G; S10359: Chr10_42295829 A/T; S10360: Chr10_42363621 T/A; S10361: Chr10_42434494 A/G; S10362: Chr10_42451506 A/G; S10363: Chr10_42503008 G/T; S10364: Chr10_42542275 G/T; S10365: Chr10_42554570 A/G; S10366: Chr10_42595397 C/T; S10367: Chr10_42618671 G/A; S10368: Chr10_42626320 T/C; S10369: Chr10_42658503 A/C; S10370: Chr10_42675233 A/G; S10371: Chr10_42709229 C/T; S10372: Chr10_42749525 A/G; S10373: Chr10_42808382 T/A; S10374: Chr10_42827123 A/C; S10375: Chr10_42853538 A/G; S10376: Chr10_42899466 T/C; S10377: Chr10_42901404 A/G; S10378: Chr10_42933639 A/T; S10379: Chr10_42958937 T/C; S10380: Chr10_42980871 G/A; S10381: Chr10_43016403 G/A; S10382: Chr10_43037423 G/T; S10383: Chr10_43070821 T/C; S10384: Chr10_43078218 G/A; S10385: Chr10_43106722 T/A; S10386: Chr10_43132487 A/T; S10387: Chr10_43150121 T/A; S10388: Chr10_43269596 A/C; S10389: Chr10_43301160 G/A; S10390: Chr10_43395294 G/C; S10391: Chr10_43459815 T/C; S10392: Chr10_43478454 A/G; S10393: Chr10_43524047 A/T; S10394: Chr10_43535408 G/T; S10395: Chr10_43595992 S10396: Chr10_43607214 G/A; S10397: Chr10_43633151 G/C; S10398: Chr10_43757485 G/T; S10399: Chr10_43784579 T/C; S10400: Chr10_43850629 A/G; S10401: Chr10_43937803 A/G; S10402: Chr10_43971514 G/A; S10403: Chr10_43990938 G/A; S10404: Chr10_44086905 G/A; S10405: Chr10_44151691 G/T; S10406: Chr10_44242211 C/T; S10407: Chr10_44267560 G/T; S10408: Chr10_44287403 G/C; S10409: Chr10_44362118 A/T; S10410: Chr10_44394936 A/G; S10411: Chr10_44460265 A/T; S10412: Chr10_44475203 C/G; S10413: Chr10_44501316 A/G; S10414: Chr10_44548961 C/T; S10415: Chr10_44556312 A/T; S10416: Chr10_44575003 T/C; S10417: Chr10_44616633 G/A; S10418: Chr10_44625266 A/G; S10419: Chr10_44653299 T/G; S10420: Chr10_44678039 T/C; S10421: Chr10_44728735 A/T; S10422: Chr10_214754336 A/G; S10423: Chr10_44777383 C/A; S10424: Chr10_44828287 C/A; S10425: Chr10_44856151 C/T; S10426: Chr10_44920131 G/A; S10427: Chr10_44956340 C/T; S10428: Chr10_44997549 T/A; S10429: Chr10_45010987 T/G; S10430: Chr10_45026735 C/T; S10431: Chr10_45082937 A/G; S10432: Chr10_45109345 T/C; S10433: Chr10_45127748 T/C; S10434: Chr10_45150445 C/G; S10435: Chr10_45175769 G/A; S10436: Chr10_45214117 C/T; S10437: Chr10_45253388 C/A; S10438: Chr10_45276682 G/A; S10439: Chr10_45305285 A/G; S10440: Chr10_45325143 G/A; S10441: Chr10_45373188 C/T; S10442: Chr10_45451718 C/T; S10443: Chr10_45550230 T/C; S10444: Chr10_45622801 T/C; S10445: Chr10_45629506 T/C; S10446: Chr10_45653187 T/C; S10447: Chr10_215678759 A/G; S10448: Chr10_45706817 T/A; S10449: Chr10_45725437 A/G; S10450: Chr10_45818488 C/T; S10451: Chr10_45825055 G/A; S10452: Chr10_45903960 A/G; S10453: Chr10_45954113 A/G; S10454: Chr10_45976767 A/G; S10455: Chr10_46102059 G/A; S10456: Chr10_46127980 A/G; S10457: Chr10_46223524 G/A; S10458: Chr10_46227628 A/C; S10459: Chr10_46297373 G/A; S10460: Chr10_46307275 T/G; S10461: Chr10_46325076 A/G; S10462: Chr10_216417960 G/A; S10463: Chr10_46455250 C/A; S10464: Chr10_216491503 C/T; S10465: Chr10_46500055 T/C; S10466: Chr10_46541827 C/T; S10467: Chr10_46561144 A/G; S10468: Chr10_46582977 G/A; S10469: Chr10_46607729 G/C; S10470: Chr10_46628106 G/A; S10471: Chr10_46669619 G/C; S10472: Chr10_46681050 A/C; S10473: Chr10_46709472 G/A; S10474: Chr10_46728149 G/A; S10475: Chr10_46755940 G/A; S10476: Chr10_46824507 A/T; S10477: Chr10_46872534 A/T; S10478: Chr10_46902903 G/C; S10479: Chr10_46943747 A/G; S10480: Chr10_46976047 T/C; S10481: Chr10_47002353 G/T; S10482: Chr10_47033722 G/T; S10483: Chr10_47053768 G/A; S10484: Chr10_47099455 T/C; S10485: Chr10_47102662 T/A; S10486: Chr10_47200521 T/C; S10487: Chr10_47227094 T/C; S10488: Chr10_47250145 T/A; S10489: Chr10_47279181 T/C; S10490: Chr10_47352507 C/A; S10491: Chr10_47384285 G/A; S10492: Chr10_47462923 C/T; S10493: Chr10_47493071 A/G; S10494: Chr10_47500165 G/T; S10495: Chr10_47636017 A/G; S10496: Chr10_47694947 C/T; S10497: Chr10_47715021 C/G; S10498: Chr10_47725534 T/C; S10499: Chr10_47750431 T/C; S10500: Chr10_47776017 G/A; S10501: Chr10_47804075 A/G; S10502: Chr10_47847000 T/C; S10503: Chr10_47851277 A/G; S10504: Chr10_47909564 T/C; S10505: Chr10_47925782 C/A; S10506: Chr10_47961242 T/A; S10507: Chr10_47981671 C/T; S10508: Chr10_48009970 G/A; S10509: Chr10_48035532 C/T; S10510: Chr10_48050029 T/C; S10511:

Chr10_48086773 A/C; S10512: Chr10_48101363 T/G; S10513: Chr10_48126385 A/C; S10514: Chr10_48150244 A/G; S10515: Chr10_48180671 A/C; S10516: Chr10_48212375 T/C; S10517: Chr10_48238429 T/C; S10518: Chr10_218256879 T/C; S10519: Chr10_48281092 T/C; S10520: Chr10_48308210 G/T; S10521: Chr10_48326406 T/A; S10522: Chr10_48353297 G/A; S10523: Chr10_48375657 T/A; S10524: Chr10_48400891 C/T; S10525: Chr10_48448324 T/A; S10526: Chr10_48464090 C/T; S10527: Chr10_48478016 T/G; S10528: Chr10_48502393 C/T; S10529: Chr10_48532363 A/C; S10530: Chr10_48554069 C/T; S10531: Chr10_48575078 G/A; S10532: Chr10_48613389 A/G; S10533: Chr10_48626281 G/A; S10534: Chr10_48651316 T/A; S10535: Chr10_48680937 A/C; S10536: Chr10_48701284 T/G; S10537: Chr10_48731730 T/C; S10538: Chr10_48754709 T/C; S10539: Chr10_48785134 G/T; S10540: Chr10_48801452 G/C; S10541: Chr10_48826415 G/A; S10542: Chr10_48854596 G/A; S10543: Chr10_48878389 G/A; S10544: Chr10_48900690 T/C; S10545: Chr10_48926597 G/A; S10546: Chr10_48950475 A/G; S10547: Chr10_48979145 C/T; S10548: Chr10_49000046 T/C; S10549: Chr10_49031606 T/G; S10550: Chr10_49050505 A/G; S10551: Chr10_49081258 G/A; S10552: Chr10_49110083 C/T; S10553: Chr10_49126592 G/T; S10554: Chr10_49165269 G/A; S10555: Chr10_49213289 T/C; S10556: Chr10_49256007 A/G; S10557: Chr10_49283496 C/T; S10558: Chr10_49302884 T/C; S10559: Chr10_49343783 C/T; S10560: Chr10_49350822 C/A; S10561: Chr10_49384169 G/A; S10562: Chr10_49403402 G/A; S10563: Chr10_49429776 C/T; S10564: Chr10_49468790 G/A; S10565: Chr10_49499602 C/G; S10566: Chr10_49519551 G/A; S10567: Chr10_49531784 C/T; S10568: Chr10_49559906 T/G; S10569: Chr10_49589849 T/C; S10570: Chr10_49622671 A/C; S10571: Chr10_49647824 G/T; S10572: Chr10_49660566 A/C; S10573: Chr10_49690721 G/A; S10574: Chr10_49704857 C/G; S10575: Chr10_49729301 T/G; S10576: Chr10_49755930 A/T; S10577: Chr10_49783225 G/A; S10578: Chr10_49801446 T/A; S10579: Chr10_49825836 A/G; S10580: Chr10_49852679 C/G; S10581: Chr10_49877594 G/T; S10582: Chr10_49902605 G/A; S10583: Chr10_49926990 G/A; S10584: Chr10_49950798 T/C; S10585: Chr10_49978021 T/C; S10586: Chr10_50004678 C/T; S10587: Chr10_50036402 G/A; S10588: Chr10_50056088 A/G; S10589: Chr10_50075074 A/C; S10590: Chr10_50101823 C/G; S10591: Chr10_50132610 A/G; S10592: Chr10_50153249 G/C; S10593: Chr10_50176988 G/A; S10594: Chr10_50202871 G/C; S10595: Chr10_50241385 G/A; S10596: Chr10_50257636 A/G; S10597: Chr10_50300250 T/C; S10598: Chr10_50326994 C/T; S10599: Chr10_50360946 T/C; S10600: Chr10_50378285 G/A; S10601: Chr10_50418275 T/C; S10602: Chr10_50442096 G/A; S10603: Chr10_50450003 G/A; S10604: Chr10_50501432 G/A; S10605: Chr10_50539235 T/A; S10606: Chr10_50556531 C/T; S10607: Chr10_50583200 G/T; S10608: Chr10_50603791 A/G; S10609: Chr10_50629784 T/C; S10610: Chr10_50654731 T/C; S10611: Chr10_50676319 G/A; S10612: Chr10_50749505 G/A; S10613: Chr10_50750003 G/A; S10614: Chr10_50776987 A/T; S10615: Chr10_50811377 G/T; S10616: Chr10_50826105 C/T; S10617: Chr10_50868906 T/C; S10618: Chr10_50891102 A/G; S10619: Chr10_50904863 A/G; S10620: Chr10_50930317 T/C; S10621: Chr10_50965060 T/C; S10622: Chr10_50981304 T/C; S10623: Chr10_51031743 T/C; S10624: Chr10_51063984 G/A; S10625: Chr10_51089310 G/T; S10626: Chr10_51100077 A/G; S10627: Chr10_51126531 A/C; S10628: Chr10_51171408 T/C; S10629: Chr10_51188301 C/T; S10630: Chr10_51266958 C/A; S10631: Chr10_51298890 A/G; S10632: Chr10_51301216 A/G; S10633: Chr10_51326203 T/G; S10634: Chr10_51354084 G/A; S10635: Chr10_51486245 A/G; S10636: Chr10_51511410 T/C; S10637: Chr10_51528562 G/T; S10638: Chr10_51550187 A/G; S10639: Chr11_00000989 T/C; S10640: Chr11_00028686 A/G; S10641: Chr11_00060238 G/C; S10642: Chr11_00104375 A/G; S10643: Chr11_00130585 G/A; S10644: Chr11_00163657 C/T; S10645: Chr11_00175001 G/A; S10646: Chr11_00200400 C/A; S10647: Chr11_00232974 G/T; S10648: Chr11_00278575 A/T; S10649: Chr11_00300782 A/C; S10650: Chr11_00330280 G/A; S10651: Chr11_00350802 C/G; S10652: Chr11_00401033 G/A; S10653: Chr11_00429839 T/C; S10654: Chr11_00456958 C/G; S10655: Chr11_00488042 T/C; S10656: Chr11_00504312 A/T; S10657: Chr11_00527851 G/T; S10658: Chr11_00551875 T/C; S10659: Chr11_00578326 T/C; S10660: Chr11_00600090 A/G; S10661: Chr11_00628458 C/G; S10662: Chr11_00676727 C/T; S10663: Chr11_00705862 C/T; S10664: Chr11_00743933 C/G; S10665: Chr11_00763543 G/T; S10666: Chr11_00778162 A/G; S10667: Chr11_00816090 T/C; S10668: Chr11_00840425 C/G; S10669: Chr11_00863884 A/G; S10670: Chr11_00875219 G/A; S10671: Chr11_00903370 A/T; S10672: Chr11_00930343 T/C; S10673: Chr11_00957200 T/C; S10674: Chr11_01020343 G/C; S10675: Chr11_01029781 A/T; S10676: Chr11_01050892 A/G; S10677: Chr11_01075377 G/A; S10678: Chr11_01104970 C/T; S10679: Chr11_01144002 A/G; S10680: Chr11_01156557 G/A; S10681: Chr11_01203429 C/T; S10682: Chr11_01241465 T/G; S10683: Chr11_01261281 G/A; S10684: Chr11_01277116 C/G; S10685: Chr11_01331991 T/G; S10686: Chr11_01353297 G/A; S10687: Chr11_01384301 A/G; S10688: Chr11_01400922 C/G; S10689: Chr11_01443512 A/G; S10690: Chr11_01495095 G/T; S10691: Chr11_01506248 T/C; S10692: Chr11_01550888 T/A; S10693: Chr11_01604659 A/T; S10694: Chr11_01637913 C/T; S10695: Chr11_01652554 T/C; S10696: Chr11_01688204 T/C; S10697: Chr11_01702304 G/A; S10698: Chr11_01732001 C/T; S10699: Chr11_01751115 A/T; S10700: Chr11_01775487 T/A; S10701: Chr11_01828233 A/G; S10702: Chr11_01869636 G/T; S10703: Chr11_01889560 A/G; S10704: Chr11_01911806 C/T; S10705: Chr11_01926460 G/A; S10706: Chr11_01966387 A/G; S10707: Chr11_02011216 A/G; S10708: Chr11_02036614 C/G; S10709: Chr11_02091363 T/C; S10710: Chr11_02104739 T/C; S10711: Chr11_02125131 C/G; S10712:

Chr11_02167163 T/G; S10713: Chr11_02177285 G/T; S10714: Chr11_02235068 C/G; S10715: Chr11_02298985 A/G; S10716: Chr11_02302391 G/A; S10717: Chr11_02328250 G/A; S10718: Chr11_02363066 C/T; S10719: Chr11_02378114 G/A; S10720: Chr11_02401786 T/C; S10721: Chr11_02432665 G/A; S10722: Chr11_02451815 T/A; S10723: Chr11_02475049 A/G; S10724: Chr11_02508323 G/A; S10725: Chr11_02525815 A/G; S10726: Chr11_02568120 G/C; S10727: Chr11_02575356 C/G; S10728: Chr11_02600437 C/T; S10729: Chr11_02630521 T/G; S10730: Chr11_02654938 G/A; S10731: Chr11_02677845 T/A; S10732: Chr11_02722866 A/G; S10733: Chr11_02726026 T/A; S10734: Chr11_02752865 C/G; S10735: Chr11_02780890 C/T; S10736: Chr11_02801209 G/T; S10737: Chr11_02865509 G/A; S10738: Chr11_02944962 G/C; S10739: Chr11_02982365 A/G; S10740: Chr11_03040946 A/C; S10741: Chr11_03050406 G/A; S10742: Chr11_03088464 T/G; S10743: Chr11_03101299 A/G; S10744: Chr11_03127479 C/T; S10745: Chr11_03210411 C/T; S10746: Chr11_03245369 T/C; S10747: Chr11_03275116 C/G; S10748: Chr11_03345025 T/C; S10749: Chr11_03350033 T/C; S10750: Chr11_03497751 C/T; S10751: Chr11_03507011 C/A; S10752: Chr11_03583784 G/A; S10753: Chr11_03604398 T/C; S10754: Chr11_03634790 A/G; S10755: Chr11_03652647 C/T; S10756: Chr11_03688082 A/C; S10757: Chr11_03717583 T/A; S10758: Chr11_03733610 G/A; S10759: Chr11_03769192 G/A; S10760: Chr11_03775949 A/G; S10761: Chr11_03808080 C/T; S10762: Chr11_03932987 T/C; S10763: Chr11_03956041 G/A; S10764: Chr11_03995083 G/C; S10765: Chr11_04000226 A/G; S10766: Chr11_04100355 G/T; S10767: Chr11_04153990 C/T; S10768: Chr11_04198332 A/T; S10769: Chr11_04237236 G/A; S10770: Chr11_04273387 G/A; S10771: Chr11_04306322 T/C; S10772: Chr11_04326464 T/C; S10773: Chr11_04353882 C/T; S10774: Chr11_04375571 A/C; S10775: Chr11_04411689 A/G; S10776: Chr11_04426923 C/G; S10777: Chr11_04454249 A/G; S10778: Chr11_04485099 T/C; S10779: Chr11_04504963 A/T; S10780: Chr11_04527604 T/C; S10781: Chr11_04562849 G/C; S10782: Chr11_04576176 A/G; S10783: Chr11_04607394 G/A; S10784: Chr11_04632928 T/C; S10785: Chr11_04654612 T/C; S10786: Chr11_04675962 G/C; S10787: Chr11_04701200 G/T; S10788: Chr11_04760533 C/T; S10789: Chr11_04776271 C/T; S10790: Chr11_04810963 G/C; S10791: Chr11_04831552 C/T; S10792: Chr11_04850027 G/C; S10793: Chr11_04875418 G/T; S10794: Chr11_04910261 G/C; S10795: Chr11_04930134 A/C; S10796: Chr11_04951621 T/G; S10797: Chr11_04995920 A/T; S10798: Chr11_05008590 G/A; S10799: Chr11_05025690 C/T; S10800: Chr11_05050943 T/G; S10801: Chr11_05089256 C/T; S10802: Chr11_05100420 A/G; S10803: Chr11_05132968 T/C; S10804: Chr11_05152014 T/C; S10805: Chr11_05215329 C/G; S10806: Chr11_05238225 T/C; S10807: Chr11_05261070 T/A; S10808: Chr11_05279687 G/A; S10809: Chr11_05301216 C/T; S10810: Chr11_05340029 G/C; S10811: Chr11_05351312 C/T; S10812: Chr11_05431199 T/G; S10813: Chr11_05480333 C/T; S10814: Chr11_05535897 C/G; S10815: Chr11_05552573 C/T; S10816: Chr11_05576317 A/G; S10817: Chr11_05608417 C/T; S10818: Chr11_05659703 T/G; S10819: Chr11_05680261 T/G; S10820: Chr11_05712326 G/A; S10821: Chr11_05733279 C/T; S10822: Chr11_05750045 T/C; S10823: Chr11_05776737 A/G; S10824: Chr11_05824301 T/C; S10825: Chr11_05846479 C/T; S10826: Chr11_05859788 T/C; S10827: Chr11_05886407 T/G; S10828: Chr11_05900170 C/T; S10829: Chr11_05925409 G/A; S10830: Chr11_05955316 G/A; S10831: Chr11_05980469 A/C; S10832: Chr11_06019335 A/T; S10833: Chr11_06028013 A/T; S10834: Chr11_06059314 G/C; S10835: Chr11_06081506 C/G; S10836: Chr11_06101132 G/A; S10837: Chr11_06133119 G/T; S10838: Chr11_06151164 C/G; S10839: Chr11_06178608 C/T; S10840: Chr11_06222493 C/T; S10841: Chr11_06232723 A/G; S10842: Chr11_06254452 A/G; S10843: Chr11_06275374 C/T; S10844: Chr11_06304945 A/C; S10845: Chr11_06328675 A/C; S10846: Chr11_06351267 T/C; S10847: Chr11_06380477 G/T; S10848: Chr11_06453029 G/C; S10849: Chr11_06476610 A/T; S10850: Chr11_06500761 C/T; S10851: Chr11_06525196 C/A; S10852: Chr11_06575704 G/A; S10853: Chr11_06600074 C/T; S10854: Chr11_06625234 C/A; S10855: Chr11_06662674 C/A; S10856: Chr11_06689411 A/G; S10857: Chr11_06702752 G/A; S10858: Chr11_06763024 T/A; S10859: Chr11_06785247 T/C; S10860: Chr11_06801280 G/C; S10861: Chr11_06844009 A/T; S10862: Chr11_06855001 A/G; S10863: Chr11_06877244 G/A; S10864: Chr11_06903111 C/T; S10865: Chr11_06981640 A/G; S10866: Chr11_07001838 G/T; S10867: Chr11_07112092 C/T; S10868: Chr11_07137027 T/G; S10869: Chr11_07151831 T/C; S10870: Chr11_07177529 A/T; S10871: Chr11_07202433 C/T; S10872: Chr11_07237037 A/G; S10873: Chr11_07250439 G/A; S10874: Chr11_07275835 C/T; S10875: Chr11_07344485 G/A; S10876: Chr11_07352805 G/C; S10877: Chr11_07386495 A/T; S10878: Chr11_07404559 C/T; S10879: Chr11_07426930 T/G; S10880: Chr11_07461105 A/G; S10881: Chr11_07484586 T/A; S10882: Chr11_07543360 C/G; S10883: Chr11_07562581 T/A; S10884: Chr11_07580201 G/A; S10885: Chr11_07609142 T/C; S10886: Chr11_07626429 T/C; S10887: Chr11_07652141 G/A; S10888: Chr11_07675766 A/G; S10889: Chr11_07703510 T/C; S10890: Chr11_07726008 C/T; S10891: Chr11_07752105 A/C; S10892: Chr11_07775265 T/G; S10893: Chr11_07804841 T/A; S10894: Chr11_07828647 C/T; S10895: Chr11_07850665 C/T; S10896: Chr11_07887588 C/G; S10897: Chr11_07906374 G/T; S10898: Chr11_07941260 A/C; S10899: Chr11_07952027 A/G; S10900: Chr11_07978460 T/G; S10901: Chr11_08009383 C/A; S10902: Chr11_08039047 A/G; S10903: Chr11_08053181 G/T; S10904: Chr11_08082887 T/C; S10905: Chr11_08116076 C/T; S10906: Chr11_08143238 T/C; S10907: Chr11_08150055 C/T; S10908: Chr11_08185968 C/T; S10909: Chr11_08203966 T/C; S10910: Chr11_08238232 C/T; S10911: Chr11_08252578 T/C; S10912: Chr11_08277026 T/A; S10913:

Chr11_08301902 T/C; S10914: Chr11_08333380 G/T; S10915: Chr11_08350789 T/A; S10916: Chr11_08384532 T/C; S10917: Chr11_08400858 T/C; S10918: Chr11_08425380 T/A; S10919: Chr11_08452987 C/T; S10920: Chr11_08477487 A/C; S10921: Chr11_08502588 T/C; S10922: Chr11_08531155 G/A; S10923: Chr11_08551742 T/A; S10924: Chr11_08602395 T/C; S10925: Chr11_08667040 G/C; S10926: Chr11_08679012 A/G; S10927: Chr11_08777751 G/A; S10928: Chr11_08876414 T/A; S10929: Chr11_08927808 C/T; S10930: Chr11_08957295 C/T; S10931: Chr11_08979943 A/G; S10932: Chr11_09000162 T/A; S10933: Chr11_09030901 G/T; S10934: Chr11_09067433 C/T; S10935: Chr11_09082959 T/A; S10936: Chr11_09128037 C/T; S10937: Chr11_09174504 G/C; S10938: Chr11_09176049 A/G; S10939: Chr11_09218497 T/G; S10940: Chr11_09225803 G/C; S10941: Chr11_09281018 G/A; S10942: Chr11_09304246 T/A; S10943: Chr11_09340733 T/C; S10944: Chr11_09354910 G/C; S10945: Chr11_09375018 C/A; S10946: Chr11_09520947 T/G; S10947: Chr11_09531963 T/A; S10948: Chr11_09550757 C/T; S10949: Chr11_09577260 G/A; S10950: Chr11_09602706 T/C; S10951: Chr11_09632890 T/C; S10952: Chr11_09651815 T/C; S10953: Chr11_09702671 A/G; S10954: Chr11_09796245 A/G; S10955: Chr11_09821617 A/G; S10956: Chr11_09896347 G/T; S10957: Chr11_09925631 G/A; S10958: Chr11_09954019 G/A; S10959: Chr11_09993857 G/A; S10960: Chr11_10001565 T/C; S10961: Chr11_10054045 T/C; S10962: Chr11_10076966 G/A; S10963: Chr11_10184787 T/C; S10964: Chr11_10223209 G/A; S10965: Chr11_10298413 G/T; S10966: Chr11_10306924 G/A; S10967: Chr11_10383858 G/A; S10968: Chr11_10492106 T/C; S10969: Chr11_10535154 G/C; S10970: Chr11_10561561 C/T; S10971: Chr11_10589735 C/G; S10972: Chr11_10700423 G/C; S10973: Chr11_10749671 A/T; S10974: Chr11_10812023 T/C; S10975: Chr11_10880104 T/A; S10976: Chr11_11090964 C/T; S10977: Chr11_11102324 T/C; S10978: Chr11_11159242 G/A; S10979: Chr11_11205174 T/C; S10980: Chr11_11226030 T/G; S10981: Chr11_11263471 T/C; S10982: Chr11_11290061 C/T; S10983: Chr11_11301829 C/T; S10984: Chr11_11331064 A/G; S10985: Chr11_11356587 T/G; S10986: Chr11_11389352 C/T; S10987: Chr11_11408553 G/A; S10988: Chr11_11441988 A/G; S10989: Chr11_11450141 C/T; S10990: Chr11_11518887 T/C; S10991: Chr11_11525141 T/G; S10992: Chr11_11633187 C/T; S10993: Chr11_11704744 C/T; S10994: Chr11_11749253 A/T; S10995: Chr11_11808897 T/C; S10996: Chr11_11843081 C/T; S10997: Chr11_11889501 A/T; S10998: Chr11_11910808 A/G; S10999: Chr11_11960802 T/C; S11000: Chr11_11989132 T/C; S11001: Chr11_12026236 T/C; S11002: Chr11_12075895 T/C; S11003: Chr11_12119547 G/A; S11004: Chr11_12136272 A/G; S11005: Chr11_12183275 C/A; S11006: Chr11_12242556 T/G; S11007: Chr11_12274543 A/T; S11008: Chr11_12276345 C/T; S11009: Chr11_12314168 G/A; S11010: Chr11_12334320 C/T; S11011: Chr11_12359800 G/C; S11012: Chr11_12375033 T/A; S11013: Chr11_12401814 T/C; S11014: Chr11_12430450 A/T; S11015: Chr11_12450079 T/C; S11016: Chr11_12507296 A/C; S11017: Chr11_12530195 T/C; S11018: Chr11_12550107 A/G; S11019: Chr11_12631856 G/A; S11020: Chr11_12681882 G/A; S11021: Chr11_12747827 G/C; S11022: Chr11_12762487 A/G; S11023: Chr11_12777928 T/C; S11024: Chr11_12856338 C/T; S11025: Chr11_13477259 G/A; S11026: Chr11_13555267 G/A; S11027: Chr11_13575411 G/T; S11028: Chr11_13719291 G/T; S11029: Chr11_13725148 A/G; S11030: Chr11_13875462 G/A; S11031: Chr11_13954281 A/G; S11032: Chr11_14025541 C/T; S11033: Chr11_14182602 T/C; S11034: Chr11_14330858 A/G; S11035: Chr11_14478081 G/A; S11036: Chr11_14554199 C/A; S11037: Chr11_14664471 G/C; S11038: Chr11_14677218 A/T; S11039: Chr11_14742910 G/A; S11040: Chr11_14750030 A/T; S11041: Chr11_14843937 A/G; S11042: Chr11_14854207 T/C; S11043: Chr11_14893537 T/C; S11044: Chr11_14936642 T/C; S11045: Chr11_14982952 A/G; S11046: Chr11_15071082 T/G; S11047: Chr11_15090412 T/G; S11048: Chr11_15100008 A/T; S11049: Chr11_15176070 A/G; S11050: Chr11_15203356 C/G; S11051: Chr11_15319554 A/G; S11052: Chr11_15349972 A/G; S11053: Chr11_15376039 C/T; S11054: Chr11_15508913 C/T; S11055: Chr11_15565340 A/G; S11056: Chr11_15605319 C/T; S11057: Chr11_15653250 T/G; S11058: Chr11_15716912 C/T; S11059: Chr11_15755147 G/A; S11060: Chr11_15820457 C/T; S11061: Chr11_15865077 T/C; S11062: Chr11_15891309 A/G; S11063: Chr11_15917002 T/C; S11064: Chr11_15942410 G/C; S11065: Chr11_15950167 A/C; S11066: Chr11_16100441 G/C; S11067: Chr11_16175866 G/C; S11068: Chr11_16310819 A/C; S11069: Chr11_16493472 T/C; S11070: Chr11_16500627 G/A; S11071: Chr11_16648606 T/C; S11072: Chr11_16665839 T/G; S11073: Chr11_16694419 T/C; S11074: Chr11_16700461 A/C; S11075: Chr11_16847620 A/G; S11076: Chr11_16852835 T/A; S11077: Chr11_16990840 T/C; S11078: Chr11_17001408 A/G; S11079: Chr11_17151109 T/C; S11080: Chr11_17241298 A/G; S11081: Chr11_17330622 T/G; S11082: Chr11_17351447 T/C; S11083: Chr11_17575017 A/C; S11084: Chr11_17689514 T/C; S11085: Chr11_17717079 C/A; S11086: Chr11_17934310 T/C; S11087: Chr11_18001836 A/T; S11088: Chr11_18039301 A/G; S11089: Chr11_18067154 G/C; S11090: Chr11_18080228 T/G; S11091: Chr11_18100105 T/C; S11092: Chr11_18245843 A/G; S11093: Chr11_18258616 A/G; S11094: Chr11_18352498 G/A; S11095: Chr11_18385599 G/C; S11096: Chr11_18436427 T/A; S11097: Chr11_18476512 C/T; S11098: Chr11_18520027 A/C; S11099: Chr11_18525958 C/T; S11100: Chr11_18629685 T/C; S11101: Chr11_18663502 T/C; S11102: Chr11_18698869 T/C; S11103: Chr11_18705996 C/T; S11104: Chr11_18725716 A/T; S11105: Chr11_18811212 T/A; S11106: Chr11_18880108 A/G; S11107: Chr11_18959448 G/A; S11108: Chr11_19030834 A/G; S11109: Chr11_19102321 T/C; S11110: Chr11_19175993 C/T; S11111: Chr11_19555170 C/T; S11112: Chr11_19703109 C/T; S11113: Chr11_19850114 G/C; S11114:

Chr11_20093323 G/A; S11115: Chr11_20803785 A/G; S11116: Chr11_20888879 A/G; S11117: Chr11_21191356 A/G; S11118: Chr11_21298996 G/A; S11119: Chr11_21331392 A/G; S11120: Chr11_21421408 C/T; S11121: Chr11_21494261 A/G; S11122: Chr11_21827282 C/T; S11123: Chr11_21883962 A/G; S11124: Chr11_21954041 G/A; S11125: Chr11_22122061 T/C; S11126: Chr11_22415946 A/G; S11127: Chr11_22477372 C/T; S11128: Chr11_22573646 G/A; S11129: Chr11_23003924 T/G; S11130: Chr11_23122947 C/T; S11131: Chr11_23176813 T/A; S11132: Chr11_23346837 T/C; S11133: Chr11_23412714 A/G; S11134: Chr11_23559372 A/G; S11135: Chr11_23627520 G/A; S11136: Chr11_23896386 G/A; S11137: Chr11_24088159 T/C; S11138: Chr11_24326692 A/T; S11139: Chr11_24414560 T/A; S11140: Chr11_24483066 C/T; S11141: Chr11_24530681 A/C; S11142: Chr11_24571364 G/A; S11143: Chr11_24612326 G/T; S11144: Chr11_24772890 T/C; S11145: Chr11_24776056 C/G; S11146: Chr11_24860833 T/A; S11147: Chr11_24925957 G/A; S11148: Chr11_25045597 G/C; S11149: Chr11_25051098 C/T; S11150: Chr11_25129730 A/T; S11151: Chr11_25153172 A/G; S11152: Chr11_25231209 G/C; S11153: Chr11_25290419 T/A; S11154: Chr11_25311421 A/G; S11155: Chr11_25364951 A/G; S11156: Chr11_25393345 C/T; S11157: Chr11_25437227 C/T; S11158: Chr11_25451456 G/T; S11159: Chr11_25612738 C/A; S11160: Chr11_25698979 A/C; S11161: Chr11_25760860 T/G; S11162: Chr11_25827157 T/C; S11163: Chr11_25952133 T/G; S11164: Chr11_25984276 A/G; S11165: Chr11_26036004 G/A; S11166: Chr11_26050119 C/T; S11167: Chr11_26085910 A/C; S11168: Chr11_26171883 G/A; S11169: Chr11_26175100 C/G; S11170: Chr11_26257312 C/G; S11171: Chr11_26300602 G/A; S11172: Chr11_26326631 C/T; S11173: Chr11_26414380 G/T; S11174: Chr11_26450337 C/G; S11175: Chr11_26492774 C/T; S11176: Chr11_26573959 C/T; S11177: Chr11_26636276 C/G; S11178: Chr11_26660359 A/T; S11179: Chr11_26733204 C/T; S11180: Chr11_26779181 T/C; S11181: Chr11_26801188 A/T; S11182: Chr11_26885201 C/G; S11183: Chr11_26960064 A/G; S11184: Chr11_27037266 C/T; S11185: Chr11_27093587 A/G; S11186: Chr11_27100403 C/T; S11187: Chr11_27130862 T/C; S11188: Chr11_27173052 T/A; S11189: Chr11_27228521 T/C; S11190: Chr11_27309240 A/G; S11191: Chr11_27388420 T/C; S11192: Chr11_27566529 C/T; S11193: Chr11_27578019 G/C; S11194: Chr11_27730895 C/T; S11195: Chr11_27880043 G/A; S11196: Chr11_28009896 C/T; S11197: Chr11_28076792 G/A; S11198: Chr11_28144108 T/C; S11199: Chr11_28150156 A/G; S11200: Chr11_28331818 G/A; S11201: Chr11_28360688 G/A; S11202: Chr11_28393380 C/A; S11203: Chr11_28401707 T/C; S11204: Chr11_28437430 T/A; S11205: Chr11_28463708 T/A; S11206: Chr11_28477245 T/C; S11207: Chr11_28612899 T/C; S11208: Chr11_28625999 T/C; S11209: Chr11_28769688 T/A; S11210: Chr11_28805896 G/A; S11211: Chr11_28825780 A/G; S11212: Chr11_28930480 T/C; S11213: Chr11_29005291 T/C; S11214: Chr11_29025760 A/G; S11215: Chr11_29101100 A/C; S11216: Chr11_29250070 C/G; S11217: Chr11_29355391 G/T; S11218: Chr11_29376624 A/T; S11219: Chr11_29450450 G/A; S11220: Chr11_29526057 C/T; S11221: Chr11_29650548 G/A; S11222: Chr11_29727557 T/C; S11223: Chr11_29775020 A/T; S11224: Chr11_29859722 T/C; S11225: Chr11_29876349 A/G; S11226: Chr11_30022087 C/T; S11227: Chr11_30058972 A/G; S11228: Chr11_30084576 A/G; S11229: Chr11_30189377 A/G; S11230: Chr11_30207369 G/A; S11231: Chr11_30225540 A/G; S11232: Chr11_30282294 G/C; S11233: Chr11_30300359 G/T; S11234: Chr11_30380679 A/T; S11235: Chr11_30403708 G/A; S11236: Chr11_30454098 A/C; S11237: Chr11_30521919 C/T; S11238: Chr11_30526422 A/T; S11239: Chr11_30550847 T/A; S11240: Chr11_30575972 A/T; S11241: Chr11_30654375 T/G; S11242: Chr11_30695358 C/T; S11243: Chr11_30726558 A/G; S11244: Chr11_30750167 G/C; S11245: Chr11_30780028 A/G; S11246: Chr11_30887656 C/G; S11247: Chi-11_30915295 A/G; S11248: Chr11_31020057 G/A; S11249: Chr11_31026476 G/A; S11250: Chr11_31052813 T/C; S11251: Chr11_31099297 T/C; S11252: Chr11_31107364 G/A; S11253: Chr11_31183242 C/T; S11254: Chr11_31201983 G/A; S11255: Chr11_31227367 A/G; S11256: Chr11_31314095 C/A; S11257: Chr11_31342445 T/C; S11258: Chr11_31352567 G/C; S11259: Chr11_31411659 T/C; S11260: Chr11_31468494 A/T; S11261: Chr11_31475960 C/A; S11262: Chr11_31555666 G/T; S11263: Chr11_31633100 A/G; S11264: Chr11_31656448 T/C; S11265: Chr11_31695829 G/A; S11266: Chr11_31700752 C/T; S11267: Chr11_31738766 C/T; S11268: Chr11_31769637 A/G; S11269: Chr11_31813218 T/C; S11270: Chr11_31828881 A/G; S11271: Chr11_31893947 G/A; S11272: Chr11_31916586 T/C; S11273: Chr11_31938719 T/A; S11274: Chr11_31957128 A/G; S11275: Chr11_32015563 G/T; S11276: Chr11_32056085 G/A; S11277: Chr11_32115772 A/G; S11278: Chr11_32127323 A/T; S11279: Chr11_32189049 T/G; S11280: Chr11_32201444 T/A; S11281: Chr11_32278359 A/G; S11282: Chr11_32305514 A/G; S11283: Chr11_32347619 A/G; S11284: Chr11_32376132 G/A; S11285: Chr11_32402605 G/T; S11286: Chr11_32432239 G/A; S11287: Chr11_32464089 A/G; S11288: Chr11_32496183 A/G; S11289: Chr11_32506058 C/T; S11290: Chr11_32527931 G/C; S11291: Chr11_32551250 C/G; S11292: Chr11_32578995 G/C; S11293: Chr11_32621730 C/G; S11294: Chr11_32633549 T/C; S11295: Chr11_32667748 T/G; S11296: Chr11_32680923 T/C; S11297: Chr11_32702098 G/C; S11298: Chr11_32727353 G/T; S11299: Chr11_32751396 T/C; S11300: Chr11_32776301 G/A; S11301: Chr11_32831996 I/O; S11302: Chr11_32850193 C/A; S11303: Chr11_32915680 A/T; S11304: Chr11_32929777 C/T; S11305: Chr11_33045385 C/T; S11306: Chr11_33050019 T/C; S11307: Chr11_33157466 A/G; S11308: Chr11_33176134 T/0; S11309: Chr11_33210066 T/A; S11310: Chr11_33241645 C/G; S11311: Chr11_33253245 G/T; S11312: Chr11_33278282 C/T; S11313: Chr11_33310823 T/A; S11314: Chr11_33338527 A/T; S11315:

Chr11_33351189 G/A; S11316: Chr11_33375205 T/C; S11317: Chr11_33410992 T/C; S11318: Chr11_33427782 G/A; S11319: Chr11_33463133 A/G; S11320: Chr11_33492121 T/C; S11321: Chr11_33527121 C/T; S11322: Chr11_33552593 G/C; S11323: Chr11_33575329 T/G; S11324: Chr11_33601762 G/A; S11325: Chr11_33650868 C/G; S11326: Chr11_33680747 T/C; S11327: Chr11_33727131 T/G; S11328: Chr11_33752196 G/C; S11329: Chr11_33778594 G/C; S11330: Chr11_33812735 A/G; S11331: Chr11_33825333 T/C; S11332: Chr11_33857564 G/A; S11333: Chr11_33888106 C/T; S11334: Chr11_33927404 A/C; S11335: Chr11_33980542 T/A; S11336: Chr11_34040969 G/A; S11337: Chr11_34053077 G/A; S11338: Chr11_34079325 G/T; S11339: Chr11_34100147 G/A; S11340: Chr11_34127072 A/T; S11341: Chr11_34153084 C/T; S11342: Chr11_34181786 A/C; S11343: Chr11_34203032 G/C; S11344: Chr11_34254516 G/C; S11345: Chr11_34282112 C/A; S11346: Chr11_34303386 T/G; S11347: Chr11_34332014 T/C; S11348: Chr11_34351151 C/G; S11349: Chr11_34380010 C/G; S11350: Chr11_34401207 A/0; S11351: Chr11_34453671 A/T; S11352: Chr11_34477311 C/T; S11353: Chr11_34501658 T/G; S11354: Chr11_34526683 G/A; S11355: Chr11_34564401 I/O; S11356: Chr11_34577538 G/A; S11357: Chr11_34600081 C/T; S11358: Chr11_34627170 C/G; S11359: Chr11_34651740 A/C; S11360: Chr11_34677410 C/T; S11361: Chr11_34700211 G/A; S11362: Chr12_00005079 G/A; S11363: Chr12_00032990 C/T; S11364: Chr12_00061334 C/A; S11365: Chr12_00099034 C/T; S11366: Chr12_00106255 T/G; S11367: Chr12_00127759 T/C; S11368: Chr12_00151675 A/T; S11369: Chr12_00182011 C/T; S11370: Chr12_00203373 C/T; S11371: Chr12_00251265 G/T; S11372: Chr12_00276474 G/A; S11373: Chr12_00302904 T/G; S11374: Chr12_00325689 G/T; S11375: Chr12_00352717 T/A; S11376: Chr12_00396353 A/G; S11377: Chr12_00400242 T/G; S11378: Chr12_00425581 C/A; S11379: Chr12_00456791 C/T; S11380: Chr12_00486575 A/C; S11381: Chr12_00502036 A/G; S11382: Chr12_00543167 A/G; S11383: Chr12_00564456 T/A; S11384: Chr12_00575161 G/A; S11385: Chr12_00603945 G/T; S11386: Chr12_00626224 G/A; S11387: Chr12_00715141 G/A; S11388: Chr12_00744020 A/G; S11389: Chr12_00805006 T/C; S11390: Chr12_00832473 C/T; S11391: Chr12_00853423 C/T; S11392: Chr12_00877178 C/T; S11393: Chr12_00900162 C/G; S11394: Chr12_00925104 T/G; S11395: Chr12_00956918 A/G; S11396: Chr12_00976950 T/C; S11397: Chr12_01006226 C/G; S11398: Chr12_01035190 T/A; S11399: Chr12_01052838 A/G; S11400: Chr12_01075940 T/A; S11401: Chr12_01101965 A/G; S11402: Chr12_01126610 G/A; S11403: Chr12_01155548 A/G; S11404: Chr12_01175973 C/G; S11405: Chr12_01200237 G/T; S11406: Chr12_01225040 A/G; S11407: Chr12_01250455 C/A; S11408: Chr12_01275476 A/G; S11409: Chr12_01301035 C/G; S11410: Chr12_01328868 T/C; S11411: Chr12_01358766 G/A; S11412: Chr12_01375187 G/C; S11413: Chr12_01409730 G/C; S11414: Chr12_01433478 A/C; S11415: Chr12_01458130 C/G; S11416: Chr12_01477256 A/C; S11417: Chr12_01501583 C/T; S11418: Chr12_01526982 C/T; S11419: Chr12_01568134 G/A; S11420: Chr12_01602091 C/T; S11421: Chr12_01627242 G/T; S11422: Chr12_01653723 A/G; S11423: Chr12_01676080 G/A; S11424: Chr12_01704106 C/G; S11425: Chr12_01733331 C/T; S11426: Chr12_01760935 C/T; S11427: Chr12_01794493 G/A; S11428: Chr12_01801282 G/A; S11429: Chr12_01828132 C/T; S11430: Chr12_01857259 C/A; S11431: Chr12_01875304 C/T; S11432: Chr12_01904721 C/A; S11433: Chr12_01941000 A/G; S11434: Chr12_01953859 G/A; S11435: Chr12_01983525 C/T; S11436: Chr12_02010505 C/T; S11437: Chr12_02046136 A/G; S11438: Chr12_02050203 T/A; S11439: Chr12_02079954 C/G; S11440: Chr12_02102328 G/A; S11441: Chr12_02126277 A/G; S11442: Chr12_02155463 A/G; S11443: Chr12_02179948 T/A; S11444: Chr12_02214923 A/G; S11445: Chr12_02225432 T/C; S11446: Chr12_02264388 C/A; S11447: Chr12_02295516 G/T; S11448: Chr12_02307823 C/T; S11449: Chr12_02325130 T/A; S11450: Chr12_02391211 G/C; S11451: Chr12_02400093 C/T; S11452: Chr12_02512744 T/C; S11453: Chr12_02525033 C/T; S11454: Chr12_02567518 T/G; S11455: Chr12_02575615 G/T; S11456: Chr12_02621904 G/A; S11457: Chr12_02629623 T/C; S11458: Chr12_02651542 A/C; S11459: Chr12_02694809 G/A; S11460: Chr12_02717465 A/G; S11461: Chr12_02736019 G/A; S11462: Chr12_02754886 C/T; S11463: Chr12_02799604 A/T; S11464: Chr12_02804424 G/C; S11465: Chr12_02856647 T/G; S11466: Chr12_02875697 G/C; S11467: Chr12_02906270 G/A; S11468: Chr12_02970658 A/G; S11469: Chr12_02978271 A/T; S11470: Chr12_03003089 G/A; S11471: Chr12_03026625 C/T; S11472: Chr12_03050421 T/A; S11473: Chr12_03079241 T/C; S11474: Chr12_03128482 C/T; S11475: Chr12_03150012 G/T; S11476: Chr12_03175880 G/T; S11477: Chr12_03209141 C/T; S11478: Chr12_03232580 C/T; S11479: Chr12_03260310 G/T; S11480: Chr12_03311520 G/A; S11481: Chr12_03327952 G/A; S11482: Chr12_03350842 C/T; S11483: Chr12_03380679 C/T; S11484: Chr12_03402721 A/C; S11485: Chr12_03433785 T/G; S11486: Chr12_03453565 C/T; S11487: Chr12_03549242 G/A; S11488: Chr12_03556753 A/G; S11489: Chr12_03577958 A/G; S11490: Chr12_03600852 A/G; S11491: Chr12_03659899 T/G; S11492: Chr12_03680545 T/A; S11493: Chr12_03713967 T/G; S11494: Chr12_03728377 C/T; S11495: Chr12_03771115 A/G; S11496: Chr12_03778486 T/G; S11497: Chr12_03801734 C/T; S11498: Chr12_03827652 G/A; S11499: Chr12_03857461 C/T; S11500: Chr12_03886177 C/T; S11501: Chr12_03901416 C/T; S11502: Chr12_03928171 A/G; S11503: Chr12_03951770 G/A; S11504: Chr12_03975064 A/G; S11505: Chr12_04002984 A/C; S11506: Chr12_04031970 A/G; S11507: Chr12_04086887 A/G; S11508: Chr12_04126210 A/G; S11509: Chr12_04154222 A/T; S11510: Chr12_04183623 A/C; S11511: Chr12_04220682 G/A; S11512: Chr12_04240087 C/T; S11513: Chr12_04268782 C/G; S11514: Chr12_04279456 T/C; S11515: Chr12_04303683 C/A; S11516:

Chr12_04360175 C/T; S11517: Chr12_04380507 C/T; S11518: Chr12_04425897 T/C; S11519: Chr12_04489884 C/G; S11520: Chr12_04502359 A/T; S11521: Chr12_04525147 C/T; S11522: Chr12_04550063 C/T; S11523: Chr12_04592714 C/T; S11524: Chr12_04600123 T/G; S11525: Chr12_04700947 A/C; S11526: Chr12_04725500 C/G; S11527: Chr12_04780109 T/C; S11528: Chr12_04826555 G/A; S11529: Chr12_04857655 A/T; S11530: Chr12_04889616 G/A; S11531: Chr12_04901120 C/G; S11532: Chr12_04960316 G/T; S11533: Chr12_04981356 T/A; S11534: Chr12_05007131 A/G; S11535: Chr12_05066919 A/C; S11536: Chr12_05077667 G/C; S11537: Chr12_05132372 T/C; S11538: Chr12_05252014 A/G; S11539: Chr12_05356016 A/G; S11540: Chr12_05437126 C/T; S11541: Chr12_05483537 G/A; S11542: Chr12_05562132 C/T; S11543: Chr12_05632577 T/G; S11544: Chr12_05739659 A/T; S11545: Chr12_05817179 G/A; S11546: Chr12_05859714 A/G; S11547: Chr12_05904066 G/A; S11548: Chr12_06002503 A/C; S11549: Chr12_06076024 T/C; S11550: Chr12_06100273 A/G; S11551: Chr12_06126740 C/A; S11552: Chr12_06174991 G/A; S11553: Chr12_06176386 C/T; S11554: Chr12_06215036 T/C; S11555: Chr12_06239587 A/T; S11556: Chr12_06309412 G/A; S11557: Chr12_06325273 A/T; S11558: Chr12_06350067 G/C; S11559: Chr12_06376962 G/A; S11560: Chr12_06411108 A/T; S11561: Chr12_06425022 T/C; S11562: Chr12_06457440 G/A; S11563: Chr12_06491230 A/T; S11564: Chr12_06507472 G/A; S11565: Chr12_06550223 A/G; S11566: Chr12_06577797 G/A; S11567: Chr12_06651061 A/G; S11568: Chr12_06676921 T/A; S11569: Chr12_06701061 A/G; S11570: Chr12_06734278 G/A; S11571: Chr12_06789756 C/T; S11572: Chr12_06872153 C/G; S11573: Chr12_06884931 C/T; S11574: Chr12_06902782 C/G; S11575: Chr12_06926575 T/C; S11576: Chr12_06951814 G/C; S11577: Chr12_06988185 G/A; S11578: Chr12_07015539 T/C; S11579: Chr12_07092868 G/C; S11580: Chr12_07101311 C/T; S11581: Chr12_07185424 A/G; S11582: Chr12_07251568 G/A; S11583: Chr12_07285954 C/T; S11584: Chr12_07327018 T/G; S11585: Chr12_07350184 A/G; S11586: Chr12_07377020 C/T; S11587: Chr12_07465197 T/G; S11588: Chr12_07482762 A/T; S11589: Chr12_07507741 G/T; S11590: Chr12_07526882 A/G; S11591: Chr12_07553999 C/T; S11592: Chr12_07629474 C/T; S11593: Chr12_07654274 A/G; S11594: Chr12_07752275 T/C; S11595: Chr12_07808361 A/G; S11596: Chr12_07933112 C/G; S11597: Chr12_07950174 G/A; S11598: Chr12_08029174 T/C; S11599: Chr12_08084163 G/A; S11600: Chr12_08100346 T/C; S11601: Chr12_08238508 G/A; S11602: Chr12_08279331 G/C; S11603: Chr12_08315662 G/C; S11604: Chr12_08393118 T/A; S11605: Chr12_08452333 G/A; S11606: Chr12_08489124 C/T; S11607: Chr12_08521539 T/C; S11608: Chr12_08570412 A/C; S11609: Chr12_08586547 T/A; S11610: Chr12_08610261 C/A; S11611: Chr12_08649332 T/C; S11612: Chr12_08650542 T/C; S11613: Chr12_08680389 T/G; S11614: Chr12_08701248 T/A; S11615: Chr12_08752149 A/G; S11616: Chr12_08800896 T/C; S11617: Chr12_08842932 A/G; S11618: Chr12_08871780 T/C; S11619: Chr12_08889281 T/G; S11620: Chr12_08916858 T/C; S11621: Chr12_08925608 G/T; S11622: Chr12_08970353 G/T; S11623: Chr12_08975011 T/C; S11624: Chr12_09014925 T/C; S11625: Chr12_09074401 T/A; S11626: Chr12_09111844 T/A; S11627: Chr12_09149322 G/C; S11628: Chr12_09151027 T/A; S11629: Chr12_09187116 T/C; S11630: Chr12_09229120 C/T; S11631: Chr12_09250922 C/G; S11632: Chr12_09276101 A/T; S11633: Chr12_09351768 T/C; S11634: Chr12_09489441 G/C; S11635: Chr12_09535497 C/T; S11636: Chr12_09597784 A/C; S11637: Chr12_09604651 A/G; S11638: Chr12_09635671 A/T; S11639: Chr12_09673552 T/C; S11640: Chr12_09675105 A/G; S11641: Chr12_09701566 G/A; S11642: Chr12_09732837 T/C; S11643: Chr12_09797751 G/A; S11644: Chr12_09805591 A/T; S11645: Chr12_09834450 G/T; S11646: Chr12_09890371 A/G; S11647: Chr12_09900671 A/C; S11648: Chr12_09948509 T/C; S11649: Chr12_09990682 A/C; S11650: Chr12_10050286 G/A; S11651: Chr12_10125030 T/A; S11652: Chr12_10201749 C/T; S11653: Chr12_10274010 G/T; S11654: Chr12_10308599 A/G; S11655: Chr12_10325445 T/A; S11656: Chr12_10407336 C/G; S11657: Chr12_10426276 A/T; S11658: Chr12_10519159 T/A; S11659: Chr12_10525312 T/G; S11660: Chr12_10559452 T/C; S11661: Chr12_10601330 C/T; S11662: Chr12_10634846 G/T; S11663: Chr12_10653571 T/C; S11664: Chr12_10678350 T/C; S11665: Chr12_10772703 A/T; S11666: Chr12_10804038 A/T; S11667: Chr12_10836734 A/G; S11668: Chr12_10905089 G/A; S11669: Chr12_10950621 A/G; S11670: Chr12_11011618 C/T; S11671: Chr12_11064740 C/T; S11672: Chr12_11078628 G/T; S11673: Chr12_11127737 G/A; S11674: Chr12_11150969 T/C; S11675: Chr12_11175041 T/C; S11676: Chr12_11251808 G/A; S11677: Chr12_11293935 A/G; S11678: Chr12_11300069 T/C; S11679: Chr12_11392401 C/T; S11680: Chr12_11401896 T/C; S11681: Chr12_11446390 G/A; S11682: Chr12_11460703 G/T; S11683: Chr12_11497464 C/T; S11684: Chr12_11504462 C/A; S11685: Chr12_11535616 A/G; S11686: Chr12_11590050 A/G; S11687: Chr12_11600955 T/C; S11688: Chr12_11634925 C/T; S11689: Chr12_11653799 A/C; S11690: Chr12_11675090 T/A; S11691: Chr12_11713369 G/T; S11692: Chr12_11749267 A/G; S11693: Chr12_11777330 T/A; S11694: Chr12_11828545 T/C; S11695: Chr12_11914494 A/T; S11696: Chr12_11955913 C/G; S11697: Chr12_11977518 G/A; S11698: Chr12_12102523 A/T; S11699: Chr12_12193300 G/A; S11700: Chr12_12208237 C/T; S11701: Chr12_12225928 T/C; S11702: Chr12_12304150 G/C; S11703: Chr12_12375004 C/T; S11704: Chr12_12456027 T/C; S11705: Chr12_12539560 T/C; S11706: Chr12_12550874 A/G; S11707: Chr12_12680143 C/G; S11708: Chr12_12728018 T/C; S11709: Chr12_12773873 C/G; S11710: Chr12_12787301 G/T; S11711: Chr12_12800477 C/T; S11712: Chr12_12897841 T/C; S11713: Chr12_12905635 C/T; S11714: Chr12_12978842 T/C; S11715: Chr12_13052869 T/C; S11716: Chr12_13126895 T/C; S11717:

Chr12_13225274 T/C; S11718: Chr12_13250717 C/A; S11719: Chr12_13369056 A/T; S11720: Chr12_13379529 A/G; S11721: Chr12_13458013 T/C; S11722: Chr12_13531453 A/G; S11723: Chr12_13550247 A/G; S11724: Chr12_13625120 G/C; S11725: Chr12_13728741 A/G; S11726: Chr12_13801369 G/A; S11727: Chr12_13828174 T/C; S11728: Chr12_13956797 C/T; S11729: Chr12_13976075 G/A; S11730: Chr12_14059970 G/A; S11731: Chr12_14230489 C/T; S11732: Chr12_14261492 T/G; S11733: Chr12_14275588 G/T; S11734: Chr12_14330916 A/G; S11735: Chr12_14374123 C/T; S11736: Chr12_14375176 A/G; S11737: Chr12_14402623 A/G; S11738: Chr12_14425688 A/G; S11739: Chr12_14480619 C/A; S11740: Chr12_14541899 C/T; S11741: Chr12_14607357 G/A; S11742: Chr12_14633256 C/A; S11743: Chr12_14657849 A/G; S11744: Chr12_14689339 A/G; S11745: Chr12_14736862 A/G; S11746: Chr12_14757109 T/C; S11747: Chr12_14813745 G/A; S11748: Chr12_14878494 A/G; S11749: Chr12_14918485 C/T; S11750: Chr12_14925379 C/T; S11751: Chr12_14955040 C/G; S11752: Chr12_14981467 T/A; S11753: Chr12_15032559 T/C; S11754: Chr12_15070725 G/A; S11755: Chr12_15082891 C/T; S11756: Chr12_15100038 G/A; S11757: Chr12_15202184 T/G; S11758: Chr12_15253423 A/T; S11759: Chr12_15282285 T/C; S11760: Chr12_15379186 G/A; S11761: Chr12_15421824 C/T; S11762: Chr12_15425017 A/T; S11763: Chr12_15500262 G/A; S11764: Chr12_15559879 G/A; S11765: Chr12_15595221 T/G; S11766: Chr12_15603857 G/A; S11767: Chr12_15646265 T/G; S11768: Chr12_15689493 A/G; S11769: Chr12_15721724 T/C; S11770: Chr12_15726302 A/G; S11771: Chr12_15800344 A/G; S11772: Chr12_15836307 C/T; S11773: Chr12_15930752 A/C; S11774: Chr12_15958810 G/T; S11775: Chr12_15975002 C/A; S11776: Chr12_16067487 G/C; S11777: Chr12_16141147 A/T; S11778: Chr12_16150102 G/A; S11779: Chr12_16236058 C/A; S11780: Chr12_16305737 T/A; S11781: Chr12_16399922 C/T; S11782: Chr12_16411095 C/T; S11783: Chr12_16469605 A/G; S11784: Chr12_16484153 C/T; S11785: Chr12_16535627 G/A; S11786: Chr12_16640060 G/A; S11787: Chr12_16672860 C/G; S11788: Chr12_16687188 T/C; S11789: Chr12_16701221 A/G; S11790: Chr12_16775172 G/A; S11791: Chr12_16850154 T/G; S11792: Chr12_16941551 T/C; S11793: Chr12_16950146 T/C; S11794: Chr12_17155426 G/A; S11795: Chr12_17175730 G/A; S11796: Chr12_17214355 G/T; S11797: Chr12_17278956 G/A; S11798: Chr12_17324963 C/A; S11799: Chr12_17325812 T/C; S11800: Chr12_17392627 T/C; S11801: Chr12_17400590 C/T; S11802: Chr12_17476417 G/A; S11803: Chr12_17599698 C/T; S11804: Chr12_17600311 C/T; S11805: Chr12_17642382 T/G; S11806: Chr12_17692926 G/A; S11807: Chr12_17701848 G/C; S11808: Chr12_17725204 A/G; S11809: Chr12_17817812 A/G; S11810: Chr12_17827366 T/C; S11811: Chr12_17904467 A/G; S11812: Chr12_17964853 C/T; S11813: Chr12_18023200 T/G; S11814: Chr12_18025896 T/G; S11815: Chr12_18094881 T/C; S11816: Chr12_18110964 G/A; S11817: Chr12_18125563 C/T; S11818: Chr12_18211288 C/G; S11819: Chr12_18345604 G/T; S11820: Chr12_18353371 G/A; S11821: Chr12_18375054 G/T; S11822: Chr12_18489623 C/A; S11823: Chr12_18582403 A/G; S11824: Chr12_18603871 G/A; S11825: Chr12_18686333 C/T; S11826: Chr12_18904344 A/G; S11827: Chr12_19050996 G/T; S11828: Chr12_19204713 C/T; S11829: Chr12_19580870 C/T; S11830: Chr12_19725765 C/T; S11831: Chr12_19877769 G/C; S11832: Chr12_20103545 T/G; S11833: Chr12_20206831 G/A; S11834: Chr12_20310382 T/C; S11835: Chr12_20400652 A/G; S11836: Chr12_20475003 C/T; S11837: Chr12_20558392 C/T; S11838: Chr12_20587250 G/T; S11839: Chr12_20600008 A/C; S11840: Chr12_20731767 A/C; S11841: Chr12_20750026 T/C; S11842: Chr12_20825088 G/T; S11843: Chr12_20902188 C/G; S11844: Chr12_20934591 C/G; S11845: Chr12_21125450 T/C; S11846: Chr12_21208434 G/C; S11847: Chr12_21225387 A/G; S11848: Chr12_21345201 G/T; S11849: Chr12_21350413 T/C; S11850: Chr12_21563799 T/C; S11851: Chr12_21578412 G/A; S11852: Chr12_21654380 C/T; S11853: Chr12_21682332 C/T; S11854: Chr12_21915884 C/G; S11855: Chr12_22052729 G/A; S11856: Chr12_22151845 C/A; S11857: Chr12_22186654 G/A; S11858: Chr12_22580099 C/T; S11859: Chr12_22647313 T/G; S11860: Chr12_22700544 C/T; S11861: Chr12_23077901 A/T; S11862: Chr12_23304783 C/T; S11863: Chr12_23508934 T/C; S11864: Chr12_23606892 C/T; S11865: Chr12_23843637 C/T; S11866: Chr12_23908204 G/A; S11867: Chr12_24050772 G/A; S11868: Chr12_24133058 T/A; S11869: Chr12_24351831 G/A; S11870: Chr12_24586692 G/A; S11871: Chr12_24831755 C/T; S11872: Chr12_24952356 C/T; S11873: Chr12_25101479 A/G; S11874: Chr12_25253506 G/A; S11875: Chr12_25329127 G/T; S11876: Chr12_25930576 A/T; S11877: Chr12_26008392 C/A; S11878: Chr12_26153763 A/G; S11879: Chr12_26398752 G/T; S11880: Chr12_26525074 C/T; S11881: Chr12_26691804 G/A; S11882: Chr12_26813025 G/A; S11883: Chr12_27209919 T/A; S11884: Chr12_27361685 C/T; S11885: Chr12_27525954 G/A; S11886: Chr12_27604654 G/A; S11887: Chr12_27753504 T/A; S11888: Chr12_28133015 T/C; S11889: Chr12_28377245 G/A; S11890: Chr12_28485309 C/T; S11891: Chr12_28777719 C/T; S11892: Chr12_28860710 G/C; S11893: Chr12_28949497 C/T; S11894: Chr12_29320526 C/T; S11895: Chr12_29384739 G/A; S11896: Chr12_29612136 A/T; S11897: Chr12_29906266 G/T; S11898: Chr12_29976157 A/G; S11899: Chr12_30052119 G/C; S11900: Chr12_30278494 G/A; S11901: Chr12_30430896 T/C; S11902: Chr12_30506847 A/T; S11903: Chr12_30674105 G/A; S11904: Chr12_30677758 C/T; S11905: Chr12_30838521 G/A; S11906: Chr12_30979340 G/A; S11907: Chr12_31225078 C/A; S11908: Chr12_31285937 G/A; S11909: Chr12_31426667 C/T; S11910: Chr12_31577052 C/T; S11911: Chr12_31737597 G/A; S11912: Chr12_31804748 G/A; S11913: Chr12_31892271 T/C; S11914: Chr12_31972116 C/T; S11915: Chr12_32037769 C/T; S11916: Chr12_32057571 T/C; S11917: Chr12_32148292 G/A; S11918:

Chr12_32295975 C/A; S11919: Chr12_32400650 T/C; S11920: Chr12_32465033 T/A; S11921: Chr12_32557052 A/C; S11922: Chr12_32651139 A/G; S11923: Chr12_32740023 T/C; S11924: Chr12_32750339 T/C; S11925: Chr12_32836668 T/A; S11926: Chr12_33020661 G/C; S11927: Chr12_33028815 C/T; S11928: Chr12_33050531 G/C; S11929: Chr12_33110525 T/A; S11930: Chr12_33133696 T/C; S11931: Chr12_33199377 C/G; S11932: Chr12_33229845 C/T; S11933: Chr12_33250256 G/C; S11934: Chr12_33329603 C/T; S11935: Chr12_33411902 C/T; S11936: Chr12_33493453 A/T; S11937: Chr12_33538436 A/T; S11938: Chr12_33618157 T/A; S11939: Chr12_33626202 T/C; S11940: Chr12_33670721 T/G; S11941: Chr12_33750271 C/T; S11942: Chr12_33833280 A/G; S11943: Chr12_33852018 T/A; S11944: Chr12_33982625 G/C; S11945: Chr12_34057603 A/C; S11946: Chr12_34080181 C/T; S11947: Chr12_34114209 C/T; S11948: Chr12_34137308 C/T; S11949: Chr12_34152629 G/A; S11950: Chr12_34249882 T/C; S11951: Chr12_34250128 A/G; S11952: Chr12_34328053 T/C; S11953: Chr12_34371463 C/T; S11954: Chr12_34378908 A/G; S11955: Chr12_34406014 G/C; S11956: Chr12_34433000 A/G; S11957: Chr12_34457837 C/T; S11958: Chr12_34507966 T/C; S11959: Chr12_34540101 A/G; S11960: Chr12_34551562 C/T; S11961: Chr12_34588297 A/T; S11962: Chr12_34600375 T/A; S11963: Chr12_34637037 G/A; S11964: Chr12_34654465 C/G; S11965: Chr12_34675137 A/T; S11966: Chr12_34709342 A/C; S11967: Chr12_34732042 A/C; S11968: Chr12_34756687 A/C; S11969: Chr12_34775228 C/T; S11970: Chr12_34851455 A/G; S11971: Chr12_34879829 G/A; S11972: Chr12_34904656 G/T; S11973: Chr12_34941924 T/C; S11974: Chr12_34957065 T/C; S11975: Chr12_34987622 C/A; S11976: Chr12_35042749 G/C; S11977: Chr12_35062838 T/A; S11978: Chr12_35077877 C/T; S11979: Chr12_35159803 T/C; S11980: Chr12_35175317 C/G; S11981: Chr12_35265460 G/A; S11982: Chr12_35289582 G/T; S11983: Chr12_35300920 C/T; S11984: Chr12_35370710 A/T; S11985: Chr12_35425457 C/T; S11986: Chr12_35454811 G/A; S11987: Chr12_35478589 T/C; S11988: Chr12_35554502 G/A; S11989: Chr12_35578344 A/G; S11990: Chr12_35603012 A/C; S11991: Chr12_35644049 G/A; S11992: Chr12_35653956 A/G; S11993: Chr12_35691745 T/C; S11994: Chr12_35707609 T/G; S11995: Chr12_35748672 A/T; S11996: Chr12_35785862 A/G; S11997: Chr12_35804687 G/A; S11998: Chr12_35842502 C/A; S11999: Chr12_35855477 T/G; S12000: Chr12_35879322 A/G; S12001: Chr12_35924294 T/C; S12002: Chr12_35925044 G/T; S12003: Chr12_35998782 T/A; S12004: Chr12_36002065 C/T; S12005: Chr12_36041304 G/A; S12006: Chr12_36158580 T/G; S12007: Chr12_36238725 C/A; S12008: Chr12_36262953 A/T; S12009: Chr12_36276063 C/T; S12010: Chr12_36302021 C/A; S12011: Chr12_36332573 T/G; S12012: Chr12_36355223 C/G; S12013: Chr12_36375186 A/C; S12014: Chr12_36408008 C/T; S12015: Chr12_36428980 A/G; S12016: Chr12_36462737 C/G; S12017: Chr12_36500199 A/T; S12018: Chr12_36530060 G/A; S12019: Chr12_36595459 C/A; S12020: Chr12_36600526 C/A; S12021: Chr12_36658275 G/C; S12022: Chr12_36704530 G/C; S12023: Chr12_36736475 G/A; S12024: Chr12_36765947 T/G; S12025: Chr12_36848739 T/C; S12026: Chr12_36851478 C/A; S12027: Chr12_36878561 T/C; S12028: Chr12_36915547 C/A; S12029: Chr12_36928914 T/A; S12030: Chr12_36950212 T/C; S12031: Chr12_36994675 G/C; S12032: Chr12_37002441 T/C; S12033: Chr12_37028027 A/G; S12034: Chr12_37076360 C/G; S12035: Chr12_37102145 G/C; S12036: Chr12_37133420 T/C; S12037: Chr12_37151146 A/G; S12038: Chr12_37208950 C/T; S12039: Chr12_37234318 C/T; S12040: Chr12_37273591 C/A; S12041: Chr12_37311954 A/G; S12042: Chr12_37353030 A/C; S12043: Chr12_37381912 A/G; S12044: Chr12_37440171 T/C; S12045: Chr12_37467028 T/C; S12046: Chr12_37548665 G/T; S12047: Chr12_37559833 A/C; S12048: Chr12_37596077 C/T; S12049: Chr12_37654886 G/A; S12050: Chr12_37675151 C/G; S12051: Chr12_37767142 A/G; S12052: Chr12_37776504 T/G; S12053: Chr12_37803533 A/G; S12054: Chr12_37928818 C/G; S12055: Chr12_37955440 A/G; S12056: Chr12_37978616 A/T; S12057: Chr12_38006616 A/T; S12058: Chr12_38025549 A/G; S12059: Chr12_38052974 T/C; S12060: Chr12_38119614 G/A; S12061: Chr12_38125246 G/C; S12062: Chr12_38170071 T/C; S12063: Chr12_38176073 A/G; S12064: Chr12_38200628 C/T; S12065: Chr12_38231815 C/G; S12066: Chr12_38259114 T/C; S12067: Chr12_38279169 T/G; S12068: Chr12_38316538 T/G; S12069: Chr12_38327506 C/T; S12070: Chr12_38355680 A/G; S12071: Chr12_38375362 A/G; S12072: Chr12_38410004 T/C; S12073: Chr12_38432192 A/T; S12074: Chr12_38451940 A/T; S12075: Chr12_38481319 G/A; S12076: Chr12_38511413 G/C; S12077: Chr12_38539569 G/C; S12078: Chr12_38553654 A/T; S12079: Chr12_38613817 A/G; S12080: Chr12_38630449 C/A; S12081: Chr12_38650415 C/T; S12082: Chr12_38679332 C/T; S12083: Chr12_38705798 C/T; S12084: Chr12_38725913 G/A; S12085: Chr12_38758294 T/A; S12086: Chr12_38789216 A/T; S12087: Chr12_38800158 A/T; S12088: Chr12_38856491 T/A; S12089: Chr12_38898720 G/C; S12090: Chr12_38900404 T/C; S12091: Chr12_38931352 T/C; S12092: Chr12_38982736 T/C; S12093: Chr12_39007841 C/T; S12094: Chr12_39034856 T/G; S12095: Chr12_39056379 A/C; S12096: Chr12_39086188 A/G; S12097: Chr12_39108395 A/C; S12098: Chr12_39141373 A/C; S12099: Chr12_39154625 G/A; S12100: Chr12_39200936 G/A; S12101: Chr12_39228628 A/C; S12102: Chr12_39259902 C/T; S12103: Chr12_39279749 G/A; S12104: Chr12_39308600 C/T; S12105: Chr12_39327909 A/G; S12106: Chr12_39361976 T/A; S12107: Chr12_39380034 T/G; S12108: Chr12_39400458 T/C; S12109: Chr12_39427191 A/G; S12110: Chr12_39450012 T/C; S12111: Chr12_39475707 G/A; S12112: Chr12_39501613 T/C; S12113: Chr12_39525342 G/A; S12114: Chr12_39552726 T/A; S12115: Chr12_39588191 G/A; S12116: Chr12_39608018 C/A; S12117: Chr12_39625516 G/C; S12118: Chr12_39654523 A/G; S12119:

Chr12_39711068 G/A; S12120: Chr12_39725146 T/C; S12121: Chr12_39786141 T/C; S12122: Chr12_39801257 A/G; S12123: Chr12_39825680 A/T; S12124: Chr12_39850861 A/G; S12125: Chr12_39886069 T/G; S12126: Chr12_39900431 C/T; S12127: Chr12_39925130 T/C; S12128: Chr12_39955071 C/A; S12129: Chr12_39977923 T/A; S12130: Chr12_40001254 C/T; S12131: Chr12_40047427 T/C; S12132: Chr12_40052522 C/T; S12133: Chr12_40075711 T/C; S12134: Chr13_00008653 C/T; S12135: Chr13_00080773 A/G; S12136: Chr13_00100900 G/A; S12137: Chr13_00127669 G/C; S12138: Chr13_00154466 T/A; S12139: Chr13_00212915 T/C; S12140: Chr13_00247594 A/T; S12141: Chr13_00297004 C/T; S12142: Chr13_00320689 G/A; S12143: Chr13_00374872 A/G; S12144: Chr13_00419563 A/T; S12145: Chr13_00433228 A/C; S12146: Chr13_00474188 C/T; S12147: Chr13_00507692 T/A; S12148: Chr13_00565399 C/G; S12149: Chr13_00577638 T/C; S12150: Chr13_00612710 A/T; S12151: Chr13_00627743 C/T; S12152: Chr13_00650020 T/G; S12153: Chr13_00675404 G/A; S12154: Chr13_00763451 C/A; S12155: Chr13_00787817 T/C; S12156: Chr13_00800104 A/G; S12157: Chr13_00909135 G/T; S12158: Chr13_00936892 A/G; S12159: Chr13_01004014 C/T; S12160: Chr13_01045508 G/A; S12161: Chr13_01068217 T/C; S12162: Chr13_01077050 C/G; S12163: Chr13_01100257 G/A; S12164: Chr13_01205094 C/T; S12165: Chr13_01239000 T/C; S12166: Chr13_01311389 C/T; S12167: Chr13_01335210 G/A; S12168: Chr13_01364636 T/A; S12169: Chr13_01386293 T/G; S12170: Chr13_01423426 G/A; S12171: Chr13_01429865 C/A; S12172: Chr13_01457322 G/C; S12173: Chr13_01484013 G/A; S12174: Chr13_01632982 C/T; S12175: Chr13_01650198 T/C; S12176: Chr13_01725211 A/G; S12177: Chr13_01806770 C/A; S12178: Chr13_01844449 A/G; S12179: Chr13_01852696 T/C; S12180: Chr13_01933143 C/T; S12181: Chr13_01950536 G/C; S12182: Chr13_01977863 A/G; S12183: Chr13_02008773 T/C; S12184: Chr13_02029233 T/A; S12185: Chr13_02091790 T/C; S12186: Chr13_02118561 C/T; S12187: Chr13_02127379 T/C; S12188: Chr13_02152261 T/C; S12189: Chr13_02231196 T/A; S12190: Chr13_02255220 A/G; S12191: Chr13_02325175 C/T; S12192: Chr13_02440599 T/C; S12193: Chr13_02456792 T/C; S12194: Chr13_02566263 C/T; S12195: Chr13_02618209 T/C; S12196: Chr13_02625854 T/C; S12197: Chr13_02650519 G/A; S12198: Chr13_02725409 C/T; S12199: Chr13_02832533 C/A; S12200: Chr13_02887532 G/A; S12201: Chr13_02901491 T/A; S12202: Chr13_02926674 G/A; S12203: Chr13_03019380 T/C; S12204: Chr13_03025720 C/T; S12205: Chr13_04125106 T/C; S12206: Chr13_04200011 G/T; S12207: Chr13_04276284 T/A; S12208: Chr13_04351360 T/C; S12209: Chr13_04558322 C/T; S12210: Chr13_04711267 C/T; S12211: Chr13_04780177 A/G; S12212: Chr13_04925001 T/C; S12213: Chr13_05225815 A/T; S12214: Chr13_05337028 A/T; S12215: Chr13_05350120 T/C; S12216: Chr13_05479709 G/A; S12217: Chr13_05500149 C/T; S12218: Chr13_05582352 T/A; S12219: Chr13_05665491 T/G; S12220: Chr13_05675470 C/A; S12221: Chr13_05846879 A/G; S12222: Chr13_05850640 G/A; S12223: Chr13_05925587 A/C; S12224: Chr13_06056544 A/G; S12225: Chr13_06076888 A/T; S12226: Chr13_06101108 A/G; S12227: Chr13_06177658 T/C; S12228: Chr13_06404193 T/A; S12229: Chr13_06555921 A/C; S12230: Chr13_06625074 G/A; S12231: Chr13_06756398 T/G; S12232: Chr13_06777415 T/C; S12233: Chr13_06800039 A/G; S12234: Chr13_06991256 C/T; S12235: Chr13_07000061 A/G; S12236: Chr13_07075042 G/A; S12237: Chr13_07334939 C/T; S12238: Chr13_07358677 T/C; S12239: Chr13_07431999 A/G; S12240: Chr13_07450551 T/G; S12241: Chr13_07525766 A/G; S12242: Chr13_07600207 T/C; S12243: Chr13_07750146 A/G; S12244: Chr13_07975012 A/G; S12245: Chr13_08119129 G/A; S12246: Chr13_08150611 T/A; S12247: Chr13_08413327 G/T; S12248: Chr13_08426803 T/C; S12249: Chr13_08500040 T/C; S12250: Chr13_08615314 G/A; S12251: Chr13_08650213 G/A; S12252: Chr13_08725132 C/T; S12253: Chr13_08875041 A/G; S12254: Chr13_08950196 A/G; S12255: Chr13_09200028 C/T; S12256: Chr13_09428111 A/C; S12257: Chr13_09599236 T/A; S12258: Chr13_09600303 T/C; S12259: Chr13_09775850 A/T; S12260: Chr13_10039510 T/C; S12261: Chr13_10051997 G/T; S12262: Chr13_10095378 T/A; S12263: Chr13_10119708 C/T; S12264: Chr13_10138462 A/C; S12265: Chr13_10176127 C/T; S12266: Chr13_10230891 T/A; S12267: Chr13_10250126 C/T; S12268: Chr13_10278590 G/T; S12269: Chr13_10310757 T/C; S12270: Chr13_10340500 A/G; S12271: Chr13_10357231 G/T; S12272: Chr13_10386453 C/T; S12273: Chr13_10466550 A/G; S12274: Chr13_10489823 T/A; S12275: Chr13_10505110 A/G; S12276: Chr13_10531732 T/A; S12277: Chr13_10550422 C/T; S12278: Chr13_10576051 A/G; S12279: Chr13_10600096 C/A; S12280: Chr13_10656715 G/T; S12281: Chr13_10706336 T/A; S12282: Chr13_10733616 A/T; S12283: Chr13_10773567 G/A; S12284: Chr13_10786816 T/C; S12285: Chr13_10828965 T/G; S12286: Chr13_10850579 T/C; S12287: Chr13_10932499 T/A; S12288: Chr13_10968522 T/C; S12289: Chr13_10985562 C/A; S12290: Chr13_11001866 A/T; S12291: Chr13_11025115 T/C; S12292: Chr13_11106359 C/A; S12293: Chr13_11166187 G/C; S12294: Chr13_11177848 C/A; S12295: Chr13_11206849 G/A; S12296: Chr13_11279838 A/G; S12297: Chr13_11338507 A/G; S12298: Chr13_11416050 A/G; S12299: Chr13_11434291 G/A; S12300: Chr13_11458607 C/T; S12301: Chr13_11476408 T/A; S12302: Chr13_11534574 G/A; S12303: Chr13_11623642 T/C; S12304: Chr13_11625952 G/A; S12305: Chr13_11706421 G/A; S12306: Chr13_11749908 T/C; S12307: Chr13_11750306 T/C; S12308: Chr13_11792034 T/C; S12309: Chr13_11817049 G/A; S12310: Chr13_11855864 A/C; S12311: Chr13_11889317 G/A; S12312: Chr13_11958884 A/G; S12313: Chr13_12003159 C/T; S12314: Chr13_12115400 G/A; S12315: Chr13_12140896 G/A; S12316: Chr13_12196612 A/T; S12317: Chr13_12220310 T/C; S12318: Chr13_12230635 G/T; S12319: Chr13_12250117 T/G; S12320:

Chr13_12311225 A/G; S12321: Chr13_12339073 C/G; S12322: Chr13_12350008 T/C; S12323: Chr13_12425006 C/A; S12324: Chr13_12532825 A/G; S12325: Chr13_12579927 C/T; S12326: Chr13_12675110 T/C; S12327: Chr13_12750252 C/A; S12328: Chr13_12876870 A/G; S12329: Chr13_12932443 T/C; S12330: Chr13_13018419 C/T; S12331: Chr13_13086943 A/G; S12332: Chr13_13137026 T/C; S12333: Chr13_13163673 C/T; S12334: Chr13_13308150 C/T; S12335: Chr13_13331067 C/A; S12336: Chr13_13354578 C/T; S12337: Chr13_13375046 T/A; S12338: Chr13_13450643 C/T; S12339: Chr13_13516435 G/A; S12340: Chr13_13550914 A/G; S12341: Chr13_13575150 T/C; S12342: Chr13_13615511 T/C; S12343: Chr13_13632205 G/T; S12344: Chr13_13659315 C/A; S12345: Chr13_13682530 T/C; S12346: Chr13_13704534 T/G; S12347: Chr13_13735973 A/C; S12348: Chr13_13759456 A/T; S12349: Chr13_13792303 T/C; S12350: Chr13_13801771 G/A; S12351: Chr13_13849289 A/C; S12352: Chr13_13854098 G/A; S12353: Chr13_13883726 T/A; S12354: Chr13_13911835 C/T; S12355: Chr13_13926021 A/T; S12356: Chr13_13985242 C/T; S12357: Chr13_14010569 C/T; S12358: Chr13_14037483 A/G; S12359: Chr13_14065806 C/A; S12360: Chr13_14089920 T/G; S12361: Chr13_14108842 A/G; S12362: Chr13_14129219 C/A; S12363: Chr13_14161070 G/A; S12364: Chr13_14176051 A/G; S12365: Chr13_14256401 G/A; S12366: Chr13_14292073 A/C; S12367: Chr13_14300033 C/T; S12368: Chr13_14325231 C/T; S12369: Chr13_14369965 G/A; S12370: Chr13_14378072 G/A; S12371: Chr13_14409328 A/G; S12372: Chr13_14435999 T/C; S12373: Chr13_14473895 T/C; S12374: Chr13_14478389 A/G; S12375: Chr13_14510977 A/T; S12376: Chr13_14526502 A/T; S12377: Chr13_14566271 T/C; S12378: Chr13_14575308 T/G; S12379: Chr13_14609221 T/C; S12380: Chr13_14630892 A/G; S12381: Chr13_14653507 C/A; S12382: Chr13_14675637 G/A; S12383: Chr13_14701641 C/T; S12384: Chr13_14733847 G/C; S12385: Chr13_14758231 T/A; S12386: Chr13_14775971 A/C; S12387: Chr13_14876832 G/A; S12388: Chr13_14909976 T/A; S12389: Chr13_14935673 G/A; S12390: Chr13_14957312 G/A; S12391: Chr13_15005913 G/A; S12392: Chr13_15037532 A/C; S12393: Chr13_15053245 A/T; S12394: Chr13_15075811 A/C; S12395: Chr13_15111137 T/G; S12396: Chr13_15125225 A/C; S12397: Chr13_15153675 T/A; S12398: Chr13_15175142 A/T; S12399: Chr13_15216568 T/A; S12400: Chr13_15225349 A/G; S12401: Chr13_15250217 C/T; S12402: Chr13_15289101 T/G; S12403: Chr13_15329859 C/T; S12404: Chr13_15396542 C/T; S12405: Chr13_15407003 T/C; S12406: Chr13_15431271 A/T; S12407: Chr13_15488118 A/C; S12408: Chr13_15502915 C/A; S12409: Chr13_15526524 G/C; S12410: Chr13_15601195 T/C; S12411: Chr13_15630824 T/C; S12412: Chr13_15660523 C/T; S12413: Chr13_15700101 C/A; S12414: Chr13_15726422 T/C; S12415: Chr13_15750139 C/G; S12416: Chr13_15846768 A/G; S12417: Chr13_15869687 G/A; S12418: Chr13_15888172 G/A; S12419: Chr13_15901106 A/T; S12420: Chr13_16005609 C/T; S12421: Chr13_16057824 G/A; S12422: Chr13_16077010 T/A; S12423: Chr13_16154260 G/A; S12424: Chr13_16180468 T/A; S12425: Chr13_16216301 C/T; S12426: Chr13_16247730 A/T; S12427: Chr13_16254543 A/G; S12428: Chr13_16333918 T/G; S12429: Chr13_16364143 A/T; S12430: Chr13_16377715 T/C; S12431: Chr13_16400793 C/T; S12432: Chr13_16432243 C/G; S12433: Chr13_16453402 G/C; S12434: Chr13_16484275 T/C; S12435: Chr13_16570127 T/C; S12436: Chr13_16599439 A/G; S12437: Chr13_16613274 C/G; S12438: Chr13_16679996 C/A; S12439: Chr13_16704243 C/A; S12440: Chr13_16748000 G/A; S12441: Chr13_16756903 C/A; S12442: Chr13_16775618 C/T; S12443: Chr13_16810612 T/A; S12444: Chr13_16825744 G/A; S12445: Chr13_16856394 A/G; S12446: Chr13_16876054 G/C; S12447: Chr13_16918581 G/A; S12448: Chr13_16925145 A/C; S12449: Chr13_16969679 T/C; S12450: Chr13_16986819 G/A; S12451: Chr13_17001176 A/C; S12452: Chr13_17041036 G/A; S12453: Chr13_17066522 G/A; S12454: Chr13_17091658 T/C; S12455: Chr13_17107219 G/T; S12456: Chr13_17126058 C/T; S12457: Chr13_17158338 C/T; S12458: Chr13_17177160 T/C; S12459: Chr13_17220523 G/A; S12460: Chr13_17225556 A/C; S12461: Chr13_17304018 A/G; S12462: Chr13_17346765 T/C; S12463: Chr13_17356493 G/A; S12464: Chr13_17394078 T/C; S12465: Chr13_17410106 G/A; S12466: Chr13_17425003 A/T; S12467: Chr13_17554291 G/T; S12468: Chr13_17619283 T/C; S12469: Chr13_17667052 G/T; S12470: Chr13_17677431 G/A; S12471: Chr13_17762950 T/C; S12472: Chr13_17830604 C/T; S12473: Chr13_17974626 T/C; S12474: Chr13_17975733 T/A; S12475: Chr13_18011254 A/C; S12476: Chr13_18034985 C/T; S12477: Chr13_18062726 A/G; S12478: Chr13_18084797 G/A; S12479: Chr13_18124177 A/G; S12480: Chr13_18151302 A/G; S12481: Chr13_18203769 T/G; S12482: Chr13_18250495 C/A; S12483: Chr13_18284251 G/A; S12484: Chr13_18328375 A/T; S12485: Chr13_18351792 G/A; S12486: Chr13_18397824 C/T; S12487: Chr13_18400146 G/A; S12488: Chr13_18426640 C/A; S12489: Chr13_18454726 T/A; S12490: Chr13_18504679 G/C; S12491: Chr13_18552044 C/T; S12492: Chr13_18578546 C/T; S12493: Chr13_18615062 A/C; S12494: Chr13_18664102 A/C; S12495: Chr13_18682420 C/T; S12496: Chr13_18732540 G/C; S12497: Chr13_18751848 A/G; S12498: Chr13_18861112 G/A; S12499: Chr13_18891455 A/C; S12500: Chr13_18959102 T/G; S12501: Chr13_19001523 G/A; S12502: Chr13_19036151 A/T; S12503: Chr13_19054199 C/T; S12504: Chr13_19080545 A/G; S12505: Chr13_19109371 A/C; S12506: Chr13_19133915 C/T; S12507: Chr13_19214398 T/C; S12508: Chr13_19246113 G/C; S12509: Chr13_19257771 A/G; S12510: Chr13_19290099 T/C; S12511: Chr13_19303467 G/A; S12512: Chr13_19399767 T/C; S12513: Chr13_19419704 C/T; S12514: Chr13_19425153 G/T; S12515: Chr13_19460489 T/C; S12516: Chr13_19517884 A/T; S12517: Chr13_19545553 T/C; S12518: Chr13_19594201 A/G; S12519: Chr13_19691041 C/A; S12520: Chr13_19868544 A/G; S12521:

Chr13_19879001 G/A; S12522: Chr13_19958151 G/T; S12523: Chr13_20043228 G/A; S12524: Chr13_20101231 A/G; S12525: Chr13_20156435 C/G; S12526: Chr13_20229356 G/A; S12527: Chr13_20320875 T/C; S12528: Chr13_20333515 A/T; S12529: Chr13_20352448 A/T; S12530: Chr13_20408995 T/C; S12531: Chr13_20425091 C/T; S12532: Chr13_20522861 T/A; S12533: Chr13_20529307 T/C; S12534: Chr13_20565648 G/A; S12535: Chr13_20587777 C/T; S12536: Chr13_20648702 G/T; S12537: Chr13_20701914 C/T; S12538: Chr13_20725448 A/G; S12539: Chr13_20814464 A/G; S12540: Chr13_20825021 G/A; S12541: Chr13_20903822 T/A; S12542: Chr13_20936168 C/T; S12543: Chr13_20954156 C/A; S12544: Chr13_20976496 G/T; S12545: Chr13_21001120 T/A; S12546: Chr13_21083722 G/A; S12547: Chr13_21155473 G/A; S12548: Chr13_21190252 T/C; S12549: Chr13_21250914 G/T; S12550: Chr13_21287347 G/A; S12551: Chr13_21324717 A/T; S12552: Chr13_21335887 C/T; S12553: Chr13_21401538 T/C; S12554: Chr13_21484110 C/T; S12555: Chr13_21508678 A/T; S12556: Chr13_21528858 T/C; S12557: Chr13_21558148 A/G; S12558: Chr13_21582241 C/T; S12559: Chr13_21616173 G/T; S12560: Chr13_21625491 A/T; S12561: Chr13_21654981 G/A; S12562: Chr13_21679609 T/C; S12563: Chr13_21706347 G/C; S12564: Chr13_21735193 A/C; S12565: Chr13_21768219 C/G; S12566: Chr13_21775204 A/G; S12567: Chr13_21819620 T/C; S12568: Chr13_21825102 T/G; S12569: Chr13_21850726 C/A; S12570: Chr13_21905803 T/G; S12571: Chr13_21926992 A/C; S12572: Chr13_21956623 G/A; S12573: Chr13_21976654 C/T; S12574: Chr13_22002166 T/C; S12575: Chr13_22033385 C/G; S12576: Chr13_22079118 A/G; S12577: Chr13_22105530 A/G; S12578: Chr13_22191411 G/A; S12579: Chr13_22243352 T/A; S12580: Chr13_22254210 A/G; S12581: Chr13_22275813 C/T; S12582: Chr13_22319413 C/T; S12583: Chr13_22365204 T/C; S12584: Chr13_22381255 G/A; S12585: Chr13_22407197 G/A; S12586: Chr13_22445616 C/A; S12587: Chr13_22453010 G/A; S12588: Chr13_22536923 A/T; S12589: Chr13_22658926 G/A; S12590: Chr13_22689145 T/C; S12591: Chr13_22764610 A/T; S12592: Chr13_22901190 C/T; S12593: Chr13_23048942 G/A; S12594: Chr13_23067115 A/C; S12595: Chr13_23079247 C/T; S12596: Chr13_23127922 A/G; S12597: Chr13_23153881 C/G; S12598: Chr13_23223501 T/C; S12599: Chr13_23234096 T/A; S12600: Chr13_23314860 A/C; S12601: Chr13_23333581 G/A; S12602: Chr13_23364555 C/T; S12603: Chr13_23378060 A/G; S12604: Chr13_23473517 G/A; S12605: Chr13_23475002 C/A; S12606: Chr13_23500338 T/C; S12607: Chr13_23557065 T/G; S12608: Chr13_23603144 T/G; S12609: Chr13_23636700 T/C; S12610: Chr13_23667968 C/T; S12611: Chr13_23681002 A/G; S12612: Chr13_23715178 T/C; S12613: Chr13_23742543 G/A; S12614: Chr13_23808347 C/G; S12615: Chr13_23835338 A/T; S12616: Chr13_23856232 G/A; S12617: Chr13_23901375 C/A; S12618: Chr13_23925198 G/A; S12619: Chr13_23956173 G/A; S12620: Chr13_23978719 A/C; S12621: Chr13_24014248 G/T;

S12622: Chr13_24029706 T/A; S12623: Chr13_24083056 T/G; S12624: Chr13_24155092 C/T; S12625: Chr13_24243211 C/G; S12626: Chr13_24250245 C/T; S12627: Chr13_24325846 G/A; S12628: Chr13_24362094 G/A; S12629: Chr13_24429215 T/C; S12630: Chr13_24539533 C/A; S12631: Chr13_24555385 C/T; S12632: Chr13_24595862 T/C; S12633: Chr13_24606476 C/A; S12634: Chr13_24631785 G/A; S12635: Chr13_24665388 C/G; S12636: Chr13_24677825 C/T; S12637: Chr13_24703460 A/C; S12638: Chr13_24787096 A/T; S12639: Chr13_24804891 C/T; S12640: Chr13_24842133 T/A; S12641: Chr13_24850013 A/G; S12642: Chr13_24891502 T/C; S12643: Chr13_24904749 C/A; S12644: Chr13_24936869 T/C; S12645: Chr13_25019748 G/A; S12646: Chr13_25028644 A/C; S12647: Chr13_25061272 T/C; S12648: Chr13_25079243 T/C; S12649: Chr13_25111706 A/C; S12650: Chr13_25137525 C/T; S12651: Chr13_25159704 G/C; S12652: Chr13_25195887 A/G; S12653: Chr13_25216168 G/T; S12654: Chr13_25232377 C/T; S12655: Chr13_25252738 C/T; S12656: Chr13_25276894 T/G; S12657: Chr13_25301785 A/G; S12658: Chr13_25325641 T/A; S12659: Chr13_25467010 T/C; S12660: Chr13_25489234 C/T; S12661: Chr13_25521127 T/C; S12662: Chr13_25548690 G/C; S12663: Chr13_25576555 T/C; S12664: Chr13_25601973 T/C; S12665: Chr13_25635804 C/T; S12666: Chr13_25666092 A/T; S12667: Chr13_25703242 T/A; S12668: Chr13_25731419 G/A; S12669: Chr13_25751923 G/C; S12670: Chr13_25776773 A/T; S12671: Chr13_25860455 T/A; S12672: Chr13_25910837 A/G; S12673: Chr13_25929775 T/C; S12674: Chr13_25953139 T/C; S12675: Chr13_25986588 G/C; S12676: Chr13_26002753 T/C; S12677: Chr13_26041469 C/T; S12678: Chr13_26056881 A/G; S12679: Chr13_26092378 C/T; S12680: Chr13_26109851 A/T; S12681: Chr13_26127577 G/T; S12682: Chr13_26160222 C/G; S12683: Chr13_26178729 T/C; S12684: Chr13_26202426 G/A; S12685: Chr13_26275406 T/C; S12686: Chr13_26314229 C/A; S12687: Chr13_26344379 T/C; S12688: Chr13_26350308 G/C; S12689: Chr13_26427631 T/A; S12690: Chr13_26553125 T/C; S12691: Chr13_26575808 G/A; S12692: Chr13_26684044 T/G; S12693: Chr13_26717064 C/T; S12694: Chr13_26735329 T/C; S12695: Chr13_26753402 G/A; S12696: Chr13_26839061 C/G; S12697: Chr13_26856123 A/G; S12698: Chr13_26880451 T/C; S12699: Chr13_26911608 C/T; S12700: Chr13_26960899 G/C; S12701: Chr13_26979745 G/C; S12702: Chr13_27003430 G/C; S12703: Chr13_27037662 G/T; S12704: Chr13_27050562 T/C; S12705: Chr13_27093500 T/G; S12706: Chr13_27106871 T/A; S12707: Chr13_27132231 G/A; S12708: Chr13_27196920 T/C; S12709: Chr13_27230030 G/C; S12710: Chr13_27269190 C/T; S12711: Chr13_27335560 G/C; S12712: Chr13_27358724 G/T; S12713: Chr13_27382220 A/T; S12714: Chr13_27425055 T/A; S12715: Chr13_27477981 T/C; S12716: Chr13_27571004 C/T; S12717: Chr13_27577017 G/A; S12718: Chr13_27607877 A/G; S12719: Chr13_27641021 G/A; S12720: Chr13_27657877 A/G; S12721: Chr13_27676025 C/T; S12722:

Chr13_27700291 T/C; S12723: Chr13_27734228 T/A; S12724: Chr13_27751336 T/A; S12725: Chr13_27775063 A/T; S12726: Chr13_27818204 C/A; S12727: Chr13_27827765 G/T; S12728: Chr13_27851429 C/T; S12729: Chr13_27877847 C/A; S12730: Chr13_27906623 A/T; S12731: Chr13_27935606 C/A; S12732: Chr13_27958282 A/G; S12733: Chr13_27975604 G/T; S12734: Chr13_28014362 T/C; S12735: Chr13_28032046 T/C; S12736: Chr13_28059131 A/C; S12737: Chr13_28077760 A/G; S12738: Chr13_28117662 C/T; S12739: Chr13_28131612 A/G; S12740: Chr13_28152499 A/G; S12741: Chr13_28175383 G/A; S12742: Chr13_28211158 T/G; S12743: Chr13_28225439 C/A; S12744: Chr13_28250568 A/C; S12745: Chr13_28293309 G/A; S12746: Chr13_28303515 G/A; S12747: Chr13_28326731 T/A; S12748: Chr13_28350392 G/A; S12749: Chr13_28398755 G/A; S12750: Chr13_28400485 A/G; S12751: Chr13_28428400 A/G; S12752: Chr13_28507313 C/T; S12753: Chr13_28539535 C/G; S12754: Chr13_28570472 T/G; S12755: Chr13_28577222 G/A; S12756: Chr13_28609825 G/A; S12757: Chr13_28630296 T/C; S12758: Chr13_28659333 G/T; S12759: Chr13_28683703 A/G; S12760: Chr13_28720904 G/T; S12761: Chr13_28762800 G/A; S12762: Chr13_28778639 T/C; S12763: Chr13_28806052 G/T; S12764: Chr13_28830306 G/C; S12765: Chr13_28861525 T/C; S12766: Chr13_28885832 C/T; S12767: Chr13_28902747 G/T; S12768: Chr13_28927438 G/A; S12769: Chr13_28982183 A/G; S12770: Chr13_29021325 A/T; S12771: Chr13_29027068 C/T; S12772: Chr13_29060083 C/T; S12773: Chr13_29086459 A/G; S12774: Chr13_29100248 T/A; S12775: Chr13_29127518 T/A; S12776: Chr13_29159206 G/A; S12777: Chr13_29182879 C/T; S12778: Chr13_29215285 G/T; S12779: Chr13_29225516 G/A; S12780: Chr13_29257473 A/G; S12781: Chr13_29276891 G/A; S12782: Chr13_29319003 T/A; S12783: Chr13_29340883 C/T; S12784: Chr13_29350140 G/T; S12785: Chr13_29378102 C/T; S12786: Chr13_29401541 A/C; S12787: Chr13_29434242 G/A; S12788: Chr13_29450326 T/C; S12789: Chr13_29476830 A/G; S12790: Chr13_29508581 C/A; S12791: Chr13_29526531 C/T; S12792: Chr13_29550344 G/A; S12793: Chr13_29583804 C/T; S12794: Chr13_29600804 G/C; S12795: Chr13_29626514 A/C; S12796: Chr13_29650706 T/C; S12797: Chr13_29715233 A/G; S12798: Chr13_29741614 C/G; S12799: Chr13_29752733 G/A; S12800: Chr13_29784069 A/G; S12801: Chr13_29808193 C/T; S12802: Chr13_29831668 T/A; S12803: Chr13_29855760 T/A; S12804: Chr13_29875100 A/T; S12805: Chr13_29901560 C/T; S12806: Chr13_29927368 A/G; S12807: Chr13_29952924 T/C; S12808: Chr13_29982943 T/C; S12809: Chr13_30002224 A/G; S12810: Chr13_30025289 G/A; S12811: Chr13_30051056 T/G; S12812: Chr13_30077218 T/A; S12813: Chr13_30101734 T/G; S12814: Chr13_30130747 A/G; S12815: Chr13_30167754 T/C; S12816: Chr13_30188286 A/C; S12817: Chr13_30221512 G/A; S12818: Chr13_30226507 G/A; S12819: Chr13_30252259 C/T; S12820: Chr13_30276045 C/T; S12821: Chr13_30300354 G/A; S12822: Chr13_30331023 C/T; S12823: Chr13_30355203 A/G; S12824: Chr13_30388748 A/G; S12825: Chr13_30402278 A/G; S12826: Chr13_30436827 C/G; S12827: Chr13_30459876 A/G; S12828: Chr13_30482286 T/C; S12829: Chr13_30502842 A/C; S12830: Chr13_30532621 C/T; S12831: Chr13_30554041 C/A; S12832: Chr13_30577921 C/T; S12833: Chr13_30608731 G/A; S12834: Chr13_30626411 A/G; S12835: Chr13_30653526 T/C; S12836: Chr13_30677554 C/T; S12837: Chr13_30709942 T/G; S12838: Chr13_30727174 T/C; S12839: Chr13_30763940 C/T; S12840: Chr13_30787325 G/T; S12841: Chr13_30806459 C/T; S12842: Chr13_30833296 C/T; S12843: Chr13_30866652 G/A; S12844: Chr13_30875390 T/C; S12845: Chr13_30915442 T/C; S12846: Chr13_30944926 C/T; S12847: Chr13_30976033 A/G; S12848: Chr13_31000192 C/A; S12849: Chr13_31047414 T/A; S12850: Chr13_31052376 A/G; S12851: Chr13_31077604 T/G; S12852: Chr13_31110646 T/A; S12853: Chr13_31125197 T/G; S12854: Chr13_31154394 T/C; S12855: Chr13_31182046 A/G; S12856: Chr13_31203096 G/A; S12857: Chr13_31226136 C/T; S12858: Chr13_31257657 C/T; S12859: Chr13_31302765 G/A; S12860: Chr13_31341468 G/A; S12861: Chr13_31355807 C/A; S12862: Chr13_31375298 G/A; S12863: Chr13_31403449 A/G; S12864: Chr13_31428733 C/T; S12865: Chr13_31480450 G/A; S12866: Chr13_31503246 G/A; S12867: Chr13_31531965 C/T; S12868: Chr13_31550833 G/C; S12869: Chr13_31583138 T/G; S12870: Chr13_31602190 C/T; S12871: Chr13_31626375 C/T; S12872: Chr13_31652601 C/A; S12873: Chr13_31685373 T/A; S12874: Chr13_31702851 C/T; S12875: Chr13_31729478 C/T; S12876: Chr13_31794058 C/T; S12877: Chr13_31814712 C/T; S12878: Chr13_31832249 A/T; S12879: Chr13_31853369 C/T; S12880: Chr13_31881151 G/T; S12881: Chr13_31921805 C/A; S12882: Chr13_31945168 T/A; S12883: Chr13_31967121 T/C; S12884: Chr13_31981339 C/A; S12885: Chr13_32021754 A/G; S12886: Chr13_32039156 G/T; S12887: Chr13_32051842 C/G; S12888: Chr13_32083900 C/T; S12889: Chr13_32109291 A/G; S12890: Chr13_32125180 G/T; S12891: Chr13_32164527 A/T; S12892: Chr13_32177815 T/C; S12893: Chr13_32205053 T/A; S12894: Chr13_32231908 T/G; S12895: Chr13_32255526 G/T; S12896: Chr13_32286698 G/C; S12897: Chr13_32301951 G/T; S12898: Chr13_32326685 G/C; S12899: Chr13_32358866 C/G; S12900: Chr13_32375491 G/A; S12901: Chr13_32400678 T/C; S12902: Chr13_32431467 A/G; S12903: Chr13_32461178 C/A; S12904: Chr13_32479457 A/G; S12905: Chr13_32500153 A/G; S12906: Chr13_32527528 T/C; S12907: Chr13_32553021 T/C; S12908: Chr13_32583988 A/G; S12909: Chr13_32608283 T/C; S12910: Chr13_32627578 G/C; S12911: Chr13_32651163 G/A; S12912: Chr13_32675517 A/T; S12913: Chr13_32711914 C/T; S12914: Chr13_32730611 C/T; S12915: Chr13_32754469 C/T; S12916: Chr13_32783652 G/C; S12917: Chr13_32804888 G/T; S12918: Chr13_32827475 T/G; S12919: Chr13_32851160 G/C; S12920: Chr13_32875774 G/T; S12921: Chr13_32904795 G/A; S12922: Chr13_32926805 G/T; S12923:

Chr13_32961415 T/A; S12924: Chr13_32978499 C/T; S12925: Chr13_33000703 C/T; S12926: Chr13_33038763 C/A; S12927: Chr13_33052153 G/T; S12928: Chr13_33096175 T/A; S12929: Chr13_33100194 A/G; S12930: Chr13_33141264 C/G; S12931: Chr13_33192397 G/A; S12932: Chr13_33201670 T/C; S12933: Chr13_33234484 T/C; S12934: Chr13_33255133 A/G; S12935: Chr13_33279595 A/G; S12936: Chr13_33316633 G/A; S12937: Chr13_33326468 T/A; S12938: Chr13_33352834 C/T; S12939: Chr13_33375272 T/A; S12940: Chr13_33401174 T/C; S12941: Chr13_33425940 G/A; S12942: Chr13_33460138 G/A; S12943: Chr13_33484893 G/T; S12944: Chr13_33504254 T/C; S12945: Chr13_33528740 A/T; S12946: Chr13_33554154 T/C; S12947: Chr13_33578163 A/G; S12948: Chr13_33601755 T/C; S12949: Chr13_33647144 T/A; S12950: Chr13_33651633 A/G; S12951: Chr13_33675472 G/A; S12952: Chr13_33701076 G/A; S12953: Chr13_33726345 T/G; S12954: Chr13_33750361 C/T; S12955: Chr13_33793812 T/G; S12956: Chr13_33804363 A/C; S12957: Chr13_33830754 C/G; S12958: Chr13_33868713 C/T; S12959: Chr13_33875760 C/A; S12960: Chr13_33940491 C/T; S12961: Chr13_33958434 A/C; S12962: Chr13_33994684 T/C; S12963: Chr13_34006822 A/C; S12964: Chr13_34031917 T/C; S12965: Chr13_34056871 T/C; S12966: Chr13_34081972 T/A; S12967: Chr13_34104353 T/A; S12968: Chr13_34125046 A/C; S12969: Chr13_34162605 C/G; S12970: Chr13_34202773 A/C; S12971: Chr13_34235079 A/G; S12972: Chr13_34257937 A/G; S12973: Chr13_34276074 G/T; S12974: Chr13_34310487 A/G; S12975: Chr13_34325919 A/G; S12976: Chr13_34353457 G/C; S12977: Chr13_34389021 G/A; S12978: Chr13_34405437 C/G; S12979: Chr13_34433520 T/A; S12980: Chr13_34460303 T/A; S12981: Chr13_34476347 C/A; S12982: Chr13_34514531 T/G; S12983: Chr13_34526027 T/A; S12984: Chr13_34560740 A/G; S12985: Chr13_34583683 G/A; S12986: Chr13_34600443 C/T; S12987: Chr13_34634901 T/G; S12988: Chr13_34653703 T/C; S12989: Chr13_34676510 C/T; S12990: Chr13_34703414 G/A; S12991: Chr13_34738900 A/G; S12992: Chr13_34803371 A/G; S12993: Chr13_34825435 C/T; S12994: Chr13_34879814 C/T; S12995: Chr13_34904095 A/C; S12996: Chr13_34926633 C/G; S12997: Chr13_34964155 A/T; S12998: Chr13_34984119 T/A; S12999: Chr13_35060291 A/C; S13000: Chr13_35164031 C/T; S13001: Chr13_35175453 C/G; S13002: Chr13_35290188 G/T; S13003: Chr13_35339739 T/A; S13004: Chr13_35374263 A/C; S13005: Chr13_35405702 G/T; S13006: Chr13_35435230 A/G; S13007: Chr13_35460371 T/G; S13008: Chr13_35483020 C/T; S13009: Chr13_35502345 A/G; S13010: Chr13_35548524 G/A; S13011: Chr13_35557395 T/C; S13012: Chr13_35585850 G/T; S13013: Chr13_35653441 T/C; S13014: Chr13_35677879 C/T; S13015: Chr13_35704762 T/C; S13016: Chr13_35732928 A/G; S13017: Chr13_35764590 G/A; S13018: Chr13_35790749 G/C; S13019: Chr13_35811168 C/T; S13020: Chr13_35832941 C/T; S13021: Chr13_35880118 G/T; S13022: Chr13_35902968 A/C; S13023: Chr13_35932514 C/T; S13024: Chr13_35958883 T/A; S13025: Chr13_35995086 T/A; S13026: Chr13_36015321 A/C; S13027: Chr13_36035227 C/T; S13028: Chr13_36053840 G/A; S13029: Chr13_36075502 C/A; S13030: Chr13_36106613 A/G; S13031: Chr13_36134370 C/T; S13032: Chr13_36153972 C/A; S13033: Chr13_36178686 A/G; S13034: Chr13_36220257 G/A; S13035: Chr13_36244080 A/G; S13036: Chr13_36255609 C/T; S13037: Chr13_36278146 A/G; S13038: Chr13_36319615 C/T; S13039: Chr13_36334102 C/T; S13040: Chr13_36363295 C/G; S13041: Chr13_36382119 G/C; S13042: Chr13_36400081 C/T; S13043: Chr13_36483210 A/T; S13044: Chr13_36577652 T/G; S13045: Chr13_36674074 C/T; S13046: Chr13_36691282 T/C; S13047: Chr13_36712314 T/C; S13048: Chr13_36725625 T/A; S13049: Chr13_36823059 G/T; S13050: Chr13_36832041 C/T; S13051: Chr13_36850354 G/C; S13052: Chr13_36886054 A/G; S13053: Chr13_36905844 T/A; S13054: Chr13_36930904 C/T; S13055: Chr13_36955158 C/T; S13056: Chr13_36997094 G/C; S13057: Chr13_37006988 A/C; S13058: Chr13_37035854 A/G; S13059: Chr13_37056487 T/C; S13060: Chr13_37075827 G/A; S13061: Chr13_37113991 G/A; S13062: Chr13_37132620 C/T; S13063: Chr13_37167423 G/C; S13064: Chr13_37176615 G/A; S13065: Chr13_37206094 G/A; S13066: Chr13_37255696 T/C; S13067: Chr13_37283856 G/C; S13068: Chr13_37311804 T/C; S13069: Chr13_37330071 T/G; S13070: Chr13_37376016 G/A; S13071: Chr13_37407329 T/C; S13072: Chr13_37490546 G/A; S13073: Chr13_37503562 T/G; S13074: Chr13_37529531 C/T; S13075: Chr13_37558939 C/T; S13076: Chr13_37575289 T/C; S13077: Chr13_37709246 G/T; S13078: Chr13_37740952 T/A; S13079: Chr13_37750253 A/G; S13080: Chr13_37777304 T/A; S13081: Chr13_37808861 G/A; S13082: Chr13_37826023 G/A; S13083: Chr13_37857157 A/C; S13084: Chr13_37885556 C/G; S13085: Chr13_37905472 A/T; S13086: Chr13_37942305 C/G; S13087: Chr13_37952454 A/T; S13088: Chr13_37976651 A/T; S13089: Chr13_38038412 C/T; S13090: Chr13_38052453 C/T; S13091: Chr13_38147912 A/G; S13092: Chr13_38192955 C/T; S13093: Chr13_38229564 A/G; S13094: Chr13_38275385 G/C; S13095: Chr13_38305260 A/G; S13096: Chr13_38328798 C/G; S13097: Chr13_38384163 T/C; S13098: Chr13_38400137 T/C; S13099: Chr13_38426722 A/G; S13100: Chr13_38521954 C/T; S13101: Chr13_38531802 T/C; S13102: Chr13_38565964 A/T; S13103: Chr13_38586536 C/T; S13104: Chr13_38600268 A/G; S13105: Chr13_38648301 C/T; S13106: Chr13_38651306 C/T; S13107: Chr13_38686988 G/A; S13108: Chr13_38768455 C/T; S13109: Chr13_38849979 T/A; S13110: Chr13_38920120 C/T; S13111: Chr13_39002270 C/T; S13112: Chr13_39040585 C/T; S13113: Chr13_39154000 A/T; S13114: Chr13_39187726 G/C; S13115: Chr13_39200507 C/T; S13116: Chr13_39248405 A/G; S13117: Chr13_39257706 A/G; S13118: Chr13_39277718 G/A; S13119: Chr13_39307256 G/T; S13120: Chr13_39343929 G/C; S13121: Chr13_39350235 A/C; S13122: Chr13_39421191 T/A; S13123: Chr13_39425358 T/A; S13124:

Chr13_39521516 G/A; S13125: Chr13_39547692 A/G; S13126: Chr13_39571944 C/T; S13127: Chr13_39575469 C/A; S13128: Chr13_39600475 A/G; S13129: Chr13_39632647 C/A; S13130: Chr13_39650971 T/C; S13131: Chr13_39682867 A/G; S13132: Chr13_39715503 A/G; S13133: Chr13_39751242 C/T; S13134: Chr13_39783524 A/C; S13135: Chr13_39808681 G/T; S13136: Chr13_39831821 G/A; S13137: Chr13_39872502 C/T; S13138: Chr13_39891137 A/G; S13139: Chr13_39905555 G/T; S13140: Chr13_39934569 T/C; S13141: Chr13_39957212 C/G; S13142: Chr13_39975871 A/G; S13143: Chr13_40047833 C/G; S13144: Chr13_40050011 G/A; S13145: Chr13_40080005 T/C; S13146: Chr13_40113406 G/A; S13147: Chr13_40129206 A/G; S13148: Chr13_40167119 T/C; S13149: Chr13_40208360 A/G; S13150: Chr13_40229200 G/C; S13151: Chr13_40259400 T/A; S13152: Chr13_40336776 T/C; S13153: Chr13_40416548 T/C; S13154: Chr13_40425978 C/T; S13155: Chr13_40460488 T/C; S13156: Chr13_40475238 T/C; S13157: Chr13_40524310 A/G; S13158: Chr13_40534038 T/C; S13159: Chr13_40553781 T/C; S13160: Chr13_40577429 T/A; S13161: Chr13_40622156 T/C; S13162: Chr13_40635821 T/C; S13163: Chr13_40651154 T/C; S13164: Chr13_40686718 A/T; S13165: Chr13_40703458 C/T; S13166: Chr13_40726057 A/T; S13167: Chr13_40755625 A/T; S13168: Chr13_40782223 A/G; S13169: Chr13_40804365 G/A; S13170: Chr13_40849363 A/G; S13171: Chr13_40850913 C/T; S13172: Chr13_40881991 C/T; S13173: Chr13_40910452 G/A; S13174: Chr13_40933593 A/C; S13175: Chr13_40950807 C/T; S13176: Chr13_40994428 T/A; S13177: Chr13_41007458 G/A; S13178: Chr13_41028381 T/A; S13179: Chr13_41052639 T/C; S13180: Chr13_41077853 A/C; S13181: Chr13_41120172 C/G; S13182: Chr13_41130515 T/C; S13183: Chr13_41157822 A/G; S13184: Chr13_41198496 C/T; S13185: Chr13_41201646 G/A; S13186: Chr13_41228822 T/C; S13187: Chr13_41250974 G/T; S13188: Chr13_41286279 G/C; S13189: Chr13_41327102 G/A; S13190: Chr13_41358409 T/C; S13191: Chr13_41390543 C/T; S13192: Chr13_41401577 A/G; S13193: Chr13_41485730 C/T; S13194: Chr13_41576144 C/T; S13195: Chr13_41635861 C/T; S13196: Chr13_41654346 G/C; S13197: Chr13_41688510 T/C; S13198: Chr13_41716504 G/A; S13199: Chr13_41775097 G/A; S13200: Chr13_41807124 G/A; S13201: Chr13_41920932 A/T; S13202: Chr13_41925528 A/G; S13203: Chr13_41963558 C/T; S13204: Chr13_41988187 C/T; S13205: Chr13_42009810 A/T; S13206: Chr13_42028098 A/C; S13207: Chr13_42050209 T/A; S13208: Chr13_42076334 A/G; S13209: Chr13_42111517 C/T; S13210: Chr13_42150995 C/T; S13211: Chr13_42189529 C/A; S13212: Chr13_42216053 C/T; S13213: Chr13_212276334 T/C; S13214: Chr13_42325942 A/G; S13215: Chr13_42371551 A/G; S13216: Chr13_42383660 C/A; S13217: Chr13_42410927 A/G; S13218: Chr13_42464296 G/A; S13219: Chr13_42496589 A/C; S13220: Chr13_42515437 G/A; S13221: Chr13_42526429 C/A; S13222: Chr13_42550196 A/G; S13223: Chr13_42643435 T/C; S13224: Chr13_42650401 T/C; S13225: Chr13_42675203 A/G; S13226: Chr13_212711332 G/A; S13227: Chr13_42740451 A/T; S13228: Chr13_42790637 T/C; S13229: Chr13_42807826 A/T; S13230: Chr13_42826125 C/A; S13231: Chr13_42906651 C/A; S13232: Chr13_42926179 G/A; S13233: Chr13_42993020 A/G; S13234: Chr13_43006188 G/A; S13235: Chr13_43103438 C/A; S13236: Chr13_43125199 G/A; S13237: Chr13_43203259 A/C; S13238: Chr13_213246319 A/T; S13239: Chr13_43251240 G/A; S13240: Chr13_43286850 T/G; S13241: Chr13_43301595 T/C; S13242: Chr13_43325422 G/T; S13243: Chr13_43350595 C/T; S13244: Chr13_43379960 C/A; S13245: Chr13_43408503 C/T; S13246: Chr13_43443174 G/A; S13247: Chr13_43467559 A/C; S13248: Chr13_43482892 C/T; S13249: Chr13_43504867 C/A; S13250: Chr13_43526500 C/T; S13251: Chr13_43559230 T/C; S13252: Chr13_43581868 A/T; S13253: Chr13_43604473 C/G; S13254: Chr13_43632387 T/C; S13255: Chr13_43657030 A/G; S13256: Chr13_43727217 T/C; S13257: Chr13_43818691 G/A; S13258: Chr13_43846857 G/A; S13259: Chr13_43863343 G/A; S13260: Chr13_43934186 T/A; S13261: Chr13_43962025 A/G; S13262: Chi-13_43979450 G/C; S13263: Chr13_44000635 T/C; S13264: Chr13_44048873 C/T; S13265: Chr13_44112040 G/A; S13266: Chr13_44130508 C/T; S13267: Chr13_44151540 C/T; S13268: Chr13_44177984 T/C; S13269: Chr13_44206131 C/T; S13270: Chr13_44232063 T/G; S13271: Chr13_44261570 G/A; S13272: Chr13_44276296 A/G; S13273: Chr13_44300416 C/T; S13274: Chr13_44345627 G/A; S13275: Chr13_44359679 C/T; S13276: Chr13_44404657 C/T; S13277: Chr13_44425046 C/T; S13278: Chr13_44483438 A/G; S13279: Chr13_44505411 G/A; S13280: Chr13_44585714 A/G; S13281: Chr13_44621614 T/C; S13282: Chr13_44636693 A/G; S13283: Chr13_44661848 &A; S13284: Chr13_44681468 A/C; S13285: Chr13_44701269 C/G; S13286: Chr13_44748437 T/A; S13287: Chr13_44762753 G/C; S13288: Chr13_44776012 T/C; S13289: Chr13_44802125 T/G; S13290: Chr13_44829419 A/G; S13291: Chr13_44857691 C/A; S13292: Chr13_44886577 G/A; S13293: Chr13_44915146 T/G; S13294: Chr13_44928223 C/G; S13295: Chr13_44962797 A/T; S13296: Chr13_44986096 A/T; S13297: Chr13_45009740 T/A; S13298: Chr13_45029402 T/C; S13299: Chr13_45066236 G/T; S13300: Chr13_45077898 G/A; S13301: Chr13_45138243 T/C; S13302: Chr13_45167250 A/C; S13303: Chr13_45184560 C/T; S13304: Chr13_45210938 A/G; S13305: Chr13_45328132 G/A; S13306: Chr13_45389186 C/A; S13307: Chr13_45427749 A/G; S13308: Chr13_45465623 C/A; S13309: Chr13_45498650 C/T; S13310: Chr13_45510929 A/G; S13311: Chr13_45527546 T/C; S13312: Chr13_45620545 C/T; S13313: Chr13_45702253 G/T; S13314: Chr13_45739372 G/T; S13315: Chr13_45794372 C/T; S13316: Chr14_00008254 A/G; S13317: Chr14_00027605 A/G; S13318: Chr14_00061332 C/T; S13319: Chr14_00076904 A/T; S13320: Chr14_00102945 C/A; S13321: Chr14_00125966 C/T; S13322: Chr14_00155839 T/G; S13323: Chr14_00191942 T/A; S13324: Chr14_00203085 C/T; S13325:

Chr14_00225957 T/A; S13326: Chr14_00252005 C/A; S13327: Chr14_00278670 G/C; S13328: Chr14_00301051 A/G; S13329: Chr14_00327226 C/T; S13330: Chr14_00351233 G/A; S13331: Chr14_00391345 T/C; S13332: Chr14_00408737 C/T; S13333: Chr14_00427669 C/A; S13334: Chr14_00454331 C/G; S13335: Chr14_00475338 C/T; S13336: Chr14_00500030 T/C; S13337: Chr14_00528288 C/T; S13338: Chr14_00560471 A/G; S13339: Chr14_00585178 T/A; S13340: Chr14_00601477 A/G; S13341: Chr14_00634072 A/G; S13342: Chr14_00651142 G/A; S13343: Chr14_00680466 A/C; S13344: Chr14_00707449 C/T; S13345: Chr14_00736668 G/A; S13346: Chr14_00753089 C/T; S13347: Chr14_00775367 T/C; S13348: Chr14_00804855 A/G; S13349: Chr14_00848084 G/A; S13350: Chr14_00851858 A/G; S13351: Chr14_00889884 A/C; S13352: Chr14_00904352 C/T; S13353: Chr14_00929692 C/G; S13354: Chr14_00950893 C/A; S13355: Chr14_00975770 G/C; S13356: Chr14_01000271 T/C; S13357: Chr14_01030462 G/T; S13358: Chr14_01058426 C/T; S13359: Chr14_01077943 T/A; S13360: Chr14_01101248 G/C; S13361: Chr14_01132141 C/G; S13362: Chr14_01155238 G/T; S13363: Chr14_01179266 A/C; S13364: Chr14_01206861 A/G; S13365: Chr14_01230610 T/A; S13366: Chr14_01256303 T/C; S13367: Chr14_01280031 G/A; S13368: Chr14_01303129 A/G; S13369: Chr14_01326978 C/T; S13370: Chr14_01350218 G/T; S13371: Chr14_01381906 T/A; S13372: Chr14_01410232 G/C; S13373: Chr14_01436266 G/A; S13374: Chr14_01470999 C/T; S13375: Chr14_01475413 A/C; S13376: Chr14_01511929 A/T; S13377: Chr14_01529917 T/G; S13378: Chr14_01554573 C/T; S13379: Chr14_01605033 C/T; S13380: Chr14_01625474 A/G; S13381: Chr14_01654006 A/G; S13382: Chr14_01692065 T/C; S13383: Chr14_01701036 A/T; S13384: Chr14_01725043 G/A; S13385: Chr14_01751251 A/G; S13386: Chr14_01777659 C/T; S13387: Chr14_01816571 T/C; S13388: Chr14_01828852 G/A; S13389: Chr14_01850964 T/C; S13390: Chr14_01878662 C/T; S13391: Chr14_01906524 C/T; S13392: Chr14_01937799 C/T; S13393: Chr14_01976478 A/C; S13394: Chr14_02004448 T/C; S13395: Chr14_02046919 A/T; S13396: Chr14_02057008 C/T; S13397: Chr14_02092624 G/T; S13398: Chr14_02102900 C/T; S13399: Chr14_02130947 G/A; S13400: Chr14_02151840 C/T; S13401: Chr14_02175127 A/G; S13402: Chr14_02205240 G/A; S13403: Chr14_02226559 C/T; S13404: Chr14_02258981 C/A; S13405: Chr14_02284411 C/T; S13406: Chr14_02307783 G/T; S13407: Chr14_02325983 C/G; S13408: Chr14_02350594 A/T; S13409: Chr14_02394331 T/C; S13410: Chr14_02401867 C/T; S13411: Chr14_02436902 C/G; S13412: Chr14_02450557 C/T; S13413: Chr14_02482722 C/T; S13414: Chr14_02500385 C/T; S13415: Chr14_02525128 C/T; S13416: Chr14_02569977 C/T; S13417: Chr14_02586989 C/T; S13418: Chr14_02620823 G/T; S13419: Chr14_02625943 T/C; S13420: Chr14_02652849 G/T; S13421: Chr14_02676035 C/T; S13422: Chr14_02720739 G/C; S13423: Chr14_02727965 A/T; S13424: Chr14_02750260 C/T; S13425: Chr14_02776855 G/T; S13426: Chr14_02802231 A/G; S13427: Chr14_02838563 T/C; S13428: Chr14_02855136 A/G; S13429: Chr14_02876612 C/A; S13430: Chr14_02909124 A/C; S13431: Chr14_02928486 G/A; S13432: Chr14_02950948 C/T; S13433: Chr14_02985797 G/A; S13434: Chr14_03015454 T/C; S13435: Chr14_03027503 T/A; S13436: Chr14_03050592 G/A; S13437: Chr14_03075548 A/G; S13438: Chr14_03106180 C/A; S13439: Chr14_03129538 A/G; S13440: Chr14_03151579 G/C; S13441: Chr14_03176478 G/T; S13442: Chr14_03201174 G/A; S13443: Chr14_03230285 G/C; S13444: Chr14_03250015 T/G; S13445: Chr14_03280590 A/T; S13446: Chr14_03300053 A/G; S13447: Chr14_03326132 T/C; S13448: Chr14_03353212 T/A; S13449: Chr14_03376375 G/A; S13450: Chr14_03402937 T/C; S13451: Chr14_03427422 C/T; S13452: Chr14_03453990 A/T; S13453: Chr14_03476154 T/C; S13454: Chr14_03503662 C/G; S13455: Chr14_03533575 A/G; S13456: Chr14_03550040 C/T; S13457: Chr14_03580412 C/G; S13458: Chr14_03606056 T/C; S13459: Chr14_03647531 G/T; S13460: Chr14_03656913 T/A; S13461: Chr14_03677003 G/C; S13462: Chr14_03713128 A/C; S13463: Chr14_03731760 G/A; S13464: Chr14_03757474 G/A; S13465: Chr14_03778127 G/T; S13466: Chr14_03801542 A/G; S13467: Chr14_03839077 A/G; S13468: Chr14_03851354 G/A; S13469: Chr14_03881270 C/A; S13470: Chr14_03904952 A/G; S13471: Chr14_03932400 T/C; S13472: Chr14_03950896 T/C; S13473: Chr14_03975170 G/A; S13474: Chr14_04002332 C/T; S13475: Chr14_04026886 T/C; S13476: Chr14_04064019 G/A; S13477: Chr14_04086211 T/G; S13478: Chr14_04103752 G/C; S13479: Chr14_04125152 G/A; S13480: Chr14_04163046 T/C; S13481: Chr14_04189909 G/A; S13482: Chr14_04222034 T/C; S13483: Chr14_04228452 T/C; S13484: Chr14_04250721 T/C; S13485: Chr14_04277526 T/C; S13486: Chr14_04340037 A/G; S13487: Chr14_04358202 C/T; S13488: Chr14_04379763 T/C; S13489: Chr14_04405030 C/G; S13490: Chr14_04425458 T/G; S13491: Chr14_04453606 A/T; S13492: Chr14_04487163 T/C; S13493: Chr14_04500489 C/G; S13494: Chr14_04565733 G/A; S13495: Chr14_04581314 G/A; S13496: Chr14_04604584 G/A; S13497: Chr14_04643048 T/A; S13498: Chr14_04651498 A/C; S13499: Chr14_04679242 G/A; S13500: Chr14_04707337 A/G; S13501: Chr14_04739905 C/A; S13502: Chr14_04759592 T/A; S13503: Chr14_04785275 A/C; S13504: Chr14_04800903 G/A; S13505: Chr14_04825904 G/T; S13506: Chr14_04872960 A/C; S13507: Chr14_04879626 C/G; S13508: Chr14_04901281 T/C; S13509: Chr14_04941855 A/G; S13510: Chr14_04954288 T/C; S13511: Chr14_04978437 A/G; S13512: Chr14_05003989 G/A; S13513: Chr14_05030918 T/C; S13514: Chr14_05072807 G/T; S13515: Chr14_05075857 G/A; S13516: Chr14_05102644 T/C; S13517: Chr14_05125061 T/A; S13518: Chr14_05152747 A/G; S13519: Chr14_05180367 T/G; S13520: Chr14_05210344 A/C; S13521: Chr14_05237488 C/T; S13522: Chr14_05256911 G/C; S13523: Chr14_05275680 A/G; S13524: Chr14_05310980 A/C; S13525: Chr14_05335822 A/C; S13526:

Chr14_05350593 A/G; S13527: Chr14_05398597 C/T; S13528: Chr14_05422204 T/C; S13529: Chr14_05431366 C/T; S13530: Chr14_05457926 G/A; S13531: Chr14_05481693 T/C; S13532: Chr14_05511725 A/C; S13533: Chr14_05528989 T/A; S13534: Chr14_05568490 T/C; S13535: Chr14_05575324 C/T; S13536: Chr14_05658766 T/C; S13537: Chr14_05681691 A/G; S13538: Chr14_05704584 T/C; S13539: Chr14_05725016 G/A; S13540: Chr14_05752132 T/C; S13541: Chr14_05778697 G/A; S13542: Chr14_05844360 G/A; S13543: Chr14_05855420 G/A; S13544: Chr14_05884688 G/T; S13545: Chr14_05900153 C/G; S13546: Chr14_05950171 A/C; S13547: Chr14_06018928 A/G; S13548: Chr14_06044435 G/A; S13549: Chr14_06089633 T/C; S13550: Chr14_06102112 T/G; S13551: Chr14_06133026 T/C; S13552: Chr14_06151609 A/G; S13553: Chr14_06195767 T/A; S13554: Chr14_06273314 T/C; S13555: Chr14_06278464 T/C; S13556: Chr14_06324987 T/C; S13557: Chr14_06338666 C/A; S13558: Chr14_06355150 T/G; S13559: Chr14_06428414 G/T; S13560: Chr14_06450290 T/C; S13561: Chr14_06509210 A/C; S13562: Chr14_06555620 T/C; S13563: Chr14_06589603 G/A; S13564: Chr14_06605215 G/C; S13565: Chr14_06642527 G/T; S13566: Chr14_06652985 G/A; S13567: Chr14_06696891 G/T; S13568: Chr14_06701862 C/A; S13569: Chr14_06730211 G/T; S13570: Chr14_06763016 T/G; S13571: Chr14_06776245 C/T; S13572: Chr14_06823902 T/C; S13573: Chr14_06842541 A/G; S13574: Chr14_06856344 A/G; S13575: Chr14_06907760 A/T; S13576: Chr14_06945025 G/A; S13577: Chr14_06966377 G/A; S13578: Chr14_06975016 A/G; S13579: Chr14_07001177 A/T; S13580: Chr14_07025099 G/T; S13581: Chr14_07064829 C/T; S13582: Chr14_07079587 G/T; S13583: Chr14_07131740 T/C; S13584: Chr14_07158424 G/C; S13585: Chr14_07176229 A/G; S13586: Chr14_07201590 T/C; S13587: Chr14_07240626 G/T; S13588: Chr14_07252079 A/G; S13589: Chr14_07278199 C/T; S13590: Chr14_07327665 G/T; S13591: Chr14_07371272 T/A; S13592: Chr14_07401505 T/G; S13593: Chr14_07426690 A/C; S13594: Chr14_07454002 C/G; S13595: Chr14_07475599 G/T; S13596: Chr14_07502180 G/A; S13597: Chr14_07532019 G/A; S13598: Chr14_07558385 C/G; S13599: Chr14_07587737 T/C; S13600: Chr14_07617971 A/G; S13601: Chr14_07635150 T/G; S13602: Chr14_07678903 A/G; S13603: Chr14_07715279 C/T; S13604: Chr14_07730609 C/T; S13605: Chr14_07754774 A/T; S13606: Chr14_07788593 T/C; S13607: Chr14_07817880 C/T; S13608: Chr14_07837756 T/C; S13609: Chr14_07861590 G/T; S13610: Chr14_07879760 A/G; S13611: Chr14_07910420 A/G; S13612: Chr14_07972211 T/C; S13613: Chr14_08003502 A/G; S13614: Chr14_08025039 C/A; S13615: Chr14_08130844 G/A; S13616: Chr14_08187901 C/T; S13617: Chr14_08204148 T/A; S13618: Chr14_08275510 A/G; S13619: Chr14_08351692 A/G; S13620: Chr14_08460108 C/A; S13621: Chr14_08492539 C/T; S13622: Chr14_08529596 C/T; S13623: Chr14_08554688 A/G; S13624: Chr14_08597825 T/G; S13625: Chr14_08663178 G/A; S13626: Chr14_08675824

A/G; S13627: Chr14_08700324 A/T; S13628: Chr14_08728922 G/C; S13629: Chr14_08754806 G/T; S13630: Chr14_08790646 T/C; S13631: Chr14_08803526 T/C; S13632: Chr14_08825156 A/G; S13633: Chr14_08850726 A/C; S13634: Chr14_08879534 C/A; S13635: Chr14_08940572 A/C; S13636: Chr14_08963143 A/G; S13637: Chr14_08983837 T/A; S13638: Chr14_09006432 A/G; S13639: Chr14_09047143 A/T; S13640: Chr14_09068169 A/G; S13641: Chr14_09109017 G/T; S13642: Chr14_09125304 A/G; S13643: Chr14_09172821 A/C; S13644: Chr14_09180994 A/T; S13645: Chr14_09211097 T/G; S13646: Chr14_09234257 T/C; S13647: Chr14_09250920 T/C; S13648: Chr14_09296883 C/A; S13649: Chr14_09312762 G/A; S13650: Chr14_09391207 A/T; S13651: Chr14_09434565 C/T; S13652: Chr14_09510886 G/C; S13653: Chr14_09527182 G/A; S13654: Chr14_09608995 T/C; S13655: Chr14_09630230 C/T; S13656: Chr14_09650015 T/C; S13657: Chr14_09719106 C/G; S13658: Chr14_09729364 T/G; S13659: Chr14_09799425 G/T; S13660: Chr14_09800838 A/G; S13661: Chr14_09839798 A/G; S13662: Chr14_09884737 A/G; S13663: Chr14_09926195 G/T; S13664: Chr14_09954871 C/T; S13665: Chr14_09991820 T/C; S13666: Chr14_10020513 C/G; S13667: Chr14_10025867 T/C; S13668: Chr14_10058614 T/A; S13669: Chr14_10076857 C/A; S13670: Chr14_10100122 A/G; S13671: Chr14_10176854 A/G; S13672: Chr14_10237420 A/G; S13673: Chr14_10251747 T/C; S13674: Chr14_10303295 T/C; S13675: Chr14_10325013 T/C; S13676: Chr14_10433423 A/G; S13677: Chr14_10489620 C/G; S13678: Chr14_10508755 T/A; S13679: Chr14_10626432 C/T; S13680: Chr14_10674152 G/A; S13681: Chr14_10675352 T/C; S13682: Chr14_10702329 A/G; S13683: Chr14_10751022 T/C; S13684: Chr14_10799289 C/T; S13685: Chr14_10849585 A/G; S13686: Chr14_10917769 A/G; S13687: Chr14_10925351 T/A; S13688: Chr14_11000492 G/A; S13689: Chr14_11110367 C/G; S13690: Chr14_11149332 A/G; S13691: Chr14_11151032 T/C; S13692: Chr14_11175113 T/C; S13693: Chr14_11319533 A/G; S13694: Chr14_11327043 T/C; S13695: Chr14_11429215 T/C; S13696: Chr14_11526493 C/G; S13697: Chr14_11825849 G/A; S13698: Chr14_11908839 C/G; S13699: Chr14_12021338 T/A; S13700: Chr14_12028707 T/A; S13701: Chr14_12200123 A/G; S13702: Chr14_12302517 C/T; S13703: Chr14_12377870 A/G; S13704: Chr14_12408250 A/T; S13705: Chr14_12517116 C/G; S13706: Chr14_12575934 G/A; S13707: Chr14_12602041 T/C; S13708: Chr14_12699122 C/T; S13709: Chr14_12700213 A/G; S13710: Chr14_12747033 T/C; S13711: Chr14_12757687 A/C; S13712: Chr14_12894476 A/G; S13713: Chr14_12914910 A/T; S13714: Chr14_12929652 G/C; S13715: Chr14_12950000 A/G; S13716: Chr14_13100804 C/T; S13717: Chr14_13197349 G/C; S13718: Chr14_13202538 A/G; S13719: Chr14_13297944 T/C; S13720: Chr14_13302417 G/A; S13721: Chr14_13365435 G/C; S13722: Chr14_13402705 C/A; S13723: Chr14_13425319 A/G; S13724: Chr14_13554799 C/T; S13725: Chr14_13582441 A/G; S13726: Chr14_13635782 C/T; S13727:

Chr14_13682699 G/A; S13728: Chr14_13756587 G/C; S13729: Chr14_13776500 C/A; S13730: Chr14_13854685 C/T; S13731: Chr14_13926508 A/G; S13732: Chr14_14078240 G/A; S13733: Chr14_14168965 G/T; S13734: Chr14_14248308 C/T; S13735: Chr14_14309614 G/T; S13736: Chr14_14531605 C/T; S13737: Chr14_14675666 T/C; S13738: Chr14_15050729 A/C; S13739: Chr14_15350215 G/A; S13740: Chr14_15438953 A/C; S13741: Chr14_15524500 C/T; S13742: Chr14_15530299 T/A; S13743: Chr14_15559078 C/A; S13744: Chr14_15620568 C/T; S13745: Chr14_15700032 A/G; S13746: Chr14_15891676 G/T; S13747: Chr14_15900175 G/A; S13748: Chr14_16052816 T/A; S13749: Chr14_16140087 G/A; S13750: Chr14_16246512 C/G; S13751: Chr14_16256888 T/C; S13752: Chr14_16325262 G/A; S13753: Chr14_16412361 T/C; S13754: Chr14_16526063 A/G; S13755: Chr14_16614014 T/C; S13756: Chr14_16631118 G/A; S13757: Chr14_16728242 T/A; S13758: Chr14_16750561 G/A; S13759: Chr14_16862164 A/T; S13760: Chr14_16913078 G/T; S13761: Chr14_16944874 G/A; S13762: Chr14_16972117 T/C; S13763: Chr14_16975134 A/G; S13764: Chr14_17050531 T/C; S13765: Chr14_17096411 C/T; S13766: Chr14_17133372 T/A; S13767: Chr14_17150006 A/G; S13768: Chr14_17303358 T/C; S13769: Chr14_17401303 C/T; S13770: Chr14_17429157 C/T; S13771: Chr14_17500142 C/T; S13772: Chr14_17530043 T/C; S13773: Chr14_17550732 T/C; S13774: Chr14_17613124 T/A; S13775: Chr14_17701149 A/G; S13776: Chr14_17778351 G/A; S13777: Chr14_17804353 A/T; S13778: Chr14_17835835 T/C; S13779: Chr14_17971471 T/A; S13780: Chr14_17975211 G/C; S13781: Chr14_18050503 A/C; S13782: Chr14_18125266 G/T; S13783: Chr14_18275046 G/A; S13784: Chr14_18381351 T/G; S13785: Chr14_18401070 T/G; S13786: Chr14_18519908 T/G; S13787: Chr14_18526221 A/C; S13788: Chr14_18634876 G/A; S13789: Chr14_18650025 C/T; S13790: Chr14_18874799 C/T; S13791: Chr14_18875444 C/T; S13792: Chr14_18953251 T/C; S13793: Chr14_18975386 G/A; S13794: Chr14_19061852 G/A; S13795: Chr14_19090314 C/G; S13796: Chr14_19325560 G/T; S13797: Chr14_19400353 G/T; S13798: Chr14_19475314 G/A; S13799: Chr14_19559232 A/T; S13800: Chr14_19605953 G/A; S13801: Chr14_19625226 T/G; S13802: Chr14_19716090 C/T; S13803: Chr14_20009427 T/C; S13804: Chr14_20151189 G/A; S13805: Chr14_20291454 T/C; S13806: Chr14_20300157 G/A; S13807: Chr14_20379197 A/C; S13808: Chr14_20603226 G/A; S13809: Chr14_20755221 A/G; S13810: Chr14_20870971 C/A; S13811: Chr14_20954235 A/G; S13812: Chr14_21037520 C/T; S13813: Chr14_21193353 C/A; S13814: Chr14_21255970 T/C; S13815: Chr14_21332909 C/A; S13816: Chr14_21492643 G/A; S13817: Chr14_21674464 T/A; S13818: Chr14_21680925 A/G; S13819: Chr14_21758521 A/G; S13820: Chr14_21851834 G/T; S13821: Chr14_21919067 C/T; S13822: Chr14_22050016 G/T; S13823: Chr14_22153520 C/T; S13824: Chr14_22255211 G/A; S13825: Chr14_22404217 T/C; S13826: Chr14_22440625 G/A; S13827: Chr14_22562620 A/G; S13828: Chr14_22585237 A/G; S13829: Chr14_22614129 T/G; S13830: Chr14_22685368 C/T; S13831: Chr14_22705326 G/A; S13832: Chr14_22792151 C/T; S13833: Chr14_22800108 G/A; S13834: Chr14_22890019 A/G; S13835: Chr14_22950153 C/T; S13836: Chr14_23035371 G/A; S13837: Chr14_23115585 T/G; S13838: Chr14_23125383 A/T; S13839: Chr14_23200322 A/G; S13840: Chr14_23275009 C/T; S13841: Chr14_23358229 A/C; S13842: Chr14_23494240 A/G; S13843: Chr14_23513533 A/G; S13844: Chr14_23624103 A/G; S13845: Chr14_23625924 C/G; S13846: Chr14_23676496 G/A; S13847: Chr14_23729819 T/C; S13848: Chr14_23781044 G/A; S13849: Chr14_23827879 T/C; S13850: Chr14_23917782 C/T; S13851: Chr14_23926475 G/A; S13852: Chr14_24088544 G/A; S13853: Chr14_24169597 C/T; S13854: Chr14_24189787 G/A; S13855: Chr14_24389067 G/A; S13856: Chr14_24557652 A/T; S13857: Chr14_24627151 A/G; S13858: Chr14_24778177 C/G; S13859: Chr14_24930156 T/A; S13860: Chr14_25007323 A/C; S13861: Chr14_25086539 C/T; S13862: Chr14_25231028 G/A; S13863: Chr14_25303569 C/G; S13864: Chr14_25455179 A/G; S13865: Chr14_25602611 C/A; S13866: Chr14_25679613 T/A; S13867: Chr14_25906550 C/T; S13868: Chr14_26354740 C/T; S13869: Chr14_26425159 A/C; S13870: Chr14_26626945 A/G; S13871: Chr14_26655477 C/T; S13872: Chr14_26877514 G/A; S13873: Chr14_26954277 A/T; S13874: Chr14_27055337 G/A; S13875: Chr14_27359082 A/G; S13876: Chr14_27599999 C/T; S13877: Chr14_27648603 T/C; S13878: Chr14_27741942 C/G; S13879: Chr14_27754592 T/A; S13880: Chr14_27836825 A/T; S13881: Chr14_27986039 G/A; S13882: Chr14_28300471 G/A; S13883: Chr14_28425424 A/G; S13884: Chr14_28581011 C/T; S13885: Chr14_28651597 G/A; S13886: Chr14_28737414 T/C; S13887: Chr14_29026845 A/G; S13888: Chr14_29181542 T/G; S13889: Chr14_29254796 G/C; S13890: Chr14_29333125 C/A; S13891: Chr14_29410132 T/A; S13892: Chr14_30076762 C/T; S13893: Chr14_30164960 C/T; S13894: Chr14_30257575 G/A; S13895: Chr14_30459179 G/A; S13896: Chr14_30702344 C/T; S13897: Chr14_30825490 G/A; S13898: Chr14_30901699 G/A; S13899: Chr14_30980859 G/C; S13900: Chr14_31053112 G/A; S13901: Chr14_31201958 C/T; S13902: Chr14_31353376 A/G; S13903: Chr14_31435518 A/G; S13904: Chr14_31502482 A/G; S13905: Chr14_31582331 G/T; S13906: Chr14_31669620 C/T; S13907: Chr14_31882984 T/C; S13908: Chr14_31964435 A/G; S13909: Chr14_32036667 A/C; S13910: Chr14_32105943 C/T; S13911: Chr14_32175533 G/A; S13912: Chr14_32312494 T/A; S13913: Chr14_32378431 C/T; S13914: Chr14_32471713 C/T; S13915: Chr14_32475472 C/T; S13916: Chr14_32550660 C/T; S13917: Chr14_32704874 G/T; S13918: Chr14_32775508 G/A; S13919: Chr14_32890240 G/C; S13920: Chr14_32943278 C/T; S13921: Chr14_32968850 C/T; S13922: Chr14_32994366 C/T; S13923: Chr14_33039130 C/T; S13924: Chr14_33050091 T/C; S13925: Chr14_33132571 T/C; S13926: Chr14_33158099 G/A; S13927: Chr14_33275184 A/C; S13928:

Chr14_33358904 A/T; S13929: Chr14_33434036 T/A; S13930: Chr14_33457921 A/G; S13931: Chr14_33515194 T/A; S13932: Chr14_33543673 T/C; S13933: Chr14_33550145 T/G; S13934: Chr14_33705422 C/T; S13935: Chr14_33782963 T/C; S13936: Chr14_33853372 T/C; S13937: Chr14_33965721 C/T; S13938: Chr14_33975942 T/A; S13939: Chr14_34059648 G/A; S13940: Chr14_34143976 G/A; S13941: Chr14_34251951 T/C; S13942: Chr14_34292263 G/A; S13943: Chr14_34310916 G/A; S13944: Chr14_34400168 C/T; S13945: Chr14_34492541 A/G; S13946: Chr14_34506644 A/G; S13947: Chr14_34525140 A/G; S13948: Chr14_34662278 G/A; S13949: Chr14_34677204 C/T; S13950: Chr14_34742075 T/C; S13951: Chr14_34750007 T/A; S13952: Chr14_34850582 A/G; S13953: Chr14_34915554 G/A; S13954: Chr14_34936040 A/G; S13955: Chr14_34984234 A/G; S13956: Chr14_35025505 T/C; S13957: Chr14_35125765 T/C; S13958: Chr14_35203338 G/A; S13959: Chr14_35275011 T/C; S13960: Chr14_35350624 A/T; S13961: Chr14_35501137 A/G; S13962: Chr14_35576497 A/T; S13963: Chr14_35796032 G/A; S13964: Chr14_35805846 A/G; S13965: Chr14_35825101 C/T; S13966: Chr14_35975029 C/G; S13967: Chr14_36171406 G/C; S13968: Chr14_36325318 G/A; S13969: Chr14_36482960 T/A; S13970: Chr14_36575029 T/G; S13971: Chr14_36699097 C/T; S13972: Chr14_36711657 T/C; S13973: Chr14_36725038 A/C; S13974: Chr14_36875181 C/A; S13975: Chr14_36983994 A/C; S13976: Chr14_37009694 G/A; S13977: Chr14_37075045 G/A; S13978: Chr14_37150417 C/A; S13979: Chr14_37237129 A/G; S13980: Chr14_37250119 C/T; S13981: Chr14_37369392 T/C; S13982: Chr14_37375044 C/T; S13983: Chr14_37456748 C/G; S13984: Chr14_37475178 T/C; S13985: Chr14_37794707 T/C; S13986: Chr14_37828576 A/G; S13987: Chr14_37850411 T/C; S13988: Chr14_37954406 A/T; S13989: Chr14_37975234 A/G; S13990: Chr14_38051131 C/A; S13991: Chr14_38126799 G/A; S13992: Chr14_38166442 G/T; S13993: Chr14_38175029 T/C; S13994: Chr14_38280314 T/C; S13995: Chr14_38300055 T/C; S13996: Chr14_38483139 A/G; S13997: Chr14_38519824 T/C; S13998: Chr14_38575073 C/G; S13999: Chr14_38681447 A/G; S14000: Chr14_38860853 T/C; S14001: Chr14_38950482 T/A; S14002: Chr14_39034298 T/C; S14003: Chr14_39216348 G/A; S14004: Chr14_39225002 T/G; S14005: Chr14_39325929 C/T; S14006: Chr14_39511857 A/C; S14007: Chr14_39656891 C/A; S14008: Chr14_39844091 T/A; S14009: Chr14_39890539 C/T; S14010: Chr14_39911850 G/T; S14011: Chr14_39999365 C/A; S14012: Chr14_40000554 G/A; S14013: Chr14_40083076 C/T; S14014: Chr14_40100046 G/A; S14015: Chr14_40176176 C/T; S14016: Chr14_40315698 C/T; S14017: Chr14_40326884 A/G; S14018: Chr14_40422851 G/A; S14019: Chr14_40445914 C/T; S14020: Chr14_40510553 T/C; S14021: Chr14_40525119 T/C; S14022: Chr14_40679441 A/G; S14023: Chr14_40851242 C/T; S14024: Chr14_40878582 T/C; S14025: Chr14_40964438 T/C; S14026: Chr14_41036283 G/A; S14027: Chr14_41124028 G/A; S14028: Chr14_41162037 T/C; S14029: Chr14_41176654 G/C; S14030: Chr14_41309990 T/A; S14031: Chr14_41365143 C/T; S14032: Chr14_41383085 G/T; S14033: Chr14_41490754 T/C; S14034: Chr14_41527330 G/T; S14035: Chr14_41550132 T/A; S14036: Chr14_41645868 C/A; S14037: Chr14_41682945 A/G; S14038: Chr14_41700244 A/G; S14039: Chr14_41823681 G/A; S14040: Chr14_41877360 C/T; S14041: Chr14_41917417 C/G; S14042: Chr14_41937739 C/T; S14043: Chr14_41960654 G/A; S14044: Chr14_42028541 C/T; S14045: Chr14_42070398 A/G; S14046: Chr14_42116369 A/T; S14047: Chr14_42143156 A/G; S14048: Chr14_42192178 T/A; S14049: Chr14_42232306 C/A; S14050: Chr14_42284498 G/A; S14051: Chr14_42305669 T/C; S14052: Chr14_42389056 T/G; S14053: Chr14_42400045 T/C; S14054: Chr14_42497522 G/T; S14055: Chr14_42500241 C/G; S14056: Chr14_42588976 T/C; S14057: Chr14_42600026 A/G; S14058: Chr14_42687624 T/C; S14059: Chr14_42719420 A/C; S14060: Chr14_42725581 G/A; S14061: Chr14_42785961 A/G; S14062: Chr14_42801091 A/G; S14063: Chr14_42880111 G/A; S14064: Chr14_42956549 C/T; S14065: Chr14_43100415 G/A; S14066: Chr14_43178378 A/C; S14067: Chr14_43313468 C/G; S14068: Chr14_43332785 C/T; S14069: Chr14_43424479 G/T; S14070: Chr14_43425239 G/C; S14071: Chr14_43451298 T/C; S14072: Chr14_43475248 T/A; S14073: Chr14_43565928 G/T; S14074: Chr14_43578964 T/G; S14075: Chr14_43611892 T/G; S14076: Chr14_43661510 T/C; S14077: Chr14_43679531 A/C; S14078: Chr14_43732839 A/C; S14079: Chr14_43756095 C/T; S14080: Chr14_43776993 A/G; S14081: Chr14_43805398 A/T; S14082: Chr14_43825033 A/C; S14083: Chr14_43921812 C/A; S14084: Chr14_43963651 T/A; S14085: Chr14_43978693 G/A; S14086: Chr14_44013597 G/A; S14087: Chr14_44031329 T/C; S14088: Chr14_44061753 G/A; S14089: Chr14_44115737 G/A; S14090: Chr14_44125046 T/C; S14091: Chr14_44229950 T/C; S14092: Chr14_44254036 C/T; S14093: Chr14_44286445 T/A; S14094: Chr14_44300356 G/T; S14095: Chr14_44446348 C/G; S14096: Chr14_44456710 T/A; S14097: Chr14_44475410 G/A; S14098: Chr14_44500688 A/T; S14099: Chr14_44527437 T/A; S14100: Chr14_44551378 T/C; S14101: Chr14_44648864 A/C; S14102: Chr14_44651744 G/A; S14103: Chr14_44681822 A/T; S14104: Chr14_44703084 G/A; S14105: Chr14_44749018 G/T; S14106: Chr14_44750988 T/C; S14107: Chr14_44775357 T/A; S14108: Chr14_44803306 T/A; S14109: Chr14_44883463 G/A; S14110: Chr14_44971960 G/A; S14111: Chr14_44977506 C/T; S14112: Chr14_45052676 T/C; S14113: Chr14_45140058 T/C; S14114: Chr14_45222119 A/T; S14115: Chr14_45239923 C/T; S14116: Chr14_45339315 T/G; S14117: Chr14_45350447 C/T; S14118: Chr14_45410804 T/C; S14119: Chr14_45438596 A/G; S14120: Chr14_45450364 G/T; S14121: Chr14_45479087 A/G; S14122: Chr14_45503125 A/G; S14123: Chr14_45537479 G/A; S14124: Chr14_45567917 C/T; S14125: Chr14_45577121 G/A; S14126: Chr14_45610988 G/A; S14127: Chr14_45644389 A/T; S14128: Chr14_45658890 T/C; S14129:

Chr14_215681110 C/A; S14130: Chr14_45715371 A/C; S14131: Chr14_45733966 G/T; S14132: Chr14_45764802 C/T; S14133: Chr14_45792631 G/A; S14134: Chr14_45800101 G/A; S14135: Chr14_45834911 G/C; S14136: Chr14_45860975 A/T; S14137: Chr14_45884593 A/G; S14138: Chr14_45922205 T/C; S14139: Chr14_45927002 A/T; S14140: Chr14_45951852 A/C; S14141: Chr14_45976170 G/A; S14142: Chr14_46004562 A/G; S14143: Chr14_46026528 G/C; S14144: Chr14_46051117 T/C; S14145: Chr14_46090973 C/T; S14146: Chr14_46120905 G/A; S14147: Chr14_46125741 T/A; S14148: Chr14_46152352 C/A; S14149: Chr14_46184665 A/T; S14150: Chr14_46204452 T/A; S14151: Chr14_46239556 T/G; S14152: Chr14_46269688 T/C; S14153: Chr14_46280351 T/G; S14154: Chr14_46303938 C/T; S14155: Chr14_46327265 A/G; S14156: Chr14_46352178 G/A; S14157: Chr14_46378839 G/A; S14158: Chr14_46406128 G/A; S14159: Chr14_46427013 C/T; S14160: Chr14_46459430 A/G; S14161: Chr14_46481282 C/G; S14162: Chr14_46506482 A/C; S14163: Chr14_46525690 A/G; S14164: Chr14_46557588 T/C; S14165: Chr14_46583472 C/T; S14166: Chr14_46614414 A/G; S14167: Chr14_46637506 A/G; S14168: Chr14_46674564 C/T; S14169: Chr14_46675012 A/C; S14170: Chr14_46703357 C/T; S14171: Chr14_46728740 A/G; S14172: Chr14_46750140 T/G; S14173: Chr14_46775040 C/T; S14174: Chr14_46804377 C/T; S14175: Chr14_46827091 C/T; S14176: Chr14_46852568 G/A; S14177: Chr14_46883348 T/C; S14178: Chr14_46909270 T/C; S14179: Chr14_46940018 G/A; S14180: Chr14_46951762 C/T; S14181: Chr14_46984083 T/A; S14182: Chr14_47000767 G/C; S14183: Chr14_47025048 C/G; S14184: Chr14_47080012 A/G; S14185: Chr14_47123681 A/G; S14186: Chr14_47148299 G/A; S14187: Chr14_47158642 T/C; S14188: Chr14_47194370 A/G; S14189: Chr14_47200317 G/T; S14190: Chr14_47296603 C/T; S14191: Chr14_47305727 T/G; S14192: Chr14_217326511 G/A; S14193: Chr14_47366232 T/C; S14194: Chr14_47376480 C/A; S14195: Chr14_47413621 T/C; S14196: Chr14_47437728 A/C; S14197: Chr14_47450074 C/T; S14198: Chr14_47508319 T/C; S14199: Chr14_47525916 T/C; S14200: Chr14_47551214 G/A; S14201: Chr14_217580440 T/C; S14202: Chr14_47608148 G/A; S14203: Chr14_47627419 G/A; S14204: Chr14_47660595 C/T; S14205: Chr14_47691854 A/C; S14206: Chr14_47730806 T/G; S14207: Chr14_47759609 A/G; S14208: Chr14_47779860 A/T; S14209: Chr14_47802875 A/G; S14210: Chr14_47825549 A/G; S14211: Chr14_47858442 C/A; S14212: Chr14_47875287 A/G; S14213: Chr14_47921356 A/G; S14214: Chr14_47954300 A/G; S14215: Chr14_47978901 G/A; S14216: Chr14_48003009 C/T; S14217: Chr14_48030891 G/A; S14218: Chr14_48065827 G/T; S14219: Chr14_48088831 T/G; S14220: Chr14_48145141 C/T; S14221: Chr14_48150956 G/C; S14222: Chr14_48175108 C/T; S14223: Chr14_48209561 T/G; S14224: Chr14_48228754 A/T; S14225: Chr14_48310916 C/A; S14226: Chr14_48325654 C/G; S14227: Chr14_48354923 C/T; S14228: Chr14_48395420 C/G; S14229: Chr14_48430089 T/G; S14230: Chr14_48462362 G/C; S14231: Chr14_48477050 G/A; S14232: Chr14_48509197 A/G; S14233: Chr14_48558876 C/T; S14234: Chr14_48603754 A/G; S14235: Chr14_48626477 A/T; S14236: Chr14_48662428 C/A; S14237: Chr14_48676354 A/G; S14238: Chr14_48751017 T/C; S14239: Chr14_48831408 C/T; S14240: Chr14_48850248 T/C; S14241: Chr14_48882689 G/A; S14242: Chr14_48908579 G/A; S14243: Chr14_48976653 A/G; S14244: Chr15_00072262 C/T; S14245: Chr15_00102796 G/A; S14246: Chr15_00193419 A/C; S14247: Chr15_00207098 A/G; S14248: Chr15_00282154 T/C; S14249: Chr15_00330562 C/T; S14250: Chr15_00355157 C/T; S14251: Chr15_00441817 G/A; S14252: Chr15_00474286 T/C; S14253: Chr15_00525236 C/A; S14254: Chr15_00609427 C/T; S14255: Chr15_00627521 C/A; S14256: Chr15_00655209 C/A; S14257: Chr15_00675207 A/T; S14258: Chr15_00706790 A/T; S14259: Chr15_00725450 A/G; S14260: Chr15_00752100 A/T; S14261: Chr15_00802850 T/C; S14262: Chr15_00830119 A/G; S14263: Chr15_00864718 T/C; S14264: Chr15_00892356 A/G; S14265: Chr15_00908803 A/G; S14266: Chr15_00940779 A/T; S14267: Chr15_00965021 C/G; S14268: Chr15_00997576 T/C; S14269: Chr15_01038587 G/A; S14270: Chr15_01056408 G/T; S14271: Chr15_01117409 G/A; S14272: Chr15_01133658 C/T; S14273: Chr15_01160347 C/A; S14274: Chr15_01298695 G/T; S14275: Chr15_01325244 C/G; S14276: Chr15_01469294 C/T; S14277: Chr15_01477046 A/T; S14278: Chr15_01507399 G/A; S14279: Chr15_01528828 G/A; S14280: Chr15_01551421 T/C; S14281: Chr15_01576124 C/A; S14282: Chr15_01604344 G/T; S14283: Chr15_01630265 C/A; S14284: Chr15_01650042 A/T; S14285: Chr15_01675352 T/C; S14286: Chr15_01712542 A/T; S14287: Chr15_01726457 G/T; S14288: Chr15_01752030 A/G; S14289: Chr15_01778615 T/C; S14290: Chr15_01804528 A/G; S14291: Chr15_01835915 T/C; S14292: Chr15_01856253 A/C; S14293: Chr15_01889751 C/G; S14294: Chr15_01905241 T/C; S14295: Chr15_01926315 G/A; S14296: Chr15_01954579 C/T; S14297: Chr15_01976306 A/G; S14298: Chr15_02000942 C/A; S14299: Chr15_02030959 G/C; S14300: Chr15_02051442 T/C; S14301: Chr15_02075079 A/T; S14302: Chr15_02101292 G/A; S14303: Chr15_02126141 T/G; S14304: Chr15_02154788 C/T; S14305: Chr15_02178320 T/C; S14306: Chr15_02204583 G/A; S14307: Chr15_02263175 G/T; S14308: Chr15_02277272 A/C; S14309: Chr15_02313354 G/C; S14310: Chr15_02328756 G/T; S14311: Chr15_02350482 A/G; S14312: Chr15_02377885 T/A; S14313: Chr15_02403039 C/A; S14314: Chr15_02428037 C/T; S14315: Chr15_02450413 T/C; S14316: Chr15_02475536 T/G; S14317: Chr15_02516541 T/C; S14318: Chr15_02528392 C/T; S14319: Chr15_02555770 C/T; S14320: Chr15_02577240 A/G; S14321: Chr15_02608939 G/C; S14322: Chr15_02629768 C/T; S14323: Chr15_02653171 T/A; S14324: Chr15_02676201 A/G; S14325: Chr15_02701601 C/G; S14326: Chr15_02725475 G/A; S14327: Chr15_02756823 C/T; S14328: Chr15_02776159 G/T; S14329: Chr15_02805388 T/C; S14330:

Chr15_02825631 G/A; S14331: Chr15_02857924 T/G; S14332: Chr15_02923012 T/C; S14333: Chr15_02934524 C/T; S14334: Chr15_02951738 G/A; S14335: Chr15_02978928 C/G; S14336: Chr15_03001256 A/G; S14337: Chr15_03025067 C/T; S14338: Chr15_03060384 G/A; S14339: Chr15_03094800 T/C; S14340: Chr15_03100306 A/G; S14341: Chr15_03125683 A/T; S14342: Chr15_03159743 C/T; S14343: Chr15_03239056 C/T; S14344: Chr15_03258659 A/G; S14345: Chr15_03322917 C/G; S14346: Chr15_03380859 T/A; S14347: Chr15_03438388 C/A; S14348: Chr15_03450565 T/G; S14349: Chr15_03545424 C/T; S14350: Chr15_03588197 T/C; S14351: Chr15_03604296 C/T; S14352: Chr15_03630889 C/G; S14353: Chr15_03660345 T/C; S14354: Chr15_03684533 G/T; S14355: Chr15_03705971 A/T; S14356: Chr15_03728571 G/A; S14357: Chr15_03756020 A/G; S14358: Chr15_03776027 A/C; S14359: Chr15_03852619 C/T; S14360: Chr15_03900110 A/G; S14361: Chr15_03964390 A/G; S14362: Chr15_03989240 G/C; S14363: Chr15_04106368 T/C; S14364: Chr15_04127450 A/G; S14365: Chr15_04157473 A/C; S14366: Chr15_04177098 T/A; S14367: Chr15_04206805 T/C; S14368: Chr15_04260899 A/T; S14369: Chr15_04275014 C/T; S14370: Chr15_04300090 C/T; S14371: Chr15_04331085 A/G; S14372: Chr15_04356804 T/C; S14373: Chr15_04384714 A/G; S14374: Chr15_04424471 A/C; S14375: Chr15_04428133 G/A; S14376: Chr15_04478296 G/A; S14377: Chr15_04500363 A/C; S14378: Chr15_04541989 G/C; S14379: Chr15_04550829 A/G; S14380: Chr15_04629758 C/T; S14381: Chr15_04653468 A/T; S14382: Chr15_04756007 G/T; S14383: Chr15_04778614 G/A; S14384: Chr15_04901229 G/A; S14385: Chr15_04932020 A/G; S14386: Chr15_04950581 A/G; S14387: Chr15_04977120 G/A; S14388: Chr15_05011525 T/C; S14389: Chr15_05055149 C/G; S14390: Chr15_05078446 T/A; S14391: Chr15_05184340 A/T; S14392: Chr15_05211748 A/G; S14393: Chr15_05228130 G/A; S14394: Chr15_05251935 A/G; S14395: Chr15_05280848 T/A; S14396: Chr15_05306620 C/A; S14397: Chr15_05328210 T/G; S14398: Chr15_05357313 A/G; S14399: Chr15_05378602 T/G; S14400: Chr15_05424851 T/C; S14401: Chr15_05429334 T/C; S14402: Chr15_05451557 A/C; S14403: Chr15_05478992 C/G; S14404: Chr15_05527752 A/G; S14405: Chr15_05562667 G/A; S14406: Chr15_05575711 G/A; S14407: Chr15_05616471 T/C; S14408: Chr15_05648225 G/A; S14409: Chr15_05654620 A/C; S14410: Chr15_05675075 C/T; S14411: Chr15_05734117 G/A; S14412: Chr15_05754674 G/A; S14413: Chr15_05788010 T/C; S14414: Chr15_05805470 T/C; S14415: Chr15_05836866 A/C; S14416: Chr15_05867965 A/G; S14417: Chr15_05875852 T/C; S14418: Chr15_05901971 C/T; S14419: Chr15_05939078 G/A; S14420: Chr15_05951406 C/T; S14421: Chr15_05986572 C/A; S14422: Chr15_06012555 C/T; S14423: Chr15_06035187 G/A; S14424: Chr15_06070810 C/A; S14425: Chr15_06075802 G/C; S14426: Chr15_06118832 C/T; S14427: Chr15_06128796 C/G; S14428: Chr15_06171168 C/G; S14429: Chr15_06177803 T/G; S14430: Chr15_06215436 A/G; S14431: Chr15_06228408 A/G; S14432: Chr15_06252435 A/G; S14433: Chr15_06291081 T/C; S14434: Chr15_06341570 G/T; S14435: Chr15_06368385 A/C; S14436: Chr15_06458464 A/C; S14437: Chr15_06478225 T/C; S14438: Chr15_06500604 T/C; S14439: Chr15_06525219 G/C; S14440: Chr15_06566885 T/A; S14441: Chr15_06595813 T/G; S14442: Chr15_06616900 C/T; S14443: Chr15_06627693 T/G; S14444: Chr15_06651021 C/T; S14445: Chr15_06680230 C/G; S14446: Chr15_06725540 A/C; S14447: Chr15_06750342 G/A; S14448: Chr15_06779998 C/G; S14449: Chr15_06800909 A/G; S14450: Chr15_06834700 G/T; S14451: Chr15_06853445 T/C; S14452: Chr15_06882556 G/A; S14453: Chr15_06912827 C/A; S14454: Chr15_06928095 T/G; S14455: Chr15_06954920 A/C; S14456: Chr15_06975046 A/G; S14457: Chr15_07037263 C/T; S14458: Chr15_07050937 T/A; S14459: Chr15_07085710 G/A; S14460: Chr15_07119879 A/G; S14461: Chr15_07125030 T/C; S14462: Chr15_07178993 C/T; S14463: Chr15_07200116 C/G; S14464: Chr15_07228378 C/T; S14465: Chr15_07288161 C/T; S14466: Chr15_07304049 A/G; S14467: Chr15_07333789 T/A; S14468: Chr15_07351567 T/C; S14469: Chr15_07384311 A/T; S14470: Chr15_07403605 C/T; S14471: Chr15_07428802 C/T; S14472: Chr15_07452040 C/T; S14473: Chr15_07499443 G/A; S14474: Chr15_07502361 G/T; S14475: Chr15_07531839 T/C; S14476: Chr15_07555484 T/A; S14477: Chr15_07575020 G/A; S14478: Chr15_07605129 C/T; S14479: Chr15_07633711 G/A; S14480: Chr15_07653389 T/G; S14481: Chr15_07679197 G/T; S14482: Chr15_07700104 T/C; S14483: Chr15_07725956 G/T; S14484: Chr15_07751014 T/A; S14485: Chr15_07776327 A/G; S14486: Chr15_07813167 G/C; S14487: Chr15_07829010 G/C; S14488: Chr15_07873099 C/T; S14489: Chr15_07888917 A/C; S14490: Chr15_07902404 G/A; S14491: Chr15_07926855 G/T; S14492: Chr15_07980099 T/C; S14493: Chr15_08006254 G/C; S14494: Chr15_08025334 G/A; S14495: Chr15_08101527 G/A; S14496: Chr15_08197918 A/C; S14497: Chr15_08203160 A/T; S14498: Chr15_08244865 T/C; S14499: Chr15_08270907 T/G; S14500: Chr15_08396417 A/G; S14501: Chr15_08401336 T/A; S14502: Chr15_08435379 C/T; S14503: Chr15_08464881 T/A; S14504: Chr15_08475046 C/T; S14505: Chr15_08505212 G/A; S14506: Chr15_08537120 G/A; S14507: Chr15_08553863 T/C; S14508: Chr15_08576234 G/A; S14509: Chr15_08620771 C/T; S14510: Chr15_08638836 T/C; S14511: Chr15_08671170 C/T; S14512: Chr15_08678412 A/G; S14513: Chr15_08701042 C/T; S14514: Chr15_08729762 T/A; S14515: Chr15_08754860 T/C; S14516: Chr15_08775120 G/A; S14517: Chr15_08804644 T/C; S14518: Chr15_08842788 G/C; S14519: Chr15_08856165 A/T; S14520: Chr15_08908980 T/G; S14521: Chr15_08946576 G/C; S14522: Chr15_08960884 T/G; S14523: Chr15_08981420 C/T; S14524: Chr15_09000881 A/G; S14525: Chr15_09028205 A/G; S14526: Chr15_09056376 T/C; S14527: Chr15_09077137 C/G; S14528: Chr15_09108212 G/A; S14529: Chr15_09138650 T/C; S14530: Chr15_09161044 A/C; S14531:

Chr15_09176525 G/A; S14532: Chr15_09205620 G/A; S14533: Chr15_09227435 G/A; S14534: Chr15_09250075 A/C; S14535: Chr15_09275579 G/C; S14536: Chr15_09303248 C/A; S14537: Chr15_09325304 C/T; S14538: Chr15_09384518 G/A; S14539: Chr15_09402560 C/T; S14540: Chr15_09434389 A/G; S14541: Chr15_09473113 A/G; S14542: Chr15_09483998 T/A; S14543: Chr15_09504513 C/T; S14544: Chr15_09527760 A/C; S14545: Chr15_09550196 G/A; S14546: Chr15_09575379 C/A; S14547: Chr15_09604387 A/G; S14548: Chr15_09632956 A/G; S14549: Chr15_09650039 G/A; S14550: Chr15_09709385 G/A; S14551: Chr15_09725132 T/A; S14552: Chr15_09750107 T/G; S14553: Chr15_09779774 C/T; S14554: Chr15_09803623 T/A; S14555: Chr15_09845752 C/T; S14556: Chr15_09865235 C/T; S14557: Chr15_09875074 G/A; S14558: Chr15_09905045 T/C; S14559: Chr15_09928289 T/C; S14560: Chr15_09950434 A/G; S14561: Chr15_09975185 C/T; S14562: Chr15_10014572 A/G; S14563: Chr15_10030285 A/G; S14564: Chr15_10050118 T/C; S14565: Chr15_10080061 T/C; S14566: Chr15_10109864 T/G; S14567: Chr15_10128698 T/G; S14568: Chr15_10150011 G/T; S14569: Chr15_10185754 G/T; S14570: Chr15_10206497 G/C; S14571: Chr15_10229679 T/C; S14572: Chr15_10265679 T/G; S14573: Chr15_10294077 T/C; S14574: Chr15_10300062 T/C; S14575: Chr15_10359216 A/C; S14576: Chr15_10404041 T/A; S14577: Chr15_10439114 T/C; S14578: Chr15_10454469 G/A; S14579: Chr15_10490636 G/T; S14580: Chr15_10514206 G/T; S14581: Chr15_10532453 C/G; S14582: Chr15_10555580 C/G; S14583: Chr15_10584781 T/C; S14584: Chr15_10605120 G/A; S14585: Chr15_10630845 C/T; S14586: Chr15_10667944 C/T; S14587: Chr15_10680812 A/G; S14588: Chr15_10700663 G/T; S14589: Chr15_10726400 A/C; S14590: Chr15_10755188 A/C; S14591: Chr15_10777703 T/A; S14592: Chr15_10821236 T/A; S14593: Chr15_10855195 T/C; S14594: Chr15_10888060 A/G; S14595: Chr15_10922355 A/C; S14596: Chr15_10946495 G/C; S14597: Chr15_11008951 G/A; S14598: Chr15_11026793 G/A; S14599: Chr15_11054370 G/A; S14600: Chr15_11075148 A/G; S14601: Chr15_11187836 A/T; S14602: Chr15_11213229 C/T; S14603: Chr15_11225288 T/C; S14604: Chr15_11284233 A/G; S14605: Chr15_11305323 G/T; S14606: Chr15_11356554 G/A; S14607: Chr15_11399195 A/G; S14608: Chr15_11441207 C/T; S14609: Chr15_11495305 T/A; S14610: Chr15_11522371 G/A; S14611: Chr15_11526643 A/C; S14612: Chr15_11554331 C/T; S14613: Chr15_11578806 A/G; S14614: Chr15_11600837 A/G; S14615: Chr15_11659055 A/G; S14616: Chr15_11690593 A/T; S14617: Chr15_11706586 C/T; S14618: Chr15_11744994 C/A; S14619: Chr15_11756214 T/C; S14620: Chr15_11812679 G/A; S14621: Chr15_11831418 G/A; S14622: Chr15_11850516 A/G; S14623: Chr15_11875811 A/G; S14624: Chr15_11907225 C/G; S14625: Chr15_11932044 G/A; S14626: Chr15_11950034 T/C; S14627: Chr15_12031299 C/T; S14628: Chr15_12102871 A/G; S14629: Chr15_12134264 C/A; S14630: Chr15_12150934 T/C; S14631: Chr15_12181115 G/A; S14632: Chr15_12217849 A/T; S14633: Chr15_12226332 C/T; S14634: Chr15_12257421 C/T; S14635: Chr15_12276728 A/T; S14636: Chr15_12311964 C/T; S14637: Chr15_12333146 T/G; S14638: Chr15_12358461 C/G; S14639: Chr15_12375153 G/C; S14640: Chr15_12436754 C/T; S14641: Chr15_12452535 A/C; S14642: Chr15_12480394 A/G; S14643: Chr15_12501887 T/G; S14644: Chr15_12547827 G/A; S14645: Chr15_12557945 A/G; S14646: Chr15_12583608 A/G; S14647: Chr15_12614466 T/G; S14648: Chr15_12633085 A/T; S14649: Chr15_12650280 A/G; S14650: Chr15_12681180 C/A; S14651: Chr15_12709425 C/G; S14652: Chr15_12725263 G/A; S14653: Chr15_12752392 C/G; S14654: Chr15_12793869 C/T; S14655: Chr15_12816590 A/G; S14656: Chr15_12832578 G/A; S14657: Chr15_12853642 G/A; S14658: Chr15_12884156 T/C; S14659: Chr15_12925076 T/G; S14660: Chr15_12974474 T/C; S14661: Chr15_12986787 C/G; S14662: Chr15_13002347 A/G; S14663: Chr15_13039055 G/A; S14664: Chr15_13077075 G/C; S14665: Chr15_13100026 G/A; S14666: Chr15_13127492 C/T; S14667: Chr15_13172018 G/C; S14668: Chr15_13184663 C/T; S14669: Chr15_13204723 T/C; S14670: Chr15_13227803 C/T; S14671: Chr15_13252405 T/A; S14672: Chr15_13293588 G/A; S14673: Chr15_13304978 G/A; S14674: Chr15_13337257 A/G; S14675: Chr15_13364591 G/A; S14676: Chr15_13392488 G/T; S14677: Chr15_13416532 A/C; S14678: Chr15_13468020 C/T; S14679: Chr15_13528990 A/T; S14680: Chr15_13586984 T/C; S14681: Chr15_13621378 T/G; S14682: Chr15_13625630 G/C; S14683: Chr15_13654337 G/A; S14684: Chr15_13679389 T/A; S14685: Chr15_13714510 C/T; S14686: Chr15_13752892 C/T; S14687: Chr15_13776924 C/T; S14688: Chr15_13802933 C/A; S14689: Chr15_13832167 T/C; S14690: Chr15_13858249 A/T; S14691: Chr15_13926569 T/C; S14692: Chr15_13974298 A/G; S14693: Chr15_13975807 G/A; S14694: Chr15_14010941 G/A; S14695: Chr15_14031139 C/T; S14696: Chr15_14055733 G/A; S14697: Chr15_14077959 T/C; S14698: Chr15_14104475 G/T; S14699: Chr15_14129270 G/A; S14700: Chr15_14153982 G/A; S14701: Chr15_14241535 A/G; S14702: Chr15_14263522 G/A; S14703: Chr15_14275699 G/A; S14704: Chr15_14311295 G/A; S14705: Chr15_14334110 A/C; S14706: Chr15_14351448 G/A; S14707: Chr15_14381232 A/G; S14708: Chr15_14405207 T/A; S14709: Chr15_14435739 C/A; S14710: Chr15_14461932 C/A; S14711: Chr15_14489369 G/T; S14712: Chr15_14525948 T/C; S14713: Chr15_14551414 A/G; S14714: Chr15_14583490 A/G; S14715: Chr15_14656674 A/C; S14716: Chr15_14682391 C/T; S14717: Chr15_14700303 A/C; S14718: Chr15_14778932 A/T; S14719: Chr15_14820323 C/T; S14720: Chr15_14825880 A/T; S14721: Chr15_14868474 G/A; S14722: Chr15_14890673 A/G; S14723: Chr15_14917106 C/T; S14724: Chr15_14925034 T/C; S14725: Chr15_15000053 T/C; S14726: Chr15_15029971 C/T; S14727: Chr15_15072976 C/T; S14728: Chr15_15092623 A/G; S14729: Chr15_15125044 T/G; S14730: Chr15_15163386 G/A; S14731: Chr15_15199848 C/T; S14732:

Chr15_15201886 A/T; S14733: Chr15_15232943 C/A; S14734: Chr15_15271446 T/G; S14735: Chr15_15275058 G/A; S14736: Chr15_15307347 G/A; S14737: Chr15_15411778 A/C; S14738: Chr15_15436616 A/G; S14739: Chr15_15478303 G/T; S14740: Chr15_15510438 C/T; S14741: Chr15_15538777 T/C; S14742: Chr15_15556974 T/G; S14743: Chr15_15605194 T/C; S14744: Chr15_15630969 T/G; S14745: Chr15_15650029 A/G; S14746: Chr15_15675119 C/T; S14747: Chr15_15700387 G/A; S14748: Chr15_15734161 A/T; S14749: Chr15_15780152 C/T; S14750: Chr15_15809633 A/G; S14751: Chr15_15848279 C/A; S14752: Chr15_15854711 A/T; S14753: Chr15_15883025 T/C; S14754: Chr15_15966263 T/G; S14755: Chr15_15986190 C/T; S14756: Chr15_16050046 G/C; S14757: Chr15_16128258 C/A; S14758: Chr15_16187778 G/A; S14759: Chr15_16213595 T/G; S14760: Chr15_16227486 T/A; S14761: Chr15_16251329 A/T; S14762: Chr15_16380801 A/G; S14763: Chr15_16432616 T/G; S14764: Chr15_16487725 C/G; S14765: Chr15_16525169 G/A; S14766: Chr15_16612256 G/A; S14767: Chr15_16699094 A/G; S14768: Chr15_16706254 T/C; S14769: Chr15_16745595 C/G; S14770: Chr15_16752209 G/A; S14771: Chr15_16793506 A/T; S14772: Chr15_16821787 A/G; S14773: Chr15_16825423 C/A; S14774: Chr15_16853644 T/G; S14775: Chr15_16877578 T/C; S14776: Chr15_16922917 T/C; S14777: Chr15_16960951 T/C; S14778: Chr15_17003417 G/A; S14779: Chr15_17034597 A/G; S14780: Chr15_17074503 G/A; S14781: Chr15_17103421 C/T; S14782: Chr15_17132476 A/C; S14783: Chr15_17173057 C/T; S14784: Chr15_17184809 C/T; S14785: Chr15_17208898 C/T; S14786: Chr15_17227877 G/A; S14787: Chr15_17334450 A/C; S14788: Chr15_17367554 G/A; S14789: Chr15_17386752 T/C; S14790: Chr15_17427683 C/G; S14791: Chr15_17453701 A/T; S14792: Chr15_17483406 C/G; S14793: Chr15_17510106 G/A; S14794: Chr15_17549772 C/A; S14795: Chr15_17551549 A/C; S14796: Chr15_17610472 A/G; S14797: Chr15_17637511 T/A; S14798: Chr15_17657743 G/C; S14799: Chr15_17681904 A/G; S14800: Chr15_17701173 G/A; S14801: Chr15_17750455 C/T; S14802: Chr15_17780080 T/C; S14803: Chr15_17833496 C/T; S14804: Chr15_17874791 G/A; S14805: Chr15_17877673 A/C; S14806: Chr15_17913152 A/C; S14807: Chr15_17973916 G/A; S14808: Chr15_17975437 T/C; S14809: Chr15_18020867 T/C; S14810: Chr15_18033106 C/G; S14811: Chr15_18072177 G/A; S14812: Chr15_18075503 C/A; S14813: Chr15_18174451 G/A; S14814: Chr15_18197700 T/C; S14815: Chr15_18241525 C/T; S14816: Chr15_18266607 T/C; S14817: Chr15_18275982 G/A; S14818: Chr15_18300014 C/T; S14819: Chr15_18336185 G/A; S14820: Chr15_18368748 T/A; S14821: Chr15_18393293 A/G; S14822: Chr15_18466646 G/A; S14823: Chr15_18485323 G/T; S14824: Chr15_18546126 T/A; S14825: Chr15_18556298 C/T; S14826: Chr15_18597342 A/T; S14827: Chr15_18600324 T/G; S14828: Chr15_18675034 C/A; S14829: Chr15_18750405 C/G; S14830: Chr15_18885806 G/C; S14831: Chr15_18900129 G/T; S14832: Chr15_18975645 G/C; S14833: Chr15_19145871 T/G; S14834: Chr15_19156477 A/G; S14835: Chr15_19190761 C/T; S14836: Chr15_19200667 A/T; S14837: Chr15_19290127 C/T; S14838: Chr15_19313620 A/T; S14839: Chr15_19326509 C/A; S14840: Chr15_19405683 G/A; S14841: Chr15_19425319 T/C; S14842: Chr15_19504572 T/C; S14843: Chr15_19570372 T/C; S14844: Chr15_19582544 A/G; S14845: Chr15_19606577 G/A; S14846: Chr15_19638270 G/C; S14847: Chr15_19716513 T/G; S14848: Chr15_19738224 A/G; S14849: Chr15_19767498 G/A; S14850: Chr15_19775155 A/C; S14851: Chr15_19863255 T/C; S14852: Chr15_19875075 A/G; S14853: Chr15_19997771 T/C; S14854: Chr15_20000197 T/C; S14855: Chr15_20099488 T/C; S14856: Chr15_20101220 A/G; S14857: Chr15_20131068 A/G; S14858: Chr15_20178534 G/A; S14859: Chr15_20200252 T/G; S14860: Chr15_20231449 A/G; S14861: Chr15_20250182 G/T; S14862: Chr15_20315356 T/C; S14863: Chr15_20325687 C/G; S14864: Chr15_20455856 C/A; S14865: Chr15_20492025 C/T; S14866: Chr15_20567865 C/G; S14867: Chr15_20629834 G/A; S14868: Chr15_20686801 G/A; S14869: Chr15_20773277 T/C; S14870: Chr15_20791509 G/A; S14871: Chr15_20813570 A/T; S14872: Chr15_20899681 A/G; S14873: Chr15_20930636 C/A; S14874: Chr15_20965879 C/A; S14875: Chr15_20989108 G/C; S14876: Chr15_21039651 G/C; S14877: Chr15_21075226 G/A; S14878: Chr15_21108412 C/T; S14879: Chr15_21175332 G/A; S14880: Chr15_21212610 G/A; S14881: Chr15_21259962 T/C; S14882: Chr15_21277170 G/C; S14883: Chr15_21324461 C/T; S14884: Chr15_21325072 A/C; S14885: Chr15_21419417 A/G; S14886: Chr15_21478526 C/A; S14887: Chr15_21507743 A/C; S14888: Chr15_21582110 C/T; S14889: Chr15_21600043 T/C; S14890: Chr15_21715291 G/A; S14891: Chr15_21725016 T/C; S14892: Chr15_21803281 A/G; S14893: Chr15_21883005 T/C; S14894: Chr15_21900073 G/A; S14895: Chr15_22093349 A/G; S14896: Chr15_22100102 G/A; S14897: Chr15_22191802 G/A; S14898: Chr15_22258593 G/T; S14899: Chr15_22328321 A/T; S14900: Chr15_22369412 C/T; S14901: Chr15_22381431 T/A; S14902: Chr15_22400647 G/C; S14903: Chr15_22511404 C/T; S14904: Chr15_22600093 C/A; S14905: Chr15_22678437 T/C; S14906: Chr15_22716254 A/G; S14907: Chr15_22761718 G/A; S14908: Chr15_22775466 A/G; S14909: Chr15_22867701 G/A; S14910: Chr15_22898105 A/T; S14911: Chr15_22901530 C/G; S14912: Chr15_22928479 T/A; S14913: Chr15_23038040 T/C; S14914: Chr15_23084706 G/A; S14915: Chr15_23117391 T/C; S14916: Chr15_23128512 A/C; S14917: Chr15_23174476 G/A; S14918: Chr15_23246712 G/T; S14919: Chr15_23250055 T/C; S14920: Chr15_23292043 C/T; S14921: Chr15_23346106 G/A; S14922: Chr15_23350503 A/T; S14923: Chr15_23411855 C/T; S14924: Chr15_23429408 T/C; S14925: Chr15_23537058 T/C; S14926: Chr15_23665550 T/A; S14927: Chr15_23675460 C/T; S14928: Chr15_23806791 G/A; S14929: Chr15_23827508 C/T; S14930: Chr15_23940382 G/C; S14931: Chr15_23950006 C/T; S14932: Chr15_24039112 G/A; S14933:

Chr15_24136915 C/A; S14934: Chr15_24193189 A/G; S14935: Chr15_24257235 T/C; S14936: Chr15_24345166 A/G; S14937: Chr15_24355722 G/A; S14938: Chr15_24375003 T/A; S14939: Chr15_24455819 T/C; S14940: Chr15_24478164 A/C; S14941: Chr15_24524290 C/T; S14942: Chr15_24527967 C/T; S14943: Chr15_24605855 C/T; S14944: Chr15_24691043 G/A; S14945: Chr15_24737404 G/A; S14946: Chr15_24761351 A/G; S14947: Chr15_24786595 T/C; S14948: Chr15_24836833 G/A; S14949: Chr15_24917767 T/C; S14950: Chr15_24929380 A/G; S14951: Chr15_25222812 A/T; S14952: Chr15_25225200 T/A; S14953: Chr15_25414621 C/G; S14954: Chr15_25547620 C/T; S14955: Chr15_25550493 C/T; S14956: Chr15_25671077 G/T; S14957: Chr15_25675125 C/T; S14958: Chr15_25765882 C/A; S14959: Chr15_25783552 G/T; S14960: Chr15_25840871 A/G; S14961: Chr15_25850063 C/A; S14962: Chr15_26003638 A/G; S14963: Chr15_26057089 G/T; S14964: Chr15_26075163 A/G; S14965: Chr15_26167069 T/A; S14966: Chr15_26175304 G/T; S14967: Chr15_26250078 T/C; S14968: Chr15_26407880 A/C; S14969: Chr15_26425213 A/G; S14970: Chr15_26515296 A/G; S14971: Chr15_26550494 T/C; S14972: Chr15_26850154 A/T; S14973: Chr15_26956594 C/G; S14974: Chr15_26975274 A/G; S14975: Chr15_27109357 T/C; S14976: Chr15_27281173 C/T; S14977: Chr15_27325661 T/G; S14978: Chr15_27395089 G/A; S14979: Chr15_27407117 A/T; S14980: Chr15_27494950 C/G; S14981: Chr15_27799282 A/T; S14982: Chr15_27802590 T/C; S14983: Chr15_28700099 G/C; S14984: Chr15_28960244 C/T; S14985: Chr15_28975002 C/T; S14986: Chr15_29179080 G/A; S14987: Chr15_29256268 A/G; S14988: Chr15_29326577 T/C; S14989: Chr15_29375845 C/T; S14990: Chr15_29424075 C/T; S14991: Chr15_29426073 A/G; S14992: Chr15_29566344 G/C; S14993: Chr15_29589124 C/T; S14994: Chr15_29600629 G/A; S14995: Chr15_29687588 A/G; S14996: Chr15_29721102 C/G; S14997: Chr15_29727241 T/C; S14998: Chr15_29815634 G/A; S14999: Chr15_29829719 G/T; S15000: Chr15_29879571 C/T; S15001: Chr15_30131694 T/C; S15002: Chr15_30150160 T/C; S15003: Chr15_30240949 T/G; S15004: Chr15_30475033 C/A; S15005: Chr15_30586659 G/A; S15006: Chr15_30600816 T/C; S15007: Chr15_31071820 T/C; S15008: Chr15_31075236 G/C; S15009: Chr15_31315557 C/T; S15010: Chr15_31390200 G/A; S15011: Chr15_31462350 C/T; S15012: Chr15_31550270 C/G; S15013: Chr15_31750390 A/T; S15014: Chr15_31885686 A/G; S15015: Chr15_31982201 C/T; S15016: Chr15_32159127 A/T; S15017: Chr15_32196466 G/T; S15018: Chr15_32206521 C/T; S15019: Chr15_32230626 C/G; S15020: Chr15_32263174 C/T; S15021: Chr15_32337022 C/T; S15022: Chr15_32400055 G/T; S15023: Chr15_32480729 A/T; S15024: Chr15_32500143 A/T; S15025: Chr15_32575253 G/A; S15026: Chr15_32661589 A/G; S15027: Chr15_32751580 C/A; S15028: Chr15_32828529 C/A; S15029: Chr15_32886473 T/C; S15030: Chr15_32954707 C/A; S15031: Chr15_32976003 G/A; S15032: Chr15_33098457 C/A; S15033: Chr15_33108787 G/T; S15034: Chr15_33148081 G/A; S15035: Chr15_33404531 A/G; S15036: Chr15_33431041 A/G; S15037: Chr15_33465973 C/T; S15038: Chr15_33542438 A/C; S15039: Chr15_33587928 G/A; S15040: Chr15_33600087 A/G; S15041: Chr15_33694150 G/A; S15042: Chr15_33747569 G/C; S15043: Chr15_33750400 C/T; S15044: Chr15_33825165 C/T; S15045: Chr15_34070247 C/T; S15046: Chr15_34077981 A/G; S15047: Chr15_34100974 A/G; S15048: Chr15_34175176 C/T; S15049: Chr15_34499855 C/G; S15050: Chr15_34500326 C/G; S15051: Chr15_34525213 A/T; S15052: Chr15_34600217 T/C; S15053: Chr15_34688767 T/C; S15054: Chr15_34829990 G/A; S15055: Chr15_34875858 A/G; S15056: Chr15_34936021 C/T; S15057: Chr15_34983211 G/C; S15058: Chr15_35030287 G/A; S15059: Chr15_35183197 C/G; S15060: Chr15_35265749 C/T; S15061: Chr15_35277731 C/T; S15062: Chr15_35321555 C/G; S15063: Chr15_35328205 G/A; S15064: Chr15_35368912 T/G; S15065: Chr15_35383043 C/T; S15066: Chr15_35439131 A/G; S15067: Chr15_35537923 A/G; S15068: Chr15_35590943 T/C; S15069: Chr15_35612314 A/G; S15070: Chr15_35671114 C/T; S15071: Chr15_35854106 T/C; S15072: Chr15_35914664 G/T; S15073: Chr15_35930038 T/A; S15074: Chr15_35955290 T/C; S15075: Chr15_36101157 C/T; S15076: Chr15_36302245 A/G; S15077: Chr15_36325341 A/G; S15078: Chr15_36406641 A/G; S15079: Chr15_36479415 C/T; S15080: Chr15_36512255 T/C; S15081: Chr15_36550200 C/T; S15082: Chr15_36668137 A/G; S15083: Chr15_36825052 C/T; S15084: Chr15_36901595 G/A; S15085: Chr15_37016776 G/T; S15086: Chr15_37089941 C/G; S15087: Chr15_37148420 A/G; S15088: Chr15_37171746 G/A; S15089: Chr15_37183721 A/G; S15090: Chr15_37350025 G/A; S15091: Chr15_37463575 A/G; S15092: Chr15_37475697 A/G; S15093: Chr15_37715514 C/T; S15094: Chr15_37775619 C/T; S15095: Chr15_37800206 C/T; S15096: Chr15_37886429 G/T; S15097: Chr15_37901128 T/A; S15098: Chr15_38021598 C/T; S15099: Chr15_38032903 C/A; S15100: Chr15_38153377 A/G; S15101: Chr15_38238636 T/C; S15102: Chr15_38325063 T/C; S15103: Chr15_38437820 C/A; S15104: Chr15_38459574 C/T; S15105: Chr15_38475857 C/T; S15106: Chr15_38550158 T/C; S15107: Chr15_38636235 G/A; S15108: Chr15_38779880 C/T; S15109: Chr15_39003512 C/T; S15110: Chr15_39155091 T/C; S15111: Chr15_39308110 T/G; S15112: Chr15_39375024 C/A; S15113: Chr15_39450654 A/T; S15114: Chr15_39525026 A/C; S15115: Chr15_39654983 A/C; S15116: Chr15_39678428 G/T; S15117: Chr15_39770397 G/A; S15118: Chr15_39880154 A/G; S15119: Chr15_39930385 C/T; S15120: Chr15_39952281 C/A; S15121: Chr15_39992195 T/C; S15122: Chr15_40068386 C/T; S15123: Chr15_40075051 T/C; S15124: Chr15_40113775 A/G; S15125: Chr15_40125295 A/G; S15126: Chr15_40314000 C/T; S15127: Chr15_40353675 T/A; S15128: Chr15_40417682 T/A; S15129: Chr15_40455695 G/A; S15130: Chr15_40507603 A/T; S15131: Chr15_40550182 C/T; S15132: Chr15_40603853 G/C; S15133: Chr15_40626160 C/T; S15134:

Chr15_40704399 C/T; S15135: Chr15_40768315 G/A; S15136: Chr15_40781712 A/G; S15137: Chr15_40827536 C/T; S15138: Chr15_40856795 T/C; S15139: Chr15_40875090 C/T; S15140: Chr15_40900014 C/T; S15141: Chr15_411030949 C/T; S15142: Chr15_41058192 G/A; S15143: Chr15_41075093 G/A; S15144: Chr15_41200200 G/A; S15145: Chr15_41225044 G/A; S15146: Chr15_41329857 C/T; S15147: Chr15_41366193 T/C; S15148: Chr15_41406679 G/A; S15149: Chr15_41461094 A/G; S15150: Chr15_41498979 A/T; S15151: Chr15_41526046 G/T; S15152: Chr15_41550637 G/A; S15153: Chr15_41602892 G/C; S15154: Chr15_41625385 G/A; S15155: Chr15_41662158 G/A; S15156: Chr15_41697336 T/G; S15157: Chr15_41741625 A/G; S15158: Chr15_41825120 A/C; S15159: Chr15_41877554 G/T; S15160: Chr15_41900119 C/G; S15161: Chr15_41990639 G/A; S15162: Chr15_42044870 A/G; S15163: Chr15_42050020 T/A; S15164: Chr15_42143724 A/T; S15165: Chr15_42162615 C/G; S15166: Chr15_42199126 T/A; S15167: Chr15_42200002 A/T; S15168: Chr15_42308897 G/A; S15169: Chr15_42325356 C/G; S15170: Chr15_42400064 A/G; S15171: Chr15_42500317 A/T; S15172: Chr15_42589640 C/T; S15173: Chr15_42696140 T/A; S15174: Chr15_42701253 T/C; S15175: Chr15_42803888 T/A; S15176: Chr15_42907433 T/A; S15177: Chr15_42977290 T/C; S15178: Chr15_43040983 G/A; S15179: Chr15_43050285 T/C; S15180: Chr15_43118214 T/C; S15181: Chr15_43140708 A/G; S15182: Chr15_43150017 A/C; S15183: Chr15_43192100 G/A; S15184: Chr15_43205952 G/A; S15185: Chr15_43228398 C/A; S15186: Chr15_43287117 G/A; S15187: Chr15_43379119 A/C; S15188: Chr15_43417406 G/A; S15189: Chr15_43432052 G/A; S15190: Chr15_43522418 G/A; S15191: Chr15_43536097 A/G; S15192: Chr15_43564644 T/C; S15193: Chr15_43591611 G/T; S15194: Chr15_43604919 A/G; S15195: Chr15_43630923 A/T; S15196: Chr15_43651082 G/A; S15197: Chr15_43692991 C/T; S15198: Chr15_43700210 C/T; S15199: Chr15_43797590 C/T; S15200: Chr15_43800219 C/G; S15201: Chr15_43847535 G/T; S15202: Chr15_43920543 T/A; S15203: Chr15_43928085 T/G; S15204: Chr15_43971750 T/C; S15205: Chr15_43975082 T/C; S15206: Chr15_44008978 G/A; S15207: Chr15_44029296 T/C; S15208: Chr15_44062774 G/T; S15209: Chr15_44075659 A/G; S15210: Chr15_44104570 A/G; S15211: Chr15_44130593 T/G; S15212: Chr15_44198497 T/A; S15213: Chr15_44200091 A/T; S15214: Chr15_44258966 G/A; S15215: Chr15_44295398 T/C; S15216: Chr15_44306453 C/A; S15217: Chr15_44326105 C/T; S15218: Chr15_44357271 T/C; S15219: Chr15_44416959 G/C; S15220: Chr15_44464743 T/C; S15221: Chr15_44494522 A/G; S15222: Chr15_44539211 G/C; S15223: Chr15_44562625 C/T; S15224: Chr15_44575168 T/A; S15225: Chr15_4608134 C/A; S15226: Chr15_44633148 T/C; S15227: Chr15_44650192 C/T; S15228: Chr15_44746420 A/G; S15229: Chr15_44767676 C/T; S15230: Chr15_44789385 G/A; S15231: Chr15_44801397 T/C; S15232: Chr15_44830573 T/C; S15233: Chr15_44853457 A/C; S15234: Chr15_44884147 A/C; S15235: Chr15_44912186 C/G; S15236: Chr15_44965823 T/C; S15237: Chr15_44991997 A/G; S15238: Chr15_45000090 T/C; S15239: Chr15_45085740 G/C; S15240: Chr15_45107575 T/C; S15241: Chr15_45125099 A/C; S15242: Chr15_45290420 A/G; S15243: Chr15_45375386 A/T; S15244: Chr15_45492903 C/T; S15245: Chr15_45514621 A/G; S15246: Chr15_45549987 T/G; S15247: Chr15_45617743 G/A; S15248: Chr15_45625231 A/G; S15249: Chr15_45728889 A/T; S15250: Chr15_45751981 C/T; S15251: Chr15_45775004 G/T; S15252: Chr15_45865773 T/C; S15253: Chr15_45922297 A/C; S15254: Chr15_45944151 T/G; S15255: Chr15_45961188 C/T; S15256: Chr15_46075792 G/T; S15257: Chr15_46100141 C/T; S15258: Chr15_46225525 T/G; S15259: Chr15_46259172 G/C; S15260: Chr15_46275019 T/C; S15261: Chr15_46346956 G/A; S15262: Chr15_46398927 A/C; S15263: Chr15_46403043 A/C; S15264: Chr15_46429757 A/G; S15265: Chr15_46453431 T/A; S15266: Chr15_46475060 A/T; S15267: Chr15_46508299 G/C; S15268: Chr15_46557607 G/A; S15269: Chr15_46584022 T/A; S15270: Chr15_46600890 G/A; S15271: Chr15_46633459 G/A; S15272: Chr15_46683889 G/A; S15273: Chr15_46700595 G/T; S15274: Chr15_46785481 C/T; S15275: Chr15_46813245 A/G; S15276: Chr15_46829611 A/G; S15277: Chr15_46851341 A/C; S15278: Chr15_46885900 T/C; S15279: Chr15_46913970 T/G; S15280: Chr15_46972360 A/C; S15281: Chr15_47074523 T/A; S15282: Chr15_47085516 T/A; S15283: Chr15_47164878 C/T; S15284: Chr15_47236573 A/C; S15285: Chr15_47260154 G/C; S15286: Chr15_47282415 G/T; S15287: Chr15_47313364 T/G; S15288: Chr15_47336147 A/G; S15289: Chr15_47362209 T/A; S15290: Chr15_47447261 A/G; S15291: Chr15_47456323 T/C; S15292: Chr15_47479136 T/A; S15293: Chr15_47524514 A/C; S15294: Chr15_47543323 G/C; S15295: Chr15_47562120 G/A; S15296: Chr15_47589564 A/G; S15297: Chr15_47600103 T/C; S15298: Chr15_47665896 T/C; S15299: Chr15_47675995 T/A; S15300: Chr15_47824588 A/G; S15301: Chr15_47825919 C/T; S15302: Chr15_47865665 C/T; S15303: Chr15_47893020 A/G; S15304: Chr15_47927321 G/A; S15305: Chr15_47957947 T/A; S15306: Chr15_48010774 C/T; S15307: Chr15_48026351 C/T; S15308: Chr15_48068448 T/C; S15309: Chr15_48103356 T/A; S15310: Chr15_48151171 G/A; S15311: Chr15_48218526 T/C; S15312: Chr15_48237380 A/T; S15313: Chr15_48250286 C/T; S15314: Chr15_48297124 T/A; S15315: Chr15_48310869 A/C; S15316: Chr15_48335392 T/G; S15317: Chr15_48363618 C/T; S15318: Chr15_48382668 T/C; S15319: Chr15_48407366 A/C; S15320: Chr15_48426754 C/T; S15321: Chr15_48452123 C/T; S15322: Chr15_48476245 C/G; S15323: Chr15_48500864 A/G; S15324: Chr15_48527526 G/A; S15325: Chr15_48557751 C/T; S15326: Chr15_48586087 C/T; S15327: Chr15_48615738 A/G; S15328: Chr15_48644372 T/G; S15329: Chr15_48660393 A/C; S15330: Chr15_48691383 G/T; S15331: Chr15_48700042 A/G; S15332: Chr15_48735747 C/T; S15333: Chr15_48798518 G/A; S15334: Chr15_48811101 C/T; S15335:

Chr15_48841245 A/G; S15336: Chr15_48865140 G/A; S15337: Chr15_48900542 T/G; S15338: Chr15_48925039 G/A; S15339: Chr15_48975189 G/A; S15340: Chr15_49031751 G/A; S15341: Chr15_49050973 T/A; S15342: Chr15_49075019 T/G; S15343: Chr15_49152895 T/A; S15344: Chr15_49187052 C/A; S15345: Chr15_49208218 C/T; S15346: Chr15_49256810 C/T; S15347: Chr15_49305236 C/A; S15348: Chr15_49325995 T/G; S15349: Chr15_49353850 A/G; S15350: Chr15_49389559 C/T; S15351: Chr15_49400217 T/A; S15352: Chr15_49448263 G/A; S15353: Chr15_49451358 T/C; S15354: Chr15_49484567 G/C; S15355: Chr15_49521129 G/A; S15356: Chr15_49558739 A/C; S15357: Chr15_49582929 A/G; S15358: Chr15_49630747 G/A; S15359: Chr15_49657011 A/G; S15360: Chr15_49681099 T/C; S15361: Chr15_49734668 A/G; S15362: Chr15_49754496 A/G; S15363: Chr15_49814040 G/A; S15364: Chr15_49844963 T/G; S15365: Chr15_49857566 G/A; S15366: Chr15_49881186 G/A; S15367: Chr15_49900348 C/T; S15368: Chr15_49930588 G/A; S15369: Chr15_49966279 T/C; S15370: Chr15_49977432 C/T; S15371: Chr15_50002489 G/A; S15372: Chr15_50041669 C/T; S15373: Chr15_50071018 T/C; S15374: Chr15_50090382 A/T; S15375: Chr15_50108394 G/T; S15376: Chr15_50178346 G/A; S15377: Chr15_50200254 A/C; S15378: Chr15_50225406 A/G; S15379: Chr15_50297493 G/A; S15380: Chr15_50303850 G/C; S15381: Chr15_50325488 T/C; S15382: Chr15_50357591 A/G; S15383: Chr15_50377398 T/C; S15384: Chr15_50400336 C/T; S15385: Chr15_50434685 C/T; S15386: Chr15_50452575 A/T; S15387: Chr15_50483125 A/G; S15388: Chr15_50500519 T/C; S15389: Chr15_50532317 A/G; S15390: Chr15_50553346 G/C; S15391: Chr15_50592087 T/C; S15392: Chr15_50617686 G/C; S15393: Chr15_50637705 T/C; S15394: Chr15_50658553 A/G; S15395: Chr15_50683560 A/C; S15396: Chr15_50716985 A/G; S15397: Chr15_50729148 G/A; S15398: Chr15_50758305 A/T; S15399: Chr15_50776870 A/T; S15400: Chr15_50802991 A/T; S15401: Chr15_50825857 T/A; S15402: Chr15_50850173 C/T; S15403: Chr15_50883739 G/T; S15404: Chr15_50900177 G/T; S15405: Chr15_50927269 G/A; S15406: Chr15_50951836 G/A; S15407: Chr15_50979764 T/A; S15408: Chr15_51008987 A/C; S15409: Chr15_51030922 T/G; S15410: Chr15_51053006 T/C; S15411: Chr15_51080848 G/T; S15412: Chr15_51102128 T/G; S15413: Chr15_51133704 G/T; S15414: Chr15_51153004 A/C; S15415: Chr15_51181112 C/A; S15416: Chr15_51221946 C/T; S15417: Chr15_51235890 T/C; S15418: Chr15_51265058 C/A; S15419: Chr15_51292364 A/G; S15420: Chr15_51300712 T/C; S15421: Chr15_51339574 A/G; S15422: Chr15_51351343 T/A; S15423: Chr15_51404142 G/T; S15424: Chr15_51491635 T/C; S15425: Chr15_51500148 G/A; S15426: Chr15_51534024 G/A; S15427: Chr15_51551156 G/A; S15428: Chr15_51579178 G/A; S15429: Chr15_51604743 T/C; S15430: Chr15_51636145 T/A; S15431: Chr15_51701949 C/T; S15432: Chr15_51725579 T/C; S15433: Chr15_51750156 C/A; S15434: Chr16_00014685 C/T; S15435: Chr16_00027033 G/C;

S15436: Chr16_00055282 T/A; S15437: Chr16_00080533 T/C; S15438: Chr16_00100925 C/T; S15439: Chr16_00128223 T/A; S15440: Chr16_00152101 C/G; S15441: Chr16_00175190 G/C; S15442: Chr16_00201816 T/A; S15443: Chr16_00229717 G/A; S15444: Chr16_00250446 T/C; S15445: Chr16_00275008 A/C; S15446: Chr16_00302842 C/T; S15447: Chr16_00325525 T/A; S15448: Chr16_00361425 T/C; S15449: Chr16_00379832 G/A; S15450: Chr16_00401296 A/G; S15451: Chr16_00425000 T/C; S15452: Chr16_00453491 A/T; S15453: Chr16_00533373 G/T; S15454: Chr16_00637971 A/G; S15455: Chr16_00659516 T/A; S15456: Chr16_00675922 G/A; S15457: Chr16_00723148 T/C; S15458: Chr16_00735936 A/G; S15459: Chr16_00762601 G/T; S15460: Chr16_00775049 G/A; S15461: Chr16_00802469 C/T; S15462: Chr16_00894917 C/A; S15463: Chr16_00921488 A/T; S15464: Chr16_00949779 C/T; S15465: Chr16_00951175 A/G; S15466: Chr16_01002898 A/C; S15467: Chr16_01031843 T/C; S15468: Chr16_01065074 A/G; S15469: Chr16_01111752 T/C; S15470: Chr16_01125091 T/C; S15471: Chr16_01152934 A/G; S15472: Chr16_01176114 T/C; S15473: Chr16_01201997 T/G; S15474: Chr16_01228140 T/G; S15475: Chr16_01250592 A/G; S15476: Chr16_01276875 T/C; S15477: Chr16_01300294 C/G; S15478: Chr16_01335381 T/G; S15479: Chr16_01352963 T/A; S15480: Chr16_01375668 G/A; S15481: Chr16_01401112 T/A; S15482: Chr16_01450936 T/G; S15483: Chr16_01484520 G/A; S15484: Chr16_01513158 A/G; S15485: Chr16_01527472 T/A; S15486: Chr16_01554533 A/T; S15487: Chr16_01578056 G/A; S15488: Chr16_01602541 C/T; S15489: Chr16_01634422 T/C; S15490: Chr16_01658785 G/T; S15491: Chr16_01675803 T/C; S15492: Chr16_01726943 T/C; S15493: Chr16_01770145 T/C; S15494: Chr16_01803493 G/A; S15495: Chr16_01831565 A/G; S15496: Chr16_01878432 G/A; S15497: Chr16_01966211 A/G; S15498: Chr16_01975010 C/A; S15499: Chr16_02054505 A/G; S15500: Chr16_02125127 A/G; S15501: Chr16_02242126 C/A; S15502: Chr16_02281019 C/T; S15503: Chr16_02321725 C/T; S15504: Chr16_02336659 C/T; S15505: Chr16_02359718 T/C; S15506: Chr16_02375224 G/A; S15507: Chr16_02403980 G/T; S15508: Chr16_02429395 A/G; S15509: Chr16_02457217 G/A; S15510: Chr16_02482849 G/C; S15511: Chr16_02502099 C/T; S15512: Chr16_02537675 A/G; S15513: Chr16_02551575 G/A; S15514: Chr16_02609793 A/G; S15515: Chr16_02633447 C/T; S15516: Chr16_02654770 G/A; S15517: Chr16_02703458 C/T; S15518: Chr16_02726504 C/A; S15519: Chr16_02763622 G/A; S15520: Chr16_02790526 G/A; S15521: Chr16_02801357 A/C; S15522: Chr16_02825192 C/T; S15523: Chr16_02856452 T/G; S15524: Chr16_02879298 G/A; S15525: Chr16_02900520 T/C; S15526: Chr16_02929849 C/T; S15527: Chr16_02954086 C/T; S15528: Chr16_02975020 A/G; S15529: Chr16_03022942 A/T; S15530: Chr16_03025002 C/T; S15531: Chr16_03051997 C/T; S15532: Chr16_03080296 T/A; S15533: Chr16_03116212 C/A; S15534: Chr16_03128065 C/A; S15535: Chr16_03152476 C/G; S15536:

Chr16_03175232 A/C; S15537: Chr16_03215568 A/C; S15538: Chr16_03229865 T/A; S15539: Chr16_03254485 G/T; S15540: Chr16_03275674 T/C; S15541: Chr16_03312432 C/T; S15542: Chr16_03327949 G/A; S15543: Chr16_03371079 T/C; S15544: Chr16_03378027 C/G; S15545: Chr16_03434702 G/C; S15546: Chr16_03452635 A/G; S15547: Chr16_03482793 A/G; S15548: Chr16_03517619 A/T; S15549: Chr16_03533529 A/G; S15550: Chr16_03562330 A/G; S15551: Chr16_03581770 T/C; S15552: Chr16_03620877 G/T; S15553: Chr16_03626618 A/G; S15554: Chr16_03669083 T/C; S15555: Chr16_03694925 G/C; S15556: Chr16_03702707 A/G; S15557: Chr16_03725529 A/G; S15558: Chr16_03754928 C/T; S15559: Chr16_03788397 C/A; S15560: Chr16_03821993 G/T; S15561: Chr16_03836844 A/T; S15562: Chr16_03852285 T/C; S15563: Chr16_03892680 A/G; S15564: Chr16_03905889 G/A; S15565: Chr16_03934191 G/A; S15566: Chr16_03959883 A/C; S15567: Chr16_03982748 C/A; S15568: Chr16_04025208 T/G; S15569: Chr16_04059617 T/C; S15570: Chr16_04075059 A/T; S15571: Chr16_04168773 C/G; S15572: Chr16_04226707 C/A; S15573: Chr16_04262242 G/A; S15574: Chr16_04277748 G/T; S15575: Chr16_04307868 T/C; S15576: Chr16_04334403 G/T; S15577: Chr16_04369302 C/A; S15578: Chr16_04377305 A/G; S15579: Chr16_04427570 G/A; S15580: Chr16_04462530 T/G; S15581: Chr16_04476121 C/T; S15582: Chr16_04505495 C/A; S15583: Chr16_04526608 T/A; S15584: Chr16_04554503 G/C; S15585: Chr16_04575619 T/C; S15586: Chr16_04610264 A/G; S15587: Chr16_04652989 A/T; S15588: Chr16_04686976 G/A; S15589: Chr16_04705707 G/A; S15590: Chr16_04737972 T/C; S15591: Chr16_04779800 G/C; S15592: Chr16_04800305 T/C; S15593: Chr16_04854062 C/T; S15594: Chr16_04894714 A/G; S15595: Chr16_04909026 C/T; S15596: Chr16_04941403 T/C; S15597: Chr16_04953367 T/C; S15598: Chr16_04977033 T/G; S15599: Chr16_05009505 C/A; S15600: Chr16_05050221 T/C; S15601: Chr16_05076558 A/T; S15602: Chr16_05107286 C/T; S15603: Chr16_05126613 C/G; S15604: Chr16_05217368 C/T; S15605: Chr16_05255849 C/A; S15606: Chr16_05279196 A/G; S15607: Chr16_05301435 G/A; S15608: Chr16_05406664 T/C; S15609: Chr16_05427988 C/T; S15610: Chr16_05451800 G/C; S15611: Chr16_05500199 C/T; S15612: Chr16_05526157 T/C; S15613: Chr16_05581173 C/T; S15614: Chr16_05628082 A/G; S15615: Chr16_05651033 C/T; S15616: Chr16_05677574 T/C; S15617: Chr16_05723223 C/A; S15618: Chr16_05729811 G/T; S15619: Chr16_05754735 G/T; S15620: Chr16_05786787 G/A; S15621: Chr16_05827068 A/G; S15622: Chr16_05859049 T/C; S15623: Chr16_05883835 C/T; S15624: Chr16_05909595 C/T; S15625: Chr16_05940565 G/A; S15626: Chr16_05957479 C/T; S15627: Chr16_05990133 C/T; S15628: Chr16_06024557 C/T; S15629: Chr16_06026215 A/C; S15630: Chr16_06105221 C/G; S15631: Chr16_06140990 G/A; S15632: Chr16_06183752 T/C; S15633: Chr16_06216130 G/T; S15634: Chr16_06228375 A/G; S15635: Chr16_06256078 C/A; S15636: Chr16_06283634 A/G; S15637: Chr16_06308508 A/T; S15638: Chr16_06325150 G/A; S15639: Chr16_06355760 T/A; S15640: Chr16_06379886 T/G; S15641: Chr16_06402391 A/T; S15642: Chr16_06425586 T/C; S15643: Chr16_06463426 T/C; S15644: Chr16_06484969 A/C; S15645: Chr16_06501591 T/C; S15646: Chr16_06528833 T/C; S15647: Chr16_06558870 T/C; S15648: Chr16_06575386 C/T; S15649: Chr16_06600685 A/G; S15650: Chr16_06627167 A/C; S15651: Chr16_06651276 A/G; S15652: Chr16_06683101 T/A; S15653: Chr16_06700263 T/A; S15654: Chr16_06729705 C/T; S15655: Chr16_06761706 C/A; S15656: Chr16_06781855 T/A; S15657: Chr16_06803823 T/C; S15658: Chr16_06830104 C/T; S15659: Chr16_06857140 T/C; S15660: Chr16_06895187 C/T; S15661: Chr16_06917627 T/C; S15662: Chr16_06931275 C/T; S15663: Chr16_07021859 G/A; S15664: Chr16_07026287 C/A; S15665: Chr16_07052711 T/C; S15666: Chr16_07179111 C/T; S15667: Chr16_07229817 A/G; S15668: Chr16_07264068 C/A; S15669: Chr16_07275026 A/G; S15670: Chr16_07353226 A/T; S15671: Chr16_07380689 G/T; S15672: Chr16_07406969 C/A; S15673: Chr16_07442495 T/C; S15674: Chr16_07452233 A/G; S15675: Chr16_07478117 A/T; S15676: Chr16_07529026 C/T; S15677: Chr16_07558236 A/G; S15678: Chr16_07576668 T/C; S15679: Chr16_07601528 A/G; S15680: Chr16_07628784 T/G; S15681: Chr16_07653194 C/A; S15682: Chr16_07725602 A/C; S15683: Chr16_07751727 T/C; S15684: Chr16_07776045 C/T; S15685: Chr16_07834303 A/T; S15686: Chr16_07862773 &A; S15687: Chr16_07886689 G/A; S15688: Chr16_07902693 T/A; S15689: Chr16_07925881 C/T; S15690: Chr16_07950366 A/T; S15691: Chr16_08002445 G/T; S15692: Chr16_08027917 C/T; S15693: Chr16_08062553 A/T; S15694: Chr16_08079322 T/A; S15695: Chr16_08103550 A/G; S15696: Chr16_08126809 T/C; S15697: Chr16_08176834 C/T; S15698: Chr16_08263728 T/A; S15699: Chr16_08280671 A/G; S15700: Chr16_08301196 T/A; S15701: Chr16_08375209 T/A; S15702: Chr16_08507700 A/G; S15703: Chr16_08560360 G/A; S15704: Chr16_08576998 T/C; S15705: Chr16_08636710 G/A; S15706: Chr16_08655971 A/G; S15707: Chr16_08706536 T/A; S15708: Chr16_08748984 G/A; S15709: Chr16_08750924 G/A; S15710: Chr16_08792088 T/C; S15711: Chr16_08808447 C/T; S15712: Chr16_08849687 A/G; S15713: Chr16_08854291 G/A; S15714: Chr16_08879158 C/T; S15715: Chr16_08900057 G/A; S15716: Chr16_09050023 G/A; S15717: Chr16_09199247 &A; S15718: Chr16_09202385 A/G; S15719: Chr16_09228251 T/G; S15720: Chr16_09320233 A/G; S15721: Chr16_09332067 A/T; S15722: Chr16_09367611 T/C; S15723: Chr16_09380826 T/C; S15724: Chr16_09403559 A/T; S15725: Chr16_09442552 C/T; S15726: Chr16_09460315 C/T; S15727: Chr16_09485672 A/T; S15728: Chr16_09538231 A/G; S15729: Chr16_09553253 A/T; S15730: Chr16_09681285 T/G; S15731: Chr16_09703115 G/T; S15732: Chr16_09765521 G/T; S15733: Chr16_09800419 A/T; S15734: Chr16_09886790 G/T; S15735: Chr16_09956811 A/C; S15736: Chr16_10020783 G/C; S15737:

Chr16_10100044 C/T; S15738: Chr16_10327632 C/T; S15739: Chr16_10405055 G/C; S15740: Chr16_10503619 A/G; S15741: Chr16_10537497 A/T; S15742: Chr16_10567251 C/T; S15743: Chr16_10577251 C/T; S15744: Chr16_10600897 T/C; S15745: Chr16_10679828 G/A; S15746: Chr16_10700059 G/A; S15747: Chr16_10860455 C/T; S15748: Chr16_10988295 G/A; S15749: Chr16_11002309 T/C; S15750: Chr16_11033967 G/A; S15751: Chr16_11061594 T/A; S15752: Chr16_11077018 A/G; S15753: Chr16_11153152 C/T; S15754: Chr16_11185265 A/G; S15755: Chr16_11229178 A/C; S15756: Chr16_11396058 G/A; S15757: Chr16_11446841 A/C; S15758: Chr16_11600159 T/C; S15759: Chr16_11804787 C/T; S15760: Chr16_11825171 G/A; S15761: Chr16_12043569 G/C; S15762: Chr16_12250320 G/A; S15763: Chr16_12350363 G/C; S15764: Chr16_12425544 C/T; S15765: Chr16_12535017 G/T; S15766: Chr16_13016987 C/T; S15767: Chr16_13050983 A/G; S15768: Chr16_13075614 A/G; S15769: Chr16_13237318 G/A; S15770: Chr16_13300247 A/C; S15771: Chr16_13675270 T/C; S15772: Chr16_13750035 C/G; S15773: Chr16_13825025 G/T; S15774: Chr16_13950210 A/C; S15775: Chr16_13975186 T/G; S15776: Chr16_14125060 T/C; S15777: Chr16_14200182 T/A; S15778: Chr16_14467750 G/A; S15779: Chr16_14480813 G/A; S15780: Chr16_14515526 A/G; S15781: Chr16_14525142 A/C; S15782: Chr16_14743424 C/A; S15783: Chr16_14764974 G/A; S15784: Chr16_14827989 A/G; S15785: Chr16_14850121 C/G; S15786: Chr16_14875013 A/T; S15787: Chr16_15000053 G/C; S15788: Chr16_15098130 T/C; S15789: Chr16_15146778 C/T; S15790: Chr16_15152862 C/A; S15791: Chr16_15250200 G/A; S15792: Chr16_15328609 C/G; S15793: Chr16_15401310 G/C; S15794: Chr16_15625032 T/C; S15795: Chr16_15765961 T/A; S15796: Chr16_15844303 C/T; S15797: Chr16_15922214 T/C; S15798: Chr16_15925446 C/T; S15799: Chr16_16463743 C/A; S15800: Chr16_16522488 C/T; S15801: Chr16_16527396 A/C; S15802: Chr16_16584752 A/G; S15803: Chr16_16724085 G/A; S15804: Chr16_16727871 G/T; S15805: Chr16_16881071 T/G; S15806: Chr16_16916788 G/A; S15807: Chr16_16974065 G/T; S15808: Chr16_16975544 C/G; S15809: Chr16_17011382 T/C; S15810: Chr16_17025997 T/G; S15811: Chr16_17100291 T/C; S15812: Chr16_17175190 T/C; S15813: Chr16_17250066 A/G; S15814: Chr16_17325273 T/C; S15815: Chr16_17401148 G/A; S15816: Chr16_17514428 A/G; S15817: Chr16_17525194 T/C; S15818: Chr16_17604552 G/A; S15819: Chr16_17710807 T/C; S15820: Chr16_17875139 G/T; S15821: Chr16_17950253 T/C; S15822: Chr16_18025020 A/G; S15823: Chr16_18101583 T/C; S15824: Chr16_18246040 T/C; S15825: Chr16_18250004 T/C; S15826: Chr16_18350123 T/A; S15827: Chr16_18638956 G/T; S15828: Chr16_18681277 C/T; S15829: Chr16_18734295 A/C; S15830: Chr16_18768475 A/G; S15831: Chr16_18775723 G/A; S15832: Chr16_18816068 T/G; S15833: Chr16_18832728 C/T; S15834: Chr16_18856775 G/A; S15835: Chr16_18919758 G/C; S15836: Chr16_18927621 A/G; S15837: Chr16_18970818

G/A; S15838: Chr16_18981027 A/C; S15839: Chr16_19023503 T/A; S15840: Chr16_19030660 T/G; S15841: Chr16_19051011 G/A; S15842: Chr16_19077660 C/A; S15843: Chr16_19130872 A/G; S15844: Chr16_19150455 C/T; S15845: Chr16_19249122 A/G; S15846: Chr16_19253129 A/G; S15847: Chr16_19350353 G/A; S15848: Chr16_19464894 T/C; S15849: Chr16_19475579 G/A; S15850: Chr16_19550020 T/G; S15851: Chr16_19639202 C/T; S15852: Chr16_19650362 C/A; S15853: Chr16_19725512 T/C; S15854: Chr16_19800355 A/G; S15855: Chr16_19939093 G/C; S15856: Chr16_19951089 G/A; S15857: Chr16_20100122 C/T; S15858: Chr16_20367118 A/G; S15859: Chr16_20382636 T/C; S15860: Chr16_20405170 G/A; S15861: Chr16_20425215 T/C; S15862: Chr16_20502915 C/T; S15863: Chr16_20636019 C/T; S15864: Chr16_20651107 T/C; S15865: Chr16_20801718 A/G; S15866: Chr16_20858468 G/C; S15867: Chr16_20890024 T/C; S15868: Chr16_20921696 C/G; S15869: Chr16_20943654 A/T; S15870: Chr16_20954534 T/C; S15871: Chr16_20991520 C/G; S15872: Chr16_21015532 T/A; S15873: Chr16_21093217 G/A; S15874: Chr16_21152590 T/C; S15875: Chr16_21200550 A/G; S15876: Chr16_21260537 A/G; S15877: Chr16_21275556 C/T; S15878: Chr16_21303486 G/A; S15879: Chr16_21361269 T/C; S15880: Chr16_21409065 T/A; S15881: Chr16_21436888 T/C; S15882: Chr16_21451029 C/T; S15883: Chr16_21497558 T/C; S15884: Chr16_21510243 C/T; S15885: Chr16_21576601 T/G; S15886: Chr16_21636489 C/T; S15887: Chr16_21685447 T/C; S15888: Chr16_21752958 A/C; S15889: Chr16_21778109 C/T; S15890: Chr16_21800058 C/A; S15891: Chr16_21875451 A/G; S15892: Chr16_21970284 A/G; S15893: Chr16_21978618 A/G; S15894: Chr16_22001114 T/C; S15895: Chr16_22075034 G/C; S15896: Chr16_22225743 T/C; S15897: Chr16_22344648 C/A; S15898: Chr16_22350102 T/C; S15899: Chr16_22433686 T/C; S15900: Chr16_22571422 G/A; S15901: Chr16_22575316 A/G; S15902: Chr16_22650525 T/A; S15903: Chr16_22800129 G/A; S15904: Chr16_22895481 A/G; S15905: Chr16_22901903 T/C; S15906: Chr16_22975281 C/T; S15907: Chr16_23050483 G/T; S15908: Chr16_23132857 G/T; S15909: Chr16_23150144 G/A; S15910: Chr16_23481742 T/C; S15911: Chr16_23645426 G/C; S15912: Chr16_23660216 T/C; S15913: Chr16_23675247 A/C; S15914: Chr16_23796142 A/G; S15915: Chr16_23822808 C/T; S15916: Chr16_23993407 G/A; S15917: Chr16_24028759 T/C; S15918: Chr16_24050007 A/G; S15919: Chr16_24138275 T/C; S15920: Chr16_24200009 A/G; S15921: Chr16_24308244 T/C; S15922: Chr16_24358277 A/C; S15923: Chr16_24436678 G/C; S15924: Chr16_24458157 T/C; S15925: Chr16_24499408 A/G; S15926: Chr16_24500795 C/T; S15927: Chr16_24547869 A/G; S15928: Chr16_24550063 A/C; S15929: Chr16_24632950 T/C; S15930: Chr16_24716641 C/T; S15931: Chr16_24726808 C/T; S15932: Chr16_24765848 C/T; S15933: Chr16_24788196 T/C; S15934: Chr16_24800069 G/A; S15935: Chr16_24897194 C/G; S15936: Chr16_24958668 A/G; S15937: Chr16_25001902 A/G; S15938:

Chr16_25034698 C/A; S15939: Chr16_25067443 G/A; S15940: Chr16_25112409 C/G; S15941: Chr16_25125453 T/C; S15942: Chr16_25152988 C/T; S15943: Chr16_25180280 T/C; S15944: Chr16_25249647 T/C; S15945: Chr16_25313126 T/G; S15946: Chr16_25328194 T/C; S15947: Chr16_25351217 G/A; S15948: Chr16_25419442 C/G; S15949: Chr16_25438723 T/C; S15950: Chr16_25483002 C/A; S15951: Chr16_25507691 A/G; S15952: Chr16_25583890 C/A; S15953: Chr16_25604863 G/A; S15954: Chr16_25628740 T/G; S15955: Chr16_25662449 T/G; S15956: Chr16_25678404 A/G; S15957: Chr16_25728130 G/A; S15958: Chr16_25782577 C/T; S15959: Chr16_25802239 C/T; S15960: Chr16_25851413 C/T; S15961: Chr16_25897633 T/A; S15962: Chr16_25902450 T/A; S15963: Chr16_25925006 C/T; S15964: Chr16_26045218 C/T; S15965: Chr16_26057335 C/G; S15966: Chr16_26103950 T/A; S15967: Chr16_26132215 A/G; S15968: Chr16_26150832 T/G; S15969: Chr16_26226952 T/C; S15970: Chr16_26280357 G/C; S15971: Chr16_26317847 T/A; S15972: Chr16_26335860 T/C; S15973: Chr16_26350002 G/A; S15974: Chr16_26444186 T/A; S15975: Chr16_26451197 G/C; S15976: Chr16_26497653 T/C; S15977: Chr16_26500476 C/A; S15978: Chr16_26527021 A/C; S15979: Chr16_26626771 C/A; S15980: Chr16_26684933 T/C; S15981: Chr16_26751708 T/G; S15982: Chr16_26775496 C/T; S15983: Chr16_26806735 T/C; S15984: Chr16_26826861 T/C; S15985: Chr16_26852312 C/T; S15986: Chr16_26885998 T/C; S15987: Chr16_26910031 C/T; S15988: Chr16_26938944 A/G; S15989: Chr16_26952456 G/A; S15990: Chr16_26985940 T/C; S15991: Chr16_27007271 T/G; S15992: Chr16_27061748 C/T; S15993: Chr16_27105003 G/A; S15994: Chr16_27125179 T/G; S15995: Chr16_27176740 T/A; S15996: Chr16_27217879 G/A; S15997: Chr16_27236909 A/T; S15998: Chr16_27269391 T/C; S15999: Chr16_27284875 A/G; S16000: Chr16_27304987 G/A; S16001: Chr16_27338693 T/A; S16002: Chr16_27366724 C/T; S16003: Chr16_27411219 G/A; S16004: Chr16_27441257 A/G; S16005: Chr16_27510099 T/C; S16006: Chr16_27557430 G/A; S16007: Chr16_27605015 C/A; S16008: Chr16_27645096 G/A; S16009: Chr16_27708494 G/C; S16010: Chr16_27727853 T/C; S16011: Chr16_27759059 C/T; S16012: Chr16_27775145 G/T; S16013: Chr16_27803269 A/G; S16014: Chr16_27878678 C/T; S16015: Chr16_27908093 A/T; S16016: Chr16_27943208 T/A; S16017: Chr16_27950367 T/C; S16018: Chr16_27975124 T/C; S16019: Chr16_28004444 G/C; S16020: Chr16_28027990 G/A; S16021: Chr16_28051006 T/G; S16022: Chr16_28077778 G/A; S16023: Chr16_28111120 G/A; S16024: Chr16_28174652 C/A; S16025: Chr16_28175016 G/A; S16026: Chr16_28228948 T/A; S16027: Chr16_28275568 A/T; S16028: Chr16_28308916 C/T; S16029: Chr16_28341181 T/A; S16030: Chr16_28393195 A/G; S16031: Chr16_28423819 A/T; S16032: Chr16_28425249 A/T; S16033: Chr16_28457304 T/A; S16034: Chr16_28487257 A/T; S16035: Chr16_28513423 G/C; S16036: Chr16_28555207 G/C; S16037: Chr16_28610516 C/T; S16038: Chr16_28633517 C/T; S16039: Chr16_28662557 C/T; S16040: Chr16_28681292 T/C; S16041: Chr16_28739828 T/C; S16042: Chr16_28752453 C/T; S16043: Chr16_28775183 C/T; S16044: Chr16_28858362 A/G; S16045: Chr16_28904652 C/T; S16046: Chr16_28926721 T/C; S16047: Chr16_28950119 G/T; S16048: Chr16_28977194 C/A; S16049: Chr16_29005893 A/C; S16050: Chr16_29035313 T/C; S16051: Chr16_29050592 A/G; S16052: Chr16_29096952 C/T; S16053: Chr16_29100169 C/T; S16054: Chr16_29125853 G/T; S16055: Chr16_29169439 G/A; S16056: Chr16_29182741 T/C; S16057: Chr16_29219376 A/T; S16058: Chr16_29248906 G/C; S16059: Chr16_29251379 C/T; S16060: Chr16_29287099 C/G; S16061: Chr16_29321785 G/A; S16062: Chr16_29347676 G/A; S16063: Chr16_29350032 C/T; S16064: Chr16_29378974 A/C; S16065: Chr16_29407813 T/G; S16066: Chr16_29425798 C/G; S16067: Chr16_29450424 C/T; S16068: Chr16_29481011 T/C; S16069: Chr16_29509872 G/A; S16070: Chr16_29527399 T/C; S16071: Chr16_29575980 C/T; S16072: Chr16_29621947 A/C; S16073: Chr16_29632615 C/T; S16074: Chr16_29672784 A/T; S16075: Chr16_29689908 A/C; S16076: Chr16_29738571 T/C; S16077: Chr16_29752813 A/G; S16078: Chr16_29837245 G/A; S16079: Chr16_29851101 T/C; S16080: Chr16_29895938 C/T; S16081: Chr16_29961102 A/G; S16082: Chr16_29975936 G/T; S16083: Chr16_30007081 A/G; S16084: Chr16_30045546 T/C; S16085: Chr16_30067405 T/G; S16086: Chr16_30142557 C/T; S16087: Chr16_30202844 T/C; S16088: Chr16_30232673 A/T; S16089: Chr16_30274842 A/G; S16090: Chr16_30275595 C/T; S16091: Chr16_30338142 C/T; S16092: Chr16_30370368 C/T; S16093: Chr16_30380593 G/A; S16094: Chr16_30400320 T/G; S16095: Chr16_30433508 G/T; S16096: Chr16_30457762 T/G; S16097: Chr16_30475002 C/G; S16098: Chr16_30502232 C/T; S16099: Chr16_30549742 T/A; S16100: Chr16_30552631 C/A; S16101: Chr16_30587474 G/A; S16102: Chr16_30604814 C/A; S16103: Chr16_30632931 A/G; S16104: Chr16_30652839 A/T; S16105: Chr16_30677411 C/T; S16106: Chr16_30702527 T/G; S16107: Chr16_30726029 C/T; S16108: Chr16_30758141 G/A; S16109: Chr16_30775316 C/A; S16110: Chr16_30810750 C/T; S16111: Chr16_30833058 T/C; S16112: Chr16_30856227 A/C; S16113: Chr16_30878823 A/G; S16114: Chr16_30903345 G/A; S16115: Chr16_30958463 T/C; S16116: Chr16_30993331 C/T; S16117: Chr16_31003707 G/A; S16118: Chr16_31030214 T/A; S16119: Chr16_31057087 C/G; S16120: Chr16_31087123 G/A; S16121: Chr16_31102611 C/A; S16122: Chr16_31149002 T/C; S16123: Chr16_31151688 G/A; S16124: Chr16_31181814 T/C; S16125: Chr16_31200547 G/T; S16126: Chr16_31233972 A/G; S16127: Chr16_31264852 A/G; S16128: Chr16_31299901 A/G; S16129: Chr16_31302679 G/A; S16130: Chr16_31325573 A/G; S16131: Chr16_31359359 G/A; S16132: Chr16_31376138 C/T; S16133: Chr16_31409184 C/G; S16134: Chr16_31432171 A/G; S16135: Chr16_31450336 G/A; S16136: Chr16_31475368 C/G; S16137: Chr16_31503410 A/G; S16138: Chr16_31535179 A/T; S16139:

Chr16_31557876 C/T; S16140: Chr16_31580495 G/A; S16141: Chr16_31601354 A/T; S16142: Chr16_31630013 G/A; S16143: Chr16_31659958 A/G; S16144: Chr16_31675884 T/A; S16145: Chr16_31700689 G/A; S16146: Chr16_31729796 A/G; S16147: Chr16_31765205 G/A; S16148: Chr16_31784576 G/A; S16149: Chr16_31818490 A/G; S16150: Chr16_31825010 A/G; S16151: Chr16_31854599 G/A; S16152: Chr16_31875053 C/A; S16153: Chr16_31906318 C/A; S16154: Chr16_31925900 A/G; S16155: Chr16_31951879 T/A; S16156: Chr16_31977185 G/T; S16157: Chr16_32004518 C/G; S16158: Chr16_32028334 C/G; S16159: Chr16_32052897 C/G; S16160: Chr16_32077963 A/G; S16161: Chr16_32101959 A/C; S16162: Chr16_32125398 A/T; S16163: Chr16_32151089 C/G; S16164: Chr16_32179023 A/G; S16165: Chr16_32214034 G/T; S16166: Chr16_32259125 A/C; S16167: Chr16_32276015 G/A; S16168: Chr16_32302680 T/C; S16169: Chr16_32349457 A/T; S16170: Chr16_32358486 C/T; S16171: Chr16_32379115 T/C; S16172: Chr16_32415874 C/T; S16173: Chr16_32425309 C/T; S16174: Chr16_32453251 A/G; S16175: Chr16_32482530 G/A; S16176: Chr16_32516100 A/G; S16177: Chr16_32534986 C/G; S16178: Chr16_32565714 A/G; S16179: Chr16_32581835 A/G; S16180: Chr16_32600062 A/G; S16181: Chr16_32631280 C/T; S16182: Chr16_32662218 C/G; S16183: Chr16_32688040 G/A; S16184: Chr16_32707283 C/T; S16185: Chr16_32731793 T/A; S16186: Chr16_32767876 G/A; S16187: Chr16_32775055 C/T; S16188: Chr16_32811336 C/T; S16189: Chr16_32825021 C/T; S16190: Chr16_32850536 A/G; S16191: Chr16_32896269 T/A; S16192: Chr16_32911332 G/C; S16193: Chr16_32933657 C/G; S16194: Chr16_32950832 C/T; S16195: Chr16_32975476 C/G; S16196: Chr16_33010822 T/G; S16197: Chr16_33047951 C/T; S16198: Chr16_33050891 C/G; S16199: Chr16_33095172 C/T; S16200: Chr16_33101280 G/A; S16201: Chr16_33135695 T/C; S16202: Chr16_33152519 T/C; S16203: Chr16_33176270 A/T; S16204: Chr16_33209606 C/A; S16205: Chr16_33225878 T/C; S16206: Chr16_33271999 A/C; S16207: Chr16_33283560 C/T; S16208: Chr16_33308448 A/G; S16209: Chr16_33325243 C/T; S16210: Chr16_33353078 C/T; S16211: Chr16_33386998 A/G; S16212: Chr16_33400746 A/G; S16213: Chr16_33431180 C/T; S16214: Chr16_33454512 T/A; S16215: Chr16_33478375 G/C; S16216: Chr16_33535324 G/A; S16217: Chr16_33568479 A/T; S16218: Chr16_33588217 C/G; S16219: Chr16_33616264 C/T; S16220: Chr16_33625575 C/G; S16221: Chr16_33654918 T/A; S16222: Chr16_33682382 C/T; S16223: Chr16_33701089 T/A; S16224: Chr16_33726162 G/A; S16225: Chr16_33754660 C/A; S16226: Chr16_33777727 T/G; S16227: Chr16_33803276 T/G; S16228: Chr16_33828286 C/G; S16229: Chr16_33850505 G/A; S16230: Chr16_33878955 T/C; S16231: Chr16_33901868 C/T; S16232: Chr16_33926299 C/T; S16233: Chr16_33950384 G/A; S16234: Chr16_33985962 A/T; S16235: Chr16_34011155 T/G; S16236: Chr16_34041415 C/T; S16237: Chr16_34053346 T/A; S16238: Chr16_34075555 C/T; S16239: Chr16_34106026 C/T; S16240: Chr16_34132614 A/T; S16241: Chr16_34170959 T/A; S16242: Chr16_34178741 T/C; S16243: Chr16_34204838 T/C; S16244: Chr16_34228498 G/A; S16245: Chr16_34252062 T/G; S16246: Chr16_34275534 A/G; S16247: Chr16_34300135 A/G; S16248: Chr16_34325301 C/T; S16249: Chr16_34350182 C/A; S16250: Chr16_34380152 A/T; S16251: Chr16_34409447 G/T; S16252: Chr16_34579528 T/G; S16253: Chr16_34648139 A/T; S16254: Chr16_34650208 A/C; S16255: Chr16_34758097 C/T; S16256: Chr16_34801942 G/C; S16257: Chr16_34913631 G/C; S16258: Chr16_34953254 C/T; S16259: Chr16_35139454 T/A; S16260: Chr16_35163546 C/T; S16261: Chr16_35179544 G/A; S16262: Chr16_35201496 T/C; S16263: Chr16_35226772 G/C; S16264: Chr16_35269248 C/A; S16265: Chr16_35289818 A/T; S16266: Chr16_35307796 A/T; S16267: Chr16_35333529 C/A; S16268: Chr16_35405458 T/A; S16269: Chr16_35436781 A/T; S16270: Chr16_35556808 G/C; S16271: Chr16_35578661 A/G; S16272: Chr16_35620276 A/G; S16273: Chr16_35625925 C/T; S16274: Chr16_35661095 T/A; S16275: Chr16_35687276 G/T; S16276: Chr16_35722498 A/C; S16277: Chr16_35728649 A/G; S16278: Chr16_35774059 T/C; S16279: Chr16_35782827 T/G; S16280: Chr16_35809331 A/G; S16281: Chr16_35826487 C/T; S16282: Chr16_35850306 T/C; S16283: Chr16_35884064 C/G; S16284: Chr16_35901219 A/G; S16285: Chr16_35928775 A/T; S16286: Chr16_35958855 C/T; S16287: Chr16_35992276 T/C; S16288: Chr16_36006407 A/G; S16289: Chr16_36031343 T/C; S16290: Chr16_36055848 G/A; S16291: Chr16_36085057 G/T; S16292: Chr16_36102518 T/A; S16293: Chr16_36127849 C/A; S16294: Chr16_36151825 A/G; S16295: Chr16_36175282 A/C; S16296: Chr16_36219434 C/T; S16297: Chr16_36231836 A/G; S16298: Chr16_36250620 T/A; S16299: Chr16_36275524 T/G; S16300: Chr16_36302861 C/T; S16301: Chr16_36328046 T/C; S16302: Chr16_36350055 G/A; S16303: Chr16_36383799 G/T; S16304: Chr16_36400882 C/T; S16305: Chr16_36427284 A/G; S16306: Chr16_36450965 A/G; S16307: Chr16_36488370 C/T; S16308: Chr16_36510916 C/G; S16309: Chr16_36528241 T/G; S16310: Chr16_36570735 C/T; S16311: Chr16_36583155 C/G; S16312: Chr16_36607850 G/A; S16313: Chr16_36626757 G/A; S16314: Chr16_36652854 A/G; S16315: Chr16_36677992 A/G; S16316: Chr16_36701948 C/G; S16317: Chr16_36729677 T/C; S16318: Chr16_36750257 G/C; S16319: Chr16_36777207 T/G; S16320: Chr16_36808147 A/G; S16321: Chr16_36827194 A/C; S16322: Chr16_36854499 C/T; S16323: Chr16_36875049 C/A; S16324: Chr16_36903270 A/G; S16325: Chr16_36929105 A/T; S16326: Chr16_36950027 G/A; S16327: Chr16_36978556 G/A; S16328: Chr16_37003627 G/A; S16329: Chr16_37027212 A/G; S16330: Chr16_37051219 T/A; S16331: Chr16_37081216 G/A; S16332: Chr16_37100205 G/C; S16333: Chr16_37126645 A/C; S16334: Chr16_37154729 C/G; S16335: Chr16_37175079 G/T; S16336: Chr16_37208853 G/A; S16337: Chr16_37225158 A/C; S16338: Chr16_37262005 C/A; S16339: Chr16_37277060 C/T; S16340:

Chr16_37305101 T/G; S16341: Chr16_37327289 C/T; S16342: Chr16_37350310 T/A; S16343: Chr16_37382445 T/C; S16344: Chr16_37402359 G/A; S16345: Chr16_37425027 A/G; S16346: Chr16_37459869 A/G; S16347: Chr16_37500306 T/C; S16348: Chr16_37529627 T/C; S16349: Chr16_37550849 T/A; S16350: Chr16_37581020 A/G; S16351: Chr16_37603102 A/T; S16352: Chr16_37634666 T/C; S16353: Chr16_37651362 T/C; S16354: Chr16_37711680 T/C; S16355: Chr16_37727086 T/A; S16356: Chr16_37765044 A/G; S16357: Chr16_37775840 G/A; S16358: Chr16_37811857 C/A; S16359: Chr16_37839002 C/G; S16360: Chr16_37861633 T/A; S16361: Chr17_00011341 A/G; S16362: Chr17_00160618 A/G; S16363: Chr17_00217289 G/A; S16364: Chr17_00254933 C/G; S16365: Chr17_00275217 T/C; S16366: Chr17_00306314 A/T; S16367: Chr17_00341237 A/T; S16368: Chr17_00350307 G/A; S16369: Chr17_00379073 G/T; S16370: Chr17_00403499 T/C; S16371: Chr17_00429463 G/A; S16372: Chr17_00461138 A/G; S16373: Chr17_00487393 C/T; S16374: Chr17_00501837 G/C; S16375: Chr17_00528741 G/C; S16376: Chr17_00551912 T/C; S16377: Chr17_00587273 C/G; S16378: Chr17_00608239 C/T; S16379: Chr17_00637561 T/C; S16380: Chr17_00660705 C/A; S16381: Chr17_00695500 G/A; S16382: Chr17_00702453 C/T; S16383: Chr17_00731515 C/T; S16384: Chr17_00763490 C/T; S16385: Chr17_00807987 G/C; S16386: Chr17_00829501 A/C; S16387: Chr17_00877201 C/T; S16388: Chr17_00917899 C/T; S16389: Chr17_01042381 C/T; S16390: Chr17_01060119 G/C; S16391: Chr17_01078928 G/T; S16392: Chr17_01118225 T/C; S16393: Chr17_01125199 A/G; S16394: Chr17_01248898 C/T; S16395: Chr17_01278373 G/A; S16396: Chr17_01410478 G/T; S16397: Chr17_01456784 A/G; S16398: Chr17_01487746 C/A; S16399: Chr17_01570502 A/T; S16400: Chr17_01631933 C/T; S16401: Chr17_01667065 G/A; S16402: Chr17_01680401 T/A; S16403: Chr17_01706058 C/T; S16404: Chr17_01730340 A/G; S16405: Chr17_01808929 G/A; S16406: Chr17_01847759 C/T; S16407: Chr17_01909481 C/T; S16408: Chr17_01930007 C/G; S16409: Chr17_01951334 C/T; S16410: Chr17_01985700 A/G; S16411: Chr17_02022280 G/A; S16412: Chr17_02078415 A/T; S16413: Chr17_02150368 A/T; S16414: Chr17_02193662 T/C; S16415: Chr17_02201362 A/G; S16416: Chr17_02231582 T/C; S16417: Chr17_02270406 C/T; S16418: Chr17_02275574 T/G; S16419: Chr17_02304992 C/T; S16420: Chr17_02325511 A/T; S16421: Chr17_02350021 C/G; S16422: Chr17_02379418 C/G; S16423: Chr17_02405419 A/T; S16424: Chr17_02425632 T/G; S16425: Chr17_02452515 A/T; S16426: Chr17_02492420 T/A; S16427: Chr17_02513973 T/C; S16428: Chr17_02534564 G/A; S16429: Chr17_02694316 G/A; S16430: Chr17_02766231 T/G; S16431: Chr17_02839005 G/A; S16432: Chr17_02875861 G/T; S16433: Chr17_02912573 T/C; S16434: Chr17_02931198 G/A; S16435: Chr17_02950737 C/T; S16436: Chr17_03000808 T/A; S16437: Chr17_03028948 T/C; S16438: Chr17_03069052 T/A; S16439: Chr17_03080989 T/A; S16440: Chr17_03103082 T/C; S16441: Chr17_03138146 T/G; S16442: Chr17_03201711 A/G; S16443: Chr17_03225031 T/C; S16444: Chr17_03258476 C/A; S16445: Chr17_03283438 T/C; S16446: Chr17_03300591 C/T; S16447: Chr17_03325907 A/G; S16448: Chr17_03382589 A/G; S16449: Chr17_03409424 A/G; S16450: Chr17_03425189 G/A; S16451: Chr17_03450387 T/C; S16452: Chr17_03477445 C/T; S16453: Chr17_03514377 A/G; S16454: Chr17_03529655 G/A; S16455: Chr17_03566468 T/C; S16456: Chr17_03579839 G/C; S16457: Chr17_03600603 T/C; S16458: Chr17_03629604 A/G; S16459: Chr17_03650643 C/A; S16460: Chr17_03692916 C/G; S16461: Chr17_03703979 T/G; S16462: Chr17_03735886 C/T; S16463: Chr17_03755395 T/C; S16464: Chr17_03775660 A/G; S16465: Chr17_03836310 T/C; S16466: Chr17_03850687 G/A; S16467: Chr17_03889125 A/G; S16468: Chr17_03907247 C/T; S16469: Chr17_03928173 C/T; S16470: Chr17_03955716 A/G; S16471: Chr17_03976107 C/T; S16472: Chr17_04016954 T/G; S16473: Chr17_04036342 T/C; S16474: Chr17_04054733 A/C; S16475: Chr17_04077693 T/C; S16476: Chr17_04120689 T/G; S16477: Chr17_04128714 C/A; S16478: Chr17_04151713 C/A; S16479: Chr17_04179272 C/A; S16480: Chr17_04218353 A/T; S16481: Chr17_04231146 C/A; S16482: Chr17_04251564 T/A; S16483: Chr17_04275211 T/G; S16484: Chr17_04300084 G/C; S16485: Chr17_04329295 G/T; S16486: Chr17_04350163 C/T; S16487: Chr17_04386685 C/T; S16488: Chr17_04405655 T/C; S16489: Chr17_04426273 C/T; S16490: Chr17_04451572 G/A; S16491: Chr17_04475531 G/C; S16492: Chr17_04501890 A/G; S16493: Chr17_04534755 G/C; S16494: Chr17_04551479 C/T; S16495: Chr17_04575427 A/G; S16496: Chr17_04600692 C/G; S16497: Chr17_04625109 T/C; S16498: Chr17_04651149 T/A; S16499: Chr17_04684960 A/C; S16500: Chr17_04701357 T/A; S16501: Chr17_04730419 G/A; S16502: Chr17_04753728 G/A; S16503: Chr17_04813560 G/C; S16504: Chr17_04831528 G/A; S16505: Chr17_04855730 T/A; S16506: Chr17_04884351 T/A; S16507: Chr17_04901383 G/A; S16508: Chr17_04935456 G/A; S16509: Chr17_04953867 G/T; S16510: Chr17_04975729 C/T; S16511: Chr17_05021725 C/A; S16512: Chr17_05033019 A/G; S16513: Chr17_05063941 T/G; S16514: Chr17_05088557 C/T; S16515: Chr17_05106093 T/C; S16516: Chr17_05132503 C/T; S16517: Chr17_05160917 T/C; S16518: Chr17_05176903 C/G; S16519: Chr17_05208908 T/A; S16520: Chr17_05228473 T/C; S16521: Chr17_05264187 G/C; S16522: Chr17_05289164 T/G; S16523: Chr17_05308042 G/A; S16524: Chr17_05337586 C/T; S16525: Chr17_05350847 C/G; S16526: Chr17_05383144 T/A; S16527: Chr17_05401632 T/C; S16528: Chr17_05440778 A/G; S16529: Chr17_05454591 T/C; S16530: Chr17_05475487 G/A; S16531: Chr17_05504494 C/T; S16532: Chr17_05525889 T/C; S16533: Chr17_05556327 G/A; S16534: Chr17_05575883 G/T; S16535: Chr17_05600004 T/C; S16536: Chr17_05628840 T/C; S16537: Chr17_05650976 T/C; S16538: Chr17_05675941 G/C; S16539: Chr17_05700196 C/G; S16540: Chr17_05727599 A/C; S16541:

Chr17_05750373 A/G; S16542: Chr17_05778829 A/G; S16543: Chr17_05807423 C/T; S16544: Chr17_05825758 C/T; S16545: Chr17_05850523 T/C; S16546: Chr17_05894617 T/C; S16547: Chr17_05904479 C/A; S16548: Chr17_05931130 A/G; S16549: Chr17_05974992 T/C; S16550: Chr17_05981755 G/A; S16551: Chr17_06051036 G/A; S16552: Chr17_06113095 C/T; S16553: Chr17_06177843 C/T; S16554: Chr17_06299640 A/G; S16555: Chr17_06300940 C/T; S16556: Chr17_06326239 T/C; S16557: Chr17_06408361 T/C; S16558: Chr17_06436543 A/T; S16559: Chr17_06461031 G/A; S16560: Chr17_06509236 G/A; S16561: Chr17_06526967 C/T; S16562: Chr17_06565253 G/C; S16563: Chr17_06578113 C/T; S16564: Chr17_06601326 A/C; S16565: Chr17_06667437 A/T; S16566: Chr17_06733809 C/T; S16567: Chr17_06760299 T/C; S16568: Chr17_06779679 A/G; S16569: Chr17_06802545 C/T; S16570: Chr17_06833408 A/T; S16571: Chr17_06852773 A/G; S16572: Chr17_06878865 A/G; S16573: Chr17_06902725 C/T; S16574: Chr17_06954938 T/C; S16575: Chr17_06976972 G/A; S16576: Chr17_07067588 G/A; S16577: Chr17_07094370 C/A; S16578: Chr17_07117839 T/A; S16579: Chr17_07128624 T/C; S16580: Chr17_07153856 G/C; S16581: Chr17_07193780 T/G; S16582: Chr17_07217017 G/A; S16583: Chr17_07265569 A/G; S16584: Chr17_07280075 C/T; S16585: Chr17_07306892 T/C; S16586: Chr17_07380145 G/T; S16587: Chr17_07442253 C/T; S16588: Chr17_07462240 C/T; S16589: Chr17_07491036 T/A; S16590: Chr17_07500935 T/C; S16591: Chr17_07575914 A/G; S16592: Chr17_07604329 A/G; S16593: Chr17_07736869 A/G; S16594: Chr17_07780377 T/C; S16595: Chr17_07800831 G/A; S16596: Chr17_07839675 C/T; S16597: Chr17_07862329 A/G; S16598: Chr17_07879648 A/T; S16599: Chr17_07900546 C/T; S16600: Chr17_07927328 T/C; S16601: Chr17_07978594 T/C; S16602: Chr17_08022010 T/C; S16603: Chr17_08025105 T/A; S16604: Chr17_08076941 T/C; S16605: Chr17_08118589 T/C; S16606: Chr17_08129418 T/A; S16607: Chr17_08153882 T/C; S16608: Chr17_08201099 T/C; S16609: Chr17_08232457 G/A; S16610: Chr17_08253214 A/G; S16611: Chr17_08286360 C/G; S16612: Chr17_08312752 G/A; S16613: Chr17_08328369 C/T; S16614: Chr17_08350510 G/C; S16615: Chr17_08455888 G/A; S16616: Chr17_08475676 G/A; S16617: Chr17_08506733 C/G; S16618: Chr17_08529959 G/A; S16619: Chr17_08555800 G/A; S16620: Chr17_08623316 A/C; S16621: Chr17_08625406 C/T; S16622: Chr17_08654251 G/T; S16623: Chr17_08684034 G/T; S16624: Chr17_08706845 A/T; S16625: Chr17_08729740 C/T; S16626: Chr17_08750018 T/C; S16627: Chr17_08783402 T/A; S16628: Chr17_08808025 A/G; S16629: Chr17_08841393 G/A; S16630: Chr17_08858290 C/T; S16631: Chr17_08881730 T/C; S16632: Chr17_08909151 C/G; S16633: Chr17_08926382 A/G; S16634: Chr17_08986106 T/C; S16635: Chr17_09008173 G/A; S16636: Chr17_09035542 C/T; S16637: Chr17_09056780 A/G; S16638: Chr17_09075599 C/A; S16639: Chr17_09101770 T/A; S16640: Chr17_09138374 A/T; S16641: Chr17_09150176 T/C; S16642: Chr17_09203728 G/A; S16643: Chr17_09226195 C/T; S16644: Chr17_09254360 G/T; S16645: Chr17_09291943 A/G; S16646: Chr17_09304175 A/C; S16647: Chr17_09338171 C/A; S16648: Chr17_09363900 T/A; S16649: Chr17_09402808 G/A; S16650: Chr17_09456638 A/G; S16651: Chr17_09482221 G/A; S16652: Chr17_09615940 T/G; S16653: Chr17_09635988 G/A; S16654: Chr17_09661735 C/T; S16655: Chr17_09716365 G/A; S16656: Chr17_09728125 T/C; S16657: Chr17_09764051 A/C; S16658: Chr17_09779938 G/A; S16659: Chr17_09812136 C/A; S16660: Chr17_09838390 A/T; S16661: Chr17_09916973 C/T; S16662: Chr17_09936811 C/T; S16663: Chr17_09950922 A/T; S16664: Chr17_09991880 C/T; S16665: Chr17_10089325 G/C; S16666: Chr17_10148611 C/T; S16667: Chr17_10206759 T/C; S16668: Chr17_10225165 A/G; S16669: Chr17_10313969 C/T; S16670: Chr17_10433088 C/T; S16671: Chr17_10470199 T/C; S16672: Chr17_10545210 C/T; S16673: Chr17_10554577 G/A; S16674: Chr17_10637978 G/A; S16675: Chr17_10706023 C/T; S16676: Chr17_10804269 A/T; S16677: Chr17_10847218 C/A; S16678: Chr17_10871828 C/T; S16679: Chr17_10945429 C/T; S16680: Chr17_10985735 C/G; S16681: Chr17_11000909 C/A; S16682: Chr17_11025426 T/C; S16683: Chr17_11058656 T/C; S16684: Chr17_11077244 T/A; S16685: Chr17_11100619 G/C; S16686: Chr17_11126475 T/C; S16687: Chr17_11224393 G/A; S16688: Chr17_11226748 C/T; S16689: Chr17_11250440 T/C; S16690: Chr17_11275022 T/C; S16691: Chr17_11312603 G/T; S16692: Chr17_11345747 G/A; S16693: Chr17_11353635 A/G; S16694: Chr17_11385561 C/A; S16695: Chr17_11417438 A/T; S16696: Chr17_11447489 A/C; S16697: Chr17_11452008 G/A; S16698: Chr17_11490884 A/C; S16699: Chr17_11517052 G/A; S16700: Chr17_11529486 A/T; S16701: Chr17_11550279 C/T; S16702: Chr17_11576799 A/G; S16703: Chr17_11602977 T/G; S16704: Chr17_11629450 C/G; S16705: Chr17_11656116 T/C; S16706: Chr17_11676224 T/C; S16707: Chr17_11744129 C/T; S16708: Chr17_11759563 T/A; S16709: Chr17_11782616 T/A; S16710: Chr17_11801522 G/C; S16711: Chr17_11839621 G/A; S16712: Chr17_11868466 G/A; S16713: Chr17_11955083 C/T; S16714: Chr17_12029252 A/C; S16715: Chr17_12050075 C/A; S16716: Chr17_12107006 C/T; S16717: Chr17_12125019 A/C; S16718: Chr17_12150960 T/C; S16719: Chr17_12188595 C/G; S16720: Chr17_12213440 C/T; S16721: Chr17_12226185 C/G; S16722: Chr17_12258670 G/A; S16723: Chr17_12291308 T/G; S16724: Chr17_12304456 A/G; S16725: Chr17_12352279 G/A; S16726: Chr17_12375076 C/T; S16727: Chr17_12404257 G/A; S16728: Chr17_12433143 C/T; S16729: Chr17_12453557 T/A; S16730: Chr17_12475327 A/G; S16731: Chr17_12532754 G/A; S16732: Chr17_12570442 G/A; S16733: Chr17_12595702 T/A; S16734: Chr17_12602542 G/A; S16735: Chr17_12625978 G/C; S16736: Chr17_12665036 C/T; S16737: Chr17_12705146 A/G; S16738: Chr17_12738323 T/C; S16739: Chr17_12775112 G/T; S16740: Chr17_12814479 T/A; S16741: Chr17_12829175 C/T; S16742:

Chr17_12874440 A/C; S16743: Chr17_12878614 T/C; S16744: Chr17_12914642 G/A; S16745: Chr17_12925637 A/C; S16746: Chr17_12968626 T/A; S16747: Chr17_12987262 C/A; S16748: Chr17_13022723 C/A; S16749: Chr17_13027116 A/G; S16750: Chr17_13054121 T/G; S16751: Chr17_13092608 T/A; S16752: Chr17_13112981 T/C; S16753: Chr17_13135238 G/T; S16754: Chr17_13164246 C/T; S16755: Chr17_13179902 A/T; S16756: Chr17_13218453 G/A; S16757: Chr17_13234616 C/T; S16758: Chr17_13252434 G/C; S16759: Chr17_13287425 A/G; S16760: Chr17_13313035 A/T; S16761: Chr17_13327286 C/T; S16762: Chr17_13350308 A/T; S16763: Chr17_13375986 A/C; S16764: Chr17_13462328 G/A; S16765: Chr17_13477838 G/A; S16766: Chr17_13515659 T/A; S16767: Chr17_13595868 A/T; S16768: Chr17_13601504 C/T; S16769: Chr17_13676730 G/A; S16770: Chr17_13751395 T/G; S16771: Chr17_13790908 T/C; S16772: Chr17_13805053 G/A; S16773: Chr17_13845235 G/C; S16774: Chr17_13862640 A/G; S16775: Chr17_13898570 A/T; S16776: Chr17_13905963 A/G; S16777: Chr17_13939962 C/T; S16778: Chr17_13950521 C/G; S16779: Chr17_14000629 C/T; S16780: Chr17_14077396 G/T; S16781: Chr17_14112455 G/A; S16782: Chr17_14137190 A/T; S16783: Chr17_14151638 C/T; S16784: Chr17_14175193 C/A; S16785: Chr17_14278942 G/T; S16786: Chr17_14363796 G/A; S16787: Chr17_14432370 G/A; S16788: Chr17_14474169 G/A; S16789: Chr17_14501495 A/G; S16790: Chr17_14528096 G/T; S16791: Chr17_14586674 G/A; S16792: Chr17_14606720 C/T; S16793: Chr17_14650655 G/A; S16794: Chr17_14690114 C/G; S16795: Chr17_14701474 T/C; S16796: Chr17_14749525 C/T; S16797: Chr17_14782777 G/A; S16798: Chr17_14804951 A/G; S16799: Chr17_14877163 C/T; S16800: Chr17_14983404 C/A; S16801: Chr17_15030575 C/A; S16802: Chr17_15052283 T/C; S16803: Chr17_15083000 T/C; S16804: Chr17_15105609 A/G; S16805: Chr17_15149183 A/G; S16806: Chr17_15161422 C/T; S16807: Chr17_15209936 C/T; S16808: Chr17_15230298 C/G; S16809: Chr17_15250595 C/A; S16810: Chr17_15312678 G/T; S16811: Chr17_15369169 C/G; S16812: Chr17_15433180 G/A; S16813: Chr17_15464503 C/A; S16814: Chr17_15480307 G/A; S16815: Chr17_15519406 G/A; S16816: Chr17_15526738 T/C; S16817: Chr17_15554945 G/C; S16818: Chr17_15585203 G/T; S16819: Chr17_15622586 A/G; S16820: Chr17_15630390 A/T; S16821: Chr17_15652166 T/A; S16822: Chr17_15680201 G/C; S16823: Chr17_15718732 T/C; S16824: Chr17_15734105 T/G; S16825: Chr17_15844951 T/G; S16826: Chr17_15850207 T/G; S16827: Chr17_15975787 G/A; S16828: Chr17_16048876 C/A; S16829: Chr17_16050101 A/G; S16830: Chr17_16091805 C/T; S16831: Chr17_16169791 G/A; S16832: Chr17_16202476 A/T; S16833: Chr17_16225263 C/T; S16834: Chr17_16307787 T/G; S16835: Chr17_16325403 A/G; S16836: Chr17_16415488 T/C; S16837: Chr17_16483230 A/T; S16838: Chr17_16500253 G/A; S16839: Chr17_16601297 G/A; S16840: Chr17_16644094 C/G; S16841: Chr17_16650764 T/A; S16842: Chr17_16772561 T/A; S16843: Chr17_16775301 A/G; S16844: Chr17_17100212 A/G; S16845: Chr17_17241543 T/C; S16846: Chr17_17265448 G/A; S16847: Chr17_17322837 C/T; S16848: Chr17_17325010 A/C; S16849: Chr17_17624642 A/G; S16850: Chr17_17626768 T/G; S16851: Chr17_17676937 C/T; S16852: Chr17_17700179 C/T; S16853: Chr17_17776304 C/T; S16854: Chr17_17800021 G/A; S16855: Chr17_17882874 A/T; S16856: Chr17_17900599 T/C; S16857: Chr17_17933084 A/T; S16858: Chr17_17988919 C/G; S16859: Chr17_18042716 G/A; S16860: Chr17_18081763 C/A; S16861: Chr17_18107174 A/G; S16862: Chr17_18153514 C/G; S16863: Chr17_18186469 T/C; S16864: Chr17_18201229 G/C; S16865: Chr17_18258105 C/T; S16866: Chr17_18294579 C/T; S16867: Chr17_18301861 G/A; S16868: Chr17_18329035 T/C; S16869: Chr17_18356133 T/C; S16870: Chr17_18431069 C/G; S16871: Chr17_18487573 A/G; S16872: Chr17_18509672 G/A; S16873: Chr17_18525570 A/T; S16874: Chr17_18600466 T/C; S16875: Chr17_18701344 C/A; S16876: Chr17_18725633 A/G; S16877: Chr17_18797361 G/A; S16878: Chr17_18800974 C/T; S16879: Chr17_18875060 G/T; S16880: Chr17_18953309 G/A; S16881: Chr17_19041453 G/A; S16882: Chr17_19058919 T/C; S16883: Chr17_19101204 C/G; S16884: Chr17_19135917 C/T; S16885: Chr17_19159896 C/T; S16886: Chr17_19205480 C/T; S16887: Chr17_19281233 A/G; S16888: Chr17_19317226 C/T; S16889: Chr17_19328444 T/C; S16890: Chr17_19382135 G/T; S16891: Chr17_19400178 G/A; S16892: Chr17_19484160 T/C; S16893: Chr17_19530937 A/C; S16894: Chr17_19682617 A/C; S16895: Chr17_19744163 G/A; S16896: Chr17_19750168 A/G; S16897: Chr17_19901858 A/T; S16898: Chr17_20017319 T/C; S16899: Chr17_20051888 A/G; S16900: Chr17_20088171 G/A; S16901: Chr17_20108392 C/G; S16902: Chr17_20209446 T/A; S16903: Chr17_20225174 C/T; S16904: Chr17_20384150 G/A; S16905: Chr17_20405717 G/A; S16906: Chr17_20490052 C/T; S16907: Chr17_20578478 T/G; S16908: Chr17_20659138 C/T; S16909: Chr17_20730261 T/G; S16910: Chr17_20750081 G/T; S16911: Chr17_20825868 C/G; S16912: Chr17_20928589 A/T; S16913: Chr17_21035426 T/G; S16914: Chr17_21325134 T/G; S16915: Chr17_21413690 A/G; S16916: Chr17_21455548 A/C; S16917: Chr17_21541312 G/A; S16918: Chr17_21659305 C/T; S16919: Chr17_21838399 G/A; S16920: Chr17_21882605 C/G; S16921: Chr17_21900034 A/G; S16922: Chr17_22056388 A/G; S16923: Chr17_22122582 C/T; S16924: Chr17_22125521 C/T; S16925: Chr17_22216099 T/C; S16926: Chr17_22226696 G/A; S16927: Chr17_22425520 C/T; S16928: Chr17_22452424 C/A; S16929: Chr17_22525043 T/C; S16930: Chr17_22613019 A/G; S16931: Chr17_22653854 A/T; S16932: Chr17_22704255 C/T; S16933: Chr17_22859618 C/T; S16934: Chr17_22937132 C/T; S16935: Chr17_22982560 G/C; S16936: Chr17_23008617 C/T; S16937: Chr17_23065578 A/G; S16938: Chr17_23075075 C/T; S16939: Chr17_23192082 A/G; S16940: Chr17_23200827 A/T; S16941: Chr17_23290851 C/G; S16942: Chr17_23434268 A/T; S16943:

Chr17_23450111 G/C; S16944: Chr17_23502378 G/A; S16945: Chr17_23526699 C/G; S16946: Chr17_23553333 T/A; S16947: Chr17_23592353 C/G; S16948: Chr17_23635599 G/A; S16949: Chr17_23720894 C/T; S16950: Chr17_23747081 C/T; S16951: Chr17_23797466 T/C; S16952: Chr17_23865088 T/C; S16953: Chr17_23875337 T/A; S16954: Chr17_23988643 C/T; S16955: Chr17_24004652 G/A; S16956: Chr17_24100727 G/T; S16957: Chr17_24173490 A/G; S16958: Chr17_24200055 C/T; S16959: Chr17_24337642 A/G; S16960: Chr17_24351375 G/C; S16961: Chr17_24387159 G/A; S16962: Chr17_24454657 C/G; S16963: Chr17_24484841 T/G; S16964: Chr17_24650127 T/C; S16965: Chr17_24792497 A/G; S16966: Chr17_24800545 A/G; S16967: Chr17_24919872 T/C; S16968: Chr17_24925330 G/A; S16969: Chr17_25000095 G/T; S16970: Chr17_25225009 T/C; S16971: Chr17_25394994 T/C; S16972: Chr17_25502136 A/G; S16973: Chr17_25529120 G/A; S16974: Chr17_25550281 T/A; S16975: Chr17_25655717 T/G; S16976: Chr17_25825669 T/C; S16977: Chr17_25900013 A/T; S16978: Chr17_25975659 T/C; S16979: Chr17_26200230 A/T; S16980: Chr17_26352190 G/A; S16981: Chr17_26550908 A/G; S16982: Chr17_26577261 G/T; S16983: Chr17_26600370 T/C; S16984: Chr17_26715017 A/C; S16985: Chr17_26725251 A/G; S16986: Chr17_26866872 G/A; S16987: Chr17_26882680 T/C; S16988: Chr17_26900412 A/G; S16989: Chr17_27075623 T/A; S16990: Chr17_27175231 A/G; S16991: Chr17_27200272 T/C; S16992: Chr17_27283444 A/G; S16993: Chr17_27305728 T/C; S16994: Chr17_27332726 C/T; S16995: Chr17_27350318 G/A; S16996: Chr17_27459343 T/C; S16997: Chr17_27475006 T/G; S16998: Chr17_27563433 A/C; S16999: Chr17_27590299 A/G; S17000: Chr17_27698970 G/A; S17001: Chr17_27706975 A/G; S17002: Chr17_27762140 C/T; S17003: Chr17_27919226 G/A; S17004: Chr17_27925053 T/A; S17005: Chr17_28200062 G/A; S17006: Chr17_28271572 T/C; S17007: Chr17_28287725 A/C; S17008: Chr17_28312120 C/T; S17009: Chr17_28329246 C/T; S17010: Chr17_28354844 A/G; S17011: Chr17_28520697 T/A; S17012: Chr17_28525194 T/C; S17013: Chr17_28750001 G/A; S17014: Chr17_28911449 C/T; S17015: Chr17_28985249 C/T; S17016: Chr17_29066346 C/A; S17017: Chr17_29134873 G/A; S17018: Chr17_29220858 A/G; S17019: Chr17_29235609 C/T; S17020: Chr17_29314202 G/A; S17021: Chr17_29346255 A/G; S17022: Chr17_29350026 C/A; S17023: Chr17_29933908 C/G; S17024: Chr17_29974939 A/G; S17025: Chr17_29975171 T/G; S17026: Chr17_30130327 A/G; S17027: Chr17_30172772 G/A; S17028: Chr17_30232201 G/A; S17029: Chr17_30300888 C/T; S17030: Chr17_30338149 C/A; S17031: Chr17_30350560 A/G; S17032: Chr17_30408030 C/T; S17033: Chr17_30490798 G/A; S17034: Chr17_30500027 T/A; S17035: Chr17_30670775 G/A; S17036: Chr17_30686217 G/A; S17037: Chr17_30724374 T/C; S17038: Chr17_30726236 T/A; S17039: Chr17_30751430 A/G; S17040: Chr17_30780112 T/C; S17041: Chr17_30802644 A/G; S17042: Chr17_30935577 G/A; S17043: Chr17_30951206 A/T; S17044: Chr17_30975200 C/T; S17045: Chr17_31103228 T/A; S17046: Chr17_31141442 T/C; S17047: Chr17_31200274 T/C; S17048: Chr17_31249456 A/T; S17049: Chr17_31297957 A/C; S17050: Chr17_31303135 A/G; S17051: Chr17_31346743 G/A; S17052: Chr17_31383072 A/C; S17053: Chr17_31405250 C/T; S17054: Chr17_31478065 A/C; S17055: Chr17_31503950 A/G; S17056: Chr17_31567167 G/T; S17057: Chr17_31577128 T/C; S17058: Chr17_31600002 G/T; S17059: Chr17_31675629 G/A; S17060: Chr17_31751563 T/C; S17061: Chr17_31949486 G/C; S17062: Chr17_31950643 C/T; S17063: Chr17_31985330 T/G; S17064: Chr17_32011956 A/G; S17065: Chr17_32025175 G/A; S17066: Chr17_32063621 C/G; S17067: Chr17_32075878 A/G; S17068: Chr17_32166476 T/A; S17069: Chr17_32190886 T/C; S17070: Chr17_32244471 C/T; S17071: Chr17_32343366 C/T; S17072: Chr17_32358699 C/T; S17073: Chr17_32381696 T/C; S17074: Chr17_32451087 C/T; S17075: Chr17_32522076 A/T; S17076: Chr17_32534815 T/C; S17077: Chr17_32606845 A/G; S17078: Chr17_32625085 T/C; S17079: Chr17_32869197 A/C; S17080: Chr17_32877464 C/T; S17081: Chr17_32911412 C/T; S17082: Chr17_32925258 T/C; S17083: Chr17_33005955 C/T; S17084: Chr17_33084420 C/G; S17085: Chr17_33100437 T/C; S17086: Chr17_33221731 C/A; S17087: Chr17_33225661 A/G; S17088: Chr17_33288990 A/G; S17089: Chr17_33323367 G/A; S17090: Chr17_33325930 T/C; S17091: Chr17_33371013 C/T; S17092: Chr17_33375064 A/T; S17093: Chr17_33471874 G/A; S17094: Chr17_33481320 T/C; S17095: Chr17_33530875 G/C; S17096: Chr17_33581107 A/T; S17097: Chr17_33612838 A/T; S17098: Chr17_33655511 T/G; S17099: Chr17_33737055 A/T; S17100: Chr17_33750065 C/T; S17101: Chr17_33851505 G/A; S17102: Chr17_33876076 C/T; S17103: Chr17_33920837 T/G; S17104: Chr17_33931087 G/T; S17105: Chr17_33973313 A/G; S17106: Chr17_33981446 G/C; S17107: Chr17_34020460 A/C; S17108: Chr17_34033452 G/A; S17109: Chr17_34050741 C/T; S17110: Chr17_34093995 C/G; S17111: Chr17_34108428 C/T; S17112: Chr17_34145499 C/G; S17113: Chr17_34201757 C/T; S17114: Chr17_34225185 T/C; S17115: Chr17_34285079 C/T; S17116: Chr17_34327220 A/G; S17117: Chr17_34366640 C/T; S17118: Chr17_34435276 G/A; S17119: Chr17_34471586 A/G; S17120: Chr17_34586801 A/G; S17121: Chr17_34600223 A/G; S17122: Chr17_34631297 T/C; S17123: Chr17_34665718 C/T; S17124: Chr17_34746818 C/A; S17125: Chr17_34757118 T/A; S17126: Chr17_34785227 C/T; S17127: Chr17_34813393 T/G; S17128: Chr17_34877574 G/T; S17129: Chr17_34900308 C/G; S17130: Chr17_34925387 T/C; S17131: Chr17_34959977 A/G; S17132: Chr17_34975104 G/A; S17133: Chr17_35064681 A/G; S17134: Chr17_35076282 C/T; S17135: Chr17_35207323 T/C; S17136: Chr17_35354440 T/G; S17137: Chr17_35375892 T/G; S17138: Chr17_35590641 C/T; S17139: Chr17_35600021 G/T; S17140: Chr17_35675200 G/A; S17141: Chr17_35768759 G/T; S17142: Chr17_35807752 C/T; S17143: Chr17_35825052 T/C; S17144:

Chr17_35867930 A/C; S17145: Chr17_35878508 T/C; S17146: Chr17_35900259 A/C; S17147: Chr17_35925122 T/C; S17148: Chr17_36078229 T/A; S17149: Chr17_36127107 G/A; S17150: Chr17_36164172 G/A; S17151: Chr17_36216748 A/G; S17152: Chr17_36297604 C/T; S17153: Chr17_36325572 A/G; S17154: Chr17_36354958 C/G; S17155: Chr17_36393214 T/A; S17156: Chr17_36422327 C/T; S17157: Chr17_36440107 A/G; S17158: Chr17_36465041 A/T; S17159: Chr17_36493357 G/T; S17160: Chr17_36505178 G/A; S17161: Chr17_36553958 A/G; S17162: Chr17_36601695 G/A; S17163: Chr17_36628893 C/T; S17164: Chr17_36652396 A/C; S17165: Chr17_36716731 C/T; S17166: Chr17_36740682 A/G; S17167: Chr17_36771812 A/T; S17168: Chr17_36783573 C/T; S17169: Chr17_36826958 A/C; S17170: Chr17_36880709 G/A; S17171: Chr17_36910170 A/T; S17172: Chr17_36976917 A/G; S17173: Chr17_37030631 G/A; S17174: Chr17_37083454 C/T; S17175: Chr17_37126338 T/C; S17176: Chr17_37181751 G/A; S17177: Chr17_37204819 G/A; S17178: Chr17_37248086 A/G; S17179: Chr17_37250895 G/A; S17180: Chr17_37300508 A/G; S17181: Chr17_37333508 G/A; S17182: Chr17_37367123 A/G; S17183: Chr17_37392776 T/C; S17184: Chr17_37400068 T/A; S17185: Chr17_37441590 G/A; S17186: Chr17_37481033 T/G; S17187: Chr17_37513852 G/A; S17188: Chr17_37541864 A/T; S17189: Chr17_37552520 A/C; S17190: Chr17_37578310 A/G; S17191: Chr17_37651410 A/G; S17192: Chr17_37684489 G/C; S17193: Chr17_37732657 G/A; S17194: Chr17_37755972 A/G; S17195: Chr17_37797897 G/C; S17196: Chr17_37801850 G/C; S17197: Chr17_37840622 G/A; S17198: Chr17_37853628 G/T; S17199: Chr17_37905877 C/T; S17200: Chr17_37956810 C/T; S17201: Chr17_38006581 A/G; S17202: Chr17_38074662 G/C; S17203: Chr17_38078798 T/G; S17204: Chr17_38130352 A/T; S17205: Chr17_38163113 G/A; S17206: Chr17_38176257 T/C; S17207: Chr17_38209056 T/A; S17208: Chr17_38276618 C/T; S17209: Chr17_38307270 A/G; S17210: Chr17_38333832 A/G; S17211: Chr17_38350306 T/G; S17212: Chr17_38383587 A/G; S17213: Chr17_38408300 G/A; S17214: Chr17_38426318 C/T; S17215: Chr17_38455100 A/T; S17216: Chr17_38477660 T/C; S17217: Chr17_38503311 C/A; S17218: Chr17_38525959 T/C; S17219: Chr17_38550082 T/C; S17220: Chr17_38602224 A/G; S17221: Chr17_38627978 C/G; S17222: Chr17_38655404 C/G; S17223: Chr17_38690973 C/T; S17224: Chr17_38700535 G/T; S17225: Chr17_38755483 A/C; S17226: Chr17_38807749 A/G; S17227: Chr17_38826185 A/G; S17228: Chr17_38970150 T/A; S17229: Chr17_39008718 C/T; S17230: Chr17_39048221 A/G; S17231: Chr17_39053360 A/C; S17232: Chr17_39075624 C/T; S17233: Chr17_39112839 A/G; S17234: Chr17_39140960 G/T; S17235: Chr17_39152440 A/C; S17236: Chr17_39177410 G/C; S17237: Chr17_39204303 T/A; S17238: Chr17_39257059 C/A; S17239: Chr17_39306002 G/C; S17240: Chr17_39326954 G/C; S17241: Chr17_39350335 T/G; S17242: Chr17_39389331 T/C; S17243: Chr17_39425435 C/T; S17244: Chr17_39450816 T/C; S17245: Chr17_39477960 G/T; S17246: Chr17_39501475 A/C; S17247: Chr17_39530836 A/G; S17248: Chr17_39551099 G/A; S17249: Chr17_39575104 T/C; S17250: Chr17_39604754 G/A; S17251: Chr17_39632330 C/T; S17252: Chr17_39686805 A/C; S17253: Chr17_39714045 G/A; S17254: Chr17_39725113 A/G; S17255: Chr17_39751334 G/T; S17256: Chr17_39816465 A/T; S17257: Chr17_39846050 T/A; S17258: Chr17_39855193 T/A; S17259: Chr17_39883098 T/C; S17260: Chr17_39904407 G/C; S17261: Chr17_39936548 T/C; S17262: Chr17_39950851 G/A; S17263: Chr17_39987601 A/C; S17264: Chr17_40011274 C/T; S17265: Chr17_40026424 C/A; S17266: Chr17_40053140 T/C; S17267: Chr17_40078123 G/A; S17268: Chr17_40101009 G/T; S17269: Chr17_40126120 G/A; S17270: Chr17_40164023 C/T; S17271: Chr17_40190680 C/T; S17272: Chr17_40210707 C/T; S17273: Chr17_40272459 A/T; S17274: Chr17_40275100 A/C; S17275: Chr17_40303159 A/G; S17276: Chr17_40333307 C/T; S17277: Chr17_40351842 G/T; S17278: Chr17_40386409 G/A; S17279: Chr17_40410230 C/T; S17280: Chr17_40431549 T/C; S17281: Chr17_40455458 C/T; S17282: Chr17_40479516 G/T; S17283: Chr17_40511428 C/T; S17284: Chr17_40528253 A/G; S17285: Chr17_40551942 A/G; S17286: Chr17_40578159 C/T; S17287: Chr17_40606398 G/T; S17288: Chr17_40626582 T/C; S17289: Chr17_40650839 A/G; S17290: Chr17_40676829 C/G; S17291: Chr17_40703474 A/G; S17292: Chr17_40740596 G/A; S17293: Chr17_40752439 C/T; S17294: Chr17_40775426 C/T; S17295: Chr17_40814153 C/T; S17296: Chr17_40828186 T/C; S17297: Chr17_40862217 C/G; S17298: Chr17_40878700 A/T; S17299: Chr17_40924268 C/T; S17300: Chr17_40929365 G/C; S17301: Chr17_40953864 T/A; S17302: Chr17_40983367 G/T; S17303: Chr17_41004326 T/C; S17304: Chr17_41025913 C/A; S17305: Chr17_41078465 T/C; S17306: Chr17_41108480 C/T; S17307: Chr17_41197113 T/C; S17308: Chr17_41200400 A/C; S17309: Chr17_41240625 A/G; S17310: Chr17_41275912 C/T; S17311: Chr17_41302725 T/C; S17312: Chr17_41368944 C/T; S17313: Chr17_41393066 C/T; S17314: Chr17_41407995 A/C; S17315: Chr17_41440373 T/C; S17316: Chr17_41457969 A/G; S17317: Chr17_41490859 G/A; S17318: Chr17_41570317 G/A; S17319: Chr17_41597488 C/T; S17320: Chr17_41600558 G/A; S17321: Chr18_00003911 T/C; S17322: Chr18_00034098 T/G; S17323: Chr18_00060921 T/A; S17324: Chr18_00084027 T/A; S17325: Chr18_00104576 C/T; S17326: Chr18_00135388 T/C; S17327: Chr18_00152732 C/T; S17328: Chr18_00177107 G/T; S17329: Chr18_00200311 T/A; S17330: Chr18_00228565 A/G; S17331: Chr18_00257570 G/A; S17332: Chr18_00278074 T/C; S17333: Chr18_00301694 T/G; S17334: Chr18_00327659 T/A; S17335: Chr18_00350689 A/G; S17336: Chr18_00380928 G/A; S17337: Chr18_00441782 C/T; S17338: Chr18_00453852 T/C; S17339: Chr18_00487941 C/T; S17340: Chr18_00506721 C/G; S17341: Chr18_00526373 C/T; S17342: Chr18_00565172 T/C; S17343: Chr18_00576814 C/G; S17344: Chr18_00603706 A/G; S17345:

Chr18_00630834 A/G; S17346: Chr18_00650460 T/G; S17347: Chr18_00681708 C/A; S17348: Chr18_00719418 G/T; S17349: Chr18_00731866 G/T; S17350: Chr18_00753527 T/C; S17351: Chr18_00777674 A/T; S17352: Chr18_00801932 T/C; S17353: Chr18_00825123 G/A; S17354: Chr18_00858994 C/T; S17355: Chr18_00880682 C/A; S17356: Chr18_00902916 T/G; S17357: Chr18_00925834 C/G; S17358: Chr18_00952111 C/T; S17359: Chr18_00977566 A/G; S17360: Chr18_01013949 A/G; S17361: Chr18_01026084 G/A; S17362: Chr18_01052588 T/C; S17363: Chr18_01075238 C/A; S17364: Chr18_01100586 T/A; S17365: Chr18_01128490 G/A; S17366: Chr18_01152844 C/T; S17367: Chr18_01182971 A/G; S17368: Chr18_01201931 C/T; S17369: Chr18_01226284 T/C; S17370: Chr18_01258159 C/T; S17371: Chr18_01285987 C/T; S17372: Chr18_01314053 A/G; S17373: Chr18_01331239 T/A; S17374: Chr18_01350832 T/C; S17375: Chr18_01375974 A/C; S17376: Chr18_01404786 G/T; S17377: Chr18_01432454 C/T; S17378: Chr18_01450525 T/A; S17379: Chr18_01476101 A/G; S17380: Chr18_01507352 C/T; S17381: Chr18_01537515 A/G; S17382: Chr18_01553751 C/T; S17383: Chr18_01578528 T/C; S17384: Chr18_01605824 C/A; S17385: Chr18_01648996 A/C; S17386: Chr18_01673531 T/G; S17387: Chr18_01681959 A/G; S17388: Chr18_01703661 A/G; S17389: Chr18_01727468 A/T; S17390: Chr18_01769569 A/G; S17391: Chr18_01780172 T/C; S17392: Chr18_01802055 C/T; S17393: Chr18_01831724 C/T; S17394: Chr18_01860886 A/G; S17395: Chr18_01875144 T/C; S17396: Chr18_01911617 C/A; S17397: Chr18_01928710 C/T; S17398: Chr18_01953836 T/C; S17399: Chr18_01982703 A/T; S17400: Chr18_02013908 T/G; S17401: Chr18_02025537 A/G; S17402: Chr18_02050240 C/G; S17403: Chr18_02076713 G/A; S17404: Chr18_02112595 C/T; S17405: Chr18_02125759 C/T; S17406: Chr18_02156834 C/T; S17407: Chr18_02180465 T/G; S17408: Chr18_02207634 T/G; S17409: Chr18_02232970 T/G; S17410: Chr18_02270439 T/C; S17411: Chr18_02306213 C/T; S17412: Chr18_02331177 G/A; S17413: Chr18_02355846 C/A; S17414: Chr18_02377373 G/C; S17415: Chr18_02408380 C/A; S17416: Chr18_02439263 A/T; S17417: Chr18_02459613 C/T; S17418: Chr18_02482239 A/G; S17419: Chr18_02500789 G/A; S17420: Chr18_02527916 A/G; S17421: Chr18_02576350 A/G; S17422: Chr18_02601324 G/A; S17423: Chr18_02625222 A/G; S17424: Chr18_02650245 C/T; S17425: Chr18_02692919 A/G; S17426: Chr18_02702240 G/A; S17427: Chr18_02728682 T/C; S17428: Chr18_02751300 T/G; S17429: Chr18_02775422 G/A; S17430: Chr18_02813504 C/A; S17431: Chr18_02840755 G/T; S17432: Chr18_02855518 T/A; S17433: Chr18_02878350 A/G; S17434: Chr18_02904831 G/A; S17435: Chr18_02925011 C/T; S17436: Chr18_03000999 G/T; S17437: Chr18_03049395 T/C; S17438: Chr18_03050361 G/A; S17439: Chr18_03076629 C/G; S17440: Chr18_03146237 C/T; S17441: Chr18_03153368 G/A; S17442: Chr18_03183609 C/T; S17443: Chr18_03209193 C/T; S17444: Chr18_03237889 A/G; S17445: Chr18_03280055 G/C; S17446: Chr18_03319598 A/G; S17447: Chr18_03378184 A/T; S17448: Chr18_03446193 A/T; S17449: Chr18_03472444 A/G; S17450: Chr18_03493254 T/C; S17451: Chr18_03509756 A/C; S17452: Chr18_03533103 C/T; S17453: Chr18_03558252 G/A; S17454: Chr18_03589034 G/A; S17455: Chr18_03600811 C/T; S17456: Chr18_03631683 G/A; S17457: Chr18_03668279 T/C; S17458: Chr18_03688356 T/C; S17459: Chr18_03706100 T/A; S17460: Chr18_03735102 C/A; S17461: Chr18_03768174 C/G; S17462: Chr18_03780542 A/T; S17463: Chr18_03809951 G/T; S17464: Chr18_03836352 G/C; S17465: Chr18_03850436 C/T; S17466: Chr18_03881663 A/C; S17467: Chr18_03900882 T/C; S17468: Chr18_03931555 A/T; S17469: Chr18_03950694 T/C; S17470: Chr18_03978970 A/G; S17471: Chr18_04004360 G/A; S17472: Chr18_04028343 C/T; S17473: Chr18_04062079 A/G; S17474: Chr18_04081785 C/T; S17475: Chr18_04118891 G/C; S17476: Chr18_04132219 A/T; S17477: Chr18_04162535 C/T; S17478: Chr18_04228095 A/G; S17479: Chr18_04259505 T/C; S17480: Chr18_04287411 T/C; S17481: Chr18_04310120 T/A; S17482: Chr18_04326472 C/G; S17483: Chr18_04354694 A/C; S17484: Chr18_04432205 G/A; S17485: Chr18_04472002 A/G; S17486: Chr18_04476345 A/G; S17487: Chr18_04504528 A/G; S17488: Chr18_04528225 T/C; S17489: Chr18_04574001 A/G; S17490: Chr18_04588056 T/A; S17491: Chr18_04601454 T/G; S17492: Chr18_04637381 G/A; S17493: Chr18_04651339 C/A; S17494: Chr18_04710908 C/T; S17495: Chr18_04751253 T/C; S17496: Chr18_04775910 C/T; S17497: Chr18_04801125 T/C; S17498: Chr18_04828051 G/A; S17499: Chr18_04854001 C/T; S17500: Chr18_04904234 C/T; S17501: Chr18_04925009 G/A; S17502: Chr18_04952948 T/C; S17503: Chr18_04989633 C/G; S17504: Chr18_05019585 T/G; S17505: Chr18_05031464 T/G; S17506: Chr18_05050402 G/A; S17507: Chr18_05081075 C/A; S17508: Chr18_05114224 A/G; S17509: Chr18_05125126 T/A; S17510: Chr18_05165899 A/G; S17511: Chr18_05188702 A/T; S17512: Chr18_05201035 C/T; S17513: Chr18_05225669 A/G; S17514: Chr18_05267339 G/A; S17515: Chr18_05288971 C/T; S17516: Chr18_05350257 C/T; S17517: Chr18_05427788 A/T; S17518: Chr18_05472286 C/A; S17519: Chr18_05541268 T/C; S17520: Chr18_05550072 C/T; S17521: Chr18_05576077 C/T; S17522: Chr18_05601082 A/G; S17523: Chr18_05683089 G/A; S17524: Chr18_05724930 G/A; S17525: Chr18_05725334 G/C; S17526: Chr18_05752905 C/T; S17527: Chr18_05779492 C/G; S17528: Chr18_05800188 A/G; S17529: Chr18_05829757 G/C; S17530: Chr18_05850655 T/C; S17531: Chr18_05884607 T/G; S17532: Chr18_05923015 T/C; S17533: Chr18_05928226 A/G; S17534: Chr18_05957508 T/C; S17535: Chr18_06027212 C/T; S17536: Chr18_06068033 T/C; S17537: Chr18_06077090 C/T; S17538: Chr18_06122987 G/A; S17539: Chr18_06125009 C/T; S17540: Chr18_06165170 C/T; S17541: Chr18_06198192 T/A; S17542: Chr18_06201727 G/A; S17543: Chr18_06226137 T/C; S17544: Chr18_06253966 A/C; S17545: Chr18_06276129 T/C; S17546:

Chr18_06362971 A/C; S17547: Chr18_06417247 T/C; S17548: Chr18_06425019 A/G; S17549: Chr18_06504913 A/T; S17550: Chr18_06527284 T/G; S17551: Chr18_06560044 C/G; S17552: Chr18_06575191 C/G; S17553: Chr18_06602221 A/G; S17554: Chr18_06630041 G/A; S17555: Chr18_06668122 T/C; S17556: Chr18_06684325 A/T; S17557: Chr18_06712702 T/G; S17558: Chr18_06725512 T/C; S17559: Chr18_06768169 T/C; S17560: Chr18_06786167 T/C; S17561: Chr18_06801571 G/A; S17562: Chr18_06825701 A/T; S17563: Chr18_06858368 A/G; S17564: Chr18_06876165 A/T; S17565: Chr18_06901761 A/G; S17566: Chr18_06975143 G/A; S17567: Chr18_07012979 T/C; S17568: Chr18_07030568 C/T; S17569: Chr18_07050206 T/C; S17570: Chr18_07080864 A/G; S17571: Chr18_07106970 C/T; S17572: Chr18_07125822 A/G; S17573: Chr18_07150155 A/G; S17574: Chr18_07181049 T/A; S17575: Chr18_07203689 G/A; S17576: Chr18_07229695 T/C; S17577: Chr18_07262003 T/C; S17578: Chr18_07275017 A/G; S17579: Chr18_07308163 A/C; S17580: Chr18_07325063 T/C; S17581: Chr18_07356843 C/T; S17582: Chr18_07375327 C/T; S17583: Chr18_07412590 G/A; S17584: Chr18_07442115 T/A; S17585: Chr18_07457331 C/T; S17586: Chr18_07484055 G/A; S17587: Chr18_07505756 A/G; S17588: Chr18_07537482 T/C; S17589: Chr18_07554233 C/G; S17590: Chr18_07595645 A/C; S17591: Chr18_07600207 C/T; S17592: Chr18_07626703 A/G; S17593: Chr18_07653552 T/C; S17594: Chr18_07684488 G/A; S17595: Chr18_07700038 A/C; S17596: Chr18_07728407 C/T; S17597: Chr18_07758619 A/G; S17598: Chr18_07803634 A/G; S17599: Chr18_07828843 T/C; S17600: Chr18_07856107 A/G; S17601: Chr18_07894691 A/G; S17602: Chr18_07919184 T/A; S17603: Chr18_07932681 A/G; S17604: Chr18_07959037 A/G; S17605: Chr18_08019056 A/T; S17606: Chr18_08074754 G/A; S17607: Chr18_08118720 G/A; S17608: Chr18_08190060 G/T; S17609: Chr18_08228210 T/C; S17610: Chr18_08262967 G/A; S17611: Chr18_08280287 C/T; S17612: Chr18_08352588 C/T; S17613: Chr18_08377201 A/C; S17614: Chr18_08400874 A/C; S17615: Chr18_08431260 T/G; S17616: Chr18_08471290 C/A; S17617: Chr18_08475560 G/T; S17618: Chr18_08500935 A/T; S17619: Chr18_08564984 C/G; S17620: Chr18_08636391 T/A; S17621: Chr18_08671202 A/G; S17622: Chr18_08694084 C/T; S17623: Chr18_08702855 A/G; S17624: Chr18_08814348 G/T; S17625: Chr18_08846760 G/A; S17626: Chr18_08856074 G/T; S17627: Chr18_08879736 A/G; S17628: Chr18_08923787 A/G; S17629: Chr18_08934188 A/G; S17630: Chr18_08956602 A/C; S17631: Chr18_08996493 G/A; S17632: Chr18_09000143 G/A; S17633: Chr18_09044950 G/A; S17634: Chr18_09050617 G/A; S17635: Chr18_09082537 T/C; S17636: Chr18_09110265 C/T; S17637: Chr18_09135924 G/T; S17638: Chr18_09165638 C/A; S17639: Chr18_09184391 T/G; S17640: Chr18_09236884 G/A; S17641: Chr18_09265457 G/A; S17642: Chr18_09279762 G/A; S17643: Chr18_09300229 G/A; S17644: Chr18_09344928 A/T; S17645: Chr18_09362578 T/C; S17646: Chr18_09412592 T/A; S17647: Chr18_09426406 C/T; S17648: Chr18_09493043 G/A; S17649: Chr18_09501393 G/C; S17650: Chr18_09538274 A/G; S17651: Chr18_09585995 G/T; S17652: Chr18_09618316 A/T; S17653: Chr18_09625481 A/T; S17654: Chr18_09655462 C/G; S17655: Chr18_09704832 G/T; S17656: Chr18_09735339 T/C; S17657: Chr18_09752095 C/T; S17658: Chr18_09775162 G/A; S17659: Chr18_09853550 G/T; S17660: Chr18_09878834 A/G; S17661: Chr18_09929801 A/T; S17662: Chr18_09968430 T/G; S17663: Chr18_09975008 A/G; S17664: Chr18_10008076 C/T; S17665: Chr18_10138786 G/A; S17666: Chr18_10177446 T/C; S17667: Chr18_10205593 C/T; S17668: Chr18_10278991 T/C; S17669: Chr18_10303447 T/G; S17670: Chr18_10327349 C/T; S17671: Chr18_10377564 G/A; S17672: Chr18_10451603 C/A; S17673: Chr18_10513513 A/T; S17674: Chr18_10532022 A/G; S17675: Chr18_10555152 G/A; S17676: Chr18_10629081 A/G; S17677: Chr18_10650158 A/T; S17678: Chr18_10679273 G/A; S17679: Chr18_10746722 A/G; S17680: Chr18_10768439 A/G; S17681: Chr18_10800425 C/G; S17682: Chr18_10842449 T/C; S17683: Chr18_10855900 A/G; S17684: Chr18_10879063 A/T; S17685: Chr18_10906648 A/T; S17686: Chr18_10933168 C/G; S17687: Chr18_10957136 T/G; S17688: Chr18_11027811 C/A; S17689: Chr18_11053669 G/A; S17690: Chr18_11116879 G/A; S17691: Chr18_11125092 A/T; S17692: Chr18_11234833 T/A; S17693: Chr18_11264531 A/G; S17694: Chr18_11309483 T/C; S17695: Chr18_11341701 A/G; S17696: Chr18_11350447 T/C; S17697: Chr18_11413829 A/G; S17698: Chr18_11527608 C/A; S17699: Chr18_11598078 A/G; S17700: Chr18_11657238 C/T; S17701: Chr18_11681480 C/G; S17702: Chr18_11702852 A/G; S17703: Chr18_11731335 A/G; S17704: Chr18_11773998 G/A; S17705: Chr18_11817988 T/C; S17706: Chr18_11916660 T/G; S17707: Chr18_11928667 C/A; S17708: Chr18_11950190 A/C; S17709: Chr18_12024166 A/T; S17710: Chr18_12047334 A/C; S17711: Chr18_12060496 C/T; S17712: Chr18_12094805 A/C; S17713: Chr18_12117325 C/T; S17714: Chr18_12125053 C/T; S17715: Chr18_12208313 G/T; S17716: Chr18_12225164 T/A; S17717: Chr18_12256721 C/T; S17718: Chr18_12309493 A/G; S17719: Chr18_12349933 C/G; S17720: Chr18_12350322 C/T; S17721: Chr18_12375610 C/T; S17722: Chr18_12410412 C/T; S17723: Chr18_12426991 A/C; S17724: Chr18_12478334 C/T; S17725: Chr18_12542389 A/T; S17726: Chr18_12582546 A/G; S17727: Chr18_12600009 A/C; S17728: Chr18_12625962 G/T; S17729: Chr18_12650040 G/T; S17730: Chr18_12689557 G/T; S17731: Chr18_12757784 C/G; S17732: Chr18_12780719 T/C; S17733: Chr18_12815423 A/C; S17734: Chr18_12825207 A/G; S17735: Chr18_12850023 T/C; S17736: Chr18_12928329 T/C; S17737: Chr18_13018653 C/T; S17738: Chr18_13060136 T/C; S17739: Chr18_13132779 A/G; S17740: Chr18_13179342 C/A; S17741: Chr18_13234615 T/A; S17742: Chr18_13272828 T/G; S17743: Chr18_13279179 C/T; S17744: Chr18_13309556 G/A; S17745: Chr18_13335134 A/G; S17746: Chr18_13399170 G/A; S17747:

Chr18_13425047 A/G; S17748: Chr18_13455312 A/G; S17749: Chr18_13527312 T/A; S17750: Chr18_13617606 T/A; S17751: Chr18_13671983 C/T; S17752: Chr18_13683130 C/T; S17753: Chr18_13758668 T/C; S17754: Chr18_13794380 G/A; S17755: Chr18_13805328 C/A; S17756: Chr18_13972058 C/T; S17757: Chr18_13978987 T/C; S17758: Chr18_14000159 T/C; S17759: Chr18_14040033 A/G; S17760: Chr18_14088856 C/T; S17761: Chr18_14111711 A/T; S17762: Chr18_14177518 G/A; S17763: Chr18_14227170 T/G; S17764: Chr18_14250911 T/C; S17765: Chr18_14275149 C/A; S17766: Chr18_14334860 A/G; S17767: Chr18_14361695 G/T; S17768: Chr18_14436745 G/A; S17769: Chr18_14472613 A/G; S17770: Chr18_14492505 A/G; S17771: Chr18_14525397 G/C; S17772: Chr18_14563118 A/G; S17773: Chr18_14575467 C/T; S17774: Chr18_14650266 T/A; S17775: Chr18_14675385 A/G; S17776: Chr18_14701235 G/C; S17777: Chr18_14751500 G/A; S17778: Chr18_14783663 G/A; S17779: Chr18_14822362 G/A; S17780: Chr18_14866471 T/G; S17781: Chr18_14889727 A/G; S17782: Chr18_14911568 T/G; S17783: Chr18_14929496 G/A; S17784: Chr18_15004921 G/A; S17785: Chr18_15086477 T/A; S17786: Chr18_15148911 G/A; S17787: Chr18_15181783 A/T; S17788: Chr18_15230069 C/T; S17789: Chr18_15277901 T/A; S17790: Chr18_15346633 C/A; S17791: Chr18_15404893 A/C; S17792: Chr18_15465731 T/C; S17793: Chr18_15475290 C/T; S17794: Chr18_15614133 T/C; S17795: Chr18_15640129 A/G; S17796: Chr18_15650035 C/T; S17797: Chr18_15753276 T/C; S17798: Chr18_15832905 G/A; S17799: Chr18_15867503 C/A; S17800: Chr18_15880883 A/T; S17801: Chr18_15900040 C/T; S17802: Chr18_16018506 A/G; S17803: Chr18_16025688 G/A; S17804: Chr18_16111507 A/G; S17805: Chr18_16188206 C/G; S17806: Chr18_16216755 A/G; S17807: Chr18_16232076 T/A; S17808: Chr18_16264417 T/A; S17809: Chr18_16338723 A/C; S17810: Chr18_16370557 A/G; S17811: Chr18_16379622 A/C; S17812: Chr18_16408957 T/A; S17813: Chr18_16472970 C/A; S17814: Chr18_16528867 T/G; S17815: Chr18_16675458 G/A; S17816: Chr18_16724202 G/A; S17817: Chr18_16725547 A/G; S17818: Chr18_16779662 A/C; S17819: Chr18_16833237 C/T; S17820: Chr18_16902633 A/T; S17821: Chr18_16926026 C/T; S17822: Chr18_17049337 A/C; S17823: Chr18_17093391 G/A; S17824: Chr18_17105268 G/A; S17825: Chr18_17153191 G/C; S17826: Chr18_17211316 G/C; S17827: Chr18_17235820 C/T; S17828: Chr18_17286945 C/T; S17829: Chr18_17300053 A/G; S17830: Chr18_17338097 A/T; S17831: Chr18_17357715 T/A; S17832: Chr18_17415667 G/A; S17833: Chr18_17435648 A/C; S17834: Chr18_17462853 G/A; S17835: Chr18_17533864 A/G; S17836: Chr18_17554506 T/G; S17837: Chr18_17575013 C/T; S17838: Chr18_17682513 C/A; S17839: Chr18_17700022 A/G; S17840: Chr18_17950278 C/T; S17841: Chr18_18035459 C/T; S17842: Chr18_18118497 G/A; S17843: Chr18_18125133 T/G; S17844: Chr18_18152113 T/C; S17845: Chr18_18197629 G/A; S17846: Chr18_18202806 A/G; S17847: Chr18_18291922 A/C; S17848: Chr18_18302983 A/G; S17849: Chr18_18325492 T/C; S17850: Chr18_18355102 T/C; S17851: Chr18_18406598 A/G; S17852: Chr18_18433396 T/C; S17853: Chr18_18456076 T/A; S17854: Chr18_18485519 T/C; S17855: Chr18_18527063 A/G; S17856: Chr18_18612505 C/A; S17857: Chr18_18670005 A/G; S17858: Chr18_18684582 A/T; S17859: Chr18_18775116 G/A; S17860: Chr18_18850036 G/A; S17861: Chr18_18929473 A/G; S17862: Chr18_19007812 T/C; S17863: Chr18_19074352 G/C; S17864: Chr18_19075123 G/A; S17865: Chr18_19109576 C/T; S17866: Chr18_19167866 G/C; S17867: Chr18_19207557 T/C; S17868: Chr18_19226081 T/C; S17869: Chr18_19254719 C/T; S17870: Chr18_19317282 G/A; S17871: Chr18_19347704 A/G; S17872: Chr18_19352347 C/T; S17873: Chr18_19421774 G/A; S17874: Chr18_19425026 A/C; S17875: Chr18_19607584 G/C; S17876: Chr18_19644341 T/C; S17877: Chr18_19671508 G/C; S17878: Chr18_19691931 A/G; S17879: Chr18_19700301 C/T; S17880: Chr18_19816659 C/G; S17881: Chr18_19844473 C/T; S17882: Chr18_19850081 C/T; S17883: Chr18_19906787 A/T; S17884: Chr18_19991723 T/A; S17885: Chr18_20000876 T/A; S17886: Chr18_20070998 T/A; S17887: Chr18_20093539 A/G; S17888: Chr18_20100282 T/C; S17889: Chr18_20159099 T/G; S17890: Chr18_20193721 T/G; S17891: Chr18_20201610 A/T; S17892: Chr18_20245220 C/T; S17893: Chr18_20278704 G/A; S17894: Chr18_20301639 C/T; S17895: Chr18_20325512 C/T; S17896: Chr18_20416992 G/A; S17897: Chr18_20473835 G/T; S17898: Chr18_20475020 G/A; S17899: Chr18_20550317 T/A; S17900: Chr18_20602366 G/A; S17901: Chr18_20629597 T/C; S17902: Chr18_20776881 A/T; S17903: Chr18_20819303 A/G; S17904: Chr18_20854783 C/T; S17905: Chr18_20930317 C/A; S17906: Chr18_20966040 C/A; S17907: Chr18_20977694 G/T; S17908: Chr18_21100852 A/G; S17909: Chr18_21171968 A/G; S17910: Chr18_21188176 C/A; S17911: Chr18_21200375 C/A; S17912: Chr18_21225369 C/T; S17913: Chr18_21314859 G/T; S17914: Chr18_21361476 T/C; S17915: Chr18_21375016 G/T; S17916: Chr18_21509590 G/A; S17917: Chr18_21750039 T/A; S17918: Chr18_21825076 G/A; S17919: Chr18_21901799 G/A; S17920: Chr18_22030315 T/A; S17921: Chr18_22055775 G/A; S17922: Chr18_22213590 C/T; S17923: Chr18_22240491 A/G; S17924: Chr18_22250226 G/A; S17925: Chr18_22275381 T/C; S17926: Chr18_22375351 G/C; S17927: Chr18_22406861 T/C; S17928: Chr18_22520117 T/C; S17929: Chr18_22525078 C/T; S17930: Chr18_22635990 T/A; S17931: Chr18_22696079 G/A; S17932: Chr18_22700155 A/C; S17933: Chr18_22832243 A/G; S17934: Chr18_22900702 A/G; S17935: Chr18_22957710 A/T; S17936: Chr18_23063313 C/T; S17937: Chr18_23078023 A/T; S17938: Chr18_23164314 C/G; S17939: Chr18_23302656 A/T; S17940: Chr18_23360278 A/G; S17941: Chr18_23404035 G/A; S17942: Chr18_23512207 A/C; S17943: Chr18_23552973 T/C; S17944: Chr18_23594493 G/A; S17945: Chr18_23655474 C/T; S17946: Chr18_23755983 C/T; S17947: Chr18_23900198 C/T; S17948:

Chr18_23997068 C/A; S17949: Chr18_24054917 C/G; S17950: Chr18_24092899 C/T; S17951: Chr18_24150129 G/A; S17952: Chr18_24255171 C/G; S17953: Chr18_24296585 C/A; S17954: Chr18_24300032 A/T; S17955: Chr18_24414217 T/G; S17956: Chr18_24468456 C/T; S17957: Chr18_24512751 C/G; S17958: Chr18_24673711 T/C; S17959: Chr18_24745654 A/G; S17960: Chr18_24789528 T/C; S17961: Chr18_24804301 T/C; S17962: Chr18_24893335 A/G; S17963: Chr18_24900874 T/C; S17964: Chr18_24925052 C/G; S17965: Chr18_25025959 G/T; S17966: Chr18_25141343 A/G; S17967: Chr18_25151072 T/A; S17968: Chr18_25239498 G/A; S17969: Chr18_25256826 A/G; S17970: Chr18_25316993 A/G; S17971: Chr18_25389337 G/A; S17972: Chr18_25552568 C/T; S17973: Chr18_25587353 A/C; S17974: Chr18_25675350 A/G; S17975: Chr18_25762957 T/C; S17976: Chr18_25836768 A/G; S17977: Chr18_25913343 C/T; S17978: Chr18_25925092 C/G; S17979: Chr18_26075006 G/T; S17980: Chr18_26358567 G/A; S17981: Chr18_26392508 G/T; S17982: Chr18_26403797 C/T; S17983: Chr18_26518995 T/A; S17984: Chr18_26525089 A/T; S17985: Chr18_26729139 A/C; S17986: Chr18_26864788 T/C; S17987: Chr18_26907144 T/C; S17988: Chr18_26925062 G/A; S17989: Chr18_27105469 T/C; S17990: Chr18_27125023 G/A; S17991: Chr18_27238770 T/A; S17992: Chr18_27250148 A/G; S17993: Chr18_27508243 C/A; S17994: Chr18_27618989 G/C; S17995: Chr18_27625001 G/T; S17996: Chr18_27723286 C/T; S17997: Chr18_27784135 T/C; S17998: Chr18_27800125 G/A; S17999: Chr18_27875076 G/A; S18000: Chr18_28047850 G/A; S18001: Chr18_28050902 A/G; S18002: Chr18_28188676 G/A; S18003: Chr18_28200001 C/T; S18004: Chr18_28281638 T/C; S18005: Chr18_28308965 G/A; S18006: Chr18_28397342 C/T; S18007: Chr18_28411008 G/T; S18008: Chr18_28733593 A/G; S18009: Chr18_28762718 T/C; S18010: Chr18_28898610 T/G; S18011: Chr18_28972908 G/A; S18012: Chr18_28975004 C/T; S18013: Chr18_29125992 G/T; S18014: Chr18_29275253 C/T; S18015: Chr18_29375017 G/A; S18016: Chr18_29400421 A/G; S18017: Chr18_29652855 C/T; S18018: Chr18_29750317 C/T; S18019: Chr18_30105901 A/C; S18020: Chr18_30125379 G/C; S18021: Chr18_30238095 T/G; S18022: Chr18_30400017 T/C; S18023: Chr18_30509636 C/G; S18024: Chr18_30561170 T/A; S18025: Chr18_30619674 G/A; S18026: Chr18_30670616 T/G; S18027: Chr18_31087642 C/T; S18028: Chr18_31102882 C/G; S18029: Chr18_31392254 G/T; S18030: Chr18_31400324 C/A; S18031: Chr18_31580375 C/G; S18032: Chr18_31839561 C/G; S18033: Chr18_31904166 G/A; S18034: Chr18_32203382 G/A; S18035: Chr18_32232259 T/A; S18036: Chr18_32300159 G/C; S18037: Chr18_32554428 C/T; S18038: Chr18_33165230 A/C; S18039: Chr18_33175221 C/T; S18040: Chr18_33827464 C/A; S18041: Chr18_33995748 A/G; S18042: Chr18_34000969 C/G; S18043: Chr18_34025102 C/T; S18044: Chr18_34160009 T/C; S18045: Chr18_34175125 G/C; S18046: Chr18_34260043 G/A; S18047: Chr18_34512819 A/G; S18048: Chr18_34525316 C/T; S18049: Chr18_34703039 A/G; S18050: Chr18_34725738 G/T; S18051: Chr18_34848982 C/G; S18052: Chr18_34852591 T/C; S18053: Chr18_34925110 G/A; S18054: Chr18_35073006 A/G; S18055: Chr18_35099637 G/T; S18056: Chr18_35125335 C/T; S18057: Chr18_35157565 G/A; S18058: Chr18_35219783 T/C; S18059: Chr18_35236266 T/C; S18060: Chr18_35261315 A/T; S18061: Chr18_35314258 G/A; S18062: Chr18_35328890 T/G; S18063: Chr18_35350118 C/T; S18064: Chr18_35426853 C/A; S18065: Chr18_35470656 G/C; S18066: Chr18_35475211 G/T; S18067: Chr18_35962135 A/G; S18068: Chr18_35975719 G/A; S18069: Chr18_36110071 T/G; S18070: Chr18_36170512 G/A; S18071: Chr18_36179707 G/C; S18072: Chr18_36216522 C/G; S18073: Chr18_36225149 G/A; S18074: Chr18_36525306 T/C; S18075: Chr18_36675060 G/A; S18076: Chr18_36819463 G/A; S18077: Chr18_37100782 G/A; S18078: Chr18_37282110 A/G; S18079: Chr18_37409468 G/T; S18080: Chr18_37502538 T/A; S18081: Chr18_37577697 A/G; S18082: Chr18_38025163 T/C; S18083: Chr18_38116604 A/T; S18084: Chr18_38188053 G/A; S18085: Chr18_38208532 C/A; S18086: Chr18_38225034 C/T; S18087: Chr18_38315146 A/G; S18088: Chr18_38325290 G/A; S18089: Chr18_38400062 T/C; S18090: Chr18_38476127 A/G; S18091: Chr18_38668850 G/C; S18092: Chr18_38675560 T/C; S18093: Chr18_38760077 A/G; S18094: Chr18_38810581 C/T; S18095: Chr18_38833612 T/C; S18096: Chr18_38859956 G/C; S18097: Chr18_38962455 T/C; S18098: Chr18_38983972 T/C; S18099: Chr18_39083587 T/C; S18100: Chr18_39100713 A/G; S18101: Chr18_39177571 C/A; S18102: Chr18_39246807 T/C; S18103: Chr18_39303770 T/C; S18104: Chr18_39463187 T/C; S18105: Chr18_39530650 C/G; S18106: Chr18_39643994 A/G; S18107: Chr18_39651448 T/C; S18108: Chr18_39735088 A/T; S18109: Chr18_39750520 G/A; S18110: Chr18_39870504 T/C; S18111: Chr18_39880046 A/G; S18112: Chr18_40017557 A/G; S18113: Chr18_40033303 A/G; S18114: Chr18_40098253 T/C; S18115: Chr18_40100480 A/T; S18116: Chr18_40217721 G/A; S18117: Chr18_40280114 A/G; S18118: Chr18_40371469 G/A; S18119: Chr18_40397421 A/T; S18120: Chr18_40400304 A/G; S18121: Chr18_40492993 T/A; S18122: Chr18_40500434 G/A; S18123: Chr18_40655350 C/A; S18124: Chr18_40725714 T/C; S18125: Chr18_40941045 A/G; S18126: Chr18_41019534 C/T; S18127: Chr18_41025035 T/C; S18128: Chr18_41100662 A/G; S18129: Chr18_41189419 A/G; S18130: Chr18_41202997 C/A; S18131: Chr18_41245134 C/G; S18132: Chr18_41298384 A/G; S18133: Chr18_41300300 A/G; S18134: Chr18_41332173 C/T; S18135: Chr18_41377036 T/A; S18136: Chr18_41416665 C/T; S18137: Chr18_41454669 A/C; S18138: Chr18_41481473 T/C; S18139: Chr18_41506471 A/G; S18140: Chr18_41580392 A/G; S18141: Chr18_41652260 C/T; S18142: Chr18_41733883 C/T; S18143: Chr18_41821506 T/G; S18144: Chr18_41894467 C/T; S18145: Chr18_41960026 G/A; S18146: Chr18_42038586 T/G; S18147: Chr18_42089173 T/C; S18148: Chr18_42100782 C/T; S18149:

Chr18_42187133 C/T; S18150: Chr18_42245325 T/G; S18151: Chr18_42254065 T/C; S18152: Chr18_42325094 G/A; S18153: Chr18_42358156 T/C; S18154: Chr18_42409314 A/G; S18155: Chr18_42425026 G/A; S18156: Chr18_42515515 T/C; S18157: Chr18_42528089 A/G; S18158: Chr18_42609709 A/T; S18159: Chr18_42683405 A/G; S18160: Chr18_42730947 C/A; S18161: Chr18_42750158 C/G; S18162: Chr18_42829446 T/G; S18163: Chr18_42975046 G/T; S18164: Chr18_43119820 A/G; S18165: Chr18_43125189 A/G; S18166: Chr18_43223477 A/C; S18167: Chr18_43225824 C/T; S18168: Chr18_43283420 T/C; S18169: Chr18_43319012 T/C; S18170: Chr18_43333468 A/G; S18171: Chr18_43357075 T/C; S18172: Chr18_43410372 T/C; S18173: Chr18_43425776 C/G; S18174: Chr18_43474688 T/C; S18175: Chr18_43488440 C/T; S18176: Chr18_43554188 G/A; S18177: Chr18_43588297 C/A; S18178: Chr18_43600114 T/C; S18179: Chr18_43689637 A/G; S18180: Chr18_43729590 A/G; S18181: Chr18_43752908 T/C; S18182: Chr18_43843850 T/G; S18183: Chr18_43869943 T/A; S18184: Chr18_43881371 G/A; S18185: Chr18_43900004 A/T; S18186: Chr18_43998358 A/G; S18187: Chr18_44000486 A/C; S18188: Chr18_44119271 G/T; S18189: Chr18_44127440 A/T; S18190: Chr18_44194515 T/C; S18191: Chr18_44272449 C/T; S18192: Chr18_44278070 C/T; S18193: Chr18_44302348 T/C; S18194: Chr18_44365654 T/C; S18195: Chr18_44375006 C/T; S18196: Chr18_44454894 C/G; S18197: Chr18_44478439 T/C; S18198: Chr18_44567016 A/G; S18199: Chr18_44589095 A/C; S18200: Chr18_44608347 T/C; S18201: Chr18_44693466 A/C; S18202: Chr18_44701012 T/C; S18203: Chr18_44726044 A/G; S18204: Chr18_44807048 G/T; S18205: Chr18_44830345 A/T; S18206: Chr18_44884370 A/G; S18207: Chr18_44965067 C/T; S18208: Chr18_44980155 A/G; S18209: Chr18_45005198 C/T; S18210: Chr18_45090047 T/A; S18211: Chr18_45119009 C/A; S18212: Chr18_45125168 A/T; S18213: Chr18_45221227 G/A; S18214: Chr18_45279506 C/T; S18215: Chr18_45352079 T/C; S18216: Chr18_45429589 T/C; S18217: Chr18_45601220 A/G; S18218: Chr18_45662570 A/T; S18219: Chr18_45822791 C/T; S18220: Chr18_45915906 C/G; S18221: Chr18_45950159 A/G; S18222: Chr18_46034742 G/T; S18223: Chr18_46087278 G/A; S18224: Chr18_46125782 T/C; S18225: Chr18_46160671 T/A; S18226: Chr18_46321747 A/C; S18227: Chr18_46447029 T/A; S18228: Chr18_46487731 A/G; S18229: Chr18_46530335 C/T; S18230: Chr18_46603358 T/C; S18231: Chr18_46708398 C/T; S18232: Chr18_46733883 A/G; S18233: Chr18_46755200 C/T; S18234: Chr18_46838729 G/A; S18235: Chr18_46852077 A/G; S18236: Chr18_46928805 C/T; S18237: Chr18_46950521 C/T; S18238: Chr18_46981085 T/A; S18239: Chr18_47017322 T/C; S18240: Chr18_47026852 A/T; S18241: Chr18_47092499 G/A; S18242: Chr18_47134584 T/C; S18243: Chr18_47150014 T/G; S18244: Chr18_47245119 T/C; S18245: Chr18_47251073 C/A; S18246: Chr18_47300691 G/C; S18247: Chr18_47327162 &A; S18248: Chr18_47379948 T/A; S18249: Chr18_47410034 A/G; S18250: Chr18_47429162 G/T; S18251: Chr18_47450240 A/G; S18252: Chr18_47565725 A/C; S18253: Chr18_47593122 G/C; S18254: Chr18_47656646 A/G; S18255: Chr18_47680692 T/C; S18256: Chr18_47765010 A/G; S18257: Chr18_47801223 T/A; S18258: Chr18_47830714 T/A; S18259: Chr18_47887506 A/T; S18260: Chr18_217924378 C/G; S18261: Chr18_47938136 A/T; S18262: Chr18_47970688 C/T; S18263: Chr18_47994179 G/A; S18264: Chr18_48017092 T/C; S18265: Chr18_48056177 T/C; S18266: Chr18_48078560 C/T; S18267: Chr18_48115553 A/G; S18268: Chr18_48125071 G/A; S18269: Chr18_48153620 C/T; S18270: Chr18_48175828 C/A; S18271: Chr18_48259512 A/G; S18272: Chr18_48297982 G/T; S18273: Chr18_48353057 A/G; S18274: Chr18_48376703 T/C; S18275: Chr18_48401259 A/T; S18276: Chr18_48437039 A/G; S18277: Chr18_48460718 A/G; S18278: Chr18_48517253 G/T; S18279: Chr18_48525002 G/T; S18280; Chr18_48622339 A/G; S18281: Chr18_48625051 T/A; S18282: Chr18_48652585 A/G; S18283: Chr18_48678056 G/C; S18284: Chr18_48700177 C/T; S18285: Chr18_48726579 C/A; S18286: Chr18_48758325 T/A; S18287: Chr18_218790598 T/C; S18288: Chr18_48814477 G/A; S18289: Chr18_48840921 T/A; S18290: Chr18_48865999 C/T; S18291: Chr18_48902770 G/C; S18292: Chr18_48925186 T/G; S18293: Chr18_48970058 A/T; S18294: Chr18_48985966 A/T; S18295: Chr18_49009694 T/C; S18296: Chr18_49025337 C/T; S18297: Chr18_49055752 T/C; S18298: Chr18_49086429 C/A; S18299: Chr18_49101315 C/A; S18300: Chr18_49199710 G/A; S18301: Chr18_49256211 A/G; S18302: Chr18_49289170 C/T; S18303: Chr18_49305095 A/G; S18304: Chr18_49329293 G/T; S18305: Chr18_49353230 T/G; S18306: Chr18_49394141 T/C; S18307: Chr18_49411942 C/G; S18308: Chr18_49427701 C/T; S18309: Chr18_49461993 T/A; S18310: Chr18_49517530 A/G; S18311: Chr18_49531256 C/T; S18312: Chr18_49550077 G/A; S18313: Chr18_49690668 T/C; S18314: Chr18_49719884 G/T; S18315: Chr18_49725195 G/C; S18316: Chr18_49760162 A/G; S18317: Chr18_49780539 G/A; S18318: Chr18_49800666 C/T; S18319: Chr18_49825477 G/A; S18320: Chr18_49850374 T/A; S18321: Chr18_49881386 A/G; S18322: Chr18_49917635 T/C; S18323: Chr18_49925828 T/C; S18324: Chr18_49993979 G/C; S18325: Chr18_50014733 A/G; S18326: Chr18_50037385 A/G; S18327: Chr18_50059570 T/C; S18328: Chr18_50078242 G/A; S18329: Chr18_50112999 C/A; S18330: Chr18_50126802 T/C; S18331: Chr18_50169967 C/G; S18332: Chr18_50213360 C/T; S18333: Chr18_50246686 G/A; S18334: Chr18_50257198 T/C; S18335: Chr18_50283253 A/T; S18336: Chr18_50306751 T/C; S18337: Chr18_50326879 G/A; S18338: Chr18_50354943 A/T; S18339: Chr18_50376665 A/T; S18340: Chr18_50402963 C/T; S18341: Chr18_50431795 G/C; S18342: Chr18_50451315 T/A; S18343: Chr18_50476758 A/G; S18344: Chr18_50504231 C/T; S18345: Chr18_50526685 G/A; S18346: Chr18_50554508 T/C; S18347: Chr18_50577547 C/T; S18348: Chr18_50604772 G/T; S18349: Chr18_50644512 G/T; S18350:

Chr18_50651797 A/G; S18351: Chr18_50679331 A/T; S18352: Chr18_50709417 C/A; S18353: Chr18_50727402 G/C; S18354: Chr18_50750100 G/A; S18355: Chr18_50783533 C/A; S18356: Chr18_50819327 G/T; S18357: Chr18_50828602 C/T; S18358: Chr18_50856036 G/A; S18359: Chr18_50899887 G/A; S18360: Chr18_50900172 G/C; S18361: Chr18_50939530 T/C; S18362: Chr18_50954877 C/T; S18363: Chr18_50981827 T/C; S18364: Chr18_51003789 C/T; S18365: Chr18_51028222 T/C; S18366: Chr18_51120636 T/A; S18367: Chr18_51137543 A/G; S18368: Chr18_51154266 T/A; S18369: Chr18_51181702 T/A; S18370: Chr18_51200487 C/A; S18371: Chr18_51270946 T/A; S18372: Chr18_51277816 A/G; S18373: Chr18_51308084 T/C; S18374: Chr18_51344406 G/T; S18375: Chr18_51358142 C/A; S18376: Chr18_51392537 A/G; S18377: Chr18_51426799 C/A; S18378: Chr18_51455346 C/T; S18379: Chr18_51480644 A/C; S18380: Chr18_51520475 C/G; S18381: Chr18_51528962 T/A; S18382: Chr18_51599876 T/A; S18383: Chr18_51605977 T/A; S18384: Chr18_51640237 G/A; S18385: Chr18_51651500 G/A; S18386: Chr18_51682723 A/C; S18387: Chr18_51700022 T/C; S18388: Chr18_51727796 A/G; S18389: Chr18_51751232 C/T; S18390: Chr18_51782717 T/G; S18391: Chr18_51803879 G/T; S18392: Chr18_51826512 C/T; S18393: Chr18_51853435 A/G; S18394: Chr18_51875599 A/C; S18395: Chr18_51900852 A/C; S18396: Chr18_51926941 G/C; S18397: Chr18_51952557 A/G; S18398: Chr18_51979685 T/C; S18399: Chr18_52019415 G/A; S18400: Chr18_52025626 G/T; S18401: Chr18_52050483 T/A; S18402: Chr18_52094769 C/A; S18403: Chr18_52123860 G/A; S18404: Chr18_52126322 G/C; S18405: Chr18_52157617 G/A; S18406: Chr18_52175054 G/T; S18407: Chr18_52202086 G/A; S18408: Chr18_52234721 A/G; S18409: Chr18_52255725 G/A; S18410: Chr18_52276598 G/A; S18411: Chr18_52307014 T/C; S18412: Chr18_52343901 G/A; S18413: Chr18_52357137 C/T; S18414: Chr18_52380082 T/C; S18415: Chr18_52409067 A/G; S18416: Chr18_52430134 G/A; S18417: Chr18_52461087 T/C; S18418: Chr18_52559344 G/A; S18419: Chr18_52581795 T/A; S18420: Chr18_52607151 T/C; S18421: Chr18_52625402 C/T; S18422: Chr18_52659364 T/C; S18423: Chr18_52682153 T/C; S18424: Chr18_52727191 A/G; S18425: Chr18_52751060 C/G; S18426: Chr18_52784503 G/T; S18427: Chr18_52800915 T/C; S18428: Chr18_52830128 C/T; S18429: Chr18_52850124 T/A; S18430: Chr18_52894066 G/T; S18431: Chr18_52900515 G/A; S18432: Chr18_52925616 G/T; S18433: Chr18_52960249 C/T; S18434: Chr18_52987956 G/T; S18435: Chr18_53002111 T/C; S18436: Chr18_53027716 G/A; S18437: Chr18_53053875 C/G; S18438: Chr18_53075481 A/C; S18439: Chr18_53109281 G/A; S18440: Chr18_53135873 C/T; S18441: Chr18_53152265 C/T; S18442: Chr18_53176450 G/T; S18443: Chr18_53200858 T/G; S18444: Chr18_53226340 T/C; S18445: Chr18_53252051 A/C; S18446: Chr18_53275333 C/T; S18447: Chr18_53300589 T/C; S18448: Chr18_53326982 A/C; S18449: Chr18_53368752 G/A; S18450: Chr18_53376980 A/G; S18451: Chr18_53402745 T/G; S18452: Chr18_53425738 T/A; S18453: Chr18_53457807 T/G; S18454: Chr18_53478465 T/G; S18455: Chr18_53504757 G/A; S18456: Chr18_53528879 A/T; S18457: Chr18_53553606 G/A; S18458: Chr18_53576029 T/C; S18459: Chr18_53624805 C/G; S18460: Chr18_53640248 G/T; S18461: Chr18_53676463 G/A; S18462: Chr18_53702257 T/A; S18463: Chr18_53725588 C/A; S18464: Chr18_53750083 C/A; S18465: Chr18_53798549 C/T; S18466: Chr18_53820056 A/G; S18467: Chr18_53832360 A/C; S18468: Chr18_53855831 A/T; S18469: Chr18_53882022 C/T; S18470: Chr18_53905333 A/G; S18471: Chr18_53927173 A/T; S18472: Chr18_53957389 T/G; S18473: Chr18_53977481 C/T; S18474: Chr18_54003174 C/T; S18475: Chr18_54049719 T/A; S18476: Chr18_54067650 A/G; S18477: Chr18_54100459 C/T; S18478: Chr18_54133882 G/T; S18479: Chr18_54154199 C/T; S18480: Chr18_54200329 G/A; S18481: Chr18_54225156 G/C; S18482: Chr18_54253157 A/T; S18483: Chr18_54275068 G/A; S18484: Chr18_54310381 G/A; S18485: Chr18_54328017 C/T; S18486: Chr18_54351586 C/T; S18487: Chr18_54375671 C/T; S18488: Chr18_54401544 G/A; S18489: Chr18_54427376 G/A; S18490: Chr18_54463869 G/A; S18491: Chr18_54476621 A/G; S18492: Chr18_54545638 G/A; S18493: Chr18_54572826 T/G; S18494: Chr18_54578575 C/T; S18495: Chr18_54612343 T/C; S18496: Chr18_54625059 C/A; S18497: Chr18_54660893 C/T; S18498: Chr18_54675348 T/C; S18499: Chr18_54703004 C/G; S18500: Chr18_54740194 T/C; S18501: Chr18_54760970 G/A; S18502: Chr18_54779845 T/C; S18503: Chr18_54801747 T/G; S18504: Chr18_54825090 A/T; S18505: Chr18_54853314 T/C; S18506: Chr18_54875469 C/T; S18507: Chr18_54903396 C/T; S18508: Chr18_54937497 T/C; S18509: Chr18_54950751 G/T; S18510: Chr18_54976521 A/G; S18511: Chr18_55004331 A/G; S18512: Chr18_55026765 C/A; S18513: Chr18_55053763 C/T; S18514: Chr18_55080051 C/T; S18515: Chr18_55105642 T/G; S18516: Chr18_55127852 G/C; S18517: Chr18_55152519 C/G; S18518: Chr18_55175339 T/C; S18519: Chr18_55200435 T/A; S18520: Chr18_55226765 A/C; S18521: Chr18_55255518 T/G; S18522: Chr18_55278952 T/G; S18523: Chr18_55300040 G/A; S18524: Chr18_55329576 T/A; S18525: Chr18_55367357 T/G; S18526: Chr18_55426153 T/C; S18527: Chr18_55455824 A/C; S18528: Chr18_55475856 A/C; S18529: Chr18_55505232 A/G; S18530: Chr18_55552164 G/T; S18531: Chr18_55575980 G/A; S18532: Chr18_55604880 A/G; S18533: Chr18_55638538 G/A; S18534: Chr18_55651375 A/C; S18535: Chr18_55677868 C/T; S18536: Chr18_55708159 T/G; S18537: Chr18_55727744 C/T; S18538: Chr18_55750431 A/C; S18539: Chr18_55787507 C/T; S18540: Chr18_55800924 A/G; S18541: Chr18_55829158 A/G; S18542: Chr18_55853215 C/T; S18543: Chr18_55885497 A/G; S18544: Chr18_55913929 A/G; S18545: Chr18_55932095 G/A; S18546: Chr18_55950786 C/T; S18547: Chr18_55980844 T/G; S18548: Chr18_56000284 C/A; S18549: Chr18_56025108 T/C; S18550: Chr18_56050521 T/A; S18551:

Chr18_56085636 A/T; S18552: Chr18_56107330 G/A; S18553: Chr18_56125043 C/G; S18554: Chr18_56160603 G/A; S18555: Chr18_56182068 G/C; S18556: Chr18_56201329 T/A; S18557: Chr18_56235199 T/C; S18558: Chr18_56265303 T/C; S18559: Chr18_56277844 G/A; S18560: Chr18_56305183 T/C; S18561: Chr18_56337693 C/A; S18562: Chr18_56353723 A/G; S18563: Chr18_56378833 A/G; S18564: Chr18_56405126 T/C; S18565: Chr18_56428643 G/A; S18566: Chr18_56450287 A/G; S18567: Chr18_56478373 G/A; S18568: Chr18_56504745 T/A; S18569: Chr18_56530090 A/T; S18570: Chr18_56550143 T/A; S18571: Chr18_56576131 A/G; S18572: Chr18_56611854 A/G; S18573: Chr18_56625365 T/C; S18574: Chr18_56657585 C/T; S18575: Chr18_56681396 T/G; S18576: Chr18_56705167 G/C; S18577: Chr18_56725199 G/A; S18578: Chr18_56750635 C/T; S18579: Chr18_56783022 C/T; S18580: Chr18_56800381 A/G; S18581: Chr18_56825608 A/C; S18582: Chr18_56850069 T/A; S18583: Chr18_56875576 T/C; S18584: Chr18_56906122 T/G; S18585: Chr18_56925239 C/G; S18586: Chr18_56964255 G/T; S18587: Chr18_56975394 G/A; S18588: Chr18_57009954 T/C; S18589: Chr18_57039233 T/C; S18590: Chr18_57052458 T/C; S18591: Chr18_57077104 C/A; S18592: Chr18_57102408 A/T; S18593: Chr18_57126326 T/A; S18594: Chr18_57158498 T/G; S18595: Chr18_57176141 T/C; S18596: Chr18_57206018 T/C; S18597: Chr18_57225847 T/G; S18598: Chr18_57251737 T/C; S18599: Chr18_57275339 C/T; S18600: Chr18_57305459 C/T; S18601: Chr18_57377908 C/A; S18602: Chr18_57405184 T/C; S18603: Chr18_57480469 G/A; S18604: Chr18_57502196 T/C: S18605: Chr18_57533306 A/G; S18606: Chr18_57557744 T/C; S18607: Chr18_57575203 G/C; S18608: Chr18_57614442 C/G; S18609: Chr18_57634020 C/T; S18610: Chr18_57658516 T/G; S18611: Chr18_57676948 A/G; S18612: Chr18_57721186 C/T; S18613: Chr18_57743617 A/C; S18614: Chr18_57756354 C/T; S18615: Chr18_57781456 C/T; S18616: Chr18_57803648 A/G; S18617: Chr18_57825072 A/T; S18618: Chr18_57854458 T/A; S18619: Chr18_57903930 T/A; S18620: Chr18_57942405 A/G; S18621: Chr18_57950660 G/A; S18622: Chr18_58010368 C/T; S18623: Chr19_00005221 C/T; S18624: Chr19_00063119 T/A; S18625: Chr19_00078582 G/T; S18626: Chr19_00105312 T/C; S18627: Chr19_00128723 C/T; S18628: Chr19_00163989 T/C; S18629: Chr19_00177534 T/C; S18630: Chr19_00206583 A/T; S18631: Chr19_00241321 C/A; S18632: Chr19_00259869 G/A; S18633: Chr19_00279864 G/A; S18634: Chr19_00313820 T/C; S18635: Chr19_00378152 T/A; S18636: Chr19_00435252 G/C; S18637: Chr19_00457864 A/C; S18638: Chr19_00475129 C/A; S18639: Chr19_00507488 C/G; S18640: Chr19_00525742 A/G; S18641: Chr19_00554823 G/C; S18642: Chr19_00596422 T/C; S18643: Chr19_00643383 C/T; S18644: Chr19_00661836 C/G; S18645: Chr19_00677651 C/T; S18646: Chr19_00717943 T/A; S18647: Chr19_00743065 C/T; S18648: Chr19_00769001 C/T; S18649: Chr19_00780588 A/G; S18650: Chr19_00806319 T/C; S18651: Chr19_00838479 A/T; S18652: Chr19_00850245 G/A; S18653: Chr19_00878494 T/C; S18654: Chr19_00903698 T/C; S18655: Chr19_00926723 G/A; S18656: Chr19_00959020 T/G; S18657: Chr19_00975886 T/C; S18658: Chr19_01003521 A/C; S18659: Chr19_01055907 T/G; S18660: Chr19_01084229 T/C; S18661: Chr19_01100195 G/A; S18662: Chr19_01129398 T/C; S18663: Chr19_01155933 G/A; S18664: Chr19_01198529 G/A; S18665: Chr19_01252659 C/T; S18666: Chr19_01276857 T/C; S18667: Chr19_01318478 G/A; S18668: Chr19_01326593 A/C; S18669: Chr19_01403853 A/T; S18670: Chr19_01465001 G/A; S18671: Chr19_01500647 G/A; S18672: Chr19_01539365 G/T; S18673: Chr19_01587017 C/T; S18674: Chr19_01608469 A/G; S18675: Chr19_01631810 T/C; S18676: Chr19_01693175 A/G; S18677: Chr19_01729702 C/T; S18678: Chr19_01814806 T/G; S18679: Chr19_01827472 C/A; S18680: Chr19_01850896 C/T; S18681: Chr19_01989302 G/A; S18682: Chr19_02003152 A/C; S18683: Chr19_02033354 C/T; S18684: Chr19_02052052 C/T; S18685: Chr19_02096058 T/G; S18686: Chr19_02101719 A/G; S18687: Chr19_02125440 G/A; S18688: Chr19_02168810 T/A; S18689: Chr19_02175886 G/A; S18690: Chr19_02215576 C/T; S18691: Chr19_02238565 C/T; S18692: Chr19_02273246 T/A; S18693: Chr19_02281855 T/C; S18694: Chr19_02303903 A/G; S18695: Chr19_02405229 T/C; S18696: Chr19_02451973 C/T; S18697: Chr19_02482838 C/T; S18698: Chr19_02508204 C/T; S18699: Chr19_02577990 A/G; S18700: Chr19_02673465 G/A; S18701: Chr19_02688713 T/C; S18702: Chr19_02722670 C/T; S18703: Chr19_02786533 T/C; S18704: Chr19_02894171 G/A; S18705: Chr19_02909622 C/T; S18706: Chr19_02925360 G/A; S18707: Chr19_03073252 C/T; S18708: Chr19_03079867 G/A; S18709: Chr19_03100003 A/G; S18710: Chr19_03180152 T/C; S18711: Chr19_03205373 T/G; S18712: Chr19_03231633 A/C; S18713: Chr19_03268138 T/C; S18714: Chr19_03275348 T/G; S18715: Chr19_03308417 C/T; S18716: Chr19_03331578 G/A; S18717: Chr19_03353156 A/C; S18718: Chr19_03395293 A/G; S18719: Chr19_03418739 A/G; S18720: Chr19_03454550 T/G; S18721: Chr19_03486812 G/A; S18722: Chr19_03507500 A/T; S18723: Chr19_03544076 C/A; S18724: Chr19_03550853 G/C; S18725: Chr19_03607754 C/A; S18726: Chr19_03664553 T/G; S18727: Chr19_03681607 C/T; S18728: Chr19_03709762 A/T; S18729: Chr19_03728347 G/A; S18730: Chr19_03753949 A/T; S18731: Chr19_03795186 C/T; S18732: Chr19_03839394 C/T; S18733: Chr19_03850732 A/T; S18734: Chr19_03936176 T/C; S18735: Chr19_03997739 T/C; S18736: Chr19_04000685 T/C; S18737: Chr19_04026013 T/C; S18738: Chr19_04055461 T/A; S18739: Chr19_04166846 T/A; S18740: Chr19_04175417 G/A; S18741: Chr19_04225883 C/T; S18742: Chr19_04260111 T/A; S18743: Chr19_04275389 A/G; S18744: Chr19_04308800 G/A; S18745: Chr19_04326571 G/C; S18746: Chr19_04355049 A/G; S18747: Chr19_04393064 T/C; S18748: Chr19_04459540 C/A; S18749: Chr19_04568981 C/T; S18750: Chr19_04620074 A/T; S18751: Chr19_04676584 T/G; S18752:

Chr19_04761980 T/A; S18753: Chr19_04830992 C/G; S18754: Chr19_05052554 A/C; S18755: Chr19_05131157 G/A; S18756: Chr19_05278439 T/C; S18757: Chr19_05366588 A/G; S18758: Chr19_05430323 C/A; S18759: Chr19_05539565 A/G; S18760: Chr19_05557750 C/T; S18761: Chr19_05700878 G/A; S18762: Chr19_05775475 A/T; S18763: Chr19_05855426 C/T; S18764: Chr19_05934046 G/A; S18765: Chr19_06005025 T/C; S18766: Chr19_06109166 A/G; S18767: Chr19_06141626 T/C; S18768: Chr19_06212053 A/G; S18769: Chr19_06255221 T/C; S18770: Chr19_06275051 T/C; S18771: Chr19_06370928 A/G; S18772: Chr19_06402283 T/C; S18773: Chr19_06444051 C/T; S18774: Chr19_06478164 A/G; S18775: Chr19_06527374 C/T; S18776: Chr19_06550361 C/T; S18777: Chr19_06626161 T/C; S18778: Chr19_06725549 A/G; S18779: Chr19_06752464 G/A; S18780: Chr19_06775155 T/A; S18781: Chr19_06812946 C/A; S18782: Chr19_06826484 T/C; S18783: Chr19_06900724 C/A; S18784: Chr19_06975736 T/C; S18785: Chr19_07119717 T/C; S18786: Chr19_07141030 A/G; S18787: Chr19_07165716 C/A; S18788: Chr19_07175326 T/C; S18789: Chr19_07280323 C/T; S18790: Chr19_07355423 T/C; S18791: Chr19_07375045 C/A; S18792: Chr19_07452184 A/T; S18793: Chr19_07502575 G/A; S18794: Chr19_07542341 A/G; S18795: Chr19_07550048 C/T; S18796: Chr19_07709913 T/C; S18797: Chr19_07766618 C/T; S18798: Chr19_07776576 T/C; S18799: Chr19_07871263 C/A; S18800: Chr19_07909803 T/G; S18801: Chr19_08016187 T/C; S18802: Chr19_08041617 T/C; S18803: Chr19_08080477 A/G; S18804: Chr19_08130844 C/G; S18805: Chr19_08157408 C/G; S18806: Chr19_08210976 A/T; S18807: Chr19_08236048 G/A; S18808: Chr19_08261702 A/G; S18809: Chr19_08296910 C/A; S18810: Chr19_08318821 G/A; S18811: Chr19_08336286 T/G; S18812: Chr19_08373854 G/T; S18813: Chr19_08379737 C/A; S18814: Chr19_08439506 T/C; S18815: Chr19_08478714 G/A; S18816: Chr19_08505496 A/G; S18817: Chr19_08525371 T/C; S18818: Chr19_08551650 G/A; S18819: Chr19_08579688 G/A; S18820: Chr19_08614225 C/T; S18821: Chr19_08720117 G/A; S18822: Chr19_08752119 C/T; S18823: Chr19_08814290 G/A; S18824: Chr19_08835414 G/C; S18825: Chr19_08882399 C/A; S18826: Chr19_08954105 A/G; S18827: Chr19_08985400 T/C; S18828: Chr19_09000169 A/T; S18829: Chr19_09085202 A/T; S18830: Chr19_09126456 T/G; S18831: Chr19_09162494 T/C; S18832: Chr19_09203615 A/T; S18833: Chr19_09281354 C/T; S18834: Chr19_09309756 T/A; S18835: Chr19_09343878 C/T; S18836: Chr19_09353133 C/T; S18837: Chr19_09382144 C/A; S18838: Chr19_09400021 C/T; S18839: Chr19_09550150 A/G; S18840: Chr19_09714086 G/A; S18841: Chr19_09725096 C/T; S18842: Chr19_09852171 T/C; S18843: Chr19_09896136 C/T; S18844: Chr19_09900012 C/T; S18845: Chr19_09975094 G/A; S18846: Chr19_10194311 C/T; S18847: Chr19_10200262 G/C; S18848: Chr19_10297867 T/C; S18849: Chr19_10305656 C/T; S18850: Chr19_10352610 G/A; S18851: Chr19_10403337 A/G; S18852: Chr19_10444389 G/T; S18853: Chr19_10450012 A/C; S18854: Chr19_10535671 G/T; S18855: Chr19_10625044 C/A; S18856: Chr19_10855011 G/A; S18857: Chr19_10875116 C/T; S18858: Chr19_10955525 T/C; S18859: Chr19_11010436 G/A; S18860: Chr19_11025129 C/A; S18861: Chr19_11100252 C/T; S18862: Chr19_11201613 C/T; S18863: Chr19_11328358 A/C; S18864: Chr19_11498741 C/G; S18865: Chr19_11507343 C/G; S18866: Chr19_11635186 T/C; S18867: Chr19_11665707 G/A; S18868: Chr19_11759480 C/A; S18869: Chr19_11844481 G/T; S18870: Chr19_11918151 A/6; S18871: Chr19_11970777 C/T; S18872: Chr19_12000725 C/T; S18873: Chr19_12112696 T/C; S18874: Chr19_12180815 C/T; S18875: Chr19_12254599 C/T; S18876: Chr19_12275130 G/A; S18877: Chr19_12500036 C/T; S18878: Chr19_12595172 G/A; S18879: Chr19_12600564 G/T; S18880: Chr19_12779228 C/A; S18881: Chr19_12925048 T/G; S18882: Chr19_13043601 C/T; S18883: Chr19_13057275 A/G; S18884: Chr19_13181859 G/A; S18885: Chr19_13200404 C/T; S18886: Chr19_13343443 G/A; S18887: Chr19_13394127 T/G; S18888: Chr19_13405246 T/C; S18889: Chr19_13425312 A/G; S18890: Chr19_13450974 A/T; S18891: Chr19_13475069 A/C; S18892: Chr19_13581026 A/T; S18893: Chr19_13600214 T/C; S18894: Chr19_13715465 G/T; S18895: Chr19_13727503 C/A; S18896: Chr19_13900003 C/T; S18897: Chr19_13975127 A/C; S18898: Chr19_14054452 G/A; S18899: Chr19_14107115 C/T; S18900: Chr19_14132809 A/G; S18901: Chr19_14573763 G/A; S18902: Chr19_14642042 C/T; S18903: Chr19_14672873 A/G; S18904: Chr19_14844154 T/C; S18905: Chr19_14850122 G/T; S18906: Chr19_15075201 T/C; S18907: Chr19_15159488 T/C; S18908: Chr19_15175067 G/A; S18909: Chr19_15267644 T/C; S18910: Chr19_15350016 A/C; S18911: Chr19_15425089 C/T; S18912: Chr19_15575061 C/T; S18913: Chr19_15926358 C/G; S18914: Chr19_15950128 C/T; S18915: Chr19_16100096 C/T; S18916: Chr19_16365462 G/A; S18917: Chr19_16375265 G/A; S18918: Chr19_16450033 G/A; S18919: Chr19_16566904 T/C; S18920: Chr19_16575051 C/T; S18921: Chr19_16650146 A/T; S18922: Chr19_16866720 G/A; S18923: Chr19_16877792 A/T; S18924: Chr19_17200833 G/A; S18925: Chr19_17226217 C/T; S18926: Chr19_17250343 T/A; S18927: Chr19_17325137 C/T; S18928: Chr19_17596308 A/G; S18929: Chr19_17600051 T/C; S18930: Chr19_17675104 A/T; S18931: Chr19_17825271 T/C; S18932: Chr19_17969591 A/G; S18933: Chr19_17997038 A/G; S18934: Chr19_18000036 T/C; S18935: Chr19_18170955 C/A; S18936: Chr19_18175000 C/T; S18937: Chr19_18373518 T/A; S18938: Chr19_18386154 G/A; S18939: Chr19_18400533 G/C; S18940: Chr19_18468017 A/C; S18941: Chr19_18769510 A/G; S18942: Chr19_18776286 C/T; S18943: Chr19_18881673 C/A; S18944: Chr19_18918863 A/C; S18945: Chr19_19038613 C/T; S18946: Chr19_19108513 T/G; S18947: Chr19_19131220 C/T; S18948: Chr19_19342268 C/A; S18949: Chr19_19350975 A/T; S18950: Chr19_19650255 T/C; S18951: Chr19_19874322 C/T; S18952: Chr19_19875865 T/C; S18953:

Chr19_20050036 C/A; S18954: Chr19_20125149 G/A; S18955: Chr19_20275441 A/T; S18956: Chr19_20854467 T/C; S18957: Chr19_20875105 G/C; S18958: Chr19_20969537 C/G; S18959: Chr19_21013897 A/G; S18960: Chr19_21025754 G/A; S18961: Chr19_21100046 T/A; S18962: Chr19_21391533 C/T; S18963: Chr19_21400925 G/A; S18964: Chr19_21437979 C/T; S18965: Chr19_21551271 C/A; S18966: Chr19_21650030 G/C; S18967: Chr19_22232312 C/A; S18968: Chr19_22337953 C/T; S18969: Chr19_22350069 C/G; S18970: Chr19_22705757 G/A; S18971: Chr19_22726832 C/A; S18972: Chr19_22771980 C/T; S18973: Chr19_22794524 G/T; S18974: Chr19_22875411 C/A; S18975: Chr19_22900011 T/C; S18976: Chr19_23053197 T/G; S18977: Chr19_23096850 C/T; S18978: Chr19_23100826 G/A; S18979: Chr19_23190410 G/A; S18980: Chr19_23200220 T/G; S18981: Chr19_23500177 T/G; S18982: Chr19_23580335 C/T; S18983: Chr19_23878647 C/T; S18984: Chr19_24016983 C/G; S18985: Chr19_24044056 G/T; S18986: Chr19_24051700 A/G; S18987: Chr19_24075129 A/C; S18988: Chr19_24185322 T/C; S18989: Chr19_24200311 G/A; S18990: Chr19_24615925 G/A; S18991: Chr19_24625270 A/G; S18992: Chr19_24775057 A/T; S18993: Chr19_25075239 G/T; S18994: Chr19_25225266 T/C; S18995: Chr19_25325144 A/G; S18996: Chr19_25400061 C/G; S18997: Chr19_25481853 T/C; S18998: Chr19_25501860 T/C; S18999: Chr19_25661004 C/A; S19000: Chr19_25960058 T/C; S19001: Chr19_26102842 G/A; S19002: Chr19_26191291 T/C; S19003: Chr19_26249213 T/G; S19004: Chr19_26263657 C/G; S19005: Chr19_26303118 G/T; S19006: Chr19_26325070 C/A; S19007: Chr19_26725565 G/C; S19008: Chr19_26815303 G/A; S19009: Chr19_26847192 C/T; S19010: Chr19_27004957 A/G; S19011: Chr19_27036099 A/G; S19012: Chr19_27069347 G/A; S19013: Chr19_27124980 A/G; S19014: Chr19_27175207 C/A; S19015: Chr19_27200141 T/C; S19016: Chr19_27263458 C/T; S19017: Chr19_27278505 G/A; S19018: Chr19_27300024 T/C; S19019: Chr19_27368131 C/G; S19020: Chr19_27398685 A/G; S19021: Chr19_27407125 A/T; S19022: Chr19_27494055 G/A; S19023: Chr19_27515450 G/C; S19024: Chr19_27527846 G/T; S19025: Chr19_27580235 A/C; S19026: Chr19_27658329 G/A; S19027: Chr19_27698039 C/G; S19028: Chr19_27724732 G/T; S19029: Chr19_27731998 A/T; S19030: Chr19_27763782 G/T; S19031: Chr19_27794254 T/A; S19032: Chr19_27800207 C/G; S19033: Chr19_27888953 A/G; S19034: Chr19_27908017 G/C; S19035: Chr19_27983175 C/A; S19036: Chr19_28014956 C/T; S19037: Chr19_28032428 A/G; S19038: Chr19_28051067 A/G; S19039: Chr19_28149484 C/T; S19040: Chr19_28162650 A/T; S19041: Chr19_28175488 C/T; S19042: Chr19_28330627 T/G; S19043: Chr19_28411219 G/C; S19044: Chr19_28425869 T/G; S19045: Chr19_28575296 A/G; S19046: Chr19_28722068 T/C; S19047: Chr19_28742305 A/G; S19048: Chr19_28783962 C/T; S19049: Chr19_28800166 T/G; S19050: Chr19_28917054 A/G; S19051: Chr19_28941320 A/T; S19052: Chr19_28955493 G/A; S19053: Chr19_28975057 G/A; S19054: Chr19_29106230 T/C; S19055: Chr19_29125060 T/C; S19056: Chr19_29200028 A/G; S19057: Chr19_29275422 C/G; S19058: Chr19_29326750 T/C; S19059: Chr19_29357909 G/A; S19060: Chr19_29375081 G/A; S19061: Chr19_29450038 C/A; S19062: Chr19_29596614 T/G; S19063: Chr19_29617526 C/G; S19064: Chr19_29658579 T/C; S19065: Chr19_29687671 A/G; S19066: Chr19_29720954 A/G; S19067: Chr19_29726258 A/G; S19068: Chr19_29786394 C/G; S19069: Chr19_29800017 A/G; S19070: Chr19_29907391 G/A; S19071: Chr19_29936268 A/G; S19072: Chr19_30021224 A/1'; S19073: Chr19_30066802 T/A; S19074: Chr19_30094274 T/C; S19075: Chr19_30101987 T/A; S19076: Chr19_30126861 A/T; S19077: Chr19_30150091 C/A; S19078: Chr19_30181051 G/A; S19079: Chr19_30246923 G/A; S19080: Chr19_30260249 C/T; S19081: Chr19_30301006 G/A; S19082: Chr19_30328077 T/C; S19083: Chr19_30381189 A/T; S19084: Chr19_30405416 C/T; S19085: Chr19_30430126 G/A; S19086: Chr19_30461190 T/A; S19087: Chr19_30491394 A/G; S19088: Chr19_30500217 G/C; S19089: Chr19_30577699 A/G; S19090: Chr19_30603167 T/C; S19091: Chr19_30653791 C/T; S19092: Chr19_30677425 C/G; S19093: Chr19_30700726 C/T; S19094: Chr19_30793330 T/C; S19095: Chr19_30800801 T/A; S19096: Chr19_30860939 C/T; S19097: Chr19_31048583 G/A; S19098: Chr19_31088125 C/T; S19099: Chr19_31110503 C/T; S19100: Chr19_31148670 G/A; S19101: Chr19_31150496 A/G; S19102: Chr19_31176086 G/T; S19103: Chr19_31242644 T/C; S19104: Chr19_31257372 A/C; S19105: Chr19_31291828 T/A; S19106: Chr19_31368028 C/T; S19107: Chr19_31441613 T/C; S19108: Chr19_31528372 C/T; S19109: Chr19_31659152 C/T; S19110: Chr19_31689003 C/T; S19111: Chr19_31721360 C/T; S19112: Chr19_31726613 G/A; S19113: Chr19_31842574 T/A; S19114: Chr19_31896830 G/C; S19115: Chr19_31903374 C/T; S19116: Chr19_31930179 G/T; S19117: Chr19_32022221 G/A; S19118: Chr19_32045110 G/A; S19119: Chr19_32067714 G/T; S19120: Chr19_32088196 A/C; S19121: Chr19_32101047 C/T; S19122: Chr19_32154302 T/A; S19123: Chr19_32193961 A/T; S19124: Chr19_32243070 G/A; S19125: Chr19_32293617 G/A; S19126: Chr19_32335333 A/G; S19127: Chr19_32378488 G/T; S19128: Chr19_32415899 G/C; S19129: Chr19_32425270 C/T; S19130: Chr19_32477951 C/T; S19131: Chr19_32538668 T/A; S19132: Chr19_32567424 C/T; S19133: Chr19_32613236 G/A; S19134: Chr19_32675253 T/C; S19135: Chr19_32758325 C/G; S19136: Chr19_32776848 C/T; S19137: Chr19_32800283 A/G; S19138: Chr19_32976165 C/T; S19139: Chr19_33009401 T/C; S19140: Chr19_33034612 A/G; S19141: Chr19_33050005 T/A; S19142: Chr19_33188821 T/C; S19143: Chr19_33203920 A/T; S19144: Chr19_33320233 G/A; S19145: Chr19_33325012 A/T; S19146: Chr19_33428338 G/A; S19147: Chr19_33459146 G/A; S19148: Chr19_33500715 G/A; S19149: Chr19_33534004 A/G; S19150: Chr19_33607701 T/C; S19151: Chr19_33643839 C/T; S19152: Chr19_33696326 T/C; S19153: Chr19_33700704 A/T; S19154:

Chr19_33791249 A/G; S19155: Chr19_33843043 C/T; S19156: Chr19_33875968 G/A; S19157: Chr19_33900801 G/A; S19158: Chr19_33956971 A/G; S19159: Chr19_34001811 A/G; S19160: Chr19_34041728 G/T; S19161: Chr19_34124996 A/T; S19162: Chr19_34125446 T/G; S19163: Chr19_34179715 G/A; S19164: Chr19_34219414 G/A; S19165: Chr19_34294271 A/G; S19166: Chr19_34318797 G/A; S19167: Chr19_34325862 A/G; S19168: Chr19_34354303 T/C; S19169: Chr19_34388576 G/A; S19170: Chr19_34400023 A/C; S19171: Chr19_34475899 A/G; S19172: Chr19_34529906 A/G; S19173: Chr19_34574726 C/T; S19174: Chr19_34575694 G/T; S19175: Chr19_34636368 A/C; S19176: Chr19_34685480 A/G; S19177: Chr19_34763536 G/A; S19178: Chr19_34843169 C/T; S19179: Chr19_34880091 T/C; S19180: Chr19_34973897 T/C; S19181: Chr19_34980822 C/T; S19182: Chr19_35014092 T/C; S19183: Chr19_35025192 G/T; S19184: Chr19_35067284 T/C; S19185: Chr19_35089737 T/C; S19186: Chr19_35100145 A/G; S19187: Chr19_35131055 A/T; S19188: Chr19_35170391 G/C; S19189: Chr19_35181144 A/G; S19190: Chr19_35209141 T/A; S19191: Chr19_35239220 G/A; S19192: Chr19_35250098 C/T; S19193: Chr19_35347476 C/T; S19194: Chr19_35350078 T/C; S19195: Chr19_35431183 G/A; S19196: Chr19_35452918 T/C; S19197: Chr19_35493058 A/G; S19198: Chr19_35543291 T/G; S19199: Chr19_35568818 T/A; S19200: Chr19_35615472 C/T; S19201: Chr19_35655752 G/T; S19202: Chr19_35687741 T/C; S19203: Chr19_35706469 T/C; S19204: Chr19_35730436 T/C; S19205: Chr19_35767268 T/A; S19206: Chr19_35816487 T/A; S19207: Chr19_35826131 G/A; S19208: Chr19_35854660 T/C; S19209: Chr19_35880993 A/T; S19210: Chr19_35917582 G/A; S19211: Chr19_35941291 A/G; S19212: Chr19_35969990 A/G; S19213: Chr19_35980215 G/T; S19214: Chr19_36024101 A/G; S19215: Chr19_36049214 A/G; S19216: Chr19_36093997 A/C; S19217: Chr19_36103456 T/C; S19218: Chr19_36125339 T/G; S19219: Chr19_36153349 T/A; S19220: Chr19_36247695 C/G; S19221: Chr19_36252439 C/T; S19222: Chr19_36313774 G/T; S19223: Chr19_36326293 G/C; S19224: Chr19_36355563 C/A; S19225: Chr19_36395421 T/C; S19226: Chr19_36402360 A/G; S19227: Chr19_36437093 A/G; S19228: Chr19_36450464 G/A; S19229: Chr19_36512056 A/T; S19230: Chr19_36547439 C/A; S19231: Chr19_36556067 C/T; S19232: Chr19_36580105 T/C; S19233: Chr19_36600949 T/C; S19234: Chr19_36695338 T/C; S19235: Chr19_36722268 A/C; S19236: Chr19_36726968 T/A; S19237: Chr19_36753884 A/T; S19238: Chr19_36797568 G/A; S19239: Chr19_36851002 G/A; S19240: Chr19_36875380 A/T; S19241: Chr19_36901570 C/G; S19242: Chr19_36968192 A/G; S19243: Chr19_36982341 G/C; S19244: Chr19_37000974 C/A; S19245: Chr19_37031903 C/T; S19246: Chr19_37072909 A/G; S19247: Chr19_37080453 G/C; S19248: Chr19_37110184 T/G; S19249: Chr19_37153893 T/C; S19250: Chr19_37183580 G/T; S19251: Chr19_37238996 A/T; S19252: Chr19_37272376 A/G; S19253: Chr19_37343772 T/A; S19254: Chr19_37359486 G/C; S19255: Chr19_37378532 A/C; S19256: Chr19_37406260 T/G; S19257: Chr19_37437688 T/C; S19258: Chr19_37471206 A/G; S19259: Chr19_37508697 C/T; S19260: Chr19_37575120 G/T; S19261: Chr19_37651499 T/C; S19262: Chr19_37677817 G/A; S19263: Chr19_37702985 G/A; S19264: Chr19_37726147 G/A; S19265: Chr19_37774127 C/T; S19266: Chr19_37776976 C/T; S19267: Chr19_37806091 C/T; S19268: Chr19_37838313 C/T; S19269: Chr19_37872006 A/G; S19270: Chr19_37908258 A/T; S19271: Chr19_37942299 A/T; S19272: Chr19_37950416 C/T; S19273: Chr19_38043103 A/T; S19274: Chr19_38057939 T/G; S19275: Chr19_38084288 G/A; S19276: Chr19_38110872 C/T; S19277: Chr19_38137560 T/C; S19278: Chr19_38152220 G/A; S19279: Chr19_38175389 C/T; S19280: Chr19_38204344 T/C; S19281: Chr19_38226098 A/G; S19282: Chr19_38273660 C/A; S19283: Chr19_38283720 A/G; S19284: Chr19_38300861 A/C; S19285: Chr19_38346651 A/G; S19286: Chr19_38412837 C/T; S19287: Chr19_38427738 G/A; S19288: Chr19_38455144 G/A; S19289: Chr19_38480634 T/C; S19290: Chr19_38506792 A/T; S19291: Chr19_38547811 A/G; S19292: Chr19_38557316 C/A; S19293: Chr19_38575125 T/C; S19294: Chr19_38615287 A/G; S19295: Chr19_38633264 C/T; S19296: Chr19_38658892 G/A; S19297: Chr19_38717537 G/A; S19298: Chr19_38728774 A/G; S19299: Chr19_38765004 T/A; S19300: Chr19_38775776 G/A; S19301: Chr19_38819427 C/A; S19302: Chr19_38836296 T/C; S19303: Chr19_38875286 A/T; S19304: Chr19_38908316 T/C; S19305: Chr19_38943716 C/T; S19306: Chr19_38951289 C/T; S19307: Chr19_39070025 G/A; S19308: Chr19_39103847 A/G; S19309: Chr19_39125429 C/T; S19310: Chr19_39204022 G/T; S19311: Chr19_39285181 G/C; S19312: Chr19_39328554 A/G; S19313: Chr19_39351065 A/G; S19314: Chr19_39376171 C/G; S19315: Chr19_39423929 T/C; S19316: Chr19_39431142 A/G; S19317: Chr19_39450573 G/C; S19318: Chr19_39479984 T/A; S19319: Chr19_39500364 A/G; S19320: Chr19_39525034 C/T; S19321: Chr19_39551975 C/T; S19322: Chr19_39576709 C/A; S19323: Chr19_39632522 G/A; S19324: Chr19_39651869 T/C; S19325: Chr19_39675377 C/G; S19326: Chr19_39707771 A/T; S19327: Chr19_39726627 C/T; S19328: Chr19_39780428 G/C; S19329: Chr19_39804154 T/C; S19330: Chr19_39826359 T/C; S19331: Chr19_39850091 C/T; S19332: Chr19_39876181 T/C; S19333: Chr19_39900613 A/G; S19334: Chr19_39926510 T/A; S19335: Chr19_39951878 G/C; S19336: Chr19_39978309 C/T; S19337: Chr19_40005621 T/C; S19338: Chr19_40043613 A/G; S19339: Chr19_40050844 G/C; S19340: Chr19_40078384 T/C; S19341: Chr19_40107624 A/G; S19342: Chr19_40127559 T/C; S19343: Chr19_40165135 A/G; S19344: Chr19_40177289 G/T; S19345: Chr19_40200329 G/C; S19346: Chr19_40228778 A/C; S19347: Chr19_40253966 T/C; S19348: Chr19_40281293 C/G; S19349: Chr19_40301909 C/T; S19350: Chr19_210334909 A/T; S19351: Chr19_40357227 T/G; S19352: Chr19_40394368 T/C; S19353: Chr19_40407684 A/T; S19354: Chr19_40426854 G/A; S19355:

Chr19_40450491 G/A; S19356: Chr19_40475339 C/T; S19357: Chr19_40507980 G/A; S19358: Chr19_40533785 G/C; S19359: Chr19_40555456 A/G; S19360: Chr19_40580203 A/T; S19361: Chr19_210600373 T/G; S19362: Chr19_40639042 A/T; S19363: Chr19_40655855 G/A; S19364: Chr19_40675343 A/T; S19365: Chr19_40707346 A/G; S19366: Chr19_40725765 G/T; S19367: Chr19_40801654 C/T; S19368: Chr19_40842973 A/G; S19369: Chr19_40860658 T/A; S19370: Chr19_40884904 A/C; S19371: Chr19_40906019 A/C; S19372: Chr19_40925018 G/A; S19373: Chr19_40966416 A/T; S19374: Chr19_40977319 G/A; S19375: Chr19_41006210 T/C; S19376: Chr19_41036642 G/A; S19377: Chr19_41060305 G/A; S19378: Chr19_41082358 G/A; S19379: Chr19_41124053 T/C; S19380: Chr19_41142193 C/A; S19381: Chr19_41150809 T/C; S19382: Chr19_41187714 A/G; S19383: Chr19_41250914 G/A; S19384: Chr19_41275372 T/C; S19385: Chr19_41302042 C/A; S19386: Chr19_41336035 T/C; S19387: Chr19_41384809 G/T; S19388: Chr19_41413225 G/A; S19389: Chr19_41425873 T/C; S19390: Chr19_41471856 A/C; S19391: Chr19_41487751 T/C; S19392: Chr19_41527548 G/A; S19393: Chr19_41564721 C/G; S19394: Chr19_41587297 T/A; S19395: Chr19_41612193 A/T; S19396: Chr19_41658929 T/G; S19397: Chr19_41680285 G/A; S19398: Chr19_41717804 C/A; S19399: Chr19_41727372 T/C; S19400: Chr19_41766068 G/T; S19401: Chr19_41822681 C/T; S19402: Chr19_41831441 T/C; S19403: Chr19_41858227 T/C; S19404: Chr19_41877767 G/A; S19405: Chr19_41909713 T/C; S19406: Chr19_41953046 G/C; S19407: Chr19_41994038 G/C; S19408: Chr19_42016901 C/T; S19409: Chr19_42025090 T/C; S19410: Chr19_42065013 A/T; S19411: Chr19_42084832 T/C; S19412: Chr19_42103596 A/C; S19413: Chr19_42125657 T/C; S19414: Chr19_42152609 G/T; S19415: Chr19_42196703 T/C; S19416: Chr19_42201464 A/G; S19417: Chr19_42235017 A/T; S19418: Chr19_42255979 T/C; S19419: Chr19_42275755 T/C; S19420: Chr19_42306211 A/T; S19421: Chr19_42328417 A/T; S19422: Chr19_42358444 T/C; S19423: Chr19_42456535 T/A; S19424: Chr19_42496895 G/A; S19425: Chr19_42503083 C/T; S19426: Chr19_42533861 A/T; S19427: Chr19_42560112 G/A; S19428: Chr19_42592704 C/G; S19429: Chr19_42636604 C/A; S19430: Chr19_42700535 A/G; S19431: Chr19_42732180 C/T; S19432: Chr19_42752759 G/A; S19433: Chr19_42856417 A/T; S19434: Chr19_42881304 G/A; S19435: Chr19_42901824 T/A; S19436: Chr19_42937706 C/T; S19437: Chr19_42955783 T/C; S19438: Chr19_42993011 T/C; S19439: Chr19_43008495 G/C; S19440: Chr19_43064220 A/G; S19441: Chr19_43075222 G/A; S19442: Chr19_43102345 T/C; S19443: Chr19_43144060 G/C; S19444: Chr19_43220051 A/T; S19445: Chr19_43230762 G/A; S19446: Chr19_43315661 C/T; S19447: Chr19_43325754 G/T; S19448: Chr19_43376867 T/G; S19449: Chr19_43437970 T/A; S19450: Chr19_43502037 G/T; S19451: Chr19_43584012 T/C; S19452: Chr19_43692912 T/A; S19453: Chr19_43734510 T/C; S19454: Chr19_43755860 G/C; S19455: Chr19_43830488 C/T; S19456: Chr19_43856774 G/A; S19457: Chr19_43942072 C/T; S19458: Chr19_44047586 C/T; S19459: Chr19_44051646 C/T; S19460: Chr19_44160674 A/T; S19461: Chr19_44246121 A/C; S19462: Chr19_44255141 T/C; S19463: Chr19_44279810 G/C; S19464: Chr19_44393911 C/T; S19465: Chr19_44400049 G/C; S19466: Chr19_44426763 C/T; S19467: Chr19_44462993 G/A; S19468: Chr19_44500753 C/T; S19469: Chr19_44533654 T/A; S19470: Chr19_44551904 A/G; S19471: Chr19_44575639 G/A; S19472: Chr19_44600856 T/C; S19473: Chr19_44628812 C/T; S19474: Chr19_44656967 C/T; S19475: Chr19_44675241 A/G; S19476: Chr19_44713372 A/T; S19477: Chr19_44731672 G/A; S19478: Chr19_44761453 G/A; S19479: Chr19_44776851 C/T; S19480: Chr19_44803709 C/T; S19481: Chr19_44826476 A/G; S19482: Chr19_44850606 A/G; S19483: Chr19_44876395 C/T; S19484: Chr19_44907180 A/G; S19485: Chr19_44929202 A/G; S19486: Chr19_44958538 G/T; S19487: Chr19_44975289 G/A; S19488: Chr19_45071789 G/T; S19489: Chr19_45075111 T/C; S19490: Chr19_45100983 A/G; S19491: Chr19_45142333 A/C; S19492: Chr19_45164521 A/T; S19493: Chr19_45184804 C/A; S19494: Chr19_45200508 A/T; S19495: Chr19_45227843 A/G; S19496: Chr19_45256468 G/T; S19497: Chr19_45275032 A/G; S19498: Chr19_45305342 C/A; S19499: Chr19_45328509 T/C; S19500: Chr19_45374771 G/C; S19501: Chr19_45384318 T/C; S19502: Chr19_45403922 C/A; S19503: Chr19_45429114 G/A; S19504: Chr19_45465977 C/T; S19505: Chr19_45501348 A/G; S19506: Chr19_45532121 A/G; S19507: Chr19_45565837 C/T; S19508: Chr19_45575841 G/A; S19509: Chr19_45624712 T/A; S19510: Chr19_45649932 A/T; S19511: Chr19_45680886 A/C; S19512: Chr19_45728338 A/G; S19513: Chr19_45769759 C/A; S19514: Chr19_45799027 C/T; S19515: Chr19_45806345 T/A; S19516: Chr19_45825001 C/T; S19517: Chr19_45856533 C/A; S19518: Chr19_45888920 C/A; S19519: Chr19_45914350 T/C; S19520: Chr19_45932807 T/A; S19521: Chr19_45999764 A/C; S19522: Chr19_46000120 T/G; S19523: Chr19_46047212 C/T; S19524: Chr19_46074678 C/T; S19525: Chr19_46094608 A/T; S19526: Chr19_46110862 A/G; S19527: Chr19_46127564 G/T; S19528: Chr19_46160913 C/T; S19529: Chr19_46194077 A/G; S19530: Chr19_46201093 C/G; S19531: Chr19_46231927 T/C; S19532: Chr19_46252805 A/C; S19533: Chr19_46285255 G/T; S19534: Chr19_46316113 G/A; S19535: Chr19_46345304 C/T; S19536: Chr19_46350574 T/C; S19537: Chr19_46383795 G/A; S19538: Chr19_46400340 A/T; S19539: Chr19_46425993 A/G; S19540: Chr19_46478837 A/G; S19541: Chr19_46507363 T/A; S19542: Chr19_46530081 T/G; S19543: Chr19_46559089 G/C; S19544: Chr19_46576863 A/T; S19545: Chr19_46605076 T/C; S19546: Chr19_46629986 C/T; S19547: Chr19_46653537 C/G; S19548: Chr19_46682837 G/T; S19549: Chr19_46714389 A/G; S19550: Chr19_46727566 C/T; S19551: Chr19_46753282 G/A; S19552: Chr19_46784752 C/T; S19553: Chr19_46807344 A/T; S19554: Chr19_46838314 A/G; S19555: Chr19_46856156 G/A; S19556:

Chr19_46879327 T/C; S19557: Chr19_46900345 A/T; S19558: Chr19_46936139 T/G; S19559: Chr19_46952128 T/C; S19560: Chr19_47008899 G/A; S19561: Chr19_47030307 A/G; S19562: Chr19_47057094 G/T; S19563: Chr19_47082265 C/T; S19564: Chr19_47105006 G/A; S19565: Chr19_47127967 G/A; S19566: Chr19_47157255 A/G; S19567: Chr19_47179506 G/T; S19568: Chr19_47200473 C/T; S19569: Chr19_47225028 G/A; S19570: Chr19_47267849 G/C; S19571: Chr19_47284576 G/T; S19572: Chr19_47305458 C/G; S19573: Chr19_47341234 A/G; S19574: Chr19_47350110 G/T; S19575: Chr19_47376769 T/C; S19576: Chr19_47406466 C/T; S19577: Chr19_47439860 G/A; S19578: Chr19_47456188 T/A; S19579: Chr19_47482154 C/A; S19580: Chr19_47504797 G/A; S19581: Chr19_47526134 C/G; S19582: Chr19_47563367 G/A; S19583: Chr19_47575059 G/A; S19584: Chr19_47600163 G/A; S19585: Chr19_47625022 A/T; S19586: Chr19_47656381 A/G; S19587: Chr19_47680091 G/A; S19588: Chr19_47723311 A/C; S19589: Chr19_47728451 G/A; S19590: Chr19_47752307 A/G; S19591: Chr19_47777022 C/T; S19592: Chr19_47801975 A/G; S19593: Chr19_47843762 G/A; S19594: Chr19_47853708 G/T; S19595: Chr19_47879217 A/G; S19596: Chr19_47900340 T/C; S19597: Chr19_47930535 G/C; S19598: Chr19_47953671 A/G; S19599: Chr19_47988748 G/C; S19600: Chr19_48002778 T/C; S19601: Chr19_48028651 T/C; S19602: Chr19_48052071 T/G; S19603: Chr19_48075287 C/T; S19604: Chr19_48105121 C/T; S19605: Chr19_48127495 A/G; S19606: Chr19_48152631 T/C; S19607: Chr19_48176591 G/A; S19608: Chr19_48200071 G/A; S19609: Chr19_48225452 G/A; S19610: Chr19_48251845 T/C; S19611: Chr19_48289871 T/G; S19612: Chr19_48300242 T/A; S19613: Chr19_48332138 A/G; S19614: Chr19_48354039 A/G; S19615: Chr19_48377490 G/A; S19616: Chr19_48406537 T/C; S19617: Chr19_48449710 A/G; S19618: Chr19_48459727 A/G; S19619: Chr19_48475085 T/C; S19620: Chr19_48506793 G/A; S19621: Chr19_48530391 C/G; S19622: Chr19_48554451 G/T; S19623: Chr19_48580728 G/C; S19624: Chr19_48600849 A/G; S19625: Chr19_48625600 G/A; S19626: Chr19_48651086 T/A; S19627: Chr19_48680007 A/G; S19628: Chr19_48700996 A/G; S19629: Chr19_48729330 T/C; S19630: Chr19_48760452 G/A; S19631: Chr19_48775245 A/T; S19632: Chr19_48800971 A/T; S19633: Chr19_48825557 C/T; S19634: Chr19_48862160 A/T; S19635: Chr19_48877280 C/T; S19636: Chr19_48929070 G/A; S19637: Chr19_48965048 A/G; S19638: Chr19_48975302 G/C; S19639: Chr19_49001417 A/C; S19640: Chr19_49076176 C/T; S19641: Chr19_49100675 A/T; S19642: Chr19_49125099 C/T; S19643: Chr19_49168972 T/C; S19644: Chr19_49176689 A/G; S19645: Chr19_49202413 A/T; S19646: Chr19_49233500 C/A; S19647: Chr19_49251774 C/G; S19648: Chr19_49275710 G/A; S19649: Chr19_49307582 G/T; S19650: Chr19_49327351 G/C; S19651: Chr19_49355418 T/A; S19652: Chr19_49378647 C/T; S19653: Chr19_49418462 T/A; S19654: Chr19_49467073 G/C; S19655: Chr19_49489855 C/T; S19656: Chr19_49513596 G/A; S19657: Chr19_49528388 A/C; S19658: Chr19_49551087 T/C; S19659: Chr19_49575441 A/G; S19660: Chr19_49617152 A/G; S19661: Chr19_49630445 A/T; S19662: Chr19_49671217 G/C; S19663: Chr19_49693040 C/T; S19664: Chr19_49726500 G/A; S19665: Chr19_49766319 G/A; S19666: Chr19_49782531 A/C; S19667: Chr19_49852132 A/G; S19668: Chr19_49877045 T/G; S19669: Chr19_49903600 A/G; S19670: Chr19_49925071 G/C; S19671: Chr19_49972042 G/C; S19672: Chr19_49982876 G/A; S19673: Chr19_50000155 C/T; S19674: Chr19_50027436 C/T; S19675: Chr19_50056805 G/T; S19676: Chr19_50088142 T/A; S19677: Chr19_50108046 G/C; S19678: Chr19_50136693 T/A; S19679: Chr19_50197786 T/C; S19680: Chr19_50208858 C/A; S19681: Chr19_50233967 A/G; S19682: Chr19_50272705 G/T; S19683: Chr19_50297670 G/A; S19684: Chr19_50309507 A/G; S19685: Chr19_50325877 A/G; S19686: Chr19_50356418 G/A; S19687: Chr19_50386373 A/G; S19688: Chr19_50409329 T/A; S19689: Chr19_50429392 A/G; S19690: Chr19_50485758 G/A; S19691: Chr19_50505580 C/T; S19692: Chr19_50529740 G/T; S19693: Chr19_50554902 A/G; S19694: Chr19_50575125 C/A; S19695: Chr19_50601588 G/A; S19696: Chr19_50637571 C/A; S19697: Chr19_50654438 T/C; S19698: Chr19_50731991 T/C; S19699: Chr20_00000944 C/G; S19700: Chr20_00043416 G/A; S19701: Chr20_00051891 A/T; S19702: Chr20_00076944 G/C; S19703: Chr20_00108578 T/C; S19704: Chr20_00126314 C/A; S19705: Chr20_00150781 C/G; S19706: Chr20_00202321 C/T; S19707: Chr20_00264414 A/C; S19708: Chr20_00275700 A/G; S19709: Chr20_00313315 G/A; S19710: Chr20_00331774 C/G; S19711: Chr20_00351117 T/C; S19712: Chr20_00387416 C/T; S19713: Chr20_00401919 C/T; S19714: Chr20_00476464 A/C; S19715: Chr20_00511464 T/C; S19716: Chr20_00525105 G/A; S19717: Chr20_00569170 A/T; S19718: Chr20_00608620 C/T; S19719: Chr20_00649658 T/C; S19720: Chr20_00650776 C/A; S19721: Chr20_00686368 A/T; S19722: Chr20_00700996 G/A; S19723: Chr20_00781601 A/T; S19724: Chr20_00801984 C/G; S19725: Chr20_00830461 A/T; S19726: Chr20_00867525 C/T; S19727: Chr20_00884135 A/G; S19728: Chr20_00900603 T/G; S19729: Chr20_00925880 A/G; S19730: Chr20_00970374 T/A; S19731: Chr20_00975164 A/G; S19732: Chr20_01032743 T/A; S19733: Chr20_01056866 A/T; S19734: Chr20_01083700 A/G; S19735: Chr20_01120527 C/T; S19736: Chr20_01134869 A/T; S19737: Chr20_01157442 A/G; S19738: Chr20_01178086 G/A; S19739: Chr20_01204198 A/T; S19740: Chr20_01240594 G/A; S19741: Chr20_01251277 T/A; S19742: Chr20_01290519 T/C; S19743: Chr20_01355746 A/C; S19744: Chr20_01375485 T/C; S19745: Chr20_01407347 C/T; S19746: Chr20_01473019 T/A; S19747: Chr20_01478117 G/A; S19748: Chr20_01519538 C/T; S19749: Chr20_01536910 A/G; S19750: Chr20_01567172 C/T; S19751: Chr20_01577377 G/A; S19752: Chr20_01624381 G/A; S19753: Chr20_01625190 A/T; S19754: Chr20_01707985 G/A; S19755: Chr20_01727686 G/T; S19756: Chr20_01750542 G/T; S19757:

Chr20_01844099 C/A; S19758: Chr20_01894103 C/T; S19759: Chr20_01907880 G/A; S19760: Chr20_01929858 C/A; S19761: Chr20_01960816 G/C; S19762: Chr20_01980332 A/C; S19763: Chr20_02000817 C/T; S19764: Chr20_02033417 G/T; S19765: Chr20_02054421 T/C; S19766: Chr20_02075232 C/T; S19767: Chr20_02113111 T/A; S19768: Chr20_02130214 C/G; S19769: Chr20_02151620 C/G; S19770: Chr20_02197394 A/G; S19771: Chr20_02201421 T/A; S19772: Chr20_02243234 G/T; S19773: Chr20_02263020 T/C; S19774: Chr20_02292167 A/C; S19775: Chr20_02331737 T/C; S19776: Chr20_02357620 G/A; S19777: Chr20_02441830 T/G; S19778: Chr20_02462160 G/T; S19779: Chr20_02475048 A/G; S19780: Chr20_02506316 G/A; S19781: Chr20_02548084 A/G; S19782: Chr20_02608000 G/A; S19783: Chr20_02638053 G/A; S19784: Chr20_02662984 T/G; S19785: Chr20_02676778 C/T; S19786: Chr20_02743355 G/A; S19787: Chr20_02752818 G/A; S19788: Chr20_02777992 G/C; S19789: Chr20_02850044 C/A; S19790: Chr20_02902437 A/G; S19791: Chr20_02926407 A/C; S19792: Chr20_02969041 T/C; S19793: Chr20_03003215 T/C; S19794: Chr20_03050056 C/T; S19795: Chr20_03079123 T/A; S19796: Chr20_03112161 C/T; S19797: Chr20_03141054 A/G; S19798: Chr20_03153315 T/C; S19799: Chr20_03181914 T/C; S19800: Chr20_03205260 C/A; S19801: Chr20_03225673 C/T; S19802: Chr20_03306874 G/A; S19803: Chr20_03413871 A/G; S19804: Chr20_03497374 C/T; S19805: Chr20_03500462 A/G; S19806: Chr20_03583596 G/A; S19807: Chr20_03680655 C/T; S19808: Chr20_03701022 C/T; S19809: Chr20_03777792 T/C; S19810: Chr20_03880969 G/A; S19811: Chr20_03903086 A/G; S19812: Chr20_03932121 T/C; S19813: Chr20_04037274 C/T; S19814: Chr20_04114296 T/A; S19815: Chr20_04130930 C/T; S19816: Chr20_04153959 C/T; S19817: Chr20_04180546 G/A; S19818: Chr20_04208983 G/C; S19819: Chr20_04246470 T/C; S19820: Chr20_04275077 A/G; S19821: Chr20_04409675 A/G; S19822: Chr20_04427553 T/C; S19823: Chr20_04459009 G/T; S19824: Chr20_04485545 T/C; S19825: Chr20_04524037 C/G; S19826: Chr20_04525044 T/A; S19827: Chr20_04550513 A/G; S19828: Chr20_04580124 C/G; S19829: Chr20_04602150 T/C; S19830: Chr20_04640975 T/C; S19831: Chr20_04665512 A/G; S19832: Chr20_04737372 A/G; S19833: Chr20_04756895 G/T; S19834: Chr20_04780806 A/G; S19835: Chr20_04927677 A/T; S19836: Chr20_05007737 C/T; S19837: Chr20_05201723 T/C; S19838: Chr20_05407163 T/C; S19839: Chr20_05489169 C/T; S19840: Chr20_05661306 G/A; S19841: Chr20_05725086 T/C; S19842: Chr20_05810132 A/G; S19843: Chr20_05962709 T/A; S19844: Chr20_06159997 C/T; S19845: Chr20_06201297 G/A; S19846: Chr20_06277552 A/G; S19847: Chr20_06356334 G/A; S19848: Chr20_06438031 C/G; S19849: Chr20_06501071 T/C; S19850: Chr20_06652969 C/T; S19851: Chr20_06734638 C/T; S19852: Chr20_06899700 G/A; S19853: Chr20_07172770 T/C; S19854: Chr20_07181332 G/A; S19855: Chr20_07252823 C/T; S19856: Chr20_07490490 T/C; S19857: Chr20_07551654 T/A; S19858: Chr20_07646020 A/T; S19859: Chr20_07703616 G/A; S19860: Chr20_07871174 T/C; S19861: Chr20_07935977 T/C; S19862: Chr20_08076579 A/G; S19863: Chr20_08185710 C/T; S19864: Chr20_08203632 C/T; S19865: Chr20_08280241 C/A; S19866: Chr20_08428023 T/A; S19867: Chr20_08506562 C/G; S19868: Chr20_08583291 G/A; S19869: Chr20_08699240 G/A; S19870: Chr20_08776946 G/A; S19871: Chr20_08878681 A/G; S19872: Chr20_09057531 T/C; S19873: Chr20_09101769 A/G; S19874: Chr20_09190572 G/A; S19875: Chr20_09262063 G/T; S19876: Chr20_09486716 C/A; S19877: Chr20_09504709 T/A; S19878: Chr20_09651553 G/C; S19879: Chr20_09744852 C/T; S19880: Chr20_10025864 C/T; S19881: Chr20_10254295 T/A; S19882: Chr20_10676879 A/T; S19883: Chr20_11008133 G/A; S19884: Chr20_11088599 C/T; S19885: Chr20_11161785 C/T; S19886: Chr20_11231588 A/G; S19887: Chr20_11384760 C/T; S19888: Chr20_11454900 T/A; S19889: Chr20_11535176 G/A; S19890: Chr20_11616717 C/G; S19891: Chr20_11723639 C/A; S19892: Chr20_11776280 C/T; S19893: Chr20_11869184 C/T; S19894: Chr20_11888844 C/T; S19895: Chr20_11957808 C/T; S19896: Chr20_11983948 C/A; S19897: Chr20_12015273 G/A; S19898: Chr20_12039471 G/A; S19899: Chr20_12188171 C/A; S19900: Chr20_12302257 T/C; S19901: Chr20_12347981 A/G; S19902: Chr20_12396550 T/C; S19903: Chr20_12412419 C/T; S19904: Chr20_12488095 G/A; S19905: Chr20_12549121 C/A; S19906: Chr20_12550621 A/T; S19907: Chr20_12627023 G/A; S19908: Chr20_12725646 T/G; S19909: Chr20_12800186 T/G; S19910: Chr20_12908522 T/A; S19911: Chr20_12925759 C/T; S19912: Chr20_13079727 T/G; S19913: Chr20_13215920 A/G; S19914: Chr20_13238536 G/A; S19915: Chr20_13250208 T/G; S19916: Chr20_13325028 C/T; S19917: Chr20_13483907 C/G; S19918: Chr20_13736021 C/T; S19919: Chr20_13826015 G/A; S19920: Chr20_13900741 G/A; S19921: Chr20_14053473 G/A; S19922: Chr20_14350552 T/C; S19923: Chr20_14777018 G/A; S19924: Chr20_14809632 A/C; S19925: Chr20_14830625 C/T; S19926: Chr20_14850012 G/C; S19927: Chr20_15000221 A/G; S19928: Chr20_15150092 C/A; S19929: Chr20_15300078 C/A; S19930: Chr20_15450095 G/A; S19931: Chr20_15600394 G/A; S19932: Chr20_15726702 C/A; S19933: Chr20_15825471 C/T; S19934: Chr20_15974064 T/C; S19935: Chr20_15975033 T/G; S19936: Chr20_16075841 T/C; S19937: Chr20_16525288 G/A; S19938: Chr20_16600140 G/A; S19939: Chr20_16684855 A/G; S19940: Chr20_16700463 G/A; S19941: Chr20_16870468 A/G; S19942: Chr20_16896963 T/C; S19943: Chr20_16900777 G/A; S19944: Chr20_16925865 A/G; S19945: Chr20_17042154 A/G; S19946: Chr20_17125945 T/C; S19947: Chr20_17249566 T/C; S19948: Chr20_17251129 G/C; S19949: Chr20_17275947 T/C; S19950: Chr20_17350440 C/T; S19951: Chr20_17549368 T/A; S19952: Chr20_17574704 G/T; S19953: Chr20_17575000 G/T; S19954: Chr20_17712510 G/A; S19955: Chr20_17731721 T/A; S19956: Chr20_17750159 G/C; S19957: Chr20_17851290 G/A; S19958:

Chr20_17905062 C/A; S19959: Chr20_17987540 T/G; S19960: Chr20_18040109 T/G; S19961: Chr20_18092831 G/T; S19962: Chr20_18100208 A/G; S19963: Chr20_18433657 G/A; S19964: Chr20_18594378 T/G; S19965: Chr20_18644809 C/T; S19966: Chr20_18658011 C/A; S19967: Chr20_18675456 C/T; S19968: Chr20_18967014 G/A; S19969: Chr20_18975155 A/G; S19970: Chr20_19066934 C/A; S19971: Chr20_19159489 C/A; S19972: Chr20_19548120 A/T; S19973: Chr20_20201525 A/G; S19974: Chr20_20281316 T/C; S19975: Chr20_20510713 A/T; S19976: Chr20_20655452 G/A; S19977: Chr20_20802732 T/A; S19978: Chr20_21177298 T/C; S19979: Chr20_21340257 G/A; S19980: Chr20_21558323 A/T; S19981: Chr20_21635581 T/A; S19982: Chr20_21776986 T/C; S19983: Chr20_22323280 C/G; S19984: Chr20_22381977 C/T; S19985: Chr20_22471252 A/T; S19986: Chr20_22527102 T/G; S19987: Chr20_22675271 T/C; S19988: Chr20_22906725 G/T; S19989: Chr20_23012151 A/C; S19990: Chr20_23041049 A/G; S19991: Chr20_23175177 C/T; S19992: Chr20_23257525 T/C; S19993: Chr20_23328397 G/A; S19994: Chr20_23432950 G/A; S19995: Chr20_23483667 G/A; S19996: Chr20_23626242 G/A; S19997: Chr20_23701985 G/A; S19998: Chr20_23777413 G/A; S19999: Chr20_23850863 T/C; S20000: Chr20_24076093 T/G; S20001: Chr20_24181753 A/C; S20002: Chr20_24220452 T/C; S20003: Chr20_24228420 G/T; S20004: Chr20_24334103 T/A; S20005: Chr20_24358807 T/A; S20006: Chr20_24507630 A/T; S20007: Chr20_24647324 A/G; S20008: Chr20_24676840 G/T; S20009: Chr20_24700266 A/G; S20010: Chr20_24778289 A/G; S20011: Chr20_25113130 G/T; S20012: Chr20_25155460 G/A; S20013: Chr20_25202930 A/G; S20014: Chr20_25287901 T/G; S20015: Chr20_25352346 G/T; S20016: Chr20_25425687 G/A; S20017: Chr20_25547432 A/G; S20018: Chr20_25551664 A/G; S20019: Chr20_25596218 C/G; S20020: Chr20_25602592 C/T; S20021: Chr20_25700548 G/A; S20022: Chr20_25787165 T/A; S20023: Chr20_25869789 C/T; S20024: Chr20_25891950 G/A; S20025: Chr20_25900157 G/A; S20026: Chr20_25925452 A/G; S20027: Chr20_25950355 T/C; S20028: Chr20_26123464 A/G; S20029: Chr20_26219822 G/T; S20030: Chr20_26225043 C/T; S20031: Chr20_26348441 T/G; S20032: Chr20_26371443 C/T; S20033: Chr20_26375993 T/C; S20034: Chr20_26400311 T/C; S20035: Chr20_26618779 G/A; S20036: Chr20_26656290 A/T; S20037: Chr20_26717958 G/A; S20038: Chr20_26909703 G/A; S20039: Chr20_26925112 A/G; S20040: Chr20_27024610 G/A; S20041: Chr20_27025578 T/A; S20042: Chr20_27162992 A/T; S20043: Chr20_27253803 A/G; S20044: Chr20_27288977 C/G; S20045: Chr20_27309375 C/T; S20046: Chr20_27337698 C/A; S20047: Chr20_27364379 T/A; S20048: Chr20_27397589 G/A; S20049: Chr20_27454594 T/G; S20050: Chr20_27475047 G/C; S20051: Chr20_27582416 A/G; S20052: Chr20_27647370 C/T; S20053: Chr20_27651428 A/G; S20054: Chr20_27675123 A/C; S20055: Chr20_27702040 T/G; S20056: Chr20_27773342 C/T; S20057: Chr20_27781817 G/A; S20058: Chr20_27826206 G/A; S20059: Chr20_27997157 G/A; S20060: Chr20_28040731 C/T; S20061: Chr20_28050166 A/T; S20062: Chr20_28150751 G/A; S20063: Chr20_28400111 C/A; S20064: Chr20_28549094 G/A; S20065: Chr20_28551096 T/C; S20066: Chr20_28575005 C/A; S20067: Chr20_28725135 G/A; S20068: Chr20_28800384 A/G; S20069: Chr20_28941455 A/T; S20070: Chr20_29042395 G/A; S20071: Chr20_29062075 T/C; S20072: Chr20_29080867 A/G; S20073: Chr20_29175283 G/A; S20074: Chr20_29275038 A/G; S20075: Chr20_29363107 A/G; S20076: Chr20_29378881 C/T; S20077: Chr20_29407044 A/G; S20078: Chr20_29425168 T/G; S20079: Chr20_29500029 T/A; S20080: Chr20_29592427 G/A; S20081: Chr20_29608925 A/G; S20082: Chr20_29656009 G/A; S20083: Chr20_29675135 A/G; S20084: Chr20_29797545 A/T; S20085: Chr20_29800115 G/A; S20086: Chr20_29937723 G/A; S20087: Chr20_30027580 G/A; S20088: Chr20_30128509 T/C; S20089: Chr20_30210574 A/G; S20090: Chr20_30226970 G/T; S20091: Chr20_30415537 G/T; S20092: Chr20_30446476 A/C; S20093: Chr20_30468681 G/C; S20094: Chr20_30504515 C/G; S20095: Chr20_30615675 A/T; S20096: Chr20_30625171 C/A; S20097: Chr20_30755234 T/C; S20098: Chr20_30793925 C/T; S20099: Chr20_30818197 C/T; S20100: Chr20_30868263 G/A; S20101: Chr20_30945767 G/A; S20102: Chr20_31002409 G/T; S20103: Chr20_31025435 C/T; S20104: Chr20_31137575 A/G; S20105: Chr20_31153820 C/A; S20106: Chr20_31278084 C/T; S20107: Chr20_31337423 T/C; S20108: Chr20_31378405 C/T; S20109: Chr20_31417092 G/A; S20110: Chr20_31451903 T/A; S20111: Chr20_31503569 C/T; S20112: Chr20_31590291 G/A; S20113: Chr20_31667676 A/G; S20114: Chr20_31676441 C/T; S20115: Chr20_31824746 G/C; S20116: Chr20_31975416 C/T; S20117: Chr20_32161821 G/A; S20118: Chr20_32221251 A/G; S20119: Chr20_32230354 T/C; S20120: Chr20_32301061 T/C; S20121: Chr20_32377940 C/T; S20122: Chr20_32473342 A/G; S20123: Chr20_32525051 A/G; S20124: Chr20_32601336 G/A; S20125: Chr20_32766620 T/A; S20126: Chr20_32854838 C/T; S20127: Chr20_32974934 T/G; S20128: Chr20_33009358 T/C; S20129: Chr20_33117202 T/G; S20130: Chr20_33134327 G/A; S20131: Chr20_33203444 C/A; S20132: Chr20_33279583 T/C; S20133: Chr20_33380766 C/T; S20134: Chr20_33429114 G/A; S20135: Chr20_33504024 G/A; S20136: Chr20_33593731 T/G; S20137: Chr20_33664539 T/A; S20138: Chr20_33682709 A/G; S20139: Chr20_33730673 C/T; S20140: Chr20_33753554 T/C; S20141: Chr20_33798169 T/G; S20142: Chr20_33802894 G/C; S20143: Chr20_33871559 A/C; S20144: Chr20_33906854 A/C; S20145: Chr20_33927670 G/C; S20146: Chr20_33958248 G/C; S20147: Chr20_33997097 C/A; S20148: Chr20_34017305 T/C; S20149: Chr20_34026890 A/G; S20150: Chr20_34074523 C/T; S20151: Chr20_34078756 G/C; S20152: Chr20_34120495 G/A; S20153: Chr20_34129587 T/C; S20154: Chr20_34152864 G/A; S20155: Chr20_34183139 T/G; S20156: Chr20_34244236 G/A; S20157: Chr20_34258085 C/G; S20158: Chr20_34277931 T/G; S20159:

Chr20_34302257 G/T; S20160: Chr20_34327545 T/A; S20161: Chr20_34355124 T/C; S20162: Chr20_34389969 C/T; S20163: Chr20_34433864 A/G; S20164: Chr20_34450003 C/T; S20165: Chr20_34482682 T/A; S20166: Chr20_34502253 C/T; S20167: Chr20_34529976 G/A; S20168: Chr20_34553826 C/T; S20169: Chr20_34580637 A/G; S20170: Chr20_34605904 A/T; S20171: Chr20_34631184 T/G; S20172: Chr20_34650623 C/T; S20173: Chr20_34675420 A/G; S20174: Chr20_34703521 C/T; S20175: Chr20_34728961 G/A; S20176: Chr20_34757622 A/G; S20177: Chr20_34802649 G/A; S20178: Chr20_34825299 A/G; S20179: Chr20_34863851 G/A; S20180: Chr20_34876085 C/A; S20181: Chr20_34914983 A/G; S20182: Chr20_34926255 G/A; S20183: Chr20_34962497 G/A; S20184: Chr20_34977235 G/A; S20185: Chr20_35009808 A/G; S20186: Chr20_35026183 G/A; S20187: Chr20_35058025 T/C; S20188: Chr20_35076216 T/G; S20189: Chr20_35101716 T/C; S20190: Chr20_35139124 A/G; S20191: Chr20_35151397 T/C; S20192: Chr20_35175021 A/G; S20193: Chr20_35223825 G/A; S20194: Chr20_35227653 A/T; S20195: Chr20_35261306 G/A; S20196: Chr20_35278446 T/G; S20197: Chr20_35301668 G/A; S20198: Chr20_35352091 G/A; S20199: Chr20_35396383 C/A; S20200: Chr20_35407554 A/G; S20201: Chr20_35426826 T/C; S20202: Chr20_35458898 C/A; S20203: Chr20_35480916 C/A; S20204: Chr20_35505229 G/A; S20205: Chr20_35525574 C/G; S20206: Chr20_35550298 G/T; S20207: Chr20_35576957 C/T; S20208: Chr20_35603778 C/T; S20209: Chr20_35626667 G/A; S20210: Chr20_35682473 G/A; S20211: Chr20_35701728 C/A; S20212: Chr20_35733276 C/T; S20213: Chr20_35750653 T/G; S20214: Chr20_35810349 T/G; S20215: Chr20_35828042 G/C; S20216: Chr20_35852520 G/A; S20217: Chr20_35927617 T/C; S20218: Chr20_35953325 T/C; S20219: Chr20_35975492 C/T; S20220: Chr20_36011033 G/C; S20221: Chr20_36027516 G/A; S20222: Chr20_36052996 G/T; S20223: Chr20_36084338 A/G; S20224: Chr20_36100265 T/C; S20225: Chr20_36146230 A/T; S20226: Chr20_36152456 A/T; S20227: Chr20_36206573 T/C; S20228: Chr20_36235038 C/G; S20229: Chr20_36252317 T/G; S20230: Chr20_36281244 G/A; S20231: Chr20_36301215 T/G; S20232: Chr20_36334945 C/T; S20233: Chr20_36351399 T/G; S20234: Chr20_36385665 A/G; S20235: Chr20_36404709 A/C; S20236: Chr20_36428198 A/T; S20237: Chr20_36459602 T/G; S20238: Chr20_36484431 A/G; S20239: Chr20_36506899 C/T; S20240: Chr20_36525266 G/A; S20241: Chr20_36581362 C/T; S20242: Chr20_36601175 T/C; S20243: Chr20_36627124 C/T; S20244: Chr20_36653406 T/C; S20245: Chr20_36680890 T/C; S20246: Chr20_36700060 G/A; S20247: Chr20_36725432 A/C; S20248: Chr20_36779726 A/G; S20249: Chr20_36802296 G/A; S20250: Chr20_36831801 G/A; S20251: Chr20_36856754 A/T; S20252: Chr20_36877099 G/C; S20253: Chr20_36925562 G/T; S20254: Chr20_36951105 G/T; S20255: Chr20_36987986 A/G; S20256: Chr20_37005688 T/C; S20257: Chr20_37034068 A/G; S20258: Chr20_37050187 C/T; S20259: Chr20_37075639 T/C; S20260: Chr20_37101848 C/T; S20261: Chr20_37130798 G/A; S20262: Chr20_37167430 G/A; S20263: Chr20_37183935 A/C; S20264: Chr20_37201537 C/A; S20265: Chr20_37235915 G/A; S20266: Chr20_37251990 C/T; S20267: Chr20_37289147 G/T; S20268: Chr20_37304318 T/G; S20269: Chr20_37334502 G/C; S20270: Chr20_37350570 A/G; S20271: Chr20_37389877 A/G; S20272: Chr20_37405401 C/T; S20273: Chr20_37455088 T/C; S20274: Chr20_37479515 C/T; S20275: Chr20_37504668 G/T; S20276: Chr20_37528119 C/G; S20277: Chr20_37557651 T/A; S20278: Chr20_37580846 C/T; S20279: Chr20_37611475 G/A; S20280: Chr20_37638064 G/A; S20281: Chr20_37652141 C/T; S20282: Chr20_37719411 G/A; S20283: Chr20_37733858 T/G; S20284: Chr20_37756436 G/C; S20285: Chr20_37776497 A/C; S20286: Chr20_37805994 G/T; S20287: Chr20_37825516 T/C; S20288: Chr20_37850268 T/C; S20289: Chr20_37877485 G/A; S20290: Chr20_37901272 C/T; S20291: Chr20_37926904 G/A; S20292: Chr20_37956490 C/T; S20293: Chr20_37987980 G/C; S20294: Chr20_38021576 T/A; S20295: Chr20_38026292 A/G; S20296: Chr20_38051950 G/T; S20297: Chr20_38081111 T/A; S20298: Chr20_38100085 G/A; S20299: Chr20_38135465 A/G; S20300: Chr20_38155215 T/C; S20301: Chr20_38205572 A/G; S20302: Chr20_38273477 C/A; S20303: Chr20_38292951 A/G; S20304: Chr20_38318011 C/T; S20305: Chr20_38335608 A/G; S20306: Chr20_38365200 A/C; S20307: Chr20_38383336 T/C; S20308: Chr20_38420045 A/G; S20309: Chr20_38430419 G/T; S20310: Chr20_38458539 T/C; S20311: Chr20_38522687 T/A; S20312: Chr20_38545201 T/G; S20313: Chr20_38550104 A/G; S20314: Chr20_38587257 G/A; S20315: Chr20_38608520 A/G; S20316: Chr20_38645659 G/A; S20317: Chr20_38650339 G/A; S20318: Chr20_38727587 C/T; S20319: Chr20_38751759 G/T; S20320: Chr20_38777204 T/G; S20321: Chr20_38801931 G/A; S20322: Chr20_38864763 T/C; S20323: Chr20_38907078 A/T; S20324: Chr20_38933919 A/T; S20325: Chr20_38974774 A/G; S20326: Chr20_38979111 C/T; S20327: Chr20_39017498 T/A; S20328: Chr20_39053499 C/T; S20329: Chr20_39078734 C/G; S20330: Chr20_39111855 T/G; S20331: Chr20_39128867 C/T; S20332: Chr20_39154016 A/G; S20333: Chr20_39202149 A/G; S20334: Chr20_39235337 A/G; S20335: Chr20_39251402 C/A; S20336: Chr20_39275104 A/G; S20337: Chr20_39301269 T/C; S20338: Chr20_39327310 T/C; S20339: Chr20_39350113 T/A; S20340: Chr20_39385023 G/C; S20341: Chr20_39405197 C/T; S20342: Chr20_39428668 C/T; S20343: Chr20_39453136 C/T; S20344: Chr20_39493065 T/A; S20345: Chr20_39500345 C/T; S20346: Chr20_39531946 A/C; S20347: Chr20_39589387 C/T; S20348: Chr20_39604945 T/C; S20349: Chr20_39630375 G/A; S20350: Chr20_39650111 C/T; S20351: Chr20_39680045 G/A; S20352: Chr20_39706382 T/G; S20353: Chr20_39726636 T/G; S20354: Chr20_39751814 G/A; S20355: Chr20_39790357 G/A; S20356: Chr20_39804202 A/G; S20357: Chr20_39830489 C/T; S20358: Chr20_39851825 C/T; S20359: Chr20_39875486 T/A; S20360:

Chr20_39903345 G/A; S20361: Chr20_39926016 G/A; S20362: Chr20_39950035 G/A; S20363: Chr20_40007957 A/G; S20364: Chr20_40028104 C/G; S20365: Chr20_40054170 C/T; S20366: Chr20_40075715 C/A; S20367: Chr20_40105233 C/G; S20368: Chr20_40134300 A/C; S20369: Chr20_40159722 A/C; S20370: Chr20_40182367 G/A; S20371: Chr20_40211114 T/C; S20372: Chr20_40275226 G/A; S20373: Chr20_40365176 G/A; S20374: Chr20_40385478 T/C; S20375: Chr20_40501012 C/T; S20376: Chr20_40549190 T/G; S20377: Chr20_40554137 G/C; S20378: Chr20_40576133 C/A; S20379: Chr20_40605901 C/T; S20380: Chr20_40640647 G/A; S20381: Chr20_40650878 C/T; S20382: Chr20_40681899 A/G; S20383: Chr20_40725804 G/A; S20384: Chr20_40757489 G/A; S20385: Chr20_40820870 G/A; S20386: Chr20_40856365 G/C; S20387: Chr20_40877765 C/T; S20388: Chr20_40924096 C/T; S20389: Chr20_40937949 T/C; S20390: Chr20_40969090 T/A; S20391: Chr20_40984801 A/G; S20392: Chr20_41000529 C/G; S20393: Chr20_41026009 G/A; S20394: Chr20_41065393 T/C; S20395: Chr20_41089460 A/G; S20396: Chr20_41101939 G/A; S20397: Chr20_41125158 A/G; S20398: Chr20_41159295 A/G; S20399: Chr20_41194444 A/C; S20400: Chr20_41204706 C/T; S20401: Chr20_41239819 A/T; S20402: Chr20_41254187 C/G; S20403: Chr20_41278396 A/G; S20404: Chr20_41303102 C/T; S20405: Chr20_41332228 C/A; S20406: Chr20_41364163 G/A; S20407: Chr20_41377212 G/T; S20408: Chr20_41402482 G/A; S20409: Chr20_41426357 C/T; S20410: Chr20_41470056 C/T; S20411: Chr20_41519089 G/A; S20412: Chr20_41530556 T/G; S20413: Chr20_41565514 G/A; S20414: Chr20_41575282 A/C; S20415: Chr20_41612322 C/G; S20416: Chr20_41680974 G/A; S20417: Chr20_41704905 T/G; S20418: Chr20_41762854 G/A; S20419: Chr20_41782778 A/T; S20420: Chr20_41834658 C/A; S20421: Chr20_41867235 G/A; S20422: Chr20_41883841 G/A; S20423: Chr20_41911571 G/A; S20424: Chr20_41927172 G/C; S20425: Chr20_41962204 A/T; S20426: Chr20_41981063 G/T; S20427: Chr20_42024476 A/G; S20428: Chr20_42041117 G/T; S20429: Chr20_42058590 C/T; S20430: Chr20_42083562 C/T; S20431: Chr20_42106157 C/T; S20432: Chr20_42129155 G/C; S20433: Chr20_42152117 G/A; S20434: Chr20_42180115 G/T; S20435: Chr20_42203876 C/A; S20436: Chr20_42233295 G/A; S20437: Chr20_42262999 A/G; S20438: Chr20_42279852 C/T; S20439: Chr20_42329954 T/C; S20440: Chr20_42353547 G/A; S20441: Chr20_42380467 C/G; S20442: Chr20_42406087 T/A; S20443: Chr20_42429795 C/T; S20444: Chr20_42460444 A/G; S20445: Chr20_42482953 G/C; S20446: Chr20_42533528 T/C; S20447: Chr20_42552365 T/A; S20448: Chr20_42602487 T/C; S20449: Chr20_42628338 C/T; S20450: Chr20_42665897 T/G; S20451: Chr20_42685613 C/T; S20452: Chr20_42719079 A/G; S20453: Chr20_42726921 A/G; S20454: Chr20_42761316 C/A; S20455: Chr20_42780643 T/A; S20456: Chr20_42800295 C/A; S20457: Chr20_42825553 G/T; S20458: Chr20_42868031 T/C; S20459: Chr20_42880576 C/T; S20460: Chr20_42907304 G/C; S20461: Chr20_42925208 T/C; S20462: Chr20_42965482 G/T; S20463: Chr20_42997045 A/C; S20464: Chr20_43006921 G/A; S20465: Chr20_43033812 T/A; S20466: Chr20_43072556 G/A; S20467: Chr20_43097335 G/C; S20468: Chr20_43103154 C/T; S20469: Chr20_43138432 G/A; S20470: Chr20_43158972 A/G; S20471: Chr20_43181855 T/A; S20472: Chr20_43216182 T/C; S20473: Chr20_43286952 A/G; S20474: Chr20_43309033 T/A; S20475: Chr20_43333610 C/T; S20476: Chr20_43360955 A/T; S20477: Chr20_43375019 G/T; S20478: Chr20_43400781 C/G; S20479: Chr20_43427903 A/G; S20480: Chr20_43451405 G/T; S20481: Chr20_43486380 A/G; S20482: Chr20_43507346 T/C; S20483: Chr20_213525748 G/A; S20484: Chr20_43614265 A/G; S20485: Chr20_43637162 A/G; S20486: Chr20_43676703 T/A; S20487: Chr20_43706827 T/C; S20488: Chr20_43732208 G/T; S20489: Chr20_43757258 A/T; S20490: Chr20_43783169 A/G; S20491: Chr20_43804681 G/A; S20492: Chr20_43836535 G/A; S20493: Chr20_43853063 A/G; S20494: Chr20_43887733 A/G; S20495: Chr20_43921707 G/A; S20496: Chr20_43941844 C/A; S20497: Chr20_43964097 T/C; S20498: Chr20_43989218 G/C; S20499: Chr20_44003388 G/T; S20500: Chr20_44044310 C/T; S20501: Chr20_44060915 C/G; S20502: Chr20_44090033 G/A; S20503: Chr20_44106133 G/T; S20504: Chr20_44142345 T/C; S20505: Chr20_44168873 A/G; S20506: Chr20_44182474 C/T; S20507: Chr20_44200336 C/T; S20508: Chr20_44237011 C/T; S20509: Chr20_44254665 C/T; S20510: Chr20_44285161 C/T; S20511: Chr20_44303846 A/G; S20512: Chr20_44327415 A/C; S20513: Chr20_44354378 A/C; S20514: Chr20_44377869 G/A; S20515: Chr20_44407089 T/C; S20516: Chr20_44430226 C/T; S20517: Chr20_44451396 C/T; S20518: Chr20_44478825 C/A; S20519: Chr20_44501019 A/G; S20520: Chr20_44540434 A/T; S20521: Chr20_44565015 A/G; S20522: Chr20_44578453 A/C; S20523: Chr20_44604545 T/A; S20524: Chr20_44625275 T/C; S20525: Chr20_44685396 T/A; S20526: Chr20_44712297 A/T; S20527: Chr20_44730738 G/A; S20528: Chr20_44754432 C/G; S20529: Chr20_44784324 A/G; S20530: Chr20_44807903 T/C; S20531: Chr20_44828994 G/A; S20532: Chr20_44862758 G/A; S20533: Chr20_44883487 T/G; S20534: Chr20_44911039 A/G; S20535: Chr20_44933435 A/G; S20536: Chr20_44959479 G/A; S20537: Chr20_44978868 C/A; S20538: Chr20_45000326 C/T; S20539: Chr20_45025309 C/G; S20540: Chr20_45051284 C/T; S20541: Chr20_45084202 A/T; S20542: Chr20_45108986 T/G; S20543: Chr20_45139632 T/C; S20544: Chr20_45152900 T/A; S20545: Chr20_45187416 G/C; S20546: Chr20_45204661 T/C; S20547: Chr20_45235280 G/A; S20548: Chr20_45262779 T/G; S20549: Chr20_45275520 C/T; S20550: Chr20_45312720 C/T; S20551: Chr20_45340883 C/T; S20552: Chr20_45351776 C/T; S20553: Chr20_45388940 C/G; S20554: Chr20_45400227 C/G; S20555: Chr20_45428753 A/G; S20556: Chr20_45474895 G/T; S20557: Chr20_45475930 G/A; S20558: Chr20_45500896 A/G; S20559: Chr20_45539232 A/C; S20560: Chr20_45550116 T/C; S20561:

Chr20_45575644 G/A; S20562: Chr20_45605462 C/G; S20563: Chr20_45628186 A/T; S20564: Chr20_45655266 G/A; S20565: Chr20_45677308 T/C; S20566: Chr20_45700759 G/A; S20567: Chr20_45734560 T/G; S20568: Chr20_45753560 A/T; S20569: Chr20_45784422 C/A; S20570: Chr20_45801421 T/A; S20571: Chr20_45831365 A/G; S20572: Chr20_45852714 T/C; S20573: Chr20_45880350 T/C; S20574: Chr20_45904952 G/C; S20575: Chr20_45926858 C/G; S20576: Chr20_45952408 C/T; S20577: Chr20_45975031 A/G; S20578: Chr20_46001841 G/A; S20579: Chr20_46032216 C/A; S20580: Chr20_46070349 T/A; S20581: Chr20_46108379 G/A; S20582: Chr20_46128429 T/C; S20583: Chr20_46165965 A/G; S20584: Chr20_46196615 G/A; S20585: Chr20_46206427 T/C; S20586: Chr20_46227244 G/C; S20587: Chr20_46260059 A/G; S20588: Chr20_46275367 C/T; S20589: Chr20_46301478 T/A; S20590: Chr20_46325006 A/G; S20591: Chr20_46352566 A/T; S20592: Chr20_46381757 T/C; S20593: Chr20_46418756 A/G; S20594: Chr20_46431733 A/T; S20595: Chr20_46450866 T/C; S20596: Chr20_46481302 A/G; S20597: Chr20_46503748 T/C; S20598: Chr20_46553853 C/T; S20599: Chr20_46579463 T/G; S20600: Chr20_46601171 G/A; S20601: Chr20_46625010 A/G; S20602: Chr20_46659014 C/A; S20603: Chr20_46675415 C/T; S20604: Chr20_46703874 T/A; S20605: Chr20_46744870 G/A; S20606: Chr20_46782443 G/A; S20607: Chr20_216802522 G/A; S20608: Chr20_46825298 C/T; S20609: Chr20_46860748 A/T; S20610: Chr20_46879741 A/T; S20611: Chr20_46905958 A/T; S20612: Chr20_46929944 T/C; S20613: Chr20_46951448 T/A; S20614: Chr20_46981555 T/G; S20615: Chr20_47000944 T/G; S20616: Chr20_47026395 G/A; S20617: Chr20_47050203 G/T; S20618: Chr20_47079980 A/G; S20619: Chr20_47104666 A/G; S20620: Chr20_47125714 C/T; S20621: Chr20_47156438 T/C; S20622: Chr20_47176109 C/T; S20623: Chr20_47209850 C/T; S20624: Chr20_47231043 A/T; S20625: Chr20_47267615 C/T; S20626: Chr20_47277493 C/A; S20627: Chr20_47304026 C/T; S20628: Chr20_47332686 C/T; S20629: Chr20_47355516 A/T; S20630: Chr20_47387960 G/A; S20631: Chr20_47408465 T/A; S20632: Chr20_47434149 T/C; S20633: Chr20_47454286 C/T; S20634: Chr20_47480812 T/C; S20635: Chr20_47534635 T/C; S20636: Chr20_47565461 T/C; S20637: Chr20_47576274 T/A; S20638: Chr20_47602009 T/A; S20639: Chr20_47638103 T/C; S20640: Chr20_47651694 G/A; S20641: Chr20_47675487 G/A; S20642: Chr20_47703018 T/A; S20643: Chr20_47737448 T/A; S20644: Chr20_47754389 A/G; S20645: Chr20_47800065 T/A; S20646: Chr20_47825341 T/C; S20647: Chr20_47892164 C/A; S20648: Chr20_47901325 C/T;

A set of probes for detecting the combination of soybean whole genome SNP loci.

A gene chip for detecting the combination soybean whole genome SNP loci, wherein the gene chip is a liquid-phase chip containing a set of nucleotide probes for detecting the SNP loci.

Furthermore, the solution system of the liquid-phase chip is nuclease-free water, and the concentration of the probes in the solution system is 60 ng/μL.

Use of the combination of soybean whole genome SNP loci in preparation of a soybean whole genome SNP gene chip.

Use of the combination of soybean whole genome SNP loci in any one of marker-assisted major gene selection, backcross breeding and its background selection, molecular assisted breeding, whole genome breeding, seed purity detection, transgenic component identification, genome-wide association study, QTL analysis, species evolution analysis, and germplasm resource identification.

Use of the probes in preparation of a soybean whole genome SNP gene chip.

Use of the probes in any one of marker-assisted major gene selection, backcross breeding and its background selection, molecular assisted breeding, whole genome breeding, seed purity detection, transgenic component identification, genome-wide association study, QTL analysis, species evolution analysis, and germplasm resource identification.

Use of the gene chip in genome-wide association study, molecular assisted breeding or whole genome breeding.

Use of the gene chip in any one of marker-assisted major gene selection, backcross breeding and its background selection, seed purity detection, transgenic component identification, QTL analysis, species evolution analysis, and germplasm resource identification.

Compared with the prior art, the present invention attains the following beneficial effects:

1. Most of the marker loci selected for the gene chip in the present invention are functionally associated loci, and preferably functional markers such as GWAS and QTL, etc. are selected.
2. The 20,648 SNP markers used in the present invention are evenly distributed on the chromosomes in the soybean genome, with 1.1 Mb maximum distance, 205 bp minimum distance, and 46 kb average distance between the markers; thus, there will be no loss of loci when the present invention is applied to QTL positioning and GWAS analysis, etc.
3. The gene chip provided by the present invention has extremely high coverage on functional genes, the SNP marker loci cover 17,096 functional genes of soybean, accounting for about 31% of the total number of soybean genes, and the SNP marker loci are located in gene coding regions. Among the 20,648 SNP marker loci, 17,588 SNP marker loci are located on genes, accounting for 85% of the total number of the SNP marker loci. Therefore, when those SNP marker loci are applied in molecular assisted breeding or whole genome selective breeding, they can accelerate the breeding process.
4. The gene chip provided by the present invention employs genotyping by target sequencing (GBTS) as the latest marker genotyping, which has the advantages of low cost, high accuracy, and high detection sensitivity, etc.

DETAILED DESCRIPTION

Figure 1:
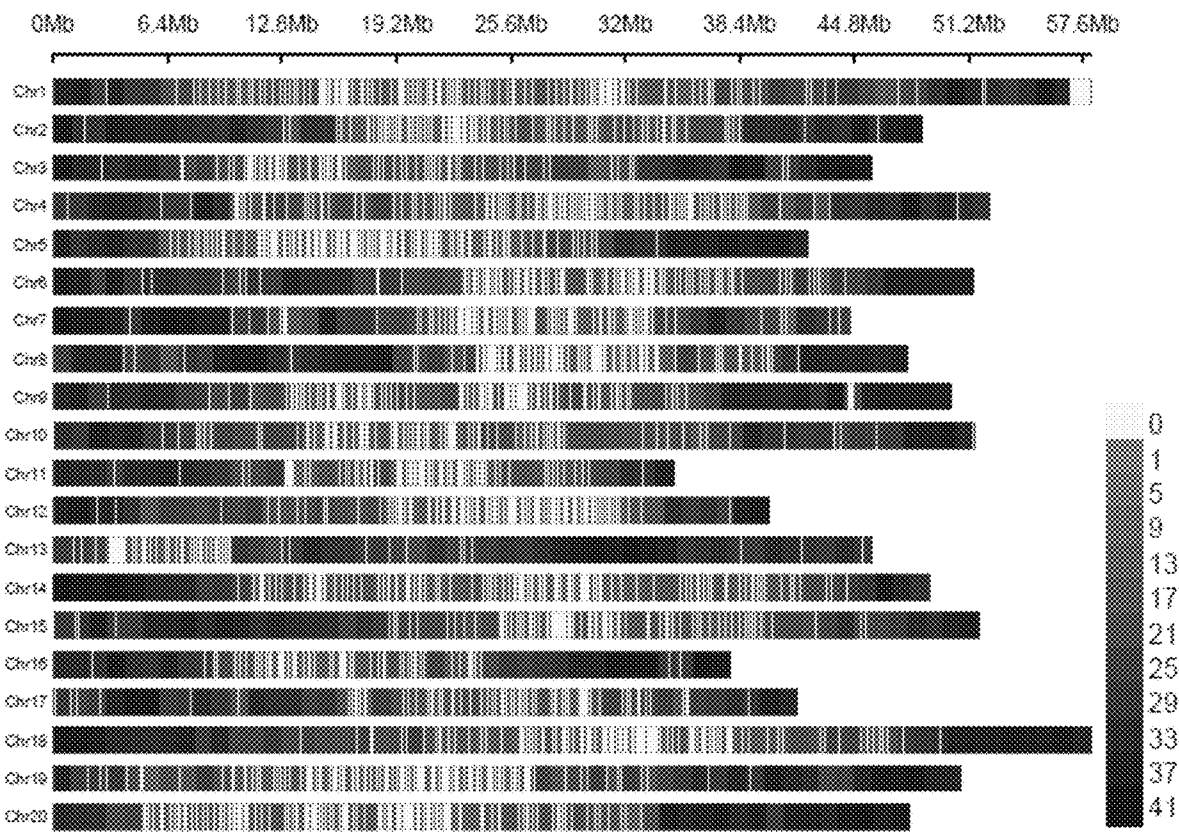
FIG. 1 shows the distribution of the 20,648 SNP loci in the soybean whole genome.

Hereunder the present invention will be further detailed in embodiments.

Embodiment 1

A combination of soybean whole genome SNP marker loci, including 20,648 SNP loci, each of SNP marker loci includes two different nucleotide variation positions for detecting allelic changes of the locus, wherein the physical positions of the 20,648 SNP loci are determined on the basis of the whole genome sequence alignment of soybean variety Williams82, the version number of the whole genome sequence of the soybean variety Williams82 is *Glycine max* Wm82.a2.v1, the whole genome sequence of the soybean variety Williams82 can be obtained from the website phytozome.jgi.doe.gov; the 20,648 SNP loci are shown as S00001-20648 in the section Summary.

In this embodiment, the combination of soybean whole genome SNP marker loci (i.e., 20,648 SNP loci) is derived from the information of whole genome resequencing and related GWAS loci of 270 cultivated soybean varieties, and is obtained with the following method:

1) Sample collection and acquisition: 270 core soybean germplasm resources were sown in an experimental field of Northeast Institute of Geography and Agroecology, Chinese Academy of Sciences and tendered normally in 2018; the data of ten important agronomic traits, including plant height, grain weight per hundred, bottom pod height, number of seeds per plant, number of pods per plant, weight of seeds per plant, number of main stem nodes, number of branches, fat content and protein content, were obtained.
2) SNP testing: high-quality soybean genomic DNAs were extracted from young leaves of V4 stage soybeans with a CTAB method. The DNAs were used for genome resequencing, the high-quality clean data volume obtained in sequencing was 8,100 Gb, with an average of 30 G per sample, and the sequencing depth was about 30 times; the sequencing data was compared with a reference soybean genome (version number: *Glycine max* Wm82.a2.v1) by means of BWA software, and was processed with PICARD software for deduplication, then high-quality SNP loci were obtained with GATK software; the SNP testing result was annotated with ANNORVAR software.
3) Genome-wide association study: genome-wide association study was carried out for the obtained SNP marker loci with measured phenotype information with TASSEL analytical software in a mixed linear model.
4) Acquisition of 20 K loci: the 20 K marker loci were acquired from the genes with genotype deletion lower than 20%, heterozygous genotypes less than 30%, maximum allele frequency lower than 95%, and minimum allele frequency higher than 5% in the 270 cultivated soybean varieties, by selecting the GWAS marker loci preferably, and then selecting the markers in the gene coding regions, in a manner of selecting one marker in every 25 kb; or selecting markers in non-coding regions if neither of the two types of markers was found in continuous 75 kb; finally, 20,648 SNP marker loci were obtained, among which 17,588 markers were located on functional genes, covering 31% of soybean coding genes; and the SNP molecular markers were evenly distributed, with an average inter-marker distance of 46 kb.

Embodiment 2

Use of the soybean whole genome SNP marker locus combination in genome-wide association study, including the following steps:

1. Genotyping

Based on the 20,648 SNP loci obtained in the embodiment 1, probes were designed and a liquid-phase gene chip for detecting the 20,648 SNP loci was prepared; the 20,648 SNP marker loci of the 270 main varieties were detected with the liquid-state chip utilizing genotyping by target sequencing (GBTS), and the density of distribution of the 20,648 SNP marker loci on the chromosomes was analyzed. The result of analysis is shown in FIG. 1. The 20,648 SNP marker loci were used as a genotype file for building up a genome selection model.

2. Phenotyping

Ten agronomic traits of the 270 main soybean varieties, including plant height, grain weight per hundred, bottom pod height, number of seeds per plant, number of pods per plant, weight of seeds per plant, number of main stem nodes, number of branches, fat content, and protein content, were detected and used as a phenotype input file for building up a genome selection model. The ten agronomic traits were detected with the following methods:

Plant height: the length from the ground surface to the apical growing point of the main stem was measured.

Grain weight per hundred: 100 well-developed seeds were taken randomly and weighed to 0.01 g accuracy, and the weight was converted to weight of seed with 13% moisture content.

Bottom pod height: the length from the ground surface to the first effective pod was measured.

Number of seeds per plant: the number of effective seeds per plant was counted.

Number of pods per plant: the number of effective pods per plant was counted.

Weight of seeds per plant: the weight of effective seeds per plant was counted.

Number of main stem nodes: the actual number of nodes from the cotyledonary node to the top of the main stem (excluding the top inflorescence) was counted.

Number of branches: the number of first-level branches with one or more nodes and pods was counted.

Fat content: the crude fat content in soybean was detected with the near-infrared technique.

Protein content: the crude protein content in soybean was detected with the near-infrared technique.

3. Building Up a Whole Genome Selection Model and Obtaining Marker Effects

The 20,648 SNP marker loci were used as genotypes, together with the 10 detected phenotypic values of soybean traits, to build up a whole genome selection model for each trait, then the effect size of each SNP marker locus in the obtained 20,648 SNP marker loci on the traits was analyzed.

4. Screening Dominant Alleles and Obtaining the Association Between Phenotypic Traits and Dominant Alleles The first 300 dominant alleles in the ranking of the absolute values of the marker effects associated to each of the 10 traits were analyzed and obtained by utilizing whole genome selection, i.e., 300 dominant alleles associated to each phenotypic trait were obtained, altogether 3,000 dominant alleles were obtained for the 10 phenotypic traits; the result of association was as follows:

The dominant alleles were represented in the form of chromosome number_physical position_dominant genotype;

The obtained 300 dominant alleles associated to protein content were as follows:

Chr01_1533882_G; Chr01_49903973_A; Chr01_52980806_T; Chr01_53127107_C; Chr01_53884130_A; Chr01_54065323_T; Chr01_7375671_G; Chr02_15034734_G; Chr02_2729755_G; Chr02_3231033_G; Chr02_351278_C; Chr02_43594093_T; Chr02_43779773_A; Chr02_44041696_C; Chr02_5225452_S; Chr02_6300927_S; Chr03_18107159_G; Chr03_1968306_G; Chr03_31175433_A; Chr03_36421392_G; Chr03_36426626_S; Chr03_36451021_A; Chr03_36504983_A; Chr03_36789422_C; Chr03_37484920 Chr03_37706557_A; Chr03_42802419_A; Chr03_45659041_S; Chr03_45778731_A; Chr03_6235821_A; Chr03_7454850_G; Chr03_8686487_T; Chr04_11425102_A; Chr04_3350250_A; Chr04_44202428_G; Chr04_45575047_T; Chr04_5155506_C; Chr04_5432335_C; Chr04_5784670_G; Chr04_5839404_A; Chr04_6151552_G; Chr04_6380579_G; Chr04_8354618_G; Chr04_8375562_C; Chr04_8460910_G; Chr04_8520847_G; Chr04_8569889_J; Chr04_8577960_A; Chr04_8600187_T; Chr04_8627986_T; Chr04_874413 LC; Chr04_8834618_G; Chr05_16077781_G; Chr05_18929941_T; Chr05_22058564_G; Chr05_22500310_G; Chr05_24544617_T; Chr05_2612793_G; Chr05_2667653_G; Chr05_33002251_G; Chr05_34110946_A; Chr05_3531115_G; Chr05_3614833_A; Chr05_3814056_A; Chr05_40476259_G; Chr05_41165218_A; Chr05_41175611_S; Chr05_41213590_A; Chr05_41231598_C; Chr05_41330573_A; Chr05_41586392_A; Chr05_41626230_C; Chr05_9750287_A; Chr06_1052684_G; Chr06_10988551_T; Chr06_11002280_A; Chr06_1129202_A; Chr06_1150126_T; Chr06_1203733_A; Chr06_1230529_J; Chr06_1280468_J; Chr06_13412419_T; Chr06_13906051_G; Chr06_1404953_T; Chr06_15643320_T; Chr06_15968336_A; Chr06_17154269_A; Chr06_17279302_G; Chr06_17382650_T; Chr06_17425051_T; Chr06_17582094_G; Chr06_17602402_J; Chr06_17626369_T; Chr06_19251651_T; Chr06_19275883_S; Chr06_2100577_J; Chr06_2158432_G; Chr06_23410068_A; Chr06_26741334_S; Chr06_27625128_G; Chr06_28928355_T; Chr06_3286909_C; Chr06_42252843_J; Chr06_4241219_G; Chr06_4298131_S; Chr06_46800208_A; Chr06_48019540_G; Chr06_48242356_S; Chr06_5453753_S; Chr06_5549522_A; Chr06_5606322_G; Chr06_5631221_G; Chr06_5766823_S; Chr06_6036370_A; Chr06_6078531_G; Chr06_6100733_C; Chr06_6134887_A; Chr06_6321130_G; Chr06_6479162_T; Chr06_7825328_T; Chr07_1952143_S; Chr07_30100016_A; Chr07_43276630_T; Chr07_5825087_S; Chr07_7200900_G; Chr08_10706589_G; Chr08_1130502_T; Chr08_12126511_S; Chr08_2781099_A; Chr08_3440456_S; Chr08_3450747_G; Chr08_35225469_T; Chr08_4201119_G; Chr08_42760680_S; Chr08_42904239_S; Chr08_44611328_J; Chr08_44625940_C; Chr09_1128170_T; Chr09_2288589_A; Chr09_3165826_G; Chr09_34552898_S; Chr09_40052962_A; Chr09_40110685_A; Chr09_40375594_T; Chr09_40442407_S; Chr09_40496435_A; Chr09_40521623_S; Chr09_41311400_C; Chr09_41558984_A; Chr09_41576646_T; Chr09_41601643_J; Chr09_41676859_G; Chr09_41801924_S; Chr09_4265011_T; Chr09_4301068_A; Chr09_4350271_T; Chr09_6653411_A; Chr09_925073_G; Chr10_1707438_T; Chr10_1903082_C; Chr10_1925335_A; Chr10_31900041_C; Chr10_331641_T; Chr10_40494875_G; Chr10_40614858_A; Chr10_42363621_A; Chr10_44777383_A; Chr10_4603708_G; Chr10_4651103_C; Chr11_25760860_G; Chr11_2630521_T; Chr11_30915295_A; Chr12_1375187_G; Chr12_13801369_A; Chr12_28860710_G; Chr12_30506847_A; Chr12_34675137_J; Chr12_34775228_T; Chr12_34851455_G; Chr12_34879829_A; Chr12_34904656_J; Chr12_34941924_C; Chr12_34957065_S; Chr12_35042749_S; Chr12_36736475_G; Chr12_39279749_G; Chr13_11958884_G; Chr13_19460489_T; Chr13_33375272_A; Chr13_33484893_T; Chr13_41807124_G; Chr13_42807826_A; Chr13_43526500_C; Chr13_44000635_T; Chr13_44130508_T; Chr14_11149332_G; Chr14_17429157_T; Chr14_18526221_A; Chr14_19325560_G; Chr14_46775040_S; Chr14_48228754_J; Chr14_48354923_C; Chr14_4978437_G; Chr15_11284233_G; Chr15_11305323_T; Chr15_11441207_C; Chr15_11495305_J; Chr15_11522371_G; Chr15_16227486_A; Chr15_17173057_T; Chr15_2204583_A; Chr15_2263175_T; Chr15_2277272_C; Chr15_2313354_C; Chr15_2328756_J; Chr15_2350482_G; Chr15_2377885_A; Chr15_2403039_A; Chr15_2428037_J; Chr15_2450413_S; Chr15_2475536_G; Chr15_2528392_T; Chr15_2555770_T; Chr15_2577240_G; Chr15_2608939_C; Chr15_2629768_J; Chr15_2701601_C; Chr15_3239056_J; Chr15_3258659_G; Chr15_3438388_A; Chr15_3450565_G; Chr15_3545424_S; Chr15_3588197_S: Chr15_3630889_G; Chr15_3660345_S; Chr15_3900110_G; Chr15_43522418_A; Chr16_1250592_G; Chr16_19023503_T; Chr16_21093217_G; Chr16_33950384_A; Chr16_37839002_C; Chr16_4075059_A; Chr16_4277748_T; Chr16_8176834_S; Chr17_12107006_J; Chr17_15230298_G; Chr17_15250595_A; Chr17_15312678_T; Chr17_15464503_C; Chr17_15844951_G; Chr17_1680401_A; Chr17_2078415_A; Chr17_2513973_T;

Chr17_40828186_T; Chr17_79273283; Chr17_8286360_G; Chr17_8312752_A; Chr17_8350510_C; Chr17_8623316_C; Chr17_8625406_T; Chr17_8654251_T; Chr17_9779938_G; Chr17_9838390_A; Chr18_48297982_T; Chr18_48840921_A; Chr18_53504757_G; Chr18_53624805_C; Chr18_53640248_G; Chr18_54801747_G; Chr18_54937497_S; Chr18_55329576_T; Chr18_55604880_G; Chr18_55727744_C; Chr18_55800924_G; Chr18_56025108_S; Chr18_56085636_A; Chr18_56405126_T; Chr18_7758619_G; Chr18_8352588_C; Chr18_8671202_G; Chr19_177534_T; Chr19_19650255_T; Chr19_30793330_T; Chr19_34843169_C; Chr19_34880091_S; Chr19_38633264_S; Chr19_40127559_S; Chr19_49168972_T; Chr19_50409329_T; Chr19_5221_S; Chr19_7542341_G; Chr20_1407347_T; Chr20_1624381_A; Chr20_1844099_C; Chr20_1894103_S; Chr20_1907880_G; Chr20_1980332_A; Chr20_23328397_A; Chr20_46744870_A.

The obtained 300 dominant alleles associated to the number of pods per plant were as follows: Chr01_2300212_C; Chr01_2350193_A; Chr01_38755673_G; Chr01_39306935_A; Chr01_39573984_T; Chr01_39860894_T; Chr01_4026903_G; Chr01_4050717_A; Chr01_4092615_G; Chr01_4125368_C; Chr01_50431852_S; Chr01_51134158_T; Chr01_52980806_A; Chr01_54252843_C; Chr01_7677753_C; Chr02_11276103_A; Chr02_13151764_A; Chr02_13979499_T; Chr02_14349056_S; Chr02_40831974 A, Chr02_40859063_S; Chr02_40977632_G; Chr02_42953049_S; Chr02_42977015_T; Chr02_43011936_C; Chr02_43559616_G; Chr02_43890012_A; Chr02_47227119_A; Chr02_47525859_A; Chr02_48012289_A; Chr02_6387459_G; Chr03_1004948_A; Chr03_2202492_S; Chr03_2357646_A; Chr03_2488291_G; Chr03_2531823_C; Chr03_28656001_S; Chr03_29000132_S; Chr03_3355927_A; Chr03_3403141_G; Chr03_35877582_G; Chr03_38305381_A; Chr03_44668318_T; Chr03_44850673_S; Chr04_11186208_A; Chr04_11656669_S; Chr04_12039123_A; Chr04_12897766_S; Chr04_12991694_G; Chr04_13145679_G; Chr04_13913892_G; Chr04_16473219_G; Chr04_44202428_G; Chr04_44612012_C; Chr04_446251613; Chr04_45234196_G; Chr04_45498316_A; Chr04_45546221_G; Chr04_45569116_A; Chr04_45658472_G; Chr04_46559968_S; Chr04_46582419_T; Chr04_46682467_C; Chr04_47254706_S; Chr04_49451089_G; Chr04_49625290_S; Chr04_51134738_C; Chr04_5276150_T; Chr06_10505562_A; Chr06_10988551_T; Chr06_11002280_A; Chr06_11029572_G; Chr06_12157998_T; Chr06_12185351_C; Chr06_12381008_T; Chr06_12937960_A; Chr06_12977788_T; Chr06_13202926_A; Chr06_14058279_3; Chr06_15681367_G; Chr06_17279302_A; Chr06_19445340_A; Chr06_20963053_G; Chr06_2636926_S; Chr06_3132988_T; Chr06_3226536_A; Chr06_3264626_G; Chr06_3286909_T; Chr06_3315550_G; Chr06_3353659_G; Chr06_3403481_T; Chr06_3453914_T; Chr06_3510973_T; Chr06_4134589_A; Chr06_4157597_G; Chr06_47814558_C; Chr06_48026477 Chr06_50975144_G; Chr06_51002402_J; Chr06_51051522_A; Chr07_14784346_A; Chr07_18525025_A; Chr07_19025998_T; Chr07_19051769_G; Chr07_19475119_G; Chr07_24050419_T; Chr07_26125231_T; Chr07_27325378_A; Chr07_29725064_T; Chr07_29876789_T; Chr07_30473399_A; Chr07_42658523_G; Chr07_6026285_G; Chr07_8226456_G; Chr07_8425687_S; Chr08_1028572_A; Chr08_3777218_S; Chr08_3801869_G; Chr08_43328129_G; Chr08_46056956_J; Chr08_46384244_G; Chr08_46400699_G; Chr08_46442484_S; Chr08_47002324_S; Chr08_47351566_T; Chr08_47407551_A; Chr08_47512843_C; Chr08_47581457_T; Chr08_47621530_G; Chr08_47707980_A; Chr08_47755831_A; Chr08_5075393_T; Chr08_734307_T; Chr08_776002_T; Chr08_920550_S; Chr08_928095_A; Chr09_38588298_S; Chr09_38843968_T; Chr09_39350396_S; Chr09_46327123_C; Chr09_46478149_T; Chr09_46571264_A; Chr09_46589096_T; Chr09_46836433_A; Chr09_49551816_A; Chr10_10070324_S; Chr10_12834195_5; Chr10_13087478_S; Chr10_27371513_S; Chr10_47847000_S; Chr10_48035532_T; Chr10_48180671_C; Chr10_49000046_C; Chr10_49384169_A; Chr11_31769637_A; Chr11_32376132_G; Chr11_32402605_T; Chr11_32929777_S; Chr12_10274010_1; Chr12_10407336_G; Chr12_33050531_S; Chr12_33110525_A; Chr12_33133696_S; Chr12_34637037_G; Chr12_36276063_S; Chr12_3659899_G; Chr12_36704530_S; Chr12_36736475_A; Chr12_36765947_G; Chr12_3680545_A; Chr12_36915547_A; Chr12_36928914_A; Chr12_36950212_S; Chr12_36994675_S; Chr12_37028027_G; Chr12_37955440_A; Chr12_9535497_J; Chr12_9597784_S; Chr12_9635671_J; Chr12_9673552_C; Chr12_9675105_G; Chr12_9732837_C; Chr12_9797751_A; Chr12_9900671_S; Chr12_9948509_S; Chr13_13759456_T; Chr13_14089920_G; Chr13_14129219_A; Chr13_14478389_G; Chr13_14630892_A; Chr13_14675637_G; Chr13_18426640_A; Chr13_18454726_A; Chr13_18615062_S; Chr13_21735193_C; Chr13_21768219_G; Chr13_21775204_G; Chr13_21850726_A; Chr13_28830306_G; Chr13_28885832_S; Chr13_31341468_A; Chr13_31550833_G; Chr13_31853369_T; Chr13_32461178_A; Chr13_41157822_G; Chr13_42111517_J; Chr13_42325942_G; Chr13_42383660_A; Chr13_42410927_G; Chr13_42496589_S; Chr14_1410232_C; Chr14_4604584_A; Chr14_46525690_G; Chr14_4785275_A; Chr14_4872960_A; Chr14_6018928_A; Chr14_736668_A; Chr14_753089_S;

Chr14_848084_A; Chr14_929692_G; Chr15_17034597_A; Chr15_17132476_A; Chr15_17173057_S; Chr15_17184809_S; Chr15_17208898_S; Chr15_207098_A; Chr15_21259962_T; Chr15_21324461_C; Chr15_282154_T; Chr15_44008978_A; Chr15_474286_T; Chr15_48218526_S; Chr15_49582929_A; Chr16_1152934_G; Chr16_1176114_S; Chr16_152101_G; Chr16_17175190_T; Chr16_17401148_G; Chr16_17604552_G; Chr16_18101583_T; Chr16_18246040_T; Chr16_18350123_J; Chr16_18681277_C; Chr16_18768475_A; Chr16_19023503_T; Chr16_19051011_G; Chr16_19350353_G; Chr16_20502915_S; Chr16_27033_S; Chr16_275008_S; Chr16_302842_T; Chr16_379832_A; Chr16_4505495_A; Chr16_5909595_S; Chr17_12029252_S; Chr17_40078123_G; Chr17_41368944_T; Chr17_8312752_A; Chr18_10008076_S; Chr18_1226284_J; Chr18_1331239_T; Chr18_46838729_G; Chr18_48017092_J; Chr18_49993979_G; Chr18_50213360_S; Chr18_50257198_T; Chr18_50326879_G; Chr18_50354943_A; Chr18_50451315_T; Chr18_50504231_S; Chr18_50526685_G; Chr18_50554508_T; Chr18_50644512_G; Chr18_50679331_A; Chr18_51803879_G; Chr18_57405184_S; Chr18_57825072_T; Chr18_5957508_T; Chr18_6602221_A; Chr18_6725512_T; Chr18_6786167_T; Chr18_7758619_A; Chr18_7894691_A; Chr18_8471290_C; Chr18_9878834_A; Chr18_9975008_A; Chr19_35100145_A; Chr19_35170391_G; Chr19_42496895_A; Chr19_46285255_G; Chr19_46507363_T; Chr20_10254295_A; Chr20_1407347_S; Chr20_14830625_J; Chr20_37557651_A; Chr20_39680045_G; Chr20_40501012_S; Chr20_42761316_A; Chr20_42800295_A; Chr20_45235280_A.

The obtained 300 dominant alleles associated to plant height were as follows:

Chr01_47726965_G; Chr01_49576766_A; Chr01_001182_A; Chr01_50851685_C; Chr01_51838674_G; Chr01_55547694_A; Chr02_10279884_S; Chr02_10384204_A; Chr02_10404552_T; Chr0212531538_C; Chr02_37064827_T; Chr02_43425791_T; Chr02_47127707_T; Chr02_6300927_S; Chr03_129878_J; Chr03_155260_S; Chr03_1633588_S; Chr03_1688207_A; Chr03_1730161_A; Chr03_1968306_G; Chr03_225286_G; Chr03_253508_T; Chr03_2550027_G; Chr03_38654695_J; Chr03_38904011_A; Chr03_40127610_G; Chr03_42456210_A; Chr03_42575014_S; Chr03_430947_S; Chr03_43232_C; Chr03_43479607_G; Chr03_43750939_T; Chr03_43775000_T; Chr03_43984693_A; Chr03_44602100_T; Chr03_44668318_T; Chr03_44704477_T; Chr03_44725448_T; Chr03_44777470_G; Chr03_44800197_S; Chr03_44833104_A; Chr03_44881299_G; Chr03_44904696_S; Chr03_44975858_T; Chr03_45644558_T; Chr03_45659041_C; Chr03_525137_J; Chr03_53784_G; Chr03_558044_S; Chr03_76396_G; Chr04_50850178_G; Chr04_52316114_G; Chr05_11320014_G; Chr05_17506173_S; Chr05_18929941_J; Chr05_24905880_A; Chr05_25750555_A; Chr05_27352879_6; Chr05_27903879_C; Chr05_33054818_A; Chr05_34977447_C; Chr05_35800521_T; Chr05_39207458_A; Chr05_39604331_S; Chr05_39788521_S; Chr05_40075652_T; Chr05_5626085_G; Chr05_7677592_A; Chr05_8413351_G; Chr06_13029242_G; Chr06_13127505_A; Chr06_15034972_G; Chr06_15132070_C; Chr06_15231313_G; Chr06_15251974_A; Chr06_15968336_A; Chr06_16011956_G; Chr06_16128371_S; Chr06_2636926_S; Chr06_2678061_S; Chr06_2714420_G; Chr06_2772954_G; Chr06_2778790_S; Chr06_45721923_A; Chr06_46153054_A; Chr06_49075014_T; Chr06_49707587_S; Chr06_50525361_A; Chr06_50975144_G; Chr06_7703276_G; Chr06_7900374_A; Chr06_9938533_C; Chr07_42047915_G; Chr07_43553458_C; Chr07_6050545_S; Chr07_6525158_T; Chr07_6562483_A; Chr07_6575085_S; Chr07_8226456_G; Chr07_9052198_G; Chr07_9201345_G; Chr07_9326561_S; Chr07_9483132_A; Chr08_12350897_G; Chr08_22078860_S; Chr08_46177116_C; Chr08_46239110_G; Chr08_7389352_T; Chr08_7457393_A; Chr08_7512438_A; Chr08_7525546_T; Chr08_7675196_A; Chr08_7805605_A; Chr08_7876236_J; Chr08_7903178_A; Chr08_9776456_S; Chr08_9803231_S; Chr09_37877689_T; Chr09_40040735_A; Chr09_40927352_S; Chr09_47305353_T; Chr10_2158340_S; Chr10_2375462_A; Chr10_2452668_T; Chr10_2508817_S; Chr10_2525602_A; Chr10_2560868_G; Chr10_2591501_S; Chr10_2601476_T; Chr10_2626212_S; Chr10_2750802_G; Chr10_2825776_T; Chr10_2870996_S; Chr10_2887410_A; Chr10_2901283_S; Chr10_2927284_T; Chr10_3032473_A; Chr10_3100684_A; Chr10_3303531_T; Chr10_3485289_S; Chr10_3533037_T; Chr10_3737967_S; Chr10_3775180_A; Chr10_45082937_A; Chr10_45127748_C; Chr10_45150445_G; Chr10_45175769_A; Chr10_45214117_T; Chr10_45451718_T; Chr10_46127980_A; Chr10_47500165_G; Chr10_48575078_A; Chr10_48900690_S; Chr10_48926597_A; Chr10_48979145_T; Chr10_49000046_C; Chr10_49213289_S; Chr10_49256007_G; Chr10_49302884_C; Chr10_49343783_J; Chr10_49429776_T; Chr10_49499602_G; Chr10_49531784_T; Chr10_49559906_G; Chr10_49647824_T; Chr10_49660566_C; Chr10_50981304_S; Chr10_51188301_T; Chr10_5870074_G; Chr11_1020343_C; Chr11_1050892_S; Chr11_1075377_A; Chr11_1104970_T; Chr11_1652554_C; Chr11_3245369_T; Chr11_34453671_A; Chr11_3956041_A; Chr11_4100355_S; Chr11_4153990_C; Chr11_4273387_G; Chr11_4306322_T; Chr11_9896347_S; Chr12_2970658 A;

Chr12_2978271_A; Chr12_3003089_G; Chr12_3026625_T; Chr12_3079241_S; Chr12_35370710_A; Chr12_35804687_G; Chr12_36002065_C; Chr12_9900671_S; Chr13_15888172_G; Chr13_28683703_A; Chr13_29215285_T; Chr13_29450326_T; Chr13_29550344_A; Chr13_29952924_S; Chr13_30866652_S; Chr13_31480450_A; Chr13_33804363_C; Chr13_34104353_A; Chr13_44483438_A; Chr14_22792151_T; Chr14_22800108_A; Chr14_22890019_G; Chr14_23035371_S; Chr14_23115585_S; Chr14_23125383_T; Chr14_23275009_T; Chr14_26877514_A; Chr14_26954277_T; Chr14_45860975_T; Chr14_46525690_G; Chr14_46675012_S; Chr14_46827091_J; Chr14_475338_T; Chr14_47551214_A; Chr14_47779860_T; Chr14_7201590 J: Chr14_7401505_J; Chr14_7426690_A; Chr14_7558385_S; Chr14_9109017_S; Chr14_9211097_T; Chr14_9234257_T; Chr14_9250920_T; Chr14_9391207_A; Chr14_9434565_S; Chr14_9527182 S: Chr15_13364591_S; Chr15_13416532_A; Chr15_15436616_A; Chr15_15478303_G; Chr15_282154_T; Chr15_49814040_S; Chr15_49881186_A; Chr15_49930588_A; Chr15_50041669_T; Chr15_50108394_T; Chr15_50297493_A; Chr15_50303850_S; Chr15_51181112_A; Chr16_28610516_T; Chr16_28633517_T; Chr16_28775183_T; Chr16_29481011_T; Chr16_33803276_G; Chr16_34228498_G; Chr16_34275534_A; Chr17_28985249_S; Chr17_379073_G; Chr17_39140960_J; Chr17_39177410_C; Chr17_39257059_C; Chr17_41457969_A; Chr17_41490859_A; Chr17_41597488_S; Chr18_2904831_G; Chr18_3472444_A; Chr18_3493254_T; Chr18_3509756_A; Chr18_47970688_T; Chr18_48056177_C; Chr18_48125071_A; Chr18_51782717_S; Chr18_52025626_G; Chr18_52607151_S; Chr18_54801747_G; Chr18_54976521_G; Chr18_55026765_A; Chr18_55127852_G; Chr18_55552164_G; Chr18_55575980_A; Chr18_55727744_C; Chr18_55800924_G; Chr18_56085636_A; Chr18_56182068_G; Chr19_1276857_T; Chr19_34575694_G; Chr19_3507500_T; Chr19_40005621_S; Chr19_45624712_T; Chr19_46231927_T; Chr19_46530081_T; Chr19_46856156_G; Chr19_46879327_T; Chr19_46900345_A; Chr19_46952128_T; Chr19_47030307_A; Chr19_47105006_G; Chr19_47200473_S; Chr19_47284576_G; Chr19_47305458_S; Chr19_47350110_G; Chr19_47988748_G; Chr20_1407347_J; Chr20_1624381_A; Chr20_35026183_A; Chr20_44168873_G; Chr20_46381757_T.

The obtained 300 dominant alleles associated to fat content were as follows:

Chr01_1204481_C; Chr01_1302531_C; Chr01_1430369_J; Chr01_1460795_S; Chr01_1533882_A; Chr01_1550268_C; Chr01_45292957_G; Chr01_45677056_T; Chr01_46700299_G; Chr01_49903973_G; Chr01_52238119_G; Chr01_52306999_G;

Chr01_53884130_C; Chr01_54530855_G; Chr01_54558891_A; Chr01_7375671_A; Chr02_2576855_G; Chr02_2661597_G; Chr02_29450123 Chr02_3200625_G; Chr02_3231033_A; Chr02_44041696_T; Chr02_5225452_T; Chr02_5284208_A; Chr02_5654145_A; Chr02_6300927_T; Chr03_13225866_A; Chr03_18107159_A; Chr03_25891807_T; Chr03_31175433_G; Chr03_336514601; Chr03_36421392_A; Chr03_36426626_T; Chr03_36451021_G; Chr03_36504983_C; Chr03_36789422_G; Chr03_36860656_S; Chr03_37706557_T; Chr03_3826007_G; Chr03_42802419_G; Chr03_43061605_S; Chr03_43232301_A; Chr03_44800197_T; Chr03_44833104_G; Chr03_44850673_G; Chr03_44881299_A; Chr03_44904696_T; Chr03_44975858_C; Chr03_45003578_T; Chr03_45081603_J; Chr03_45151144_A; Chr03_45252972_S; Chr03_45280678_A; Chr03_45778731_G; Chr03_6235821_G; Chr03_7454850_1; Chr04_3350250_S; Chr04_44202428_S; Chr04_49655228_S; Chr04_5155506_J; Chr04_5432335_G; Chr04_5839404_T; Chr04_6151552_A; Chr04_6380579_S; Chr04_8375562_T; Chr04_8460910_C; Chr04_8520847_A; Chr04_8569889_A; Chr04_8577960_G; Chr04_8600187_C; Chr04_8627986_S; Chr04_8744131_T; Chr04_8834618_T; Chr05_13088208_C; Chr05_2667653_A; Chr05_33002251_A; Chr05_33075008_S; Chr05_33376715_T; Chr05_33468570_T; Chr05_33525340_T; Chr05_33630915_G; Chr05_34063554_T; Chr05_34110946_9; Chr05_36275125_G; Chr05_3725956_A; Chr05_3814056_S; Chr05_39207458_S; Chr05_40476259_A; Chr05_41165218_G; Chr05_41175611_T; Chr05_41213590_G; Chr05_41231598_T; Chr05_41254151_A; Chr05_41330573_G; Chr05_41626230_T; Chr05_9828221_S; Chr06_14691651_9; Chr06_15403340_S; Chr06_17382650_S; Chr06_17626369_A; Chr06_19600014_T; Chr06_19781007_T; Chr06_2100577_S; Chr06_21275222_A; Chr06_2158432_C; Chr06_27625128_A; Chr06_28175922_S; Chr06_28928355_G; Chr06_3430462_A; Chr06_3453914_T; Chr06_3510973_J; Chr06_3525384_G; Chr06_37624463_T; Chr06_39583427_A; Chr06_41790617_G; Chr06_42000621_S; Chr06_4241219_A; Chr06_4298131_T; Chr06_4319355_T; Chr06_4334059_S; Chr06_4351486_A; Chr06_48019540_T; Chr06_48242356_A; Chr06_526813_J; Chr06_5766823_J; Chr06_6078531_A; Chr06_6100733_A; Chr06_6134887_S; Chr06_8325839_A; Chr06_875297_T; Chr07_15986465_A; Chr07_1952143_T; Chr07_30100016_T; Chr07_35977735_C; Chr07_36906380_C; Chr07_36934673_A; Chr07_36951473_C; Chr07_37077520_G; Chr07_7200900_A; Chr08_14519320_T; Chr08_1798324_T; Chr08_1801713_G; Chr08_2104023_A; Chr08_3450747_S; Chr08_35225469_A; Chr08_38926845_A;

Chr08_4201119_A; Chr08_42760680_T; Chr08_44625940_T; Chr08_46093989_S; Chr08_46177116_C; Chr08_46278339_1; Chr08_46311293_A; Chr08_46326275_G; Chr08_46863453_J; Chr08_46885184_G; Chr08_46900170_A; Chr08_5655781_S; Chr08_6633155_G; Chr08_6659330_G; Chr09_1563510_G; Chr09_2288589_T; Chr09_2878505_A; Chr09_2909053_G; Chr09_34552898_T; Chr09_38553476_T; Chr09_41558984_G; Chr09_41576646_S; Chr09_41601643_G; Chr09_41676859_A; Chr09_41777476_G; Chr09_41801924_G; Chr09_4201884_C; Chr09_4283906_S; Chr09_44123069_G; Chr09_46779824_G; Chr09_5001601_T; Chr09_6305537_A; Chr09_6653411_J; Chr10_1707438_A; Chr10_2746072_G; Chr10_31900041_T; Chr10_331641_G; Chr10_44777383_C; Chr10_44828287_A; Chr11_2630521_G; Chr12_1375187_C; Chr12_34057603_S; Chr12_34080181_T; Chr12_34137308_T; Chr12_34152629_A; Chr12_34775228_C; Chr12_34851455_A; Chr12_34879829_G; Chr12_34904656_G; Chr12_34941924_T; Chr12_36332573_J; Chr12_36355223_S; Chr12_36736475_A; Chr12_5483537_A; Chr13_19460489_C; Chr13_30388748_G; Chr13_33234484_S; Chr13_33316633_G; Chr13_33326468_A; Chr13_33484893_G; Chr13_41807124_A; Chr13_43526500_J; Chr14_18526221_S; Chr14_18874799_S; Chr14_19325560_T; Chr14_26954277_A; Chr14_48354923_1; Chr14_4978437_A; Chr14_8254_A; Chr15_10454469_A; Chr15_11284233_A; Chr15_11305323_G; Chr15_11356554_G; Chr15_11441207_T; Chr15_12793869_T; Chr15_14682391_S; Chr15_2204583_G; Chr15_2263175_G; Chr15_2277272_A; Chr15_2313354_G; Chr15_2328756_G; Chr15_2350482_A; Chr15_2377885_J; Chr15_2403039_S; Chr15_2428037_S; Chr15_2450413_T; Chr15_2475536_J; Chr15_2528392_S; Chr15_2555770_C; Chr15_2577240_A; Chr15_2608939_G; Chr15_2701601_G; Chr15_3239056_C; Chr15_3258659_A; Chr15_3438388_S; Chr15_3450565_T; Chr15_3545424_J; Chr15_3588197_1; Chr15_3630889_S; Chr15_3660345_T; Chr15_38550158_S; Chr15_3900110_A; Chr16_32565714_G; Chr16_33950384_G; Chr16_35556808_S; Chr16_37081216_A; Chr16_37839002_G; Chr16_4075059_J; Chr16_4277748_G; Chr16_8176834_T; Chr16_949779_1; Chr17_10945429_C; Chr17_11025426_J; Chr17_12029252_S; Chr17_12107006_S; Chr17_13092608_1; Chr17_15230298_S; Chr17_15250595_S; Chr17_2078415_1; Chr17_23434268_A; Chr17_7927328_S; Chr17_8286360_S; Chr17_8312752_G; Chr17_8328369_C; Chr17_8350510_G; Chr17_8623316_A; Chr17_8654251_G; Chr17_9203728_G; Chr17_9779938_A; Chr17_9838390_1; Chr18_48297982_G; Chr18_48840921_1; Chr18_51200487_A; Chr18_54100459_C; Chr18_54801747_1; Chr18_55604880_A; Chr18_55727744_1; Chr18_55800924_A; Chr18_8671202_A; Chr18_8702855_G; Chr19_15350016_S; Chr19_19650255_S; Chr19_241321_A; Chr19_259869_A; Chr19_279864_A; Chr19_32154302_A; Chr19_34843169_T; Chr19_34880091_J; Chr19_40127559_J; Chr19_5221_1; Chr20_1894103_T; Chr20_23328397_G; Chr20_37201537_S; Chr20_4180546_G.

The obtained 300 dominant alleles associated to the number of main stem nodes were as follows:

Chr01_38782697_1; Chr01_39586209_G; Chr01_39600198_A; Chr01_39802257_G; Chr01_39860894_T; Chr01_4292947_J; Chr01_4301032_S; Chr01_45292957_G; Chr01_50030807_A; Chr01_50067658_G; Chr01_50079414_S; Chr01_50502058_G; Chr01_50572793_C; Chr01_50602779_S; Chr01_50653236_G; Chr01_50689878_G; Chr01_50702185_S; Chr01_50834469_G; Chr01_50851685_S; Chr01_51315364_G; Chr01_52011140_A; Chr01_52078418_1; Chr02_12531538_S; Chr02_38904196_G; Chr02_40658010_G; Chr02_40701107_A; Chr02_40726991_G; Chr02_40831974_A; Chr02_40859063_S; Chr02_40955346_G; Chr02_40977632_G; Chr02_41000605_G; Chr02_41066386_A; Chr02_41077148_G; Chr02_41104941_A; Chr02_45300532_A; Chr02_45476100_G; Chr02_45606962_A; Chr02_45625797_J; Chr02_48491652_G; Chr03_114996_C; Chr03_36421392_A; Chr03_42127054_C; Chr03_42530214_G; Chr03_42575014_C; Chr03_42692363_1; Chr03_43232_C; Chr03_446683181; Chr03_44975858_1; Chr03_525137_1; Chr03_558044_S; Chr03_76396_G; Chr04_2236262_S; Chr04_52188714_J; Chr04_5257081_G; Chr04_5276150_1; Chr04_9308835_C; Chr05_2963065_S; Chr05_38376405_S; Chr05_39002106_G; Chr05_39132561_A; Chr05_39479733_G; Chr05_39604331_C; Chr05_39788521_S; Chr05_40019733_G; Chr05_40051231_C; Chr05_40075652_T; Chr05_40326384_J; Chr05_5558466_T; Chr05_5575650_G; Chr05_5626085_G; Chr06_12283364_J; Chr06_12381008_T; Chr06_12784181_G; Chr06_12937960_A; Chr06_12977788_J; Chr06_13029242_G; Chr06_13093038_G; Chr06_13105258_A; Chr06_13127505_A; Chr06_13151489_G; Chr06_13175906_A; Chr06_13202926_A; Chr06_15968336_A; Chr06_1756279_A; Chr06_2636926_C; Chr06_2650044_S; Chr06_2678061_S; Chr06_2714420_G; Chr06_2725187_G; Chr06_2772954_G; Chr06_3179722_T; Chr06_49001498_S; Chr06_49075014_T; Chr06_9938533_C; Chr07_10160518_A; Chr08_21149631_J; Chr08_21153685_A; Chr0821749534_A; Chr08_22078860_G; Chr08_38101241_A; Chr08_38229046_A; Chr08_38850879_T; Chr08_43361138_T; Chr08_43375195_G; Chr08_43428478_S; Chr08_46056956_T; Chr08_46177116_C; Chr08_5001757_J; Chr09_3251850_S;

Chr09_3729069_A; Chr09_37756366_T; Chr09_39343182_T; Chr09_41207254_T; Chr09_45107106_T; Chr09_46200899_S; Chr09_46276810_J; Chr09_47156687_S; Chr09_47977625_G; Chr09_5500100_A; Chr09_6800411_T; Chr10_18575802_G; Chr10_2750802_G; Chr10_2870996_G; Chr10_2887410_A; Chr10_2901283_G; Chr10_2927284_T; Chr10_3303531_T; Chr10_34094035_G; Chr10_3485289_C; Chr10_3533037_J; Chr10_3775180_A; Chr10_4003143_A; Chr10_48900690_C; Chr10_48926597_A; Chr10_49213289_C; Chr10_49256007_G; Chr10_49302884_C; Chr10_49343783_J; Chr10_49384169_A; Chr10_49429776_T; Chr10_49531784_T; Chr11_10001565_T; Chr11_34526683_G; Chr11_34577538_G; Chr11_34677410_C; Chr11_5301216_C; Chr11_9896347_G; Chr11_9993857_G; Chr12_10325445_A; Chr12_13956797_C; Chr12_32400650_C; Chr12_35370710_A; Chr12_36765947_G; Chr12_37654886_G; Chr12_37675151_C; Chr12_37767142_A; Chr12_37776504_1; Chr12_37803533_A; Chr12_37978616_A; Chr12_38025549_A; Chr12_39450012_T; Chr12_9675105_G; Chr13_21735193_S; Chr13_21768219_G; Chr13_21775204_G; Chr13_29215285_T; Chr13_29808193_C; Chr13_30532621_T; Chr13_30875390_T; Chr13_32500153_A; Chr13_42550196_G; Chr13_42643435_S; Chr13_42650401_C; Chr13_42906651_A; Chr14_45860975_T; Chr14_46303938_T; Chr14_46352178_A; Chr14_46525690_G; Chr14_46583472_T; Chr14_46614414_G; Chr14_46750140_T; Chr14_46827091_T; Chr14_46852568_A; Chr14_46940018_A; Chr14_47627419_G; Chr14_47779860_1; Chr14_4785275_A; Chr14_9250920_J; Chr14_9391207_A; Chr15_193419_A; Chr15_207098_A; Chr15_282154_J; Chr15_49448263_A; Chr15_49521129_G; Chr15_49558739_S; Chr15_49630747_A; Chr15_49844963_G; Chr15_49857566_A; Chr15_50041669_J; Chr15_50071018_S; Chr15_50090382_T; Chr15_50108394_T; Chr15_50225406_A; Chr15_50297493_A; Chr15_50303850_C; Chr15_50325488_S; Chr15_50357591_G; Chr15_50377398_S; Chr15_50400336_S; Chr15_50434685_C; Chr15_50532317_A; Chr15_5986572_S; Chr15_6291081_T; Chr16_13675270_T; Chr16_18246040_T; Chr16_28752453_C; Chr16_28858362_A; Chr16_28950119_G; Chr16_28977194_S; Chr16_29035313_T; Chr16_29481011_J; Chr16_31675884_T; Chr16_32911332_G; Chr16_34228498_G; Chr16_34275534_A; Chr17_13805053_A; Chr17_13845235_G; Chr17_1570502_A; Chr17_39257059_S; Chr17_41457969_A; Chr17_41597488_S; Chr17_4901383_G; Chr17_5021725_A; Chr18_1331239_T; Chr18_257570_G; Chr18_453852_1; Chr18_54976521_G; Chr18_55026765_A; Chr18_55127852_G; Chr18_55575980_A; Chr18_55604880_G; Chr18_55727744_S; Chr18_55800924_G; Chr18_56906122_T; Chr18_56925239_S; Chr18_56975394_G; Chr18_57721186_S; Chr18_5957508_T; Chr18_6602221_A; Chr18_6712702_T; Chr18_6725512_T; Chr18_6786167_T; Chr18_6801571_G; Chr18_6825701_A; Chr18_6858368_A; Chr18_6975143_G; Chr18_7030568_T; Chr18_7050206_S; Chr18_7125822_G; Chr18_7375327_T; Chr18_7537482_S; Chr18_7894691_A; Chr18_8879736_A; Chr18_9000143_G; Chr18_9050617_G; Chr18_9165638_S; Chr19_1198529_G; Chr19_1252659_S; Chr19_1276857_T; Chr19_34318797_G; Chr19_34475899_A; Chr19_34529906_A; Chr19_34574726_S; Chr19_34575694_G; Chr19_3507500_T; Chr19_35100145_A; Chr19_35250098_S; Chr19_35452918_J; Chr19_46231927_T; Chr19_46879327_T; Chr19_47267849_G; Chr19_47284576_G; Chr19_5221_S; Chr20_34389969_T; Chr20_34605904_T; Chr20_34703521_T; Chr20_34962497_A; Chr20_34977235_A; Chr20_35009808_G; Chr20_35026183_A; Chr20_35151397_C; Chr20_35301668_A; Chr20_35480916_S; Chr20_35525574_G; Chr20_38292951_A; Chr20_38335608_A; Chr20_38383336_T; Chr20_39751814_A; Chr20_39926016_G.

The obtained 300 dominant alleles associated to the grain weight per hundred were as follows:

Chr01_2753365_C; Chr01_2782130_G; Chr01_2877051_T; Chr01_3038334_A; Chr01_3051719_C; Chr01_47726965_G; Chr01_48510140_T; Chr01_50602779_A; Chr01_51175986_T; Chr01_51315364_A; Chr01_51507836_T; Chr01_51528414_T; Chr01_51553036_G; Chr01_51600690_G; Chr01_51634033_A; Chr01_52011140_G; Chr01_53054125_G; Chr01_53509482_G; Chr01_53787487_S; Chr01_54681333_G; Chr02_14414245_G; Chr02_34053527_T; Chr02_3912545_A; Chr02_39560572_T; Chr02_434019_A; Chr02_43594093_T; Chr02_4526649_T; Chr02_474929_T; Chr02_475192_T; Chr02_48284401_G; Chr02_48304951_T; Chr02_48352600_A; Chr02_503569_T; Chr02_531882_T; Chr02_605426_C; Chr02_626869_A; Chr02_662230_G; Chr02_688019_A; Chr02_7802661_G; Chr02_7852038_A; Chr02_8124168_G; Chr02_8175874_S; Chr02_826621_A; Chr02_8505964_S; Chr03_1404553_A; Chr03_1452056_T; Chr03_1536380_T; Chr03_1633588_A; Chr03_177571_A; Chr03_21945332_A; Chr03_2531823_T; Chr03_333082_G; Chr03_36421392_G; Chr03_36451021_A; Chr03_37027494_A; Chr03_37484920_A; Chr03_42754587_C; Chr03_43630368_G; Chr03_43703324_A; Chr03_43726576_T; Chr03_630212_T; Chr04_134959_G; Chr04_3536354_S; Chr04_47900156_T; Chr04_47925101_A; Chr04_48485665_C; Chr04_49204713_S; Chr04_49601333_S; Chr04_5155506_C; Chr04_6545493_T; Chr04_7467876_T; Chr04_7608019_T; Chr05_2477128_A; Chr05_2505712_S;

Chr05_2525824_G; Chr05_33002251_A; Chr05_33054818_A; Chr05_33257198_A; Chr05_33359743_A; Chr05_33852440_S; Chr05_33893210_A; Chr05_33920665_C; Chr05_33926353_S; Chr05_34539965_C; Chr05_34635952_G; Chr05_35283498_G; Chr05_41912828_S; Chr05_41984546_G; Chr05_42019019_T; Chr05_5558466_C; Chr05_5575650_A; Chr05_6730320_S; Chr06_12425353_T; Chr06_12450074_G; Chr06_12525745_G; Chr06_12555111_T; Chr06_12575606_A; Chr06_13231992_C; Chr06_13481784_T; Chr06_15681367_T; Chr06_17154269_A; Chr06_17175049_S; Chr06_19445340_G; Chr06_19461588_S; Chr06_4134589_A; Chr06_46778730_T; Chr06_47527814_S; Chr06_48880873_G; Chr06_970242_T; Chr07_29475322_G; Chr07_31692_G; Chr07_355715_S; Chr07_3753_T; Chr07_39355101_T; Chr07_39679761_J; Chr07_42119515_T; Chr07_42256379_A; Chr07_42689775_T; Chr07_42700692_J; Chr07_42732051_G; Chr07_42782332_T; Chr07_42836543_A; Chr07_42870671_A; Chr07_42925545_T; Chr07_42959812_G; Chr07_43127874_C; Chr07_43196784_T; Chr07_43200777_A; Chr07_7659934_S; Chr07_89336_G; Chr07_9125085_S; Chr08_19262396_T; Chr08_19353170_A; Chr08_19375087_T; Chr08_19492544_T; Chr08_19536081_G; Chr08_19777852_A; Chr08_34976194_S; Chr08_35082500_A; Chr08_776002_S; Chr09_34981876_C; Chr09_35674085_A; Chr10_12834195_S; Chr10_1677025_A; Chr10_34434459_A; Chr10_4528519_T; Chr10_50539235_A; Chr11_10492106_S; Chr11_10561561_S; Chr11_10589735_G; Chr11_28331818_G; Chr11_30521919_T; Chr11_30526422_T; Chr11_30550847_A; Chr11_30575972_T; Chr11_31020057_G; Chr11_31107364_G; Chr11_31183242_C; Chr12_3128482_C; Chr12_3150012_J; Chr12_35265460_G; Chr12_35289582_G; Chr12_35300920_S; Chr12_35370710_T; Chr12_35454811_A; Chr12_35478589_T; Chr12_35554502_G; Chr12_35578344_A; Chr12_35653956_G; Chr12_37776504_G; Chr12_8916858_T; Chr12_9900671_A; Chr12_9948509_T; Chr13_13883726_T; Chr13_20814464_A; Chr13_28428400_G; Chr13_30787325_G; Chr13_31550833_S; Chr13_31602190_T; Chr14_10675352_T; Chr14_10779431; Chr14_1326978_1; Chr14_1410232_G; Chr14_1850964_S; Chr14_1906524_T; Chr14_2258981_A; Chr14_47437728_A; Chr14_47450074_S; Chr14_47508319 J: Chr14_47525916_T; Chr14_753089_T; Chr14_8663178_A; Chr14_8700324_T; Chr14_8728922_C; Chr15_15163386_A; Chr15_15199848_J; Chr15_15201886_T; Chr15_15232943_A: Chr15_15275058_A; Chr15_15411778_S; Chr15_15848279_A; Chr15_15854711_T; Chr15_15966263_G; Chr15_16752209_A; Chr15_16793506_T; Chr15_48476245_G; Chr15_49521129_A; Chr15_49558739_A; Chr15_49630747_G; Chr15_5251935_G; Chr16_1176114_T; Chr16_30433508_G; Chr16_33152519_S; Chr16_33225878_S; Chr16_37225158_S; Chr16_921488_T; Chr17_12029252_A; Chr17_13601504_S; Chr17_13805053_G; Chr17_37905877_T; Chr17_38074662_S; Chr17_38078798_G; Chr17_38130352_T; Chr17_38163113_A; Chr17_38176257_C; Chr17_38209056_A; Chr17_38307270_A; Chr17_38333832_A; Chr17_38350306_T; Chr17_38383587_A; Chr17_38627978_S; Chr17_39987601_S; Chr17_40578159_S; Chr17_40606398_T; Chr17_4120689_G; Chr17_41368944_S; Chr17_8312752_G; Chr17_8350510_G; Chr18_200311_T; Chr18_453852_S; Chr18_47245119_C; Chr18_47251073_A; Chr18_47656646_G; Chr18_47765010_G; Chr18_47801223_A; Chr18_47830714_A; Chr18_47938136_T; Chr18_47970688_T; Chr18_48017092_C; Chr18_48056177_S; Chr18_48125071_A; Chr18_48153620_T; Chr18_49353230_G; Chr18_49394141_S; Chr18_49411942_G; Chr18_49427701_T; Chr18_49461993_A; Chr18_49725195_S; Chr18_49760162_G; Chr18_49917635_S; Chr18_49925828_C; Chr18_50169967_G; Chr18_50577547_T; Chr18_51751232_S; Chr18_51979685_T; Chr18_54427376_A; Chr18_54703004_S; Chr18_54740194_T; Chr18_56681396_G; Chr18_7203689_G; Chr19_11759480_A; Chr19_25661004_A; Chr19_27263458_T; Chr19_27300024_C; Chr19_27398685_G; Chr19_27407125_T; Chr19_34400023_S; Chr19_36049214_A; Chr19_36125339_T; Chr19_39651869_S; Chr19_40005621_S; Chr19_40707346_G; Chr19_42700535_G; Chr19_42732180_T; Chr19_42937706_S; Chr19_43075222_G; Chr19_43144060_G; Chr19_43230762_G; Chr19_4459540_A; Chr19_46110862_G; Chr19_46160913_T; Chr19_4620074_T; Chr19_46231927_C; Chr19_46952128_S; Chr19_47008899_A; Chr19_47082265_S; Chr19_4761980_A; Chr19_8080477_A; Chr19_9343878_T; Chr20_37251990_T.

The obtained 300 dominant alleles associated to the weight of seeds per plant were as follows:

Chr01_2484626_G; Chr01_27750349_A; Chr01_27893663_A; Chr01_38755673_G; Chr01_39450786_G; Chr01_39586209_6; Chr01_4026903_G; Chr01_4050717_A; Chr01_4092615_G; Chr01_4125368_S; Chr01_50431852_S; Chr01_53979152_T; Chr01_8533425_T; Chr01_8656269_S; Chr01_8775411_T; Chr01_9053888_T; Chr02_10900886_T; Chr02_10925940_A; Chr02_11020666_T; Chr02_11075770_A; Chr02_13151764_A; Chr02_1450107_T; Chr02_1482658_G; Chr02_15034734_6; Chr02_40029226_T; Chr02_40058782_A; Chr02_40831974_A; Chr02_40859063_S; Chr02_41077148_G; Chr02_41104941_A; Chr02_45541258_T; Chr02_45625797_T; Chr02_4800624_G; Chr02_48012289_A; Chr02_5200074_S; Chr02_7928221_T; Chr02_9659990_S; Chr02_9675960_T;

Chr03_1875617_A; Chr03_1917125_T; Chr03_2000327_J; Chr03_2043169_S; Chr03_42127054_S; Chr03_42530214_G; Chr03_42575014_S; Chr03_44176052_A; Chr03_44881299_G; Chr03_44975858_T; Chr04_11186208_A; Chr04_11225993_T; Chr04_11252437_T; Chr04_12991694_G; Chr04_13488853_G; Chr04_13575150_C; Chr04_13755707_A; Chr04_13818399_T; Chr04_13913892_G; Chr04_45498316_A; Chr04_45658472_G; Chr04_46878018_G; Chr04_47875842_A; Chr04_48109645_J; Chr04_48133794_G; Chr04_48382310_A; Chr04_48428892_A; Chr04_48485665_S; Chr04_51103827_J; Chr04_51134738_C; Chr04_51176069_C; Chr04_51201999_T; Chr04_51554352_C; Chr04_51579450_G; Chr04_9326798_S; Chr04_9378161_G; Chr04_9412752_T; Chr04_9501636_A; Chr04_9877995_A; Chr05_37737672_S; Chr05_38063211_C; Chr05_41175611_T; Chr06_12937960_A; Chr06_13029242_G; Chr06_13105258_A; Chr06_13127505_A; Chr06_13231992_C; Chr06_13308460_A; Chr06_13356169_A; Chr06_13378329_C; Chr06_13432800_S; Chr06_13455439_A; Chr06_13481784_T; Chr06_17279302_A; Chr06_2714420_G; Chr06_3226536_A; Chr06_4134589_A; Chr06_48428377_S; Chr06_48526587_A; Chr06_48910052_A; Chr06_48956197_A; Chr06_49530212_1; Chr06_49877389_A; Chr06_49925613_T; Chr06_49953938_A; Chr06_49982968_A; Chr06_50029281_A; Chr06_50145253_C; Chr06_50163774_G; Chr06_50975144_G; Chr06_51051522_A; Chr07_10918261_A; Chr07_13502229_S; Chr07_13680710_A; Chr07_14091972_S; Chr07_140995_G; Chr07_176543_A; Chr07_19025998_1; Chr07_19051769_G; Chr07_19640899_S; Chr07_19650904_A; Chr07_31692_G; Chr07_3753_J; Chr07_41078590_A; Chr07_41184660_A; Chr07_42630478_C; Chr07_42658523_G; Chr07_42975287_T; Chr07_43553458_S; Chr07_44302019_T; Chr07_44443942_A; Chr07_5257022_A; Chr07_5403591_J; Chr07_5432458_G; Chr07_5575080_S; Chr07_5825087_T; Chr07_5858750_A; Chr07_89336_G; Chr08_1028572_A; Chr08_3709318_C; Chr08_3777218_C; Chr08_3836330_T; Chr08_40820397_S; Chr08_43328129_G; Chr08_43361138 Chr08_43375195_G; Chr08_43428478_S; Chr08_43453091_S; Chr08_44625940_T; Chr08_44706029_G; Chr08_44802718_G; Chr08_47284810_A; Chr08_47332464_S; Chr08_47581457_T; Chr08_734307_T; Chr09_1850879_1; Chr09_1904702_G; Chr09_2040426_A; Chr09_35582172_S; Chr09_38751029_C; Chr09_38843968_J; Chr09_39343182_T; Chr09_39350396_S; Chr09_39411135_G; Chr09_45975341_S; Chr09_46200899_S; Chr09_46308505_A; Chr09_46478149_T; Chr09_46544673_G; Chr09_46571264_A; Chr09_46589096_T; Chr09_46836433_A; Chr09_47527188_T; Chr09_47575242_C; Chr09_47637297_T; Chr09_47677967_A; Chr09_47977625_G; Chr09_48003816_G; Chr09_48251278_G; Chr09_48275347_T; Chr09_49162387_1; Chr09_49185455_G; Chr10_2988733_T; Chr10_3755179_J; Chr10_40960388_A; Chr10_43269596_A; Chr10_48900690_S; Chr10_48926597_A; Chr11_31026476_G; Chr11_32376132_G; Chr11_32402605_T; Chr11_32506058_C; Chr11_628458_C; Chr12_36704530_S; Chr12_36736475_A; Chr12_36765947_G; Chr13_14129219_A; Chr13_14630892_A; Chr13_14653507_S; Chr13_14733847_G; Chr13_16484275_C; Chr13_17356493_A; Chr13_19425153_T; Chr13_20936168_T; Chr13_21735193_C; Chr13_21768219_G; Chr13_21775204_G; Chr13_22689145_T; Chr13_41775097_A; Chr13_41963558_T; Chr13_42028098_S; Chr13_42050209_A; Chr13_42111517_J; Chr13_42150995_T; Chr13_42216053_T; Chr13_42325942_G; Chr13_42371551_G; Chr13_42383660_A; Chr13_42410927_G; Chr13_9200028_S; Chr14_3731760_A; Chr14_427669_A; Chr14_45052676_S; Chr14_46750140_T; Chr14_47779860_T; Chr15_207098_A; Chr15_282154_T; Chr15_3989240_G; Chr15_4106368_T; Chr15_6368385_A; Chr16_14685_T; Chr16_17011382_T; Chr16_17325273_T; Chr16_18025020_A; Chr16_18101583_T; Chr16_18246040_T; Chr16_19150455_S; Chr16_19464894_T; Chr16_20943654_A; Chr16_27033_C; Chr16_31675884_T; Chr16_325525_A; Chr16_361425_C; Chr16_379832_A; Chr16_5406664_J; Chr16_5427988_S; Chr16_5451800_G; Chr16_55282_A; Chr16_5581173_C; Chr16_5859049_T; Chr16_5883835_C; Chr16_5909595_S; Chr16_5940565_G; Chr16_5957479_S; Chr16_5990133_S; Chr16_6024557_C; Chr16_6026215_A; Chr16_6216130_G; Chr16_6325150_G; Chr17_12475327_G; Chr17_37578310_G; Chr18_10008076_S; Chr18_1331239_T; Chr18_1537515_G; Chr18_27508243_S; Chr18_2855518_T; Chr18_50257198_T; Chr18_50326879_G; Chr18_50504231_S; Chr18_50526685_G; Chr18_50554508_T; Chr18_50604772_T; Chr18_50644512_G; Chr18_50651797_A; Chr18_5957508_J; Chr18_6575191_C; Chr18_6602221_A; Chr18_6786167_J; Chr18_6825701_A; Chr18_7554233_S; Chr18_7758619_A; Chr18_7894691_A; Chr18_8471290_S; Chr18_9300229_G; Chr18_9968430_T; Chr18_9975008_A; Chr19_38110872_J; Chr19_45575841_G; Chr19_47575059_G; Chr19_47600163_G; Chr19_47680091_G; Chr19_47728451_G; Chr20_2243234_T; Chr20_33664539_J; Chr20_33682709_A; Chr20_33730673_C; Chr20_34017305_T; Chr20_42800295_A; Chr20_43006921_A; Chr20_43033812_A; Chr20_43158972_G; Chr20_45204661_S.

The obtained 300 dominant alleles associated to the number of seeds per plant were as follows:

Chr01_38782697_T; Chr01_39100017_G;
Chr01_39450786_G; Chr01_39586209_G;
Chr01_39600198_A; Chr01_39628619_S;
Chr01_39860894_T; Chr01_39914433_T;
Chr01_39969229_S; Chr01_40040195_J;
Chr01_40130345_C; Chr01_4026903_G;
Chr01_4050717_A; Chr01_4092615_G;
Chr01_4125368_C; Chr01_52250882_A;
Chr01_56407141_C; Chr02_10925940_A;
Chr02_11020666_T; Chr02_11276103_A;
Chr02_12531538_S; Chr02_13151764_A;
Chr02_1333828_G; Chr02_13357583_G;
Chr02_13922538_T; Chr02_14349056_S;
Chr02_15034734_G; Chr02_40029226_T;
Chr02_40831974_A; Chr02_4277591_A;
Chr02_42977015_T; Chr02_45083910_G;
Chr02_45541258_T; Chr02_45625797_T;
Chr02_4800624_G; Chr03_2834232_S;
Chr03_2886359_S; Chr03_3483680_J;
Chr03_38305381_A; Chr03_42575014_S;
Chr03_44550993_S; Chr03_44668318_J;
Chr03_44725448_T; Chr03_44800197_S;
Chr03_44881299_G; Chr03_44975858 J;
Chr03_45003578_G; Chr03_45081603_S;
Chr03_5250137_G; Chr03_7454850_T;
Chr04_10450193_G; Chr04_10789432_A;
Chr04_13145679_G; Chr04_13818399_T;
Chr04_13913892_G; Chr04_45546221_G;
Chr04_45569116_A; Chr04_45658472_G;
Chr04_46582419_T; Chr04_46878018_S;
Chr04_47254706_S; Chr04_47537209_G;
Chr04_47555835_S; Chr04_48726633_T;
Chr04_51134738_C; Chr04_51176069_C;
Chr04_5155506_T; Chr04_5276150_T;
Chr04_9378161_G; Chr04_9501636_A;
Chr05_1545337_C; Chr06_10505562_A;
Chr06_10988551_T; Chr06_11002280_A;
Chr06_12232760_A; Chr06_13151489_S;
Chr06_17154269_S; Chr06_19461588_T;
Chr06_3132988_T; Chr06_3226536_A;
Chr06_3453914_T; Chr06_44785999_S;
Chr06_47814558_S; Chr06_48026477_T;
Chr06_48976326_G; Chr06_49530212_J;
Chr06_49877389_A; Chr06_49908711_A;
Chr06_49925613_T; Chr06_49982968_A;
Chr06_50029281_A; Chr06_50051628_C;
Chr06_50119980_A; Chr06_50145253_S;
Chr06_50163774_S; Chr06_50179369_A;
Chr06_50975144_G; Chr06_51150774_G;
Chr07_10918261_A; Chr07_14784346_A;
Chr07_14943741_G; Chr07_15801743_G;
Chr07_19025998_J; Chr07_19051769_G;
Chr07_19196212_A; Chr07_19435779_G;
Chr07_19475119_G; Chr07_27233175_T;
Chr07_30473399_A; Chr07_41858206_1;
Chr07_43276630_C; Chr07_43553458_S;
Chr07_44443942_A; Chr07_5403591_T;
Chr07_5432458_G; Chr07_5500763_S;
Chr07_5575080_S; Chr07_5601319_A;
Chr07_5650442_A; Chr07_5825087_J;
Chr08_1028572_A; Chr08_37025145_S;
Chr08_3777218_C; Chr08_3801869_S;
Chr08_43283434_S; Chr08_43300853_A;
Chr08_43328129_G; Chr08_43361138_T;
Chr08_43375195_G; Chr08_43808487_G;
Chr08_44579046_A; Chr08_44673111_T;
Chr08_44683661_S; Chr08_44706029_G;
Chr08_44725861_S; Chr08_44754026_J;
Chr08_44795785_S; Chr08_44802718_G;
Chr08_44825547_T; Chr08_45184902_C;
Chr08_45427974_A; Chr08_45459064_G;
Chr08_45490743_A; Chr08_45506182_C;
Chr08_47284810_A; Chr08_47332464_S;
Chr08_734307_T; Chr08_776002_T;
Chr08_840319_S; Chr08_888019_S;
Chr08_920550_C; Chr08_928095_A;
Chr09_35879535_S; Chr09_36928428_S;
Chr09_37567588_A; Chr09_38843968_J;
Chr09_39300088_A; Chr09_39350396_C;
Chr09_39454893_G; Chr09_43202321_S;
Chr09_43575272_G; Chr09_45975341_S;
Chr09_46200899_S; Chr09_46308505_A;
Chr09_46327123_S; Chr09_46478149_T;
Chr09_46544673_G; Chr09_46571264_A;
Chr09_46589096_1; Chr09_46836433_A;
Chr09_47156687_C: Chr09_48003816_G;
Chr09_49162387_T; Chr09_49185455_G;
Chr10_12834195_T; Chr10_13087478_S;
Chr10_1380442_S; Chr10_14430405_T;
Chr10_38258505_S; Chr10_43269596_A;
Chr10_7840956_S; Chr10_7856251_T;
Chr11_1637913_T; Chr11_1652554_C;
Chr11_31555666_G; Chr11_31633100_A;
Chr11_32376132_G; Chr11_32402605_T;
Chr11_32506058_C; Chr11_33727131_T;
Chr11_3733610_G; Chr11_5050943_T;
Chr11_628458_C; Chr12_26153763_A;
Chr12_32400650_S; Chr12_34637037_G;
Chr12_36595459_S; Chr12_36704530_S;
Chr12_36736475_A; Chr12_36765947_G;
Chr12_36915547_A; Chr12_37028027_G;
Chr12_37978616_A; Chr12_9673552_S;
Chr12_9675105_G; Chr13_14129219_A;
Chr13_14630892_A; Chr13_16484275_C;
Chr13_17126058_T; Chr13_17177160_S;
Chr13_17356493_A; Chr13_17410106_A;
Chr13_17425003_1; Chr13_18011254_S;
Chr13_18034985_T; Chr13_18124177_G;
Chr13_18284251_A; Chr13_18454726_A;
Chr13_18552044_J; Chr13_18615062_C;
Chr13_18751848_G; Chr13_21735193_C;
Chr13_21768219_G; Chr13_21775204_G;
Chr13_41775097_A; Chr13_41988187_S;
Chr13_42028098_S; Chr13_42050209_A;
Chr13_42111517_T; Chr13_42150995_T;
Chr13_42216053_J; Chr13_42325942_G;
Chr13_42371551_G; Chr13_42383660_A;
Chr13_42410927_G; Chr13_42496589_S;
Chr14_47551214_A; Chr14_47779860_T;
Chr14_48603754_G; Chr15_207098_A;
Chr15_282154_T; Chr15_3989240_G;
Chr15_4106368_T; Chr15_474286_J;
Chr15_6368385_A; Chr16_17175190_J;
Chr16_18246040_1; Chr16_18768475_A;
Chr16_18981027_A; Chr16_19077660_S;
Chr16_19350353_G; Chr16_19464894_T;
Chr16_21200550_A; Chr16_5909595_C;
Chr16_5957479_S; Chr16_5990133_S;
Chr16_6026215_A; Chr16_6216130_G;
Chr17_12029252_S; Chr17_37552520_A;
Chr17_37578310_G; Chr17_39987601_A;
Chr17_41490859_A; Chr17_8286360_G;
Chr17_8312752_A; Chr17_8350510_S;
Chr17_8623316_S; Chr17_9150176_T;

Chr17_9991880_S; Chr18_1331239_T; Chr18_48017092_T; Chr18_48153620_S; Chr18_50213360_S; Chr18_50326879_G; Chr18_50354943_A; Chr18_50504231_S; Chr18_50526685_G; Chr18_50554508_T; Chr18_50750100_G; Chr18_57502196_S; Chr18_57557744_S; Chr18_5957508_J; Chr18_6602221_A; Chr18_6725512_J; Chr18_6786167_T; Chr18_7894691_A; Chr18_9300229_G; Chr19_38175389_T; Chr19_42496895_A; Chr19_42732180_S; Chr19_4676584_T; Chr19_47600163_G; Chr20_126314_A; Chr20_1407347_S; Chr20_40501012_C; Chr20_42761316_A; Chr20_42780643_A; Chr20_42800295_A; Chr20_43181855_A; Chr20_45204661_S.

The obtained 300 dominant alleles associated to the number of branches were as follows:

Chr01_10708262_G; Chr01_11225614_T; Chr01_17413412_G; Chr01_19950120_G; Chr01_27551480_T; Chr01_3150979_T; Chr01_48359406_A; Chr01_50572793_C; Chr01_50653236_G; Chr01_50689878_G; Chr01_50702185_C; Chr01_54065323_T; Chr01_54109018_A; Chr01_54126679_C; Chr02_10113138_T; Chr02_10141061_T; Chr02_10216169_T; Chr02_10279884_S; Chr02_10304650_T; Chr02_13294039_S; Chr02_3650992_G; Chr02_37235724_S; Chr02_44058992_S; Chr02_44113985_G; Chr02_44131383_A; Chr02_4526649_T; Chr02_7263449_S; Chr03_1140747_G; Chr03_1280334_S; Chr03_33604283_S; Chr03_3540421_C; Chr03_37015622_S; Chr03_5009142_G; Chr03_5050657_G; Chr03_5621695_T; Chr04_17777645_G; Chr04_3125194_C; Chr04_3175161_T; Chr04_3308493_G; Chr04_50757517_G; Chr04_51176069_C; Chr04_5321180_T; Chr04_6144091_T; Chr05_2729896_A; Chr05_30201810_A; Chr05_32075424_T; Chr05_32127005_T; Chr05_32150188_G; Chr05_33844667_G; Chr05_33852440_S; Chr05_34000026_A; Chr05_34025706_A; Chr05_34377218_A; Chr05_36371924_T; Chr05_37375076_T; Chr05_37414974_A; Chr05_37557447_G; Chr05_37653121_T; Chr05_37737672_G; Chr05_37794902_S; Chr05_37827649_G; Chr05_37879985_G; Chr05_41175611_T; Chr05_41213590_G; Chr05_41254151_A; Chr05_41330573_G; Chr05_5843476_T; Chr06_13308460_A; Chr06_13378329_S; Chr06_13432800_S; Chr06_13455439_A; Chr06_13481784_T; Chr06_13535265_S; Chr06_13803027_S; Chr06_45403673_C; Chr06_45489483_A; Chr06_45500186_C; Chr06_45756814_G; Chr06_47814558_S; Chr06_6958945_S; Chr06_976127_G; Chr07_15215367_T; Chr07_15375316_C; Chr07_40654148_A; Chr07_40951249_C; Chr07_41411439_G; Chr07_42047915_G; Chr07_5432458_G; Chr07_5500763_S; Chr07_5825087_T; Chr07_5954603_S; Chr07_8226456_G; Chr07_8425687_S; Chr08_16795090_C; Chr08_45075520_G; Chr08_45225436_T; Chr09_38902705_T; Chr09_458254_G; Chr09_475009_G; Chr09_500375_T; Chr09_6511413_G; Chr09_673239_A; Chr10_331641_T; Chr10_37308624_G; Chr10_38779021_A; Chr10_43269596_A; Chr10_45082937_A; Chr10_45127748_C; Chr10_46227628_A; Chr10_46628106_G; Chr10_46872534_A; Chr10_47200521_S; Chr10_47227094_S; Chr10_48180671_S; Chr10_48256879_S; Chr10_48281092_C; Chr10_48353297_A; Chr11_33527121_C; Chr11_6981640_A; Chr11_7137027_G; Chr12_2970658_A; Chr12_2978271_A; Chr12_3003089_G; Chr12_34057603_S; Chr12_34080181_T; Chr12_34152629_A; Chr12_36765947_G; Chr12_39007841_T; Chr12_3951770_A; Chr12_4086887_G; Chr12_4154222_T; Chr12_4183623_S; Chr12_4220682_A; Chr12_4725500_S; Chr12_4826555_G; Chr13_10489823_1; Chr13_11623642_T; Chr13_11625952_G; Chr13_11706421_G; Chr13_12230635_G; Chr13_18284251_A; Chr13_18426640_A; Chr13_18454726_A; Chr13_18552044_T; Chr13_18615062_C; Chr13_22002166_S; Chr13_22033385_G; Chr13_22365204_S; Chr13_22381255_A; Chr13_22407197_A; Chr13_22445616_A; Chr13_37113991_G; Chr13_37167423_G; Chr13_42550196_A; Chr13_44915146_G; Chr13_44928223_G; Chr13_44962797_T; Chr13_44986096_T; Chr13_45009740_A; Chr13_45029402_C; Chr13_45066236_T; Chr15_10014572_A; Chr15_10050118_T; Chr15_10109864_T; Chr15_10128698_T; Chr15_10206497_G; Chr15_10359216_S; Chr15_10404041_T; Chr15_10439114_T; Chr15_10605120_G; Chr15_10726400_A; Chr15_10777703_T; Chr15_10821236_A; Chr15_10922355_A; Chr15_10946495_G; Chr15_11522371_A; Chr15_4300090_C; Chr15_4478296_G; Chr15_4550829_A; Chr15_49558739_S; Chr15_49630747_A; Chr15_49657011_A; Chr15_50041669_T; Chr15_50090382_T; Chr15_50200254_S; Chr15_50225406_A; Chr15_50297493_A; Chr15_50303850_S; Chr15_50400336_S; Chr15_50500519_T; Chr15_50532317_A; Chr15_8396417_A; Chr15_8464881_T; Chr15_8537120_G; Chr15_8553863_T; Chr15_8576234_G; Chr15_8620771_S; Chr15_8638836_T; Chr15_8678412_A; Chr15_8701042_S; Chr15_8775120_G; Chr15_8842788_S; Chr15_8856165_T; Chr15_8908980_G; Chr15_8946576_S; Chr15_8960884_G; Chr15_8981420_T; Chr15_9000881_G; Chr15_9028205_G; Chr15_9077137_S; Chr15_9108212_A; Chr15_9138650_S; Chr15_9176525_A; Chr15_9250075_A; Chr15_9303248_S; Chr15_9325304_T; Chr15_9384518_G; Chr15_9402560_S; Chr15_9473113_A; Chr15_9483998_T; Chr15_9504513_S; Chr15_9527760_A; Chr15_9550196_G; Chr15_9575379_S; Chr15_9632956_A; Chr15_9650039_G; Chr15_9709385_G; Chr15_9750107_T; Chr15_9779774_S; Chr15_9845752_S; Chr15_9865235_S; Chr15_9905045_T;

Chr15_9928289_T; Chr15_9950434_A; Chr16_1966211_G; Chr16_1975010_A; Chr16_2359718_T; Chr16_2375224_G; Chr16_28681292_S; Chr16_32581835_A; Chr16_32631280_T; Chr16_32850536_G; Chr16_33135695_C; Chr16_33152519_C; Chr16_33225878_S; Chr16_35661095_A; Chr16_7902693_T; Chr17_11490884_C; Chr17_11517052_A; Chr17_13135238_G; Chr17_14501495_A; Chr17_15464503_S; Chr17_2405419_T; Chr17_2513973_T; Chr17_33371013_T; Chr17_34285079_T; Chr18_1928710_S; Chr18_1953836_T; Chr18_2207634_T; Chr18_50651797_A; Chr18_51028222_T; Chr18_51426799_C; Chr18_51599876_A; Chr18_51640237_A; Chr18_51782717_G; Chr18_56800381_G; Chr18_5957508_T; Chr18_9853550_G; Chr18_9878834_A; Chr19_1198529_G; Chr19_1252659_S; Chr19_1276857_T; Chr19_1318478_G; Chr19_1326593_A; Chr19_2003152_C; Chr19_31148670_A; Chr19_31176086_T; Chr19_3231633_C; Chr19_3728347_A; Chr19_42456535_A; Chr20_31337423_C; Chr20_31451903_A; Chr20_34605904_T; Chr20_34703521_T; Chr20_35480916_C; Chr20_35505229_G; Chr20_35525574_G; Chr20_35550298_T; Chr20_36653406_T; Chr20_36680890_T; Chr20_37334502_S; Chr20_39453136_C; Chr20_39493065_T; Chr20_39531946_A; Chr20_39604945_T; Chr20_39650111_C; Chr20_39680045_G; Chr20_47209850_T; Chr20_47267615_T; Chr20_47277493_A.

The obtained 300 dominant alleles associated to the bottom pod height were as follows:

Chr01_281981_C; Chr01_50689878_G; Chr02_2177579_S; Chr02_2250172_T; Chr02_38904196_G; Chr02_38935935_A; Chr02_38957458_T; Chr02_43825349_A; Chr02_44753024_G; Chr02_44850928_G; Chr02_44889728_T; Chr02_44902984_S; Chr02_44953925_S; Chr02_45012265_T; Chr02_45035957_S; Chr02_45083910_S; Chr0245106877_A; Chr02_45225277_T; Chr02_45300532_A; Chr02_45460408_S; Chr02_45476100_G; Chr02_45500945_T; Chr02_45675678_C; Chr02_45701878_T; Chr02_46050021_S; Chr02_47626392_T; Chr02_605426_A; Chr02_6910331_T; Chr02_702221_S; Chr02_7145800_G; Chr02_7181578_T; Chr02_7928221_T; Chr03_1452056_S; Chr03_1842018_C; Chr03_2202492_T; Chr03_35729726_G; Chr03_39976930_J; Chr03_40028464_A; Chr03_42083901_G; Chr03_42754587_T; Chr04_13575150_T; Chr04_1886636_G; Chr04_1906362_A; Chr04_1929171_G; Chr04_2464452_A; Chr04_45569116_G; Chr04_45575047_T; Chr04_45658472_T; Chr04_48707587_T; Chr04_51504477_T; Chr04_51554352_A; Chr04_5432335_S; Chr04_9914276_T; Chr05_2626909_S; Chr05_31756235_S; Chr05_34141257_A; Chr05_40147705_S; Chr05_41384000_C; Chr05_5558466_T; Chr05_5575650_G; Chr05_5613716_S; Chr05_5953531_S; Chr06_10505562_T; Chr06_10988551_C; Chr06_12232760_S; Chr06_15164880_A; Chr06_1948936_A; Chr06_2678061_S; Chr06_27950335_T; Chr06_3430462_J; Chr06_3510973_C; Chr06_3525384_T; Chr06_3629797_G; Chr06_432211_G; Chr06_44427481_S; Chr06_44680491_T; Chr06_452705_A; Chr06_45403673_A; Chr06_45721923_A; Chr06_46328232_S; Chr06_526813_T; Chr06_9125060_A; Chr07_13413417_A; Chr07_13431779_J; Chr07_15059227_S; Chr07_15215367_T; Chr07_15402604_C; Chr07_15480093_T; Chr07_15500002_G; Chr07_16130074_A; Chr07_39200003_G; Chr07_42047915_G; Chr07_6171429_A; Chr07_6864441_T; Chr07_8285590_G; Chr07_9550118_T; Chr08_17844333_T; Chr08_17908686_G; Chr08_17942655_T; Chr08_1801713_A; Chr08_19746885_S; Chr08_19853041_G; Chr08_21306156_T; Chr08_21506648_T; Chr08_21651195_A; Chr08_4952152_A; Chr08_7409094_G; Chr08_7425128_T; Chr08_7457393_A; Chr08_7512438_A; Chr08_7525546_J; Chr08_7574487_C; Chr08_7725294_T; Chr08_7805605_A; Chr08_7876236_T; Chr08_7903178_A; Chr08_7980043_J; Chr08_9170262_A; Chr08_9185800_G; Chr08_9229556_G; Chr08_9290677_A; Chr08_9307384_G; Chr08_9481603_A; Chr08_9526669_T; Chr08_9803231_G; Chr09_22525012_T; Chr09_27725186_C; Chr09_3354335_J; Chr09_38776058_T; Chr09_5108019_G; Chr10_12425641_A; Chr10_12869555_A; Chr10_12928422_G; Chr10_13000075_G; Chr10_13153732_T; Chr10_13409537_T; Chr10_13430170_A; Chr10_13553542_G; Chr10_13876671_S; Chr10_15550212_T; Chr10_18078705_A; Chr10_18501504_A; Chr10_1898584_S; Chr10_1903082_S; Chr10_24002695_T; Chr10_24143408_T; Chr10_24239878_C; Chr10_2750802_G; Chr10_2870996_G; Chr10_2927284_T; Chr10_40852908_A; Chr10_43269596_A; Chr10_43301160_G; Chr10_43990938_G; Chr10_45082937_A; Chr10_45127748_C; Chr10_45150445_G; Chr10_45175769_A; Chr10_45214117_J; Chr10_45451718_J; Chr10_45706817_A; Chr10_46491503_T; Chr10_46561144_G; Chr10_46681050_S; Chr10_47053768_A; Chr10_48900690_C; Chr10_49343783_T; Chr10_49499602_G; Chr10_49647824_T; Chr10_49660566_S; Chr10_7809194_S; Chr11_10001565_T; Chr11_1029781_T; Chr11_1050892_G; Chr11_1075377_A; Chr11_1104970_T; Chr11_1241465_G; Chr11_1261281_A; Chr11_1400922_G; Chr11_18525958_S; Chr11_2104739_T; Chr11_2167163_T; Chr11_2177285_G; Chr11_27566529_C; Chr11_28686_G; Chr11_32506058_T; Chr11_33857564_A; Chr11_429839_C; Chr11_456958_G; Chr11_5576317_A; Chr11_578326_S; Chr11_628458_G; Chr11_676727_T; Chr11_7151831_C; Chr11_7237037_G; Chr11_7275835_T;

Chr11_9896347_G; Chr12_11535616_A; Chr12_37133420_S; Chr13_14089920_J; Chr13_14129219_C; Chr13_14478389_A; Chr13_14675637_A; Chr13_16484275_J; Chr13_17346765_T; Chr13_17356493_G; Chr13_19303467_A; Chr13_19868544_6; Chr13_21976654_S; Chr13_28428400_G; Chr13_28570472_G; Chr13_29215285_T; Chr13_33804363_S; Chr13_33830754_6; Chr13_34104353_A; Chr13_34460303_A; Chr13_34653703_S; Chr13_34926633_G; Chr13_35164031_T; Chr13_45510929_G; Chr13_45620545_T; Chr13_45794372_T; Chr14_2226559_T; Chr14_225957_A; Chr14_278670_S; Chr14_7475599_G; Chr14_753089_T; Chr14_7678903_A; Chr14_7715279_S; Chr15_11225288_T; Chr15_11441207_T; Chr15_3728571_A; Chr15_49075019_G; Chr15_49152895_T; Chr15_49448263_A; Chr15_5986572_S; Chr15_6834700_T; Chr15_6912827_A; Chr15_7653389_T; Chr15_7679197_G; Chr16_1002898_A; Chr16_1125091_T; Chr16_1201997_J; Chr16_1276875_T; Chr16_27033_G; Chr16_27411219_A; Chr16_27950367_S; Chr16_28111120_A; Chr16_28513423_S; Chr16_5406664_C; Chr16_5451800_C; Chr16_5581173_J; Chr16_5628082_G; Chr16_5909595_T; Chr16_6355760_A; Chr16_6627167_S; Chr16_80533_T; Chr17_1278373_G; Chr17_25000095_T; Chr17_32381696_S; Chr17_32625085_S; Chr17_33325930_J; Chr17_38176257_T; Chr17_39450816_S; Chr17_39632330_T; Chr17_39725113_G; Chr17_39883098_S; Chr17_39936548_S; Chr17_39950851_A; Chr17_40011274_T; Chr17_40101009_T; Chr18_10008076_S; Chr18_1703661_G; Chr18_1831724_T; Chr18_19607584_G; Chr18_47924378_S; Chr18_52559344_6; Chr18_52607151_C; Chr18_54476621_A; Chr18_7595645_A; Chr18_9878834_A; Chr19_1403853_A; Chr19_2673465_A; Chr19_3073252_T; Chr19_36580105_S; Chr19_36797568_A; Chr19_38226098_G; Chr19_39707771_A; Chr19_47526134_S; Chr19_48002778_J; Chr19_48225452_G; Chr19_49693040_T; Chr19_7355423_S; Chr19_7550048_T; Chr19_8210976_J; Chr20_34389969_T; Chr20_34502253_T; Chr20_38318011_C; Chr20_40075715_S; Chr20_8076579 A.

Embodiment 3

2,193 SNP marker loci were obtained by performing deduplication of the 3000 dominant alleles obtained in the embodiment 2, probes for detecting the 2,193 SNP marker loci were designed on the basis of the obtained 2,193 SNP marker loci, and a liquid-phase gene chip for detecting the 2,193 SNP marker loci was prepared.

Embodiment 4

Figure 2:
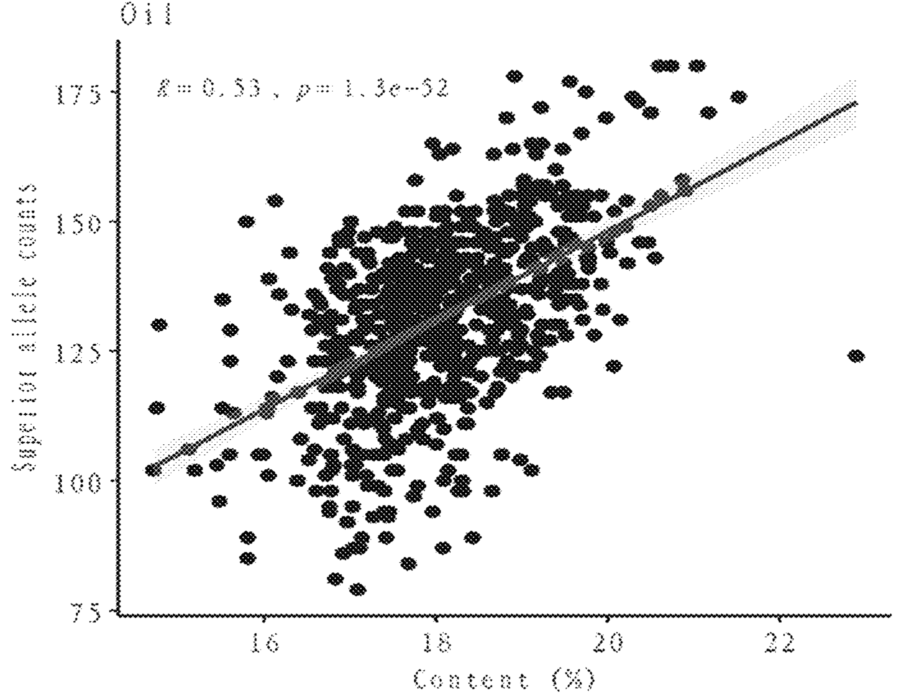
FIG. 2 is a diagram of analysis on the association between soybean fat content and dominant alleles.

For example, for the trait index of fat content, the degree of association of the 300 dominant alleles associated to the fat content in soybean, which were obtained in the embodiment 2, was verified, with the following method:

1) High-oil soybean variety FNGS0217 and low-oil soybean variety FNGS0301 that were confirmed by phenotypic traits were selected as the materials for implementation; a population of 1,000 plants of F4 generation was established by using the high-oil soybean variety FNGS0217 and the low-oil soybean variety FNGS0301, and the fat content of each plant was detected with near infrared technique;
2) The genotypes of 2,193 SNP marker loci associated to fat content in soybean in the 1,000 plants of F4 generation established from the high-oil soybean variety FNGS0217 and the low-oil soybean variety FNGS0301 were determined;
3) The aggregation of the 300 dominant alleles associated to the fat content in soybean in the Loan plants of F4 generation established from the high-oil soybean variety FNGS0217 and the low-oil soybean variety FNGS0301 was analyzed. The result is shown in FIG. 2, and indicates: the more dominant alleles associated to the fat trait are aggregated in one plant, the higher its oil content is. Therefore, the dominant alleles of the corresponding phenotypic traits obtained in the embodiment 2 can be used to evaluate the phenotypic traits of the soybean plants, and the more dominant alleles are aggregated with the associated phenotypic traits, the better the performance of the target plants in the associated phenotypic traits is.

Embodiment 5

In this embodiment, with screening high-oil varieties as an example, the method for applying the 2,193 SNP marker loci obtained in the embodiment 3 in molecular assisted breeding is introduced. The method includes the following steps:

1. Obtaining target plants to be tested: a cross-population of 1000 plants (the average fat content in the population is 18.05%) was established by using the high-oil soybean variety FNGS0217 (with 21.97% fat content) and the low-oil soybean variety FNGS0301 (with 18.06% fat content) for breeding a high-oil line;
2. The genomic DNA of each sample was extracted and a sample library is established;
3. The genotypes of the samples at the 2,193 SNP marker loci were determined with the liquid-phase gene chip prepared in the embodiment 3;
4. The determined genotypes of each sample at the 2,193 SNP marker loci were compared with the dominant alleles associated to the phenotypic traits obtained in the embodiment 2 to screen top 10 plants in terms of the number of dominant alleles associated to the fat content trait, thereby 10 high-oil soybean lines were obtained; then, after the plants in the 10 high-oil soybean lines matured, the fat contents of the 10 high-oil soybean lines were measured and verified. The result was shown in the following table. Finally, 10 high-oil soybean lines were screened out finally, with 20.36% average fat content, which was apparently higher than the average value 18.05% of the population. Thus, it is proved that the method is of high practical value.

| Variety No. | Number of dominant alleles associated to fat content | Fat content (%) |
|---|---|---|
| F4GS4-16119-267 | 180 | 21.04 |
| F4GS4-16119-373 | 180 | 20.74 |
| F4GS4-16119-781 | 180 | 20.60 |
| F4GS4-16119-922 | 178 | 19.91 |
| F4GS4-16119-472 | 177 | 19.55 |
| F4GS4-16119-497 | 175 | 19.74 |
| F4GS4-16119-159 | 174 | 21.52 |
| F4GS4-16119-596 | 174 | 20.29 |
| F4GS4-16119-625 | 173 | 20.35 |
| F4GS4-16119-59 | 172 | 19.82 |

Embodiment 6

When molecular breeding is to be carried out for traits that are not covered by the 2,193 SNP marker loci obtained in the embodiment 2, the 20,648 SNP marker loci obtained in the embodiment 1 can be directly applied in molecular assisted breeding alternatively.

While the present invention is described in some preferred embodiments above, those embodiments are not exhaustive. Those having ordinary skills in the art can make obvious modifications and variations without departing from the principle and spirit of the present invention; however, all of such modifications and variations shall be deemed as included in the protection scope of the present invention as defined by the claims.

The invention claimed is:

1. A gene chip for detecting a combination of soybean whole genome single nucleotide polymorphism (SNP) loci, wherein the gene chip is a liquid-phase chip containing a set of polynucleotide probes for the soybean whole genome SNP loci that comprise 20,648 SNP loci, wherein each of SNP loci contains two different nucleotide variation positions for detecting allelic changes of the locus, wherein the physical positions of the 20,648 SNP loci are determined on the basis of the whole genome sequence alignment of soybean variety Williams82, the version number of the whole genome sequence of the soybean variety Williams82 is *Glycine max* Wm82.a2.v1, and the 20,648 SNP loci are shown as S00001-20648.

2. The gene chip according to claim 1, wherein a solution system of the liquid-phase chip is nuclease-free water, and the concentration of the probes in the solution system is 60 ng/μL.

* * * * *